US008277804B2

(12) United States Patent
Smith

(10) Patent No.: US 8,277,804 B2

(45) Date of Patent: Oct. 2, 2012

(54) ANTAGONISTS OF IL-6 TO PREVENT OR TREAT THROMBOSIS

(75) Inventor: Jeffrey T. L. Smith, Redmond, WA (US)

(73) Assignee: Alderbio Holdings LLC, Las Vegas, NV (US)

( * ) Notice: Subject to any disclaimer, the term of this patent is extended or adjusted under 35 U.S.C. 154(b) by 368 days.

(21) Appl. No.: 12/624,830

(22) Filed: Nov. 24, 2009

(65) Prior Publication Data

US 2010/0143294 A1 Jun. 10, 2010

Related U.S. Application Data

(63) Continuation-in-part of application No. 12/502,581, filed on Jul. 14, 2009, and a continuation-in-part of application No. 12/399,156, filed on Mar. 6, 2009, and a continuation-in-part of application No. 12/391,717, filed on Feb. 24, 2009, and a continuation-in-part of application No. 12/366,567, filed on Feb. 5, 2009.

(60) Provisional application No. 61/117,861, filed on Nov. 25, 2008, provisional application No. 61/117,839, filed on Nov. 25, 2008, provisional application No. 61/117,811, filed on Nov. 25, 2008.

(51) Int. Cl.
*A61K 39/395* (2006.01)
*C07K 16/24* (2006.01)
*C12P 21/08* (2006.01)

(52) U.S. Cl. ............... 424/133.1; 424/135.1; 424/145.1; 530/350; 530/387.3; 530/388.23

(58) Field of Classification Search ........................ None
See application file for complete search history.

(56) References Cited

U.S. PATENT DOCUMENTS 7,169,573 B2 1/2007 Kurosawa et al.
2006/0257407 A1 11/2006 Chen et al.

FOREIGN PATENT DOCUMENTS

WO 2008/144763 A2 11/2008

OTHER PUBLICATIONS

Nishimoto et al. "Improvement in Castleman's disease by humanized anti-interleukin-6 receptor antibody therapy"; Blood, Jan. 1, 2000, vol. 95, No. 1, pp. 56-61.

Lab Tests Online, D-Dimer: The Test, Oct. 20, 2008 [Retrieved form the internet Jun. 17, 2010; <URL:http://web.archive.org/web/20071020065024/http://www.laptestsonline.org/understanding/analytes/d_dimer/test.html>]; pp. 1-2.

Blay et al. "Role of Interleukin-6 in the Paraneoplastic Inflammatory Syndrome Associate with Renal-Cell Carcinoma" In J. Cancer 72, 1997, pp. 424-430.

Cata et al. "The effects of thalidomide and minocycline on taxol-induced hyperalgesia in rats" Brain Res 2008, Sep. 10, 2008, pp. 1-18.

Ridker et al. "Rosuvastatin to Prevent Vascular Events in Men and Women with Elevated C-Reactive Protein" The New England Journal of Medicine, Nov. 20, 2008, vol. 359, No. 21, pp. 2195-2207.

Nishimoto et al. "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease" BI00D, Nov. 15, 2008, vol. 112, No. 10, pp. 3959-3964.

Lab Tests Online, Hypercoagulable Disorders, Mar. 1, 2008 [Retrieved from the internet Jun. 17, 2010: ,URL: http://web.archive.org/web/20080301224129/http://www.labtestsonline.org/understaning/conditions/hypercoagulable_disorders-6.html>.

International Search Report dated Jul. 14, 2010 (PCT/US09/06266).

Haddad et al. Chemotherapy-Induced thrombosis. Thrombosis Research, 118: 555-568 (2006).

Ito, et al. HMG-C0A reductase inhibitors reduce interleukin-6 synthesis in human vascular smooth muscle cells. Cardiovascular Drugs and Therapy, 16: 121-126 (2002).

*Primary Examiner* — Bridget E Bunner
*Assistant Examiner* — Fozia Hamud
(74) *Attorney, Agent, or Firm* — Hunton & Williams LLP

(57) ABSTRACT

The present invention is directed to therapeutic methods using IL-6 antagonists such as antibodies and fragments thereof having binding specificity for IL-6 to prevent or treat thrombosis in diseases associated with abnormal blood coagulation or fibrinolysis. In preferred embodiments these patients will comprise those exhibiting elevated D-dimer or other coagulation cascade related proteins and optionally will further exhibit elevated C reactive protein prior to treatment. The subject therapies also may include the administration of other actives such as chemotherapeutics, anti-coagulants, statins, et al.

46 Claims, 55 Drawing Sheets

Figure 2

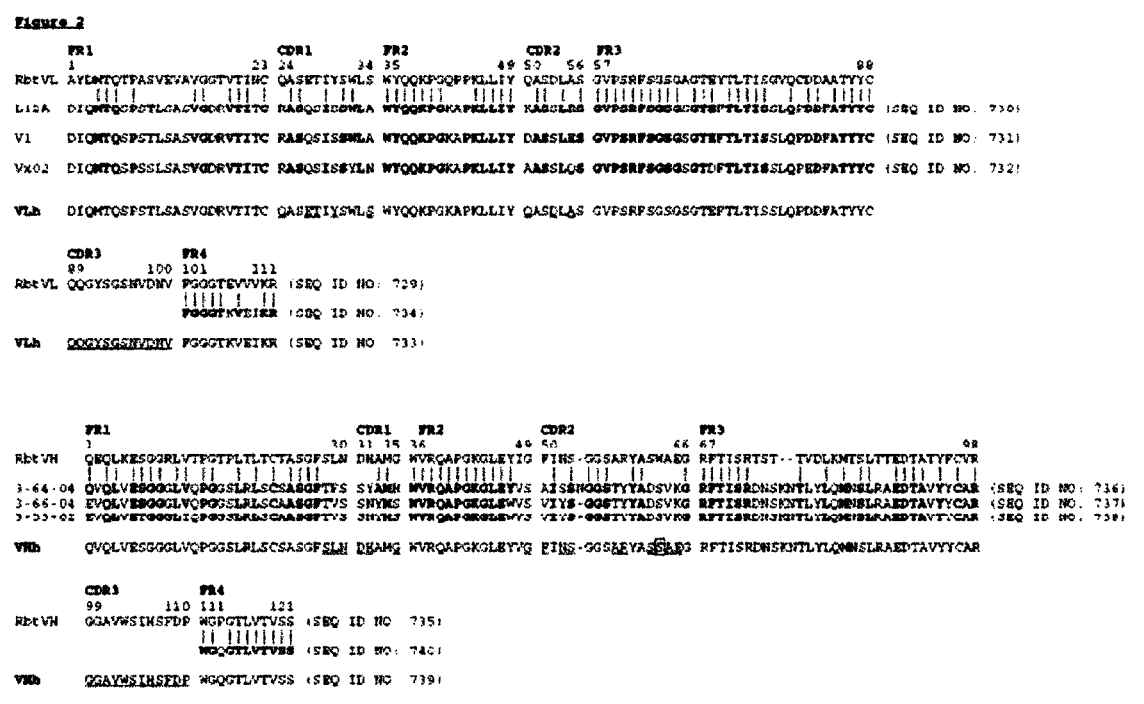

```
       FR1                      CDR1        FR2             CDR2     FR3
       1                     23 24       34 35           49 50    56 57                               88
RbtVL  AYDMTQTPASVEVAVGGTVTINC QASETIYSWLS WYQQKPGQPPKLLIY QASDLAS GVPSRFSGSGAGTEYTLTISGVQCDDAATYYC
L12A   DIQMTQSPSTLSASVGDRVTITC RASQSISSWLA WYQQKPGKAPKLLIY KASSLES GVPSRFSGSGSGTEFTLTISSLQPDDFATYYC (SEQ ID NO: 730)

V1     DIQMTQSPSTLSASVGDRVTITC RASQSISSWLA WYQQKPGKAPKLLIY DASSLES GVPSRFSGSGSGTEFTLTISSLQPDDFATYYC (SEQ ID NO: 731)

Vx02   DIQMTQSPSSLSASVGDRVTITC RASQSISSYLN WYQQKPGKAPKLLIY AASSLQS GVPSRFSGSGSGTDFTLTISSLQPEDFATYYC (SEQ ID NO: 732)

VLh    DIQMTQSPSTLSASVGDRVTITC QASETIYSWLS WYQQKPGKAPKLLIY QASDLAS GVPSRFSGSGSGTEFTLTISSLQPDDFATYYC

       CDR3         FR4
       89       100 101       111
RbtVL  QQGYSGSNVDNV FGGGTEVVVKR (SEQ ID NO: 729)
                    FGGGTKVEIKR (SEQ ID NO: 734)

VLh    QQGYSGSNVDNV FGGGTKVEIKR (SEQ ID NO: 733)


         FR1                           CDR1  FR2            CDR2              FR3
         1                          30 31 35 36          49 50              66 67                              98
RbtVH    QEQLKESGGRLVTPGTPLTLTCTASGFSLN DHAMG WVRQAPGKGLEYIG FINS-GGSARYASWAEG RFTISRTST--TVDLKMTSLTTEDTATYFCVR
3-64-04  QVQLVESGGGLVQPGGSLRLSCSASGFTFS SYAMH WVRQAPGKGLEYVS AISSNGGSTYYADSVKG RFTISRDNSKNTLYLQMNSLRAEDTAVYYCAR (SEQ ID NO: 736)
3-66-04  EVQLVESGGGLVQPGGSLRLSCAASGFTVS SNYMS WVRQAPGKGLEWVS VIYS-GGSTYYADSVKG RFTISRDNSKNTLYLQMNSLRAEDTAVYYCAR (SEQ ID NO: 737)
3-53-02  EVQLVETGGGLIQPGGSLRLSCAASGFTVS SNYMS WVRQAPGKGLEWVS VIYS-GGSTYYADSVKG RFTISRDNSKNTLYLQMNSLRAEDTAVYYCAR (SEQ ID NO: 738)

VHh      QVQLVESGGGLVQPGGSLRLSCSASGFSLN DHAMG WVRQAPGKGLEYVG FINS-GGSAEYASSAEG RFTISRDNSKNTLYLQMNSLRAEDTAVYYCAR

         CDR3         FR4
         99       110 111       121
RbtVH    GGAVWSIHSFDP WGPGTLVTVSS (SEQ ID NO: 735)
                      WGQGTLVTVSS (SEQ ID NO: 740)

VHh      GGAVWSIHSFDP WGQGTLVTVSS (SEQ ID NO: 739)
```

FIG. 11

| Antibody | Blocks IL6 binding to R1 | Blocks IL6 binding to GP130 | Reference |
|---|---|---|---|
| Ab1 | Yes | Yes | 021051 |
| Ab2 | No | Partial | 021050 |
| Ab3 | No | Yes | 021030 |
| Ab4 | No | Yes | 021050 |
| Ab6 | Yes | Yes | 021051 |
| Ab7 | Yes | Yes | 021051 |
| Ab8 | No | Yes | 021051 |

FIG. 12

| | | |
|---|---|---|
| 1 VPPGEDSKDVAAPHR (SEQ ID NO: 590) | 20 ENNLNLPKMAEKDGC (SEQ ID NO: 609) | 39 QMSTKVLIQFLQKKA (SEQ ID NO: 628) |
| 2 GEDSKDVAAPHRQPL (SEQ ID NO: 591) | 21 LNLPKMAEKDGCFQS (SEQ ID NO: 610) | 40 TKVLIQFLQKKAKNL (SEQ ID NO: 629) |
| 3 SKDVAAPHRQPLTSS (SEQ ID NO: 592) | 22 PKMAEKDGCFQSGFN (SEQ ID NO: 611) | 41 LIQFLQKKAKNLDAI (SEQ ID NO: 630) |
| 4 VAAPHRQPLTSSERI (SEQ ID NO: 593) | 23 AEKDGCFQSGFNEET (SEQ ID NO: 612) | 42 FLQKKAKNLDAITTP (SEQ ID NO: 631) |
| 5 PHRQPLTSSERIDKQ (SEQ ID NO: 594) | ■24 DGCFQSGFNEETCLV (SEQ ID NO: 613) | 43 KKAKNLDAITTPDPT (SEQ ID NO: 632) |
| 6 QPLTSSERIDKQIRY (SEQ ID NO: 595) | 25 FQSGFNEETCLVKII (SEQ ID NO: 614) | 44 KNLDAITTPDPTTNA (SEQ ID NO: 633) |
| 7 TSSERIDKQIRYILD (SEQ ID NO: 596) | 26 GFNEETCLVKIITGL (SEQ ID NO: 615) | 45 DAITTPDPTTNASLL (SEQ ID NO: 634) |
| 8 ERIDKQIRYILDGIS (SEQ ID NO: 597) | 27 EETCLVKIITGLLEF (SEQ ID NO: 616) | 46 TTPDPTTNASLLTKL (SEQ ID NO: 635) |
| 9 DKQIRYILDGISALR (SEQ ID NO: 598) | 28 CLVKIITGLLEFEVY (SEQ ID NO: 617) | 47 DPTTNASLLTKLQAQ (SEQ ID NO: 636) |
| 10 IRYILDGISALRKET (SEQ ID NO: 599) | 29 KIITGLLEFEVYLEY (SEQ ID NO: 618) | 48 TNASLLTKLQAQNQW (SEQ ID NO: 637) |
| 11 ILDGISALRKETCNK (SEQ ID NO: 600) | 30 TGLLEFEVYLEYLQN (SEQ ID NO: 619) | 49 SLLTKLQAQNQWLQD (SEQ ID NO: 638) |
| 12 GISALRKETCNKSNM (SEQ ID NO: 601) | 31 LEFEVYLEYLQNRFE (SEQ ID NO: 620) | 50 TKLQAQNQWLQDMTT (SEQ ID NO: 639) |
| ■13 ALRKETCNKSNMCES (SEQ ID NO: 602) | 32 EVYLEYLQNRFESSE (SEQ ID NO: 621) | 51 QAQNQWLQDMTTHLI (SEQ ID NO: 640) |
| 14 KETCNKSNMCESSKE (SEQ ID NO: 603) | 33 LEYLQNRFESSEEQA (SEQ ID NO: 622) | 52 NQWLQDMTTHLILRS (SEQ ID NO: 641) |
| 15 CNKSNMCESSKEALA (SEQ ID NO: 604) | 34 LQNRFESSEEQARAV (SEQ ID NO: 623) | 53 LQDMTTHLILRSFKE (SEQ ID NO: 642) |
| 16 SNMCESSKEALAENN (SEQ ID NO: 605) | 35 RFESSEEQARAVQMS (SEQ ID NO: 624) | 54 MTTHLILRSFKEFLQ (SEQ ID NO: 643) |
| 17 CESSKEALAENNLNL (SEQ ID NO: 606) | 36 SSEEQARAVQMSTKV (SEQ ID NO: 625) | 55 HLILRSFKEFLQSSL (SEQ ID NO: 644) |
| 18 SKEALAENNLNLPKM (SEQ ID NO: 607) | 37 EQARAVQMSTKVLIQ (SEQ ID NO: 626) | 56 LRSFKEFLQSSLRAL (SEQ ID NO: 645) |
| 19 ALAENNLNLPKMAEK (SEQ ID NO: 608) | 38 RAVQMSTKVLIQFLQ (SEQ ID NO: 627) | ■57 FKEFLQSSLRALRQM (SEQ ID NO: 646) |

FIG. 15

A. Surface Plasmon Resonance: Averaged binding constants determined at 25 ° C for Ab1 to IL-6.

| Species (IL-6) | $K_a$ ($M^{-1}s^{-1}$) | $K_d$ ($s^{-1}$) | $K_D$ |
|---|---|---|---|
| Rat | $1.6e^6$ | $2.2e^{-3}$ | 1.4 nM |
| Mouse | $1.1e^6$ | $4.0e^{-4}$ | 0.4 nM |
| Dog | Below LOQ[a] | Below LOQ[a] | Below LOQ[a] |
| Human | $1.6e^5$ | $5e^{-7}$ | 4 pM |
| Cynomolgus monkey | $9.6e^4$ | $3e^{-6}$ | 31 pM |

a. Below Limit of Quantitation

B. IC50 values for Ab1 against human, cynomolgus monkey, mouse, rat and dog IL-6 in the T1165 assay.

| IL-6 Species | IC50 (pM) |
|---|---|
| Human | 13 |
| Cynomolgus monkey | 12 |
| Mouse | 1840 |
| Rat | 2060 |
| Dog | No inhibition of cell proliferation |

FIG. 19

Summary of Ab1 Pharmacokinetics in Healthy Human Volunteers

| Dose of Ab1 | $T_{1/2}$ (days) | AUC (µg · h / mL) | $C_{max}$ (µg / mL) | $T_{max}$ |
|---|---|---|---|---|
| 1mg | 10.3 | 35 | 0.1 | 8 |
| 3mg | 11.6 | 229 | 0.7 | 4 |
| 10mg | 22.4 | 1473 | 4.0 | 4 |
| 30mg | 25.1 | 9076 | 19.4 | 4 |
| 100mg | 30.3 | 26128 | 48.0 | 12 |
| 300mg | 26.2 | 92891 | 188.0 | 12 |
| 640mg | 30.2 | 175684 | 306.0 | 12 |

Mean plasma concentration of Ab1 given as a single IV infusion of 80 mg (n=2) or 160 mg (n=3) (Mean +/- SEM)

FIG. 21

Unprecedented Elimination Half-life of Ab1

| | **Cynomolgus Monkey (days)** | **Human (days)** |
|---|---|---|
| Ab1 | 15-21 | ~31 |
| Actemra (Tocilizumab) | 7 | 6 |
| Remicade | 5 | 8 to 9.5 |
| Synagis | 8.6 | 20 |
| Erbitux | 3 to 7 | 5 |
| Zenapax | 7 | 20 |
| Avastin | 10 | 20 |
| Pertuzumab | 10 | 18 to 22 |

Single IV infusion of 80 mg, 160 mg, or 320 mg Ab1 (n=8) (Mean +/- SEM)

Ab1 Prevents Weight Loss in a Mouse Cancer Cachexia Model

FIGURE 34 - PREFERRED ANTI-IL-6 ANTIBODY HUMANIZATION

| | FR1 | CDR1 | FR2 | CDR2 | FR3 |
|---|---|---|---|---|---|
| SEQ ID NO:647 | AYDMTQTPASVSAAVGGTVTIKC | QASQSINNELS | WYQQKPGQRPKLLIY | RASTLAS | GVSSRFKGSGSGTEFTLTISDLECADAATYYC |
| SEQ ID NO:648 | AIQMTQSPSSLSASVGDRVTITC | RASQGIRNDLG | WYQQKPGKAPKLLIY | AASSLQS | GVPSRFSGSGSGTDFTLTISSLQPEDFATYYC |
| SEQ ID NO:649 | DIQMTQSPSSLSASVGDRVTITC | RASQGISNYLA | WYQQKPGKVPKLLIY | AASTLQS | GVPSRFSGSGSGTDFTLTISSLQPEDVATYYC |
| SEQ ID NO:650 | DIQMTQSPSTLSASVGDRVTITC | RASQSISSWLA | WYQQKPGKAPKLLIY | KASSLES | GVPSRFSGSGSGTEFTLTISSLQPDDFATYYC |
| SEQ ID NO:651 | AIQMTQSPSSLSASVGDRVTITC | QASQSINNELS | WYQQKPGKAPKLLIY | RASTLAS | GVPSRFSGSGSGTDFTLTISSLQPEDFATYYC |
| SEQ ID NO:651 | AIQMTQSPSSLSASVGDRVTITC | QASQSINNELS | WYQQKPGKAPKLLIY | RASTLAS | GVPSRFSGSGSGTDFTLTISSLQPEDFATYYC |

| | CDR3 | FR4 |
|---|---|---|
| SEQ ID NO:647 | QQGYSLRNIDNA | FGGGTEVVVKR |
| SEQ ID NO:648 | | |
| SEQ ID NO:649 | | FGGGTKVEIKR |
| SEQ ID NO:650 | | |
| SEQ ID NO:651 | QQGYSLRNIDNA | FGGGTKVEIKR |
| SEQ ID NO:651 | QQGYSLRNIDNA | FGGGTKVEIKR |

| | FR1 | CDR1 | FR2 | CDR2 | FR3 |
|---|---|---|---|---|---|
| SEQ ID NO:652 | -QSLEESGGRLVTPGTPLTLTCTASGFSLS | NYYVT | WVRQAPGKGLEWIG | IIYG-SDETAYATWAIG | RFTISKTST--TVDLKMTSLTAADTATYFCAR |
| SEQ ID NO:653 | EVQLVESGGGLVQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO:654 | EVQLVESGGGLIQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO:655 | EVQLLESGGGLVQPGGSLRLSCAASGFTFS | SYAMS | WVRQAPGKGLEWVS | VIYSGGSSTYYADSVKG | RFTISRDNSKNTLYLQMNSLRAEDTAVYYCAK |
| SEQ ID NO:656 | EVQLVESGGGLVQPGGSLRLSCAASGFSLS | NYYVT | WVRQAPGKGLEWVG | IIYG-SDETAYATWAIG | RFTISRDNSKNTLYLQMNSLRAEDTAVYYCAR |
| SEQ ID NO:657 | EVQLVESGGGLVQPGGSLRLSCAASGFSLS | NYYVT | WVRQAPGKGLEWVG | IIYG-SDETAYATSAIG | RFTISRDNSKNTLYLQMNSLRAEDTAVYYCAR |

| | CDR3 | FR4 |
|---|---|---|
| SEQ ID NO:652 | DDSSDWDAKFNL | WGQGTLVTVSS |
| SEQ ID NO:653 | | |
| SEQ ID NO:654 | | WGQGTLVTVSS |
| SEQ ID NO:655 | | |
| SEQ ID NO:656 | DDSSDWDAKFNL | WGQGTLVTVSS |
| SEQ ID NO:657 | DDSSDWDAKFNL | WGQGTLVTVSS |

FIGURE 35 - PREFERRED ANTI-IL-6 ANTIBODY HUMANIZATION

| | FR1 | CDR1 | FR2 | CDR2 | FR3 |
|---|---|---|---|---|---|
| SEQ ID NO:647 | AYDMTQTPASVSAAVGGTVTIKC | QASQSINNELS | WYQQKPGQRPKLLIY | RASTLAS | GVSSRFKGSGSGTEFTLTISDLECADAATYYC |
| SEQ ID NO:648 | AIQMTQSPSSLSASVGDRVTITC | RASQGIRNDLG | WYQQKPGKAPKLLIY | AASSLQS | GVPSRFSGSGSGTDFTLTISSLQPEDFATYYC |
| SEQ ID NO:649 | DIQMTQSPSSLSASVGDRVTITC | RASQGISNYLA | WYQQKPGKVPKLLIY | AASTLQS | GVPSRFSGSGSGTDFTLTISSLQPEDVATYYC |
| SEQ ID NO:650 | DIQMTQSPSTLSASVGDRVTITC | RASQSISSWLA | WYQQKPGKAPKLLIY | KASSLES | GVPSRFSGSGSGTEFTLTISSLQPDDFATYYC |
| SEQ ID NO:709 | AIQMTQSPSSLSASVGDRVTITC | QASQSINNELS | WYQQKPGKAPKLLIY | RASTLAS | GVPSRFSGSGSGTDFTLTISSLQPDDFATYYC |
| SEQ ID NO:709 | AIQMTQSPSSLSASVGDRVTITC | QASQSINNELS | WYQQKPGKAPKLLIY | RASTLAS | GVPSRFSGSGSGTDFTLTISSLQPDDFATYYC |

| | CDR3 | FR4 |
|---|---|---|
| SEQ ID NO:647 | QQGYSLRNIDNA | FGGGTEVVVKR |
| SEQ ID NO:648 | | |
| SEQ ID NO:649 | | FGGGTKVEIKR |
| SEQ ID NO:650 | | |
| SEQ ID NO:709 | QQGYSLRNIDNA | FGGGTKVEIKR |
| SEQ ID NO:709 | QQGYSLRNIDNA | FGGGTKVEIKR |

| | FR1 | CDR1 | FR2 | CDR2 | FR3 |
|---|---|---|---|---|---|
| SEQ ID NO:652 | -QSLEESGGRLVTPGTPLTLTCTASGFSLS | NYYVT | WVRQAPGKGLEWIG | IIYG-SDETAYATWAIG | RFTISKTST--TVDLKMTSLTAADTATYFCAR |
| SEQ ID NO:653 | EVQLVESGGGLVQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO:654 | EVQLVESGGGLIQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO:655 | EVQLLESGGGLVQPGGSLRLSCAASGFTFS | SYAMS | WVRQAPGKGLEWVS | VIYSGGSSTYYADSVKG | RFTISRDNSKNTLYLQMNSLRAEDTAVYYCAK |
| SEQ ID NO:656 | EVQLVESGGGLVQPGGSLRLSCAASGFSLS | NYYVT | WVRQAPGKGLEWVG | IIYG-SDETAYATWAIG | RFTISRDNSKNTLYLQMNSLRAEDTAVYYCAR |
| SEQ ID NO:657 | EVQLVESGGGLVQPGGSLRLSCAASGFSLS | NYYVT | WVRQAPGKGLEWVG | IIYG-SDETAYATSAIG | RFTISRDNSKNTLYLQMNSLRAEDTAVYYCAR |

| | CDR3 | FR4 |
|---|---|---|
| SEQ ID NO:652 | DDSSDWDAKFNL | WGQGTLVTVSS |
| SEQ ID NO:653 | | |
| SEQ ID NO:654 | | WGQGTLVTVSS |
| SEQ ID NO:655 | | |
| SEQ ID NO:656 | DDSSDWDAKFNL | WGQGTLVTVSS |
| SEQ ID NO:657 | DDSSDWDAKFNL | WGQGTLVTVSS |

FIGURE 36A - Alignment of Ab1 light chains

| | | FR1 | CDR1 | FR2 |
|---|---|---|---|---|
| SEQ ID NO:2 | MDTRAPTQLLGLLLLWLPGARC | AYDMTQTPASVSAAVGGTVTIKC | QASQSINNELS | WYQQKPGQRPKLLIY |
| SEQ ID NO:20 | | IQMTQSPSSLSASVGDRVTITC | QASQSINNELS | WYQQKPGKAPKLLIY |
| SEQ ID NO:647 | | AYDMTQTPASVSAAVGGTVTIKC | QASQSINNELS | WYQQKPGQRPKLLIY |
| SEQ ID NO:651 | | AIQMTQSPSSLSASVGDRVTITC | QASQSINNELS | WYQQKPGKAPKLLIY |
| SEQ ID NO:660 | MDTRAPTQLLGLLLLWLPGARC | AYDMTQTPASVSAAVGGTVTIKC | QASQSINNELS | WYQQKPGQRPKLLIY |
| SEQ ID NO:666 | | IQMTQSPSSLSASVGDRVTITC | QASQSINNELS | WYQQKPGKAPKLLIY |
| SEQ ID NO:699 | | AIQMTQSPSSLSASVGDRVTITC | QASQSINNELS | WYQQKPGKAPKLLIY |
| SEQ ID NO:702 | | AIQMTQSPSSLSASVGDRVTITC | QASQSINNELS | WYQQKPGKAPKLLIY |
| SEQ ID NO:706 | MKWVTFISLLFLFSSAYS | AIQMTQSPSSLSASVGDRVTITC | QASQSINNELS | WYQQKPGKAPKLLIY |
| SEQ ID NO:709 | | AIQMTQSPSSLSASVGDRVTITC | QASQSINNELS | WYQQKPGKAPKLLIY |

| | CDR2 | FR3 | CDR3 |
|---|---|---|---|
| SEQ ID NO:2 | RASTLAS | GVSSRFKGSGSGTEFTLTISDLECADAATYYC | QQGYSLRNIDNA |
| SEQ ID NO:20 | RASTLAS | GVPSRFSGSGSGTDFTLTISSLQPDDFATYYC | QQGYSLRNIDNA |
| SEQ ID NO:647 | RASTLAS | GVSSRFKGSGSGTEFTLTISDLECADAATYYC | QQGYSLRNIDNA |
| SEQ ID NO:651 | RASTLAS | GVPSRFSGSGSGTDFTLTISSLQPEDFATYYC | QQGYSLRNIDNA |
| SEQ ID NO:660 | RASTLAS | GVSSRFKGSGSGTEFTLTISDLECADAATYYC | QQGYSLRNIDNA |
| SEQ ID NO:666 | RASTLAS | GVPSRFSGSGSGTDFTLTISSLQPDDFATYYC | QQGYSLRNIDNA |
| SEQ ID NO:699 | RASTLAS | GVPSRFSGSGSGTDFTLTISSLQPDDFATYYC | QQGYSLRNIDNA |
| SEQ ID NO:702 | RASTLAS | GVPSRFSGSGSGTDFTLTISSLQPDDFATYYC | QQGYSLRNIDNA |
| SEQ ID NO:706 | RASTLAS | GVPSRFSGSGSGTDFTLTISSLQPDDFATYYC | QQGYSLRNIDNA |
| SEQ ID NO:709 | RASTLAS | GVPSRFSGSGSGTDFTLTISSLQPDDFATYYC | QQGYSLRNIDNA |

FIGURE 36B - Alignment of Ab1 light chains (continued)

```
                    FR4             kappa constant light chain
SEQ ID NO:2    FGGGTEVVVKR T VAAPSVFIFPPSDEQLKSGTASVVCLLNN
SEQ ID NO:20
SEQ ID NO:647 FGGGTEVVVKR
SEQ ID NO:651 FGGGTKVEIKR
SEQ ID NO:660
SEQ ID NO:666 FGGGTKVEIKR T VAAPSVFIFPPSDEQLKSGTASVVCLLNNFYPREAKVQWKVDNALQSGN
SEQ ID NO:699 FGGGTKVEIKR T
SEQ ID NO:702 FGGGTKVEIKR T VAAPSVFIFPPSDEQLKSGTASVVCLLNNFYPREAKVQWKVDNALQSGN
SEQ ID NO:706 FGGGTKVEIKR T VAAPSVFIFPPSDEQLKSGTASVVCLLNNFYPREAKVQWKVDNALQSGN
SEQ ID NO:709 FGGGTKVEIKR

                 kappa constant light chain (continued)
SEQ ID NO:2
SEQ ID NO:20
SEQ ID NO:647
SEQ ID NO:651
SEQ ID NO:660
SEQ ID NO:666 SQESVTEQDSKDSTYSLSSTLTLSKADYEKHKVYACEVTHQGLSSPVTKSFNRGEC
SEQ ID NO:699
SEQ ID NO:702 SQESVTEQDSKDSTYSLSSTLTLSKADYEKHKVYACEVTHQGLSSPVTKSFNRGEC
SEQ ID NO:706 SQESVTEQDSKDSTYSLSSTLTLSKADYEKHKVYACEVTHQGLSSPVTKSFNRGEC
SEQ ID NO:709
```

FIGURE 37A - Alignment of Ab1 heavy chains

| | | FR1 | CDR1 | FR2 |
|---|---|---|---|---|
| SEQ ID NO:3 | METGLRWLLLVAVLKGVQC | -QSLEESGGRLVTPGTPLTLTCTASGFSLS | NYYVT | WVRQAPGKGLEWIG |
| SEQ ID NO:18 | | EVQLVESGGGLVQPGGSLRLSCAASGFSLS | NYYVT | WVRQAPGKGLEWVG |
| SEQ ID NO:19 | | EVQLVESGGGLVQPGGSLRLSCAASGFSLS | NYYVT | WVRQAPGKGLEWVG |
| SEQ ID NO:652 | | -QSLEESGGRLVTPGTPLTLTCTASGFSLS | NYYVT | WVRQAPGKGLEWIG |
| SEQ ID NO:656 | | EVQLVESGGGLVQPGGSLRLSCAASGFSLS | NYYVT | WVRQAPGKGLEWVG |
| SEQ ID NO:657 | | EVQLVESGGGLVQPGGSLRLSCAASGFSLS | NYYVT | WVRQAPGKGLEWVG |
| SEQ ID NO:658 | METGLRWLLLVAVLKGVQC | -QSLEESGGRLVTPGTPLTLTCTASGFSLS | NYYVT | WVRQAPGKGLEWIG |
| SEQ ID NO:661 | METGLRWLLLVAVLKGVQC | -QSLEESGGRLVTPGTPLTLTCTASGFSLS | NYYVT | WVRQAPGKGLEWIG |
| SEQ ID NO:664 | | EVQLVESGGGLVQPGGSLRLSCAASGFSLS | NYYVT | WVRQAPGKGLEWVG |
| SEQ ID NO:665 | | EVQLVESGGGLVQPGGSLRLSCAASGFSLS | NYYVT | WVRQAPGKGLEWVG |
| SEQ ID NO:704 | | EVQLVESGGGLVQPGGSLRLSCAASGFSLS | NYYVT | WVRQAPGKGLEWVG |
| SEQ ID NO:708 | MKWVTFISLLFLFSSAYS | EVQLVESGGGLVQPGGSLRLSCAASGFSLS | NYYVT | WVRQAPGKGLEWVG |

| | CDR2 | FR3 | CDR3 | FR4 |
|---|---|---|---|---|
| SEQ ID NO:3 | IIYG-SDETAYATWAIG | RFTISKTST--TVDLKMTSLTAADTATYFCAR | DDSSDWDAKFNL | WGQGTLVTVSS |
| SEQ ID NO:18 | IIYG-SDETAYATWAIG | RFTISRDNSKNTLYLQMNSLRAEDTAVYYCAR | DDSSDWDAKFNL | |
| SEQ ID NO:19 | IIYG-SDETAYATSAIG | RFTISRDNSKNTLYLQMNSLRAEDTAVYYCAR | DDSSDWDAKFNL | |
| SEQ ID NO:652 | IIYG-SDETAYATWAIG | RFTISKTST--TVDLKMTSLTAADTATYFCAR | DDSSDWDAKFNL | WGQGTLVTVSS |
| SEQ ID NO:656 | IIYG-SDETAYATWAIG | RFTISRDNSKNTLYLQMNSLRAEDTAVYYCAR | DDSSDWDAKFNL | WGQGTLVTVSS |
| SEQ ID NO:657 | IIYG-SDETAYATSAIG | RFTISRDNSKNTLYLQMNSLRAEDTAVYYCAR | DDSSDWDAKFNL | WGQGTLVTVSS |
| SEQ ID NO:658 | IIYG-SDETAYATSAIG | RFTISKTST--TVDLKMTSLTAADTATYFCAR | DDSSDWDAKFNL | WGQGTLVTVSS |
| SEQ ID NO:661 | IIYG-SDETAYATWAIG | RFTISKTST--TVDLKMTSLTAADTATYFCAR | DDSSDWDAKFNL | |
| SEQ ID NO:664 | IIYG-SDETAYATWAIG | RFTISRDNSKNTLYLQMNSLRAEDTAVYYCAR | DDSSDWDAKFNL | WGQGTLVTVSS |
| SEQ ID NO:665 | IIYG-SDETAYATSAIG | RFTISRDNSKNTLYLQMNSLRAEDTAVYYCAR | DDSSDWDAKFNL | WGQGTLVTVSS |
| SEQ ID NO:704 | IIYG-SDETAYATSAIG | RFTISRDNSKNTLYLQMNSLRAEDTAVYYCAR | DDSSDWDAKFNL | WGQGTLVTVSS |
| SEQ ID NO:708 | IIYG-SDETAYATSAIG | RFTISRDNSKNTLYLQMNSLRAEDTAVYYCAR | DDSSDWDAKFNL | WGQGTLVTVSS |

FIGURE 37B - Alignment of Ab1 heavy chains, continued

```
                  gamma-1 constant heavy chain polypeptide
SEQ ID NO:3       ASTKGPSVFPLAPSSKSTSGGTAALGCLVK
SEQ ID NO:658     ASTKGPSVFPLAPSSKSTSGGTAALGCLVK

SEQ ID NO:664     ASTKGPSVFPLAPSSKSTSGGTAALGCLVKDYFPEPVTVSWNSGALTSGVHTFPAVLQSSGLYSLSSVVTVPSSS
SEQ ID NO:665     ASTKGPSVFPLAPSSKSTSGGTAALGCLVKDYFPEPVTVSWNSGALTSGVHTFPAVLQSSGLYSLSSVVTVPSSS
SEQ ID NO:704     ASTKGPSVFPLAPSSKSTSGGTAALGCLVKDYFPEPVTVSWNSGALTSGVHTFPAVLQSSGLYSLSSVVTVPSSS
SEQ ID NO:708     ASTKGPSVFPLAPSSKSTSGGTAALGCLVKDYFPEPVTVSWNSGALTSGVHTFPAVLQSSGLYSLSSVVTVPSSS

                  gamma-1 constant heavy chain polypeptide, continued
SEQ ID NO:664     LGTQTYICNVNHKPSNTKVDKRVEPKSCDKTHTCPPCPAPELLGGPSVFLFPPKPKDTLMISRTPEVTCVVVDVS
SEQ ID NO:665     LGTQTYICNVNHKPSNTKVDKRVEPKSCDKTHTCPPCPAPELLGGPSVFLFPPKPKDTLMISRTPEVTCVVVDVS
SEQ ID NO:704     LGTQTYICNVNHKPSNTKVDKRVEPKSCDKTHTCPPCPAPELLGGPSVFLFPPKPKDTLMISRTPEVTCVVVDVS
SEQ ID NO:708     LGTQTYICNVNHKPSNTKVDKRVEPKSCDKTHTCPPCPAPELLGGPSVFLFPPKPKDTLMISRTPEVTCVVVDVS

                  gamma-1 constant heavy chain polypeptide, continued
SEQ ID NO:664     HEDPEVKFNWYVDGVEVHNAKTKPREEQYASTYRVVSVLTVLHQDWLNGKEYKCKVSNKALPAPIEKTISKAKGQ
SEQ ID NO:665     HEDPEVKFNWYVDGVEVHNAKTKPREEQYASTYRVVSVLTVLHQDWLNGKEYKCKVSNKALPAPIEKTISKAKGQ
SEQ ID NO:704     HEDPEVKFNWYVDGVEVHNAKTKPREEQYASTYRVVSVLTVLHQDWLNGKEYKCKVSNKALPAPIEKTISKAKGQ
SEQ ID NO:708     HEDPEVKFNWYVDGVEVHNAKTKPREEQYASTYRVVSVLTVLHQDWLNGKEYKCKVSNKALPAPIEKTISKAKGQ

                  gamma-1 constant heavy chain polypeptide, continued
SEQ ID NO:664     PREPQVYTLPPSRDELTKNQVSLTCLVKGFYPSDIAVEWESNGQPENNYKTTPPVLDSDGSFFLYSKLTVDKSRW
SEQ ID NO:665     PREPQVYTLPPSRDELTKNQVSLTCLVKGFYPSDIAVEWESNGQPENNYKTTPPVLDSDGSFFLYSKLTVDKSRW
SEQ ID NO:704     PREPQVYTLPPSREEMTKNQVSLTCLVKGFYPSDIAVEWESNGQPENNYKTTPPVLDSDGSFFLYSKLTVDKSRW
SEQ ID NO:708     PREPQVYTLPPSREEMTKNQVSLTCLVKGFYPSDIAVEWESNGQPENNYKTTPPVLDSDGSFFLYSKLTVDKSRW

                  gamma-1 constant heavy chain polypeptide, continued
SEQ ID NO:664     QQGNVFSCSVMHEALHNHYTQKSLSLSPGK
SEQ ID NO:665     QQGNVFSCSVMHEALHNHYTQKSLSLSPGK
SEQ ID NO:704     QQGNVFSCSVMHEALHNHYTQKSLSLSPGK
SEQ ID NO:708     QQGNVFSCSVMHEALHNHYTQKSLSLSPGK
```

ANTAGONISTS OF IL-6 TO PREVENT OR TREAT THROMBOSIS

CROSS-REFERENCE TO RELATED APPLICATIONS

This application claims the benefit of priority to U.S. provisional patent application No. 61/117,811, 61/117,861, and 61/117,839 all filed on Nov. 25, 2008 the disclosure of each of which is herein incorporated by reference in its entirety.

The sequence listing file named "67858o708001v1.txt" having a size of 342,443 bytes which was created on May 21, 2012 is hereby incorporated by reference in its entirety.

BACKGROUND OF THE INVENTION

1. Field of the Invention

This invention is an extension of Applicants' prior invention disclosed in the above-referenced patent applications relating to novel anti-IL-6 antibodies and novel therapies and therapeutic protocols using anti-IL-6 antibodies, preferably those described herein. In particular, this invention pertains to methods of preventing or treating thrombosis in a patient in need thereof, comprising administering to the patient an IL-6 antagonist, e.g., an anti-IL-6 antibody as disclosed in applicants' earlier applications referenced herein whereby the patient's coagulation profile is improved.

In another embodiment the invention provides novel combination therapies wherein thrombosis is prevented or treated by the administration of at least one IL-6 antagonist and at least one other therapeutic compound e.g., a statin compound including but not limited to atorvastatin, cerivastatin, fluvastatin, lovastatin, mevastatin, pitavastatin, pravastatin, rosuvastatin, simvastatin, or any combination thereof.

In another embodiment, this invention relates to methods of preventing or treating thrombosis in a patient in a state of hypercoagulation, comprising administering to the patient an anti-IL-6 antibody or antibody fragment, whereby the patient's coagulation profile is improved or restored to a normal condition, and monitoring the patient to assess coagulation profile, wherein the anti-IL-6 antibody or antibody fragment specifically binds to the same linear or conformational epitope(s) and/or competes for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies. Preferably these antibodies are aglycosylated.

This invention further pertains to novel methods of preventing or treating thrombosis in a patient in need thereof using anti-IL-6 antibodies, preferably humanized antibodies possessing an elimination half-life which is at least about 25 days.

2. Description of Related Art

Thrombosis is a significant cause of mortality in cancer patients. Bick, N Engl Med 349:109-111 (2003). For example, serious, life-threatening thrombotic events occur in approximately 6% of lung cancer patients. Alguire et al., J Clin Oncol 2004 Vol (July 15th Supplement) No. 14S: 8082. Cancer patients often exhibit hypercoagulation, in which the coagulation system has an increased clotting tendency. Rickles and Edwards, Blood 62:14-31 (1983). Markers of hypercoagulation correlate with poor patient outcome for at least some cancers. Bick, Semin Thromb Hemostat 18:353-372 (1992); Buccheri et al., Cancer 97:3044-3052 (2003); Wojtukiewicz, Blood Coagul Fibrinolysis 3:429-437 (1992). Causes of hypercoagulation include the cancer itself and the cancer treatments (e.g., chemotherapy). Hypercoagulation results in an increased risk of thrombotic events, which can be further exacerbated when patients become bed-ridden. When not contraindicated, anticoagulant therapy has conferred survival benefit in some cancers. Lebeau et al., Cancer 74:38-45 (1994); Chahinian et al., J Clin Oncol 7:993-1002 (1989). However, therapeutic options are often limited because many cancer patients are at an elevated risk of major bleeding, precluding administration of anticoagulants that could otherwise be given prophylactically to reduce the risk of thrombosis. In summary, the available methods for prevention of thrombosis in cancer patients are unsatisfactory, and thus there is a need for new therapies. Such therapies would enhance cancer patient survival and promote better quality of life.

Thrombosis can also be a significant cause of adverse events and mortality in other patient groups, including those with chronic illness or chronic inflammation, surgical patients, bed-ridden individuals, and orthopedic patients. When they are not otherwise contraindicated, preventative methods include calf compression and anticoagulants (e.g. low molecular weight heparin). These preventative methods can reduce—but not eliminate—the risk of thrombosis. Because these preventative methods are not always effective and are contraindicated for some patients, and because anticoagulants can cause potentially lethal side-effects such as major bleeding, there is a need for alternative methods to prevent thrombosis in these patients. Such methods should improve patient outcomes.

Interleukin-6 (hereinafter "IL-6") (also known as interferon-$\beta_2$; B-cell differentiation factor; B-cell stimulatory factor-2; hepatocyte stimulatory factor; hybridoma growth factor; and plasmacytoma growth factor) is a multifunctional cytokine involved in numerous biological processes such as the regulation of the acute inflammatory response, the modulation of specific immune responses including B- and T-cell differentiation, bone metabolism, thrombopoiesis, epidermal proliferation, menses, neuronal cell differentiation, neuroprotection, aging, cancer, and the inflammatory reaction occurring in Alzheimer's disease. See A. Papassotiropoulos et al, Neurobiology of Aging, 22:863-871 (2001).

IL-6 is a member of a family of cytokines that promote cellular responses through a receptor complex consisting of at least one subunit of the signal-transducing glycoprotein gp130 and the IL-6 receptor ("IL-6R") (also known as gp80). The IL-6R may also be present in a soluble form ("sIL-6R"). IL-6 binds to IL-6R, which then dimerizes the signal-transducing receptor gp130. See Jones, S A, J. Immunology, 175: 3463-3468 (2005).

In humans, the gene encoding IL-6 is organized in five exons and four introns, and maps to the short arm of chromosome 7 at 7p21. Translation of IL-6 RNA and post-translational processing result in the formation of a 21 to 28 kDa protein with 184 amino acids in its mature form. See A. Papassotiropoulos, et al, Neurobiology of Aging, 22:863-871 (2001).

As set forth in greater detail herein IL-6 is believed to play a role in the development of a multitude of diseases and disorders, including but not limited to fatigue, cachexia, autoimmune diseases, diseases of the skeletal system, cancer, heart disease, obesity, diabetes, asthma, alzheimer's disease and multiple sclerosis. Due to the perceived involvement of IL-6 in a wide range of diseases and disorders, there remains a need in the art for compositions and methods useful for preventing or treating diseases associated with IL-6, as well as methods of screening to identify patients having diseases or disorders associated with IL-6. Particularly preferred anti-IL-6 compositions are those having minimal or minimizing adverse reactions when administered to the patient. Compositions or methods that reduce or inhibit diseases or disorders associated with IL-6 are beneficial to the patient in need thereof.

The function of IL-6 is not restricted to the immune response as it acts in hematopoiesis, thrombopoiesis, osteoclast formation, elicitation of hepatic acute phase response resulting in the elevation of C-reactive protein (CRP) and serum amyloid A (SAA) protein. It is known to be a growth factor for epidermal keratinocytes, renal mesangial cells, myeloma and plasmacytoma cells (Grossman et al., 1989 Prot Natl Acad. Sci., 86, (16) 6367-6371; Horii et al., 1989, J Immunol, 143, 12, 3949-3955; Kawano et al., 1988, Nature 332, 6159, 83-85). IL-6 is produced by a wide range of cell types including monocytes/macrophages, fibroblasts, epidermal keratinocytes, vascular endothelial cells, renal messangial cells, glial cells, condrocytes, T and B-cells and some tumor cells (Akira et al, 1990, FASEB J., 4, 11, 2860-2867). Except for tumor cells that constitutively produce IL-6, normal cells do not express IL-6 unless appropriately stimulated.

Elevated IL-6 levels have been observed in many types of cancer, including breast cancer, leukemia, ovarian cancer, prostate cancer, pancreatic cancer, lymphoma, lung cancer, renal cell carcinoma, colorectal cancer, and multiple myeloma (e.g., Chopra et al., 2004, MJAFI 60:45-49; Songur et al., 2004, Tumori 90:196-200; Blay et al., 1992, Cancer Research 52:3317-3322; Nikiteas et al., 2005, World J. Gasterenterol. 11:1639-1643; reviewed in Heikkila et al., 2008, Eur J Cancer, 44:937-945). As noted above, IL-6 is known or suspected to play a role in promoting proliferation or survival of at least some types of cancer. Moreover, some of these studies have demonstrated correlation between IL-6 levels and patient outcome. Together, these results suggest the possibility that inhibition of IL-6 can be therapeutically beneficial. Indeed, clinical studies (reviewed in Trikha et al., 2003, Clinical Cancer Research 9:4653-4665) have shown some improvement in patient outcomes due to administration of various anti-IL-6 antibodies, particularly in those cancers in which IL-6 plays a direct role promoting cancer cell proliferation or survival.

As noted above, IL-6 stimulates the hepatic acute phase response, resulting in increased production of CRP and elevated serum CRP levels. For this reason, C-reactive protein (CRP) has been reported to comprise a surrogate marker of IL-6 activity. Thus, elevated IL-6 activity can be detected through measurement of serum CRP. Conversely, effective suppression of IL-6 activity, e.g., through administration of a neutralizing anti-IL-6 antibody, can be detected by the resulting decrease in serum CRP levels.

A recent clinical trial demonstrated that administration of rosuvastatin to apparently healthy individuals having elevated CRP (greater than 2.0 mg/l) reduced their CRP levels by 37% and greatly decreased the incidence of myocardial infarction, stroke, arterial revascularization, hospitalization for unstable angina, or death from cardiovascular causes. Ridker et al., N Engl J. Med. 2008 Nov. 9 [Epub ahead of print].

In addition to its direct role in pathogenesis of some cancers and other diseases, chronically elevated IL-6 levels appear to adversely affect patient well-being and quality of life. For example, elevated IL-6 levels have been reported to be associated with cachexia and fever, and reduced serum albumin. Gauldie et al., 1987, PNAS 84:7251-7253; Heinric et al., 1990, 265:621-636; Zamir et al., 1993, Metabolism 42:204-208; Zamir et al., 1992, Arch Surg, 127:170-174. Inhibition of IL-6 by a neutralizing antibody has been reported to ameliorate fever and cachexia in cancer patients, though improvement in these patients' serum albumin level has not been reported (Emille et al., 1994, Blood, 84:2472-2479; Blay et al., 1992, Cancer Research 52:3317-3322; Bataille et al., 1995, Blood, 86: 685-691).

Numerous studies have suggested that CRP is a valuable prognostic factor in cancer patients, with elevated CRP levels predicting poor outcome. See, e.g., Hefler et al, Clin Cancer Res, 2008 Feb. 1; 14(3):710-4; Nagaoka et al, Liver Int, 2007 October; 27(8):1091-7; Heikkilä et al, J Epidemiol Community Health, 2007 September; 61(9):824-33, Review; Hara et al, Anticancer Res, 2007 July-August; 27(4C):3001-4; Polterauer et al, Gynecol Oncol, 2007 October; 107(1):114-7, Epub 2007 Jul. 6; Tingstedt et al, Scand J Gastroenterol, 2007 June; 42(6):754-9; Suh et al, Support Care Cancer, 2007 June; 15(6):613-20, Epub 2007 Jan. 18; Gerhardt et al, World J Gastroenterol, 2006 Sep. 14; 12(34):5495-500; McArdle et al, Urol Int, 2006; 77(2):127-9; Guillem et al, Dis Esophagus, 2005; 18(3):146-50; Brown et al, Cancer, 2005 Jan. 15; 103 (2):377-82. Decreased serum albumin (hypoalbuminemia) is also associated with increased morbidity and mortality in many critical illnesses, including cancers (e.g., Vigano et al., Arch Intern Med, 2000 Mar. 27; 160(6):861-8; Hauser et al., Support Care Cancer, 2006 October; 14(10):999-1011; Seve et al., Cancer, 2006 Dec. 1; 107(11):2698-705). The apparent link between hypoalbuminemia and poor patient outcome suggests that restoring albumin levels through direct albumin infusion could promote patient survival, however, albumin infusion has not improved survival of patients with advanced cancer (Demirkazik et al., Proc Am Soc Clin Oncol 21: 2002 (abstr 2892)) or other critically ill patients groups (reviewed in Wilkes et al., Ann Intern Med, 2001 Aug. 7; 135(3):149-64).

The Glasgow Prognostic Score (GPS) is an inflammation-based prognostic score that combines levels of albumin (<35 mg/L=1 point) and CRP (>10 mg/L=1 point) (Forrest et al., Br J Cancer, 2004 May 4; 90(9):1704-6). Since its introduction in 2004, the Glasgow Prognostic Score has already been shown to have prognostic value as a predictor of mortality in numerous cancers, including gastro-oesophageal cancer, non-small-cell lung cancer, colorectal cancer, breast cancer, ovarian cancer, bronchogenic cancer, and metastatic renal cancer (Forrest et al., Br J Cancer, 2004 May 4; 90(9):1704-6; Sharma et al., Clin Colorectal Cancer, 2008 September; 7(5): 331-7; Sharma et al., Eur J Cancer, 2008 January; 44(2):251-6; McMillan et al., Nutr Cancer, 2001; 41(1-2):64-9; McMillan, Proc Nutr Soc, 2008 August; 67(3):257-62; Ramsey et al., Cancer, 2007 Jan. 15; 109(2):205-12). Because the combination of elevated CRP and reduced albumin predicts cancer patient mortality, a treatment that both lowers CRP and raises albumin would suggest a strong possibility of also promoting patient survival.

U.S. patent application publication no. 20080081041 (relating to treatment of cancer using an anti-IL-6 antibody) discloses that since IL-6 is associated with disease activity and since CRP is a surrogate marker of IL-6 activity, sustained suppression of CRP by neutralization of IL-6 by their anti-IL-6 antibody (CNTO 328, Zaki et al., Int J Cancer, 2004 Sep. 10; 111(4):592-5) may be assumed necessary to achieve biological activity.

The same patent application indicates that the relationship between IL-6 and CRP in patients with benign and malignant prostate disease was previously examined by McArdle (McArdle et al. 2004 Br J Cancer 91(10):1755-1757). McArdle reportedly found no significant differences between the concentrations of IL-6 and CRP in the patients with benign disease compared with prostate cancer patients, in the cancer patients there was a significant increase in both IL-6 and CRP concentration with increasing tumor grade. The median serum CRP value for the 86 subjects with prostate cancer was 1.8 mg/L. Based thereon the inventors in this patent application postulate a proposed dose and schedule wherein 6 mg/kg of an anti-IL-6 antibody (CNTO 328) is administered every 2 weeks and allege that this is likely to achieve sustained suppression of CRP in subjects with metastatic HRPC.

IL-6 signaling is mediated by the Jak-Tyk family of cytoplasmic tyrosine kinases, including JAK1, JAK2, and JAK3 (reviewed in Murray J. Immunol. 2007 Mar. 1; 178(5):2623-9). Sivash et al. report abrogation of IL-6-mediated JAK signaling by the cyclopentenone prostaglandin 15d-$PGJ_2$ in oral squamous carcinoma cells. British Journal of Cancer (2004) 91, 1074-1080. These results suggest that inhibitors of JAK1, JAK2, or JAK3 could be employed as antagonists of IL-6.

Ulanova et al. report that inhibition of the nonreceptor protein tyrosine kinase Syk (using siRNA) decreased production of IL-6 by epithelial cells. Am J Physiol Lung Cell Mol. Physiol. 2005 March; 288(3):L497-507. These results suggest that an inhibitor of Syk could be employed as an antagonist of IL-6.

Kedar et al. report that treatment with thalidomide significantly reduced serum levels of CRP and IL-6 to normal or near normal levels in a substantial fraction of renal cell carcinoma patients. Int J. Cancer. 2004 Jun. 10; 110(2):260-5. These results suggest that thalidomide, and possibly derivatives thereof, such as lenalidomide, may be useful antagonists of IL-6.

In addition, another published patent application, US 20070292420 teaches a Phase I dose escalating study using an anti-IL-6 (cCLB-8) antibody for treating refractory patients with advanced stage multiple myeloma (N=12) and indicate that this study demonstrated that some patients had disease stabilization. The application also reports that after discontinuation of treatment there was acceleration in the increase of M protein levels, suggesting disease re-bound after the withdrawal of therapy. Anti-IL-6 cCLB-8 antibody inhibited free circulating IL-6.

The application also indicates that this antibody trial resulted in no toxicity (except transient thrombocytopenia in two heavily pretreated patients) or allergic reactions were observed and that C-reactive protein (CRP) decreased below detection level in all patients. Their antibody (cCLB-8 antibody) reportedly possessed a circulating half-life of 17.8 days, and that there was no human anti-chimeric antibody (HACA) immune response observed (van Zaanen et al. 1998). They allege that the administration of CNTO 328 did not cause changes in blood pressure, pulse rate, temperature, hemoglobin, liver functions and renal functions. Except for transient thrombocytopenia in two heavily pretreated patients, no toxicity or allergic reactions allegedly were observed, and there was no human anti-chimeric antibody (HACA) immune response observed. Three patients in their study reportedly developed infection-related complications during therapy, however, a possible relation with anti-IL-6 cCLB-8 antibody was concluded by the inventors to be unlikely because infectious complications are reportedly common in end stage multiple myeloma and are a major cause of death. They conclude based on their results that this anti-IL-6 cCLB-8 antibody was safe in multiple myeloma patients.

BRIEF SUMMARY OF THE INVENTION

The present invention is an extension of Applicants' previous invention which is directed to specific antibodies and fragments thereof having binding specificity for IL-6, in particular antibodies having specific epitopic specificity and/or functional properties and novel therapies using these and other anti-IL-6 antibodies. One embodiment of the prior invention encompasses specific humanized antibodies and fragments thereof capable of binding to IL-6 and/or the IL-6/IL-6R complex. These antibodies may bind soluble IL-6 or cell surface expressed IL-6. Also, these antibodies may inhibit the formation or the biological effects of one or more of IL-6, IL-6/IL-6R complexes, IL-6/IL-6R/gp130 complexes and/or multimers of IL-6/IL-6R/gp130. The present invention relates to novel therapies and therapeutic protocols using anti-IL-6 antibodies, preferably those described herein and in Applicants' earlier applications incorporated by reference herein. In particular, the present invention pertains to methods of preventing or treating thrombosis in a patient in need thereof, e.g., a patient showing elevated D-dimer and/or CRP levels prior to treatment, comprising administering to the patient an IL-6 antagonist, such as those identified infra, e.g., an anti-IL-6 antibody or antibody fragment, whereby the patient's coagulation profile is improved or restored to a normal condition. In some embodiments these methods may further include the administration of other actives such as statins that may further help (synergize) with the IL-6 antagonist and thereby more effectively treat or prevent thrombosis.

In a preferred embodiment this is effected by the administration of the antibodies described herein, comprising the sequences of the $V_H$, $V_L$ and CDR polypeptides described herein, and the polynucleotides encoding them. In more specific embodiments of the invention these antibodies will block gp130 activation and/or possess binding affinities (Kds) less than 50 picomolar and/or $K_{off}$ values less than or equal to $10^{-4}$ $S^{-1}$.

In another embodiment of the invention these antibodies and humanized versions will be derived from rabbit immune cells (B lymphocytes) and may be selected based on their homology (sequence identity) to human germ line sequences. These antibodies may require minimal or no sequence modifications, thereby facilitating retention of functional properties after humanization.

In another embodiment of the invention the subject antibodies may be selected based on their activity in functional assays such as IL-6 driven T1165 proliferation assays, IL-6 simulated HepG2 haptoglobin production assays, and the like. A further embodiment of the invention is directed to fragments from anti-IL-6 antibodies encompassing $V_H$, $V_L$ and CDR polypeptides, e.g., derived from rabbit immune cells and the polynucleotides encoding the same, as well as the use of these antibody fragments and the polynucleotides encoding them in the creation of novel antibodies and polypeptide compositions capable of recognizing IL-6 and/or IL-6/IL-6R complexes or IL-6/IL-6R/gp130 complexes and/or multimers thereof.

The invention also contemplates the administration of conjugates of anti-IL-6 antibodies and binding fragments thereof conjugated to one or more functional or detectable moieties. The invention also contemplates methods of making said humanized anti-IL-6 or anti-IL-6/IL-6R complex antibodies and binding fragments thereof. In one embodiment, binding fragments include, but are not limited to, Fab, Fab', $F(ab')_2$, Fv and scFv fragments.

Embodiments of the invention pertain to the use of anti-IL-6 antibodies for the diagnosis, assessment and treatment of diseases and disorders associated with IL-6 or aberrant expression thereof. The invention also contemplates the use of fragments of anti-IL-6 antibodies for the diagnosis, assessment and treatment of diseases and disorders associated with IL-6 or aberrant expression thereof. Preferred usages of the subject antibodies are the treatment and prevention of cancer associated fatigue, and/or cachexia and rheumatoid arthritis.

Other embodiments of the invention relate to the production of anti-IL-6 antibodies in recombinant host cells, preferably diploid yeast such as diploid *Pichia* and other yeast strains.

Another embodiment of the invention relates to methods of improving survivability or quality of life of a patient diagnosed with cancer, comprising administering to the patient an anti-IL-6 antibody or antibody fragment, whereby the patient's serum C-reactive protein ("CRP") level is reduced, and monitoring the patient to assess the reduction in the patient's serum CRP level, wherein the anti-IL-6 antibody or antibody fragment may specifically bind to the same linear or conformational epitope(s) and/or compete for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies which preferably are aglycosylated.

Another embodiment of the invention relates to methods of improving muscular strength in a patient diagnosed with cancer, comprising administering to the patient an anti-IL-6 antibody or antibody fragment, whereby the patient's muscular strength is improved, and monitoring the patient to assess muscular strength, wherein the anti-IL-6 antibody or antibody fragment may specifically bind to the same linear or conformational epitope(s) and/or compete for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies, which preferably are aglycosylated. In such methods preferably the patient's muscular strength is improved by at least about 15% within approximately 4 weeks of administering the anti-IL-6 antibody or antibody fragment, as measured by the Hand Grip Strength test and more preferably the patient's muscular strength is improved by at least about 20% within approximately 4 weeks of administering the anti-IL-6 antibody or antibody fragment, as measured by the Hand Grip Strength test.

Another embodiment of the invention relates to methods of increasing serum albumin in a patient in need thereof, comprising administering to the patient an anti-IL-6 antibody or antibody fragment, whereby the patient's serum albumin level is improved, and monitoring the patient to assess serum albumin level, wherein the anti-IL-6 antibody or antibody fragment may specifically bind to the same linear or conformational epitope(s) and/or compete for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies, which preferably are aglycosylated. Preferably, these methods are effected under conditions whereby the patient's survivability is improved, and/or under conditions wherein the serum albumin level is increased by about 5 g/L within approximately 6 weeks of administering the anti-IL-6 antibody or antibody fragment. These patients will include, without limitation thereto, those diagnosed with rheumatoid arthritis, cancer, advanced cancer, liver disease, renal disease, inflammatory bowel disease, celiac's disease, trauma, burns, other diseases associated with reduced serum albumin, or any combination thereof.

Another embodiment of the invention relates to methods of preventing or treating thrombosis in a patient in a state of hypercoagulation or susceptible to hypercoagulation because of disease or therapeutic regimen (e.g., chemotherapy), comprising administering to the patient an IL-6 antagonist, e.g. an anti-IL-6 antibody or antibody fragment, whereby the patient's coagulation profile is improved or restored to a normal condition, and monitoring the patient to assess coagulation profile. In such methods if the IL-6 antagonist is an anti-IL-6 antibody or antibody fragment preferably this antibody may specifically bind to the same linear or conformational epitope(s) and/or compete for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies which preferably are aglycosylated. In the inventive methods of preventing or treating thrombosis, the patient's coagulation profile is assessed by measurement of the patient's serum level of one or more of D-dimer, Factor II, Factor V, Factor VIII, Factor IX, Factor XI, Factor XII, F/fibrin degradation products, thrombin-antithrombin III complex, fibrinogen, plasminogen, prothrombin, and von Willebrand factor and preferably by a method including measuring the patient's serum D-dimer level prior to administration of the anti-IL-6 antibody, and administering the anti-IL-6 antibody or antibody fragment if the patient's serum D-dimer level is elevated. In addition, the levels of C reactive protein may also be assessed in the patient prior to treatment and if elevated this may be used as a further indicator as to an increased risk of thrombosis in the patient.

An embodiment of the invention relates to methods of treating a patient having a disease or condition associated with hypercoagulation, which may comprise administering to the patient an IL-6 antagonist, whereby the patient's coagulation profile is improved or restored to normal, and monitoring the patient to assess coagulation profile.

In an embodiment of the invention, the patient may have elevated serum D-dimer levels prior to treatment.

In an embodiment of the invention, the patient may have elevated C-reactive protein (CRP) levels prior to treatment.

In an embodiment of the invention, the method may further comprise the administration of at least one statin.

In an embodiment of the invention, the IL-6 antagonist may target IL-6, IL-6 receptor alpha, gp130, p38 MAP kinase, JAK1, JAK2, JAK3, SYK, or any combination thereof.

In an embodiment of the invention, the IL-6 antagonist may comprise an antibody, an antibody fragment, a peptide, a glycoalkoid, an antisense nucleic acid, a ribozyme, a retinoid, an avemir, a small molecule, or any combination thereof.

In an embodiment of the invention, the IL-6 antagonist may comprise an anti-IL-6R, anti-gp130, anti-p38 MAP kinase, anti-JAK1, anti-JAK2, anti-JAK3, or anti-SYK antibody or antibody fragment.

In one embodiment of the invention, the IL-6 antagonist may comprise a small molecule comprising thalidomide, lenalidomide, or any combination thereof.

In an embodiment of the invention, the antagonist may comprise an anti-IL-6 antibody or antibody fragment.

In an embodiment of the invention, the anti-IL-6 antibody or antibody fragment may specifically bind to the same linear or conformational epitope(s) and/or compete for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies which preferably are aglycosylated.

In an embodiment of the invention, the anti-IL-6 antibody may bind to the same linear or conformational epitope(s) and/or compete for binding to the same linear or conformational epitope(s) on an intact human IL-6 polypeptide or a fragment thereof as Ab1.

In an embodiment of the invention, the anti-IL-6 antibody or antibody fragment may specifically bind to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, and Ab36 and chimeric, human, humanized antibodies or antibody fragments containing most or all of the CDRs of the afore-identified antibodies which preferably are aglycosylated.

In an embodiment of the invention, the anti-IL-6 antibody or antibody fragment may specifically bind to the same linear or conformational epitope(s) on an intact human IL-6 polypeptide or a fragment thereof as Ab1 or an antibody comprising the same CDRs as Ab1.

Another embodiment of the invention relates to Ab1, including rabbit and humanized forms thereof, as well as heavy chains, light chains, fragments, variants, and CDRs thereof. In the human clinical trials presented in the Examples, a humanized form of Ab1 was administered.

In a preferred embodiment the humanized anti-IL-6 antibody will comprise the variable heavy and variable light chain sequences respectively contained in SEQ ID NO:657 and SEQ ID NO:709, and preferably further comprising the heavy chain and light chain constant regions respectively contained in SEQ ID NO:588 and SEQ ID NO:586, or any of the VH and VL sequences contained in FIGS. 34-37 and variants thereof comprising one or more amino acid substitutions or deletions that do not substantially affect IL-6 binding and/or desired effector function. This embodiment also contemplates polynucleotides comprising, or alternatively consisting of, one or more of the nucleic acids encoding the variable heavy chain (SEQ ID NO: 700) and variable light chain (SEQ ID NO:723) sequences and the constant region heavy chain (SEQ ID NO: 589) and constant region light chain (SEQ ID NO:587) sequences. This embodiment further contemplates nucleic acids encoding variants comprising one or more amino acid substitutions or deletions to the variable heavy and variable light chain sequences respectively contained in SEQ ID NO:657 and SEQ ID NO:709 and the heavy chain and light chain constant regions respectively contained in SEQ ID NO:588 and SEQ ID NO:586, that do not substantially affect IL-6 binding and/or desired effector function.

In an embodiment of the invention, the anti-IL-6 antibody or antibody fragment may specifically bind to the same linear or conformational epitopes on an intact IL-6 polypeptide or antibody fragment thereof that is (are) specifically bound by Ab1 and wherein said epitope(s) when ascertained by epitopic mapping using overlapping linear peptide fragments which span the full length of the native human IL-6 polypeptide includes one or more residues comprised in IL-6 fragments selected from those respectively encompassing amino acid residues 37-51, amino acid residues 70-84, amino acid residues 169-183, amino acid residues 31-45 and/or amino acid residues 58-72.

In an embodiment of the invention, the anti-IL-6 antibody or antibody fragment may comprise at least 2 complementarity determining regions (CDRs) in each the variable light and the variable heavy regions which are identical to those contained in an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies which preferably are aglycosylated.

In an embodiment of the invention, the anti-IL-6 antibody or antibody fragment may comprise at least 2 complementarity determining regions (CDRs) in each the variable light and the variable heavy regions which are identical to those contained in Ab1.

In an embodiment of the invention, all of the CDRs in the anti-IL-6 antibody or antibody fragment may be identical to the CDRs contained in an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, human, humanized antibodies or antibody fragments containing most or all of the CDRs of the afore-identified antibodies which preferably are aglycosylated.

In an embodiment of the invention, all of the CDRs in the anti-IL-6 antibody or antibody fragment may be identical to the CDRs contained in Ab1.

In an embodiment of the invention, the anti-IL-6 antibody or antibody fragment may be aglycosylated.

In an embodiment of the invention, the anti-IL-6 antibody or antibody fragment may contain an Fc region that has been modified to alter effector function, half-life, proteolysis, and/or glycosylation. Preferably the Fc region if present is modified to eliminate glycosylation.

In an embodiment of the invention, the anti-IL-6 antibody or antibody fragment may be a human, humanized, single chain or chimeric antibody.

In an embodiment of the invention, the anti-IL-6 antibody or antibody fragment may be a humanized antibody derived from a rabbit (parent) anti-IL-6 antibody.

In an embodiment of the invention, the framework regions (FRs) in the variable light region and the variable heavy regions of said anti-IL-6 antibody or antibody fragment respectively may be human FRs which are unmodified or which have been modified by the substitution of at most 2 or 3 human FR residues in the variable light or heavy chain region with the corresponding FR residues of the parent rabbit antibody, and the human FRs may have been derived from human variable heavy and light chain antibody sequences which have been selected from a library of human germline antibody sequences based on their high level of homology to the corresponding rabbit variable heavy or light chain regions relative to other human germline antibody sequences contained in the library.

In an embodiment of the invention, the anti-IL-6 antibody or antibody fragment may be administered to the patient with a frequency at most once per period of approximately four weeks, approximately eight weeks, approximately twelve weeks, approximately sixteen weeks, approximately twenty weeks, or approximately twenty-four weeks.

In an embodiment of the invention, the patient's coagulation profile may remain improved for an entire period intervening two consecutive anti-IL-6 antibody administrations.

In an embodiment of the invention, the patient may have been diagnosed with cancer selected from Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Müllerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Szary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In an embodiment of the invention, the patient may have been diagnosed with a cancer selected from Colorectal Cancer, Non-Small Cell Lung Cancer, Cholangiocarcinoma, Mesothelioma, Castleman's disease, Renal Cell Carcinoma, or any combination thereof.

In an embodiment of the invention, the anti-IL-6 antibody or antibody fragment may comprise a VH polypeptide sequence comprising: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708 or the VH sequences contained in the antibodies depicted in FIGS. 34-37; and may further comprise a VL polypeptide sequence comprising: SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or any of the variable heavy and light chain sequences in FIGS. 34-37 or a variant thereof wherein one or more of the framework residues (FR residues) in said VH or VL polypeptide may have been substituted with another amino acid residue resulting in an anti-IL-6 antibody or antibody fragment that specifically binds human IL-6. Preferably the variable heavy and light sequences comprise those in SEQ ID NO:657 and 709.

In an embodiment of the invention, one or more of said FR residues may be substituted with an amino acid present at the corresponding site in a parent rabbit anti-IL-6 antibody from which the complementarity determining regions (CDRs) contained in said VH or VL polypeptides have been derived or by a conservative amino acid substitution.

In an embodiment of the invention, said anti-IL-6 antibody or antibody fragment may be humanized.

In an embodiment of the invention, said anti-IL-6 antibody or antibody fragment may be chimeric.

In an embodiment of the invention, said anti-IL-6 antibody or antibody fragment further may comprise a human Fc.

In an embodiment of the invention, said human Fc may be derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19.

In an embodiment of the invention, the anti-IL-6 antibody or antibody fragment may comprise a polypeptide having at least 90% sequence homology to one or more of the polypeptide sequences of SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, 708, 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709 or to any of the VH and VL sequences contained in FIGS. 34-37.

In an embodiment of the invention, the anti-IL-6 antibody or antibody fragment may have an elimination half-life of at least about 22 days, at least about 25 days, or at least about 30 days.

In an embodiment of the invention, the IL-6 antagonist may be co-administered with a chemotherapy agent or as part of a therapeutic regimen including chemotherapy, including without limitation thereto: VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux™, Avastin™, Pertuzumab, anti-CD20 antibodies, Rituxan®, ocrelizumab, ofatumumab, DXL625, Herceptin®, or any combination thereof.

In an embodiment of the invention, the another therapeutic compound may be a statin.

In an embodiment of the invention, the anti-IL-6 antibody or antibody fragment may be directly or indirectly attached to a detectable label or therapeutic agent.

In an embodiment of the invention, the anti-IL-6 antibody or antibody fragment may be Ab1 or a fragment thereof.

In an embodiment of the invention, the disease or condition may be selected from acute venous thrombosis, pulmonary embolism, thrombosis during pregnancy, hemorrhagic skin necrosis, acute or chronic disseminated intravascular coagulation (DIC), clot formation from surgery, long bed rest, long periods of immobilization, venous thrombosis, fulminant meningococcemia, acute thrombotic stroke, acute coronary occlusion, acute peripheral arterial occlusion, massive pulmonary embolism, axillary vein thrombosis, massive iliofemoral vein thrombosis, occluded arterial cannulae, occluded venous cannulae, cardiomyopathy, venoocclusive disease of the liver, hypotension, decreased cardiac output, decreased vascular resistance, pulmonary hypertension, diminished lung compliance, leukopenia, thrombocytopenia, heparin-induced thrombocytopenia (HIT), heparin-induced thrombocytopenia and thrombosis (HITT), atrial fibrillation, implantation of a prosthetic heart valve, genetic susceptibility to thrombosis, factor V Leiden, prothrombin gene mutation, methylenetetrahydrofolate reductase (MTHFR) polymorphism, platelet-receptor polymorphism, trauma, fractures, burns, or any combination thereof.

In an embodiment of the invention, may include administration of one or more anti-coagulants or statins.

In an embodiment of the invention, the one or more anti-coagulants may be selected from abciximab (ReoPro™), acenocoumarol, antithrombin III, argatroban, aspirin, bivalirudin (Angiomax™), clopidogrel, dabigatran, dabigatran etexilate (Pradaxa™/Pradax™), desirudin (Revasc™/Iprivask™), dipyridamole, eptifibatide (Integrilin™), fondaparinux, heparin, hirudin, idraparinux, lepirudin (Refludan™), low molecular weight heparin, melagatran, phenindione, phenprocoumon, ticlopidine, tirofiban (Aggrastat™), warfarin, ximelagatran, ximelagatran (Exanta™/Exarta™), or any combination thereof.

In an embodiment of the invention, the one or more statins may be selected from atorvastatin, cerivastatin, fluvastatin, lovastatin, mevastatin, pitavastatin, pravastatin, rosuvastatin, simvastatin, or any combination thereof.

In an embodiment of the invention, the patient's coagulation profile may be assessed by measurement of the patient's serum level of one or more of D-dimer, Factor II, Factor V, Factor VIII, Factor IX, Factor XI, Factor XII, F/fibrin degradation products, thrombin-antithrombin III complex, fibrinogen, plasminogen, prothrombin, and von Willebrand factor.

In an embodiment of the invention, the patient's coagulation profile may be assessed by a functional measurement of clotting ability.

In an embodiment of the invention, the functional measurement of clotting ability may be selected from prothrombin time (PT), prothrombin ratio (PR), international normalized ratio (INR), or any combination thereof.

In an embodiment of the invention, the method may include measuring the patient's international normalized ratio (INR) prior to administration of the IL-6 antagonist, and administering to the patient an IL-6 antagonist if the patient's INR is less than about 0.9.

In an embodiment of the invention, the invention may include measuring the patient's international normalized ratio (INR) prior to administration of the IL-6 antagonist, and administering to the patient an IL-6 antagonist if the patient's INR is less than about 0.5 or 0.9.

In an embodiment of the invention, the patient's INR may be raised to more than approximately 0.9 within 4 weeks of administering to the patient an IL-6 antagonist.

In an embodiment of the invention, the method may include measuring the patient's serum D-dimer level prior to administration of the IL-6 antagonist, and administering the IL-6 antagonist if the patient's serum D-dimer level is above the normal reference range.

In an embodiment of the invention, the patient's serum D-dimer level may be lowered to less than the upper limit of the normal reference range within 4 weeks of administering to the patient an IL-6 antagonist.

In an embodiment of the invention, the method may result in a prolonged improvement in the patient's coagulation profile.

In an embodiment of the invention, the patient's coagulation profile may be measurably improved within about 2 weeks of administration of the IL-6 antagonist.

In an embodiment of the invention, the patient's coagulation profile may remain measurably improved approximately 12 weeks after administering to the patient an IL-6 antagonist.

In an embodiment of the invention, the patient's survivability may be improved.

In an embodiment of the invention, the IL-6 antagonist may be an antisense nucleic acid.

In an embodiment of the invention, the IL-6 antagonist may be an antisense nucleic acid, for example comprising at least approximately 10 nucleotides of a sequence encoding IL-6, IL-6 receptor alpha, gp130, p38 MAP kinase, JAK1, JAK2, JAK3, or SYK.

In an embodiment of the invention, the antisense nucleic acid or interfering RNA (iRNA) may comprise DNA, RNA, peptide nucleic acid, locked nucleic acid, morpholino (phosphorodiamidate morpholino oligo), glycerol nucleic acid, threose nucleic acid, or any combination thereof.

In an embodiment of the invention, the IL-6 antagonist may comprise Actemra™ (Tocilizumab), Remicade®, Zenapax™ (daclizumab), or any combination thereof.

In an embodiment of the invention, the IL-6 antagonist may comprise a polypeptide having a sequence comprising a fragment of IL-6, IL-6 receptor alpha, gp130, p38 MAP kinase, JAK1, JAK2, JAK3, SYK, or any combination thereof, such as a fragment or full-length polypeptide that is at least 40 amino acids in length.

In an embodiment of the invention, the IL-6 antagonist may comprise a soluble IL-6, IL-6 receptor alpha, gp130, p38 MAP kinase, JAK1, JAK2, JAK3, SYK, or any combination thereof.

In an embodiment of the invention, the IL-6 antagonist may be coupled to a half-life increasing moiety.

In an embodiment of the invention, the method may further comprise administration of one or more statins to the patient, including without limitation thereto atorvastatin, cerivastatin, fluvastatin, lovastatin, mevastatin, pitavastatin, pravastatin, rosuvastatin, simvastatin, or any combination thereof.

Another embodiment of the invention relates to a composition comprising an IL-6 antagonist, and an anti-coagulant. In an embodiment of the invention, the one or more anti-coagulants may be selected from abciximab (ReoPro™), acenocoumarol, antithrombin III, argatroban, aspirin, bivalirudin (Angiomax™), clopidogrel, dabigatran, dabigatran etexilate (Pradaxa™/Pradax™), desirudin (Revasc™/Iprivask™), dipyridamole, eptifibatide (Integrilin™), fondaparinux, heparin, hirudin, idraparinux, lepirudin (Refludan™), low molecular weight heparin, melagatran, phenindione, phenprocoumon, ticlopidine, tirofiban (Aggrastat™), warfarin, ximelagatran, ximelagatran (Exanta™/Exarta™), or any combination thereof.

Another embodiment of the invention relates to a composition comprising an IL-6 antagonist, and a chemotherapy agent. In an embodiment of the invention, the chemotherapy agent may be selected from VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux™, Avastin™, Pertuzumab, anti-CD20 antibodies, Rituxan®, ocrelizumab, ofatumumab, DXL625, Herceptin®, or any combination thereof.

BRIEF DESCRIPTION OF THE SEVERAL VIEWS OF THE DRAWINGS

FIG. 2 shows alignments of variable light and variable heavy sequences between a rabbit antibody variable light and variable heavy sequences and homologous human sequences and the final humanized sequences. Framework regions are identified FR1-FR4. Complementarity determining regions are identified as CDR1-CDR3. Amino acid residues are numbered as shown. The initial rabbit sequences are called RbtVL and RbtVH for the variable light and variable heavy sequences respectively. Three of the most similar human germline antibody sequences, spanning from Framework 1 through to the end of Framework 3, are aligned below the rabbit sequences. The human sequence that is considered the most similar to the rabbit sequence is shown first. In this example those most similar sequences are L12A for the light chain and 3-64-04 for the heavy chain. Human CDR3 sequences are not shown. The closest human Framework 4 sequence is aligned below the rabbit Framework 4 sequence. The vertical dashes indicate a residue where the rabbit residue is identical with one or more of the human residues at the same position. The bold residues indicate that the human residue at that position is identical to the rabbit residue at the same position. The final humanized sequences are called VLh and VHh for the variable light and variable heavy sequences respectively. The underlined residues indicate that the residue is the same as the rabbit residue at that position but different than the human residues at that position in the three aligned human sequences.

FIG. 10 E provides binding data for antibodies Ab1, Ab6 and Ab7.

FIG. 11 summarizes the binding data of FIG. 10 (A-E) in tabular form.

FIG. 12 presents the sequences of the 15 amino acid peptides used in the peptide mapping experiment of Example 14.

FIG. 15A shows affinity and binding kinetics of Ab1 for IL-6 of various species.

FIG. 15B demonstrates inhibition of IL-6 by Ab1 in the T1165 cell proliferation assay.

FIG. 19 summarizes Ab1 pharmacokinetic measurements of the dosage groups shown in FIG. 16.

FIG. 21 illustrates the unprecedented elimination half-life of Ab1 compared with other anti-IL-6 antibodies.

FIGS. 34 and 35 show alignments between a rabbit antibody light and variable heavy sequences and homologous human sequences and the final humanized sequences. Framework regions are identified FR1-FR4. Complementarity determining regions are identified as CDR1-CDR3.

FIGS. 36 (A-B) and 37 (A-B) show alignments between light and variable heavy sequences, respectively, of different forms of Ab1. Framework regions are identified FR1-FR4. Complementarity determining regions are identified as CDR1-CDR3. Sequence differences within the CDR regions highlighted.

DETAILED DESCRIPTION OF PREFERRED EMBODIMENTS

Definitions

Figure 1:
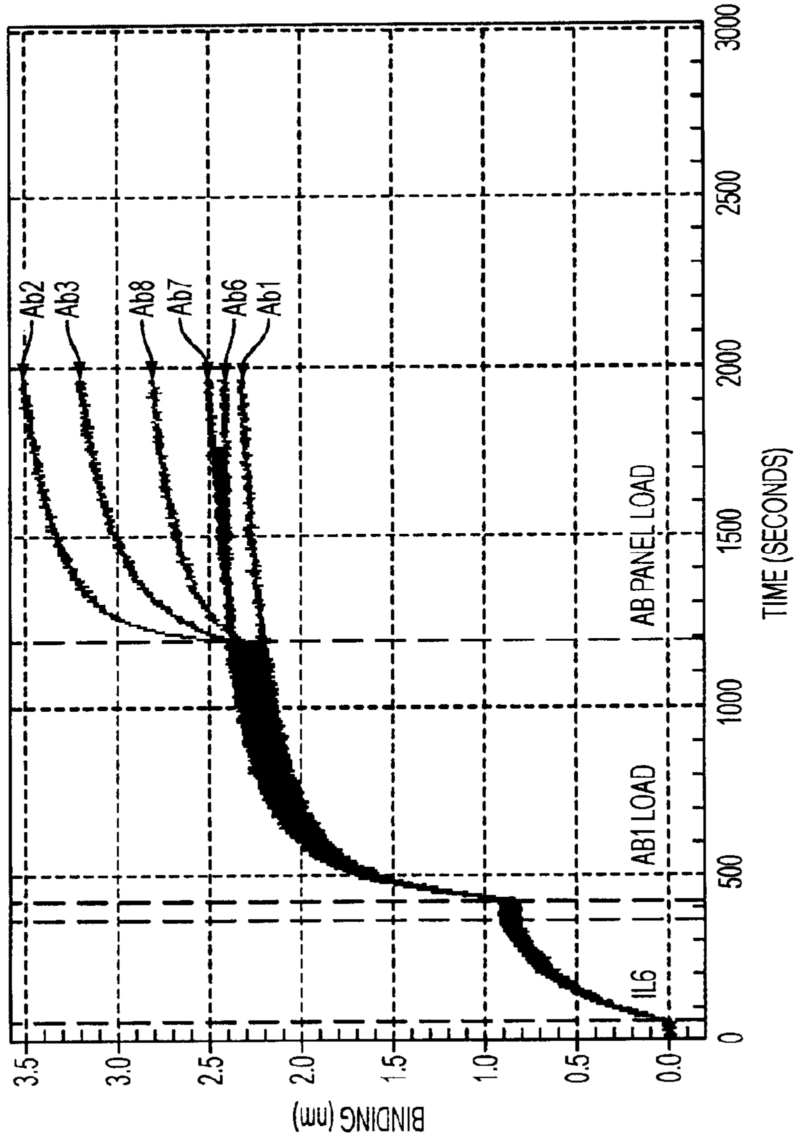
FIG. 1 shows that a variety of unique epitopes were recognized by the collection of anti-IL-6 antibodies prepared by the antibody selection protocol. Epitope variability was confirmed by antibody-IL-6 binding competition studies (ForteBio Octet).

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Interleukin-6 (IL-6): As used herein, interleukin-6 (IL-6) encompasses not only the following 212 amino acid sequence available as GenBank Protein Accession No. NP_000591: MNSFSTSAFGPVAFSLGLLLVLPAAFPA-PVPPGEDSKDVAAPHRQPLTSSERIDKQ IRYILDGIS-ALRKETCNKSNMCESSKEALAENNLNLP-KMAEKDGCFQSGFNEETC LVKIITGLLEFEVYLEYLQNRFES SEEQARAVQMST-KVLIQFLQKKAKNLDAITTP DPTTNASLLTKLQAQN-QWLQDMTTEILILRSFKEFLQSSLRALRQM (SEQ ID NO: 1), but also any pre-pro, pro- and mature forms of this IL-6 amino acid sequence, as well as mutants and variants including allelic variants of this sequence.

IL-6 antagonist: As used herein, the terms "IL-6 antagonist," and grammatical variants thereof include any composition that prevents, inhibits, or lessens the effect(s) of IL-6 signaling. Generally, such antagonists may reduce the levels or activity of IL-6, IL-6 receptor alpha, gp130, or a molecule involved in IL-6 signal transduction, or may reduce the levels or activity complexes between the foregoing (e.g., reducing the activity of an IL-6/IL-6 receptor complex). Antagonists include antisense nucleic acids, including DNA, RNA, or a nucleic acid analogue such as a peptide nucleic acid, locked nucleic acid, morpholino (phosphorodiamidate morpholino oligo), glycerol nucleic acid, or threose nucleic acid. See Heasman, Dev Biol. 2002 Mar. 15; 243(2):209-14; Hannon and Rossi, Nature. 2004 Sep. 16; 431(7006):371-8; Paul et al., Nat. Biotechnol. 2002 May; 20(5):505-8; Zhang et al., J Am Chem. Soc. 2005 Mar. 30; 127(12):4174-5; Wahlestedt et al., Proc Natl Acad Sci USA. 2000 May 9; 97(10):5633-8; Hanvey et al., 1992 Nov. 27; 258(5087):1481-5; Braasch et al., Biochemistry. 2002 Apr. 9; 41(14):4503-10; Schoning et al., Science. 2000 Nov. 17; 290(5495):1347-51. In addition IL-6 antagonists specifically include peptides that block IL-6 signaling such as those described in any of U.S. Pat. Nos. 6,599,875; 6,172,042; 6,838,433; 6,841,533; 5,210,075 et al. Also, IL-6 antagonists according to the invention may include p38 MAP kinase inhibitors such as those reported in US20070010529 et al. given this kinase's role in cytokine production and more particularly IL-6 production. Further, IL-6 antagonists according to the invention include the glycoalkaloid compounds reported in US20050090453 as well as other IL-6 antagonist compounds isolatable using the IL-6 antagonist screening assays reported therein. Other IL-6 antagonists include antibodies, such as anti-IL-6 antibodies, anti-IL-6 receptor alpha antibodies, anti-gp130 antibodies, and anti-p38 MAP kinase antibodies including (but not limited to) the anti-IL-6 antibodies disclosed herein, Actemra™ (Tocilizumab), Remicade®, Zenapax™ (daclizumab), or any combination thereof. Other IL-6 antagonists include portions or fragments of molecules involved in IL-6 signaling, such as IL-6, IL-6 receptor alpha, and gp130, which may be native, mutant, or variant sequence, and may optionally be coupled to other moieties (such as half-life-increasing moieties, e.g. an Fc domain). For example, an IL-6 antagonist may be a soluble IL-6 receptor or fragment, a soluble IL-6 receptor:Fc fusion protein, a small molecule inhibitor of IL-6, an anti-IL-6 receptor antibody or antibody fragment, antisense nucleic acid, etc. Other IL-6 antagonists include avemirs, such as C326 (Silverman et al., Nat. Biotechnol. 2005 December; 23(12):1556-61) and small molecules, such as synthetic retinoid AM80 (tamibarotene) (Takeda et al., Arterioscler Thromb Vasc Biol. 2006 May; 26(5):1177-83). Such IL-6 antagonists may be administered by any means known in the art, including contacting a subject with nucleic acids which encode or cause to be expressed any of the foregoing polypeptides or antisense sequences.

Thrombosis: As used herein, thrombosis refers to a thrombus (blood clot) inside a blood vessel. The term encompasses, without limitation, arterial and venous thrombosis, including deep vein thrombosis, portal vein thrombosis, jugular vein thrombosis, renal vein thrombosis, stroke, myocardial infarction, Budd-Chiari syndrome, Paget-Schroetter disease, and cerebral venous sinus thrombosis. Diseases and conditions associated with thrombosis include, without limitation, acute venous thrombosis, pulmonary embolism, thrombosis during pregnancy, hemorrhagic skin necrosis, acute or chronic disseminated intravascular coagulation (DIC), clot formation from surgery, long bed rest, long periods of immobilization, venous thrombosis, fulminant meningococcemia, acute thrombotic stroke, acute coronary occlusion, acute peripheral arterial occlusion, massive pulmonary embolism, axillary vein thrombosis, massive iliofemoral vein thrombosis, occluded arterial cannulae, occluded venous cannulae, cardiomyopathy, venoocclusive disease of the liver, hypotension, decreased cardiac output, decreased vascular resistance, pulmonary hypertension, diminished lung compliance, leukopenia, and thrombocytopenia.

D-Dimer: As used herein, D-dimer refers to a fibrin degradation product produced during the break down of blood clots by the enzyme plasmin. Monoclonal antibodies specifically reactive against D-dimer are readily available, e.g. DD-3B6/22 (Elms et al., 1986, Am J Clin Pathol. 85:360-4). Clinical measurements of D-dimer levels are routinely performed, e.g., using a red blood cell agglutination test, ELISA, etc.

(reviewed in Dempfle, Semin Vasc Med, 2005 November; 5(4):315-20). Measurements of D-dimer may vary depending on the measurement method and testing lab; nonetheless, a normal "reference range" may be readily established for any particular method and testing lab, e.g. by taking measurements from healthy individuals. Accordingly, an elevated D-dimer level is understood by persons skilled in the art to refer to a D-dimer level that is above the reference range for the particular method and testing lab.

Coagulation profile: As used herein, coagulation profile refers generally to the functioning of the coagulation system. Both the tissue factor (extrinsic) and contact activation (intrinsic) pathways of clotting are components of the coagulation profile. A normal coagulation profile refers to coagulation functioning as in a normal, healthy individual, i.e., maintaining balance between ability to control bleeding and tendency towards excessive clotting (thrombotic tendency). An abnormal coagulation profile may be a decrease or an increase in coagulation tendency. One particularly abnormal coagulation profile is hypercoagulation, which refers to a greatly increased risk of excessive clot formation, resulting in high risk of thrombosis. Coagulation profile may be assessed by various tests and assays known in the art, such as: the activated partial thromboplastin time (aPTT) test; prothrombin time (PT) test (typical reference range of 12 to 15 second); measurements derived from the PT test, such as prothrombin ratio (PR) and international normalized ratio (INR) (typical reference range 0.8 to 1.2); fibrinogen testing (e.g. the Clauss method (Clauss A, "Rapid Physiological Coagulation Method for the Determination of Fibrinogen [German]," Acta Haematol, 1957, 17:237-46) or the Ellis method (Ellis B C and Stransky A, "A Quick and Accurate Method for the Determination of Fibrinogen in Plasma," J Lab Clin Med, 1961, 58:477-88); assays for activated protein C resistance, protein C, protein S, and antithrombin; assays for antiphospholipid antibodies (lupus anticoagulant and anticardiolipin antibodies); elevated homocysteine; assays for plasminogen, dysfibrinogenemia, heparin cofactor II, or platelet hyperaggregability. Other assays useful to assess coagulation profile include measurement of clotting factors and/or indicators of clotting, such as serum levels of D-dimer, Factor II, Factor V, Factor VIII, Factor IX, Factor XI, Factor XII, F/fibrin degradation products, thrombin-antithrombin III complex, thrombocytosis, fibrinogen, plasminogen, prothrombin, and von Willebrand factor. Worsening in coagulation profile refers to a measureable change in an indicator of coagulation, e.g., any of the aforementioned assays, that reflects a deterioration of the normal coagulation tendency, such that the measured value becomes abnormal or deviates farther from the normal range than previously. Improvement in coagulation profile refers to a measureable change in an indicator of coagulation, e.g., any of the aforementioned assays, that reflects a partial or full restoration of the normal coagulation tendency, i.e., after a therapeutic intervention, such as administration of an anti-IL-6 antibody, the measured value is in the normal range or closer to the normal range than prior to the therapeutic intervention. Disease or condition: As used herein, "disease or condition" refers to a disease or condition that a patient has been diagnosed with or is suspected of having, particularly a disease or condition associated with elevated IL-6. A disease or condition encompasses, without limitation thereto, the side-effects of medications or treatments (such as radiation therapy), as well as idiopathic conditions characterized by symptoms that include elevated IL-6.

Cachexia: As used herein, cachexia, also known as wasting disease, refers to any disease marked especially by progressive emaciation, weakness, general ill health, malnutrition, loss of body mass, loss of muscle mass, or an accelerated loss of skeletal muscle in the context of a chronic inflammatory response (reviewed in Kotler, Ann Intern Med. 2000 Oct. 17; 133(8):622-34). Diseases and conditions in which cachexia is frequently observed include cancer, rheumatoid arthritis, AIDS, heart disease, dehydration, malnutrition, lead exposure, malaria, respiratory disease, old age, hypothyroidism, tuberculosis, hypopituitarism, neurasthenia, hypernatremia, hyponatremia, renal disease, splenica, ankylosing spondylitis, failure to thrive (faltering growth) and other diseases, particularly chronic diseases. Cachexia may also be idiopathic (arising from an uncertain cause). Weight assessment in a patient is understood to exclude growths or fluid accumulations, e.g. tumor weight, extravascular fluid accumulation, etc. Cachexia may be assessed by measurement of a patient's total body mass (exclusive of growths or fluid accumulations), total lean (fat-free) body mass, lean mass of the arms and legs (appendicular lean mass, e.g. measured using dual-energy x-ray absorptiometry or bioelectric impedance spectroscopy), and/or lean body mass index (lean body mass divided by the square of the patient's height). See Kotler, Ann Intern Med. 2000 Oct. 17; 133(8):622-34; Marcora et al., Rheumatology (Oxford). 2006 November; 45(11):1385-8.

Weakness: As used herein, weakness refers physical fatigue, which typically manifests as a loss of muscle strength and/or endurance. Weakness may be central (affecting most or all of the muscles in the body) or peripheral (affecting a subset of muscles). Weakness includes "true weakness," in which a patient's muscles have a decrease in some measure of peak and/or sustained force output, and "perceived weakness," in which a patient perceives that a greater effort is required for performance of a task even though objectively measured strength remains nearly the same, and may be objectively measured or self-reported by the patient. For example, weakness may be objectively measured using the hand grip strength test (a medically recognized test for evaluating muscle strength), typically employing a handgrip dynamometer.

Fatigue: As used herein, fatigue refers to mental fatigue (for physical fatigue see "weakness"). Fatigue includes drowsiness (somnolence) and/or decreased attention. Fatigue may be measured using a variety of tests known in the art, such as the FACIT-F (Functional Assessment of Chronic Illness Therapy-Fatigue) test. See, e.g., Cella, D., Lai, J. S., Chang, C. H., Peterman, A., & Slavin, M. (2002). Fatigue in cancer patients compared with fatigue in the general population. Cancer, 94(2), 528-538; Cella, D., Eton, D. T., Lai, F J-S., Peterman, A. H & Merkel, D. E. (2002). Combining anchor and distribution based methods to derive minimal clinically important differences on the Functional Assessment of Cancer Therapy anemia and fatigue scales. Journal of Pain & Symptom Management, 24 (6) 547-561.

Fever: As used herein, "fever" refers to a body temperature set-point that is elevated by at least 1 to 2 degrees Celsius. Fever is often associated with a subjective feeling of hypothermia exhibited as a cold sensation, shivering, increased heart rate and respiration rate by which the individual's body reaches the increased set-point. As is well understood in the medical arts, normal body temperature typically varies with activity level and time of day, with highest temperatures observed in the afternoon and early evening hours, and lowest temperatures observed during the second half of the sleep cycle, and temperature measurements may be influenced by external factors such as mouth breathing, consumption of food or beverage, smoking, or ambient temperature (depending on the type of measurement). Moreover, the normal temperature set point for individuals may vary by up to about 0.5 degrees Celsius, thus a medical professional may interpret an individual's temperature in view of these factors to diagnose whether a fever is present. Generally speaking, a fever is typically diagnosed by a core body temperature above 38.0 degrees Celsius, an oral temperature above 37.5 degrees Celsius, or an axillary temperature above 37.2 degrees Celsius.

Improved: As used herein, "improved," "improvement," and other grammatical variants, includes any beneficial change resulting from a treatment. A beneficial change is any way in which a patient's condition is better than it would have been in the absence of the treatment. "Improved" includes prevention of an undesired condition, slowing the rate at which a condition worsens, delaying the development of an undesired condition, and restoration to an essentially normal condition. For example, improvement in cachexia encompasses any increase in patient's mass, such as total body mass (excluding weight normally excluded during assessment of cachexia, e.g. tumor weight, extravascular fluid accumulation, etc.), lean body mass, and/or appendicular lean mass, as well as any delay or slowing in the rate of loss of mass, or prevention or slowing of loss of mass associated with a disease or condition with which the patient has been diagnosed. For another example, improvement in weakness encompasses any increase in patient's strength, as well as any delay or slowing in the rate of loss of strength, or prevention or slowing of loss of strength associated with a disease or condition with which the patient has been diagnosed. For yet another example, improvement in fatigue encompasses any decrease in patient's fatigue, as well as any delay or slowing in the rate of increase of fatigue, or prevention or slowing of increase in fatigue associated with a disease or condition with which the patient has been diagnosed. For still another example, improvement in fever encompasses any decrease in patient's fever, as well as any delay or slowing in the rate of increase in fever, or prevention or slowing of increase in fever associated with a disease or condition with which the patient has been diagnosed.

C-Reactive Protein (CRP): As used herein, C-Reactive Protein (CRP) encompasses not only the following 224 amino acid sequence available as GenBank Protein Accession No. NP_000558: MEKLLCFLVLTSLSHAFGQTDMSRKAFVFPKESDTSYVSLKAPLTKPLKAFTVCL HFYTELSSTRGYSIFSYATKRQDNEILIFWSKDIGYSFTVGGSEILFEVPEVTVAPV HICTSWESASGIVEFWVDGKPRVRKSLKKGYTVGAEASIILGQEQDSF GGNFEGS QSLVGDIGNVNMWDFVLSPDEINTIYLGGPFSPNVLNRRALKYEVQGEVFTKPQ LWP (SEQ ID NO: 726), but also any pre-pro, pro- and mature forms of this CRP amino acid sequence, as well as mutants and variants including allelic variants of this sequence. CRP levels, e.g. in the serum, liver, tumor, or elsewhere in the body, can be readily measured using routine methods and commercially available reagents, e.g. ELISA, antibody test strip, immunoturbidimetry, rapid immunodiffusion, visual agglutination, Western blot, Northern blot, etc. As mentioned above CRP levels may in addition be measured in patients having or at risk of developing thrombosis according to the invention.

Interleukin-6 receptor (IL-6R); also called IL-6 receptor alpha (IL-6RA): As used herein, "interleukin-6 receptor" ("IL-6R"; also "IL-6 receptor alpha" or "IL-6RA") encompasses not only the following 468 amino acid sequence available as Swiss-Prot Protein Accession No. P08887: MLAVGCALLAALLAAPGAALAPRRCPAQEVARGVLTSLPGD SVTLTCPGVEPED NATVHWVLRKPAAGSHPSRWAGMGRRLLLRSVQLEIDSGNYSCYRAGRPAGTV EILLVDVPPEEPQLSCFRKSPLSNVVCEWGPRSTPSLTTKAVLLVRKFQNSPAEDF QEPCQYSQESQKFSCQLAVPEGDSSFYIVSMCVASSVGSKFSKTQTFQGCGILQP DPPANITVTAVARNPRWLSVTWQDPHSWNS SFYRLRFELRYRAERSKTFTTWM VKDLQHHCVIHDAWSGLRHVVQLRAQEEFGQGEWSEWSPEAMGTPWTESRSPP AENEVSTPMQALTTNKDDDNILFRDSANATSLPVQDSSSVPLPTFLVAGGSLAFG TLLCIAIVLRFKKTWKLRALKEGKTSMEPPYSLGQLVPERPRPTPVLVPLISPPVSP SSLGSDNTSSHNRPDARDPRSPYDISNTDYFFPR (SEQ ID NO: 727), but also any pre-pro, pro- and mature forms of this amino acid sequence, as well as mutants and variants including allelic variants of this sequence.

gp130: As used herein, gp130 (also called Interleukin-6 receptor subunit beta) encompasses not only the following 918 precursor amino acid sequence available as Swiss-Prot Protein Accession No. P40189: MLTLQTWVVQALFIFLTTESTGELLDPCGYISPESPVVQLHSNFTAVCVLKEKCM DYFHVNANYIVWKTNHFTIPKEQYTIINRTASSVTFTDIASLNIQLTCNILTFGQLE QNVYGITIISGLPPEKPKNLSCIVNEGKKMRCEWDGGRETHLETNFTLKSEWATH KFADCKAKRDTPTSCTVDYSTVYFVNIEVWVEAENALGKVTSDHINFDPVYKVK PNPPHNLSVINSEELSSILKLTWTNPSIKSVIILKYNIQYRTKDASTWSQIPPEDTAS TRSSFTVQDLKPFTEYVFRIRCMKEDGKGYWSDWSEEASGITYEDRPSKAPSFW YKIDP SHTQGYRTVQLVWKTLPPFEANGKILDYEVTLTRWKSHLQNYTVNATKL TVNLTNDRYLATLTVRNLVGKSDAAVLTIPACDFQATHPVMDLKAFPKDNMLW VEWTTPRESVKKYILEWCVLSDKAPCITDWQQEDGTVHRTYLRGNLAESKCYLI TVTPVYADGPGSPESIKAYLKQAPPSKGPTVRTKKVGKNEAVLEWDQLPVDVQ NGFIRNYTIFYRTIIGNETAVNVDSSHTEYTLSSLTSDTLYMVRMAAYTDEGGKD GPEFTFTTPKFAQGEIEAIVVPVCLAFLLTTLLGVLFCFNKRDLIKKHIWPNVPDPS KSHIAQWSPHTPPRHNFNSKDQMYSDGNFTDVSVVEIEANDKKPFPEDLKSLDLF KKEKINTEGHSSGIGGSSCMSSSRPSISSSDENESSQNTSSTVQYSTVVHSGYRHQ VPSVQVFSRSESTQPLLDSEERPEDLQLVDHVDGGDGILPRQQYFKQNCS QHESS PDISHFERSKQVSSVNEEDFVRLKQQISDHISQSCGSGQMKMFQEVSAADAFGPG TEGQVERFETVGMEAATDEGMPKSYLPQTVRQGGYMPQ (SEQ ID NO: 728), but also any pre-pro, pro- and mature forms of this amino acid sequence, such as the mature form encoded by amino acids 23 through 918 of the sequence shown, as well as mutants and variants including allelic variants of this sequence.

Glasgow Prognostic Score (GPS): As used herein, Glasgow Prognostic Score (GPS) refers to an inflammation-based prognostic score that awards one point for a serum albumin level less than <35 mg/L and one point for a CRP level above 10 mg/L. Thus, a GPS of 0 indicates normal albumin and CRP, a GPS of 1 indicates reduced albumin or elevated CRP, and a GPS of 2 indicates both reduced albumin and elevated CRP.

Effective amount: As used herein, "effective amount," "amount effective to," "amount of X effective to" and the like, refer to an amount of an active ingredient that is effective to relieve or reduce to some extent one or more of the symptoms of the disease in need of treatment, or to retard initiation of clinical markers or symptoms of a disease in need of prevention, when the compound is administered. Thus, an effective amount refers to an amount of the active ingredient which exhibit effects such as (i) reversing the rate of progress of a disease; (ii) inhibiting to some extent further progress of the disease; and/or, (iii) relieving to some extent (or, preferably, eliminating) one or more symptoms associated with the disease. The effective amount may be empirically determined by experimenting with the compounds concerned in known in vivo and in vitro model systems for a disease in need of treatment. The context in which the phrase “effective amount” is used may indicate a particular desired effect. For example, “an amount of an anti-IL-6 antibody effective to prevent or treat a hypercoagulable state” and similar phrases refer to an amount of anti-IL-6 antibody that, when administered to a subject, will cause a measurable improvement in the subject’s coagulation profile, or prevent, slow, delay, or arrest, a worsening of the coagulation profile for which the subject is at risk. An effective amount will vary according to the weight, sex, age and medical history of the individual, as well as the severity of the patient’s condition(s), the type of disease(s), mode of administration, and the like. An effective amount may be readily determined using routine experimentation, e.g., by titration (administration of increasing dosages until an effective dosage is found) and/or by reference to amounts that were effective for prior patients. Generally, the anti-IL-6 antibodies of the present invention will be administered in dosages ranging between about 0.1 mg/kg and about 20 to 100 mg/kg of the patient’s body-weight.

Prolonged improvement in coagulation profile: As used herein, “prolonged improvement in coagulation profile” and similar phrases refer to a measurable improvement in the subject’s coagulation profile relative to the initial coagulation profile (i.e. the coagulation profile at a time before treatment begins) that is detectable within about a week from when treatment begins (e.g. administration of an IL-6 antagonist) and remains improved for a prolonged duration, e.g., at least about 14 days, at least about 21 days, at least about 28 days, at least about 35 days, at least about 40 days, at least about 50 days, at least about 60 days, at least about 70 days, at least about 11 weeks, or at least about 12 weeks from when the treatment begins.

Prolonged reduction in serum CRP: As used herein, “prolonged reduction in serum CRP” and similar phrases refer to a measurable decrease in serum CRP level relative to the initial serum CRP level (i.e. the serum CRP level at a time before treatment begins) that is detectable within about a week from when a treatment begins (e.g. administration of an anti-IL-6 antibody) and remains below the initial serum CRP level for an prolonged duration, e.g. at least about 14 days, at least about 21 days, at least about 28 days, at least about 35 days, at least about 40 days, at least about 50 days, at least about 60 days, at least about 70 days, at least about 11 weeks, or at least about 12 weeks from when the treatment begins.

Prolonged increase in serum albumin: As used herein, “prolonged increase in serum albumin” and similar phrases refer to a measurable decrease in serum albumin level relative to the initial serum albumin level (i.e. the serum albumin level at a time before treatment begins) that is detectable within about a week from when a treatment begins (e.g. administration of an anti-IL-6 antibody) and remains above the initial serum albumin level for an prolonged duration, e.g. at least about 14 days, at least about 21 days, at least about 28 days, at least about 35 days, at least about 40 days, at least about 50 days, at least about 60 days, at least about 70 days, at least about 11 weeks, or at least about 12 weeks from when the treatment begins.

Prolonged improvement in cachexia: As used herein, “prolonged improvement in cachexia” refers to a measurable improvement patient’s body mass, lean body mass, appendicular lean body mass, and/or lean body mass index, relative to the initial level (i.e. the level at a time before treatment begins) that is detectable within about 4 weeks and remains improved for a prolonged duration, e.g. at least about 35 days, at least about 40 days, at least about 50 days, at least about 60 days, at least about 70 days, at least about 11 weeks, or at least about 12 weeks from when the treatment begins.

Prolonged improvement in weakness: As used herein, “prolonged improvement in weakness” refers to a measurable improvement in muscular strength, relative to the initial level (i.e. the level at a time before treatment begins) that is detectable within about 2 weeks and remains improved for a prolonged duration, e.g. at least about 21 days, at least about 28 days, at least about 35 days, at least about 40 days, at least about 50 days, at least about 60 days, at least about 70 days, at least about 11 weeks, or at least about 12 weeks from when the treatment begins.

Prolonged improvement in fatigue: As used herein, “prolonged improvement in fatigue” refers to a measureable improvement in fatigue, relative to the initial level (i.e. the level at a time before treatment begins) that is detectable within about 1 week and remains improved for a prolonged duration, e.g. at least about 14 days, at least about 21 days, at least about 28 days, at least about 35 days, at least about 40 days, at least about 50 days, at least about 60 days, at least about 70 days, at least about 11 weeks, or at least about 12 weeks from when the treatment begins.

Prolonged improvement in fever: As used herein, “prolonged improvement in fever” refers to a measureable decrease in fever (e.g. peak temperature or amount of time that temperature is elevated), relative to the initial level (i.e. the level at a time before treatment begins) that is detectable within about 1 week and remains improved for a prolonged duration, e.g. at least about 14 days, at least about 21 days, at least about 28 days, at least about 35 days, at least about 40 days, at least about 50 days, at least about 60 days, at least about 70 days, at least about 11 weeks, or at least about 12 weeks from when the treatment begins.

Mating competent yeast species: In the present invention this is intended to broadly encompass any diploid or tetraploid yeast which can be grown in culture. Such species of yeast may exist in a haploid, diploid, or tetraploid form. The cells of a given ploidy may, under appropriate conditions, proliferate for indefinite number of generations in that form. Diploid cells can also sporulate to form haploid cells. Sequential mating can result in tetraploid strains through further mating or fusion of diploid strains. In the present invention the diploid or polyploidal yeast cells are preferably produced by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia, Rhodosporidium, Candida, Hansenula, Filobasium, Filobasidellla, Sporidiobolus, Bullera, Leucosporidium and Filobasidella.*

In a preferred embodiment of the invention, the mating competent yeast is a member of the genus *Pichia*. In a further preferred embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* is the species *Pichia pastoris.*

Haploid Yeast Cell: A cell having a single copy of each gene of its normal genomic (chromosomal) complement.

Polyploid Yeast Cell: A cell having more than one copy of its normal genomic (chromosomal) complement.

Diploid Yeast Cell: A cell having two copies (alleles) of essentially every gene of its normal genomic complement, typically formed by the process of fusion (mating) of two haploid cells.

Tetraploid Yeast Cell: A cell having four copies (alleles) of essentially every gene of its normal genomic complement, typically formed by the process of fusion (mating) of two haploid cells. Tetraploids may carry two, three, four, or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his]×diploid [arg] to obtain a tetraploid prototroph. It will be understood by those of skill in the art that reference to the benefits and uses of diploid cells may also apply to tetraploid cells.

Yeast Mating: The process by which two haploid yeast cells naturally fuse to form one diploid yeast cell.

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

Expression Vector: These DNA vectors contain elements that facilitate manipulation for the expression of a foreign protein within the target host cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome.

In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. *Pichia* transformation is described in Cregg et al. (1985) *Mol. Cell. Biol.* 5:3376-3385.

Examples of suitable promoters from *Pichia* include the AOX1 and promoter (Cregg et al. (1989) *Mol. Cell. Biol.* 9:1316-1323); ICL1 promoter (Menendez et al. (2003) *Yeast* 20(13):1097-108); glyceraldehyde-3-phosphate dehydrogenase promoter (GAP) (Waterham et al. (1997) *Gene* 186(1): 37-44); and FLD1 promoter (Shen et al. (1998) *Gene* 216(1):

93-102). The GAP promoter is a strong constitutive promoter and the AOX and FLD1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin™ (phleomycin)) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and *E. coli* encoded recombination proteins. Recombination occurs between specific attachment (att) sites on the interacting DNA molecules. For a description of att sites see Weisberg and Landy (1983) Site-Specific Recombination in Phage Lambda, in *Lambda II*, Weisberg, ed. (Cold Spring Harbor, N.Y.:Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

The terms "desired protein" or "target protein" are used interchangeably and refer generally to a humanized antibody or a binding portion thereof described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies such as scFvs, camelbodies, nanobodies, IgNAR (single-chain antibodies derived from sharks), small-modular immunopharmaceuticals (SMIPs), and antibody fragments such as Fabs, Fab', $F(ab')_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374 (6518):168-73; Nuttall S D, et al., Isolation of the new antigen receptor from wobbegong sharks, and use as a scaffold for the display of protein loop libraries, Mol. Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', $F(ab')_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

The term "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 10-25 mg/liter and preferably substantially greater.

The term "polyploidal yeast culture that secretes desired amounts of recombinant polypeptide" refers to cultures that stably or for prolonged periods secrete at least 10-25 mg/liter of heterologous polypeptide, more preferably at least 50-500 mg/liter, and most preferably 500-1000 mg/liter or more.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes or other lipid aggregates (for polypeptides and/or polynucleotides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence. Exemplary expression vectors and techniques for their use are described in the following publications: Old et al., Principles of Gene Manipulation: An Introduction to Genetic Engineering, Blackwell Scientific Publications, 4th edition, 1989; Sambrook et al., Molecular Cloning: A Laboratory Manual, 2nd Edition, Cold Spring Harbor Laboratory Press, 1989; Sambrook et al., Molecular Cloning: A Laboratory Manual, 3rd Edition, Cold Spring Harbor Laboratory Press, 2001; Gorman, "High Efficiency Gene Transfer into Mammalian Cells," in DNA Cloning, Volume II, Glover, D. M., Ed., IRL Press, Washington, D.C., pp. 143 190 (1985).

For example, a liposomes or other lipid aggregate may comprise a lipid such as phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides, cerebrosides and combinations thereof; a cationic lipid (or other cationic amphiphile) such as 1,2-dioleyloxy-3-(trimethylamino) propane (DOTAP); N-cholesteryloxycarbaryl-3,7,12-triazapentadecane-1,15-diamine (CTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DOME); N-[1-(2,3-dioleyloxy) propyl]-N,N,N-trimethylammonium chloride (DOTMA); 3 beta [N—(N', N'-dimethylaminoethane)carbamoly] cholesterol (DC-Choi); and dimethyldioctadecylammonium (DDAB); dioleoylphosphatidyl ethanolamine (DOPE), cholesterol-containing DOPC; and combinations thereof; and/or a hydrophilic polymer such as polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and combinations thereof. Other suitable cationic lipids are described in Miller, Angew. Chem. Int. Ed. 37:1768 1785 (1998), and Cooper et al., Chem. Eur. J. 4(1): 137 151 (1998). Liposomes can be crosslinked, partially crosslinked, or free from crosslinking. Crosslinked liposomes can include crosslinked as well as non-crosslinked components. Suitable cationic liposomes or cytofectins are commercially available and can also be prepared as described in Sipkins et al., Nature Medicine, 1998, 4(5):(1998), 623 626 or as described in Miller, supra. Exemplary liposomes include a polymerizable zwitterionic or neutral lipid, a polymerizable integrin targeting lipid and a polymerizable cationic lipid suitable for binding a nucleic acid. Liposomes can optionally include peptides that provide increased efficiency, for example as described in U.S. Pat. No. 7,297,759. Additional exemplary liposomes and other lipid aggregates are described in U.S. Pat. No. 7,166,298.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_c$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ϵ (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ, (lambda). Each heavy chain class can be paired with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J. Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)). The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

Anti-IL-6 Antibodies and Binding Fragments Thereof

The invention includes antibodies having binding specificity to IL-6 and possessing a variable light chain sequence comprising the sequence set forth below:

```
                                                (SEQ ID NO: 2)
MDTRAPTQLLGLLLLWLPGARCAYDMTQTPASVSAAVGGTVTIKCQASQS

INNELSWYQQKPGQRPKLLIYRASTLASGVSSRFKGSGSGTEFTLTISDL

ECADAATYYCQQGYSLRNIDNAFGGGTEVVVKRTVAAPSVFIFPPSDEQ

LKSGTASVVCLLNN
or
                                              (SEQ ID NO: 709)
AIQMTQSPSSLSASVGDRVTITCQASQSINNELSWYQQKPGKAPKLLIY

RASTLASGVPSRFSGSGSGTDFTLTISSLQPDDFATYYCQQGYSLRNID

NAFGGGTKVEIKR.
```

The invention also includes antibodies having binding specificity to IL-6 and possessing a variable heavy chain sequence comprising the sequence set forth below:

```
                                                (SEQ ID NO: 3)
METGLRWLLLVAVLKGVQCQSLEESGGRLVTPGTPLTLTCTASGFSLSNY

YVTWVRQAPGKGLEWIGIIYGSDETAYATWAIGRFTISKTSTTVDLKMT

SLTAADTATYFCARDDSSDWDAKFNLWGQGTLVTVSSASTKGPSVFPLA

PSSKSTSGGTAALGCLVK
or
                                              (SEQ ID NO: 657)
EVQLVESGGGLVQPGGSLRLSCAASGFSLSNYYVTWVRQAPGKGLEWVG

IIYGSDETAYATSAIGRFTISRDNSKNTLYLQMNSLRAEDTAVYYCARD

DSSDWDAKFNLWGQGTLVTVSS.
```

The invention further contemplates antibodies comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2 or 709, and/or one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3 or SEQ ID NO:657 or those contained in FIGS. 34-37 or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2 or 709 or the other humanized VL sequences contained in FIGS. 34-37 and/or one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3, or combinations of these polypeptide sequences.

In another embodiment of the invention, the antibodies of the invention preferably include combinations of the CDRs and the variable heavy and light chain sequences set forth above. In a preferred embodiment the humanized anti-IL-6 antibody will comprise the variable heavy and variable light chain sequences respectively contained in SEQ ID NO:657 and SEQ ID NO:709, and preferably further comprising the heavy chain and light chain constant regions respectively contained in SEQ ID NO:588 and SEQ ID NO:586 or an anti-IL-6IL-6 antibody comprising one or more of the other variable heavy and light chain sequences in FIGS. 34-37 derived from Ab1, and variants thereof comprising one or more amino acid substitutions or deletions that do not substantially affect IL-6 binding and/or desired effector function. This embodiment also contemplates polynucleotides comprising, or alternatively consisting of, one or more of the nucleic acids encoding the variable heavy chain (SEQ ID NO: 700) and variable light chain (SEQ ID NO:723) sequences and the constant region heavy chain (SEQ ID NO: 589) and constant region light chain (SEQ ID NO:587) sequences. This embodiment further contemplates nucleic acids encoding variants comprising one or more amino acid substitutions or deletions to the variable heavy and variable light chain sequences respectively contained in SEQ ID NO:657 and SEQ ID NO:709 and the heavy chain and light chain constant regions respectively contained in SEQ ID NO:588 and SEQ ID NO:586, that do not substantially affect IL-6 binding and/or desired effector function.

The invention also contemplates fragments of the antibody having binding specificity to IL-6. In one embodiment of the invention, antibody fragments of the invention comprise, or alternatively consist of, the polypeptide sequence of SEQ ID NO: 2 or 709 In another embodiment of the invention, antibody fragments of the invention comprise, or alternatively consist of, the polypeptide sequence of SEQ ID NO: 3 or 657.

In a further embodiment of the invention, fragments of the antibody having binding specificity to IL-6 comprise, or alternatively consist of, one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2 or SEQ ID NO:709.

In a further embodiment of the invention, fragments of the antibody having binding specificity to IL-6 comprise, or alternatively consist of, one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3 or SEQ ID NO:657.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 2 or 709; the variable heavy chain region of SEQ ID NO: 3 or SEQ ID NO:657; the complementarity-determining regions (SEQ ID NO: 4; SEQ ID NO: 5; and SEQ ID NO: 6) of the variable light chain region of SEQ ID NO: 2 or 709; and the complementarity-determining regions (SEQ ID NO: 7; SEQ ID NO: 8; and SEQ ID NO: 9) of the variable heavy chain region of SEQ ID NO: 3 or 657.

The invention also contemplates variants wherein either of the heavy chain polypeptide sequences of SEQ ID NO: 18 or SEQ ID NO: 19 is substituted for the heavy chain polypeptide sequence of SEQ ID NO: 3 or 657; the light chain polypeptide sequence of SEQ ID NO: 20 is substituted for the light chain polypeptide sequence of SEQ ID NO: 2 or 709; and the heavy chain CDR sequence of SEQ ID NO: 120 is substituted for the heavy chain CDR sequence of SEQ ID NO: 8.

In a preferred embodiment of the invention, the anti-IL-6 antibody is Ab1, comprising SEQ ID NO: 2 and SEQ ID NO: 3, or more particularly an antibody comprising SEQ ID NO:657 and SEQ ID NO:709 (which are respectively encoded by the nucleic acid sequences in SEQ ID NO:700 and SEQ ID NO:723) or one comprised of the alternative SEQ ID NOs set forth in the preceding paragraph, and having at least one of the biological activities set forth herein. In a preferred embodiment, the anti-IL-6 antibody will comprise at least one humanized sequence as shown in FIGS. 34-37.

In another embodiment, the invention includes antibodies having binding specificity to IL-6 and possessing a variable light chain sequence comprising the sequence set forth below:

```
                                            (SEQ ID NO: 21)
MDTRAPTQLLGLLLLWLPGARCAYDMTQTPASVEVAVGGTVTINCQASET

IYSWLSWYQQKPGQPPKLLIYQASDLASGVPSRFSGSGAGTEYTLTISG

VQCDDAATYYCQQGYSGSNVDNVFGGGTEVVVKRTVAAPSVFIFPPSDE

QLKSGTASVVCLLNNFY
```

The invention also includes antibodies having binding specificity to IL-6 and possessing a variable heavy chain sequence comprising the sequence set forth below:

```
                                            (SEQ ID NO: 22)
METGLRWLLLVAVLKGVQCQEQLKESGGRLVTPGTPLTLTCTASGFSLN

DHAMGWVRQAPGKGLEYIGFINSGGSARYASWAEGRFTISRTSTTVDLKM

TSLTTEDTATYFCVRGGAVWSIHSFDPWGPGTLVTVSSASTKGPSVFPLA

PSSKSTSGGTAALGCLVK.
```

The invention further contemplates antibodies comprising one or more of the polypeptide sequences of SEQ ID NO: 23; SEQ ID NO: 24; and SEQ ID NO: 25 which correspond to the complementarity-determining regions (CDRs, or hypervariable regions) of the variable light chain sequence of SEQ ID NO: 21, and/or one or more of the polypeptide sequences of SEQ ID NO: 26; SEQ ID NO: 27; and SEQ ID NO: 28 which correspond to the complementarity-determining regions (CDRs, or hypervariable regions) of the variable heavy chain sequence of SEQ ID NO: 22, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 23; SEQ ID NO: 24; and SEQ ID NO: 25 which correspond to the complementarity-determining regions (CDRs, or hypervariable regions) of the variable light chain sequence of SEQ ID NO: 21, and/or one or more of the polypeptide sequences of SEQ ID NO: 26; SEQ ID NO: 27; and SEQ ID NO: 28 which correspond to the complementarity-determining regions (CDRs, or hypervariable regions) of the variable heavy chain sequence of SEQ ID NO: 22, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 21. In another embodiment of the invention, antibody fragments of the invention comprise, or alternatively consist of, the polypeptide sequence of SEQ ID NO: 22.

In a further embodiment of the invention, fragments of the antibody having binding specificity to IL-6 comprise, or alternatively consist of, one or more of the polypeptide sequences of SEQ ID NO: 23; SEQ ID NO: 24; and SEQ ID NO: 25 which correspond to the complementarity-determining regions (CDRs, or hypervariable regions) of the variable light chain sequence of SEQ ID NO: 21.

In a further embodiment of the invention, fragments of the antibody having binding specificity to IL-6 comprise, or alternatively consist of, one or more of the polypeptide sequences of SEQ ID NO: 26; SEQ ID NO: 27; and SEQ ID NO: 28 which correspond to the complementarity-determining regions (CDRs, or hypervariable regions) of the variable heavy chain sequence of SEQ ID NO: 22.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 21; the variable heavy chain region of SEQ ID NO: 22; the complementarity-determining regions (SEQ ID NO: 23; SEQ ID NO: 24; and SEQ ID NO: 25) of the variable light chain region of SEQ ID NO: 21; and the complementarity-determining regions (SEQ ID NO: 26; SEQ ID NO: 27; and SEQ ID NO: 28) of the variable heavy chain region of SEQ ID NO: 22.

In a preferred embodiment of the invention, the anti-IL-6 antibody is Ab2, comprising SEQ ID NO: 21 and SEQ ID NO: 22, and having at least one of the biological activities set forth herein.

In another embodiment, the invention includes antibodies having binding specificity to IL-6 and possessing a variable light chain sequence comprising the sequence set forth below:

(SEQ ID NO: 37)
MDTRAPTQLLGLLLLWLPGATFAAVLTQTPSPVSAAVGGTVSISCQASQS

VYDNNYLSWFQQKPGQPPKLLIYGASTLASGVPSRFVGSGSGTQFTLTIT

DVQCDDAATYYCAGVYDDDSDNAFGGGTEVVVKRTVAAPSVFIFPPSDEQ

LKSGTASVVCLLNN

The invention also includes antibodies having binding specificity to IL-6 and possessing a variable heavy chain sequence comprising the sequence set forth below:

(SEQ ID NO: 38)
METGLRWLLLVAVLKGVQCQSLEESGGRLVTPGTPLTLTCTASGFSLSVY

YMNWVRQAPGKGLEWIGFITMSDNINYASWAKGRFTISKTSTTVDLKMTS

PTTEDTATYFCARSRGWGTMGRLDLWGPGTLVTVSSASTKGPSVFPLAPS

SKSTSGGTAALGCLVK.

The invention further contemplates antibodies comprising one or more of the polypeptide sequences of SEQ ID NO: 39; SEQ ID NO: 40; and SEQ ID NO: 41 which correspond to the complementarity-determining regions (CDRs, or hypervariable regions) of the variable light chain sequence of SEQ ID NO: 37, and/or one or more of the polypeptide sequences of SEQ ID NO: 42; SEQ ID NO: 43; and SEQ ID NO: 44 which correspond to the complementarity-determining regions (CDRs, or hypervariable regions) of the variable heavy chain sequence of SEQ ID NO: 38, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 39; SEQ ID NO: 40; and SEQ ID NO: 41 which correspond to the complementarity-determining regions (CDRs, or hypervariable regions) of the variable light chain sequence of SEQ ID NO: 37, and/or one or more of the polypeptide sequences of SEQ ID NO: 42; SEQ ID NO: 43; and SEQ ID NO: 44 which correspond to the complementarity-determining regions (CDRs, or hypervariable regions) of the variable heavy chain sequence of SEQ ID NO: 38, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 37. In another embodiment of the invention, antibody fragments of the invention comprise, or alternatively consist of, the polypeptide sequence of SEQ ID NO: 38.

In a further embodiment of the invention, fragments of the antibody having binding specificity to IL-6 comprise, or alternatively consist of, one or more of the polypeptide sequences of SEQ ID NO: 39; SEQ ID NO: 40; and SEQ ID NO: 41 which correspond to the complementarity-determining regions (CDRs, or hypervariable regions) of the variable light chain sequence of SEQ ID NO: 37.

In a further embodiment of the invention, fragments of the antibody having binding specificity to IL-6 comprise, or alternatively consist of, one or more of the polypeptide sequences of SEQ ID NO: 42; SEQ ID NO: 43; and SEQ ID NO: 44 which correspond to the complementarity-determining regions (CDRs, or hypervariable regions) of the variable heavy chain sequence of SEQ ID NO: 38.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 37; the variable heavy chain region of SEQ ID NO: 38; the complementarity-determining regions (SEQ ID NO: 39; SEQ ID NO: 40; and SEQ ID NO: 41) of the variable light chain region of SEQ ID NO: 37; and the complementarity-determining regions (SEQ ID NO: 42; SEQ ID NO: 43; and SEQ ID NO: 44) of the variable heavy chain region of SEQ ID NO: 38.

In a preferred embodiment of the invention, the anti-IL-6 antibody is Ab3, comprising SEQ ID NO: 37 and SEQ ID NO: 38, and having at least one of the biological activities set forth herein.

In another embodiment, the invention includes antibodies having binding specificity to IL-6 and possessing a variable light chain sequence comprising the sequence set forth below:

(SEQ ID NO: 53)

MDTRAPTQLLGLLLLWLPGAICDPVLTQTPSPVSAPVGGTVSISCQASQS

VYENNYLSWFQQKPGQPPKLLIYGASTLDSGVPSRFKGSGSGTQFTLTIT

DVQCDDAATYYCAGVYDDDSDDAFGGGTEVVVKRTVAAPSVFIFPPSDE

QLKSGTASVVCLLNN

The invention also includes antibodies having binding specificity to IL-6 and possessing a variable heavy chain sequence comprising the sequence set forth below:

(SEQ ID NO: 54)

METGLRWLLLVAVLKGVQCQEQLKESGGGLVTPGGTLTLTCTASGFSLNA

YYMNWVRQAPGKGLEWIGFITLNNNVAYANWAKGRFTFSKTSTTVDLKMT

SPTPEDTATYFCARSRGWGAMGRLDLWGHGTLVTVSSASTKGPSVFPLAP

SSKSTSGGTAALGCLVK.

The invention further contemplates antibodies comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 53, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 54, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 53, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 54, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 53. In another embodiment of the invention, antibody fragments of the invention comprise, or alternatively consist of, the polypeptide sequence of SEQ ID NO: 54.

In a further embodiment of the invention, fragments of the antibody having binding specificity to IL-6 comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 53.

In a further embodiment of the invention, fragments of the antibody having binding specificity to IL-6 comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 54.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 53; the variable heavy chain region of SEQ ID NO: 54; the complementarity-determining regions (SEQ ID NO: 55; SEQ ID NO: 56; and SEQ ID NO: 57) of the variable light chain region of SEQ ID NO: 53; and the complementarity-determining regions (SEQ ID NO: 58; SEQ ID NO: 59; and SEQ ID NO: 60) of the variable heavy chain region of SEQ ID NO: 54.

In a preferred embodiment of the invention, the anti-IL-6 antibody is Ab4, comprising SEQ ID NO: 53 and SEQ ID NO: 54, and having at least one of the biological activities set forth herein.

In another embodiment, the invention includes antibodies having binding specificity to IL-6 and possessing a variable light chain sequence comprising the sequence set forth below:

(SEQ ID NO: 69)

MDTRAPTQLLGLLLLWLPGATFAQVLTQTPSPVSAAVGGTVTINCQASQS

VDDNNWLGWYQQKRGQPPKYLIYSASTLASGVPSRFKGSGSGTQFTLTIS

DLECDDAATYYCAGGFSGNIFAFGGGTEVVVKRTVAAPSVFIFPPSDEQL

KSGTASVVCLLNNF

The invention also includes antibodies having binding specificity to IL-6 and possessing a variable heavy chain sequence comprising the sequence set forth below:

(SEQ ID NO: 70)

METGLRWLLLVAVLKGVQCQSVEESGGRLVTPGTPLTLTCTVSGFSLSSY

AMSWVRQAPGKGLEWIGIIGGFGTTYYATWAKGRFTISKTSTTVDLRITS

PTTEDTATYFCARGGPGNGGDIWGQGTLVTVSSASTKGPSVFPLAPSSKS

TSGGTAALGCLVKD.

The invention further contemplates antibodies comprising one or more of the polypeptide sequences of SEQ ID NO: 71; SEQ ID NO: 72; and SEQ ID NO: 73 which correspond to the complementarity-determining regions (CDRs, or hypervariable regions) of the variable light chain sequence of SEQ ID NO: 69, and/or one or more of the polypeptide sequences of SEQ ID NO: 74; SEQ ID NO: 75; and SEQ ID NO: 76 which correspond to the complementarity-determining regions (CDRs, or hypervariable regions) of the variable heavy chain sequence of SEQ ID NO: 70, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 71; SEQ ID NO: 72; and SEQ ID NO: 73 which correspond to the complementarity-determining regions (CDRs, or hypervariable regions) of the variable light chain sequence of SEQ ID NO: 69, and/or one or more of the polypeptide sequences of SEQ ID NO: 74; SEQ ID NO: 75; and SEQ ID NO: 76 which correspond to the complementarity-determining regions (CDRs, or hypervariable regions) of the variable heavy chain sequence of SEQ ID NO: 70, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 69. In another embodiment of the invention, antibody fragments of the invention comprise, or alternatively consist of, the polypeptide sequence of SEQ ID NO: 70.

In a further embodiment of the invention, fragments of the antibody having binding specificity to IL-6 comprise, or alternatively consist of, one or more of the polypeptide sequences of SEQ ID NO: 71; SEQ ID NO: 72; and SEQ ID NO: 73 which correspond to the complementarity-determining regions (CDRs, or hypervariable regions) of the variable light chain sequence of SEQ ID NO: 69.

In a further embodiment of the invention, fragments of the antibody having binding specificity to IL-6 comprise, or alternatively consist of, one or more of the polypeptide sequences of SEQ ID NO: 74; SEQ ID NO: 75; and SEQ ID NO: 76 which correspond to the complementarity-determining regions (CDRs, or hypervariable regions) of the variable heavy chain sequence of SEQ ID NO: 70.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 69; the variable heavy chain region of SEQ ID NO: 70; the complementarity-determining regions (SEQ ID NO: 71; SEQ ID NO: 72; and SEQ ID NO: 73) of the variable light chain region of SEQ ID NO: 69; and the complementarity-determining regions (SEQ ID NO: 74; SEQ ID NO: 75; and SEQ ID NO: 76) of the variable heavy chain region of SEQ ID NO: 70.

In a preferred embodiment of the invention, the anti-IL-6 antibody is Ab5, comprising SEQ ID NO: 69 and SEQ ID NO: 70, and having at least one of the biological activities set forth herein.

In another embodiment, the invention includes antibodies having binding specificity to IL-6 and possessing a variable light chain sequence comprising the sequence set forth below:

(SEQ ID NO: 85)

```
MDTRAPTQLLGLLLLWLPGATFAAVLTQTPSPVSVPVGGTVTIKCQSSQS

VYNNFLSWYQQKPGQPPKLLIYQASKLASGVPDRFSGSGSGTQFTLTISG

VQCDDAATYYCLGGYDDDADNAFGGGTEVVVKRTVAAPSVFIFPPSDEQL

KSGTASVVCLLNNF
```

The invention also includes antibodies having binding specificity to IL-6 and possessing a variable heavy chain sequence comprising the sequence set forth below:

(SEQ ID NO: 86)

```
METGLRWLLLVAVLKGVQCQSVEESGGRLVTPGTPLTLTCTVSGIDLSDY

AMSWVRQAPGKGLEWIGIIYAGSGSTWYASWAKGRFTISKTSTTVDLKIT
```

-continued

```
SPTTEDTATYFCARDGYDDYGDFDRLDLWGPGTLVTVSSASTKGPSVFPL

APSSKSTSGGTAALGCLVKD.
```

The invention further contemplates antibodies comprising one or more of the polypeptide sequences of SEQ ID NO: 87; SEQ ID NO: 88; and SEQ ID NO: 89 which correspond to the complementarity-determining regions (CDRs, or hypervariable regions) of the variable light chain sequence of SEQ ID NO: 85, and/or one or more of the polypeptide sequences of SEQ ID NO: 90; SEQ ID NO: 91; and SEQ ID NO: 92 which correspond to the complementarity-determining regions (CDRs, or hypervariable regions) of the variable heavy chain sequence of SEQ ID NO: 86, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 87; SEQ ID NO: 88; and SEQ ID NO: 89 which correspond to the complementarity-determining regions (CDRs, or hypervariable regions) of the variable light chain sequence of SEQ ID NO: 85, and/or one or more of the polypeptide sequences of SEQ ID NO: 90; SEQ ID NO: 91; and SEQ ID NO: 92 which correspond to the complementarity-determining regions (CDRs, or hypervariable regions) of the variable heavy chain sequence of SEQ ID NO: 86, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 85. In another embodiment of the invention, antibody fragments of the invention comprise, or alternatively consist of, the polypeptide sequence of SEQ ID NO: 86.

In a further embodiment of the invention, fragments of the antibody having binding specificity to IL-6 comprise, or alternatively consist of, one or more of the polypeptide sequences of SEQ ID NO: 87; SEQ ID NO: 88; and SEQ ID NO: 89 which correspond to the complementarity-determining regions (CDRs, or hypervariable regions) of the variable light chain sequence of SEQ ID NO: 85.

In a further embodiment of the invention, fragments of the antibody having binding specificity to IL-6 comprise, or alternatively consist of, one or more of the polypeptide sequences of SEQ ID NO: 90; SEQ ID NO: 91; and SEQ ID NO: 92 which correspond to the complementarity-determining regions (CDRs, or hypervariable regions) of the variable heavy chain sequence of SEQ ID NO: 86.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 85; the variable heavy chain region of SEQ ID NO: 86; the complementarity-determining regions (SEQ ID NO: 87; SEQ ID NO: 88; and SEQ ID NO: 89) of the variable light chain region of SEQ ID NO: 85; and the complementarity-determining regions (SEQ ID NO: 90; SEQ ID NO: 91; and SEQ ID NO: 92) of the variable heavy chain region of SEQ ID NO: 86.

In a preferred embodiment of the invention, the anti-IL-6 antibody is Ab6, comprising SEQ ID NO: 85 and SEQ ID NO: 86, and having at least one of the biological activities set forth herein.

In another embodiment, the invention includes antibodies having binding specificity to IL-6 and possessing a variable light chain sequence comprising the sequence set forth below:

(SEQ ID NO: 101)
MDTRAPTQLLGLLLLWLPGARCAYDMTQTPASVSAAVGGTVTIKCQASQS

INNELSWYQQKSGQRPKLLIYRASTLASGVSSRFKGSGSGTEFTLTISDL

ECADAATYYCQQGYSLRNIDNAFGGGTEVVVKRTVAAPSVFIFPPSDEQL

KSGTASVVCLLNNF

The invention also includes antibodies having binding specificity to IL-6 and possessing a variable heavy chain sequence comprising the sequence set forth below:

(SEQ ID NO: 102)
METGLRWLLLVAVLSGVQCQSLEESGGRLVTPGTPLTLTCTASGFSLSNY

YMTWVRQAPGKGLEWIGMIYGSDETAYANWAIGRFTISKTSTTVDLKMTS

LTAADTATYFCARDDSSDWDAKFNLWGQGTLVTVSSASTKGPSVFPLAPS

SKSTSGGTAALGCLVK.

The invention further contemplates antibodies comprising one or more of the polypeptide sequences of SEQ ID NO: 103; SEQ ID NO: 104; and SEQ ID NO: 105 which correspond to the complementarity-determining regions (CDRs, or hypervariable regions) of the variable light chain sequence of SEQ ID NO: 101, and/or one or more of the polypeptide sequences of SEQ ID NO: 106; SEQ ID NO: 107; and SEQ ID NO: 108 which correspond to the complementarity-determining regions (CDRs, or hypervariable regions) of the variable heavy chain sequence of SEQ ID NO: 102, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 103; SEQ ID NO: 104; and SEQ ID NO: 105 which correspond to the complementarity-determining regions (CDRs, or hypervariable regions) of the variable light chain sequence of SEQ ID NO: 101, and/or one or more of the polypeptide sequences of SEQ ID NO: 106; SEQ ID NO: 107; and SEQ ID NO: 108 which correspond to the complementarity-determining regions (CDRs, or hypervariable regions) of the variable heavy chain sequence of SEQ ID NO: 102, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 101. In another embodiment of the invention, antibody fragments of the invention comprise, or alternatively consist of, the polypeptide sequence of SEQ ID NO: 102.

In a further embodiment of the invention, fragments of the antibody having binding specificity to IL-6 comprise, or alternatively consist of, one or more of the polypeptide sequences of SEQ ID NO: 103; SEQ ID NO: 104; and SEQ ID NO: 105 which correspond to the complementarity-determining regions (CDRs, or hypervariable regions) of the variable light chain sequence of SEQ ID NO: 101.

In a further embodiment of the invention, fragments of the antibody having binding specificity to IL-6 comprise, or alternatively consist of, one or more of the polypeptide sequences of SEQ ID NO: 106; SEQ ID NO: 107; and SEQ ID NO: 108 which correspond to the complementarity-determining regions (CDRs, or hypervariable regions) of the variable heavy chain sequence of SEQ ID NO: 102.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 101; the variable heavy chain region of SEQ ID NO: 102; the complementarity-determining regions (SEQ ID NO: 103; SEQ ID NO: 104; and SEQ ID NO: 105) of the variable light chain region of SEQ ID NO: 101; and the complementarity-determining regions (SEQ ID NO: 106; SEQ ID NO: 107; and SEQ ID NO: 108) of the variable heavy chain region of SEQ ID NO: 102.

The invention also contemplates variants wherein either of the heavy chain polypeptide sequences of SEQ ID NO: 117 or SEQ ID NO: 118 is substituted for the heavy chain polypeptide sequence of SEQ ID NO: 102; the light chain polypeptide sequence of SEQ ID NO: 119 is substituted for the light chain polypeptide sequence of SEQ ID NO: 101; and the heavy chain CDR sequence of SEQ ID NO: 121 is substituted for the heavy chain CDR sequence of SEQ ID NO: 107.

In a preferred embodiment of the invention, the anti-IL-6 antibody is Ab7, comprising SEQ ID NO: 101 and SEQ ID NO: 102, or the alternative SEQ ID NOs set forth in the preceding paragraph, and having at least one of the biological activities set forth herein.

In another embodiment, the invention includes antibodies having binding specificity to IL-6 and possessing a variable light chain sequence comprising the sequence set forth below:

(SEQ ID NO: 122)
MDTRAPTQLLGLLLLWLPGATFAAVLTQTPSPVSAAVGGTVTISCQSSQS

VGNNQDLSWFQQRPGQPPKLLIYEISKLESGVPSRFSGSGSGTHFTLTIS

GVQCDDAATYYCLGGYDDDADNA

The invention also includes antibodies having binding specificity to IL-6 and possessing a variable heavy chain sequence comprising the sequence set forth below:

(SEQ ID NO: 123)
METGLRWLLLVAVLKGVQCHSVEESGGRLVTPGTPLTLTCTVSGFSLSSR

TMSWVRQAPGKGLEWIGYIWSGGSTYYATWAKGRFTISKTSTTVDLKITS

PTTEDTATYFCARLGDTGGHAYATRLNL.

The invention further contemplates antibodies comprising one or more of the polypeptide sequences of SEQ ID NO: 124; SEQ ID NO: 125; and SEQ ID NO: 126 which correspond to the complementarity-determining regions (CDRs, or hypervariable regions) of the variable light chain sequence of SEQ ID NO: 122, and/or one or more of the polypeptide sequences of SEQ ID NO: 127; SEQ ID NO: 128; and SEQ ID NO: 129 which correspond to the complementarity-determining regions (CDRs, or hypervariable regions) of the variable heavy chain sequence of SEQ ID NO: 123, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 124; SEQ ID NO: 125; and SEQ ID NO: 126 which correspond to the complementarity-determining regions (CDRs, or hypervariable regions) of the variable light chain sequence of SEQ ID NO: 122, and/or one or more of the polypeptide sequences of SEQ ID NO: 127; SEQ ID NO: 128; and SEQ ID NO: 129 which correspond to the complementarity-determining regions (CDRs, or hypervariable regions) of the variable heavy chain sequence of SEQ ID NO: 123, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 122. In another embodiment of the invention, antibody fragments of the invention comprise, or alternatively consist of, the polypeptide sequence of SEQ ID NO: 123.

In a further embodiment of the invention, fragments of the antibody having binding specificity to IL-6 comprise, or alternatively consist of, one or more of the polypeptide sequences of SEQ ID NO: 124; SEQ ID NO: 125; and SEQ ID NO: 126 which correspond to the complementarity-determining regions (CDRs, or hypervariable regions) of the variable light chain sequence of SEQ ID NO: 122.

In a further embodiment of the invention, fragments of the antibody having binding specificity to IL-6 comprise, or alternatively consist of, one or more of the polypeptide sequences of SEQ ID NO: 127; SEQ ID NO: 128; and SEQ ID NO: 129 which correspond to the complementarity-determining regions (CDRs, or hypervariable regions) of the variable heavy chain sequence of SEQ ID NO: 123.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 122; the variable heavy chain region of SEQ ID NO: 123; the complementarity-determining regions (SEQ ID NO: 124; SEQ ID NO: 125; and SEQ ID NO: 126) of the variable light chain region of SEQ ID NO: 122; and the complementarity-determining regions (SEQ ID NO: 127; SEQ ID NO: 128; and SEQ ID NO: 129) of the variable heavy chain region of SEQ ID NO: 123.

In a preferred embodiment of the invention, the anti-IL-6 antibody is Ab8, comprising SEQ ID NO: 122 and SEQ ID NO: 123, and having at least one of the biological activities set forth herein.

In another embodiment, the invention includes antibodies having binding specificity to IL-6 and possessing a variable light chain sequence comprising the sequence set forth below:

```
                                          (SEQ ID NO: 138)
MDTRAPTQLLGLLLLWLPGATFAAVLTQTPSSVSAAVGGTVSISCQSSQS

VYSNKYLAWYQQKPGQPPKLLIYWTSKLASGAPSRFSGSGSGTQFTLTIS

GVQCDDAATYYCLGAYDDDADNA
```

The invention also includes antibodies having binding specificity to IL-6 and possessing a variable heavy chain sequence comprising the sequence set forth below:

```
                                          (SEQ ID NO: 139)
METGLRWLLLVAVLKGVQCQSVEESGGRLVKPDETLTLTCTASGFSLEGG

YMTWVRQAPGKGLEWIGISYDSGSTYYASWAKGRFTISKTSSTTVDLKMT

SLTTEDTATYFCVRSLKYPTVTSDDL.
```

The invention further contemplates antibodies comprising one or more of the polypeptide sequences of SEQ ID NO: 140; SEQ ID NO: 141; and SEQ ID NO: 142 which correspond to the complementarity-determining regions (CDRs, or hypervariable regions) of the variable light chain sequence of SEQ ID NO: 138, and/or one or more of the polypeptide sequences of SEQ ID NO: 143; SEQ ID NO: 144; and SEQ ID NO: 145 which correspond to the complementarity-determining regions (CDRs, or hypervariable regions) of the variable heavy chain sequence of SEQ ID NO: 139, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 140; SEQ ID NO: 141; and SEQ ID NO: 142 which correspond to the complementarity-determining regions (CDRs, or hypervariable regions) of the variable light chain sequence of SEQ ID NO: 138, and/or one or more of the polypeptide sequences of SEQ ID NO: 143; SEQ ID NO: 144; and SEQ ID NO: 145 which correspond to the complementarity-determining regions (CDRs, or hypervariable regions) of the variable heavy chain sequence of SEQ ID NO: 139, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 138. In another embodiment of the invention, antibody fragments of the invention comprise, or alternatively consist of, the polypeptide sequence of SEQ ID NO: 139.

In a further embodiment of the invention, fragments of the antibody having binding specificity to IL-6 comprise, or alternatively consist of, one or more of the polypeptide sequences of SEQ ID NO: 140; SEQ ID NO: 141; and SEQ ID NO: 142 which correspond to the complementarity-determining regions (CDRs, or hypervariable regions) of the variable light chain sequence of SEQ ID NO: 138.

In a further embodiment of the invention, fragments of the antibody having binding specificity to IL-6 comprise, or alternatively consist of, one or more of the polypeptide sequences of SEQ ID NO: 143; SEQ ID NO: 144; and SEQ ID NO: 145 which correspond to the complementarity-determining regions (CDRs, or hypervariable regions) of the variable heavy chain sequence of SEQ ID NO: 139.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 138; the variable heavy chain region of SEQ ID NO: 139; the complementarity-determining regions (SEQ ID NO: 140; SEQ ID NO: 141; and SEQ ID NO: 142) of the variable light chain region of SEQ ID NO: 138; and the complementarity-determining regions (SEQ ID NO: 143; SEQ ID NO: 144; and SEQ ID NO: 145) of the variable heavy chain region of SEQ ID NO: 139.

In a preferred embodiment of the invention, the anti-IL-6 antibody is Ab9, comprising SEQ ID NO: 138 and SEQ ID NO: 139, and having at least one of the biological activities set forth herein.

In another embodiment, the invention includes antibodies having binding specificity to IL-6 and possessing a variable light chain sequence comprising the sequence set forth below:

```
                                      (SEQ ID NO: 154)
MDTRAPTQLLGLLLLWLPGATFAAVLTQTPSPVSAAVGGTVTISCQSSQS

VYNNNDLAWYQQKPGQPPKLLIYYASTLASGVPSRFKGSGSGTQFTLTIS

GVQCDDAAAYYCLGGYDDDADNA
```

The invention also includes antibodies having binding specificity to IL-6 and possessing a variable heavy chain sequence comprising the sequence set forth below:

```
                                      (SEQ ID NO: 155)
METGLRWLLLVAVLKGVQCQSVEESGGRLVTPGTPLTLTCTVSGLSLSSN

TINWVRQAPGKGLEWIGYIWSGGSTYYASWVNGRFTISKTSTTVDLKITS

PTTEDTATYFCARGGYASGGYPYATRLDL.
```

The invention further contemplates antibodies comprising one or more of the polypeptide sequences of SEQ ID NO: 156; SEQ ID NO: 157; and SEQ ID NO: 158 which correspond to the complementarity-determining regions (CDRs, or hypervariable regions) of the variable light chain sequence of SEQ ID NO: 154, and/or one or more of the polypeptide sequences of SEQ ID NO: 159; SEQ ID NO: 160; and SEQ ID NO: 161 which correspond to the complementarity-determining regions (CDRs, or hypervariable regions) of the variable heavy chain sequence of SEQ ID NO: 155, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 156; SEQ ID NO: 157; and SEQ ID NO: 158 which correspond to the complementarity-determining regions (CDRs, or hypervariable regions) of the variable light chain sequence of SEQ ID NO: 154, and/or one or more of the polypeptide sequences of SEQ ID NO: 159; SEQ ID NO: 160; and SEQ ID NO: 161 which correspond to the complementarity-determining regions (CDRs, or hypervariable regions) of the variable heavy chain sequence of SEQ ID NO: 155, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 154. In another embodiment of the invention, antibody fragments of the invention comprise, or alternatively consist of, the polypeptide sequence of SEQ ID NO: 155.

In a further embodiment of the invention, fragments of the antibody having binding specificity to IL-6 comprise, or alternatively consist of, one or more of the polypeptide sequences of SEQ ID NO: 156; SEQ ID NO: 157; and SEQ ID NO: 158 which correspond to the complementarity-determining regions (CDRs, or hypervariable regions) of the variable light chain sequence of SEQ ID NO: 154.

In a further embodiment of the invention, fragments of the antibody having binding specificity to IL-6 comprise, or alternatively consist of, one or more of the polypeptide sequences of SEQ ID NO: 159; SEQ ID NO: 160; and SEQ ID NO: 161 which correspond to the complementarity-determining regions (CDRs, or hypervariable regions) of the variable heavy chain sequence of SEQ ID NO: 155.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 154; the variable heavy chain region of SEQ ID NO: 155; the complementarity-determining regions (SEQ ID NO: 156; SEQ ID NO: 157; and SEQ ID NO: 158) of the variable light chain region of SEQ ID NO: 154; and the complementarity-determining regions (SEQ ID NO: 159; SEQ ID NO: 160; and SEQ ID NO: 161) of the variable heavy chain region of SEQ ID NO: 155.

In a preferred embodiment of the invention, the anti-IL-6 antibody is Ab10, comprising SEQ ID NO: 154 and SEQ ID NO: 155, and having at least one of the biological activities set forth herein.

In another embodiment, the invention includes antibodies having binding specificity to IL-6 and possessing a variable light chain sequence comprising the sequence set forth below:

```
                                      (SEQ ID NO: 170)
MDTRAPTQLLGLLLLWLPGATFAAVLTQTPSSVSAAVGGTVTINCQSS

QSVYNNDYLSWYQQRPGQRPKLLIYGASKLASGVPSRFKGSGSGKQFTL

TISGVQCDDAATYYCLGDYDDDADNT
```

The invention also includes antibodies having binding specificity to IL-6 and possessing a variable heavy chain sequence comprising the sequence set forth below:

```
                                      (SEQ ID NO: 171)
METGLRWLLLVAVLKGVQCQSLEESGGRLVTPGTPLTLTCTVSGFTLSTN

YYLSWVRQAPGKGLEWIGIIYPSGNTYCAKWAKGRFTISKTSSTTVDLKM

TSPTTEDTATYFCARNYGGDESL.
```

The invention further contemplates antibodies comprising one or more of the polypeptide sequences of SEQ ID NO: 172; SEQ ID NO: 173; and SEQ ID NO: 174 which correspond to the complementarity-determining regions (CDRs, or hypervariable regions) of the variable light chain sequence of SEQ ID NO: 170, and/or one or more of the polypeptide sequences of SEQ ID NO: 175; SEQ ID NO: 176; and SEQ ID NO: 177 which correspond to the complementarity-determining regions (CDRs, or hypervariable regions) of the variable heavy chain sequence of SEQ ID NO: 171, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 172; SEQ ID NO: 173; and SEQ ID NO: 174 which correspond to the complementarity-determining regions (CDRs, or hypervariable regions) of the variable light chain sequence of SEQ ID NO: 170, and/or one or more of the polypeptide sequences of SEQ ID NO: 175; SEQ ID NO: 176; and SEQ ID NO: 177 which correspond to the complementarity-determining regions (CDRs, or hypervariable regions) of the variable heavy chain sequence of SEQ ID NO: 171, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 170. In another embodiment of the invention, antibody fragments of the invention comprise, or alternatively consist of, the polypeptide sequence of SEQ ID NO: 171.

In a further embodiment of the invention, fragments of the antibody having binding specificity to IL-6 comprise, or alternatively consist of, one or more of the polypeptide sequences of SEQ ID NO: 172; SEQ ID NO: 173; and SEQ ID NO: 174 which correspond to the complementarity-determining regions (CDRs, or hypervariable regions) of the variable light chain sequence of SEQ ID NO: 170.

In a further embodiment of the invention, fragments of the antibody having binding specificity to IL-6 comprise, or alternatively consist of, one or more of the polypeptide sequences of SEQ ID NO: 175; SEQ ID NO: 176; and SEQ ID NO: 177 which correspond to the complementarity-determining regions (CDRs, or hypervariable regions) of the variable heavy chain sequence of SEQ ID NO: 171.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 170; the variable heavy chain region of SEQ ID NO: 171; the complementarity-determining regions (SEQ ID NO: 172; SEQ ID NO: 173; and SEQ ID NO: 174) of the variable light chain region of SEQ ID NO: 170; and the complementarity-determining regions (SEQ ID NO: 175; SEQ ID NO: 176; and SEQ ID NO: 177) of the variable heavy chain region of SEQ ID NO: 171.

In a preferred embodiment of the invention, the anti-IL-6 antibody is Ab11, comprising SEQ ID NO: 170 and SEQ ID NO: 171, and having at least one of the biological activities set forth herein.

In another embodiment, the invention includes antibodies having binding specificity to IL-6 and possessing a variable light chain sequence comprising the sequence set forth below:

```
                                       (SEQ ID NO: 186)
MDTRAPTQLLGLLLLWLPGARCDVVMTQTPASVEAAVGGTVTIKCQA

SETIGNALAWYQQKSGQPPKLLIYKASKLASGVPSRFKGSGSGTEYTL

TISDLECADAATYYCQWCYFGDSV
```

The invention also includes antibodies having binding specificity to IL-6 and possessing a variable heavy chain sequence comprising the sequence set forth below:

```
                                       (SEQ ID NO: 187)
METGLRWLLLVTVLKGVQCQEQLVESGGGLVQPEGSLTLTCTASGFDF

SSGYYMCWVRQAPGKGLEWIACIFTITTNTYYASWAKGRFTISKTSSTTV

TLQMTSLTAADTATYLCARGIYSDNNYYAL.
```

The invention further contemplates antibodies comprising one or more of the polypeptide sequences of SEQ ID NO: 188; SEQ ID NO: 189; and SEQ ID NO: 190 which correspond to the complementarity-determining regions (CDRs, or hypervariable regions) of the variable light chain sequence of SEQ ID NO: 186, and/or one or more of the polypeptide sequences of SEQ ID NO: 191; SEQ ID NO: 192; and SEQ ID NO: 193 which correspond to the complementarity-determining regions (CDRs, or hypervariable regions) of the variable heavy chain sequence of SEQ ID NO: 187, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 188; SEQ ID NO: 189; and SEQ ID NO: 190 which correspond to the complementarity-determining regions (CDRs, or hypervariable regions) of the variable light chain sequence of SEQ ID NO: 186, and/or one or more of the polypeptide sequences of SEQ ID NO: 191; SEQ ID NO: 192; and SEQ ID NO: 193 which correspond to the complementarity-determining regions (CDRs, or hypervariable regions) of the variable heavy chain sequence of SEQ ID NO: 187, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 186. In another embodiment of the invention, antibody fragments of the invention comprise, or alternatively consist of, the polypeptide sequence of SEQ ID NO: 187.

In a further embodiment of the invention, fragments of the antibody having binding specificity to IL-6 comprise, or alternatively consist of, one or more of the polypeptide sequences of SEQ ID NO: 188; SEQ ID NO: 189; and SEQ ID NO: 190 which correspond to the complementarity-determining regions (CDRs, or hypervariable regions) of the variable light chain sequence of SEQ ID NO: 186.

In a further embodiment of the invention, fragments of the antibody having binding specificity to IL-6 comprise, or alternatively consist of, one or more of the polypeptide sequences of SEQ ID NO: 191; SEQ ID NO: 192; and SEQ ID NO: 193 which correspond to the complementarity-determining regions (CDRs, or hypervariable regions) of the variable heavy chain sequence of SEQ ID NO: 187.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 186; the variable heavy chain region of SEQ ID NO: 187; the complementarity-determining regions (SEQ ID NO: 188; SEQ ID NO: 189; and SEQ ID NO: 190) of the variable light chain region of SEQ ID NO: 186; and the complementarity-determining regions (SEQ ID NO: 191; SEQ ID NO: 192; and SEQ ID NO: 193) of the variable heavy chain region of SEQ ID NO: 187.

In a preferred embodiment of the invention, the anti-IL-6 antibody is Ab12, comprising SEQ ID NO: 186 and SEQ ID NO: 187, and having at least one of the biological activities set forth herein.

In another embodiment, the invention includes antibodies having binding specificity to IL-6 and possessing a variable light chain sequence comprising the sequence set forth below:

```
                                         (SEQ ID NO: 202)
MDTRAPTQLLGLLLLWLPGARCDVVMTQTPASVEAAVGGTVTIKCQA

SESIGNALAWYQQKPGQPPKLLIYKASTLASGVPSRFSGSGSGTEFTLT

ISGVQCADAAAYYCQWCYFGDSV
```

The invention also includes antibodies having binding specificity to IL-6 and possessing a variable heavy chain sequence comprising the sequence set forth below:

```
                                         (SEQ ID NO: 203)
METGLRWLLLVAVLKGVQCQQQLVESGGGLVKPGASLTLTCKASGFSFS

SGYYMCWVRQAPGKGLESIACIFTITDNTYYANWAKGRFTISKPSSPTVT

LQMTSLTAADTATYFCARGIYSTDNYYAL.
```

The invention further contemplates antibodies comprising one or more of the polypeptide sequences of SEQ ID NO: 204; SEQ ID NO: 205; and SEQ ID NO: 206 which correspond to the complementarity-determining regions (CDRs, or hypervariable regions) of the variable light chain sequence of SEQ ID NO: 202, and/or one or more of the polypeptide sequences of SEQ ID NO: 207; SEQ ID NO: 208; and SEQ ID NO: 209 which correspond to the complementarity-determining regions (CDRs, or hypervariable regions) of the variable heavy chain sequence of SEQ ID NO: 203, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 204; SEQ ID NO: 205; and SEQ ID NO: 206 which correspond to the complementarity-determining regions (CDRs, or hypervariable regions) of the variable light chain sequence of SEQ ID NO: 202, and/or one or more of the polypeptide sequences of SEQ ID NO: 207; SEQ ID NO: 208; and SEQ ID NO: 209 which correspond to the complementarity-determining regions (CDRs, or hypervariable regions) of the variable heavy chain sequence of SEQ ID NO: 203, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 202. In another embodiment of the invention, antibody fragments of the invention comprise, or alternatively consist of, the polypeptide sequence of SEQ ID NO: 203.

In a further embodiment of the invention, fragments of the antibody having binding specificity to IL-6 comprise, or alternatively consist of, one or more of the polypeptide sequences of SEQ ID NO: 204; SEQ ID NO: 205; and SEQ ID NO: 206 which correspond to the complementarity-determining regions (CDRs, or hypervariable regions) of the variable light chain sequence of SEQ ID NO: 202.

In a further embodiment of the invention, fragments of the antibody having binding specificity to IL-6 comprise, or alternatively consist of, one or more of the polypeptide sequences of SEQ ID NO: 207; SEQ ID NO: 208; and SEQ ID NO: 209 which correspond to the complementarity-determining regions (CDRs, or hypervariable regions) of the variable heavy chain sequence of SEQ ID NO: 203.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 202; the variable heavy chain region of SEQ ID NO: 203; the complementarity-determining regions (SEQ ID NO: 204; SEQ ID NO: 205; and SEQ ID NO: 206) of the variable light chain region of SEQ ID NO: 202; and the complementarity-determining regions (SEQ ID NO: 207; SEQ ID NO: 208; and SEQ ID NO: 209) of the variable heavy chain region of SEQ ID NO: 203.

In a preferred embodiment of the invention, the anti-IL-6 antibody is Ab13, comprising SEQ ID NO: 202 and SEQ ID NO: 203, and having at least one of the biological activities set forth herein.

In another embodiment, the invention includes antibodies having binding specificity to IL-6 and possessing a variable light chain sequence comprising the sequence set forth below:

```
                                         (SEQ ID NO: 218)
MDTRAPTQLLGLLLLWLPGARCDVVMTQTPASVEAAVGGTVTIKCQA

SQSVSSYLNWYQQKPGQPPKLLIYRASTLESGVPSRFKGSGSGTEFTLT

ISDLECADAATYYCQCTYGTSSSYGAA
```

The invention also includes antibodies having binding specificity to IL-6 and possessing a variable heavy chain sequence comprising the sequence set forth below:

```
                                         (SEQ ID NO: 219)
METGLRWLLLVAVLKGVQCQSVEESGGRLVTPGTPLTLTCTVSGISLSS

NAISWVRQAPGKGLEWIGIISYSGTTYYASWAKGRFTISKTSSTTVDLK

ITSPTTEDTATYFCARDDPTTVMVMLIPFGAGMDL.
```

The invention further contemplates antibodies comprising one or more of the polypeptide sequences of SEQ ID NO: 220; SEQ ID NO: 221; and SEQ ID NO: 222 which correspond to the complementarity-determining regions (CDRs, or hypervariable regions) of the variable light chain sequence of SEQ ID NO: 218, and/or one or more of the polypeptide sequences of SEQ ID NO: 223; SEQ ID NO: 224; and SEQ ID NO: 225 which correspond to the complementarity-determining regions (CDRs, or hypervariable regions) of the variable heavy chain sequence of SEQ ID NO: 219, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 220; SEQ ID NO: 221; and SEQ ID NO: 222 which correspond to the complementarity-determining regions (CDRs, or hypervariable regions) of the variable light chain sequence of SEQ ID NO: 218, and/or one or more of the polypeptide sequences of SEQ ID NO: 223; SEQ ID NO: 224; and SEQ ID NO: 225 which correspond to the complementarity-determining regions (CDRs, or hypervariable regions) of the variable heavy chain sequence of SEQ ID NO: 219, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 218. In another embodiment of the invention, antibody fragments of the invention comprise, or alternatively consist of, the polypeptide sequence of SEQ ID NO: 219.

In a further embodiment of the invention, fragments of the antibody having binding specificity to IL-6 comprise, or alternatively consist of, one or more of the polypeptide sequences of SEQ ID NO: 220; SEQ ID NO: 221; and SEQ ID NO: 222 which correspond to the complementarity-determining regions (CDRs, or hypervariable regions) of the variable light chain sequence of SEQ ID NO: 218.

In a further embodiment of the invention, fragments of the antibody having binding specificity to IL-6 comprise, or alternatively consist of, one or more of the polypeptide sequences of SEQ ID NO: 223; SEQ ID NO: 224; and SEQ ID NO: 225 which correspond to the complementarity-determining regions (CDRs, or hypervariable regions) of the variable heavy chain sequence of SEQ ID NO: 219.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 218; the variable heavy chain region of SEQ ID NO: 219; the complementarity-determining regions (SEQ ID NO: 220; SEQ ID NO: 221; and SEQ ID NO: 222) of the variable light chain region of SEQ ID NO: 218; and the complementarity-determining regions (SEQ ID NO: 223; SEQ ID NO: 224; and SEQ ID NO: 225) of the variable heavy chain region of SEQ ID NO: 219.

In a preferred embodiment of the invention, the anti-IL-6 antibody is Ab14, comprising SEQ ID NO: 218 and SEQ ID NO: 219, and having at least one of the biological activities set forth herein.

In another embodiment, the invention includes antibodies having binding specificity to IL-6 and possessing a variable light chain sequence comprising the sequence set forth below:

```
                                         (SEQ ID NO: 234)
MDTRAPTQLLGLLLLWLPGATFAQVLTQTASPVSAAVGGTVTINCQAS

QSVYKNNYLSWYQQKPGQPPKGLIYSASTLDSGVPLRFSGSGSGTQFT

LTISDVQCDDAATYYCLGSYDCSSGDCYA
```

The invention also includes antibodies having binding specificity to IL-6 and possessing a variable heavy chain sequence comprising the sequence set forth below:

```
                                         (SEQ ID NO: 235)
METGLRWLLLVAVLKGVQCQSLEESGGDLVKPEGSLTLTCTASGFSFS

SYWMCWVRQAPGKGLEWIACIVTGNGNTYYANWAKGRFTISKTSSTTVTL

QMTSLTAADTATYFCAKAYDL.
```

The invention further contemplates antibodies comprising one or more of the polypeptide sequences of SEQ ID NO: 236; SEQ ID NO: 237; and SEQ ID NO: 238 which correspond to the complementarity-determining regions (CDRs, or hypervariable regions) of the variable light chain sequence of SEQ ID NO: 234, and/or one or more of the polypeptide sequences of SEQ ID NO: 239; SEQ ID NO: 240; and SEQ ID NO: 241 which correspond to the complementarity-determining regions (CDRs, or hypervariable regions) of the variable heavy chain sequence of SEQ ID NO: 235, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 236; SEQ ID NO: 237; and SEQ ID NO: 238 which correspond to the complementarity-determining regions (CDRs, or hypervariable regions) of the variable light chain sequence of SEQ ID NO: 234, and/or one or more of the polypeptide sequences of SEQ ID NO: 239; SEQ ID NO: 240; and SEQ ID NO: 241 which correspond to the complementarity-determining regions (CDRs, or hypervariable regions) of the variable heavy chain sequence of SEQ ID NO: 235, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 234. In another embodiment of the invention, antibody fragments of the invention comprise, or alternatively consist of, the polypeptide sequence of SEQ ID NO: 235.

In a further embodiment of the invention, fragments of the antibody having binding specificity to IL-6 comprise, or alternatively consist of, one or more of the polypeptide sequences of SEQ ID NO: 236; SEQ ID NO: 237; and SEQ ID NO: 238 which correspond to the complementarity-determining regions (CDRs, or hypervariable regions) of the variable light chain sequence of SEQ ID NO: 234.

In a further embodiment of the invention, fragments of the antibody having binding specificity to IL-6 comprise, or alternatively consist of, one or more of the polypeptide sequences of SEQ ID NO: 239; SEQ ID NO: 240; and SEQ ID NO: 241 which correspond to the complementarity-determining regions (CDRs, or hypervariable regions) of the variable heavy chain sequence of SEQ ID NO: 235.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 234; the variable heavy chain region of SEQ ID NO: 235; the complementarity-determining regions (SEQ ID NO: 236; SEQ ID NO: 237; and SEQ ID NO: 238) of the variable light chain region of SEQ ID NO: 234; and the complementarity-determining regions (SEQ ID NO: 239; SEQ ID NO: 240; and SEQ ID NO: 241) of the variable heavy chain region of SEQ ID NO: 235.

In a preferred embodiment of the invention, the anti-IL-6 antibody is Ab15, comprising SEQ ID NO: 234 and SEQ ID NO: 235, and having at least one of the biological activities set forth herein.

In another embodiment, the invention includes antibodies having binding specificity to IL-6 and possessing a variable light chain sequence comprising the sequence set forth below:

```
                                        (SEQ ID NO: 250)
MDTRAPTQLLGLLLLWLPGSTFAAVLTQTPSPVSAAVGGTVSISCQAS

QSVYDNNYLSWYQQKPGQPPKLLIYGASTLASGVPSRFKGTGSGTQFT

LTITDVQCDDAATYYCAGVFNDDSDDA
```

The invention also includes antibodies having binding specificity to IL-6 and possessing a variable heavy chain sequence comprising the sequence set forth below:

```
                                        (SEQ ID NO: 251)
METGLRWLLLVAVPKGVQCQSLEESGGRLVTPGTPLTLTCTLSGFSLSA

YYMSWVRQAPGKGLEWIGFITLSDHISYARWAKGRFTISKTSTTVDLKMT

SPTTEDTATYFCARSRGWGAMGRLDL.
```

The invention further contemplates antibodies comprising one or more of the polypeptide sequences of SEQ ID NO: 252; SEQ ID NO: 253; and SEQ ID NO: 254 which correspond to the complementarity-determining regions (CDRs, or hypervariable regions) of the variable light chain sequence of SEQ ID NO: 250, and/or one or more of the polypeptide sequences of SEQ ID NO: 255; SEQ ID NO: 256; and SEQ ID NO: 257 which correspond to the complementarity-determining regions (CDRs, or hypervariable regions) of the variable heavy chain sequence of SEQ ID NO: 251, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 252; SEQ ID NO: 253; and SEQ ID NO: 254 which correspond to the complementarity-determining regions (CDRs, or hypervariable regions) of the variable light chain sequence of SEQ ID NO: 250, and/or one or more of the polypeptide sequences of SEQ ID NO: 255; SEQ ID NO: 256; and SEQ ID NO: 257 which correspond to the complementarity-determining regions (CDRs, or hypervariable regions) of the variable heavy chain sequence of SEQ ID NO: 251, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 250. In another embodiment of the invention, antibody fragments of the invention comprise, or alternatively consist of, the polypeptide sequence of SEQ ID NO: 251.

In a further embodiment of the invention, fragments of the antibody having binding specificity to IL-6 comprise, or alternatively consist of, one or more of the polypeptide sequences of SEQ ID NO: 252; SEQ ID NO: 253; and SEQ ID NO: 254 which correspond to the complementarity-determining regions (CDRs, or hypervariable regions) of the variable light chain sequence of SEQ ID NO: 250.

In a further embodiment of the invention, fragments of the antibody having binding specificity to IL-6 comprise, or alternatively consist of, one or more of the polypeptide sequences of SEQ ID NO: 255; SEQ ID NO: 256; and SEQ ID NO: 257 which correspond to the complementarity-determining regions (CDRs, or hypervariable regions) of the variable heavy chain sequence of SEQ ID NO: 251.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 250; the variable heavy chain region of SEQ ID NO: 251; the complementarity-determining regions (SEQ ID NO: 252; SEQ ID NO: 253; and SEQ ID NO: 254) of the variable light chain region of SEQ ID NO: 250; and the complementarity-determining regions (SEQ ID NO: 255; SEQ ID NO: 256; and SEQ ID NO: 257) of the variable heavy chain region of SEQ ID NO: 251.

In a preferred embodiment of the invention, the anti-IL-6 antibody is Ab16, comprising SEQ ID NO: 250 and SEQ ID NO: 251, and having at least one of the biological activities set forth herein.

In another embodiment, the invention includes antibodies having binding specificity to IL-6 and possessing a variable light chain sequence comprising the sequence set forth below:

```
                                        (SEQ ID NO: 266)
MDTRAPTQLLGLLLLWLPGATFAAVLTQTPSPVSAAVGGTVTISCQAS

QSVYNNKNLAWYQQKSGQPPKLLIYWASTLASGVSSRFSGSGSGTQF

TLTVSGVQCDDAATYYCLGVFDDDADNA
```

The invention also includes antibodies having binding specificity to IL-6 and possessing a variable heavy chain sequence comprising the sequence set forth below:

```
                                        (SEQ ID NO: 267)
METGLRWLLLVAVLKGVQCQSVEESGGRLVTPGTPLTLTCTASGFSLS

SYSMTWVRQAPGKGLEYIGVIGTSGSTYYATWAKGRFTISRTSTTVALK

ITSPTTEDTATYFCVRSLSSITFL.
```

The invention further contemplates antibodies comprising one or more of the polypeptide sequences of SEQ ID NO: 268; SEQ ID NO: 269; and SEQ ID NO: 270 which correspond to the complementarity-determining regions (CDRs, or hypervariable regions) of the variable light chain sequence of SEQ ID NO: 266, and/or one or more of the polypeptide sequences of SEQ ID NO: 271; SEQ ID NO: 272; and SEQ ID NO: 273 which correspond to the complementarity-determining regions (CDRs, or hypervariable regions) of the variable heavy chain sequence of SEQ ID NO: 267, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 268; SEQ ID NO: 269; and SEQ ID NO: 270 which correspond to the complementarity-determining regions (CDRs, or hypervariable regions) of the variable light chain sequence of SEQ ID NO: 266, and/or one or more of the polypeptide sequences of SEQ ID NO: 271; SEQ ID NO: 272; and SEQ ID NO: 273 which correspond to the complementarity-determining regions (CDRs, or hypervariable regions) of the variable heavy chain sequence of SEQ ID NO: 267, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 266. In another embodiment of the invention, antibody fragments of the invention comprise, or alternatively consist of, the polypeptide sequence of SEQ ID NO: 267.

In a further embodiment of the invention, fragments of the antibody having binding specificity to IL-6 comprise, or alternatively consist of, one or more of the polypeptide sequences of SEQ ID NO: 268; SEQ ID NO: 269; and SEQ ID NO: 270 which correspond to the complementarity-determining regions (CDRs, or hypervariable regions) of the variable light chain sequence of SEQ ID NO: 266.

In a further embodiment of the invention, fragments of the antibody having binding specificity to IL-6 comprise, or alternatively consist of, one or more of the polypeptide sequences of SEQ ID NO: 271; SEQ ID NO: 272; and SEQ ID NO: 273 which correspond to the complementarity-determining regions (CDRs, or hypervariable regions) of the variable heavy chain sequence of SEQ ID NO: 267.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 266; the variable heavy chain region of SEQ ID NO: 267; the complementarity-determining regions (SEQ ID NO: 268; SEQ ID NO: 269; and SEQ ID NO: 270) of the variable light chain region of SEQ ID NO: 266; and the complementarity-determining regions (SEQ ID NO: 271; SEQ ID NO: 272; and SEQ ID NO: 273) of the variable heavy chain region of SEQ ID NO: 267.

In a preferred embodiment of the invention, the anti-IL-6 antibody is Ab17, comprising SEQ ID NO: 266 and SEQ ID NO: 267, and having at least one of the biological activities set forth herein.

In another embodiment, the invention includes antibodies having binding specificity to IL-6 and possessing a variable light chain sequence comprising the sequence set forth below:

```
                                        (SEQ ID NO: 282)
MDTRAPTQLLGLLLLWLPGARCAFELTQTPASVEAAVGGTVTINCQASQN

IYRYLAWYQQKPGQPPKFLIYLASTLASGVPSRFKGSGSGTEFTLTISDL

ECADAATYYCQSYYSSNSVA
```

The invention also includes antibodies having binding specificity to IL-6 and possessing a variable heavy chain sequence comprising the sequence set forth below:

```
                                        (SEQ ID NO: 283)
METGLRWLLLVAVLKGVQCQEQLVESGGDLVQPEGSLTLTCTASELDFSS

GYWICWVRQVPGKGLEWIGCIYTGSSGSTFYASWAKGRFTISKTSSTTVT

LQMTSLTAADTATYFCARGYSGFGYFKL.
```

The invention further contemplates antibodies comprising one or more of the polypeptide sequences of SEQ ID NO: 284; SEQ ID NO: 285; and SEQ ID NO: 286 which correspond to the complementarity-determining regions (CDRs, or hypervariable regions) of the variable light chain sequence of SEQ ID NO: 282, and/or one or more of the polypeptide sequences of SEQ ID NO: 287; SEQ ID NO: 288; and SEQ ID NO: 289 which correspond to the complementarity-determining regions (CDRs, or hypervariable regions) of the variable heavy chain sequence of SEQ ID NO: 283, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 284; SEQ ID NO: 285; and SEQ ID NO: 286 which correspond to the complementarity-determining regions (CDRs, or hypervariable regions) of the variable light chain sequence of SEQ ID NO: 282, and/or one or more of the polypeptide sequences of SEQ ID NO: 287; SEQ ID NO: 288; and SEQ ID NO: 289 which correspond to the complementarity-determining regions (CDRs, or hypervariable regions) of the variable heavy chain sequence of SEQ ID NO: 283, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 282. In another embodiment of the invention, antibody fragments of the invention comprise, or alternatively consist of, the polypeptide sequence of SEQ ID NO: 283.

In a further embodiment of the invention, fragments of the antibody having binding specificity to IL-6 comprise, or alternatively consist of, one or more of the polypeptide sequences of SEQ ID NO: 284; SEQ ID NO: 285; and SEQ ID NO: 286 which correspond to the complementarity-determining regions (CDRs, or hypervariable regions) of the variable light chain sequence of SEQ ID NO: 282.

In a further embodiment of the invention, fragments of the antibody having binding specificity to IL-6 comprise, or alternatively consist of, one or more of the polypeptide sequences of SEQ ID NO: 287; SEQ ID NO: 288; and SEQ ID NO: 289 which correspond to the complementarity-determining regions (CDRs, or hypervariable regions) of the variable heavy chain sequence of SEQ ID NO: 283.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 282; the variable heavy chain region of SEQ ID NO: 283; the complementarity-determining regions (SEQ ID NO: 284; SEQ ID NO: 285; and SEQ ID NO: 286) of the variable light chain region of SEQ ID NO: 282; and the complementarity-determining regions (SEQ ID NO: 287; SEQ ID NO: 288; and SEQ ID NO: 289) of the variable heavy chain region of SEQ ID NO: 283.

In a preferred embodiment of the invention, the anti-IL-6 antibody is Ab18, comprising SEQ ID NO: 282 and SEQ ID NO: 283, and having at least one of the biological activities set forth herein.

In another embodiment, the invention includes antibodies having binding specificity to IL-6 and possessing a variable light chain sequence comprising the sequence set forth below:

(SEQ ID NO: 298)
MDTRAPTQLLGLLLLWLPGARCAYDMTQTPASVEVAVGGTVTIKCQASED

IYRLLAWYQQKPGQPPKLLIYDSSDLASGVPSRFKGSGSGTEFTLAISGV

QCDDAATYYCQQAWSYSDIDNA

The invention also includes antibodies having binding specificity to IL-6 and possessing a variable heavy chain sequence comprising the sequence set forth below:

(SEQ ID NO: 299)
METGLRWLLLVAVLKGVQCQSVEESGGRLVTPGTPLTLTCTASGFSLSSY

YMSWVRQAPGKGLEWIGIITTSGNTFYASWAKGRLTISRTSTTVDLKITS

PTTEDTATYFCARTSDIFYYRNL.

The invention further contemplates antibodies comprising one or more of the polypeptide sequences of SEQ ID NO: 300; SEQ ID NO: 301; and SEQ ID NO: 302 which correspond to the complementarity-determining regions (CDRs, or hypervariable regions) of the variable light chain sequence of SEQ ID NO: 298, and/or one or more of the polypeptide sequences of SEQ ID NO: 303; SEQ ID NO: 304; and SEQ ID NO: 305 which correspond to the complementarity-determining regions (CDRs, or hypervariable regions) of the variable heavy chain sequence of SEQ ID NO: 299, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 300; SEQ ID NO: 301; and SEQ ID NO: 302 which correspond to the complementarity-determining regions (CDRs, or hypervariable regions) of the variable light chain sequence of SEQ ID NO: 298, and/or one or more of the polypeptide sequences of SEQ ID NO: 303; SEQ ID NO: 304; and SEQ ID NO: 305 which correspond to the complementarity-determining regions (CDRs, or hypervariable regions) of the variable heavy chain sequence of SEQ ID NO: 299, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 298. In another embodiment of the invention, antibody fragments of the invention comprise, or alternatively consist of, the polypeptide sequence of SEQ ID NO: 299.

In a further embodiment of the invention, fragments of the antibody having binding specificity to IL-6 comprise, or alternatively consist of, one or more of the polypeptide sequences of SEQ ID NO: 300; SEQ ID NO: 301; and SEQ ID NO: 302 which correspond to the complementarity-determining regions (CDRs, or hypervariable regions) of the variable light chain sequence of SEQ ID NO: 298.

In a further embodiment of the invention, fragments of the antibody having binding specificity to IL-6 comprise, or alternatively consist of, one or more of the polypeptide sequences of SEQ ID NO: 303; SEQ ID NO: 304; and SEQ ID NO: 305 which correspond to the complementarity-determining regions (CDRs, or hypervariable regions) of the variable heavy chain sequence of SEQ ID NO: 299.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 298; the variable heavy chain region of SEQ ID NO: 299; the complementarity-determining regions (SEQ ID NO: 300; SEQ ID NO: 301; and SEQ ID NO: 302) of the variable light chain region of SEQ ID NO: 298; and the complementarity-determining regions (SEQ ID NO: 303; SEQ ID NO: 304; and SEQ ID NO: 305) of the variable heavy chain region of SEQ ID NO: 299.

In a preferred embodiment of the invention, the anti-IL-6 antibody is Ab19, comprising SEQ ID NO: 298 and SEQ ID NO: 299, and having at least one of the biological activities set forth herein.

In another embodiment, the invention includes antibodies having binding specificity to IL-6 and possessing a variable light chain sequence comprising the sequence set forth below:

(SEQ ID NO: 314)
MDTRAPTQLLGLLLLWLPGATFAAVLTQTASPVSAAVGATVTINCQSSQS

VYNDMDLAWFQQKPGQPPKLLIYSASTLASGVPSRFSGSGSGTEFTLTIS

GVQCDDAATYYCLGAFDDDADNT

The invention also includes antibodies having binding specificity to IL-6 and possessing a variable heavy chain sequence comprising the sequence set forth below:

(SEQ ID NO: 315)
METGLRWLLLVAVLKGVQCQSVEESGGRLVTPGTPLTLTCTVSGFSLTRH

AITWVRQAPGKGLEWIGCIWSGGSTYYATWAKGRFTISKTSTTVDLRITS

PTTEDTATYFCARVIGDTAGYAYFTGLDL.

The invention further contemplates antibodies comprising one or more of the polypeptide sequences of SEQ ID NO: 316; SEQ ID NO: 317; and SEQ ID NO: 318 which correspond to the complementarity-determining regions (CDRs, or hypervariable regions) of the variable light chain sequence of SEQ ID NO: 314, and/or one or more of the polypeptide sequences of SEQ ID NO: 319; SEQ ID NO: 320; and SEQ ID NO: 321 which correspond to the complementarity-determining regions (CDRs, or hypervariable regions) of the variable heavy chain sequence of SEQ ID NO: 315, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 316; SEQ ID NO: 317; and SEQ ID NO: 318 which correspond to the complementarity-determining regions (CDRs, or hypervariable regions) of the variable light chain sequence of SEQ ID NO: 314, and/or one or more of the polypeptide sequences of SEQ ID NO: 319; SEQ ID NO: 320; and SEQ ID NO: 321 which correspond to the complementarity-determining regions (CDRs, or hypervariable regions) of the variable heavy chain sequence of SEQ ID NO: 315, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 314. In another embodiment of the invention, antibody fragments of the invention comprise, or alternatively consist of, the polypeptide sequence of SEQ ID NO: 315.

In a further embodiment of the invention, fragments of the antibody having binding specificity to IL-6 comprise, or alternatively consist of, one or more of the polypeptide sequences of SEQ ID NO: 316; SEQ ID NO: 317; and SEQ ID NO: 318 which correspond to the complementarity-determining regions (CDRs, or hypervariable regions) of the variable light chain sequence of SEQ ID NO: 314.

In a further embodiment of the invention, fragments of the antibody having binding specificity to IL-6 comprise, or alternatively consist of, one or more of the polypeptide sequences of SEQ ID NO: 319; SEQ ID NO: 320; and SEQ ID NO: 321 which correspond to the complementarity-determining regions (CDRs, or hypervariable regions) of the variable heavy chain sequence of SEQ ID NO: 315.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 314; the variable heavy chain region of SEQ ID NO: 315; the complementarity-determining regions (SEQ ID NO: 316; SEQ ID NO: 317; and SEQ ID NO: 318) of the variable light chain region of SEQ ID NO: 314; and the complementarity-determining regions (SEQ ID NO: 319; SEQ ID NO: 320; and SEQ ID NO: 321) of the variable heavy chain region of SEQ ID NO: 315.

In a preferred embodiment of the invention, the anti-IL-6 antibody is Ab20, comprising SEQ ID NO: 314 and SEQ ID NO: 315, and having at least one of the biological activities set forth herein.

In another embodiment, the invention includes antibodies having binding specificity to IL-6 and possessing a variable light chain sequence comprising the sequence set forth below:

```
                                                 (SEQ ID NO: 330)
MDTRAPTQLLGLLLLWLPGARCAYDMTQTPASVEVAVGGTVTIKCQASQS

VYNWLSWYQQKPGQPPKLLIYTASSLASGVPSRFSGSGSGTEFTLTISGV

ECADAATYYCQQGYTSDVDNV
```

The invention also includes antibodies having binding specificity to IL-6 and possessing a variable heavy chain sequence comprising the sequence set forth below:

```
                                                 (SEQ ID NO: 331)
METGLRWLLLVAVLKGVQCQSLEEAGGRLVTPGTPLTLTCTVSGIDLSSY

AMGWVRQAPGKGLEYIGIISSSGSTYYATWAKGRFTISQASSTTVDLKIT

SPTTEDSATYFCARGGAGSGGVWLLDGFDP.
```

The invention further contemplates antibodies comprising one or more of the polypeptide sequences of SEQ ID NO: 332; SEQ ID NO: 333; and SEQ ID NO: 334 which correspond to the complementarity-determining regions (CDRs, or hypervariable regions) of the variable light chain sequence of SEQ ID NO: 330, and/or one or more of the polypeptide sequences of SEQ ID NO: 335; SEQ ID NO: 336; and SEQ ID NO: 337 which correspond to the complementarity-determining regions (CDRs, or hypervariable regions) of the variable heavy chain sequence of SEQ ID NO: 331, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 332; SEQ ID NO: 333; and SEQ ID NO: 334 which correspond to the complementarity-determining regions (CDRs, or hypervariable regions) of the variable light chain sequence of SEQ ID NO: 330, and/or one or more of the polypeptide sequences of SEQ ID NO: 335; SEQ ID NO: 336; and SEQ ID NO: 337 which correspond to the complementarity-determining regions (CDRs, or hypervariable regions) of the variable heavy chain sequence of SEQ ID NO: 331, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 330. In another embodiment of the invention, antibody fragments of the invention comprise, or alternatively consist of, the polypeptide sequence of SEQ ID NO: 331.

In a further embodiment of the invention, fragments of the antibody having binding specificity to IL-6 comprise, or alternatively consist of, one or more of the polypeptide sequences of SEQ ID NO: 332; SEQ ID NO: 333; and SEQ ID NO: 334 which correspond to the complementarity-determining regions (CDRs, or hypervariable regions) of the variable light chain sequence of SEQ ID NO: 330.

In a further embodiment of the invention, fragments of the antibody having binding specificity to IL-6 comprise, or alternatively consist of, one or more of the polypeptide sequences of SEQ ID NO: 335; SEQ ID NO: 336; and SEQ ID NO: 337 which correspond to the complementarity-determining regions (CDRs, or hypervariable regions) of the variable heavy chain sequence of SEQ ID NO: 331.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 330; the variable heavy chain region of SEQ ID NO: 331; the complementarity-determining regions (SEQ ID NO: 332; SEQ ID NO: 333; and SEQ ID NO: 334) of the variable light chain region of SEQ ID NO: 330; and the complementarity-determining regions (SEQ ID NO: 335; SEQ ID NO: 336; and SEQ ID NO: 337) of the variable heavy chain region of SEQ ID NO: 331.

In a preferred embodiment of the invention, the anti-IL-6 antibody is Ab21, comprising SEQ ID NO: 330 and SEQ ID NO: 331, and having at least one of the biological activities set forth herein.

In another embodiment, the invention includes antibodies having binding specificity to IL-6 and possessing a variable light chain sequence comprising the sequence set forth below:

(SEQ ID NO: 346)
MDTRAPTQLLGLLLLWLPGAKCADVVMTQTPASVSAAVGGTVTINCQASE

NIYNWLAWYQQKPGQPPKLLIYTVGDLASGVSSRFKGSGSGTEFTLTISD

LECADAATYYCQQGYSSSYVDNV

The invention also includes antibodies having binding specificity to IL-6 and possessing a variable heavy chain sequence comprising the sequence set forth below:

(SEQ ID NO: 347)
METGLRWLLLVAVLKGVQCQEQLKESGGRLVTPGTPLTLTCTVSGFSLND

YAVGWFRQAPGKGLEWIGYIRSSGTTAYATWAKGRFTISATSTTVDLKIT

SPTTEDTATYFCARGGAGSSGVWILDGFAP.

The invention further contemplates antibodies comprising one or more of the polypeptide sequences of SEQ ID NO: 348; SEQ ID NO: 349; and SEQ ID NO: 350 which correspond to the complementarity-determining regions (CDRs, or hypervariable regions) of the variable light chain sequence of SEQ ID NO: 346, and/or one or more of the polypeptide sequences of SEQ ID NO: 351; SEQ ID NO: 352; and SEQ ID NO: 353 which correspond to the complementarity-determining regions (CDRs, or hypervariable regions) of the variable heavy chain sequence of SEQ ID NO: 347, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 348; SEQ ID NO: 349; and SEQ ID NO: 350 which correspond to the complementarity-determining regions (CDRs, or hypervariable regions) of the variable light chain sequence of SEQ ID NO: 346, and/or one or more of the polypeptide sequences of SEQ ID NO: 351; SEQ ID NO: 352; and SEQ ID NO: 353 which correspond to the complementarity-determining regions (CDRs, or hypervariable regions) of the variable heavy chain sequence of SEQ ID NO: 347, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 346. In another embodiment of the invention, antibody fragments of the invention comprise, or alternatively consist of, the polypeptide sequence of SEQ ID NO: 347.

In a further embodiment of the invention, fragments of the antibody having binding specificity to IL-6 comprise, or alternatively consist of, one or more of the polypeptide sequences of SEQ ID NO: 348; SEQ ID NO: 349; and SEQ ID NO: 350 which correspond to the complementarity-determining regions (CDRs, or hypervariable regions) of the variable light chain sequence of SEQ ID NO: 346.

In a further embodiment of the invention, fragments of the antibody having binding specificity to IL-6 comprise, or alternatively consist of, one or more of the polypeptide sequences of SEQ ID NO: 351; SEQ ID NO: 352; and SEQ ID NO: 353 which correspond to the complementarity-determining regions (CDRs, or hypervariable regions) of the variable heavy chain sequence of SEQ ID NO: 347.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 346; the variable heavy chain region of SEQ ID NO: 347; the complementarity-determining regions (SEQ ID NO: 348; SEQ ID NO: 349; and SEQ ID NO: 350) of the variable light chain region of SEQ ID NO: 346; and the complementarity-determining regions (SEQ ID NO: 351; SEQ ID NO: 352; and SEQ ID NO: 353) of the variable heavy chain region of SEQ ID NO: 347.

In a preferred embodiment of the invention, the anti-IL-6 antibody is Ab22, comprising SEQ ID NO: 346 and SEQ ID NO: 347, and having at least one of the biological activities set forth herein.

In another embodiment, the invention includes antibodies having binding specificity to IL-6 and possessing a variable light chain sequence comprising the sequence set forth below:

(SEQ ID NO: 362)
MDTRAPTQLLGLLLLWLPGATFAQVLTQTPSSVSAAVGGTVTINCQASQS

VYQNNYLSWFQQKPGQPPKLLIYGAATLASGVPSRFKGSGSGTQFTLTIS

DLECDDAATYYCAGAYRDVDS

The invention also includes antibodies having binding specificity to IL-6 and possessing a variable heavy chain sequence comprising the sequence set forth below:

(SEQ ID NO: 363)
METGLRWLLLVAVLKGVQCQSLEESGGDLVKPGASLTLTCTASGFSFTST

YYIYWVRQAPGKGLEWIACIDAGSSGSTYYATWVNGRFTISKTSSTTVTL

QMTSLTAADTATYFCAKWDYGGNVGWGYDL.

The invention further contemplates antibodies comprising one or more of the polypeptide sequences of SEQ ID NO: 364; SEQ ID NO: 365; and SEQ ID NO: 366 which correspond to the complementarity-determining regions (CDRs, or hypervariable regions) of the variable light chain sequence of SEQ ID NO: 362, and/or one or more of the polypeptide sequences of SEQ ID NO: 367; SEQ ID NO: 368; and SEQ ID NO: 369 which correspond to the complementarity-determining regions (CDRs, or hypervariable regions) of the variable heavy chain sequence of SEQ ID NO: 363, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 364; SEQ ID NO: 365; and SEQ ID NO: 366 which correspond to the complementarity-determining regions (CDRs, or hypervariable regions) of the variable light chain sequence of SEQ ID NO: 362, and/or one or more of the polypeptide sequences of SEQ ID NO: 367; SEQ ID NO: 368; and SEQ ID NO: 369 which correspond to the complementarity-determining regions (CDRs, or hypervariable regions) of the variable heavy chain sequence of SEQ ID NO: 363, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 362. In another embodiment of the invention, antibody fragments of the invention comprise, or alternatively consist of, the polypeptide sequence of SEQ ID NO: 363.

In a further embodiment of the invention, fragments of the antibody having binding specificity to IL-6 comprise, or alternatively consist of, one or more of the polypeptide sequences of SEQ ID NO: 364; SEQ ID NO: 365; and SEQ ID NO: 366 which correspond to the complementarity-determining regions (CDRs, or hypervariable regions) of the variable light chain sequence of SEQ ID NO: 362.

In a further embodiment of the invention, fragments of the antibody having binding specificity to IL-6 comprise, or alternatively consist of, one or more of the polypeptide sequences of SEQ ID NO: 367; SEQ ID NO: 368; and SEQ ID NO: 369 which correspond to the complementarity-determining regions (CDRs, or hypervariable regions) of the variable heavy chain sequence of SEQ ID NO: 363.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 362; the variable heavy chain region of SEQ ID NO: 363; the complementarity-determining regions (SEQ ID NO: 364; SEQ ID NO: 365; and SEQ ID NO: 366) of the variable light chain region of SEQ ID NO: 362; and the complementarity-determining regions (SEQ ID NO: 367; SEQ ID NO: 368; and SEQ ID NO: 369) of the variable heavy chain region of SEQ ID NO: 363.

In a preferred embodiment of the invention, the anti-IL-6 antibody is Ab23, comprising SEQ ID NO: 362 and SEQ ID NO: 363, and having at least one of the biological activities set forth herein.

In another embodiment, the invention includes antibodies having binding specificity to IL-6 and possessing a variable light chain sequence comprising the sequence set forth below:

(SEQ ID NO: 378)
MDTRAPTQLLGLLLLWLPGARCAFELTQTPSSVEAAVGGTVTIKCQASQS

ISSYLAWYQQKPGQPPKFLIYRASTLASGVPSRFKGSGSGTEFTLTISDL

ECADAATYYCQSYYDSVSNP

The invention also includes antibodies having binding specificity to IL-6 and possessing a variable heavy chain sequence comprising the sequence set forth below:

(SEQ ID NO: 379)
METGLRWLLLVAVLKGVQCQSLEESGGDLVKPEGSLTLTCKASGLDLGTY

WFMCWVRQAPGKGLEWIACIYTGSSGSTFYASWVNGRFTISKTSSTTVTL

QMTSLTAADTATYFCARGYSGYGYFKL.

The invention further contemplates antibodies comprising one or more of the polypeptide sequences of SEQ ID NO: 380; SEQ ID NO: 381; and SEQ ID NO: 382 which correspond to the complementarity-determining regions (CDRs, or hypervariable regions) of the variable light chain sequence of SEQ ID NO: 378, and/or one or more of the polypeptide sequences of SEQ ID NO: 383; SEQ ID NO: 384; and SEQ ID NO: 385 which correspond to the complementarity-determining regions (CDRs, or hypervariable regions) of the variable heavy chain sequence of SEQ ID NO: 379, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 380; SEQ ID NO: 381; and SEQ ID NO: 382 which correspond to the complementarity-determining regions (CDRs, or hypervariable regions) of the variable light chain sequence of SEQ ID NO: 378, and/or one or more of the polypeptide sequences of SEQ ID NO: 383; SEQ ID NO: 384; and SEQ ID NO: 385 which correspond to the complementarity-determining regions (CDRs, or hypervariable regions) of the variable heavy chain sequence of SEQ ID NO: 379, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 378. In another embodiment of the invention, antibody fragments of the invention comprise, or alternatively consist of, the polypeptide sequence of SEQ ID NO: 379.

In a further embodiment of the invention, fragments of the antibody having binding specificity to IL-6 comprise, or alternatively consist of, one or more of the polypeptide sequences of SEQ ID NO: 380; SEQ ID NO: 381; and SEQ ID NO: 382 which correspond to the complementarity-determining regions (CDRs, or hypervariable regions) of the variable light chain sequence of SEQ ID NO: 378.

In a further embodiment of the invention, fragments of the antibody having binding specificity to IL-6 comprise, or alternatively consist of, one or more of the polypeptide sequences of SEQ ID NO: 383; SEQ ID NO: 384; and SEQ ID NO: 385 which correspond to the complementarity-determining regions (CDRs, or hypervariable regions) of the variable heavy chain sequence of SEQ ID NO: 379.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 378; the variable heavy chain region of SEQ ID NO: 379; the complementarity-determining regions (SEQ ID NO: 380; SEQ ID NO: 381; and SEQ ID NO: 382) of the variable light chain region of SEQ ID NO: 378; and the complementarity-determining regions (SEQ ID NO: 383; SEQ ID NO: 384; and SEQ ID NO: 385) of the variable heavy chain region of SEQ ID NO: 379.

In a preferred embodiment of the invention, the anti-IL-6 antibody is Ab24, comprising SEQ ID NO: 378 and SEQ ID NO: 379, and having at least one of the biological activities set forth herein.

In another embodiment, the invention includes antibodies having binding specificity to IL-6 and possessing a variable light chain sequence comprising the sequence set forth below:

(SEQ ID NO: 394)

MDTRAPTQLLGLLLLWLPGVTFAIEMTQSPFSVSAAVGGTVSISCQASQS

VYKNNQLSWYQQKSGQPPKLLIYGASALASGVPSRFKGSGSGTEFTLTIS

DVQCDDAATYYCAGAITGSIDTDG

The invention also includes antibodies having binding specificity to IL-6 and possessing a variable heavy chain sequence comprising the sequence set forth below:

(SEQ ID NO: 395)

METGLRWLLLVAVLKGVQCQSLEESGGDLVKPGASLTLTCTTSGFSFSSS

YFICWVRQAPGKGLEWIACIYGGDGSTYYASWAKGRFTISKTSSTTVTLQ

MTSLTAADTATYFCAREWAYSQGYFGAFDL.

The invention further contemplates antibodies comprising one or more of the polypeptide sequences of SEQ ID NO: 396; SEQ ID NO: 397; and SEQ ID NO: 398 which correspond to the complementarity-determining regions (CDRs, or hypervariable regions) of the variable light chain sequence of SEQ ID NO: 394, and/or one or more of the polypeptide sequences of SEQ ID NO: 399; SEQ ID NO: 400; and SEQ ID NO: 401 which correspond to the complementarity-determining regions (CDRs, or hypervariable regions) of the variable heavy chain sequence of SEQ ID NO: 395, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 396; SEQ ID NO: 397; and SEQ ID NO: 398 which correspond to the complementarity-determining regions (CDRs, or hypervariable regions) of the variable light chain sequence of SEQ ID NO: 394, and/or one or more of the polypeptide sequences of SEQ ID NO: 399; SEQ ID NO: 400; and SEQ ID NO: 401 which correspond to the complementarity-determining regions (CDRs, or hypervariable regions) of the variable heavy chain sequence of SEQ ID NO: 395, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 394. In another embodiment of the invention, antibody fragments of the invention comprise, or alternatively consist of, the polypeptide sequence of SEQ ID NO: 395.

In a further embodiment of the invention, fragments of the antibody having binding specificity to IL-6 comprise, or alternatively consist of, one or more of the polypeptide sequences of SEQ ID NO: 396; SEQ ID NO: 397; and SEQ ID NO: 398 which correspond to the complementarity-determining regions (CDRs, or hypervariable regions) of the variable light chain sequence of SEQ ID NO: 394.

In a further embodiment of the invention, fragments of the antibody having binding specificity to IL-6 comprise, or alternatively consist of, one or more of the polypeptide sequences of SEQ ID NO: 399; SEQ ID NO: 400; and SEQ ID NO: 401 which correspond to the complementarity-determining regions (CDRs, or hypervariable regions) of the variable heavy chain sequence of SEQ ID NO: 395.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 394; the variable heavy chain region of SEQ ID NO: 395; the complementarity-determining regions (SEQ ID NO: 396; SEQ ID NO: 397; and SEQ ID NO: 398) of the variable light chain region of SEQ ID NO: 394; and the complementarity-determining regions (SEQ ID NO: 399; SEQ ID NO: 400; and SEQ ID NO: 401) of the variable heavy chain region of SEQ ID NO: 395.

In a preferred embodiment of the invention, the anti-IL-6 antibody is Ab25, comprising SEQ ID NO: 394 and SEQ ID NO: 395, and having at least one of the biological activities set forth herein.

In another embodiment, the invention includes antibodies having binding specificity to IL-6 and possessing a variable light chain sequence comprising the sequence set forth below:

(SEQ ID NO: 410)

MDTRAPTQLLGLLLLWLPGARCDVVMTQTPASVEAAVGGTVTIKCQASED

ISSYLAWYQQKPGQPPKLLIYAASNLESGVSSRFKGSGSGTEYTLTISDL

ECADAATYYCQCTYGTISISDGNA

The invention also includes antibodies having binding specificity to IL-6 and possessing a variable heavy chain sequence comprising the sequence set forth below:

(SEQ ID NO: 411)

METGLRWLLLVAVLKGVQCQSVEESGGRLVTPGTPLTLTCTVSGFSLSSY

FMTWVRQAPGEGLEYIGFINPGGSAYYASWVKGRFTISKSSTTVDLKITS

PTTEDTATYFCARVLIVSYGAFTI.

The invention further contemplates antibodies comprising one or more of the polypeptide sequences of SEQ ID NO: 412; SEQ ID NO: 413; and SEQ ID NO: 414 which correspond to the complementarity-determining regions (CDRs, or hypervariable regions) of the variable light chain sequence of SEQ ID NO: 410, and/or one or more of the polypeptide sequences of SEQ ID NO: 415; SEQ ID NO: 416; and SEQ ID NO: 417 which correspond to the complementarity-determining regions (CDRs, or hypervariable regions) of the variable heavy chain sequence of SEQ ID NO: 411, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 412; SEQ ID NO: 413; and SEQ ID NO: 414 which correspond to the complementarity-determining regions (CDRs, or hypervariable regions) of the variable light chain sequence of SEQ ID NO: 410, and/or one or more of the polypeptide sequences of SEQ ID NO: 415; SEQ ID NO: 416; and SEQ ID NO: 417 which correspond to the complementarity-determining regions (CDRs, or hypervariable regions) of the variable heavy chain sequence of SEQ ID NO: 411, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 410. In another embodiment of the invention, antibody fragments of the invention comprise, or alternatively consist of, the polypeptide sequence of SEQ ID NO: 411.

In a further embodiment of the invention, fragments of the antibody having binding specificity to IL-6 comprise, or alternatively consist of, one or more of the polypeptide sequences of SEQ ID NO: 412; SEQ ID NO: 413; and SEQ ID NO: 414 which correspond to the complementarity-determining regions (CDRs, or hypervariable regions) of the variable light chain sequence of SEQ ID NO: 410.

In a further embodiment of the invention, fragments of the antibody having binding specificity to IL-6 comprise, or alternatively consist of, one or more of the polypeptide sequences of SEQ ID NO: 415; SEQ ID NO: 416; and SEQ ID NO: 417 which correspond to the complementarity-determining regions (CDRs, or hypervariable regions) of the variable heavy chain sequence of SEQ ID NO: 411.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 410; the variable heavy chain region of SEQ ID NO: 411; the complementarity-determining regions (SEQ ID NO: 412; SEQ ID NO: 413; and SEQ ID NO: 414) of the variable light chain region of SEQ ID NO: 410; and the complementarity-determining regions (SEQ ID NO: 415; SEQ ID NO: 416; and SEQ ID NO: 417) of the variable heavy chain region of SEQ ID NO: 411.

In a preferred embodiment of the invention, the anti-IL-6 antibody is Ab26, comprising SEQ ID NO: 410 and SEQ ID NO: 411, and having at least one of the biological activities set forth herein.

In another embodiment, the invention includes antibodies having binding specificity to IL-6 and possessing a variable light chain sequence comprising the sequence set forth below:

```
                                        (SEQ ID NO: 426)
MDTRAPTQLLGLLLLWLPGARCDVVMTQTPASVSAAVGGTVTIKCQASED

IESYLAWYQQKPGQPPKLLIYGASNLESGVSSRFKGSGSGTEFTLTISDL

ECADAATYYCQCTYGIISISDGNA
```

The invention also includes antibodies having binding specificity to IL-6 and possessing a variable heavy chain sequence comprising the sequence set forth below:

```
                                        (SEQ ID NO: 427)
METGLRWLLLVAVLKGVQCQSVEESGGRLVTPGTPLTLTCTVSGFSLSSY

FMTWVRQAPGEGLEYIGFMNTGDNAYYASWAKGRFTISKTSTTVDLKITS

PTTEDTATYFCARVLVVAYGAFNI.
```

The invention further contemplates antibodies comprising one or more of the polypeptide sequences of SEQ ID NO: 428; SEQ ID NO: 429; and SEQ ID NO: 430 which correspond to the complementarity-determining regions (CDRs, or hypervariable regions) of the variable light chain sequence of SEQ ID NO: 426, and/or one or more of the polypeptide sequences of SEQ ID NO: 431; SEQ ID NO: 432; and SEQ ID NO: 433 which correspond to the complementarity-determining regions (CDRs, or hypervariable regions) of the variable heavy chain sequence of SEQ ID NO: 427, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 428; SEQ ID NO: 429; and SEQ ID NO: 430 which correspond to the complementarity-determining regions (CDRs, or hypervariable regions) of the variable light chain sequence of SEQ ID NO: 426, and/or one or more of the polypeptide sequences of SEQ ID NO: 431; SEQ ID NO: 432; and SEQ ID NO: 433 which correspond to the complementarity-determining regions (CDRs, or hypervariable regions) of the variable heavy chain sequence of SEQ ID NO: 427, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 426. In another embodiment of the invention, antibody fragments of the invention comprise, or alternatively consist of, the polypeptide sequence of SEQ ID NO: 427.

In a further embodiment of the invention, fragments of the antibody having binding specificity to IL-6 comprise, or alternatively consist of, one or more of the polypeptide sequences of SEQ ID NO: 428; SEQ ID NO: 429; and SEQ ID NO: 430 which correspond to the complementarity-determining regions (CDRs, or hypervariable regions) of the variable light chain sequence of SEQ ID NO: 426.

In a further embodiment of the invention, fragments of the antibody having binding specificity to IL-6 comprise, or alternatively consist of, one or more of the polypeptide sequences of SEQ ID NO: 431; SEQ ID NO: 432; and SEQ ID NO: 433 which correspond to the complementarity-determining regions (CDRs, or hypervariable regions) of the variable heavy chain sequence of SEQ ID NO: 427.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 426; the variable heavy chain region of SEQ ID NO: 427; the complementarity-determining regions (SEQ ID NO: 428; SEQ ID NO: 429; and SEQ ID NO: 430) of the variable light chain region of SEQ ID NO: 426; and the complementarity-determining regions (SEQ ID NO: 431; SEQ ID NO: 432; and SEQ ID NO: 433) of the variable heavy chain region of SEQ ID NO: 427.

In a preferred embodiment of the invention, the anti-IL-6 antibody is Ab27, comprising SEQ ID NO: 426 and SEQ ID NO: 427, and having at least one of the biological activities set forth herein.

In another embodiment, the invention includes antibodies having binding specificity to IL-6 and possessing a variable light chain sequence comprising the sequence set forth below:

(SEQ ID NO: 442)
MDTRAPTQLLGLLLLWLPGATFAAVLTQTPSPVSEPVGGTVSISCQSSKS
VMNNNYLAWYQQKPGQPPKLLIYGASNLASGVPSRFSGSGSGTQFTLTIS
DVQCDDAATYYCQGGYTGYSDHGT

The invention also includes antibodies having binding specificity to IL-6 and possessing a variable heavy chain sequence comprising the sequence set forth below:

(SEQ ID NO: 443)
METGLRWLLLVAVLKGVQCQSVEESGGRLVKPDETLTLTCTVSGIDLSSY
PMNWVRQAPGKGLEWIGFINTGGTIVYASWAKGRFTISKTSTTVDLKMTS
PTTEDTATYFCARGSYVSSGYAYYFNV.

The invention further contemplates antibodies comprising one or more of the polypeptide sequences of SEQ ID NO: 444; SEQ ID NO: 445; and SEQ ID NO: 446 which correspond to the complementarity-determining regions (CDRs, or hypervariable regions) of the variable light chain sequence of SEQ ID NO: 442, and/or one or more of the polypeptide sequences of SEQ ID NO: 447; SEQ ID NO: 448; and SEQ ID NO: 449 which correspond to the complementarity-determining regions (CDRs, or hypervariable regions) of the variable heavy chain sequence of SEQ ID NO: 443, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 444; SEQ ID NO: 445; and SEQ ID NO: 446 which correspond to the complementarity-determining regions (CDRs, or hypervariable regions) of the variable light chain sequence of SEQ ID NO: 442, and/or one or more of the polypeptide sequences of SEQ ID NO: 447; SEQ ID NO: 448; and SEQ ID NO: 449 which correspond to the complementarity-determining regions (CDRs, or hypervariable regions) of the variable heavy chain sequence of SEQ ID NO: 443, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 442. In another embodiment of the invention, antibody fragments of the invention comprise, or alternatively consist of, the polypeptide sequence of SEQ ID NO: 443.

In a further embodiment of the invention, fragments of the antibody having binding specificity to IL-6 comprise, or alternatively consist of, one or more of the polypeptide sequences of SEQ ID NO: 444; SEQ ID NO: 445; and SEQ ID NO: 446 which correspond to the complementarity-determining regions (CDRs, or hypervariable regions) of the variable light chain sequence of SEQ ID NO: 442.

In a further embodiment of the invention, fragments of the antibody having binding specificity to IL-6 comprise, or alternatively consist of, one or more of the polypeptide sequences of SEQ ID NO: 447; SEQ ID NO: 448; and SEQ ID NO: 449 which correspond to the complementarity-determining regions (CDRs, or hypervariable regions) of the variable heavy chain sequence of SEQ ID NO: 443.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 442; the variable heavy chain region of SEQ ID NO: 443; the complementarity-determining regions (SEQ ID NO: 444; SEQ ID NO: 445; and SEQ ID NO: 446) of the variable light chain region of SEQ ID NO: 442; and the complementarity-determining regions (SEQ ID NO: 447; SEQ ID NO: 448; and SEQ ID NO: 449) of the variable heavy chain region of SEQ ID NO: 443.

In a preferred embodiment of the invention, the anti-IL-6 antibody is Ab28, comprising SEQ ID NO: 442 and SEQ ID NO: 443, and having at least one of the biological activities set forth herein.

In another embodiment, the invention includes antibodies having binding specificity to IL-6 and possessing a variable light chain sequence comprising the sequence set forth below:

(SEQ ID NO: 458)
MDTRAPTQLLGLLLLWLPGATFAAVLTQTPSPVSAAVGGTVSISCQSSQS
VYNNNWLSWFQQKPGQPPKLLIYKASTLASGVPSRFKGSGSGTQFTLTIS
DVQCDDVATYYCAGGYLDSVI

The invention also includes antibodies having binding specificity to IL-6 and possessing a variable heavy chain sequence comprising the sequence set forth below:

(SEQ ID NO: 459)
METGLRWLLLVAVLKGVQCQSVEESGGRLVTPGTPLTLTCTVSGFSLSTY
SINWVRQAPGKGLEWIGIIANSGTTFYANWAKGRFTVSKTSTTVDLKITS
PTTEDTATYFCARESGMYNEYGKFNI.

The invention further contemplates antibodies comprising one or more of the polypeptide sequences of SEQ ID NO: 460; SEQ ID NO: 461; and SEQ ID NO: 462 which correspond to the complementarity-determining regions (CDRs, or hypervariable regions) of the variable light chain sequence of SEQ ID NO: 458, and/or one or more of the polypeptide sequences of SEQ ID NO: 463; SEQ ID NO: 464; and SEQ ID NO: 465 which correspond to the complementarity-determining regions (CDRs, or hypervariable regions) of the variable heavy chain sequence of SEQ ID NO: 459, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 460; SEQ ID NO: 461; and SEQ ID NO: 462 which correspond to the complementarity-determining regions (CDRs, or hypervariable regions) of the variable light chain sequence of SEQ ID NO: 458, and/or one or more of the polypeptide sequences of SEQ ID NO: 463; SEQ ID NO: 464; and SEQ ID NO: 465 which correspond to the complementarity-determining regions (CDRs, or hypervariable regions) of the variable heavy chain sequence of SEQ ID NO: 459, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 458. In another embodiment of the invention, antibody fragments of the invention comprise, or alternatively consist of, the polypeptide sequence of SEQ ID NO: 459.

In a further embodiment of the invention, fragments of the antibody having binding specificity to IL-6 comprise, or alternatively consist of, one or more of the polypeptide sequences of SEQ ID NO: 460; SEQ ID NO: 461; and SEQ ID NO: 462 which correspond to the complementarity-determining regions (CDRs, or hypervariable regions) of the variable light chain sequence of SEQ ID NO: 458.

In a further embodiment of the invention, fragments of the antibody having binding specificity to IL-6 comprise, or alternatively consist of, one or more of the polypeptide sequences of SEQ ID NO: 463; SEQ ID NO: 464; and SEQ ID NO: 465 which correspond to the complementarity-determining regions (CDRs, or hypervariable regions) of the variable heavy chain sequence of SEQ ID NO: 459.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 458; the variable heavy chain region of SEQ ID NO: 459; the complementarity-determining regions (SEQ ID NO: 460; SEQ ID NO: 461; and SEQ ID NO: 462) of the variable light chain region of SEQ ID NO: 458; and the complementarity-determining regions (SEQ ID NO: 463; SEQ ID NO: 464; and SEQ ID NO: 465) of the variable heavy chain region of SEQ ID NO: 459.

In a preferred embodiment of the invention, the anti-IL-6 antibody is Ab29, comprising SEQ ID NO: 458 and SEQ ID NO: 459, and having at least one of the biological activities set forth herein.

In another embodiment, the invention includes antibodies having binding specificity to IL-6 and possessing a variable light chain sequence comprising the sequence set forth below:

```
                                          (SEQ ID NO: 474)
MDTRAPTQLLGLLLLWLPGARCASDMTQTPSSVSAAVGGTVTINCQASEN

IYSFLAWYQQKPGQPPKLLIFKASTLASGVSSRFKGSGSGTQFTLTISDL

ECDDAATYYCQQGATVYDIDNN
```

The invention also includes antibodies having binding specificity to IL-6 and possessing a variable heavy chain sequence comprising the sequence set forth below:

```
                                          (SEQ ID NO: 475)
METGLRWLLLVAVLKGVQCQSLEESGGRLVTPGTPLTLTCTVSGIDLSAY

AMIWVRQAPGEGLEWITIIYPNGITYYANWAKGRFTVSKTSTAMDLKITS

PTTEDTATYFCARDAESSKNAYWGYFNV.
```

The invention further contemplates antibodies comprising one or more of the polypeptide sequences of SEQ ID NO: 476; SEQ ID NO: 477; and SEQ ID NO: 478 which correspond to the complementarity-determining regions (CDRs, or hypervariable regions) of the variable light chain sequence of SEQ ID NO: 474, and/or one or more of the polypeptide sequences of SEQ ID NO: 479; SEQ ID NO: 480; and SEQ ID NO: 481 which correspond to the complementarity-determining regions (CDRs, or hypervariable regions) of the variable heavy chain sequence of SEQ ID NO: 475, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 476; SEQ ID NO: 477; and SEQ ID NO: 478 which correspond to the complementarity-determining regions (CDRs, or hypervariable regions) of the variable light chain sequence of SEQ ID NO: 474, and/or one or more of the polypeptide sequences of SEQ ID NO: 479; SEQ ID NO: 480; and SEQ ID NO: 481 which correspond to the complementarity-determining regions (CDRs, or hypervariable regions) of the variable heavy chain sequence of SEQ ID NO: 475, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 474. In another embodiment of the invention, antibody fragments of the invention comprise, or alternatively consist of, the polypeptide sequence of SEQ ID NO: 475.

In a further embodiment of the invention, fragments of the antibody having binding specificity to IL-6 comprise, or alternatively consist of, one or more of the polypeptide sequences of SEQ ID NO: 476; SEQ ID NO: 477; and SEQ ID NO: 478 which correspond to the complementarity-determining regions (CDRs, or hypervariable regions) of the variable light chain sequence of SEQ ID NO: 474.

In a further embodiment of the invention, fragments of the antibody having binding specificity to IL-6 comprise, or alternatively consist of, one or more of the polypeptide sequences of SEQ ID NO: 479; SEQ ID NO: 480; and SEQ ID NO: 481 which correspond to the complementarity-determining regions (CDRs, or hypervariable regions) of the variable heavy chain sequence of SEQ ID NO: 475.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 474; the variable heavy chain region of SEQ ID NO: 475; the complementarity-determining regions (SEQ ID NO: 476; SEQ ID NO: 477; and SEQ ID NO: 478) of the variable light chain region of SEQ ID NO: 474; and the complementarity-determining regions (SEQ ID NO: 479; SEQ ID NO: 480; and SEQ ID NO: 481) of the variable heavy chain region of SEQ ID NO: 475.

In a preferred embodiment of the invention, the anti-IL-6 antibody is Ab30, comprising SEQ ID NO: 474 and SEQ ID NO: 475, and having at least one of the biological activities set forth herein.

In another embodiment, the invention includes antibodies having binding specificity to IL-6 and possessing a variable light chain sequence comprising the sequence set forth below:

```
                                          (SEQ ID NO: 490)
MDTRAPTQLLGLLLLWLPGARCASDMTQTPSSVSAAVGGTVTINCQASEN

IYSFLAWYQQKPGQPPKLLIFRASTLASGVSSRFKGSGSGTQFTLTISDL

ECDDAATYYCQQGATVYDIDNN
```

The invention also includes antibodies having binding specificity to IL-6 and possessing a variable heavy chain sequence comprising the sequence set forth below:

```
                                          (SEQ ID NO: 491)
METGLRWLLLVAVLKGVQCQSLEESGGRLVTPGTPLTLTCTVSGIDLSAY

AMIWVRQAPGEGLEWITIIYPNGITYYANWAKGRFTVSKTSTAMDLKITS

PTTEDTATYFCARDAESSKNAYWGYFNV.
```

The invention further contemplates antibodies comprising one or more of the polypeptide sequences of SEQ ID NO: 492; SEQ ID NO: 493; and SEQ ID NO: 494 which correspond to the complementarity-determining regions (CDRs, or hypervariable regions) of the variable light chain sequence of SEQ ID NO: 490, and/or one or more of the polypeptide sequences of SEQ ID NO: 495; SEQ ID NO: 496; and SEQ ID NO: 497 which correspond to the complementarity-determining regions (CDRs, or hypervariable regions) of the variable heavy chain sequence of SEQ ID NO: 491, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 492; SEQ ID NO: 493; and SEQ ID NO: 494 which correspond to the complementarity-determining regions (CDRs, or hypervariable regions) of the variable light chain sequence of SEQ ID NO: 490, and/or one or more of the polypeptide sequences of SEQ ID NO: 495; SEQ ID NO: 496; and SEQ ID NO: 497 which correspond to the complementarity-determining regions (CDRs, or hypervariable regions) of the variable heavy chain sequence of SEQ ID NO: 491, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 490. In another embodiment of the invention, antibody fragments of the invention comprise, or alternatively consist of, the polypeptide sequence of SEQ ID NO: 491.

In a further embodiment of the invention, fragments of the antibody having binding specificity to IL-6 comprise, or alternatively consist of, one or more of the polypeptide sequences of SEQ ID NO: 492; SEQ ID NO: 493; and SEQ ID NO: 494 which correspond to the complementarity-determining regions (CDRs, or hypervariable regions) of the variable light chain sequence of SEQ ID NO: 490.

In a further embodiment of the invention, fragments of the antibody having binding specificity to IL-6 comprise, or alternatively consist of, one or more of the polypeptide sequences of SEQ ID NO: 495; SEQ ID NO: 496; and SEQ ID NO: 497 which correspond to the complementarity-determining regions (CDRs, or hypervariable regions) of the variable heavy chain sequence of SEQ ID NO: 491.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 490; the variable heavy chain region of SEQ ID NO: 491; the complementarity-determining regions (SEQ ID NO: 492; SEQ ID NO: 493; and SEQ ID NO: 494) of the variable light chain region of SEQ ID NO: 490; and the complementarity-determining regions (SEQ ID NO: 495; SEQ ID NO: 496; and SEQ ID NO: 497) of the variable heavy chain region of SEQ ID NO: 491.

In a preferred embodiment of the invention, the anti-IL-6 antibody is Ab31, comprising SEQ ID NO: 490 and SEQ ID NO: 491, and having at least one of the biological activities set forth herein.

In another embodiment, the invention includes antibodies having binding specificity to IL-6 and possessing a variable light chain sequence comprising the sequence set forth below:

```
                                          (SEQ ID NO: 506)
MDTRAPTQLLGLLLLWLPGATFAIEMTQTPSPVSAAVGGTVTINCQASES

VFNNMLSWYQQKPGHSPKLLIYDASDLASGVPSRFKGSGSGTQFTLTISG

VECDDAATYYCAGYKSDSNDGDNV
```

The invention also includes antibodies having binding specificity to IL-6 and possessing a variable heavy chain sequence comprising the sequence set forth below:

```
                                          (SEQ ID NO: 507)
METGLRWLLLVAVLKGVQCQSLEESGGRLVTPGTPLTLTCTVSGFSLNRN

SITWVRQAPGEGLEWIGIITGSGRTYYANWAKGRFTISKTSTTVDLKMTS

PTTEDTATYFCARGHPGLGSGNI.
```

The invention further contemplates antibodies comprising one or more of the polypeptide sequences of SEQ ID NO: 508; SEQ ID NO: 509; and SEQ ID NO: 510 which correspond to the complementarity-determining regions (CDRs, or hypervariable regions) of the variable light chain sequence of SEQ ID NO: 506, and/or one or more of the polypeptide sequences of SEQ ID NO: 511; SEQ ID NO: 512; and SEQ ID NO: 513 which correspond to the complementarity-determining regions (CDRs, or hypervariable regions) of the variable heavy chain sequence of SEQ ID NO: 507, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 508; SEQ ID NO: 509; and SEQ ID NO: 510 which correspond to the complementarity-determining regions (CDRs, or hypervariable regions) of the variable light chain sequence of SEQ ID NO: 506, and/or one or more of the polypeptide sequences of SEQ ID NO: 511; SEQ ID NO: 512; and SEQ ID NO: 513 which correspond to the complementarity-determining regions (CDRs, or hypervariable regions) of the variable heavy chain sequence of SEQ ID NO: 507, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 506. In another embodiment of the invention, antibody fragments of the invention comprise, or alternatively consist of, the polypeptide sequence of SEQ ID NO: 507.

In a further embodiment of the invention, fragments of the antibody having binding specificity to IL-6 comprise, or alternatively consist of, one or more of the polypeptide sequences of SEQ ID NO: 508; SEQ ID NO: 509; and SEQ ID NO: 510 which correspond to the complementarity-determining regions (CDRs, or hypervariable regions) of the variable light chain sequence of SEQ ID NO: 506.

In a further embodiment of the invention, fragments of the antibody having binding specificity to IL-6 comprise, or alternatively consist of, one or more of the polypeptide sequences of SEQ ID NO: 511; SEQ ID NO: 512; and SEQ ID NO: 513 which correspond to the complementarity-determining regions (CDRs, or hypervariable regions) of the variable heavy chain sequence of SEQ ID NO: 507.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 506; the variable heavy chain region of SEQ ID NO: 507; the complementarity-determining regions (SEQ ID NO: 508; SEQ ID NO: 509; and SEQ ID NO: 510) of the variable light chain region of SEQ ID NO: 506; and the complementarity-determining regions (SEQ ID NO: 511; SEQ ID NO: 512; and SEQ ID NO: 513) of the variable heavy chain region of SEQ ID NO: 507.

In a preferred embodiment of the invention, the anti-IL-6 antibody is Ab32, comprising SEQ ID NO: 506 and SEQ ID NO: 507, and having at least one of the biological activities set forth herein.

In another embodiment, the invention includes antibodies having binding specificity to IL-6 and possessing a variable light chain sequence comprising the sequence set forth below:

```
                                        (SEQ ID NO: 522)
MDTRAPTQLLGLLLLWLPGATFAQVLTQTASSVSAAVGGTVTINCQSS

QSVYNNYLSWYQQKPGQPPKLLIYTASSLASGVPSRFKGSGSGTQFTL

TISEVQCDDAATYYCQGYYSGPIIT
```

The invention also includes antibodies having binding specificity to IL-6 and possessing a variable heavy chain sequence comprising the sequence set forth below:

```
                                        (SEQ ID NO: 523)
METGLRWLLLVAVLKGVQCQSLEESGGRLVTPGTPLTLTCTASGFSLNNY

YIQWVRQAPGEGLEWIGIIYAGGSAYYATWANGRFTIAKTSSTTVDLKMT

SLTTEDTATYFCARGTFDGYEL.
```

The invention further contemplates antibodies comprising one or more of the polypeptide sequences of SEQ ID NO: 524; SEQ ID NO: 525; and SEQ ID NO: 526 which correspond to the complementarity-determining regions (CDRs, or hypervariable regions) of the variable light chain sequence of SEQ ID NO: 522, and/or one or more of the polypeptide sequences of SEQ ID NO: 527; SEQ ID NO: 528; and SEQ ID NO: 529 which correspond to the complementarity-determining regions (CDRs, or hypervariable regions) of the variable heavy chain sequence of SEQ ID NO: 523, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 524; SEQ ID NO: 525; and SEQ ID NO: 526 which correspond to the complementarity-determining regions (CDRs, or hypervariable regions) of the variable light chain sequence of SEQ ID NO: 522, and/or one or more of the polypeptide sequences of SEQ ID NO: 527; SEQ ID NO: 528; and SEQ ID NO: 529 which correspond to the complementarity-determining regions (CDRs, or hypervariable regions) of the variable heavy chain sequence of SEQ ID NO: 523, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 522. In another embodiment of the invention, antibody fragments of the invention comprise, or alternatively consist of, the polypeptide sequence of SEQ ID NO: 523.

In a further embodiment of the invention, fragments of the antibody having binding specificity to IL-6 comprise, or alternatively consist of, one or more of the polypeptide sequences of SEQ ID NO: 524; SEQ ID NO: 525; and SEQ ID NO: 526 which correspond to the complementarity-determining regions (CDRs, or hypervariable regions) of the variable light chain sequence of SEQ ID NO: 522.

In a further embodiment of the invention, fragments of the antibody having binding specificity to IL-6 comprise, or alternatively consist of, one or more of the polypeptide sequences of SEQ ID NO: 527; SEQ ID NO: 528; and SEQ ID NO: 529 which correspond to the complementarity-determining regions (CDRs, or hypervariable regions) of the variable heavy chain sequence of SEQ ID NO: 523.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 522; the variable heavy chain region of SEQ ID NO: 523; the complementarity-determining regions (SEQ ID NO: 524; SEQ ID NO: 525; and SEQ ID NO: 526) of the variable light chain region of SEQ ID NO: 522; and the complementarity-determining regions (SEQ ID NO: 527; SEQ ID NO: 528; and SEQ ID NO: 529) of the variable heavy chain region of SEQ ID NO: 523.

In a preferred embodiment of the invention, the anti-IL-6 antibody is Ab33, comprising SEQ ID NO: 522 and SEQ ID NO: 523, and having at least one of the biological activities set forth herein.

In another embodiment, the invention includes antibodies having binding specificity to IL-6 and possessing a variable light chain sequence comprising the sequence set forth below:

```
                                          (SEQ ID NO: 538)
MDTRAPTQLLGLLLLWLPGATFAQVLTQTPSPVSVPVGDTVTISCQSSES

VYSNNLLSWYQQKPGQPPKLLIYRASNLASGVPSRFKGSGSGTQFTLTIS

GAQCDDAATYYCQGYYSGVINS
```

The invention also includes antibodies having binding specificity to IL-6 and possessing a variable heavy chain sequence comprising the sequence set forth below:

```
                                          (SEQ ID NO: 539)
METGLRWLLLVAVLKGVQCQSVEESGGRLVTPGTPLTLTCTVSGFSLSSY

FMSWVRQAPGEGLEYIGFINPGGSAYYASWASGRLTISKTSTTVDLKITS

PTTEDTATYFCARILIVSYGAFTI.
```

The invention further contemplates antibodies comprising one or more of the polypeptide sequences of SEQ ID NO: 540; SEQ ID NO: 541; and SEQ ID NO: 542 which correspond to the complementarity-determining regions (CDRs, or hypervariable regions) of the variable light chain sequence of SEQ ID NO: 538, and/or one or more of the polypeptide sequences of SEQ ID NO: 543; SEQ ID NO: 544; and SEQ ID NO: 545 which correspond to the complementarity-determining regions (CDRs, or hypervariable regions) of the variable heavy chain sequence of SEQ ID NO: 539, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 540; SEQ ID NO: 541; and SEQ ID NO: 542 which correspond to the complementarity-determining regions (CDRs, or hypervariable regions) of the variable light chain sequence of SEQ ID NO: 538, and/or one or more of the polypeptide sequences of SEQ ID NO: 543; SEQ ID NO: 544; and SEQ ID NO: 545 which correspond to the complementarity-determining regions (CDRs, or hypervariable regions) of the variable heavy chain sequence of SEQ ID NO: 539, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 538. In another embodiment of the invention, antibody fragments of the invention comprise, or alternatively consist of, the polypeptide sequence of SEQ ID NO: 539.

In a further embodiment of the invention, fragments of the antibody having binding specificity to IL-6 comprise, or alternatively consist of, one or more of the polypeptide sequences of SEQ ID NO: 540; SEQ ID NO: 541; and SEQ ID NO: 542 which correspond to the complementarity-determining regions (CDRs, or hypervariable regions) of the variable light chain sequence of SEQ ID NO: 538.

In a further embodiment of the invention, fragments of the antibody having binding specificity to IL-6 comprise, or alternatively consist of, one or more of the polypeptide sequences of SEQ ID NO: 543; SEQ ID NO: 544; and SEQ ID NO: 545 which correspond to the complementarity-determining regions (CDRs, or hypervariable regions) of the variable heavy chain sequence of SEQ ID NO: 539.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 538; the variable heavy chain region of SEQ ID NO: 539; the complementarity-determining regions (SEQ ID NO: 540; SEQ ID NO: 541; and SEQ ID NO: 542) of the variable light chain region of SEQ ID NO: 538; and the complementarity-determining regions (SEQ ID NO: 543; SEQ ID NO: 544; and SEQ ID NO: 545) of the variable heavy chain region of SEQ ID NO: 539.

In a preferred embodiment of the invention, the anti-IL-6 antibody is Ab34, comprising SEQ ID NO: 538 and SEQ ID NO: 539, and having at least one of the biological activities set forth herein.

In another embodiment, the invention includes antibodies having binding specificity to IL-6 and possessing a variable light chain sequence comprising the sequence set forth below:

```
                                          (SEQ ID NO: 554)
MDTRAPTQLLGLLLLWLPGARCAYDMTQTPASVEVAVGGTVTIKCQATES

IGNELSWYQQKPGQAPKLLIYSASTLASGVPSRFKGSGSGTQFTLTIT

GVECDDAATYYCQQGYSSANIDNA
```

The invention also includes antibodies having binding specificity to IL-6 and possessing a variable heavy chain sequence comprising the sequence set forth below:

```
                                          (SEQ ID NO: 555)
METGLRWLLLVAVLKGVQCQSLEESGGRLVTPGTPLTLTCTVSGFSLSK

YYMSWVRQAPEKGLKYIGYIDSTTVNTYYATWARGRFTISKTSTTVDLKI

TSPTSEDTATYFCARGSTYFTDGGHRLDL.
```

The invention further contemplates antibodies comprising one or more of the polypeptide sequences of SEQ ID NO: 556; SEQ ID NO: 557; and SEQ ID NO: 558 which correspond to the complementarity-determining regions (CDRs, or hypervariable regions) of the variable light chain sequence of SEQ ID NO: 554, and/or one or more of the polypeptide sequences of SEQ ID NO: 559; SEQ ID NO: 560; and SEQ ID NO: 561 which correspond to the complementarity-determining regions (CDRs, or hypervariable regions) of the variable heavy chain sequence of SEQ ID NO: 555, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 556; SEQ ID NO: 557; and SEQ ID NO: 558 which correspond to the complementarity-determining regions (CDRs, or hypervariable regions) of the variable light chain sequence of SEQ ID NO: 554, and/or one or more of the polypeptide sequences of SEQ ID NO: 559; SEQ ID NO: 560; and SEQ ID NO: 561 which correspond to the complementarity-determining regions (CDRs, or hypervariable regions) of the variable heavy chain sequence of SEQ ID NO: 555, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 554. In another embodiment of the invention, antibody fragments of the invention comprise, or alternatively consist of, the polypeptide sequence of SEQ ID NO: 555.

In a further embodiment of the invention, fragments of the antibody having binding specificity to IL-6 comprise, or alternatively consist of, one or more of the polypeptide sequences of SEQ ID NO: 556; SEQ ID NO: 557; and SEQ ID NO: 558 which correspond to the complementarity-determining regions (CDRs, or hypervariable regions) of the variable light chain sequence of SEQ ID NO: 554.

In a further embodiment of the invention, fragments of the antibody having binding specificity to IL-6 comprise, or alternatively consist of, one or more of the polypeptide sequences of SEQ ID NO: 559; SEQ ID NO: 560; and SEQ ID NO: 561 which correspond to the complementarity-determining regions (CDRs, or hypervariable regions) of the variable heavy chain sequence of SEQ ID NO: 555.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 554; the variable heavy chain region of SEQ ID NO: 555; the complementarity-determining regions (SEQ ID NO: 556; SEQ ID NO: 557; and SEQ ID NO: 558) of the variable light chain region of SEQ ID NO: 554; and the complementarity-determining regions (SEQ ID NO: 559; SEQ ID NO: 560; and SEQ ID NO: 561) of the variable heavy chain region of SEQ ID NO: 555.

In a preferred embodiment of the invention, the anti-IL-6 antibody is Ab35, comprising SEQ ID NO: 554 and SEQ ID NO: 555, and having at least one of the biological activities set forth herein.

In another embodiment, the invention includes antibodies having binding specificity to IL-6 and possessing a variable light chain sequence comprising the sequence set forth below:

```
                                        (SEQ ID NO: 570)
MDTRAPTQLLGLLLLWLPGARCAYDMTQTPASVEVAVGGTVTIKCQATE

SIGNELSWYQQKPGQAPKLLIYSASTLASGVPSRFKGSGSGTQFTLTITG

VECDDAATYYCQQGYSSANIDNA
```

The invention also includes antibodies having binding specificity to IL-6 and possessing a variable heavy chain sequence comprising the sequence set forth below:

```
                                        (SEQ ID NO: 571)
METGLRWLLLVAVLKGVQCQSLEESGGRLVTPGTPLTLTCTVSGFSLSTY

NMGWVRQAPGKGLEWIGSITIDGRTYYASWAKGRFTVSKSSTTVDLKMTS

LTTGDTATYFCARILIVSYGAFTI.
```

The invention further contemplates antibodies comprising one or more of the polypeptide sequences of SEQ ID NO: 572; SEQ ID NO: 573; and SEQ ID NO: 574 which correspond to the complementarity-determining regions (CDRs, or hypervariable regions) of the variable light chain sequence of SEQ ID NO: 570, and/or one or more of the polypeptide sequences of SEQ ID NO: 575; SEQ ID NO: 576; and SEQ ID NO: 577 which correspond to the complementarity-determining regions (CDRs, or hypervariable regions) of the variable heavy chain sequence of SEQ ID NO: 571, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 572; SEQ ID NO: 573; and SEQ ID NO: 574 which correspond to the complementarity-determining regions (CDRs, or hypervariable regions) of the variable light chain sequence of SEQ ID NO: 570, and/or one or more of the polypeptide sequences of SEQ ID NO: 575; SEQ ID NO: 576; and SEQ ID NO: 577 which correspond to the complementarity-determining regions (CDRs, or hypervariable regions) of the variable heavy chain sequence of SEQ ID NO: 571, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 570. In another embodiment of the invention, antibody fragments of the invention comprise, or alternatively consist of, the polypeptide sequence of SEQ ID NO: 571.

In a further embodiment of the invention, fragments of the antibody having binding specificity to IL-6 comprise, or alternatively consist of, one or more of the polypeptide sequences of SEQ ID NO: 572; SEQ ID NO: 573; and SEQ ID NO: 574 which correspond to the complementarity-determining regions (CDRs, or hypervariable regions) of the variable light chain sequence of SEQ ID NO: 570.

In a further embodiment of the invention, fragments of the antibody having binding specificity to IL-6 comprise, or alternatively consist of, one or more of the polypeptide sequences of SEQ ID NO: 575; SEQ ID NO: 576; and SEQ ID NO: 577 which correspond to the complementarity-determining regions (CDRs, or hypervariable regions) of the variable heavy chain sequence of SEQ ID NO: 571.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 570; the variable heavy chain region of SEQ ID NO: 571; the complementarity-determining regions (SEQ ID NO: 572; SEQ ID NO: 573; and SEQ ID NO: 574) of the variable light chain region of SEQ ID NO: 570; and the complementarity-determining regions (SEQ ID NO: 575; SEQ ID NO: 576; and SEQ ID NO: 577) of the variable heavy chain region of SEQ ID NO: 571.

In a preferred embodiment of the invention, the anti-IL-6 antibody is Ab36, comprising SEQ ID NO: 570 and SEQ ID NO: 571, and having at least one of the biological activities set forth herein.

Sequences of anti-IL-6 antibodies of the present invention are shown in Table 1. Exemplary sequence variants other alternative forms of the heavy and light chains of Ab1 through Ab7 are shown. The antibodies of the present invention encompass additional sequence variants, including conservative substitutions, substitution of one or more CDR sequences and/or FR sequences, etc.

Exemplary Ab1 embodiments include an antibody comprising a variant of the light chain and/or heavy chain. Exemplary variants of the light chain of Ab1 include the sequence of any of the Ab1 light chains shown (i.e., any of SEQ ID NO: 2, 20, 647, 651, 660, 666, 699, 702, 706, or 709) wherein the entire CDR1 sequence is replaced or wherein one or more residues in the CDR1 sequence is substituted by the residue in the corresponding position of any of the other light chain CDR1 sequences set forth (i.e., any of SEQ ID NO: 23, 39, 55, 71, 87, 103, 124, 140, 156, 172, 188, 204, 220, 236, 252, 268, 284, 300, 316, 332, 348, 364, 380, 396, 412, 428, 444, 460, 476, 492, 508, 524, 540, 556, or 572); and/or wherein the entire CDR2 sequence is replaced or wherein one or more residues in the CDR2 sequence is substituted by the residue in the corresponding position of any of the other light chain CDR2 sequences set forth (i.e., any of SEQ ID NO: 24, 40, 56, 72, 88, 104, 125, 141, 157, 173, 189, 205, 221, 237, 253, 269, 285, 301, 317, 333, 349, 365, 381, 397, 413, 429, 445, 461, 477, 493, 509, 525, 541, 557, or 573); and/or wherein the entire CDR3 sequence is replaced or wherein one or more residues in the CDR3 sequence is substituted by the residue in the corresponding position of any of the other light chain CDR3 sequences set forth (i.e., any of SEQ ID NO: 25, 41, 57, 73, 89, 105, 126, 142, 158, 174, 190, 206, 222, 238, 254, 270, 286, 302, 318, 334, 350, 366, 382, 398, 414, 430, 446, 462, 478, 494, 510, 526, 542, 558, or 574).

Exemplary variants of the heavy chain of Ab1 include the sequence of any of the Ab1 heavy chains shown (i.e., any of SEQ ID NO: 3, 18, 19, 652, 656, 657, 658, 661, 664, 665, 704, or 708) wherein the entire CDR1 sequence is replaced or wherein one or more residues in the CDR1 sequence is substituted by the residue in the corresponding position of any of the other heavy chain CDR1 sequences set forth (i.e., any of SEQ ID NO: 26, 42, 58, 74, 90, 106, 127, 143, 159, 175, 191, 207, 223, 239, 255, 271, 287, 303, 319, 335, 351, 367, 383, 399, 415, 431, 447, 463, 479, 495, 511, 527, 543, 559, or 575); and/or wherein the entire CDR2 sequence is replaced or wherein one or more residues in the CDR2 sequence is substituted by the residue in the corresponding position of an Ab1 heavy chain CDR2, such as those set forth in Table 1 (i.e., any of SEQ ID NO: 8, or 120) or any of the other heavy chain CDR2 sequences set forth (i.e., any of SEQ ID NO: 27, 43, 59, 75, 91, 107, 121, 128, 144, 160, 176, 192, 208, 224, 240, 256, 272, 288, 304, 320, 336, 352, 368, 384, 400, 416, 432, 448, 464, 480, 496, 512, 528, 544, 560, or 576); and/or wherein the entire CDR3 sequence is replaced or wherein one or more residues in the CDR3 sequence is substituted by the residue in the corresponding position of any of the other heavy chain CDR3 sequences set forth (i.e., any of SEQ ID NO: 28, 44, 60, 76, 92, 108, 129, 145, 161, 177, 193, 209, 225, 241, 257, 273, 289, 305, 321, 337, 353, 369, 385, 401, 417, 433, 449, 465, 481, 497, 513, 529, 545, 561, or 577).

In another embodiment, the invention contemplates other antibodies, such as for example chimeric or humanized antibodies, comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or one or more of the polypeptide sequences of SEQ ID NO: 7 (CDR1); SEQ ID NO: 8 (CDR2); SEQ ID NO: 120 (CDR2); and SEQ ID NO: 9 (CDR3) which correspond to the complementarity-determining regions (CDRs, or hypervariable regions) of the variable heavy chain sequence of SEQ ID NO: 3 or SEQ ID NO: 19, or combinations of these polypeptide sequences. In another embodiment of the invention, the antibodies of the invention include combinations of the CDRs and the variable heavy and light chain sequences set forth above including those set forth in FIGS. 2 and 34-37, and those identified in Table 1.

In another embodiment the anti-IL-6 antibody of the invention is one comprising at least one of the following: a CDR1 light chain encoded by the sequence in SEQ ID NO: 12 or SEQ ID NO: 694; a light chain CDR2 encoded by the sequence in SEQ ID NO: 13; a light chain CDR3 encoded by the sequence in SEQ ID NO: 14 or SEQ ID NO: 695; a heavy chain CDR1 encoded by the sequence in SEQ ID NO: 15, a heavy chain CDR2 encoded by SEQ ID NO: 16 or SEQ ID NO: 696 and a heavy chain CDR3 encoded by SEQ ID NO: 17 or SEQ ID NO: 697. In addition the invention embraces such nucleic acid sequences and variants thereof.

In another embodiment the invention is directed to amino acid sequences corresponding to the CDRs of said anti-IL-6 antibody which are selected from SEQ ID NO: 4 (CDR1), SEQ ID NO: 5 (CDR2), SEQ ID NO: 6 (CDR3), SEQ ID NO: 7, SEQ ID NO: 120 and SEQ ID NO: 9.

In another embodiment the anti-IL-6 antibody of the invention comprises a light chain nucleic acid sequence of SEQ ID NO: 10, 662, 698, 701, 705, 720, 721, 722, or 723; and/or a heavy chain nucleic acid sequence of SEQ ID NO: 11, 663, 700, 703, 707, 724, or 725. In addition the invention is directed to the corresponding polypeptides encoded by any of the foregoing nucleic acid sequences and combinations thereof.

In a specific embodiment of the invention the anti-IL-6 antibodies or a portion thereof will be encoded by a nucleic acid sequence selected from those comprised in SEQ ID NO: 10, 12, 13, 14, 662, 694, 695, 698, 701, 705, 720, 721, 722, 723, 11, 15, 16, 17, 663, 696, 697, 700, 703, 707, 724, and 725. For example the CDR1 in the light chain may be encoded by SEQ ID NO: 12 or 694, the CDR2 in the light chain may be encoded by SEQ ID NO: 13, the CDR3 in the light chain may be encoded by SEQ ID NO: 14 or 695; the CDR1 in the heavy chain may be encoded by SEQ ID NO: 15, the CDR2 in the heavy chain may be encoded by SEQ ID NO: 16 or 696, the CDR3 in the heavy chain may be encoded by SEQ ID NO: 17 or 697. As discussed infra antibodies containing these CDRs may be constructed using appropriate human frameworks based on the humanization methods disclosed herein.

In another specific embodiment of the invention the variable light chain will be encoded by SEQ ID NO: 10, 662, 698, 701, 705, 720, 721, 722, or 723 and the variable heavy chain of the anti-IL-6 antibodies will be encoded by SEQ ID NO: 11, 663, 700, 703, 707, 724, or 725.

In a more specific embodiment variable light and heavy chains of the anti-IL-6 antibody respectively will be encoded by SEQ ID NO: 10 and 11, or SEQ ID NO: 698 and SEQ ID NO: 700, or SEQ ID NO: 701 and SEQ ID NO: 703 or SEQ ID NO: 705 and SEQ ID NO: 707.

In another specific embodiment the invention covers nucleic acid constructs containing any of the foregoing nucleic acid sequences and combinations thereof as well as recombinant cells containing these nucleic acid sequences and constructs containing wherein these nucleic acid sequences or constructs may be extrachromosomal or integrated into the host cell genome In another specific embodiment the invention covers polypeptides containing any of the CDRs or combinations thereof recited in SEQ ID NO: 4, SEQ ID NO: 5, SEQ ID NO: 6, SEQ ID NO: 7, SEQ ID NO: 8, SEQ ID NO: 120, SEQ ID NO: 9 or polypeptides comprising any of the variable light polypeptides comprised in SEQ ID NO: 2, 20, 647, 651, 660, 666, 699, 702, 706, or 709 and/or the variable heavy polypeptides comprised in SEQ ID NO: 3, 18, 19, 652, 656, 657, 658, 661, 664, 665, 704, or 708. These polypeptides optionally may be attached directly or indirectly to other immunoglobulin polypeptides or effector moieties such as therapeutic or detectable entities.

In another embodiment the anti-IL-6 antibody is one comprising at least one of the following: a variable light chain encoded by the sequence in SEQ ID NO: 10 or SEQ ID NO: 698 or SEQ ID NO: 701 or SEQ ID NO: 705 and a variable chain encoded by the sequence in SEQ ID NO: 11 or SEQ ID NO: 700 or SEQ ID NO: 703 or SEQ ID NO: 707.

In another embodiment the anti-IL-6 antibody is a variant of the foregoing sequences that includes one or more substitution in the framework and/or CDR sequences and which has one or more of the properties of Ab1 in vitro and/or upon in vivo administration.

These in vitro and in vivo properties are described in more detail in the examples below and include: competing with Ab1 for binding to IL-6 and/or peptides thereof; having a binding affinity (Kd) for IL-6 of less than about 50 picomolar, and/or a rate of dissociation ($K_{off}$) from IL-6 of less than or equal to $10^{-4}$ $S^{-1}$; having an in-vivo half-life of at least about 22 days in a healthy human subject; ability to prevent or treat hypoalbunemia; ability to prevent or treat elevated CRP; ability to prevent or treat abnormal coagulation; and/or ability to decrease the risk of thrombosis in an individual having a disease or condition associated with increased risk of thrombosis. Additional non-limiting examples of anti-IL-6 activity are set forth herein, for example, under the heading "Anti-IL-6 Activity."

In another embodiment the anti-IL-6 antibody includes one or more of the Ab1 light-chain and/or heavy chain CDR sequences (see Table 1) or variant(s) thereof which has one or more of the properties of Ab1 in vitro and/or upon in vivo administration (examples of such properties are discussed in the preceding paragraph). One of skill in the art would understand how to combine these CDR sequences to form an antigen-binding surface, e.g. by linkage to one or more scaffold which may comprise human or other mammalian framework sequences, or their functional orthologs derived from a SMIP, camelbody, nanobody, IgNAR or other immunoglobulin or other engineered antibody. For example, embodiments may specifically bind to human IL-6 and include one, two, three, four, five, six, or more of the following CDR sequences or variants thereof:

a polypeptide having at least 72.7% (i.e., 8 out of 11 amino acids) identity to the light chain CDR1 of SEQ ID NO: 4;

a polypeptide having at least 81.8% (i.e., 9 out of 11 amino acids) identity to the light chain CDR1 of SEQ ID NO: 4;

a polypeptide having at least 90.9% (i.e., 10 out of 11 amino acids) identity to the light chain CDR1 of SEQ ID NO: 4;

a polypeptide having 100% (i.e., 11 out of 11 amino acids) identity to the light chain CDR1 of SEQ ID NO: 4;

a polypeptide having at least 85.7% (i.e., 6 out of 7 amino acids) identity to the light chain CDR2 of SEQ ID NO: 5;

a polypeptide having 100% (i.e., 7 out of 7 amino acids) identity to the light chain CDR2 of SEQ ID NO: 5;

a polypeptide having at least 50% (i.e., 6 out of 12 amino acids) identity to the light chain CDR3 of SEQ ID NO: 6;

a polypeptide having at least 58.3% (i.e., 7 out of 12 amino acids) identity to the light chain CDR3 of SEQ ID NO: 6;

a polypeptide having at least 66.6% (i.e., 8 out of 12 amino acids) identity to the light chain CDR3 of SEQ ID NO: 6;

a polypeptide having at least 75% (i.e., 9 out of 12 amino acids) identity to the light chain CDR3 of SEQ ID NO: 6;

a polypeptide having at least 83.3% (i.e., 10 out of 12 amino acids) identity to the light chain CDR3 of SEQ ID NO: 6;

a polypeptide having at least 91.6% (i.e., 11 out of 12 amino acids) identity to the light chain CDR3 of SEQ ID NO: 6;

a polypeptide having 100% (i.e., 12 out of 12 amino acids) identity to the light chain CDR3 of SEQ ID NO: 6;

a polypeptide having at least 80% (i.e., 4 out of 5 amino acids) identity to the heavy chain CDR1 of SEQ ID NO: 7;

a polypeptide having 100% (i.e., 5 out of 5 amino acids) identity to the heavy chain CDR1 of SEQ ID NO: 7;

a polypeptide having at least 50% (i.e., 8 out of 16 amino acids) identity to the heavy chain CDR2 of SEQ ID NO: 120;

a polypeptide having at least 56.2% (i.e., 9 out of 16 amino acids) identity to the heavy chain CDR2 of SEQ ID NO: 120;

a polypeptide having at least 62.5% (i.e., 10 out of 16 amino acids) identity to the heavy chain CDR2 of SEQ ID NO: 120;

a polypeptide having at least 68.7% (i.e., 11 out of 16 amino acids) identity to the heavy chain CDR2 of SEQ ID NO: 120;

a polypeptide having at least 75% (i.e., 12 out of 16 amino acids) identity to the heavy chain CDR2 of SEQ ID NO: 120;

a polypeptide having at least 81.2% (i.e., 13 out of 16 amino acids) identity to the heavy chain CDR2 of SEQ ID NO: 120;

a polypeptide having at least 87.5% (i.e., 14 out of 16 amino acids) identity to the heavy chain CDR2 of SEQ ID NO: 120;

a polypeptide having at least 93.7% (i.e., 15 out of 16 amino acids) identity to the heavy chain CDR2 of SEQ ID NO: 120;

a polypeptide having 100% (i.e., 16 out of 16 amino acids) identity to the heavy chain CDR2 of SEQ ID NO: 120;

a polypeptide having at least 33.3% (i.e., 4 out of 12 amino acids) identity to the heavy chain CDR3 of SEQ ID NO: 9;

a polypeptide having at least 41.6% (i.e., 5 out of 12 amino acids) identity to the heavy chain CDR3 of SEQ ID NO: 9;

a polypeptide having at least 50% (i.e., 6 out of 12 amino acids) identity to the heavy chain CDR3 of SEQ ID NO: 9;

a polypeptide having at least 58.3% (i.e., 7 out of 12 amino acids) identity to the heavy chain CDR3 of SEQ ID NO: 9;

a polypeptide having at least 66.6% (i.e., 8 out of 12 amino acids) identity to the heavy chain CDR3 of SEQ ID NO: 9;

a polypeptide having at least 75% (i.e., 9 out of 12 amino acids) identity to the heavy chain CDR3 of SEQ ID NO: 9;

a polypeptide having at least 83.3% (i.e., 10 out of 12 amino acids) identity to the heavy chain CDR3 of SEQ ID NO: 9;

a polypeptide having at least 91.6% (i.e., 11 out of 12 amino acids) identity to the heavy chain CDR3 of SEQ ID NO: 9;

a polypeptide having 100% (i.e., 12 out of 12 amino acids) identity to the heavy chain CDR3 of SEQ ID NO: 9;

a polypeptide having at least 90.9% (i.e., 10 out of 11 amino acids) similarity to the light chain CDR1 of SEQ ID NO: 4;

a polypeptide having 100% (i.e., 11 out of 11 amino acids) similarity to the light chain CDR1 of SEQ ID NO: 4;

a polypeptide having at least 85.7% (i.e., 6 out of 7 amino acids) similarity to the light chain CDR2 of SEQ ID NO: 5;

a polypeptide having 100% (i.e., 7 out of 7 amino acids) similarity to the light chain CDR2 of SEQ ID NO: 5;

a polypeptide having at least 66.6% (i.e., 8 out of 12 amino acids) similarity to the light chain CDR3 of SEQ ID NO: 6;

a polypeptide having at least 75% (i.e., 9 out of 12 amino acids) similarity to the light chain CDR3 of SEQ ID NO: 6;

a polypeptide having at least 83.3% (i.e., 10 out of 12 amino acids) similarity to the light chain CDR3 of SEQ ID NO: 6;

a polypeptide having at least 91.6% (i.e., 11 out of 12 amino acids) similarity to the light chain CDR3 of SEQ ID NO: 6;

a polypeptide having 100% (i.e., 12 out of 12 amino acids) similarity to the light chain CDR3 of SEQ ID NO: 6;

a polypeptide having at least 80% (i.e., 4 out of 5 amino acids) similarity to the heavy chain CDR1 of SEQ ID NO: 7;

a polypeptide having 100% (i.e., 5 out of 5 amino acids) similarity to the heavy chain CDR1 of SEQ ID NO: 7;

a polypeptide having at least 56.2% (i.e., 9 out of 16 amino acids) similarity to the heavy chain CDR2 of SEQ ID NO: 120;

a polypeptide having at least 62.5% (i.e., 10 out of 16 amino acids) similarity to the heavy chain CDR2 of SEQ ID NO: 120;

a polypeptide having at least 68.7% (i.e., 11 out of 16 amino acids) similarity to the heavy chain CDR2 of SEQ ID NO: 120;

a polypeptide having at least 75% (i.e., 12 out of 16 amino acids) similarity to the heavy chain CDR2 of SEQ ID NO: 120;

a polypeptide having at least 81.2% (i.e., 13 out of 16 amino acids) similarity to the heavy chain CDR2 of SEQ ID NO: 120;

a polypeptide having at least 87.5% (i.e., 14 out of 16 amino acids) similarity to the heavy chain CDR2 of SEQ ID NO: 120;

a polypeptide having at least 93.7% (i.e., 15 out of 16 amino acids) similarity to the heavy chain CDR2 of SEQ ID NO: 120;

a polypeptide having 100% (i.e., 16 out of 16 amino acids) similarity to the heavy chain CDR2 of SEQ ID NO: 120;

a polypeptide having at least 50% (i.e., 6 out of 12 amino acids) similarity to the heavy chain CDR3 of SEQ ID NO: 9;

a polypeptide having at least 58.3% (i.e., 7 out of 12 amino acids) similarity to the heavy chain CDR3 of SEQ ID NO: 9;

a polypeptide having at least 66.6% (i.e., 8 out of 12 amino acids) similarity to the heavy chain CDR3 of SEQ ID NO: 9;

a polypeptide having at least 75% (i.e., 9 out of 12 amino acids) similarity to the heavy chain CDR3 of SEQ ID NO: 9;

a polypeptide having at least 83.3% (i.e., 10 out of 12 amino acids) similarity to the heavy chain CDR3 of SEQ ID NO: 9;

a polypeptide having at least 91.6% (i.e., 11 out of 12 amino acids) similarity to the heavy chain CDR3 of SEQ ID NO: 9;

a polypeptide having 100% (i.e., 12 out of 12 amino acids) similarity to the heavy chain CDR3 of SEQ ID NO: 9.

Other exemplary embodiments include one or more polynucleotides encoding any of the foregoing, e.g., a polynucleotide encoding a polypeptide that specifically binds to human IL-6 and includes one, two, three, four, five, six, or more of the following CDRs or variants thereof:

a polynucleotide encoding a polypeptide having at least 72.7% (i.e., 8 out of 11 amino acids) identity to the light chain CDR1 of SEQ ID NO: 4;

a polynucleotide encoding a polypeptide having at least 81.8% (i.e., 9 out of 11 amino acids) identity to the light chain CDR1 of SEQ ID NO: 4;

a polynucleotide encoding a polypeptide having at least 90.9% (i.e., 10 out of 11 amino acids) identity to the light chain CDR1 of SEQ ID NO: 4;

a polynucleotide encoding a polypeptide having 100% (i.e., 11 out of 11 amino acids) identity to the light chain CDR1 of SEQ ID NO: 4;

a polynucleotide encoding a polypeptide having at least 85.7% (i.e., 6 out of 7 amino acids) identity to the light chain CDR2 of SEQ ID NO: 5;

a polynucleotide encoding a polypeptide having 100% (i.e., 7 out of 7 amino acids) identity to the light chain CDR2 of SEQ ID NO: 5;

a polynucleotide encoding a polypeptide having at least 50% (i.e., 6 out of 12 amino acids) identity to the light chain CDR3 of SEQ ID NO: 6;

a polynucleotide encoding a polypeptide having at least 58.3% (i.e., 7 out of 12 amino acids) identity to the light chain CDR3 of SEQ ID NO: 6;

a polynucleotide encoding a polypeptide having at least 66.6% (i.e., 8 out of 12 amino acids) identity to the light chain CDR3 of SEQ ID NO: 6;

a polynucleotide encoding a polypeptide having at least 75% (i.e., 9 out of 12 amino acids) identity to the light chain CDR3 of SEQ ID NO: 6;

a polynucleotide encoding a polypeptide having at least 83.3% (i.e., 10 out of 12 amino acids) identity to the light chain CDR3 of SEQ ID NO: 6;

a polynucleotide encoding a polypeptide having at least 91.6% (i.e., 11 out of 12 amino acids) identity to the light chain CDR3 of SEQ ID NO: 6;

a polynucleotide encoding a polypeptide having 100% (i.e., 12 out of 12 amino acids) identity to the light chain CDR3 of SEQ ID NO: 6;

a polynucleotide encoding a polypeptide having at least 80% (i.e., 4 out of 5 amino acids) identity to the heavy chain CDR1 of SEQ ID NO: 7;

a polynucleotide encoding a polypeptide having 100% (i.e., 5 out of 5 amino acids) identity to the heavy chain CDR1 of SEQ ID NO: 7;

a polynucleotide encoding a polypeptide having at least 50% (i.e., 8 out of 16 amino acids) identity to the heavy chain CDR2 of SEQ ID NO: 120;

a polynucleotide encoding a polypeptide having at least 56.2% (i.e., 9 out of 16 amino acids) identity to the heavy chain CDR2 of SEQ ID NO: 120;

a polynucleotide encoding a polypeptide having at least 62.5% (i.e., 10 out of 16 amino acids) identity to the heavy chain CDR2 of SEQ ID NO: 120;

a polynucleotide encoding a polypeptide having at least 68.7% (i.e., 11 out of 16 amino acids) identity to the heavy chain CDR2 of SEQ ID NO: 120;

a polynucleotide encoding a polypeptide having at least 75% (i.e., 12 out of 16 amino acids) identity to the heavy chain CDR2 of SEQ ID NO: 120;

a polynucleotide encoding a polypeptide having at least 81.2% (i.e., 13 out of 16 amino acids) identity to the heavy chain CDR2 of SEQ ID NO: 120;

a polynucleotide encoding a polypeptide having at least 87.5% (i.e., 14 out of 16 amino acids) identity to the heavy chain CDR2 of SEQ ID NO: 120;

a polynucleotide encoding a polypeptide having at least 93.7% (i.e., 15 out of 16 amino acids) identity to the heavy chain CDR2 of SEQ ID NO: 120;

a polynucleotide encoding a polypeptide having 100% (i.e., 16 out of 16 amino acids) identity to the heavy chain CDR2 of SEQ ID NO: 120;

a polynucleotide encoding a polypeptide having at least 33.3% (i.e., 4 out of 12 amino acids) identity to the heavy chain CDR3 of SEQ ID NO: 9;

a polynucleotide encoding a polypeptide having at least 41.6% (i.e., 5 out of 12 amino acids) identity to the heavy chain CDR3 of SEQ ID NO: 9;

a polynucleotide encoding a polypeptide having at least 50% (i.e., 6 out of 12 amino acids) identity to the heavy chain CDR3 of SEQ ID NO: 9;

a polynucleotide encoding a polypeptide having at least 58.3% (i.e., 7 out of 12 amino acids) identity to the heavy chain CDR3 of SEQ ID NO: 9;

a polynucleotide encoding a polypeptide having at least 66.6% (i.e., 8 out of 12 amino acids) identity to the heavy chain CDR3 of SEQ ID NO: 9;

a polynucleotide encoding a polypeptide having at least 75% (i.e., 9 out of 12 amino acids) identity to the heavy chain CDR3 of SEQ ID NO: 9;

a polynucleotide encoding a polypeptide having at least 83.3% (i.e., 10 out of 12 amino acids) identity to the heavy chain CDR3 of SEQ ID NO: 9;

a polynucleotide encoding a polypeptide having at least 91.6% (i.e., 11 out of 12 amino acids) identity to the heavy chain CDR3 of SEQ ID NO: 9;

a polynucleotide encoding a polypeptide having 100% (i.e., 12 out of 12 amino acids) identity to the heavy chain CDR3 of SEQ ID NO: 9;

a polynucleotide encoding a polypeptide having at least 90.9% (i.e., 10 out of 11 amino acids) similarity to the light chain CDR1 of SEQ ID NO: 4;

a polynucleotide encoding a polypeptide having 100% (i.e., 11 out of 11 amino acids) similarity to the light chain CDR1 of SEQ ID NO: 4;

a polynucleotide encoding a polypeptide having at least 85.7% (i.e., 6 out of 7 amino acids) similarity to the light chain CDR2 of SEQ ID NO: 5;

a polynucleotide encoding a polypeptide having 100% (i.e., 7 out of 7 amino acids) similarity to the light chain CDR2 of SEQ ID NO: 5;

a polynucleotide encoding a polypeptide having at least 66.6% (i.e., 8 out of 12 amino acids) similarity to the light chain CDR3 of SEQ ID NO: 6;

a polynucleotide encoding a polypeptide having at least 75% (i.e., 9 out of 12 amino acids) similarity to the light chain CDR3 of SEQ ID NO: 6;

a polynucleotide encoding a polypeptide having at least 83.3% (i.e., 10 out of 12 amino acids) similarity to the light chain CDR3 of SEQ ID NO: 6;

a polynucleotide encoding a polypeptide having at least 91.6% (i.e., 11 out of 12 amino acids) similarity to the light chain CDR3 of SEQ ID NO: 6;

a polynucleotide encoding a polypeptide having 100% (i.e., 12 out of 12 amino acids) similarity to the light chain CDR3 of SEQ ID NO: 6;

a polynucleotide encoding a polypeptide having at least 80% (i.e., 4 out of 5 amino acids) similarity to the heavy chain CDR1 of SEQ ID NO: 7;

a polynucleotide encoding a polypeptide having 100% (i.e., 5 out of 5 amino acids) similarity to the heavy chain CDR1 of SEQ ID NO: 7;

a polynucleotide encoding a polypeptide having at least 56.2% (i.e., 9 out of 16 amino acids) similarity to the heavy chain CDR2 of SEQ ID NO: 120;

a polynucleotide encoding a polypeptide having at least 62.5% (i.e., 10 out of 16 amino acids) similarity to the heavy chain CDR2 of SEQ ID NO: 120;

a polynucleotide encoding a polypeptide having at least 68.7% (i.e., 11 out of 16 amino acids) similarity to the heavy chain CDR2 of SEQ ID NO: 120;

a polynucleotide encoding a polypeptide having at least 75% (i.e., 12 out of 16 amino acids) similarity to the heavy chain CDR2 of SEQ ID NO: 120;

a polynucleotide encoding a polypeptide having at least 81.2% (i.e., 13 out of 16 amino acids) similarity to the heavy chain CDR2 of SEQ ID NO: 120;

a polynucleotide encoding a polypeptide having at least 87.5% (i.e., 14 out of 16 amino acids) similarity to the heavy chain CDR2 of SEQ ID NO: 120;

a polynucleotide encoding a polypeptide having at least 93.7% (i.e., 15 out of 16 amino acids) similarity to the heavy chain CDR2 of SEQ ID NO: 120;

a polynucleotide encoding a polypeptide having 100% (i.e., 16 out of 16 amino acids) similarity to the heavy chain CDR2 of SEQ ID NO: 120;

a polynucleotide encoding a polypeptide having at least 50% (i.e., 6 out of 12 amino acids) similarity to the heavy chain CDR3 of SEQ ID NO: 9;

a polynucleotide encoding a polypeptide having at least 58.3% (i.e., 7 out of 12 amino acids) similarity to the heavy chain CDR3 of SEQ ID NO: 9;

a polynucleotide encoding a polypeptide having at least 66.6% (i.e., 8 out of 12 amino acids) similarity to the heavy chain CDR3 of SEQ ID NO: 9;

a polynucleotide encoding a polypeptide having at least 75% (i.e., 9 out of 12 amino acids) similarity to the heavy chain CDR3 of SEQ ID NO: 9;

a polynucleotide encoding a polypeptide having at least 83.3% (i.e., 10 out of 12 amino acids) similarity to the heavy chain CDR3 of SEQ ID NO: 9;

a polynucleotide encoding a polypeptide having at least 91.6% (i.e., 11 out of 12 amino acids) similarity to the heavy chain CDR3 of SEQ ID NO: 9;

a polynucleotide encoding a polypeptide having 100% (i.e., 12 out of 12 amino acids) similarity to the heavy chain CDR3 of SEQ ID NO: 9.

TABLE 1

Sequences of exemplary anti-IL-6 antibodies.

| Antibody | Antibody chains PRT. | Antibody chains Nuc. | CDR1 PRT. | CDR1 Nuc. | CDR2 PRT. | CDR2 Nuc. | CDR3 PRT. | CDR3 Nuc. |
|---|---|---|---|---|---|---|---|---|
| Ab1 light chains* | 2 | 10 | 4 | 12 | 5 | 13 | 6 | 14 |
| | 20 | 720 | 4 | 12 | 5 | 13 | 6 | 14 |
| | 647 | 721 | 4 | 12 | 5 | 13 | 6 | 14 |
| | 651 | | 4 | 12 | 5 | 13 | 6 | 14 |
| | 660 | 662 | 4 | 12 | 5 | 13 | 6 | 14 |
| | 666 | 722 | 4 | 12 | 5 | 13 | 6 | 14 |
| | 699 | 698 | 4 | 694 | 5 | 13 | 6 | 695 |
| | 702 | 701 | 4 | 694 | 5 | 13 | 6 | 695 |
| | 706 | 705 | 4 | 694 | 5 | 13 | 6 | 695 |
| | 709 | 723 | 4 | 12 | 5 | 13 | 6 | 14 |
| Human light chains | 648 | | 710 | | 713 | | | |
| used in Ab1 | 649 | | 711 | | 714 | | | |
| humanization | 650 | | 712 | | 715 | | | |
| Ab1 heavy chains | 3 | 11 | 7 | 15 | 8 | 16 | 9 | 17 |
| | 18 | | 7 | 15 | 8 | 16 | 9 | 17 |
| | 19 | 724 | 7 | 15 | 120 | 696 | 9 | 17 |
| | 652 | 725 | 7 | 15 | 8 | 16 | 9 | 17 |
| | 656 | | 7 | 15 | 8 | 16 | 9 | 17 |
| | 657 | 700 | 7 | 15 | 659 | 696 | 9 | 697 |
| | 658 | | 7 | 15 | 120 | 696 | 9 | 17 |
| | 661 | 663 | 7 | 15 | 8 | 16 | 9 | 17 |
| | 664 | | 7 | 15 | 8 | 16 | 9 | 17 |
| | 665 | | 7 | 15 | 120 | 696 | 9 | 17 |
| | 704 | 703 | 7 | 15 | 120 | 696 | 9 | 697 |
| | 708 | 707 | 7 | 15 | 120 | 696 | 9 | 697 |
| Human heavy chains | 653 | | 716 | | 717 | | | |
| used in Ab1 | 654 | | 716 | | 717 | | | |
| humanization | 655 | | 74 | 82 | 718 | | | |
| Ab2 light chains | 21 | 29 | 23 | 31 | 24 | 32 | 25 | 33 |
| | 667 | 669 | 23 | 31 | 24 | 32 | 25 | 33 |
| Ab2 heavy chains | 22 | 30 | 26 | 34 | 27 | 35 | 28 | 36 |
| | 668 | 670 | 26 | 34 | 27 | 35 | 28 | 36 |
| Ab3 light chains | 37 | 45 | 39 | 47 | 40 | 48 | 41 | 49 |
| | 671 | 673 | 39 | 47 | 40 | 48 | 41 | 49 |
| Ab3 heavy chains | 38 | 46 | 42 | 50 | 43 | 51 | 44 | 52 |
| | 672 | 674 | 42 | 50 | 43 | 51 | 44 | 52 |
| Ab4 light chains | 53 | 61 | 55 | 63 | 56 | 64 | 57 | 65 |
| | 675 | 677 | 55 | 63 | 56 | 64 | 57 | 65 |
| Ab4 heavy chains | 54 | 62 | 58 | 66 | 59 | 67 | 60 | 68 |
| | 676 | 678 | 58 | 66 | 59 | 67 | 60 | 68 |
| Ab5 light chains | 69 | 77 | 71 | 79 | 72 | 80 | 73 | 81 |
| | 679 | 681 | 71 | 79 | 72 | 80 | 73 | 81 |
| Ab5 heavy chains | 70 | 78 | 74 | 82 | 75 | 83 | 76 | 84 |
| | 680 | 682 | 74 | 82 | 75 | 83 | 76 | 84 |
| Ab6 light chains | 85 | 93 | 87 | 95 | 88 | 96 | 89 | 97 |
| | 683 | 685 | 87 | 95 | 88 | 96 | 89 | 97 |
| Ab6 heavy chains | 86 | 94 | 90 | 98 | 91 | 99 | 92 | 100 |
| | 684 | 686 | 90 | 98 | 91 | 99 | 92 | 100 |
| Ab7 light chains | 101 | 109 | 103 | 111 | 104 | 112 | 105 | 113 |
| | 119 | | 103 | 111 | 104 | 112 | 105 | 113 |
| | 687 | 689 | 103 | 111 | 104 | 112 | 105 | 113 |
| | 693 | | 103 | 111 | 104 | 112 | 105 | 113 |
| Ab7 heavy chains | 102 | 110 | 106 | 114 | 107 | 115 | 108 | 116 |
| | 117 | | 106 | 114 | 107 | 115 | 108 | 116 |
| | 118 | | 106 | 114 | 121 | | 108 | 116 |
| | 688 | 690 | 106 | 114 | 107 | 115 | 108 | 116 |
| | 691 | | 106 | 114 | 107 | 115 | 108 | 116 |
| | 692 | | 106 | 114 | 121 | | 108 | 116 |
| Ab8 light chain | 122 | 130 | 124 | 132 | 125 | 133 | 126 | 134 |
| Ab8 heavy chain | 123 | 131 | 127 | 135 | 128 | 136 | 129 | 137 |
| Ab9 light chain | 138 | 146 | 140 | 148 | 141 | 149 | 142 | 150 |
| Ab9 heavy chain | 139 | 147 | 143 | 151 | 144 | 152 | 145 | 153 |
| Ab10 light chain | 154 | 162 | 156 | 164 | 157 | 165 | 158 | 166 |
| Ab10 heavy chain | 155 | 163 | 159 | 167 | 160 | 168 | 161 | 169 |
| Ab11 light chain | 170 | 178 | 172 | 180 | 173 | 181 | 174 | 182 |
| Ab11 heavy chain | 171 | 179 | 175 | 183 | 176 | 184 | 177 | 185 |
| Ab12 light chain | 186 | 194 | 188 | 196 | 189 | 197 | 190 | 198 |
| Ab12 heavy chain | 187 | 195 | 191 | 199 | 192 | 200 | 193 | 201 |
| Ab13 light chain | 202 | 210 | 204 | 212 | 205 | 213 | 206 | 214 |
| Ab13 heavy chain | 203 | 211 | 207 | 215 | 208 | 216 | 209 | 217 |
| Ab14 light chain | 218 | 226 | 220 | 228 | 221 | 229 | 222 | 230 |
| Ab14 heavy chain | 219 | 227 | 223 | 231 | 224 | 232 | 225 | 233 |
| Ab15 light chain | 234 | 242 | 236 | 244 | 237 | 245 | 238 | 246 |

TABLE 1-continued

Sequences of exemplary anti-IL-6 antibodies.

| Antibody | Antibody chains PRT. | Antibody chains Nuc. | CDR1 PRT. | CDR1 Nuc. | CDR2 PRT. | CDR2 Nuc. | CDR3 PRT. | CDR3 Nuc. |
|---|---|---|---|---|---|---|---|---|
| Ab15 heavy chain | 235 | 243 | 239 | 247 | 240 | 248 | 241 | 249 |
| Ab16 light chain | 250 | 258 | 252 | 260 | 253 | 261 | 254 | 262 |
| Ab16 heavy chain | 251 | 259 | 255 | 263 | 256 | 264 | 257 | 265 |
| Ab17 light chain | 266 | 274 | 268 | 276 | 269 | 277 | 270 | 278 |
| Ab17 heavy chain | 267 | 275 | 271 | 279 | 272 | 280 | 273 | 281 |
| Ab18 light chain | 282 | 290 | 284 | 292 | 285 | 293 | 286 | 294 |
| Ab18 heavy chain | 283 | 291 | 287 | 295 | 288 | 296 | 289 | 297 |
| Ab19 light chain | 298 | 306 | 300 | 308 | 301 | 309 | 302 | 310 |
| Ab19 heavy chain | 299 | 307 | 303 | 311 | 304 | 312 | 305 | 313 |
| Ab20 light chain | 314 | 322 | 316 | 324 | 317 | 325 | 318 | 326 |
| Ab20 heavy chain | 315 | 323 | 319 | 327 | 320 | 328 | 321 | 329 |
| Ab21 light chain | 330 | 338 | 332 | 340 | 333 | 341 | 334 | 342 |
| Ab21 heavy chain | 331 | 339 | 335 | 343 | 336 | 344 | 337 | 345 |
| Ab22 light chain | 346 | 354 | 348 | 356 | 349 | 357 | 350 | 358 |
| Ab22 heavy chain | 347 | 355 | 351 | 359 | 352 | 360 | 353 | 361 |
| Ab23 light chain | 362 | 370 | 364 | 372 | 365 | 373 | 366 | 374 |
| Ab23 heavy chain | 363 | 371 | 367 | 375 | 368 | 376 | 369 | 377 |
| Ab24 light chain | 378 | 386 | 380 | 388 | 381 | 389 | 382 | 390 |
| Ab24 heavy chain | 379 | 387 | 383 | 391 | 384 | 392 | 385 | 393 |
| Ab25 light chain | 394 | 402 | 396 | 404 | 397 | 405 | 398 | 406 |
| Ab25 heavy chain | 395 | 403 | 399 | 407 | 400 | 408 | 401 | 409 |
| Ab26 light chain | 410 | 418 | 412 | 420 | 413 | 421 | 414 | 422 |
| Ab26 heavy chain | 411 | 419 | 415 | 423 | 416 | 424 | 417 | 425 |
| Ab27 light chain | 426 | 434 | 428 | 436 | 429 | 437 | 430 | 438 |
| Ab27 heavy chain | 427 | 435 | 431 | 439 | 432 | 440 | 433 | 441 |
| Ab28 light chain | 442 | 450 | 444 | 452 | 445 | 453 | 446 | 454 |
| Ab28 heavy chain | 443 | 451 | 447 | 455 | 448 | 456 | 449 | 457 |
| Ab29 light chain | 458 | 466 | 460 | 468 | 461 | 469 | 462 | 470 |
| Ab29 heavy chain | 459 | 467 | 463 | 471 | 464 | 472 | 465 | 473 |
| Ab30 light chain | 474 | 482 | 476 | 484 | 477 | 485 | 478 | 486 |
| Ab30 heavy chain | 475 | 483 | 479 | 487 | 480 | 488 | 481 | 489 |
| Ab31 light chain | 490 | 498 | 492 | 500 | 493 | 501 | 494 | 502 |
| Ab31 heavy chain | 491 | 499 | 495 | 503 | 496 | 504 | 497 | 505 |
| Ab32 light chain | 506 | 514 | 508 | 516 | 509 | 517 | 510 | 518 |
| Ab32 heavy chain | 507 | 515 | 511 | 519 | 512 | 520 | 513 | 521 |
| Ab33 light chain | 522 | 530 | 524 | 532 | 525 | 533 | 526 | 534 |
| Ab33 heavy chain | 523 | 531 | 527 | 535 | 528 | 536 | 529 | 537 |
| Ab34 light chain | 538 | 546 | 540 | 548 | 541 | 549 | 542 | 550 |
| Ab34 heavy chain | 539 | 547 | 543 | 551 | 544 | 552 | 545 | 553 |
| Ab35 light chain | 554 | 562 | 556 | 564 | 557 | 565 | 558 | 566 |
| Ab35 heavy chain | 555 | 563 | 559 | 567 | 560 | 568 | 561 | 569 |
| Ab36 light chain | 570 | 578 | 572 | 580 | 573 | 581 | 574 | 582 |
| Ab36 heavy chain | 571 | 579 | 575 | 583 | 576 | 584 | 577 | 585 |

*Exemplary sequence variant forms of heavy and light chains are shown on separate lines.
PRT.: Polypeptide sequence.
Nuc.: Exemplary coding sequence.

For reference, sequence identifiers other than those included in Table 1 are summarized in Table 2.

TABLE 2

Summary of sequence identifiers in this application.

| SEQ ID | Description |
|---|---|
| 1 | Human IL-6 |
| 586 | kappa constant light chain polypeptide sequence |
| 587 | kappa constant light chain polynucleotide sequence |
| 588 | gamma-1 constant heavy chain polypeptide sequence |
| 589 | gamma-1 constant heavy chain polynucleotide sequence |
| 590-646 | Human IL-6 peptides (see FIG. 12 and Example 14) |
| 719 | gamma-1 constant heavy chain polypeptide sequence (differs from SEQ ID NO: 518 at two positions) |
| 726 | C-reactive protein polypeptide sequence |
| 727 | IL-6 receptor alpha |
| 728 | IL-6 receptor beta/gp130 |

Such antibody fragments may be present in one or more of the following non-limiting forms: Fab, Fab', $F(ab')_2$, Fv and single chain Fv antibody forms. In a preferred embodiment, the anti-IL-6 antibodies described herein further comprises the kappa constant light chain sequence comprising the sequence set forth below:

```
                                            (SEQ ID NO: 586)
VAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSF

NRGEC.
```

In another preferred embodiment, the anti-IL-6 antibodies described herein further comprises the gamma-1 constant heavy chain polypeptide sequence comprising one of the sequences set forth below:

```
                                            (SEQ ID NO: 588)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS
```

-continued

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK and (SEQ ID NO: 719)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK.

Embodiments of antibodies described herein may include a leader sequence, such as a rabbit Ig leader, albumin prepeptide, a yeast mating factor pre pro secretion leader sequence (such as *P. pastoris* or *Saccharomyces cerevisiae* a or alpha factor), or human HAS leader. Exemplary leader sequences are shown offset from FR1 at the N-terminus of polypeptides shown in FIGS. 36A and 37A as follows: rabbit Ig leader sequences in SEQ ID NOs: 2 and 660 (MD . . . ) and SEQ ID NOs: 3 and 661 (ME . . . ); and an albumin prepeptide in SEQ ID NOs: 706 and 708, which facilitates secretion. Other leader sequences known in the art to confer desired properties, such as secretion, improved stability or half-life, etc. may also be used, either alone or in combinations with one another, on the heavy and/or light chains, which may optionally be cleaved prior to administration to a subject. For example, a polypeptide may be expressed in a cell or cell-free expression system that also expresses or includes (or is modified to express or include) a protease, e.g., a membrane-bound signal peptidase, that cleaves a leader sequence.

In another embodiment, the invention contemplates an isolated anti-IL-6 antibody comprising a $V_H$ polypeptide sequence comprising: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708 or any of the VH sequences depicted in FIGS. 34-37; and further comprising a $V_L$ polypeptide sequence comprising: SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709 or any of the other VL sequences depicted in FIGS. 34-37 or a variant thereof wherein one or more of the framework residues (FR residues) in said $V_{H\,or}\,V_L$ polypeptide has been substituted with another amino acid residue resulting in an anti-IL-6 antibody that specifically binds IL-6. The invention contemplates humanized and chimeric forms of these antibodies. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions and in particular a variable heavy and light chain constant region as contained in SEQ ID NO:588 and SEQ ID NO:586.

In one embodiment of the invention, the antibodies or $V_H$ or $V_L$ polypeptides originate or are selected from one or more rabbit B cell populations prior to initiation of the humanization process referenced herein.

In another embodiment of the invention, the anti-IL-6 antibodies and fragments thereof have binding specificity for primate homologs of the human IL-6 protein. Non-limiting examples of primate homologs of the human IL-6 protein are IL-6 obtained from *Macaca fascicularis* (also known as the cynomolgus monkey) and the Rhesus monkey. In another embodiment of the invention, the anti-IL-6 antibodies and fragments thereof inhibits the association of IL-6 with IL-6R, and/or the production of IL-6/IL-6R/gp130 complexes and/or the production of IL-6/IL-6R/gp130 multimers and/or antagonizes the biological effects of one or more of the foregoing.

As stated above, antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, and phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}I$), Carbon 14 (14C), Sulfur 35 ($^{35}S$), Tritium (3H) and Phosphorus 32 ($^{32}P$).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, caminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents. Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux™, Avastin™ Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}P$), Scandium-47 ($^{47}Sc$), Copper-67 ($^{67}Cu$), Gallium-67 ($^{67}Ga$), Yttrium-88 ($^{88}Y$), Yttrium-90 ($^{90}Y$), Iodine-125 ($^{125}I$) Iodine-131 ($^{131}I$) Samarium-153 ($^{153}Sm$), Lutetium-177 ($^{177}Lu$), Rhenium-186 ($^{186}Re$) or Rhenium-188 ($^{188}Re$), and alpha-emitters such as Astatine-211 ($^{211}At$), Lead-212 $^{212}Pb$), Bismuth-212 ($^{212}Bi$) or −213 ($^{213}Bi$) or Actinium-225 ($^{225}Ac$).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-IL-6 activity. Non-limiting examples of anti-IL-6 activity are set forth herein, for example, under the heading "Anti-IL-6 Activity," infra.

In another embodiment, the invention further contemplates the generation and use of anti-idiotypic antibodies that bind any of the foregoing sequences. In an exemplary embodiment, such an anti-idiotypic antibody could be administered to a subject who has received an anti-IL-6 antibody to modulate, reduce, or neutralize, the effect of the anti-IL-6 antibody. Such anti-idiotypic antibodies could also be useful for treatment of an autoimmune disease characterized by the presence of anti-IL-6 antibodies. A further exemplary use of such anti-idiotypic antibodies is for detection of the anti-IL-6 antibodies of the present invention, for example to monitor the levels of the anti-IL-6 antibodies present in a subject's blood or other bodily fluids.

The present invention also contemplates anti-IL-6 antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates one or more anti-IL-6 antibodies or antibody fragment which may specifically bind to the same linear or conformational epitope(s) and/or compete for binding to the same linear or conformational epitope(s) on an intact human IL-6 polypeptide or fragment thereof as an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36. In a preferred embodiment, the anti-IL-6 antibody or fragment may specifically bind to the same linear or conformational epitope(s) and/or compete for binding to the same linear or conformational epitope(s) on an intact human IL-6 polypeptide or a fragment thereof as Ab1.

In another embodiment of the invention, the anti-IL-6 antibody which specifically binds to the same linear or conformational epitopes on an intact IL-6 polypeptide or fragment thereof that is (are) specifically bound by Ab1 binds to a IL-6 epitope(s) ascertained by epitopic mapping using overlapping linear peptide fragments which span the full length of the native human IL-6 polypeptide. In one embodiment of the invention, the IL-6 epitope comprises, or alternatively consists of, one or more residues comprised in IL-6 fragments selected from those respectively encompassing amino acid residues 37-51, amino acid residues 70-84, amino acid residues 169-183, amino acid residues 31-45 and/or amino acid residues 58-72.

The invention is also directed to an anti-IL-6 antibody that binds with the same IL-6 epitope and/or competes with an anti-IL-6 antibody for binding to IL-6 as an antibody or antibody fragment disclosed herein, including but not limited to an anti-IL-6 antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, and Ab36 and chimeric, humanized, human or fragments containing all or most of the CDRs of the afore-identified antibodies which specifically bind IL-6, preferably aglycosylated antibodies.

In another embodiment, the invention is also directed to an isolated anti-IL-6 antibody or antibody fragment comprising one or more of the CDRs contained in the $V_H$ polypeptide sequences comprising: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708 and/or one or more of the CDRs contained in the $V_L$ polypeptide sequence consisting of: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709 or the VH and VL sequences depicted in the antibody alignments comprised in FIGS. 34-37 of this application.

In one embodiment of the invention, the anti-IL-6 antibody discussed in the two prior paragraphs comprises at least 2 complementarity determining regions (CDRs) in each the variable light and the variable heavy regions which are identical to those contained in an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, humanized, human or fragments containing all or most of the CDRs of the afore-identified antibodies which specifically bind IL-6, preferably aglycosylated antibodies. In a preferred embodiment of the invention, all of the CDRs of the anti-IL-6 antibody discussed above are identical to the CDRs contained in Ab1, e.g., an antibody comprised of the VH and VL sequences comprised in SEQ ID NO:657 and SEQ ID NO:709 respectively, or antibodies comprising any combination of the humanized sequence contained in FIGS. 34-37.

In a preferred embodiment, the anti-IL-6 antibody discussed above comprises at least 2 complementarity determining regions (CDRs) in each the variable light and the variable heavy regions which are identical to those contained in Ab1. In another embodiment, all of the CDRs of the anti-IL-6 antibody discussed above are identical to the CDRs contained in an anti-IL-6 antibody comprising Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 and chimeric, humanized, human or fragments containing all or most of the CDRs of the afore-identified antibodies which specifically bind IL-6, preferably aglycosylated antibodies.

In a preferred embodiment of the invention, all of the CDRs of the anti-IL-6 antibody discussed above are identical to the CDRs contained in Ab1 and more preferably will be comprised in one of the variable heavy and light antibody sequences depicted in FIGS. 34-37.

The invention further contemplates that the one or more anti-IL-6 antibodies discussed above are aglycosylated; that contain an Fc region that has been modified to alter effector function, half-life, proteolysis, and/or glycosylation; are human, humanized, single chain or chimeric; and are a humanized antibody derived from a rabbit (parent) anti-IL-6 antibody. Exemplary constant regions that provide for the production of aglycosylated antibodies in *Pichia* are comprised in SEQ ID NO:588 and SEQ ID NO:586 which respectively are encode by the nucleic acid sequences in SEQ ID NO:589 and SEQ ID NO:587.

The invention further contemplates one or more anti-IL-6 antibodies wherein the framework regions (FRs) in the variable light region and the variable heavy regions of said antibody respectively are human FRs which are unmodified or which have been modified by the substitution of at most 2 or 3 human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-IL-6 antibody or fragment may specifically bind to IL-6 expressing human cells and/or to circulating soluble IL-6 molecules in vivo, including IL-6 expressed on or by human cells in a patient with a disease associated with cells that express IL-6.

In another embodiment, the disease is selected from general fatigue, exercise-induced fatigue, cancer-related fatigue, stress-related fatigue, inflammatory disease-related fatigue, chronic fatigue syndrome, fibromyalgia, cancer-related cachexia, cardiac-related cachexia, respiratory-related cachexia, renal-related cachexia, age-related cachexia, rheumatoid arthritis, systemic lupus erythematosis (SLE), systemic juvenile idiopathic arthritis, psoriasis, psoriatic arthropathy, ankylosing spondylitis, inflammatory bowel disease (IBD), polymyalgia rheumatica, giant cell arteritis, autoimmune vasculitis, graft versus host disease (GVHD), Sjogren's syndrome, adult onset Still's disease, rheumatoid arthritis, systemic juvenile idiopathic arthritis, osteoarthritis, osteoporosis, Paget's disease of bone, osteoarthritis, multiple myeloma, Hodgkin's lymphoma, non-Hodgkin's lymphoma, prostate cancer, leukemia, renal cell cancer, multicentric Castleman's disease, ovarian cancer, drug resistance in cancer chemotherapy, cancer chemotherapy toxicity, ischemic heart disease, atherosclerosis, obesity, diabetes, asthma, multiple sclerosis, Alzheimer's disease, cerebrovascular disease, fever, acute phase response, allergies, anemia, anemia of inflammation (anemia of chronic disease), hypertension, depression, depression associated with a chronic illness, thrombosis, thrombocytosis, acute heart failure, metabolic syndrome, miscarriage, obesity, chronic prostatitis, glomerulonephritis, pelvic inflammatory disease, reperfusion injury, transplant rejection, graft versus host disease (GVHD), avian influenza, smallpox, pandemic influenza, adult respiratory distress syndrome (ARDS), severe acute respiratory syndrome (SARS), sepsis, and systemic inflammatory response syndrome (SIRS). In a preferred embodiment, the disease is selected from a cancer, inflammatory disorder, viral disorder, or autoimmune disorder. In a particularly preferred embodiment, the disease is arthritis, cachexia, and wasting syndrome.

The invention further contemplates anti-IL-6 antibodies or fragments directly or indirectly attached to a detectable label or therapeutic agent.

The invention also contemplates one or more nucleic acid sequences which result in the expression of an anti-IL-6 antibody or antibody fragment as set forth above, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells expressing at least one of the antibodies set forth above, including a mammalian, yeast, bacterial, and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with IL-6 expressing cells a therapeutically effective amount of at least one anti-IL-6 antibody or fragment. The diseases that may be treated are presented in the non-limiting list set forth above. In a preferred embodiment, the disease is selected from a cancer, autoimmune disease, or inflammatory condition. In a particularly preferred embodiment, the disease is cancer or viral infection. In another embodiment the treatment further includes the administration of another therapeutic agent or regimen selected from chemotherapy, radiotherapy, cytokine administration or gene therapy.

The invention further contemplates a method of in vivo imaging which detects the presence of cells which express IL-6 comprising administering a diagnostically effective amount of at least one anti-IL-6 antibody. In one embodiment, said administration further includes the administration of a radionuclide or fluorophore that facilitates detection of the antibody at IL-6 expressing disease sites. In another embodiment of the invention, the method of in vivo imaging is used to detect IL-6 expressing tumors or metastases or is used to detect the presence of sites of autoimmune disorders associated with IL-6 expressing cells. In a further embodiment, the results of said in vivo imaging method are used to facilitate design of an appropriate therapeutic regimen, including therapeutic regimens including radiotherapy, chemotherapy or a combination thereof.

Polynucleotides Encoding Anti-IL-6 Antibody Polypeptides

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 2:

(SEQ ID NO: 10)

ATGGACACGAGGGCCCCCACTCAGCTGCTGGGGCTCCTGCTGCTCTGGCT

CCCAGGTGCCAGATGTGCCTATGATATGACCCAGACTCCAGCCTCGGTGT

CTGCAGCTGTGGGAGGCACAGTCACCATCAAGTGCCAGGCCAGTCAGAGC

ATTAACAATGAATTATCCTGGTATCAGCAGAAACCAGGGCAGCGTCCCAA

GCTCCTGATCTATAGGGCATCCACTCTGGCATCTGGGGTCTCATCGCGGT

TCAAAGGCAGTGGATCTGGGACAGAGTTCACTCTCACCATCAGCGACCTG

GAGTGTGCCGATGCTGCCACTTACTACTGTCAACAGGGTTATAGTCTGAG

GAATATTGATAATGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTT

In another embodiment of the invention, polynucleotides of the invention comprise, or alternatively consist of, the following polynucleotide sequence encoding the variable heavy chain polypeptide sequence of SEQ ID NO: 3:

(SEQ ID NO: 11)

ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGCCTCTGGATTCTCCCTCAGTAACTAC

TACGTGACCTGGGTCCGCCAGGCTCCAGGGAAGGGGCTGGAATGGATCGG

AATCATTTATGGTAGTGATGAAACGGCCTACGCGACCTGGGCGATAGGCC

GATTCACCATCTCCAAAACCTCGACCACGGTGGATCTGAAAATGACCAGT

CTGACAGCCGCGGACACGGCCACCTATTTCTGTGCCAGAGATGATAGTAG

TGACTGGGATGCAAAATTTAACTTGTGGGGCCAAGGCACCCTGGTCACCG

TCTCGAGCGCCTCCACCAAGGGCCCATCGGTCTTCCCCCTGGCACCCTCC

TCCAAGAGCACCTCTGGGGGCACAGCGGCCCTGGGCTGCCTGGTCAAGG.

In another embodiment of the invention, polynucleotides of the invention further comprise, the following polynucleotide sequence encoding the variable heavy chain polypeptide sequence of SEQ ID NO: 700:

(SEQ ID NO: 700)

GAGGTGCAGCTGGTGGAGTCTGGGGGAGGCTTGGTCCAGCCTGGGGGGTC

CCTGAGACTCTCCTGTGCAGCCTCTGGATTCTCCCTCAGTAACTACTACG

TGACCTGGGTCCGTCAGGCTCCAGGGAAGGGGCTGGAGTGGGTCGGCATC

ATCTATGGTAGTGATGAAACCGCCTACGCTACCTCCGCTATAGGCCGATT

CACCATCTCCAGAGACAATTCCAAGAACACCCTGTATCTTCAAATGAACA

GCCTGAGAGCTGAGGACACTGCTGTGTATTACTGTGCTAGAGATGATAGT

AGTGACTGGGATGCAAAGTTCAACTTGTGGGGCCAAGGGACCCTCGTCAC

CGTCTCGAGC.

In another embodiment of the invention, polynucleotides of the invention further comprise, the following polynucleotide sequence encoding the variable light chain polypeptide sequence of SEQ ID NO: 723:

(SEQ ID NO: 723)

GCTATCCAGATGACCCAGTCTCCTTCCTCCCTGTCTGCATCTGTAGGAGA

CAGAGTCACCATCACTTGCCAGGCCAGTCAGAGCATTAACAATGAGTTAT

CCTGGTATCAGCAGAAACCAGGGAAAGCCCCTAAGCTCCTGATCTATAGG

GCATCCACTCTGGCATCTGGGGTCCCATCAAGGTTCAGCGGCAGTGGATC

TGGGACAGACTTCACTCTCACCATCAGCAGCCTGCAGCCTGATGATTTTG

CAACTTATTACTGCCAACAGGGTTATAGTCTGAGGAACATTGATAATGCT

TTCGGCGGAGGGACCAAGGTGGAAATCAAACGT.

In a further embodiment of the invention, polynucleotides encoding fragments of the antibody having binding specificity to IL-6 comprise, or alternatively consist of, one or more of the polynucleotide sequences of SEQ ID NO: 12; SEQ ID NO: 13; and SEQ ID NO: 14 which correspond to polynucleotides encoding the complementarity-determining regions (CDRs, or hypervariable regions) of the light chain variable sequence of SEQ ID NO: 2 or 709 or any of those contained in FIGS. 34-37.

In a further embodiment of the invention, polynucleotides encoding fragments of the antibody having binding specificity to IL-6 comprise, or alternatively consist of, one or more of the polynucleotide sequences of SEQ ID NO: 15; SEQ ID NO: 16; and SEQ ID NO: 17 which correspond to polynucleotides encoding the complementarity-determining regions (CDRs, or hypervariable regions) of the heavy chain variable sequence of SEQ ID NO: 3 or 657 or any of those contained in FIGS. 34-37.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 10 encoding the light chain variable region of SEQ ID NO: 2; the polynucleotide SEQ ID NO: 11 encoding the heavy chain variable region of SEQ ID NO: 3; the polynucleotide NO:700 encoding the VH polypeptide in SEQ ID NO:657, the polynucleotide 723 encoding the VL polypeptide contained in SEQ ID NO:709 or any of the other VL or VH polypeptides contained in FIGS. 34-37, polynucleotides encoding the complementarity-determining regions (SEQ ID NO: 12; SEQ ID NO: 13; and SEQ ID NO: 14) of the light chain variable region of SEQ ID NO: 10; and polynucleotides encoding the complementarity-determining regions (SEQ ID NO: 15; SEQ ID NO: 16; and SEQ ID NO: 17) of the heavy chain variable region of SEQ ID NO: 11.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 21:

```
                                     (SEQ ID NO: 29)
ATGGACACGAGGGCCCCCACTCAGCTGCTGGGGCTCCTGCTGCTCTGGCT

CCCAGGTGCCAGATGTGCCTATGATATGACCCAGACTCCAGCCTCTGTGG

AGGTAGCTGTGGGAGGCACAGTCACCATCAATTGCCAGGCCAGTGAGACC

ATTTACAGTTGGTTATCCTGGTATCAGCAGAAGCCAGGGCAGCCTCCCAA

GCTCCTGATCTACCAGGCATCCGATCTGGCATCTGGGGTCCCATCGCGAT

TCAGCGGCAGTGGGGCTGGGACAGAGTACACTCTCACCATCAGCGGCGTG

CAGTGTGACGATGCTGCCACTTACTACTGTCAACAGGGTTATAGTGGTAG

TAATGTTGATAATGTTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTCTATCCCAG

AGAGGCCAAAG
```

In another embodiment of the invention, polynucleotides of the invention comprise, or alternatively consist of, the following polynucleotide sequence encoding the variable heavy chain polypeptide sequence of SEQ ID NO: 22:

```
                                     (SEQ ID NO: 30)
ATGGAGACTGGGCTGCGCTGGCTTCTCCTGGTCGCTGTGCTCAAAGGTGT

CCAGTGTCAGGAGCAGCTGAAGGAGTCCGGGGGTCGCCTGGTCACGCCTG

GACACCCCTGACACTTACCTGCACAGCCTCTGGATTCTCCCTCAATGACC

ATGCAATGGGCTGGGTCCGCCAGGCTCCAGGGAAGGGGCTGGAATACATC
```

-continued

```
GGATTCATTAATAGTGGTGGTAGCGCACGCTACGCGAGCTGGGCAGAAGG

CCGATTCACCATCTCCAGAACCTCGACCACGGTGGATCTGAAAATGACCA

GTCTGACAACCGAGGACACGGCCACCTATTTCTGTGTCAGAGGGGGTGCT

GTTTGGAGTATTCATAGTTTTGATCCCTGGGGCCCAGGGACCCTGGTCAC

CGTCTCGAGCGCCTCCACCAAGGGCCCATCGGTCTTCCCCCTGGCACCCT

CCTCCAAGAGCACCTCTGGGGGCACAGCGGCCCTGGGCTGCCTGGTC

AAG.
```

In a further embodiment of the invention, polynucleotides encoding fragments of the antibody having binding specificity to IL-6 comprise, or alternatively consist of, one or more of the polynucleotide sequences of SEQ ID NO: 31; SEQ ID NO: 32; and SEQ ID NO: 33 which correspond to polynucleotides encoding the complementarity-determining regions (CDRs, or hypervariable regions) of the light chain variable sequence of SEQ ID NO: 21.

In a further embodiment of the invention, polynucleotides encoding fragments of the antibody having binding specificity to IL-6 comprise, or alternatively consist of, one or more of the polynucleotide sequences of SEQ ID NO: 34; SEQ ID NO: 35; and SEQ ID NO: 36 which correspond to polynucleotides encoding the complementarity-determining regions (CDRs, or hypervariable regions) of the heavy chain variable sequence of SEQ ID NO: 22.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 29 encoding the light chain variable region of SEQ ID NO: 21; the polynucleotide SEQ ID NO: 30 encoding the heavy chain variable region of SEQ ID NO: 22; polynucleotides encoding the complementarity-determining regions (SEQ ID NO: 31; SEQ ID NO: 32; and SEQ ID NO: 33) of the light chain variable region of SEQ ID NO: 29; and polynucleotides encoding the complementarity-determining regions (SEQ ID NO: 34; SEQ ID NO: 35; and SEQ ID NO: 36) of the heavy chain variable region of SEQ ID NO: 30.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 37:

```
                                     (SEQ ID NO: 45)
ATGGACACGAGGGCCCCCACTCAGCTGCTGGGGCTCCTGCTGCTCTGGCT

CCCAGGTGCCACATTTGCCGCCGTGCTGACCCAGACTCCATCTCCCGTGT

CTGCAGCTGTGGGAGGCACAGTCAGCATCAGTTGCCAGGCCAGTCAGAGT

GTTTATGACAACAACTACTTATCCTGGTTTCAGCAGAAACCAGGGCAGCC

TCCCAAGCTCCTGATCTATGGTGCATCCACTCTGGCATCTGGGGTCCCAT

CGCGGTTCGTGGGCAGTGGATCTGGGACACAGTTCACTCTCACCATCACA

GACGTGCAGTGTGACGATGCTGCCACTTACTATTGTGCAGGCGTTTATGA
```

-continued

TGATGATAGTGATAATGCCTTCGGCGGAGGGACCGAGGTGGTGGTCAAAC

GTACGGTAGCGGCCCCATCTGTCTTCATCTTCCCGCCATCTGATGAGCAG

TTGAAATCTGGAACTGCCTCTGTTGTGTGCCTGCTGAATAACTTCT

In another embodiment of the invention, polynucleotides of the invention comprise, or alternatively consist of, the following polynucleotide sequence encoding the variable heavy chain polypeptide sequence of SEQ ID NO: 38:

(SEQ ID NO: 46)

ATGGAGACTGGGCTGCGCTGGCTTCTCCTGGTGGCTGTGCTCAAAGGTGT

CCAGTGTCAGTCGCTGGAGGAGTCCGGGGGTCGCCTGGTCACCCCTGGGA

CACCCCTGACACTCACCTGCACAGCCTCTGGATTCTCCCTCAGTGTCTAC

TACATGAACTGGGTCCGCCAGGCTCCAGGGAAGGGGCTGGAATGGATCGG

ATTCATTACAATGAGTGATAATATAAATTACGCGAGCTGGGCGAAAGGCC

GATTCACCATCTCCAAAACCTCGACCACGGTGGATCTGAAAATGACCAGT

CCGACAACCGAGGACACGGCCACCTATTTCTGTGCCAGGAGTCGTGGCTG

GGGTACAATGGGTCGGTTGGATCTCTGGGGCCCAGGCACCCTCGTCACCG

TCTCGAGCGCCTCCACCAAGGGCCCATCGGTCTTCCCCCTGGCACCCTCC

TCCAAGAGCACCTCTGGGGGCACAGCGGCCCTGGGCTGCCTGGTCAAGG.

In a further embodiment of the invention, polynucleotides encoding fragments of the antibody having binding specificity to IL-6 comprise, or alternatively consist of, one or more of the polynucleotide sequences of SEQ ID NO: 47; SEQ ID NO: 48; and SEQ ID NO: 49 which correspond to polynucleotides encoding the complementarity-determining regions (CDRs, or hypervariable regions) of the light chain variable sequence of SEQ ID NO: 37.

In a further embodiment of the invention, polynucleotides encoding fragments of the antibody having binding specificity to IL-6 comprise, or alternatively consist of, one or more of the polynucleotide sequences of SEQ ID NO: 50; SEQ ID NO: 51; and SEQ ID NO: 52 which correspond to polynucleotides encoding the complementarity-determining regions (CDRs, or hypervariable regions) of the heavy chain variable sequence of SEQ ID NO: 38.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 45 encoding the light chain variable region of SEQ ID NO: 37; the polynucleotide SEQ ID NO: 46 encoding the heavy chain variable region of SEQ ID NO: 38; polynucleotides encoding the complementarity-determining regions (SEQ ID NO: 47; SEQ ID NO: 48; and SEQ ID NO: 49) of the light chain variable region of SEQ ID NO: 37; and polynucleotides encoding the complementarity-determining regions (SEQ ID NO: 50; SEQ ID NO: 51; and SEQ ID NO: 52) of the heavy chain variable region of SEQ ID NO: 38.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 53:

(SEQ ID NO: 61)

ATGGACACGAGGGCCCCCACTCAGCTGCTGGGGCTCCTGCTGCTCTGGCT

CCCAGGTGCCATATGTGACCCTGTGCTGACCCAGACTCCATCTCCCGTAT

CTGCACCTGTGGGAGGCACAGTCAGCATCAGTTGCCAGGCCAGTCAGAGT

GTTTATGAGAACAACTATTTATCCTGGTTTCAGCAGAAACCAGGGCAGCC

TCCCAAGCTCCTGATCTATGGTGCATCCACTCTGGATTCTGGGGTCCCAT

CGCGGTTCAAAGGCAGTGGATCTGGGACACAGTTCACTCTCACCATTACA

GACGTGCAGTGTGACGATGCTGCCACTTACTATTGTGCAGGCGTTTATGA

TGATGATAGTGATGATGCCTTCGGCGGAGGGACCGAGGTGGTGGTCAAAC

GTACGGTAGCGGCCCCATCTGTCTTCATCTTCCCGCCATCTGATGAGCAG

TTGAAATCTGGAACTGCCTCTGTTGTGTGCCTGCTGAATAACTT

In another embodiment of the invention, polynucleotides of the invention comprise, or alternatively consist of, the following polynucleotide sequence encoding the variable heavy chain polypeptide sequence of SEQ ID NO: 54:

(SEQ ID NO: 62)

ATGGAGACTGGGCTGCGCTGGCTTCTCCTGGTGGCTGTGCTCAAAGGTGT

CCAGTGTCAGGAGCAGCTGAAGGAGTCCGGAGGAGGCCTGGTAACGCCTG

GAGGAACCCTGACACTCACCTGCACAGCCTCTGGATTCTCCCTCAATGCC

TACTACATGAACTGGGTCCGCCAGGCTCCAGGGAAGGGGCTGGAATGGAT

CGGATTCATTACTCTGAATAATAATGTAGCTTACGCGAACTGGGCGAAAG

GCCGATTCACCTTCTCCAAAACCTCGACCACGGTGGATCTGAAAATGACC

AGTCCGACACCCGAGGACACGGCCACCTATTTCTGTGCCAGGAGTCGTGG

CTGGGGTGCAATGGGTCGGTTGGATCTCTGGGGCCATGGCACCCTGGTCA

CCGTCTCGAGCGCCTCCACCAAGGGCCCATCGGTCTTCCCCCTGGCACCC

TCCTCCAAGAGCACCTCTGGGGGCACAGCGGCCCTGGGCTGCCTGGTCAA

GG.

In a further embodiment of the invention, polynucleotides encoding fragments of the antibody having binding specificity to IL-6 comprise, or alternatively consist of, one or more of the polynucleotide sequences of SEQ ID NO: 63; SEQ ID NO: 64; and SEQ ID NO: 65 which correspond to polynucleotides encoding the complementarity-determining regions (CDRs, or hypervariable regions) of the light chain variable sequence of SEQ ID NO: 53.

In a further embodiment of the invention, polynucleotides encoding fragments of the antibody having binding specificity to IL-6 comprise, or alternatively consist of, one or more of the polynucleotide sequences of SEQ ID NO: 66; SEQ ID NO: 67; and SEQ ID NO: 68 which correspond to polynucleotides encoding the complementarity-determining regions (CDRs, or hypervariable regions) of the heavy chain variable sequence of SEQ ID NO: 54.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 61 encoding the light chain variable region of SEQ ID NO: 53; the polynucleotide SEQ ID NO: 62 encoding the heavy chain variable region of SEQ ID NO: 54; polynucleotides encoding the complementarity-determining regions (SEQ ID NO: 63; SEQ ID NO: 64; and SEQ ID NO: 65) of the light chain variable region of SEQ ID NO: 53; and polynucleotides encoding the complementarity-determining regions (SEQ ID NO: 66; SEQ ID NO: 67; and SEQ ID NO: 68) of the heavy chain variable region of SEQ ID NO: 54.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 69:

(SEQ ID NO: 77)

```
ATGGACACGAGGGCCCCCACTCAGCTGCTGGGGCTCCTGCTGCTCTGGCT

CCCAGGTGCCACATTTGCCCAAGTGCTGACCCAGACTCCATCGCCTGTGT

CTGCAGCTGTGGGAGGCACAGTCACCATCAACTGCCAGGCCAGTCAGAGT

GTTGATGATAACAACTGGTTAGGCTGGTATCAGCAGAAACGAGGGCAGCC

TCCCAAGTACCTGATCTATTCTGCATCCACTCTGGCATCTGGGGTCCCAT

CGCGGTTCAAAGGCAGTGGATCTGGGACACAGTTCACTCTCACCATCAGC

GACCTGGAGTGTGACGATGCTGCCACTTACTACTGTGCAGGCGGTTTTAG

TGGTAATATCTTTGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTCT
```

In another embodiment of the invention, polynucleotides of the invention comprise, or alternatively consist of, the following polynucleotide sequence encoding the variable heavy chain polypeptide sequence of SEQ ID NO: 70:

(SEQ ID NO: 78)

```
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGCTTCTCCCTCAGTAGCTAT

GCAATGAGCTGGGTCCGCCAGGCTCCAGGAAAGGGGCTGGAGTGGATCGG

AATCATTGGTGGTTTTGGTACCACATACTACGCGACCTGGGCGAAAGGCC

GATTCACCATCTCCAAAACCTCGACCACGGTGGATCTGAGAATCACCAGT

CCGACAACCGAGGACACGGCCACCTATTTCTGTGCCAGAGGTGGTCCTGG

TAATGGTGGTGACATCTGGGGCCAAGGGACCCTGGTCACCGTCTCGAGCG

CCTCCACCAAGGGCCCATCGGTCTTCCCCCTGGCACCCTCCTCCAAGAGC

ACCTCTGGGGGCACAGCGGCCCTGGGCTGCCTGGTCAAGGACT.
```

In a further embodiment of the invention, polynucleotides encoding fragments of the antibody having binding specificity to IL-6 comprise, or alternatively consist of, one or more of the polynucleotide sequences of SEQ ID NO: 79; SEQ ID NO: 80; and SEQ ID NO: 81 which correspond to polynucleotides encoding the complementarity-determining regions (CDRs, or hypervariable regions) of the light chain variable sequence of SEQ ID NO: 69.

In a further embodiment of the invention, polynucleotides encoding fragments of the antibody having binding specificity to IL-6 comprise, or alternatively consist of, one or more of the polynucleotide sequences of SEQ ID NO: 82; SEQ ID NO: 83; and SEQ ID NO: 84 which correspond to polynucleotides encoding the complementarity-determining regions (CDRs, or hypervariable regions) of the heavy chain variable sequence of SEQ ID NO: 70.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 77 encoding the light chain variable region of SEQ ID NO: 69; the polynucleotide SEQ ID NO: 78 encoding the heavy chain variable region of SEQ ID NO: 70; polynucleotides encoding the complementarity-determining regions (SEQ ID NO: 79; SEQ ID NO: 80; and SEQ ID NO: 81) of the light chain variable region of SEQ ID NO: 69; and polynucleotides encoding the complementarity-determining regions (SEQ ID NO: 82; SEQ ID NO: 83; and SEQ ID NO: 84) of the heavy chain variable region of SEQ ID NO: 70.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 85:

(SEQ ID NO: 93)

```
ATGGACACGAGGGCCCCCACTCAGCTGCTGGGGCTCCTGCTGCTCTGGCT

CCCAGGTGCCACATTTGCAGCCGTGCTGACCCAGACACCATCGCCCGTGT

CTGTACCTGTGGGAGGCACAGTCACCATCAAGTGCCAGTCCAGTCAGAGT

GTTTATAATAATTTCTTATCGTGGTATCAGCAGAAACCAGGGCAGCCTCC

CAAGCTCCTGATCTACCAGGCATCCAAACTGGCATCTGGGGTCCCAGATA

GGTTCAGCGGCAGTGGATCTGGGACACAGTTCACTCTCACCATCAGCGGC

GTGCAGTGTGACGATGCTGCCACTTACTACTGTCTAGGCGGTTATGATGA

TGATGCTGATAATGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTC
```

In another embodiment of the invention, polynucleotides of the invention comprise, or alternatively consist of, the following polynucleotide sequence encoding the variable heavy chain polypeptide sequence of SEQ ID NO: 86:

(SEQ ID NO: 94)

```
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACGCTCACCTGCACAGTCTCTGGAATCGACCTCAGTGACTAT

GCAATGAGCTGGGTCCGCCAGGCTCCAGGGAAGGGGCTGGAATGGATCGG

AATCATTTATGCTGGTAGTGGTAGCACATGGTACGCGAGCTGGGCGAAAG

GCCGATTCACCATCTCCAAAACCTCGACCACGGTGGATCTGAAAATCACC

AGTCCGACAACCGAGGACACGGCCACCTATTTCTGTGCCAGAGATGGATA
```

-continued

CGATGACTATGGTGATTTCGATCGATTGGATCTCTGGGGCCCAGGCACCC

TCGTCACCGTCTCGAGCGCCTCCACCAAGGGCCCATCGGTCTTCCCCCTG

GCACCCTCCTCCAAGAGCACCTCTGGGGGCACAGCGGCCCTGGGCTGCCT

GGTCAAGGACT.

In a further embodiment of the invention, polynucleotides encoding fragments of the antibody having binding specificity to IL-6 comprise, or alternatively consist of, one or more of the polynucleotide sequences of SEQ ID NO: 95; SEQ ID NO: 96; and SEQ ID NO: 97 which correspond to polynucleotides encoding the complementarity-determining regions (CDRs, or hypervariable regions) of the light chain variable sequence of SEQ ID NO: 85.

In a further embodiment of the invention, polynucleotides encoding fragments of the antibody having binding specificity to IL-6 comprise, or alternatively consist of, one or more of the polynucleotide sequences of SEQ ID NO: 98; SEQ ID NO: 99; and SEQ ID NO: 100 which correspond to polynucleotides encoding the complementarity-determining regions (CDRs, or hypervariable regions) of the heavy chain variable sequence of SEQ ID NO: 86.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 93 encoding the light chain variable region of SEQ ID NO: 85; the polynucleotide SEQ ID NO: 94 encoding the heavy chain variable region of SEQ ID NO: 86; polynucleotides encoding the complementarity-determining regions (SEQ ID NO: 95; SEQ ID NO: 96; and SEQ ID NO: 97) of the light chain variable region of SEQ ID NO: 85; and polynucleotides encoding the complementarity-determining regions (SEQ ID NO: 98; SEQ ID NO: 99; and SEQ ID NO: 100) of the heavy chain variable region of SEQ ID NO: 86.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 101:

(SEQ ID NO: 109)

ATGGACACGAGGGCCCCCACTCAGCTGCTGGGGCTCCTGCTGCTCTGGCT

CCCAGGTGCCAGATGTGCCTATGATATGACCCAGACTCCAGCCTCGGTGT

CTGCAGCTGTGGGAGGCACAGTCACCATCAAATGCCAGGCCAGTCAGAGC

ATTAACAATGAATTATCCTGGTATCAGCAGAAATCAGGGCAGCGTCCCAA

GCTCCTGATCTATAGGGCATCCACTCTGGCATCTGGGGTCTCATCGCGGT

TCAAAGGCAGTGGATCTGGGACAGAGTTCACTCTCACCATCAGCGACCTG

GAGTGTGCCGATGCTGCCACTTACTACTGTCAACAGGGTTATAGTCTGAG

GAATATTGATAATGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTC

In another embodiment of the invention, polynucleotides of the invention comprise, or alternatively consist of, the following polynucleotide sequence encoding the variable heavy chain polypeptide sequence of SEQ ID NO: 102:

(SEQ ID NO: 110)

ATGGAGACTGGGCTGCGCTGGCTTCTCCTGGTCGCTGTGCTCTCAGGTGT

CCAGTGTCAGTCGCTGGAGGAGTCCGGGGGTCGCCTGGTCACGCCTGGGA

CACCCCTGACACTCACCTGCACAGCCTCTGGATTCTCCCTCAGTAACTAC

TACATGACCTGGGTCCGCCAGGCTCCAGGGAAGGGGCTGGAATGGATCGG

AATGATTTATGGTAGTGATGAAACAGCCTACGCGAACTGGGCGATAGGCC

GATTCACCATCTCCAAAACCTCGACCACGGTGGATCTGAAAATGACCAGT

CTGACAGCCGCGGACACGGCCACCTATTTCTGTGCCAGAGATGATAGTAG

TGACTGGGATGCAAAATTTAACTTGTGGGGCCAAGGGACCCTCGTCACCG

TCTCGAGCGCCTCCACCAAGGGCCCATCGGTCTTCCCCCTGGCACCCTCC

TCCAAGAGCACCTCTGGGGGCACAGCGGCCCTGGGCTGCCTGGTCAAGG.

In a further embodiment of the invention, polynucleotides encoding fragments of the antibody having binding specificity to IL-6 comprise, or alternatively consist of, one or more of the polynucleotide sequences of SEQ ID NO: 111; SEQ ID NO: 112; and SEQ ID NO: 113 which correspond to polynucleotides encoding the complementarity-determining regions (CDRs, or hypervariable regions) of the light chain variable sequence of SEQ ID NO: 101.

In a further embodiment of the invention, polynucleotides encoding fragments of the antibody having binding specificity to IL-6 comprise, or alternatively consist of, one or more of the polynucleotide sequences of SEQ ID NO: 114; SEQ ID NO: 115; and SEQ ID NO: 116 which correspond to polynucleotides encoding the complementarity-determining regions (CDRs, or hypervariable regions) of the heavy chain variable sequence of SEQ ID NO: 102.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 109 encoding the light chain variable region of SEQ ID NO: 101; the polynucleotide SEQ ID NO: 110 encoding the heavy chain variable region of SEQ ID NO: 102; polynucleotides encoding the complementarity-determining regions (SEQ ID NO: 111; SEQ ID NO: 112; and SEQ ID NO: 113) of the light chain variable region of SEQ ID NO: 101; and polynucleotides encoding the complementarity-determining regions (SEQ ID NO: 114; SEQ ID NO: 115; and SEQ ID NO: 116) of the heavy chain variable region of SEQ ID NO: 102.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 122:

(SEQ ID NO: 130)

ATGGACACGAGGGCCCCCACTCAGCTGCTGGGGCTCCTGCTGCTCTGGCT

CCCAGGTGCCACATTTGCAGCCGTGCTGACCCAGACACCATCACCCGTGT

-continued

CTGCAGCTGTGGGAGGCACAGTCACCATCAGTTGCCAGTCCAGTCAGAGT

GTTGGTAATAACCAGGACTTATCCTGGTTTCAGCAGAGACCAGGGCAGCC

TCCCAAGCTCCTGATCTACGAAATATCCAAACTGGAATCTGGGGTCCCAT

CGCGGTTCAGCGGCAGTGGATCTGGGACACACTTCACTCTCACCATCAGC

GGCGTACAGTGTGACGATGCTGCCACTTACTACTGTCTAGGCGGTTATGA

TGATGATGCTGATAATGCT

In another embodiment of the invention, polynucleotides of the invention comprise, or alternatively consist of, the following polynucleotide sequence encoding the variable heavy chain polypeptide sequence of SEQ ID NO: 123:

(SEQ ID NO: 131)

ATGGAGACTGGGCTGCGCTGGCTTCTCCTGGTCGCTGTGCTCAAAGGTGT

CCAGTGTCACTCGGTGGAGGAGTCCGGGGGTCGCCTGGTCACGCCTGGGA

CACCCCTGACACTCACCTGCACAGTCTCTGGATTCTCCCTCAGTAGTCGT

ACAATGTCCTGGGTCCGCCAGGCTCCAGGGAAGGGGCTGGAGTGGATCGG

ATACATTTGGAGTGGTGGTAGCACATACTACGCGACCTGGGCGAAAGGCC

GATTCACCATCTCCAAAACCTCGACCACGGTGGATCTGAAAATCACCAGT

CCGACAACCGAGGACACGGCCACCTATTTCTGTGCCAGATTGGGCGATAC

TGGTGGTCACGCTTATGCTACTCGCTTAAATCTC.

In a further embodiment of the invention, polynucleotides encoding fragments of the antibody having binding specificity to IL-6 comprise, or alternatively consist of, one or more of the polynucleotide sequences of SEQ ID NO: 132; SEQ ID NO: 133; and SEQ ID NO: 134 which correspond to polynucleotides encoding the complementarity-determining regions (CDRs, or hypervariable regions) of the light chain variable sequence of SEQ ID NO: 122.

In a further embodiment of the invention, polynucleotides encoding fragments of the antibody having binding specificity to IL-6 comprise, or alternatively consist of, one or more of the polynucleotide sequences of SEQ ID NO: 135; SEQ ID NO: 136; and SEQ ID NO: 137 which correspond to polynucleotides encoding the complementarity-determining regions (CDRs, or hypervariable regions) of the heavy chain variable sequence of SEQ ID NO: 123.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 130 encoding the light chain variable region of SEQ ID NO: 122; the polynucleotide SEQ ID NO: 131 encoding the heavy chain variable region of SEQ ID NO: 123; polynucleotides encoding the complementarity-determining regions (SEQ ID NO: 132; SEQ ID NO: 133; and SEQ ID NO: 134) of the light chain variable region of SEQ ID NO: 122; and polynucleotides encoding the complementarity-determining regions (SEQ ID NO: 135; SEQ ID NO: 136; and SEQ ID NO: 137) of the heavy chain variable region of SEQ ID NO: 123.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 138:

(SEQ ID NO: 146)

ATGGACACGAGGGCCCCCACTCAGCTGCTGGGGCTCCTGCTGCTCTGGCT

CCCAGGTGCCACATTTGCAGCCGTGCTGACCCAGACACCATCGTCCGTGT

CTGCAGCTGTGGGAGGCACAGTCAGCATCAGTTGCCAGTCCAGTCAGAGT

GTTTATAGTAATAAGTACCTAGCCTGGTATCAGCAGAAACCAGGGCAGCC

TCCCAAGCTCCTGATCTACTGGACATCCAAACTGGCATCTGGGGCCCCAT

CACGGTTCAGCGGCAGTGGATCTGGGACACAATTCACTCTCACCATCAGC

GGCGTGCAGTGTGACGATGCTGCCACTTACTACTGTCTAGGCGCTTATGA

TGATGATGCTGATAATGCT

In another embodiment of the invention, polynucleotides of the invention comprise, or alternatively consist of, the following polynucleotide sequence encoding the variable heavy chain polypeptide sequence of SEQ ID NO: 139:

(SEQ ID NO: 147)

ATGGAGACTGGGCTGCGCTGGCTTCTCCTGGTCGCTGTGCTCAAAG

GTGTCCAGTGTCAGTCGGTGGAAGAGTCCGGGGGTCGCCTGGTCAAGC

CTGACGAAACCCTGACACTCACCTGCACAGCCTCTGGATTCTCCCTGGA

GGGCGGCTACATGACCTGGGTCCGCCAGGCTCCAGGGAAGGGGCTGGA

ATGGATCGGAATCAGTTATGATAGTGGTAGCACATACTACGCGAGCTGGG

CGAAAGGCCGATTCACCATCTCCAAGACCTCGTCGACCACGGTGGATCT

GAAAATGACCAGTCTGACAACCGAGGACACGGCCACCTATTTCTGCGTCA

GATCACTAAAATATCCTACTGTTACTTCTGATGACTTG.

In a further embodiment of the invention, polynucleotides encoding fragments of the antibody having binding specificity to IL-6 comprise, or alternatively consist of, one or more of the polynucleotide sequences of SEQ ID NO: 148; SEQ ID NO: 149; and SEQ ID NO: 150 which correspond to polynucleotides encoding the complementarity-determining regions (CDRs, or hypervariable regions) of the light chain variable sequence of SEQ ID NO: 138.

In a further embodiment of the invention, polynucleotides encoding fragments of the antibody having binding specificity to IL-6 comprise, or alternatively consist of, one or more of the polynucleotide sequences of SEQ ID NO: 151; SEQ ID NO: 152; and SEQ ID NO: 153 which correspond to polynucleotides encoding the complementarity-determining regions (CDRs, or hypervariable regions) of the heavy chain variable sequence of SEQ ID NO: 139.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 146 encoding the light chain variable region of SEQ ID NO: 138; the polynucleotide SEQ ID NO: 147 encoding the heavy chain variable region of SEQ ID NO: 139; polynucleotides encoding the complementarity-determining regions (SEQ ID NO: 148; SEQ ID NO: 149; and SEQ ID NO: 150) of the light chain variable region of SEQ ID NO: 138; and polynucleotides encoding the complementarity-determining regions (SEQ ID NO: 151; SEQ ID NO: 152; and SEQ ID NO: 153) of the heavy chain variable region of SEQ ID NO: 139.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 154:

(SEQ ID NO: 162)

```
ATGGACACGAGGGCCCCCACTCAGCTGCTGGGGCTCCTGCTGCTCT
GGCTCCCAGGTGCCACATTTGCAGCCGTGCTGACCCAGACACCATCACCC
GTGTCTGCAGCTGTGGGAGGCACAGTCACCATCAGTTGCCAGTCCAGTCA
GAGTGTTTATAATAATAACGACTTAGCCTGGTATCAGCAGAAACCAGGG
CAGCCTCCTAAACTCCTGATCTATTATGCATCCACTCTGGCATCTGGGG
TCCCATCGCGGTTCAAAGGCAGTGGATCTGGGACACAGTTCACTCTCAC
CATCAGCGGCGTGCAGTGTGACGATGCTGCCGCTTACTACTGTCTAGGC
GGTTATGATGATGATGCTGATAATGCT
```

In another embodiment of the invention, polynucleotides of the invention comprise, or alternatively consist of, the following polynucleotide sequence encoding the variable heavy chain polypeptide sequence of SEQ ID NO: 155:

(SEQ ID NO: 163)

```
ATGGAGACTGGGCTGCGCTGGCTTCTCCTGGTCGCTGTGCTCAAAG
GTGTCCAGTGTCAGTCGGTGGAGGAGTCCGGGGGTCGCCTGGTCACGCCT
GGGACACCCCTGACACTCACCTGCACAGTATCTGGATTATCCCTCAGTAG
CAATACAATAAACTGGGTCCGCCAGGCTCCAGGGAAGGGGCTGGAGTGG
ATCGGATACATTTGGAGTGGTGGTAGTACATACTACGCGAGCTGGGTGA
ATGGTCGATTCACCATCTCCAAAACCTCGACCACGGTGGATCTGAAAAT
CACCAGTCCGACAACCGAGGACACGGCCACCTATTTCTGTGCCAGAGG
GGGTTACGCTAGTGGTGGTTATCCTTATGCCACTCGGTTGGATCTC.
```

In a further embodiment of the invention, polynucleotides encoding fragments of the antibody having binding specificity to IL-6 comprise, or alternatively consist of, one or more of the polynucleotide sequences of SEQ ID NO: 164; SEQ ID NO: 165; and SEQ ID NO: 166 which correspond to polynucleotides encoding the complementarity-determining regions (CDRs, or hypervariable regions) of the light chain variable sequence of SEQ ID NO: 154.

In a further embodiment of the invention, polynucleotides encoding fragments of the antibody having binding specificity to IL-6 comprise, or alternatively consist of, one or more of the polynucleotide sequences of SEQ ID NO: 167; SEQ ID NO: 168; and SEQ ID NO: 169 which correspond to polynucleotides encoding the complementarity-determining regions (CDRs, or hypervariable regions) of the heavy chain variable sequence of SEQ ID NO: 155.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 162 encoding the light chain variable region of SEQ ID NO: 154; the polynucleotide SEQ ID NO: 163 encoding the heavy chain variable region of SEQ ID NO: 155; polynucleotides encoding the complementarity-determining regions (SEQ ID NO: 164; SEQ ID NO: 165; and SEQ ID NO: 166) of the light chain variable region of SEQ ID NO: 154; and polynucleotides encoding the complementarity-determining regions (SEQ ID NO: 167; SEQ ID NO: 168; and SEQ ID NO: 169) of the heavy chain variable region of SEQ ID NO: 155.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 170:

(SEQ ID NO: 178)

```
ATGGACACGAGGGCCCCCACTCAGCTGCTGGGGCTCCTGCTGCTCT
GGCTCCCAGGTGCCACATTTGCAGCCGTGCTGACCCAGACACCATCCTCC
GTGTCTGCAGCTGTGGGAGGCACAGTCACCATCAATTGCCAGTCCAGTCA
GAGTGTTTATAATAACGACTACTTATCCTGGTATCAACAGAGGCCAGGG
CAACGTCCCAAGCTCCTAATCTATGGTGCTTCCAAACTGGCATCTGGGG
TCCCGTCACGGTTCAAAGGCAGTGGATCTGGGAAACAGTTTACTCTCAC
CATCAGCGGCGTGCAGTGTGACGATGCTGCCACTTACTACTGTCTGGGC
GATTATGATGATGATGCTGATAATACT
```

In another embodiment of the invention, polynucleotides of the invention comprise, or alternatively consist of, the following polynucleotide sequence encoding the variable heavy chain polypeptide sequence of SEQ ID NO: 171:

(SEQ ID NO: 179)

```
ATGGAGACTGGGCTGCGCTGGCTTCTCCTGGTCGCTGTGCTCAAAG
GTGTCCAGTGTCAGTCGCTGGAGGAGTCCGGGGGTCGCCTGGTCACGCCT
GGGACACCCCTGACACTCACTTGCACAGTCTCTGGATTCACCCTCAGTA
CCAACTACTACCTGAGCTGGGTCCGCCAGGCTCCAGGGAAGGGGCTAG
AATGGATCGGAATCATTTATCCTAGTGGTAACACATATTGCGCGAAGTGG
GCGAAAGGCCGATTCACCATCTCCAAAACCTCGTCGACCACGGTGGATC
TGAAAATGACCAGTCCGACAACCGAGGACACAGCCACGTATTTCTGTGCC
AGAAATTATGGTGGTGATGAAAGTTTG.
```

In a further embodiment of the invention, polynucleotides encoding fragments of the antibody having binding specificity to IL-6 comprise, or alternatively consist of, one or more of the polynucleotide sequences of SEQ ID NO: 180; SEQ ID NO: 181; and SEQ ID NO: 182 which correspond to polynucleotides encoding the complementarity-determining regions (CDRs, or hypervariable regions) of the light chain variable sequence of SEQ ID NO: 170.

In a further embodiment of the invention, polynucleotides encoding fragments of the antibody having binding specificity to IL-6 comprise, or alternatively consist of, one or more of the polynucleotide sequences of SEQ ID NO: 183; SEQ ID NO: 184; and SEQ ID NO: 185 which correspond to polynucleotides encoding the complementarity-determining regions (CDRs, or hypervariable regions) of the heavy chain variable sequence of SEQ ID NO: 171.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 178 encoding the light chain variable region of SEQ ID NO: 170; the polynucleotide SEQ ID NO: 179 encoding the heavy chain variable region of SEQ ID NO: 171; polynucleotides encoding the complementarity-determining regions (SEQ ID NO: 180; SEQ ID NO: 181; and SEQ ID NO: 182) of the light chain variable region of SEQ ID NO: 170; and polynucleotides encoding the complementarity-determining regions (SEQ ID NO: 183; SEQ ID NO: 184; and SEQ ID NO: 185) of the heavy chain variable region of SEQ ID NO: 171.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 186:

(SEQ ID NO: 194)

```
ATGGACACGAGGGCCCCCACTCAGCTGCTGGGGCTCCTGCTGCTCT
GGCTCCCAGGTGCCAGATGTGATGTTGTGATGACCCAGACTCCAGCCTCC
GTGGAGGCAGCTGTGGGAGGCACAGTCACCATCAAGTGCCAGGCCAGTG
AGACCATTGGCAATGCATTAGCCTGGTATCAGCAGAAATCAGGGCAGCCT
CCCAAGCTCCTGATCTACAAGGCATCCAAACTGGCATCTGGGGTCCCATC
GCGGTTCAAAGGCAGTGGATCTGGGACAGAGTACACTCTCACCATCAGCG
ACCTGGAGTGTGCCGATGCTGCCACTTACTACTGTCAATGGTGTTATTTT
GGTGATAGTGTT
```

In another embodiment of the invention, polynucleotides of the invention comprise, or alternatively consist of, the following polynucleotide sequence encoding the variable heavy chain polypeptide sequence of SEQ ID NO: 187:

(SEQ ID NO: 195)

```
ATGGAGACTGGGCTGCGCTGGCTTCTCCTGGTCACTGTGCTCAAAG
GTGTCCAGTGTCAGGAGCAGCTGGTGGAGTCCGGGGGAGGCCTGGTCCAG
CCTGAGGGATCCCTGACACTCACCTGCACAGCCTCTGGATTCGACTTCAG
TAGCGGCTACTACATGTGCTGGGTCCGCCAGGCTCCAGGGAAGGGGCT
GGAGTGGATCGCGTGTATTTTCACTATTACTACTAACACTTACTACGCGA
GCTGGGCGAAAGGCCGATTCACCATCTCCAAGACCTCGTCGACCACGG
TGACTCTGCAAATGACCAGTCTGACAGCCGCGGACACGGCCACCTATCT
CTGTGCGAGAGGGATTTATTCTGATAATAATTATTATGCCTTG.
```

In a further embodiment of the invention, polynucleotides encoding fragments of the antibody having binding specificity to IL-6 comprise, or alternatively consist of, one or more of the polynucleotide sequences of SEQ ID NO: 196; SEQ ID NO: 197; and SEQ ID NO: 198 which correspond to polynucleotides encoding the complementarity-determining regions (CDRs, or hypervariable regions) of the light chain variable sequence of SEQ ID NO: 186.

In a further embodiment of the invention, polynucleotides encoding fragments of the antibody having binding specificity to IL-6 comprise, or alternatively consist of, one or more of the polynucleotide sequences of SEQ ID NO: 199; SEQ ID NO: 200; and SEQ ID NO: 201 which correspond to polynucleotides encoding the complementarity-determining regions (CDRs, or hypervariable regions) of the heavy chain variable sequence of SEQ ID NO: 187.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 194 encoding the light chain variable region of SEQ ID NO: 186; the polynucleotide SEQ ID NO: 195 encoding the heavy chain variable region of SEQ ID NO: 187; polynucleotides encoding the complementarity-determining regions (SEQ ID NO: 196; SEQ ID NO: 197; and SEQ ID NO: 198) of the light chain variable region of SEQ ID NO: 186; and polynucleotides encoding the complementarity-determining regions (SEQ ID NO: 199; SEQ ID NO: 200; and SEQ ID NO: 201) of the heavy chain variable region of SEQ ID NO: 187.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 202:

(SEQ ID NO: 210)

```
ATGGACACGAGGGCCCCCACTCAGCTGCTGGGGCTCCTGCTGCTCT
GGCTCCCAGGTGCCAGATGTGATGTTGTGATGACCCAGACTCCAGCCTCC
GTGGAGGCAGCTGTGGGAGGCACAGTCACCATCAAGTGCCAGGCCAGTG
AGAGCATTGGCAATGCATTAGCCTGGTATCAGCAGAAACCAGGGCAGCCT
CCCAAGCTCCTGATCTACAAGGCATCCACTCTGGCATCTGGGGTCCCATC
GCGGTTCAGCGGCAGTGGATCTGGGACAGAGTTCACTCTCACCATCAGCG
GCGTGCAGTGTGCCGATGCTGCCGCTTACTACTGTCAATGGTGTTATTTT
GGTGATAGTGTT
```

In another embodiment of the invention, polynucleotides of the invention comprise, or alternatively consist of, the following polynucleotide sequence encoding the variable heavy chain polypeptide sequence of SEQ ID NO: 203:

(SEQ ID NO: 211)

```
ATGGAGACTGGGCTGCGCTGGCTTCTCCTGGTCGCTGTGCTCAAAG
GTGTCCAGTGTCAGCAGCAGCTGGTGGAGTCCGGGGGAGGCCTGGTCAAG
CCGGGGGCATCCCTGACACTCACCTGCAAAGCCTCTGGATTCTCCTTCA
GTAGCGGCTACTACATGTGCTGGGTCCGCCAGGCTCCAGGGAAGGGGCT
GGAGTCGATCGCATGCATTTTTACTATTACTGATAACACTTACTACGCG
AACTGGGCGAAAGGCCGATTCACCATCTCCAAGCCCTCGTCGCCCACGG
TGACTCTGCAAATGACCAGTCTGACAGCCGCGGACACGGCCACCTATTTC
TGTGCGAGGGGGATTTATTCTACTGATAATTATTATGCCTTG.
```

In a further embodiment of the invention, polynucleotides encoding fragments of the antibody having binding specificity to IL-6 comprise, or alternatively consist of, one or more of the polynucleotide sequences of SEQ ID NO: 212; SEQ ID NO: 213; and SEQ ID NO: 214 which correspond to polynucleotides encoding the complementarity-determining regions (CDRs, or hypervariable regions) of the light chain variable sequence of SEQ ID NO: 202.

In a further embodiment of the invention, polynucleotides encoding fragments of the antibody having binding specificity to IL-6 comprise, or alternatively consist of, one or more of the polynucleotide sequences of SEQ ID NO: 215; SEQ ID NO: 216; and SEQ ID NO: 217 which correspond to polynucleotides encoding the complementarity-determining regions (CDRs, or hypervariable regions) of the heavy chain variable sequence of SEQ ID NO: 203.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 210 encoding the light chain variable region of SEQ ID NO: 202; the polynucleotide SEQ ID NO: 211 encoding the heavy chain variable region of SEQ ID NO: 203; polynucleotides encoding the complementarity-determining regions (SEQ ID NO: 212; SEQ ID NO: 213; and SEQ ID NO: 214) of the light chain variable region of SEQ ID NO: 202; and polynucleotides encoding the complementarity-determining regions (SEQ ID NO: 215; SEQ ID NO: 216; and SEQ ID NO: 217) of the heavy chain variable region of SEQ ID NO: 203.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 218:

(SEQ ID NO: 226)

ATGGACACGAGGGCCCCCACTCAGCTGCTGGGGCTCCTGCTGCTCT

GGCTCCCAGGTGCCAGATGTGATGTTGTGATGACCCAGACTCCAGCCTCC

GTGGAGGCAGCTGTGGGAGGCACAGTCACCATCAAGTGCCAGGCCAGTC

AGAGCGTTAGTAGCTACTTAAACTGGTATCAGCAGAAACCAGGGCAGCCT

CCCAAGCTCCTGATCTACAGGGCATCCACTCTGGAATCTGGGGTCCCATC

GCGGTTCAAAGGCAGTGGATCTGGGACAGAGTTCACTCTCACCATCAGCG

ACCTGGAGTGTGCCGATGCTGCCACTTACTACTGTCAATGTACTTATGGT

ACTAGTAGTAGTTATGGTGCTGCT

In another embodiment of the invention, polynucleotides of the invention comprise, or alternatively consist of, the following polynucleotide sequence encoding the variable heavy chain polypeptide sequence of SEQ ID NO: 219:

(SEQ ID NO: 227)

ATGGAGACTGGGCTGCGCTGGCTTCTCCTGGTCGCTGTGCTCAAAG

GTGTCCAGTGTCAGTCGGTGGAGGAGTCCGGGGGTCGCCTGGTCACGCCT

GGGACACCCCTGACACTCACCTGCACCGTCTCTGGTATCTCCCTCAGTA

-continued

GCAATGCAATAAGCTGGGTCCGCCAGGCTCCAGGGAAGGGGCTGGAAT

GGATCGGAATCATTAGTTATAGTGGTACCACATACTACGCGAGCTGGGC

GAAAGGCCGATTCACCATCTCCAAAACCTCGTCGACCACGGTGGATCT

GAAAATCACTAGTCCGACAACCGAGGACACGGCCACCTACTTCTGTGC

CAGAGATGACCCTACGACAGTTATGGTTATGTTGATACCTTTTGGAGCC

GGCATGGACCTC.

In a further embodiment of the invention, polynucleotides encoding fragments of the antibody having binding specificity to IL-6 comprise, or alternatively consist of, one or more of the polynucleotide sequences of SEQ ID NO: 228; SEQ ID NO: 229; and SEQ ID NO: 230 which correspond to polynucleotides encoding the complementarity-determining regions (CDRs, or hypervariable regions) of the light chain variable sequence of SEQ ID NO: 218.

In a further embodiment of the invention, polynucleotides encoding fragments of the antibody having binding specificity to IL-6 comprise, or alternatively consist of, one or more of the polynucleotide sequences of SEQ ID NO: 231; SEQ ID NO: 232; and SEQ ID NO: 233 which correspond to polynucleotides encoding the complementarity-determining regions (CDRs, or hypervariable regions) of the heavy chain variable sequence of SEQ ID NO: 219.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 226 encoding the light chain variable region of SEQ ID NO: 218; the polynucleotide SEQ ID NO: 227 encoding the heavy chain variable region of SEQ ID NO: 219; polynucleotides encoding the complementarity-determining regions (SEQ ID NO: 228; SEQ ID NO: 229; and SEQ ID NO: 230) of the light chain variable region of SEQ ID NO: 218; and polynucleotides encoding the complementarity-determining regions (SEQ ID NO: 231; SEQ ID NO: 232; and SEQ ID NO: 233) of the heavy chain variable region of SEQ ID NO: 219.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 234:

(SEQ ID NO: 242)

ATGGACACGAGGGCCCCCACTCAGCTGCTGGGGCTCCTGCTGCTCT

GGCTCCCAGGTGCCACATTTGCCCAAGTGCTGACCCAGACTGCATCGCCC

GTGTCTGCAGCTGTGGGAGGCACAGTCACCATCAACTGCCAGGCCAGTCA

GAGTGTTTATAAGAACAACTACTTATCCTGGTATCAGCAGAAACCAGGG

CAGCCTCCCAAAGGCCTGATCTATTCTGCATCGACTCTAGATTCTGGGG

TCCCATTGCGGTTCAGCGGCAGTGGATCTGGGACACAGTTCACTCTCAC

CATCAGCGACGTGCAGTGTGACGATGCTGCCACTTACTACTGTCTAGGC

AGTTATGATTGTAGTAGTGGTGATTGTTATGCT

In another embodiment of the invention, polynucleotides of the invention comprise, or alternatively consist of, the following polynucleotide sequence encoding the variable heavy chain polypeptide sequence of SEQ ID NO: 235:

(SEQ ID NO: 243)
ATGGAGACTGGGCTGCGCTGGCTTCTCCTGGTCGCTGTGCTCAAAG

GTGTCCAGTGTCAGTCGTTGGAGGAGTCCGGGGGAGACCTGGTCAAGCCT

GAGGGATCCCTGACACTCACCTGCACAGCCTCTGGATTCTCCTTCAGTAG

CTACTGGATGTGCTGGGTCCGCCAGGCTCCAGGGAAGGGGCTGGAGTGG

ATCGCATGCATTGTTACTGGTAATGGTAACACTTACTACGCGAACTGGG

CGAAAGGCCGATTCACCATCTCCAAAACCTCGTCGACCACGGTGACTC

TGCAAATGACCAGTCTGACAGCCGCGGACACGGCCACCTATTTTTGTGC

GAAAGCCTATGACTTG.

In a further embodiment of the invention, polynucleotides encoding fragments of the antibody having binding specificity to IL-6 comprise, or alternatively consist of, one or more of the polynucleotide sequences of SEQ ID NO: 244; SEQ ID NO: 245; and SEQ ID NO: 246 which correspond to polynucleotides encoding the complementarity-determining regions (CDRs, or hypervariable regions) of the light chain variable sequence of SEQ ID NO: 234.

In a further embodiment of the invention, polynucleotides encoding fragments of the antibody having binding specificity to IL-6 comprise, or alternatively consist of, one or more of the polynucleotide sequences of SEQ ID NO: 247; SEQ ID NO: 248; and SEQ ID NO: 249 which correspond to polynucleotides encoding the complementarity-determining regions (CDRs, or hypervariable regions) of the heavy chain variable sequence of SEQ ID NO: 235.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 242 encoding the light chain variable region of SEQ ID NO: 234; the polynucleotide SEQ ID NO: 243 encoding the heavy chain variable region of SEQ ID NO: 235; polynucleotides encoding the complementarity-determining regions (SEQ ID NO: 244; SEQ ID NO: 245; and SEQ ID NO: 246) of the light chain variable region of SEQ ID NO: 234; and polynucleotides encoding the complementarity-determining regions (SEQ ID NO: 247; SEQ ID NO: 248; and SEQ ID NO: 249) of the heavy chain variable region of SEQ ID NO: 235.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 250:

(SEQ ID NO: 258)
ATGGACACGAGGGCCCCCACTCAGCTGCTGGGGCTCCTGCTGCTCT

GGCTCCCAGGTTCCACATTTGCCGCCGTGCTGACCCAGACTCCATCTCC

CGTGTCTGCAGCTGTGGGAGGCACAGTCAGCATCAGTTGCCAGGCCAGT

CAGAGTGTTTATGACAACAACTATTTATCCTGGTATCAGCAGAAACCAG

-continued

GACAGCCTCCCAAGCTCCTGATCTATGGTGCATCCACTCTGGCATCTG

GGGTCCCATCGCGGTTCAAAGGCACGGGATCTGGGACACAGTTCACTC

TCACCATCACAGACGTGCAGTGTGACGATGCTGCCACTTACTATTGTGC

AGGCGTTTTTAATGATGATAGTGATGATGCC

In another embodiment of the invention, polynucleotides of the invention comprise, or alternatively consist of, the following polynucleotide sequence encoding the variable heavy chain polypeptide sequence of SEQ ID NO: 251:

(SEQ ID NO: 259)
ATGGAGACTGGGCTGCGCTGGCTTCTCCTGGTCGCTGTGCCCAAAG

GTGTCCAGTGTCAGTCGCTGGAGGAGTCCGGGGGTCGCCTGGTCACGCCT

GGGACACCCCTGACACTCACCTGCACACTCTCTGGATTCTCCCTCAGTGC

ATACTATATGAGCTGGGTCCGCCAGGCTCCAGGGAAGGGGCTGGAATGGA

TCGGATTCATTACTCTGAGTGATCATATATCTTACGCGAGGTGGGCGAAA

GGCCGATTCACCATCTCCAAAACCTCGACCACGGTGGATCTGAAAATGA

CCAGTCCGACAACCGAGGACACGGCCACCTATTTCTGTGCCAGGAGTCG

TGGCTGGGGTGCAATGGGTCGGTTGGATCTC.

In a further embodiment of the invention, polynucleotides encoding fragments of the antibody having binding specificity to IL-6 comprise, or alternatively consist of, one or more of the polynucleotide sequences of SEQ ID NO: 260; SEQ ID NO: 261; and SEQ ID NO: 262 which correspond to polynucleotides encoding the complementarity-determining regions (CDRs, or hypervariable regions) of the light chain variable sequence of SEQ ID NO: 250.

In a further embodiment of the invention, polynucleotides encoding fragments of the antibody having binding specificity to IL-6 comprise, or alternatively consist of, one or more of the polynucleotide sequences of SEQ ID NO: 263; SEQ ID NO: 264; and SEQ ID NO: 265 which correspond to polynucleotides encoding the complementarity-determining regions (CDRs, or hypervariable regions) of the heavy chain variable sequence of SEQ ID NO: 251.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 258 encoding the light chain variable region of SEQ ID NO: 250; the polynucleotide SEQ ID NO: 259 encoding the heavy chain variable region of SEQ ID NO: 251; polynucleotides encoding the complementarity-determining regions (SEQ ID NO: 260; SEQ ID NO: 261; and SEQ ID NO: 262) of the light chain variable region of SEQ ID NO: 250; and polynucleotides encoding the complementarity-determining regions (SEQ ID NO: 263; SEQ ID NO: 264; and SEQ ID NO: 265) of the heavy chain variable region of SEQ ID NO: 251.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 266:

(SEQ ID NO: 274)
ATGGACACGAGGGCCCCCACTCAGCTGCTGGGGCTCCTGCTGCTCTGG

CTCCCAGGTGCCACATTCGCAGCCGTGCTGACCCAGACACCATCGCCCGT

GTCTGCGGCTGTGGGAGGCACAGTCACCATCAGTTGCCAGGCCAGTCAGA

GTGTTTATAACAACAAAAATTTAGCCTGGTATCAGCAGAAATCAGGGCAG

CCTCCCAAGCTCCTGATCTACTGGGCATCCACTCTGGCATCTGGGGTCTC

ATCGCGGTTCAGCGGCAGTGGATCTGGGACACAGTTCACTCTCACCGTCA

GCGGCGTGCAGTGTGACGATGCTGCCACTTACTACTGTCTAGGCGTTTTT

GATGATGATGCTGATAATGCT

In another embodiment of the invention, polynucleotides of the invention comprise, or alternatively consist of, the following polynucleotide sequence encoding the variable heavy chain polypeptide sequence of SEQ ID NO: 267:

(SEQ ID NO: 275)
ATGGAGACTGGGCTGCGCTGGCTTCTCCTGGTCGCTGTGCTCAAAGGT

GTCCAATGTCAGTCGGTGGAGGAGTCCGGGGGTCGCCTGGTCACGCCTGG

GACACCCCTGACACTCACCTGCACAGCCTCTGGATTCTCCCTCAGTAGCT

ACTCCATGACCTGGGTCCGCCAGGCTCCAGGGAAGGGGCTGGAATATATC

GGAGTCATTGGTACTAGTGGTAGCACATACTACGCGACCTGGGCGAAAGG

CCGATTCACCATCTCCAGAACCTCGACCACGGTGGCTCTGAAAATCACCA

GTCCGACAACCGAGGACACGGCCACCTATTTCTGTGTCAGGAGTCTTTCT

TCTATTACTTTCTTG.

In a further embodiment of the invention, polynucleotides encoding fragments of the antibody having binding specificity to IL-6 comprise, or alternatively consist of, one or more of the polynucleotide sequences of SEQ ID NO: 276; SEQ ID NO: 277; and SEQ ID NO: 278 which correspond to polynucleotides encoding the complementarity-determining regions (CDRs, or hypervariable regions) of the light chain variable sequence of SEQ ID NO: 266.

In a further embodiment of the invention, polynucleotides encoding fragments of the antibody having binding specificity to IL-6 comprise, or alternatively consist of, one or more of the polynucleotide sequences of SEQ ID NO: 279; SEQ ID NO: 280; and SEQ ID NO: 281 which correspond to polynucleotides encoding the complementarity-determining regions (CDRs, or hypervariable regions) of the heavy chain variable sequence of SEQ ID NO: 267.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 274 encoding the light chain variable region of SEQ ID NO: 266; the polynucleotide SEQ ID NO: 275 encoding the heavy chain variable region of SEQ ID NO: 267; polynucleotides encoding the complementarity-determining regions (SEQ ID NO: 276; SEQ ID NO: 277; and SEQ ID NO: 278) of the light chain variable region of SEQ ID NO: 266; and polynucleotides encoding the complementarity-determining regions (SEQ ID NO: 279; SEQ ID NO: 280; and SEQ ID NO: 281) of the heavy chain variable region of SEQ ID NO: 267.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 282:

(SEQ ID NO: 290)
ATGGACACGAGGGCCCCCACTCAGCTGCTGGGGCTCCTGCTGCTCTGG

CTCCCAGGTGCCAGATGTGCATTCGAATTGACCCAGACTCCAGCCTCCGT

GGAGGCAGCTGTGGGAGGCACAGTCACCATCAATTGCCAGGCCAGTCA

GAACATTTATAGATACTTAGCCTGGTATCAGCAGAAACCAGGGCAGCCT

CCCAAGTTCCTGATCTATCTGGCATCTACTCTGGCATCTGGGGTCCCATC

GCGGTTTAAAGGCAGTGGATCTGGGACAGAGTTCACTCTCACCATCAGC

GACCTGGAGTGTGCCGATGCTGCCACTTACTACTGTCAAAGTTATTATAG

TAGTAATAGTGTCGCT

In another embodiment of the invention, polynucleotides of the invention comprise, or alternatively consist of, the following polynucleotide sequence encoding the variable heavy chain polypeptide sequence of SEQ ID NO: 283:

(SEQ ID NO: 291)
ATGGAGACTGGGCTGCGCTGGCTTCTCCTGGTCGCTGTGCTCAAAGGT

GTCCAGTGTCAGGAGCAGCTGGTGGAGTCCGGGGGAGACCTGGTCCAGCC

TGAGGGATCCCTGACACTCACCTGCACAGCTTCTGAGTTAGACTTCAGT

AGCGGCTACTGGATATGCTGGGTCCGCCAGGTTCCAGGGAAGGGGCTGG

AGTGGATCGGATGCATTTATACTGGTAGTAGTGGTAGCACTTTTTACGCG

AGTTGGGCGAAAGGCCGATTCACCATCTCCAAAACCTCGTCGACCACGGT

GACTCTGCAAATGACCAGTCTGACAGCCGCGGACACGGCCACCTATTTCT

GTGCGAGAGGTTATAGTGGCTTTGGTTACTTTAAGTTG.

In a further embodiment of the invention, polynucleotides encoding fragments of the antibody having binding specificity to IL-6 comprise, or alternatively consist of, one or more of the polynucleotide sequences of SEQ ID NO: 292; SEQ ID NO: 293; and SEQ ID NO: 294 which correspond to polynucleotides encoding the complementarity-determining regions (CDRs, or hypervariable regions) of the light chain variable sequence of SEQ ID NO: 282.

In a further embodiment of the invention, polynucleotides encoding fragments of the antibody having binding specificity to IL-6 comprise, or alternatively consist of, one or more of the polynucleotide sequences of SEQ ID NO: 295; SEQ ID NO: 296; and SEQ ID NO: 297 which correspond to polynucleotides encoding the complementarity-determining regions (CDRs, or hypervariable regions) of the heavy chain variable sequence of SEQ ID NO: 283.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 290 encoding the light chain variable region of SEQ ID NO: 282; the polynucleotide SEQ ID NO: 291 encoding the heavy chain variable region of SEQ ID NO: 283; polynucleotides encoding the complementarity-determining regions (SEQ ID NO: 292; SEQ ID NO: 293; and SEQ ID NO: 294) of the light chain variable region of SEQ ID NO: 282; and polynucleotides encoding the complementarity-determining regions (SEQ ID NO: 295; SEQ ID NO: 296; and SEQ ID NO: 297) of the heavy chain variable region of SEQ ID NO: 283.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 298:

```
                                          (SEQ ID NO: 306)
ATGGACACGAGGGCCCCCACTCAGCTGCTGGGGCTCCTGCTGCTCTGG

CTCCCAGGTGCCAGATGTGCCTATGATATGACCCAGACTCCAGCCTCTGT

GGAGGTAGCTGTGGGAGGCACAGTCACCATCAAGTGCCAGGCCAGTGAG

GACATTTATAGGTTATTGGCCTGGTATCAACAGAAACCAGGGCAGCCTCC

CAAGCTCCTGATCTATGATTCATCCGATCTGGCATCTGGGGTCCCATCGC

GGTTCAAAGGCAGTGGATCTGGGACAGAGTTCACTCTCGCCATCAGCGGT

GGTGCAGTGTACGATGCTGCCACTTACTACTGTCAACAGGCTTGGAGTTA

TAGTGATATTGATAATGCT
```

In another embodiment of the invention, polynucleotides of the invention comprise, or alternatively consist of, the following polynucleotide sequence encoding the variable heavy chain polypeptide sequence of SEQ ID NO: 299:

```
                                          (SEQ ID NO: 307)
ATGGAGACTGGGCTGCGCTGGCTTCTCCTGGTCGCTGTGCTCAAAGGT

GTCCAGTGTCAGTCGGTGGAGGAGTCCGGGGGTCGCCTGGTCACGCCGGG

GACACCCCTGACACTCACCTGCACAGCCTCTGGATTCTCCCTCAGTAGC

TACTACATGAGCTGGGTCCGCCAGGCTCCAGGGAAGGGGCTGGAATGGA

TCGGAATCATTACTACTAGTGGTAATACATTTTACGCGAGCTGGGCGAAA

GGCCGGCTCACCATCTCCAGAACCTCGACCACGGTGGATCTGAAAATCA

CCAGTCCGACAACCGAGGACACGGCCACCTATTTCTGTGCCAGAACTTCT

GATATTTTTTATTATCGTAACTTG.
```

In a further embodiment of the invention, polynucleotides encoding fragments of the antibody having binding specificity to IL-6 comprise, or alternatively consist of, one or more of the polynucleotide sequences of SEQ ID NO: 308; SEQ ID NO: 309; and SEQ ID NO: 310 which correspond to polynucleotides encoding the complementarity-determining regions (CDRs, or hypervariable regions) of the light chain variable sequence of SEQ ID NO: 298.

In a further embodiment of the invention, polynucleotides encoding fragments of the antibody having binding specificity to IL-6 comprise, or alternatively consist of, one or more of the polynucleotide sequences of SEQ ID NO: 311; SEQ ID NO: 312; and SEQ ID NO: 313 which correspond to polynucleotides encoding the complementarity-determining regions (CDRs, or hypervariable regions) of the heavy chain variable sequence of SEQ ID NO: 299.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 306 encoding the light chain variable region of SEQ ID NO: 298; the polynucleotide SEQ ID NO: 307 encoding the heavy chain variable region of SEQ ID NO: 299; polynucleotides encoding the complementarity-determining regions (SEQ ID NO: 308; SEQ ID NO: 309; and SEQ ID NO: 310) of the light chain variable region of SEQ ID NO: 298; and polynucleotides encoding the complementarity-determining regions (SEQ ID NO: 311; SEQ ID NO: 312; and SEQ ID NO: 313) of the heavy chain variable region of SEQ ID NO: 299.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 314:

```
                                          (SEQ ID NO: 322)
ATGGACACGAGGGCCCCCACTCAGCTGCTGGGGCTCCTGCTGCTCTGG

CTCCCAGGTGCCACGTTTGCAGCCGTGCTGACCCAGACTGCATCACCCGT

GTCTGCCGCTGTGGGAGCCACAGTCACCATCAACTGCCAGTCCAGTCAGA

GTGTTTATAATGACATGGACTTAGCCTGGTTTCAGCAGAAACCAGGGCAG

CCTCCCAAGCTCCTGATCTATTCTGCATCCACTCTGGCATCTGGGGTCCC

ATCGCGGTTCAGCGGCAGTGGATCTGGGACAGAGTTCACTCTCACCATCA

GCGGCGTGCAGTGTGACGATGCTGCCACTTACTACTGTCTAGGCGCTTTT

GATGATGATGCTGATAATACT
```

In another embodiment of the invention, polynucleotides of the invention comprise, or alternatively consist of, the following polynucleotide sequence encoding the variable heavy chain polypeptide sequence of SEQ ID NO: 315:

```
                                          (SEQ ID NO: 323)
ATGGAGACTGGGCTGCGCTGGCTTCTCCTGGTCGCTGTGCTCAAAGGT

GTCCAGTGTCAGTCGGTGGAGGAGTCCGGGGGTCGCCTGGTCACGCCTGG

GACACCCCTGACACTCACCTGCACAGTCTCTGGATTCTCCCTCACTAGGC

ATGCAATAACCTGGGTCCGCCAGGCTCCAGGGAAGGGGCTGGAATGGAT

CGGATGCATTTGGAGTGGTGGTAGCACATACTACGCGACCTGGGCGAAAG

GCCGATTCACCATCTCCAAAACCTCGACCACGGTGGATCTCAGAATCACC

AGTCCGACAACCGAGGACACGGCCACCTACTTCTGTGCCAGAGTCATTG

GCGATACTGCTGGTTATGCTTATTTTACGGGGCTTGACTTG.
```

In a further embodiment of the invention, polynucleotides encoding fragments of the antibody having binding specificity to IL-6 comprise, or alternatively consist of, one or more of the polynucleotide sequences of SEQ ID NO: 324; SEQ ID NO: 325; and SEQ ID NO: 326 which correspond to polynucleotides encoding the complementarity-determining regions (CDRs, or hypervariable regions) of the light chain variable sequence of SEQ ID NO: 314.

In a further embodiment of the invention, polynucleotides encoding fragments of the antibody having binding specificity to IL-6 comprise, or alternatively consist of, one or more of the polynucleotide sequences of SEQ ID NO: 327; SEQ ID NO: 328; and SEQ ID NO: 329 which correspond to polynucleotides encoding the complementarity-determining regions (CDRs, or hypervariable regions) of the heavy chain variable sequence of SEQ ID NO: 315.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 322 encoding the light chain variable region of SEQ ID NO: 314; the polynucleotide SEQ ID NO: 323 encoding the heavy chain variable region of SEQ ID NO: 315; polynucleotides encoding the complementarity-determining regions (SEQ ID NO: 324; SEQ ID NO: 325; and SEQ ID NO: 326) of the light chain variable region of SEQ ID NO: 314; and polynucleotides encoding the complementarity-determining regions (SEQ ID NO: 327; SEQ ID NO: 328; and SEQ ID NO: 329) of the heavy chain variable region of SEQ ID NO: 315.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 330:

(SEQ ID NO: 338)

ATGGACACGAGGGCCCCCACTCAGCTGCTGGGGCTCCTGCTGCTCTGG

CTCCCAGGTGCCAGATGTGCCTATGATATGACCCAGACTCCAGCCTCTGT

GGAGGTAGCTGTGGGAGGCACAGTCACCATCAAGTGCCAGGCCAGTCAG

AGTGTTTATAATTGGTTATCCTGGTATCAGCAGAAACCAGGGCAGCCTCC

CAAGCTCCTGATCTATACTGCATCCAGTCTGGCATCTGGGGTCCCATCGC

GGTTCAGTGGCAGTGGATCTGGGACAGAGTTCACTCTCACCATCAGCGGC

GTGGAGTGTGCCGATGCTGCCACTTACTACTGTCAACAGGGTTATACTAG

TGATGTTGATAATGTT

In another embodiment of the invention, polynucleotides of the invention comprise, or alternatively consist of, the following polynucleotide sequence encoding the variable heavy chain polypeptide sequence of SEQ ID NO: 331:

(SEQ ID NO: 339)

ATGGAGACTGGGCTGCGCTGGCTTCTCCTGGTCGCTGTGCTCAAAGGT

GTCCAGTGTCAGTCGCTGGAGGAGGCCGGGGGTCGCCTGGTCACGCCTGG

GACACCCCTGACACTCACCTGCACAGTCTCTGGAATCGACCTCAGTAGCT

ATGCAATGGGCTGGGTCCGCCAGGCTCCAGGGAAGGGGCTGGAATACATC

GGAATCATTAGTAGTAGTGGTAGCACATACTACGCGACCTGGGCGAAAGG

CCGATTCACCATCTCACAAGCCTCGTCGACCACGGTGGATCTGAAAATTA

CCAGTCCGACAACCGAGGACTCGGCCACATATTTCTGTGCCAGAGGGGG

TGCTGGTAGTGGTGGTGTTTGGCTGCTTGATGGTTTTGATCCC.

In a further embodiment of the invention, polynucleotides encoding fragments of the antibody having binding specificity to IL-6 comprise, or alternatively consist of, one or more of the polynucleotide sequences of SEQ ID NO: 340; SEQ ID NO: 341; and SEQ ID NO: 342 which correspond to polynucleotides encoding the complementarity-determining regions (CDRs, or hypervariable regions) of the light chain variable sequence of SEQ ID NO: 330.

In a further embodiment of the invention, polynucleotides encoding fragments of the antibody having binding specificity to IL-6 comprise, or alternatively consist of, one or more of the polynucleotide sequences of SEQ ID NO: 343; SEQ ID NO: 344; and SEQ ID NO: 345 which correspond to polynucleotides encoding the complementarity-determining regions (CDRs, or hypervariable regions) of the heavy chain variable sequence of SEQ ID NO: 331.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 338 encoding the light chain variable region of SEQ ID NO: 330; the polynucleotide SEQ ID NO: 339 encoding the heavy chain variable region of SEQ ID NO: 331; polynucleotides encoding the complementarity-determining regions (SEQ ID NO: 340; SEQ ID NO: 341; and SEQ ID NO: 342) of the light chain variable region of SEQ ID NO: 330; and polynucleotides encoding the complementarity-determining regions (SEQ ID NO: 343; SEQ ID NO: 344; and SEQ ID NO: 345) of the heavy chain variable region of SEQ ID NO: 331.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 346.

(SEQ ID NO: 354)

ATGGACACGAGGGCCCCCACTCAGCTGCTGGGGCTCCTGCTGCTCTGG

CTCCCAGGTGCCAAATGTGCCGATGTTGTGATGACCCAGACTCCAGCCTC

CGTGTCTGCAGCTGTGGGAGGCACAGTCACCATCAATTGCCAGGCCAGTG

AGAACATTTATAATTGGTTAGCCTGGTATCAGCAGAAACCAGGGCAGCCT

CCCAAGCTCCTGATCTATACTGTAGGCGATCTGGCATCTGGGGTCTCAT

CGCGGTTCAAAGGCAGTGGATCTGGGACAGAGTTCACTCTCACCATCAG

CGACCTGGAGTGTGCCGATGCTGCCACTTACTATTGTCAACAGGGTTATA

GTAGTAGTTATGTTGATAATGTT

In another embodiment of the invention, polynucleotides of the invention comprise, or alternatively consist of, the following polynucleotide sequence encoding the variable heavy chain polypeptide sequence of SEQ ID NO: 347:

(SEQ ID NO: 355)

ATGGAGACTGGGCTGCGCTGGCTTCTCCTGGTCGCTGTGCTCAAAGGT

GTCCAGTGTCAGGAGCAGCTGAAGGAGTCCGGGGGTCGCCTGGTCACGCC

TGGGACACCCCTGACACTCACCTGCACAGTCTCTGGATTCTCCCTCAAT

GACTATGCAGTGGGCTGGTTCCGCCAGGCTCCAGGGAAGGGGCTGGAAT

GGATCGGATACATTCGTAGTAGTGGTACCACAGCCTACGCGACCTGGGC

GAAAGGCCGATTCACCATCTCCGCTACCTCGACCACGGTGGATCTGAAAA

TCACCAGTCCGACAACCGAGGACACGGCCACCTATTTCTGTGCCAGAGG

GGGTGCTGGTAGTAGTGGTGTGTGGATCCTTGATGGTTTTGCTCCC.

In a further embodiment of the invention, polynucleotides encoding fragments of the antibody having binding specificity to IL-6 comprise, or alternatively consist of, one or more of the polynucleotide sequences of SEQ ID NO: 356; SEQ ID NO: 357; and SEQ ID NO: 358 which correspond to polynucleotides encoding the complementarity-determining regions (CDRs, or hypervariable regions) of the light chain variable sequence of SEQ ID NO: 346.

In a further embodiment of the invention, polynucleotides encoding fragments of the antibody having binding specificity to IL-6 comprise, or alternatively consist of, one or more of the polynucleotide sequences of SEQ ID NO: 359; SEQ ID NO: 360; and SEQ ID NO: 361 which correspond to polynucleotides encoding the complementarity-determining regions (CDRs, or hypervariable regions) of the heavy chain variable sequence of SEQ ID NO: 347.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 354 encoding the light chain variable region of SEQ ID NO: 346; the polynucleotide SEQ ID NO: 355 encoding the heavy chain variable region of SEQ ID NO: 347; polynucleotides encoding the complementarity-determining regions (SEQ ID NO: 356; SEQ ID NO: 357; and SEQ ID NO: 358) of the light chain variable region of SEQ ID NO: 346; and polynucleotides encoding the complementarity-determining regions (SEQ ID NO: 359; SEQ ID NO: 360; and SEQ ID NO: 361) of the heavy chain variable region of SEQ ID NO: 347.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 362:

(SEQ ID NO: 370)

ATGGACACGAGGGCCCCCACTCAGCTGCTGGGGCTCCTGCTGCTCTGG

CTCCCAGGTGCCACATTTGCTCAAGTGCTGACCCAGACTCCATCCTCCGT

GTCTGCAGCTGTGGGAGGCACAGTCACCATCAATTGCCAGGCCAGTCAG

AGTGTTTATCAGAACAACTACTTATCCTGGTTTCAGCAGAAACCAGGGCA

GCCTCCCAAGCTCCTGATCTATGGTGCGGCCACTCTGGCATCTGGGGTCC

CATCGCGGTTCAAAGGCAGTGGATCTGGGACACAGTTCACTCTCACCAT

CAGCGACCTGGAGTGTGACGATGCTGCCACTTACTACTGTGCAGGCGCT

TATAGGGATGTGGATTCT

In another embodiment of the invention, polynucleotides of the invention comprise, or alternatively consist of, the following polynucleotide sequence encoding the variable heavy chain polypeptide sequence of SEQ ID NO: 363:

(SEQ ID NO: 371)

ATGGAGACTGGGCTGCGCTGGCTTCTCCTGGTCGCTGTGCTCAAAGGT

GTCCAGTGTCAGTCGTTGGAGGAGTCCGGGGGAGACCTGGTCAAGCCTGG

GGCATCCCTGACACTCACCTGCACAGCCTCTGGATTCTCCTTTACTAGTA

CCTACTACATCTACTGGGTCCGCCAGGCTCCAGGGAAGGGGCTGGAGTG

GATCGCATGTATTGATGCTGGTAGTAGTGGTAGCACTTACTACGCGACCT

-continued

GGGTGAATGGCCGATTCACCATCTCCAAAACCTCGTCGACCACGGTGAC

TCTGCAAATGACCAGTCTGACAGCCGCGGACACGGCCACCTATTTCTGT

GCGAAATGGGATTATGGTGGTAATGTTGGTTGGGGTTATGACTTG.

In a further embodiment of the invention, polynucleotides encoding fragments of the antibody having binding specificity to IL-6 comprise, or alternatively consist of, one or more of the polynucleotide sequences of SEQ ID NO: 372; SEQ ID NO: 373; and SEQ ID NO: 374 which correspond to polynucleotides encoding the complementarity-determining regions (CDRs, or hypervariable regions) of the light chain variable sequence of SEQ ID NO: 362.

In a further embodiment of the invention, polynucleotides encoding fragments of the antibody having binding specificity to IL-6 comprise, or alternatively consist of, one or more of the polynucleotide sequences of SEQ ID NO: 375; SEQ ID NO: 376; and SEQ ID NO: 377 which correspond to polynucleotides encoding the complementarity-determining regions (CDRs, or hypervariable regions) of the heavy chain variable sequence of SEQ ID NO: 363.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 370 encoding the light chain variable region of SEQ ID NO: 362; the polynucleotide SEQ ID NO: 371 encoding the heavy chain variable region of SEQ ID NO: 363; polynucleotides encoding the complementarity-determining regions (SEQ ID NO: 372; SEQ ID NO: 373; and SEQ ID NO: 374) of the light chain variable region of SEQ ID NO: 362; and polynucleotides encoding the complementarity-determining regions (SEQ ID NO: 375; SEQ ID NO: 376; and SEQ ID NO: 377) of the heavy chain variable region of SEQ ID NO: 363.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 378:

(SEQ ID NO: 386)

ATGGACACGAGGGCCCCCACTCAGCTGCTGGGGCTCCTGCTGCTCTGG

CTCCCAGGTGCCAGATGTGCATTCGAATTGACCCAGACTCCATCCTCCGT

GGAGGCAGCTGTGGGAGGCACAGTCACCATCAAGTGCCAGGCCAGTCAG

AGCATTAGTAGTTACTTAGCCTGGTATCAGCAGAAACCAGGGCAGCCTC

CCAAGTTCCTGATCTACAGGGCGTCCACTCTGGCATCTGGGGTCCCATC

GCGATTCAAAGGCAGTGGATCTGGGACAGAGTTCACTCTCACCATCAGC

GACCTGGAGTGTGCCGATGCTGCCACTTACTACTGTCAAAGCTATTATGA

TAGTGTTTCAAATCCT

In another embodiment of the invention, polynucleotides of the invention comprise, or alternatively consist of, the following polynucleotide sequence encoding the variable heavy chain polypeptide sequence of SEQ ID NO: 379:

(SEQ ID NO: 387)
ATGGAGACTGGGCTGCGCTGGCTTCTCCTGGTCGCTGTGCTCAAAGGTGT

CCAGTGTCAGTCGTTGGAGGAGTCCGGGGGAGACCTGGTCAAGCCTGAGG

GATCCCTGACACTCACCTGCAAAGCCTCTGGACTCGACCTCGGTACCTAC

TGGTTCATGTGCTGGGTCCGCCAGGCTCCAGGGAAGGGGCTGGAGTGGAT

CGCTTGTATTTATACTGGTAGTAGTGGTTCCACTTTCTACGCGAGCTGGG

TGAATGGCCGATTCACCATCTCCAAAACCTCGTCGACCACGGTGACTCTG

CAAATGACCAGTCTGACAGCCGCGGACACGGCCACTTATTTTTGTGCGA

GAGGTTATAGTGGTTATGGTTATTTTAAGTTG.

In a further embodiment of the invention, polynucleotides encoding fragments of the antibody having binding specificity to IL-6 comprise, or alternatively consist of, one or more of the polynucleotide sequences of SEQ ID NO: 388; SEQ ID NO: 389; and SEQ ID NO: 390 which correspond to polynucleotides encoding the complementarity-determining regions (CDRs, or hypervariable regions) of the light chain variable sequence of SEQ ID NO: 378.

In a further embodiment of the invention, polynucleotides encoding fragments of the antibody having binding specificity to IL-6 comprise, or alternatively consist of, one or more of the polynucleotide sequences of SEQ ID NO: 391; SEQ ID NO: 392; and SEQ ID NO: 393 which correspond to polynucleotides encoding the complementarity-determining regions (CDRs, or hypervariable regions) of the heavy chain variable sequence of SEQ ID NO: 379.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 386 encoding the light chain variable region of SEQ ID NO: 378; the polynucleotide SEQ ID NO: 387 encoding the heavy chain variable region of SEQ ID NO: 379; polynucleotides encoding the complementarity-determining regions (SEQ ID NO: 388; SEQ ID NO: 389; and SEQ ID NO: 390) of the light chain variable region of SEQ ID NO: 378; and polynucleotides encoding the complementarity-determining regions (SEQ ID NO: 391; SEQ ID NO: 392; and SEQ ID NO: 393) of the heavy chain variable region of SEQ ID NO: 379.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 394:

(SEQ ID NO: 402)
ATGGACACGAGGGCCCCCACTCAGCTGCTGGGGCTCCTGCTGCTCTGGCT

CCCAGGTGTCACATTTGCCATCGAAATGACCCAGAGTCCATTCTCCGTGT

CTGCAGCTGTGGGAGGCACAGTCAGCATCAGTTGCCAGGCCAGTCAGAGT

GTTTATAAGAACAACCAATTATCCTGGTATCAGCAGAAATCAGGGCAGCC

TCCCAAGCTCCTGATCTATGGTGCATCGGCTCTGGCATCTGGGGTCCCAT

CGCGGTTCAAAGGCAGTGGATCTGGGACAGAGTTCACTCTCACCATCAGC

-continued

GACGTGCAGTGTGACGATGCTGCCACTTACTACTGTGCAGGCGCTATTAC

TGGTAGTATTGATACGGATGGT

In another embodiment of the invention, polynucleotides of the invention comprise, or alternatively consist of, the following polynucleotide sequence encoding the variable heavy chain polypeptide sequence of SEQ ID NO: 395:

(SEQ ID NO: 403)
ATGGAGACTGGGCTGCGCTGGCTTCTCCTGGTCGCTGTGCTCAAAGGTGT

CCAGTGTCAGTCGTTGGAGGAGTCCGGGGGAGACCTGGTCAAGCCTGGGG

CATCCCTGACACTCACCTGCACAACTTCTGGATTCTCCTTCAGTAGCAGC

TACTTCATTTGCTGGGTCCGCCAGGCTCCAGGGAAGGGGCTGGAGTGGAT

CGCATGCATTTATGGTGGTGATGGCAGCACATACTACGCGAGCTGGGCGA

AAGGCCGATTCACCATCTCCAAAACCTCGTCGACCACGGTGACGCTGCAA

ATGACCAGTCTGACAGCCGCGGACACGGCCACCTATTTCTGTGCGAGAGA

ATGGGCATATAGTCAAGGTTATTTTGGTGCTTTTGATCTC.

In a further embodiment of the invention, polynucleotides encoding fragments of the antibody having binding specificity to IL-6 comprise, or alternatively consist of, one or more of the polynucleotide sequences of SEQ ID NO: 404; SEQ ID NO: 405; and SEQ ID NO: 406 which correspond to polynucleotides encoding the complementarity-determining regions (CDRs, or hypervariable regions) of the light chain variable sequence of SEQ ID NO: 394.

In a further embodiment of the invention, polynucleotides encoding fragments of the antibody having binding specificity to IL-6 comprise, or alternatively consist of, one or more of the polynucleotide sequences of SEQ ID NO: 407; SEQ ID NO: 408; and SEQ ID NO: 409 which correspond to polynucleotides encoding the complementarity-determining regions (CDRs, or hypervariable regions) of the heavy chain variable sequence of SEQ ID NO: 395.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 402 encoding the light chain variable region of SEQ ID NO: 394; the polynucleotide SEQ ID NO: 403 encoding the heavy chain variable region of SEQ ID NO: 395; polynucleotides encoding the complementarity-determining regions (SEQ ID NO: 404; SEQ ID NO: 405; and SEQ ID NO: 406) of the light chain variable region of SEQ ID NO: 394; and polynucleotides encoding the complementarity-determining regions (SEQ ID NO: 407; SEQ ID NO: 408; and SEQ ID NO: 409) of the heavy chain variable region of SEQ ID NO: 395.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 410:

(SEQ ID NO: 418)

ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGG

AGGCAGCTGTGGGAGGCACAGTCACCATCAAGTGCCAGGCCAGTGAGGAT

ATTAGTAGCTACTTAGCCTGGTATCAGCAGAAACCAGGGCAGCCTCCCAA

GCTCCTGATCTATGCTGCATCCAATCTGGAATCTGGGGTCTCATCGCGAT

TCAAAGGCAGTGGATCTGGGACAGAGTACACTCTCACCATCAGCGACCTG

GAGTGTGCCGATGCTGCCACCTATTACTGTCAATGTACTTATGGTACTAT

TTCTATTAGTGATGGTAATGCT

In another embodiment of the invention, polynucleotides of the invention comprise, or alternatively consist of, the following polynucleotide sequence encoding the variable heavy chain polypeptide sequence of SEQ ID NO: 411:

(SEQ ID NO: 419)

ATGGAGACTGGGCTGCGCTGGCTTCTCCTGGTCGCTGTGCTCAAAGGTGT

CCAATGTCAGTCGGTGGAGGAGTCCGGGGGTCGCCTGGTCACGCCTGGGA

CACCCCTGACACTCACCTGCACAGTCTCTGGATTCTCCCTCAGTAGCTAC

TTCATGACCTGGGTCCGCCAGGCTCCAGGGGAGGGGCTGGAATACATCGG

ATTCATTAATCCTGGTGGTAGCGCTTACTACGCGAGCTGGGTGAAAGGCC

GATTCACCATCTCCAAGTCCTCGACCACGGTAGATCTGAAAATCACCAGT

CCGACAACCGAGGACACGGCCACCTATTTCTGTGCCAGGGTTCTGATTGT

TTCTTATGGAGCCTTTACCATC.

In a further embodiment of the invention, polynucleotides encoding fragments of the antibody having binding specificity to IL-6 comprise, or alternatively consist of, one or more of the polynucleotide sequences of SEQ ID NO: 420; SEQ ID NO: 421; and SEQ ID NO: 422 which correspond to polynucleotides encoding the complementarity-determining regions (CDRs, or hypervariable regions) of the light chain variable sequence of SEQ ID NO: 410.

In a further embodiment of the invention, polynucleotides encoding fragments of the antibody having binding specificity to IL-6 comprise, or alternatively consist of, one or more of the polynucleotide sequences of SEQ ID NO: 423; SEQ ID NO: 424; and SEQ ID NO: 425 which correspond to polynucleotides encoding the complementarity-determining regions (CDRs, or hypervariable regions) of the heavy chain variable sequence of SEQ ID NO: 411.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 418 encoding the light chain variable region of SEQ ID NO: 410; the polynucleotide SEQ ID NO: 419 encoding the heavy chain variable region of SEQ ID NO: 411; polynucleotides encoding the complementarity-determining regions (SEQ ID NO: 420; SEQ ID NO: 421; and SEQ ID NO: 422) of the light chain variable region of SEQ ID NO: 410; and polynucleotides encoding the complementarity-determining regions (SEQ ID NO: 423; SEQ ID NO: 424; and SEQ ID NO: 425) of the heavy chain variable region of SEQ ID NO: 411.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 426:

(SEQ ID NO: 434)

ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGT

CTGCAGCTGTGGGAGGCACAGTCACCATCAAGTGCCAGGCCAGTGAGGAC

ATTGAAAGCTATCTAGCCTGGTATCAGCAGAAACCAGGGCAGCCTCCCAA

GCTCCTGATCTATGGTGCATCCAATCTGGAATCTGGGGTCTCATCGCGGT

TCAAAGGCAGTGGATCTGGGACAGAGTTCACTCTCACCATCAGCGACCTG

GAGTGTGCCGATGCTGCCACTTACTATTGTCAATGCACTTATGGTATTAT

TAGTATTAGTGATGGTAATGCT

In another embodiment of the invention, polynucleotides of the invention comprise, or alternatively consist of, the following polynucleotide sequence encoding the variable heavy chain polypeptide sequence of SEQ ID NO: 427:

(SEQ ID NO: 435)

ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTGTCTGGATTCTCCCTCAGTAGCTAC

TTCATGACCTGGGTCCGCCAGGCTCCAGGGGAGGGGCTGGAATACATCGG

ATTCATGAATACTGGTGATAACGCATACTACGCGAGCTGGGCGAAAGGCC

GATTCACCATCTCCAAAACCTCGACCACGGTGGATCTGAAAATCACCAGT

CCGACAACCGAGGACACGGCCACCTATTTCTGTGCCAGGGTTCTTGTTGT

TGCTTATGGAGCCTTTAACATC.

In a further embodiment of the invention, polynucleotides encoding fragments of the antibody having binding specificity to IL-6 comprise, or alternatively consist of, one or more of the polynucleotide sequences of SEQ ID NO: 436; SEQ ID NO: 437; and SEQ ID NO: 438 which correspond to polynucleotides encoding the complementarity-determining regions (CDRs, or hypervariable regions) of the light chain variable sequence of SEQ ID NO: 426.

In a further embodiment of the invention, polynucleotides encoding fragments of the antibody having binding specificity to IL-6 comprise, or alternatively consist of, one or more of the polynucleotide sequences of SEQ ID NO: 439; SEQ ID NO: 440; and SEQ ID NO: 441 which correspond to polynucleotides encoding the complementarity-determining regions (CDRs, or hypervariable regions) of the heavy chain variable sequence of SEQ ID NO: 427.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 434 encoding the light chain variable region of SEQ ID NO: 426; the polynucleotide SEQ ID NO: 435 encoding the heavy chain variable region of SEQ ID NO: 427; polynucleotides encoding the complementarity-determining regions (SEQ ID NO: 436; SEQ ID NO: 437; and SEQ ID NO: 438) of the light chain variable region of SEQ ID NO: 426; and polynucleotides encoding the complementarity-determining regions (SEQ ID NO: 439; SEQ ID NO: 440; and SEQ ID NO: 441) of the heavy chain variable region of SEQ ID NO: 427.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 442:

```
                                       (SEQ ID NO: 450)
ATGGACACGAGGGCCCCCACTCAGCTGCTGGGGCTCCTGCTGCTCTGGCT

CCCAGGTGCCACATTTGCCGCCGTGCTGACCCAGACTCCATCTCCCGTGT

CTGAACCTGTGGGAGGCACAGTCAGCATCAGTTGCCAGTCCAGTAAGAGT

GTTATGAATAACAACTACTTAGCCTGGTATCAGCAGAAACCAGGGCAGCC

TCCCAAGCTCCTGATCTATGGTGCATCCAATCTGGCATCTGGGGTCCCAT

CACGGTTCAGCGGCAGTGGATCTGGGACACAGTTCACTCTCACCATCAGC

GACGTGCAGTGTGACGATGCTGCCACTTACTACTGTCAAGGCGGTTATAC

TGGTTATAGTGATCATGGGACT
```

In another embodiment of the invention, polynucleotides of the invention comprise, or alternatively consist of, the following polynucleotide sequence encoding the variable heavy chain polypeptide sequence of SEQ ID NO: 443:

```
                                       (SEQ ID NO: 451)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCAAGCCTGACG

AAACCCTGACACTCACCTGCACAGTCTCTGGAATCGACCTCAGTAGCTAT

CCAATGAACTGGGTCCGCCAGGCTCCAGGGAAGGGGCTGGAATGGATCGG

ATTCATTAATACTGGTGGTACCATAGTCTACGCGAGCTGGGCAAAAGGCC

GATTCACCATCTCCAAAACCTCGACCACGGTGGATCTGAAAATGACCAGT

CCGACAACCGAGGACACGGCCACCTATTTCTGTGCCAGAGGCAGTTATGT

TTCATCTGGTTATGCCTACTATTTTAATGTC.
```

In a further embodiment of the invention, polynucleotides encoding fragments of the antibody having binding specificity to IL-6 comprise, or alternatively consist of, one or more of the polynucleotide sequences of SEQ ID NO: 452; SEQ ID NO: 453; and SEQ ID NO: 454 which correspond to polynucleotides encoding the complementarity-determining regions (CDRs, or hypervariable regions) of the light chain variable sequence of SEQ ID NO: 442.

In a further embodiment of the invention, polynucleotides encoding fragments of the antibody having binding specificity to IL-6 comprise, or alternatively consist of, one or more of the polynucleotide sequences of SEQ ID NO: 455; SEQ ID NO: 456; and SEQ ID NO: 457 which correspond to polynucleotides encoding the complementarity-determining regions (CDRs, or hypervariable regions) of the heavy chain variable sequence of SEQ ID NO: 443.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 450 encoding the light chain variable region of SEQ ID NO: 442; the polynucleotide SEQ ID NO: 451 encoding the heavy chain variable region of SEQ ID NO: 443; polynucleotides encoding the complementarity-determining regions (SEQ ID NO: 452; SEQ ID NO: 453; and SEQ ID NO: 454) of the light chain variable region of SEQ ID NO: 442; and polynucleotides encoding the complementarity-determining regions (SEQ ID NO: 455; SEQ ID NO: 456; and SEQ ID NO: 457) of the heavy chain variable region of SEQ ID NO: 443.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 458:

```
                                       (SEQ ID NO: 466)
ATGGACACGAGGGCCCCCACTCAGCTGCTGGGGCTCCTGCTGCTCTGGCT

CCCAGGTGCCACATTTGCCGCCGTGCTGACCCAGACTCCATCTCCCGTGT

CTGCAGCTGTGGGAGGCACAGTCAGCATCAGTTGCCAGTCCAGTCAGAGT

GTTTATAATAACAACTGGTTATCCTGGTTTCAGCAGAAACCAGGGCAGCC

TCCCAAGCTCCTGATCTACAAGGCATCCACTCTGGCATCTGGGGTCCCAT

CGCGGTTCAAAGGCAGTGGATCTGGGACACAGTTCACTCTCACCATCAGC

GACGTGCAGTGTGACGATGTTGCCACTTACTACTGTGCGGGCGGTTATCT

TGATAGTGTTATT
```

In another embodiment of the invention, polynucleotides of the invention comprise, or alternatively consist of, the following polynucleotide sequence encoding the variable heavy chain polypeptide sequence of SEQ ID NO: 459:

```
                                       (SEQ ID NO: 467)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTACCTAT

TCAATAAACTGGGTCCGCCAGGCTCCAGGGAAGGGCCTGGAATGGATCGG

AATCATTGCTAATAGTGGTACCACATTCTACGCGAACTGGGCGAAAGGCC

GATTCACCGTCTCCAAAACCTCGACCACGGTGGATCTGAAAATCACCAGT

CCGACAACCGAGGACACGGCCACCTATTTCTGTGCCAGAGAGAGTGGAAT

GTACAATGAATATGGTAAATTTAACATC.
```

In a further embodiment of the invention, polynucleotides encoding fragments of the antibody having binding specificity to IL-6 comprise, or alternatively consist of, one or more of the polynucleotide sequences of SEQ ID NO: 468; SEQ ID NO: 469; and SEQ ID NO: 470 which correspond to polynucleotides encoding the complementarity-determining regions (CDRs, or hypervariable regions) of the light chain variable sequence of SEQ ID NO: 458.

In a further embodiment of the invention, polynucleotides encoding fragments of the antibody having binding specificity to IL-6 comprise, or alternatively consist of, one or more of the polynucleotide sequences of SEQ ID NO: 471; SEQ ID NO: 472; and SEQ ID NO: 473 which correspond to polynucleotides encoding the complementarity-determining regions (CDRs, or hypervariable regions) of the heavy chain variable sequence of SEQ ID NO: 459.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 466 encoding the light chain variable region of SEQ ID NO: 458; the polynucleotide SEQ ID NO: 467 encoding the heavy chain variable region of SEQ ID NO: 459; polynucleotides encoding the complementarity-determining regions (SEQ ID NO: 468; SEQ ID NO: 469; and SEQ ID NO: 470) of the light chain variable region of SEQ ID NO: 458; and polynucleotides encoding the complementarity-determining regions (SEQ ID NO: 471; SEQ ID NO: 472; and SEQ ID NO: 473) of the heavy chain variable region of SEQ ID NO: 459.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 474:

```
                                          (SEQ ID NO: 482)
ATGGACACGAGGGCCCCCACTCAGCTGCTGGGGCTCCTGCTGCTCTGGCT

CCCAGGTGCCAGATGTGCCTCTGATATGACCCAGACTCCATCCTCCGTGT

CTGCAGCTGTGGGAGGCACAGTCACCATCAATTGCCAGGCCAGTGAGAAC

ATTTATAGCTTTTTGGCCTGGTATCAGCAGAAACCAGGGCAGCCTCCCAA

GCTCCTGATCTTCAAGGCTTCCACTCTGGCATCTGGGGTCTCATCGCGGT

TCAAAGGCAGTGGATCTGGGACACAGTTCACTCTCACCATCAGCGACCTG

GAGTGTGACGATGCTGCCACTTACTACTGTCAACAGGGTGCTACTGTGTA

TGATATTGATAATAAT
```

In another embodiment of the invention, polynucleotides of the invention comprise, or alternatively consist of, the following polynucleotide sequence encoding the variable heavy chain polypeptide sequence of SEQ ID NO: 475:

```
                                          (SEQ ID NO: 483)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGTTTCTGGAATCGACCTCAGTGCCTAT

GCAATGATCTGGGTCCGCCAGGCTCCAGGGGAGGGGCTGGAATGGATCAC

AATCATTTATCCTAATGGTATCACATACTACGCGAACTGGGCGAAAGGCC

GATTCACCGTCTCCAAAACCTCGACCGCGATGGATCTGAAAATCACCAGT

CCGACAACCGAGGACACGGCCACCTATTTCTGTGCCAGAGATGCAGAAAG

TAGTAAGAATGCTTATTGGGGCTACTTTAACGTC.
```

In a further embodiment of the invention, polynucleotides encoding fragments of the antibody having binding specificity to IL-6 comprise, or alternatively consist of, one or more of the polynucleotide sequences of SEQ ID NO: 484; SEQ ID NO: 485; and SEQ ID NO: 486 which correspond to polynucleotides encoding the complementarity-determining regions (CDRs, or hypervariable regions) of the light chain variable sequence of SEQ ID NO: 474.

In a further embodiment of the invention, polynucleotides encoding fragments of the antibody having binding specificity to IL-6 comprise, or alternatively consist of, one or more of the polynucleotide sequences of SEQ ID NO: 487; SEQ ID NO: 488; and SEQ ID NO: 489 which correspond to polynucleotides encoding the complementarity-determining regions (CDRs, or hypervariable regions) of the heavy chain variable sequence of SEQ ID NO: 475.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 482 encoding the light chain variable region of SEQ ID NO: 474; the polynucleotide SEQ ID NO: 483 encoding the heavy chain variable region of SEQ ID NO: 475; polynucleotides encoding the complementarity-determining regions (SEQ ID NO: 484; SEQ ID NO: 485; and SEQ ID NO: 486) of the light chain variable region of SEQ ID NO: 474; and polynucleotides encoding the complementarity-determining regions (SEQ ID NO: 487; SEQ ID NO: 488; and SEQ ID NO: 489) of the heavy chain variable region of SEQ ID NO: 475.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 490:

```
                                          (SEQ ID NO: 498)
ATGGACACGAGGGCCCCCACTCAGCTGCTGGGGCTCCTGCTGCTCTGGCT

CCCAGGTGCCAGATGTGCCTCTGATATGACCCAGACTCCATCCTCCGTGT

CTGCAGCTGTGGGAGGCACAGTCACCATCAATTGCCAGGCCAGTGAGAAC

ATTTATAGCTTTTTGGCCTGGTATCAGCAGAAACCAGGGCAGCCTCCCAA

GCTCCTGATCTTCAGGGCTTCCACTCTGGCATCTGGGGTCTCATCGCGGT

TCAAAGGCAGTGGATCTGGGACACAGTTCACTCTCACCATCAGCGACCTG

GAGTGTGACGATGCTGCCACTTACTACTGTCAACAGGGTGCTACTGTGTA

TGATATTGATAATAAT
```

In another embodiment of the invention, polynucleotides of the invention comprise, or alternatively consist of, the following polynucleotide sequence encoding the variable heavy chain polypeptide sequence of SEQ ID NO: 491:

```
                                          (SEQ ID NO: 499)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGTTTCTGGAATCGACCTCAGTGCCTAT

GCAATGATCTGGGTCCGCCAGGCTCCAGGGGAGGGGCTGGAATGGATCAC

AATCATTTATCCTAATGGTATCACATACTACGCGAACTGGGCGAAAGGCC

GATTCACCGTCTCCAAAACCTCGACCGCGATGGATCTGAAAATCACCAGT
```

-continued

```
CCGACAACCGAGGACACGGCCACCTATTTCTGTGCCAGAGATGCAGAAAG

TAGTAAGAATGCTTATTGGGGCTACTTTAACGTC.
```

In a further embodiment of the invention, polynucleotides encoding fragments of the antibody having binding specificity to IL-6 comprise, or alternatively consist of, one or more of the polynucleotide sequences of SEQ ID NO: 500; SEQ ID NO: 501; and SEQ ID NO: 502 which correspond to polynucleotides encoding the complementarity-determining regions (CDRs, or hypervariable regions) of the light chain variable sequence of SEQ ID NO: 490.

In a further embodiment of the invention, polynucleotides encoding fragments of the antibody having binding specificity to IL-6 comprise, or alternatively consist of, one or more of the polynucleotide sequences of SEQ ID NO: 503; SEQ ID NO: 504; and SEQ ID NO: 505 which correspond to polynucleotides encoding the complementarity-determining regions (CDRs, or hypervariable regions) of the heavy chain variable sequence of SEQ ID NO: 491.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 498 encoding the light chain variable region of SEQ ID NO: 490; the polynucleotide SEQ ID NO: 499 encoding the heavy chain variable region of SEQ ID NO: 491; polynucleotides encoding the complementarity-determining regions (SEQ ID NO: 500; SEQ ID NO: 501; and SEQ ID NO: 502) of the light chain variable region of SEQ ID NO: 490; and polynucleotides encoding the complementarity-determining regions (SEQ ID NO: 503; SEQ ID NO: 504; and SEQ ID NO: 505) of the heavy chain variable region of SEQ ID NO: 491.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 506:

```
                                          (SEQ ID NO: 514)
ATGGACACGAGGGCCCCCACTCAGCTGCTGGGGCTCCTGCTGCTCTGGCT

CCCAGGTGCCACATTTGCCATTGAAATGACCCAGACTCCATCCCCCGTGT

CTGCCGCTGTGGGAGGCACAGTCACCATCAATTGCCAGGCCAGTGAGAGT

GTTTTTAATAATATGTTATCCTGGTATCAGCAGAAACCAGGGCACTCTCC

TAAGCTCCTGATCTATGATGCATCCGATCTGGCATCTGGGGTCCCATCGC

GGTTCAAAGGCAGTGGATCTGGGACACAGTTCACTCTCACCATCAGTGGC

GTGGAGTGTGACGATGCTGCCACTTACTATTGTGCAGGGTATAAAAGTGA

TAGTAATGATGGCGATAATGTT
```

In another embodiment of the invention, polynucleotides of the invention comprise, or alternatively consist of, the following polynucleotide sequence encoding the variable heavy chain polypeptide sequence of SEQ ID NO: 507:

```
                                          (SEQ ID NO: 515)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGTCTCTGGATTCTCCCTCAACAGGAAT

TCAATAACCTGGGTCCGCCAGGCTCCAGGGGAGGGGCTGGAATGGATCGG

AATCATTACTGGTAGTGGTAGAACGTACTACGCGAACTGGGCAAAAGGCC

GATTCACCATCTCCAAAACCTCGACCACGGTGGATCTGAAAATGACCAGT

CCGACAACCGAGGACACGGCCACCTATTTCTGTGCCAGAGGCCATCCTGG

TCTTGGTAGTGGTAACATC.
```

In a further embodiment of the invention, polynucleotides encoding fragments of the antibody having binding specificity to IL-6 comprise, or alternatively consist of, one or more of the polynucleotide sequences of SEQ ID NO: 516; SEQ ID NO: 517; and SEQ ID NO: 518 which correspond to polynucleotides encoding the complementarity-determining regions (CDRs, or hypervariable regions) of the light chain variable sequence of SEQ ID NO: 506.

In a further embodiment of the invention, polynucleotides encoding fragments of the antibody having binding specificity to IL-6 comprise, or alternatively consist of, one or more of the polynucleotide sequences of SEQ ID NO: 519; SEQ ID NO: 520; and SEQ ID NO: 521 which correspond to polynucleotides encoding the complementarity-determining regions (CDRs, or hypervariable regions) of the heavy chain variable sequence of SEQ ID NO: 507.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 514 encoding the light chain variable region of SEQ ID NO: 506; the polynucleotide SEQ ID NO: 515 encoding the heavy chain variable region of SEQ ID NO: 507; polynucleotides encoding the complementarity-determining regions (SEQ ID NO: 516; SEQ ID NO: 517; and SEQ ID NO: 518) of the light chain variable region of SEQ ID NO: 506; and polynucleotides encoding the complementarity-determining regions (SEQ ID NO: 519; SEQ ID NO: 520; and SEQ ID NO: 521) of the heavy chain variable region of SEQ ID NO: 507.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 522:

```
                                          (SEQ ID NO: 530)
ATGGACACGAGGGCCCCCACTCAGCTGCTGGGGCTCCTGCTGCTCTGGCT

CCCAGGTGCCACATTTGCGCAAGTGCTGACCCAGACTGCATCGTCCGTGT

CTGCAGCTGTGGGAGGCACAGTCACCATCAATTGCCAGTCCAGTCAGAGT

GTTTATAATAACTACTTATCCTGGTATCAGCAGAAACCAGGGCAGCCTCC

CAAGCTCCTGATCTATACTGCATCCAGCCTGGCATCTGGGGTCCCATCGC

GGTTCAAAGGCAGTGGATCTGGGACACAGTTCACTCTCACCATCAGCGAA

GTGCAGTGTGACGATGCTGCCACTTACTACTGTCAAGGCTATTATAGTGG

TCCTATAATTACT
```

In another embodiment of the invention, polynucleotides of the invention comprise, or alternatively consist of, the following polynucleotide sequence encoding the variable heavy chain polypeptide sequence of SEQ ID NO: 523:

(SEQ ID NO: 531)
ATGGAGACTGGGCTGCGCTGGCTTCTCCTGGTCGCTGTGCTCAAAGGTGT
CCAGTGTCAGTCGCTGGAGGAGTCCGGGGGTCGCCTGGTCACGCCTGGGA
CACCCCTGACACTCACCTGCACAGCCTCTGGATTCTCCCTCAATAACTAC
TACATACAATGGGTCCGCCAGGCTCCAGGGGAGGGGCTGGAATGGATCGG
GATCATTTATGCTGGTGGTAGCGCATACTACGCGACCTGGGCAAACGGCC
GATTCACCATCGCCAAAACCTCGTCGACCACGGTGGATCTGAAGATGACC
AGTCTGACAACCGAGGACACGGCCACCTATTTCTGTGCCAGAGGGACATT
TGATGGTTATGAGTTG.

In a further embodiment of the invention, polynucleotides encoding fragments of the antibody having binding specificity to IL-6 comprise, or alternatively consist of, one or more of the polynucleotide sequences of SEQ ID NO: 532; SEQ ID NO: 533; and SEQ ID NO: 534 which correspond to polynucleotides encoding the complementarity-determining regions (CDRs, or hypervariable regions) of the light chain variable sequence of SEQ ID NO: 522.

In a further embodiment of the invention, polynucleotides encoding fragments of the antibody having binding specificity to IL-6 comprise, or alternatively consist of, one or more of the polynucleotide sequences of SEQ ID NO: 535; SEQ ID NO: 536; and SEQ ID NO: 537 which correspond to polynucleotides encoding the complementarity-determining regions (CDRs, or hypervariable regions) of the heavy chain variable sequence of SEQ ID NO: 523.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 530 encoding the light chain variable region of SEQ ID NO: 522; the polynucleotide SEQ ID NO: 531 encoding the heavy chain variable region of SEQ ID NO: 523; polynucleotides encoding the complementarity-determining regions (SEQ ID NO: 532; SEQ ID NO: 533; and SEQ ID NO: 534) of the light chain variable region of SEQ ID NO: 522; and polynucleotides encoding the complementarity-determining regions (SEQ ID NO: 535; SEQ ID NO: 536; and SEQ ID NO: 537) of the heavy chain variable region of SEQ ID NO: 523.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 538:

(SEQ ID NO: 546)
ATGGACACGAGGGCCCCCACTCAGCTGCTGGGGCTCCTGCTGCTCTGGCT
CCCAGGTGCCACATTTGCCCAAGTGCTGACCCAGACTCCATCCCCTGTGT
CTGTCCCTGTGGGAGACACAGTCACCATCAGTTGCCAGTCCAGTGAGAGC

-continued

GTTTATAGTAATAACCTCTTATCCTGGTATCAGCAGAAACCAGGGCAGCC
TCCCAAGCTCCTGATCTACAGGGCATCCAATCTGGCATCTGGTGTCCCAT
CGCGGTTCAAAGGCAGTGGATCTGGGACACAGTTCACTCTCACCATCAGC
GGCGCACAGTGTGACGATGCTGCCACTTACTACTGTCAAGGCTATTATAG
TGGTGTCATTAATAGT

In another embodiment of the invention, polynucleotides of the invention comprise, or alternatively consist of, the following polynucleotide sequence encoding the variable heavy chain polypeptide sequence of SEQ ID NO: 539:

(SEQ ID NO: 547)
ATGGAGACTGGGCTGCGCTGGCTTCTCCTGGTCGCTGTGCTCAAAGGTGT
CCAGTGTCAGTCGGTGGAGGAGTCCGGGGGTCGCCTGGTCACGCCTGGGA
CACCCCTGACACTCACCTGCACAGTGTCTGGATTCTCCCTCAGTAGCTAC
TTCATGAGCTGGGTCCGCCAGGCTCCAGGGGAGGGGCTGGAATACATCGG
ATTCATTAATCCTGGTGGTAGCGCATACTACGCGAGCTGGGCGAGTGGCC
GACTCACCATCTCCAAAACCTCGACCACGGTAGATCTGAAAATCACCAGT
CCGACAACCGAGGACACGGCCACCTATTTCTGTGCCAGGATTCTTATTGT
TTCTTATGGAGCCTTTACCATC.

In a further embodiment of the invention, polynucleotides encoding fragments of the antibody having binding specificity to IL-6 comprise, or alternatively consist of, one or more of the polynucleotide sequences of SEQ ID NO: 548; SEQ ID NO: 549; and SEQ ID NO: 550 which correspond to polynucleotides encoding the complementarity-determining regions (CDRs, or hypervariable regions) of the light chain variable sequence of SEQ ID NO: 538.

In a further embodiment of the invention, polynucleotides encoding fragments of the antibody having binding specificity to IL-6 comprise, or alternatively consist of, one or more of the polynucleotide sequences of SEQ ID NO: 551; SEQ ID NO: 552; and SEQ ID NO: 553 which correspond to polynucleotides encoding the complementarity-determining regions (CDRs, or hypervariable regions) of the heavy chain variable sequence of SEQ ID NO: 539.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 546 encoding the light chain variable region of SEQ ID NO: 538; the polynucleotide SEQ ID NO: 547 encoding the heavy chain variable region of SEQ ID NO: 539; polynucleotides encoding the complementarity-determining regions (SEQ ID NO: 548; SEQ ID NO: 549; and SEQ ID NO: 550) of the light chain variable region of SEQ ID NO: 538; and polynucleotides encoding the complementarity-determining regions (SEQ ID NO: 551; SEQ ID NO: 552; and SEQ ID NO: 553) of the heavy chain variable region of SEQ ID NO: 539.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 554:

(SEQ ID NO: 562)
ATGGACACGAGGGCCCCCACTCAGCTGCTGGGGCTCCTGCTGCTCTGGCT
CCCAGGTGCCAGATGTGCCTATGATATGACCCAGACTCCAGCCTCTGTGG
AGGTAGCTGTGGGAGGCACAGTCACCATCAAGTGCCAGGCCACTGAGAGC
ATTGGCAATGAGTTATCCTGGTATCAGCAGAAACCAGGGCAGGCTCCCAA
GCTCCTGATCTATTCTGCATCCACTCTGGCATCTGGGGTCCCATCGCGGT
TCAAAGGCAGTGGATCTGGGACACAGTTCACTCTCACCATCACCGGCGTG
GAGTGTGATGATGCTGCCACTTACTACTGTCAACAGGGTTATAGTAGTGC
TAATATTGATAATGCT

In another embodiment of the invention, polynucleotides of the invention comprise, or alternatively consist of, the following polynucleotide sequence encoding the variable heavy chain polypeptide sequence of SEQ ID NO: 555:

(SEQ ID NO: 563)
ATGGAGACTGGGCTGCGCTGGCTTCTCCTGGTCGCTGTGCTCAAAGGTGT
CCAGTGTCAGTCGCTGGAGGAGTCCGGGGGTCGCCTGGTCACGCCTGGGA
CACCCCTGACACTCACCTGCACCGTCTCTGGATTCTCCCTCAGTAAGTAC
TACATGAGCTGGGTCCGCCAGGCTCCAGAGAAGGGGCTGAAATACATCGG
ATACATTGATAGTACTACTGTTAATACATACTACGCGACCTGGGCGAGAG
GCCGATTCACCATCTCCAAAACCTCGACCACGGTGGATCTGAAGATCACC
AGTCCGACAAGTGAGGACACGGCCACCTATTTCTGTGCCAGAGGAAGTAC
TTATTTTACTGATGGAGGCCATCGGTTGGATCTC.

In a further embodiment of the invention, polynucleotides encoding fragments of the antibody having binding specificity to IL-6 comprise, or alternatively consist of, one or more of the polynucleotide sequences of SEQ ID NO: 564; SEQ ID NO: 565; and SEQ ID NO: 566 which correspond to polynucleotides encoding the complementarity-determining regions (CDRs, or hypervariable regions) of the light chain variable sequence of SEQ ID NO: 554.

In a further embodiment of the invention, polynucleotides encoding fragments of the antibody having binding specificity to IL-6 comprise, or alternatively consist of, one or more of the polynucleotide sequences of SEQ ID NO: 567; SEQ ID NO: 568; and SEQ ID NO: 569 which correspond to polynucleotides encoding the complementarity-determining regions (CDRs, or hypervariable regions) of the heavy chain variable sequence of SEQ ID NO: 555.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 562 encoding the light chain variable region of SEQ ID NO: 554; the polynucleotide SEQ ID NO: 563 encoding the heavy chain variable region of SEQ ID NO: 555; polynucleotides encoding the complementarity-determining regions (SEQ ID NO: 564; SEQ ID NO: 565; and SEQ ID NO: 566) of the light chain variable region of SEQ ID NO: 554; and polynucleotides encoding the complementarity-determining regions (SEQ ID NO: 567; SEQ ID NO: 568; and SEQ ID NO: 569) of the heavy chain variable region of SEQ ID NO: 555.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 570:

(SEQ ID NO: 578)
ATGGACACGAGGGCCCCCACTCAGCTGCTGGGGCTCCTGCTGCTCTGGCT
CCCAGGTGCCAGATGTGCCTATGATATGACCCAGACTCCAGCCTCTGTGG
AGGTAGCTGTGGGAGGCACAGTCACCATCAAGTGCCAGGCCACTGAGAGC
ATTGGCAATGAGTTATCCTGGTATCAGCAGAAACCAGGGCAGGCTCCCAA
GCTCCTGATCTATTCTGCATCCACTCTGGCATCTGGGGTCCCATCGCGGT
TCAAAGGCAGTGGATCTGGGACACAGTTCACTCTCACCATCACCGGCGTG
GAGTGTGATGATGCTGCCACTTACTACTGTCAACAGGGTTATAGTAGTGC
TAATATTGATAATGCT

In another embodiment of the invention, polynucleotides of the invention comprise, or alternatively consist of, the following polynucleotide sequence encoding the variable heavy chain polypeptide sequence of SEQ ID NO: 571:

(SEQ ID NO: 579)
ATGGAGACTGGGCTGCGCTGGCTTCTCCTGGTCGCTGTGCTCAAAGGTGT
CCAGTGTCAGTCGCTGGAGGAGTCCGGGGGTCGCCTGGTAACGCCTGGGA
CACCCCTGACACTCACCTGCACAGTCTCTGGATTCTCCCTCAGTACCTAC
AACATGGGCTGGGTCCGCCAGGCTCCAGGGAAGGGGCTGGAATGGATCGG
AAGTATTACTATTGATGGTCGCACATACTACGCGAGCTGGGCGAAAGGCC
GATTCACCGTCTCCAAAAGCTCGACCACGGTGGATCTGAAAATGACCAGT
CTGACAACCGGGGACACGGCCACCTATTTCTGTGCCAGGATTCTTATTGT
TTCTTATGGGGCCTTTACCATC.

In a further embodiment of the invention, polynucleotides encoding fragments of the antibody having binding specificity to IL-6 comprise, or alternatively consist of, one or more of the polynucleotide sequences of SEQ ID NO: 580; SEQ ID NO: 581; and SEQ ID NO: 582 which correspond to polynucleotides encoding the complementarity-determining regions (CDRs, or hypervariable regions) of the light chain variable sequence of SEQ ID NO: 570.

In a further embodiment of the invention, polynucleotides encoding fragments of the antibody having binding specificity to IL-6 comprise, or alternatively consist of, one or more of the polynucleotide sequences of SEQ ID NO: 583; SEQ ID NO: 584; and SEQ ID NO: 585 which correspond to polynucleotides encoding the complementarity-determining regions (CDRs, or hypervariable regions) of the heavy chain variable sequence of SEQ ID NO: 571.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 578 encoding the light chain variable region of SEQ ID NO: 570; the polynucleotide SEQ ID NO: 579 encoding the heavy chain variable region of SEQ ID NO: 571; polynucleotides encoding the complementarity-determining regions (SEQ ID NO: 580; SEQ ID NO: 581; and SEQ ID NO: 582) of the light chain variable region of SEQ ID NO: 570; and polynucleotides encoding the complementarity-determining regions (SEQ ID NO: 583; SEQ ID NO: 584; and SEQ ID NO: 585) of the heavy chain variable region of SEQ ID NO: 571.

In another embodiment of the invention, polynucleotides of the invention further comprise, the following polynucleotide sequence encoding the kappa constant light chain sequence of SEQ ID NO: 586:

```
                                          (SEQ ID NO: 587)
GTGGCTGCACCATCTGTCTTCATCTTCCCGCCATCTGATGAGCAGTTGAA

ATCTGGAACTGCCTCTGTTGTGTGCCTGCTGAATAACTTCTATCCCAGAG

AGGCCAAAGTACAGTGGAAGGTGGATAACGCCCTCCAATCGGGTAACTCC

CAGGAGAGTGTCACAGAGCAGGACAGCAAGGACAGCACCTACAGCCTCAG

CAGCACCCTGACGCTGAGCAAAGCAGACTACGAGAAACACAAAGTCTACG

CCTGCGAAGTCACCCATCAGGGCCTGAGCTCGCCCGTCACAAAGAGCTTC

AACAGGGGAGAGTGT.
```

In another embodiment of the invention, polynucleotides of the invention further comprise, the following polynucleotide sequence encoding the gamma-1 constant heavy chain polypeptide sequence of SEQ ID NO: 588:

```
                                          (SEQ ID NO: 589)
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGC

AACGTGAATCACAAGCCCAGCAACACCAAGGTGGACAAGAGAGTTGAG

CCCAAATCTTGTGACAAAACTCACACATGCCCACCGTGCCCAGCACCT

GAACTCCTGGGGGGACCGTCAGTCTTCCTCTTCCCCCCAAAACCCAAG

GACACCCTCATGATCTCCCGGACCCCTGAGGTCACATGCGTGGTGGTG

GACGTGAGCCACGAAGACCCTGAGGTCAAGTTCAACTGGTACGTGGAC

GGCGTGGAGGTGCATAATGCCAAGACAAAGCCGCGGGAGGAGCAGTAC

GCCAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGG

GTAAA.
```

In another embodiment of the invention, polynucleotides of the invention further comprise, the following polynucleotide sequence encoding the variable heavy chain polypeptide sequence of SEQ ID NO: 700:

```
                                          (SEQ ID NO: 700)
GAGGTGCAGCTGGTGGAGTCTGGGGGAGGCTTGGTCCAGCCTGGGGGGTC

CCTGAGACTCTCCTGTGCAGCCTCTGGATTCTCCCTCAGTAACTACTACG

TGACCTGGGTCCGTCAGGCTCCAGGGAAGGGGCTGGAGTGGGTCGGCATC

ATCTATGGTAGTGATGAAACCGCCTACGCTACCTCCGCTATAGGCCGATT

CACCATCTCCAGAGACAATTCCAAGAACACCCTGTATCTTCAAATGAACA

GCCTGAGAGCTGAGGACACTGCTGTGTATTACTGTGCTAGAGATGATAGT

AGTGACTGGGATGCAAAGTTCAACTTGTGGGGCCAAGGGACCCTCGTCAC

CGTCTCGAGC.
```

In another embodiment of the invention, polynucleotides of the invention further comprise, the following polynucleotide sequence encoding the variable light chain polypeptide sequence of SEQ ID NO: 723:

```
                                          (SEQ ID NO: 723)
GCTATCCAGATGACCCAGTCTCCTTCCTCCCTGTCTGCATCTGTAGGAGA

CAGAGTCACCATCACTTGCCAGGCCAGTCAGAGCATTAACAATGAGTTAT

CCTGGTATCAGCAGAAACCAGGGAAAGCCCCTAAGCTCCTGATCTATAGG

GCATCCACTCTGGCATCTGGGGTCCCATCAAGGTTCAGCGGCAGTGGATC

TGGGACAGACTTCACTCTCACCATCAGCAGCCTGCAGCCTGATGATTTTG

CAACTTATTACTGCCAACAGGGTTATAGTCTGAGGAACATTGATAATGCT

TTCGGCGGAGGGACCAAGGTGGAAATCAAACGT.
```

In one embodiment, the invention is directed to an isolated polynucleotide comprising a polynucleotide encoding an anti-IL-6 $V_H$ antibody amino acid sequence selected from SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708 or another shown in FIGS. 34-37 or encoding a variant thereof wherein at least one framework residue (FR residue) has been substituted with an amino acid present at the corresponding position in a rabbit anti-IL-6 antibody $V_H$ polypeptide or a conservative amino acid substitution.

In another embodiment, the invention is directed to an isolated polynucleotide comprising the polynucleotide sequence encoding an anti-IL-6 $V_L$ antibody amino acid sequence of SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709 or another depicted in FIGS. 34-37 or encoding a variant thereof wherein at least one framework residue (FR residue) has been substituted with an amino acid present at the corresponding position in a rabbit anti-IL-6 antibody $V_L$ polypeptide or a conservative amino acid substitution.

In yet another embodiment, the invention is directed to one or more heterologous polynucleotides comprising a sequence encoding the polypeptides contained in SEQ ID NO:2 and SEQ ID NO:3; SEQ ID NO:657 and SEQ ID NO:709, SEQ ID NO:2 and SEQ ID NO:18; SEQ ID NO:2 and SEQ ID NO:19; SEQ ID NO:20 and SEQ ID NO:3; SEQ ID NO:20 and SEQ ID NO:18; SEQ ID NO:20 and SEQ ID NO:19; SEQ ID NO:21 and SEQ ID NO:22; SEQ ID NO:37 and SEQ ID NO:38; SEQ ID NO:53 and SEQ ID NO:54; SEQ ID NO:69 and SEQ ID NO:70; SEQ ID NO:85 and SEQ ID NO:86; SEQ ID NO:101 and SEQ ID NO:102; SEQ ID NO:101 and SEQ ID NO:117; SEQ ID NO:101 and SEQ ID NO:118; SEQ ID NO:119 and SEQ ID NO:102; SEQ ID NO:119 and SEQ ID NO:117; SEQ ID NO:119 and SEQ ID NO:118; SEQ ID NO:122 and SEQ ID NO:123; SEQ ID NO:138 and SEQ ID NO:139; SEQ ID NO:154 and SEQ ID NO:155; SEQ ID NO:170 and SEQ ID NO:171; SEQ ID NO:186 and SEQ ID NO:187; SEQ ID NO:202 and SEQ ID NO:203; SEQ ID NO:218 and SEQ ID NO:219; SEQ ID NO:234 and SEQ ID NO:235; SEQ ID NO:250 and SEQ ID NO:251; SEQ ID NO:266 and SEQ ID NO:267; SEQ ID NO:282 and SEQ ID NO:283; SEQ ID NO:298 and SEQ ID NO:299; SEQ ID NO:314 and SEQ ID NO:315; SEQ ID NO:330 and SEQ ID NO:331; SEQ ID NO:346 and SEQ ID NO:347; SEQ ID NO:362 and SEQ ID NO:363; SEQ ID NO:378 and SEQ ID NO:379; SEQ ID NO:394 and SEQ ID NO:395; SEQ ID NO:410 and SEQ ID NO:411; SEQ ID NO:426 and SEQ ID NO:427; SEQ ID NO:442 and SEQ ID NO:443; SEQ ID NO:458 and SEQ ID NO:459; SEQ ID NO:474 and SEQ ID NO:475; SEQ ID NO:490 and SEQ ID NO:491; SEQ ID NO:506 and SEQ ID NO:507; SEQ ID NO:522 and SEQ ID NO:523; SEQ ID NO:538 and SEQ ID NO:539; SEQ ID NO:554 and SEQ ID NO:555; or SEQ ID NO:570 and SEQ ID NO:571 and the other combinations of variable heavy and light chain sequences contained in the antibodies derived from Ab1 depicted in FIGS. 34-37. In preferred embodiments the anti-IL-6 antibody will comprises the CDRs in an anti-IL-6 antibody comprising the VH and VL in SEQ ID NO:657 and SEQ ID NO:709 respectively.

In another embodiment, the invention is directed to an isolated polynucleotide that expresses a polypeptide containing at least one CDR polypeptide derived from an anti-IL-6 antibody wherein said expressed polypeptide alone specifically binds IL-6 or specifically binds IL-6 when expressed in association with another polynucleotide sequence that expresses a polypeptide containing at least one CDR polypeptide derived from an anti-IL-6 antibody wherein said at least one CDR is selected from those contained in the $V_L$ or $V_H$ polypeptides contained in SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, 708, 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709. Exemplary nucleic acid sequence encoding the VH and VL polypeptides SEQ ID NO:657 and SEQ ID NO:709 are comprised in SEQ ID NO:700 and SEQ ID NO:723 respectively, and the variable heavy and light chain sequences contained in FIGS. 34-37.

Host cells and vectors comprising said polynucleotides are also contemplated.

In another specific embodiment the invention covers nucleic acid constructs containing any of the foregoing nucleic acid sequences and combinations thereof as well as recombinant cells containing these nucleic acid sequences and constructs containing wherein these nucleic acid sequences or constructs may be extrachromosomal or integrated into the host cell genome.

The invention further contemplates vectors comprising the polynucleotide sequences encoding the variable heavy and light chain polypeptide sequences, as well as the individual complementarity determining regions (CDRs, or hypervariable regions) set forth herein, as well as host cells comprising said sequences. In one embodiment of the invention, the host cell is a yeast cell. In another embodiment of the invention, the yeast host cell belongs to the genus *Pichia*. In particular the invention includes nucleic acid sequences and vectors containing that encode the variable heavy and light chain polypeptides in SEQ ID NO:657 and 709 and also those other variable heavy and light chain polypeptides contained in FIGS. 34-37 and especially the nucleic acid sequences contained in SEQ ID encoding SEQ ID NO:657 and 709 contained in SEQ ID NO: 700 and 723 or those encoding the other VH and VL polypeptide sequences contained in FIGS. 34-37.

In some instances, more than one exemplary polynucleotide encoding a given polypeptide sequence is provided, as summarized in Table 3.

TABLE 3

Multiple exemplary polynucleotides encoding particular polypeptides.

| Polypeptide SEQ ID NO | Exemplary coding SEQ ID NOs |
|---|---|
| 4 | 12, 111, 694 |
| 5 | 13, 112, 389, 501 |
| 6 | 14, 113, 695 |
| 9 | 17, 116, 697 |
| 39 | 47, 260 |
| 40 | 48, 261 |
| 60 | 68, 265 |
| 72 | 80, 325, 565, 581 |
| 89 | 97, 134, 166 |
| 103 | 12, 111, 694 |
| 104 | 13, 112, 389, 501 |
| 105 | 14, 113, 695 |
| 108 | 17, 116, 697 |
| 126 | 97, 134, 166 |
| 158 | 97, 134, 166 |
| 190 | 198, 214 |
| 191 | 199, 215 |
| 205 | 213, 469, 485 |
| 206 | 198, 214 |
| 207 | 199, 215 |
| 252 | 47, 260 |
| 253 | 48, 261 |
| 257 | 68, 265 |
| 317 | 80, 325, 565, 581 |
| 333 | 341, 533 |
| 381 | 13, 112, 389, 501 |
| 415 | 423, 439 |
| 431 | 423, 439 |
| 461 | 213, 469, 485 |
| 475 | 483, 499 |
| 476 | 484, 500 |
| 477 | 213, 469, 485 |
| 478 | 486, 502 |
| 479 | 487, 503 |
| 480 | 488, 504 |
| 481 | 489, 505 |
| 491 | 483, 499 |
| 492 | 484, 500 |
| 493 | 13, 112, 389, 501 |
| 494 | 486, 502 |
| 495 | 487, 503 |
| 496 | 488, 504 |
| 497 | 489, 505 |
| 525 | 341, 533 |
| 545 | 553, 585 |
| 554 | 562, 578 |

TABLE 3-continued

| Multiple exemplary polynucleotides encoding particular polypeptides. | |
|---|---|
| Polypeptide SEQ ID NO | Exemplary coding SEQ ID NOs |
| 556 | 564, 580 |
| 557 | 80, 325, 565, 581 |
| 558 | 566, 582 |
| 570 | 562, 578 |
| 572 | 564, 580 |
| 573 | 80, 325, 565, 581 |
| 574 | 566, 582 |
| 577 | 553, 585 |

In some instances, multiple sequence identifiers refer to the same polypeptide or polynucleotide sequence, as summarized in Table 4. References to these sequence identifiers are understood to be interchangeable, except where context indicates otherwise.

TABLE 4

| Repeated sequences. Each cell lists a group of repeated sequences included in the sequence listing. SEQ ID NOs of repeated sequences |
|---|
| 4, 103 |
| 5, 104, 381, 493 |
| 6, 105 |
| 9, 108 |
| 12, 111 |
| 13, 112 |
| 14, 113 |
| 17, 116 |
| 39, 252 |
| 40, 253 |
| 48, 261 |
| 60, 257 |
| 68, 265 |
| 72, 317, 557, 573 |
| 80, 325, 565, 581 |
| 89, 126, 158 |
| 97, 134, 166 |
| 120, 659 |
| 190, 206 |
| 191, 207 |
| 198, 214 |
| 199, 215 |
| 205, 461, 477 |
| 213, 469 |
| 333, 525 |
| 415, 431 |
| 423, 439 |
| 475, 491 |
| 476, 492 |
| 478, 494 |
| 479, 495 |
| 480, 496 |
| 481, 497 |
| 483, 499 |
| 484, 500 |
| 486, 502 |
| 487, 503 |
| 488, 504 |
| 489, 505 |
| 545, 577 |
| 554, 570 |
| 556, 572 |
| 558, 574 |
| 562, 578 |
| 564, 580 |
| 566, 582 |

Certain exemplary embodiments include polynucleotides that hybridize under moderately or highly stringent hybridization conditions to a polynucleotide having one of the exemplary coding sequences recited in Table 1, and also include polynucleotides that hybridize under moderately or highly stringent hybridization conditions to a polynucleotide encoding the same polypeptide as a polynucleotide having one of the exemplary coding sequences recited in Table 1, or polypeptide encoded by any of the foregoing polynucleotides.

The phrase "high stringency hybridization conditions" refers to conditions under which a probe will hybridize to its target subsequence, typically in a complex mixture of nucleic acid, but to no other sequences. High stringency conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, high stringency conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). High stringency conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). High stringency conditions may also be achieved with the addition of destabilizing agents such as formamide. For selective or specific hybridization, a positive signal is at least two times background, optionally 10 times background hybridization. Exemplary high stringency hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under high stringency conditions are still substantially related if the polypeptides that they encode are substantially related. This occurs, for example, when a copy of a nucleic acid is created using the maximum codon degeneracy permitted by the genetic code. In such cases, the nucleic acids typically hybridize under moderate stringency hybridization conditions. Exemplary "moderate stringency hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

Exemplary Embodiments of Heavy and Light Chain Polypeptides and Polynucleotides This section recites exemplary embodiments of heavy and light chain polypeptides, as well as exemplary polynucleotides encoding such polypeptides. These exemplary polynucleotides are suitable for expression in the disclosed *Pichia* expression system.

In certain embodiments, the present invention encompasses polynucleotides having at least 70%, such as at least 75%, at least 80%, at least 85%, at least 90%, at least 91%, at least 92%, at least 93%, at least 94%, at least 95%, at least 96%, at least 97%, at least 98%, at least 99%, or 100% identity to the polynucleotides recited in this application or that encode polypeptides recited in this application, or that hybridize to said polynucleotides under conditions of low-stringency, moderate-stringency, or high-stringency conditions, preferably those that encode polypeptides (e.g. an immunoglobulin heavy and light chain, a single-chain antibody, an antibody fragment, etc.) that have at least one of the biological activities set forth herein, including without limitation thereto specific binding to an IL-6 polypeptide. In another aspect, the invention encompasses a composition comprising such a polynucleotide and/or a polypeptide encoded by such a polynucleotide. In yet another aspect, the invention encompasses a method of treatment of a disease or condition associated with IL-6 or that may be prevented, treated, or ameliorated with an IL-6 antagonist such as Ab1 (e.g. cachexia, cancer fatigue, arthritis, etc.) comprising administration of a composition comprising such a polynucleotide and/or polypeptide.

In certain preferred embodiments, a heavy chain polypeptide will comprise one or more of the CDR sequences of the heavy and/or light chain polypeptides recited herein (including those contained in the heavy and light chain polypeptides recited herein) and one or more of the framework region polypeptides recited herein, including those depicted in FIGS. 2 and 34-37 or Table 1, and contained in the heavy and light chain polypeptide sequences recited herein. In certain preferred embodiments, a heavy chain polypeptide will comprise one or more Framework 4 region sequences as depicted in FIGS. 2 and 34-37 or Table 1, or as contained in a heavy or light chain polypeptide recited herein.

In certain preferred embodiments, a light chain polypeptide will comprise one or more of the CDR sequences of the heavy and/or light chain polypeptides recited herein (including those contained in the heavy and light chain polypeptides recited herein) and one or more of the Framework region polypeptides recited herein, including those depicted in FIGS. 2 and 34-37 or Table 1, and contained in the heavy and light chain polypeptide sequences recited herein. In certain preferred embodiments, a light chain polypeptide will comprise one or more Framework 4 region sequences as depicted in FIGS. 2 and 34-37 or Table 1, or as contained in a heavy or light chain polypeptide recited herein.

In any of the embodiments recited herein, certain of the sequences recited may be substituted for each other, unless the context indicates otherwise. The recitation that particular sequences may be substituted for one another, where such recitations are made, are understood to be illustrative rather than limiting, and it is also understood that such substitutions are encompassed even when no illustrative examples of substitutions are recited, For example, wherever one or more of the Ab1 light chain polypeptides is recited, e.g. any of SEQ ID NO: 2, 20, 647, 651, 660, 666, 699, 702, 706, or 709, another Ab1 light chain polypeptide may be substituted unless the context indicates otherwise. Similarly, wherever one of the Ab1 heavy chain polypeptides is recited, e.g. any of SEQ ID NO: 3, 18, 19, 652, 656, 657, 658, 661, 664, 665, 704, or 708, another Ab1 heavy chain polypeptide may be substituted unless the context indicates otherwise. Likewise, wherever one of the Ab1 light chain polynucleotides is recited, e.g. any of SEQ ID NO: 10, 662, 698, 701, or 705, another Ab1 light chain polynucleotide may be substituted unless the context indicates otherwise. Similarly, wherever one of the Ab1 heavy chain polynucleotides is recited, e.g. any of SEQ ID NO: 11, 663, 700, 703, or 707, another Ab1 heavy chain polynucleotide may be substituted unless the context indicates otherwise. Additionally, recitation of any member of any of the following groups is understood to encompass substitution by any other member of the group, as follows: Ab2 Light chain polypeptides (SEQ ID NO: 21 and 667); Ab2 Light chain polynucleotides (SEQ ID NO: 29 and 669); Ab2 Heavy chain polypeptides (SEQ ID NO: 22 and 668); Ab2 Heavy chain polynucleotides (SEQ ID NO: 30 and 670); Ab3 Light chain polypeptides (SEQ ID NO: 37 and 671); Ab3 Light chain polynucleotides (SEQ ID NO: 45 and 673); Ab3 Heavy chain polypeptides (SEQ ID NO: 38 and 672); Ab3 Heavy chain polynucleotides (SEQ ID NO: 46 and 674); Ab4 Light chain polypeptides (SEQ ID NO: 53 and 675); Ab4 Light chain polynucleotides (SEQ ID NO: 61 and 677); Ab4 Heavy chain polypeptides (SEQ ID NO: 54 and 676); Ab4 Heavy chain polynucleotides (SEQ ID NO: 62 and 678); Ab5 Light chain polypeptides (SEQ ID NO: 69 and 679); Ab5 Light chain polynucleotides (SEQ ID NO: 77 and 681); Ab5 Heavy chain polypeptides (SEQ ID NO: 70 and 680); Ab5 Heavy chain polynucleotides (SEQ ID NO: 78 and 682); Ab6 Light chain polypeptides (SEQ ID NO: 85 and 683); Ab6 Light chain polynucleotides (SEQ ID NO: 93 and 685); Ab6 Heavy chain polypeptides (SEQ ID NO: 86 and 684); Ab6 Heavy chain polynucleotides (SEQ ID NO: 94 and 686); Ab7 Light chain polypeptides (SEQ ID NO: 101, 119, 687, 693); Ab7 Light chain polynucleotides (SEQ ID NO: 109 and 689); Ab7 Heavy chain polypeptides (SEQ ID NO: 102, 117, 118, 688, 691, and 692); Ab7 Heavy chain polynucleotides (SEQ ID NO: 110 and 690); Ab1 Light Chain CDR1 polynucleotides (SEQ ID NO: 12 and 694); Ab1 Light Chain CDR3 polynucleotides (SEQ ID NO: 14 and 695); Ab1 Heavy Chain CDR2 polynucleotides (SEQ ID NO: 16 and 696) and Ab1 Heavy Chain CDR3 polynucleotides (SEQ ID NO: 17 and 697).

Anti-IL-6 Activity

As stated previously, IL-6 is a member of a family of cytokines that promote cellular responses through a receptor complex consisting of at least one subunit of the signal-transducing glycoprotein gp130 and the IL-6 receptor (IL-6R). The IL-6R may also be present in a soluble form (sIL-6R). IL-6 binds to IL-6R, which then dimerizes the signal-transducing receptor gp130.

It is believed that the anti-IL-6 antibodies of the invention, or IL-6 binding fragments thereof, are useful by exhibiting anti-IL-6 activity. In one non-limiting embodiment of the invention, the anti-IL-6 antibodies of the invention, or IL-6 binding fragments thereof, exhibit anti-IL-6 activity by binding to IL-6 which may be soluble IL-6 or cell surface expressed IL-6 and/or may prevent or inhibit the binding of IL-6 to IL-6R and/or activation (dimerization) of the gp130 signal-transducing glycoprotein and the formation of IL-6/IL-6R/gp130 multimers and the biological effects of any of the foregoing. The subject anti-IL-6 antibodies may possess different antagonistic activities based on where (i.e., epitope) the particular antibody binds IL-6 and/or how it affects the formation of the foregoing IL-6 complexes and/or multimers and the biological effects thereof. Consequently, different anti-IL-6 antibodies according to the invention e.g., may be better suited for preventing or treating conditions involving the formation and accumulation of substantial soluble IL-6 such as rheumatoid arthritis whereas other antibodies may be favored in treatments wherein the prevention of IL-6/IL-6R/gp130 or IL-6/IL-6R/gp130 multimers is a desired therapeutic outcome. This can be determined in binding and other assays.

The anti-IL-6 activity of the anti-IL-6 antibody of the present invention, and fragments thereof having binding specificity to IL-6, may also be described by their strength of binding or their affinity for IL-6. This also may affect their therapeutic properties. In one embodiment of the invention, the anti-IL-6 antibodies of the present invention, and fragments thereof having binding specificity to IL-6, bind to IL-6 with a dissociation constant ($K_D$) of less than or equal to $5\times10^{-7}$, $10^{-7}$, $5\times10^{-8}$, $10^{-8}$, $5\times10^{-9}$, $10^{-9}$, $5\times10^{-10}$, $10^{-10}$, $5\times10^{-11}$, $10^{-11}$, $5\times10^{-12}$, $10^{-12}$, $5\times10^{-13}$, $10^{-13}$, $5\times10^{-14}$, $10^{-14}$, $5\times10^{-15}$ or $10^{-15}$. Preferably, the anti-IL-6 antibodies and fragments thereof bind IL-6 with a dissociation constant of less than or equal to $5\times10^{-10}$.

In another embodiment of the invention, the anti-IL-6 activity of the anti-IL-6 antibodies of the present invention, and fragments thereof having binding specificity to IL-6, bind to IL-6 with an off-rate of less than or equal to $10^{-4}$ $S^{-1}$, $5\times10^{-5}$ $S^{-1}$, $10^{-5}$ $S^{-1}$, $5\times10^{-6}$ $S^{-1}$, $10^{-6}$ $S^{-1}$, $5\times10^{-7}$ $S^{-1}$, or $10^{-7}$ $S^{-1}$. In one embodiment of the invention, the anti-IL-6 antibodies of the invention, and fragments thereof having binding specificity to IL-6, bind to a linear or conformational IL-6 epitope.

In a further embodiment of the invention, the anti-IL-6 activity of the anti-IL-6 antibodies of the present invention, and fragments thereof having binding specificity to IL-6, exhibit anti-IL-6 activity by ameliorating or reducing the symptoms of, or alternatively treating, or preventing, diseases and disorders associated with IL-6. Non-limiting examples of diseases and disorders associated with IL-6 are set forth infra. As noted cancer-related fatigue, cachexia and rheumatoid arthritis are preferred indications for the subject anti-IL-6 antibodies.

In another embodiment of the invention, the anti-IL-6 antibodies described herein, or IL-6 binding fragments thereof, do not have binding specificity for IL-6R or the gp-130 signal-transducing glycoprotein.

B-cell Screening and Isolation

In one embodiment, the present invention provides methods of isolating a clonal population of antigen-specific B cells that may be used for isolating at least one antigen-specific cell. As described and exemplified infra, these methods contain a series of culture and selection steps that can be used separately, in combination, sequentially, repetitively, or periodically. Preferably, these methods are used for isolating at least one antigen-specific cell, which can be used to produce a monoclonal antibody, which is specific to a desired antigen, or a nucleic acid sequence corresponding to such an antibody.

In one embodiment, the present invention provides a method comprising the steps of:

a. preparing a cell population comprising at least one antigen-specific B cell;

b. enriching the cell population, e.g., by chromatography, to form an enriched cell population comprising at least one antigen-specific B cell;

c. isolating a single B cell from the enriched B cell population; and d. determining whether the single B cell produces an antibody specific to the antigen.

In another embodiment, the present invention provides an improvement to a method of isolating a single, antibody-producing B cell, the improvement comprising enriching a B cell population obtained from a host that has been immunized or naturally exposed to an antigen, wherein the enriching step precedes any selection steps, comprises at least one culturing step, and results in a clonal population of B cells that produces a single monoclonal antibody specific to said antigen.

Throughout this application, a "clonal population of B cells" refers to a population of B cells that only secrete a single antibody specific to a desired antigen. That is to say that these cells produce only one type of monoclonal antibody specific to the desired antigen.

In the present application, "enriching" a cell population cells means increasing the frequency of desired cells, typically antigen-specific cells, contained in a mixed cell population, e.g., a B cell-containing isolate derived from a host that is immunized against a desired antigen. Thus, an enriched cell population encompasses a cell population having a higher frequency of antigen-specific cells as a result of an enrichment step, but this population of cells may contain and produce different antibodies.

The general term "cell population" encompasses pre- and a post-enrichment cell populations, keeping in mind that when multiple enrichment steps are performed, a cell population can be both pre- and post-enrichment. For example, in one embodiment, the present invention provides a method:

a. harvesting a cell population from an immunized host to obtain a harvested cell population;

b. creating at least one single cell suspension from the harvested cell population;

c. enriching at least one single cell suspension to form a first enriched cell population;

d. enriching the first enriched cell population to form a second enriched cell population;

e. enriching the second enriched cell population to form a third enriched cell population; and f. selecting an antibody produced by an antigen-specific cell of the third enriched cell population.

Each cell population may be used directly in the next step, or it can be partially or wholly frozen for long- or short-term storage or for later steps. Also, cells from a cell population can be individually suspended to yield single cell suspensions. The single cell suspension can be enriched, such that a single cell suspension serves as the pre-enrichment cell population. Then, one or more antigen-specific single cell suspensions together form the enriched cell population; the antigen-specific single cell suspensions can be grouped together, e.g., re-plated for further analysis and/or antibody production.

In one embodiment, the present invention provides a method of enriching a cell population to yield an enriched cell population having an antigen-specific cell frequency that is about 50% to about 100%, or increments therein. Preferably, the enriched cell population has an antigen-specific cell frequency greater than or equal to about 50%, 60%, 70%, 75%, 80%, 90%, 95%, 99%, or 100%.

In another embodiment, the present invention provides a method of enriching a cell population whereby the frequency of antigen-specific cells is increased by at least about 2-fold, 5-fold, 10-fold, 20-fold, 50-fold, 100-fold, or increments therein.

Throughout this application, the term "increment" is used to define a numerical value in varying degrees of precision, e.g., to the nearest 10, 1, 0.1, 0.01, etc. The increment can be rounded to any measurable degree of precision, and the increment need not be rounded to the same degree of precision on both sides of a range. For example, the range 1 to 100 or increments therein includes ranges such as 20 to 80, 5 to 50, and 0.4 to 98. When a range is open-ended, e.g., a range of less than 100, increments therein means increments between 100 and the measurable limit. For example, less than 100 or increments therein means 0 to 100 or increments therein unless the feature, e.g., temperature, is not limited by 0.

Antigen-specificity can be measured with respect to any antigen. The antigen can be any substance to which an antibody can bind including, but not limited to, peptides, proteins or fragments thereof; carbohydrates; organic and inorganic molecules; receptors produced by animal cells, bacterial cells, and viruses; enzymes; agonists and antagonists of biological pathways; hormones; and cytokines. Exemplary antigens include, but are not limited to, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF) and Hepcidin. Preferred antigens include IL-6, IL-13, TNF-α, VEGF-α, Hepatocyte Growth Factor (HGF) and Hepcidin. In a method utilizing more than one enrichment step, the antigen used in each enrichment step can be the same as or different from one another. Multiple enrichment steps with the same antigen may yield a large and/or diverse population of antigen-specific cells; multiple enrichment steps with different antigens may yield an enriched cell population with cross-specificity to the different antigens.

Enriching a cell population can be performed by any cell-selection means known in the art for isolating antigen-specific cells. For example, a cell population can be enriched by chromatographic techniques, e.g., Miltenyi bead or magnetic bead technology. The beads can be directly or indirectly attached to the antigen of interest. In a preferred embodiment, the method of enriching a cell population includes at least one chromatographic enrichment step.

A cell population can also be enriched by performed by any antigen-specificity assay technique known in the art, e.g., an ELISA assay or a halo assay. ELISA assays include, but are not limited to, selective antigen immobilization (e.g., biotinylated antigen capture by streptavidin, avidin, or neutravidin coated plate), non-specific antigen plate coating, and through an antigen build-up strategy (e.g., selective antigen capture followed by binding partner addition to generate a heteromeric protein-antigen complex). The antigen can be directly or indirectly attached to a solid matrix or support, e.g., a column. A halo assay comprises contacting the cells with antigen-loaded beads and labeled anti-host antibody specific to the host used to harvest the B cells. The label can be, e.g., a fluorophore. In one embodiment, at least one assay enrichment step is performed on at least one single cell suspension. In another embodiment, the method of enriching a cell population includes at least one chromatographic enrichment step and at least one assay enrichment step.

Methods of "enriching" a cell population by size or density are known in the art. See, e.g., U.S. Pat. No. 5,627,052. These steps can be used in the present method in addition to enriching the cell population by antigen-specificity.

The cell populations of the present invention contain at least one cell capable of recognizing an antigen. Antigen-recognizing cells include, but are not limited to, B cells, plasma cells, and progeny thereof. In one embodiment, the present invention provides a clonal cell population containing a single type of antigen-specific B-cell, i.e., the cell population produces a single monoclonal antibody specific to a desired antigen.

In such embodiment, it is believed that the clonal antigen-specific population of B cells consists predominantly of antigen-specific, antibody-secreting cells, which are obtained by the novel culture and selection protocol provided herein. Accordingly, the present invention also provides methods for obtaining an enriched cell population containing at least one antigen-specific, antibody-secreting cell. In one embodiment, the present invention provides an enriched cell population containing about 50% to about 100%, or increments therein, or greater than or equal to about 60%, 70%, 80%, 90%, or 100% of antigen-specific, antibody-secreting cells.

In one embodiment, the present invention provides a method of isolating a single B cell by enriching a cell population obtained from a host before any selection steps, e.g., selecting a particular B cell from a cell population and/or selecting an antibody produced by a particular cell. The enrichment step can be performed as one, two, three, or more steps. In one embodiment, a single B cell is isolated from an enriched cell population before confirming whether the single B cell secretes an antibody with antigen-specificity and/or a desired property.

In one embodiment, a method of enriching a cell population is used in a method for antibody production and/or selection. Thus, the present invention provides a method comprising enriching a cell population before selecting an antibody. The method can include the steps of: preparing a cell population comprising at least one antigen-specific cell, enriching the cell population by isolating at least one antigen-specific cell to form an enriched cell population, and inducing antibody production from at least one antigen-specific cell. In a preferred embodiment, the enriched cell population contains more than one antigen-specific cell. In one embodiment, each antigen-specific cell of the enriched population is cultured under conditions that yield a clonal antigen-specific B cell population before isolating an antibody producing cell therefrom and/or producing an antibody using said B cell, or a nucleic acid sequence corresponding to such an antibody. In contrast to prior techniques where antibodies are produced from a cell population with a low frequency of antigen-specific cells, the present invention allows antibody selection from among a high frequency of antigen-specific cells. Because an enrichment step is used prior to antibody selection, the majority of the cells, preferably virtually all of the cells, used for antibody production are antigen-specific. By producing antibodies from a population of cells with an increased frequency of antigen specificity, the quantity and variety of antibodies are increased.

In the antibody selection methods of the present invention, an antibody is preferably selected after an enrichment step and a culture step that results in a clonal population of antigen-specific B cells. The methods can further comprise a step of sequencing a selected antibody or portions thereof from one or more isolated, antigen-specific cells. Any method known in the art for sequencing can be employed and can include sequencing the heavy chain, light chain, variable region(s), and/or complementarity determining region(s) (CDR).

In addition to the enrichment step, the method for antibody selection can also include one or more steps of screening a cell population for antigen recognition and/or antibody functionality. For example, the desired antibodies may have specific structural features, such as binding to a particular epitope or mimicry of a particular structure; antagonist or agonist activity; or neutralizing activity, e.g., inhibiting binding between the antigen and a ligand. In one embodiment, the antibody functionality screen is ligand-dependent. Screening for antibody functionality includes, but is not limited to, an in vitro protein-protein interaction assay that recreates the natural interaction of the antigen ligand with recombinant receptor protein; and a cell-based response that is ligand dependent and easily monitored (e.g., proliferation response). In one embodiment, the method for antibody selection includes a step of screening the cell population for antibody functionality by measuring the inhibitory concentration (IC50). In one embodiment, at least one of the isolated, antigen-specific cells produces an antibody having an IC50 of less than about 100, 50, 30, 25, 10 μg/mL, or increments therein.

In addition to the enrichment step, the method for antibody selection can also include one or more steps of screening a cell population for antibody binding strength. Antibody binding strength can be measured by any method known in the art (e.g., Biacore™). In one embodiment, at least one of the isolated, antigen-specific cells produces an antibody having a high antigen affinity, e.g., a dissociation constant (Kd) of less than about $5\times10^{-10}$ M-1, preferably about $1\times10^{-13}$ to $5\times10^{-10}$, $1\times10^{-12}$ to $1\times10^{-10}$, $1\times10^{-12}$ to $7.5\times10^{-11}$, $1\times10^{-11}$ to $2\times10^{-11}$, about $1.5\times10^{-11}$ or less, or increments therein. In this embodiment, the antibodies are said to be affinity mature. In a preferred embodiment, the affinity of the antibodies is comparable to or higher than the affinity of any one of Panorex® (edrecolomab), Rituxan® (rituximab), Herceptin® (traztuzumab), Mylotarg® (gentuzumab), Campath® (alemtuzumab), Zevalin™ (ibritumomab), Erbitux™ (cetuximab), Avastin™ (bevicizumab), Raptiva™ (efalizumab), Remicade® (infliximab), Humira™ (adalimumab), and Xolair™ (omalizumab). Preferably, the affinity of the antibodies is comparable to or higher than the affinity of Humira™. The affinity of an antibody can also be increased by known affinity maturation techniques. In one embodiment, at least one cell population is screened for at least one of, preferably both, antibody functionality and antibody binding strength.

In addition to the enrichment step, the method for antibody selection can also include one or more steps of screening a cell population for antibody sequence homology, especially human homology. In one embodiment, at least one of the isolated, antigen-specific cells produces an antibody that has a homology to a human antibody of about 50% to about 100%, or increments therein, or greater than about 60%, 70%, 80%, 85%, 90%, or 95% homologous. The antibodies can be humanized to increase the homology to a human sequence by techniques known in the art such as CDR grafting or selectivity determining residue grafting (SDR).

In another embodiment, the present invention also provides the antibodies themselves according to any of the embodiments described above in terms of IC50, Kd, and/or homology.

The B cell selection protocol disclosed herein has a number of intrinsic advantages versus other methods for obtaining antibody-secreting B cells and monoclonal antibodies specific to desired target antigens. These advantages include, but are not restricted to, the following:

First, it has been found that when these selection procedures are utilized with a desired antigen such as IL-6 or TNF-α, the methods reproducibly result in antigen-specific B cells capable of generating what appears to be a substantially comprehensive complement of antibodies, i.e., antibodies that bind to the various different epitopes of the antigen. Without being bound by theory, it is hypothesized that the comprehensive complement is attributable to the antigen enrichment step that is performed prior to initial B cell recovery. Moreover, this advantage allows for the isolation and selection of antibodies with different properties as these properties may vary depending on the epitopic specificity of the particular antibody.

Second, it has been found that the B cell selection protocol reproducibly yields a clonal B cell culture containing a single B cell, or its progeny, secreting a single monoclonal antibody that generally binds to the desired antigen with a relatively high binding affinity, i.e. picomolar or better antigen binding affinities. By contrast, prior antibody selection methods tend to yield relatively few high affinity antibodies and therefore require extensive screening procedures to isolate an antibody with therapeutic potential. Without being bound by theory, it is hypothesized that the protocol results in both in vivo B cell immunization of the host (primary immunization) followed by a second in vitro B cell stimulation (secondary antigen priming step) that may enhance the ability and propensity of the recovered clonal B cells to secrete a single high affinity monoclonal antibody specific to the antigen target.

Third, it has been observed (as shown herein with IL-6 specific B cells) that the B cell selection protocol reproducibly yields enriched B cells producing IgG's that are, on average, highly selective (antigen specific) to the desired target. Antigen-enriched B cells recovered by these methods are believed to contain B cells capable of yielding the desired full complement of epitopic specificities as discussed above.

Fourth, it has been observed that the B cell selection protocols, even when used with small antigens, i.e., peptides of 100 amino acids or less, e.g., 5-50 amino acids long, reproducibly give rise to a clonal B cell culture that secretes a single high affinity antibody to the small antigen, e.g., a peptide. This is highly surprising as it is generally quite difficult, labor intensive, and sometimes not even feasible to produce high affinity antibodies to small peptides. Accordingly, the invention can be used to produce therapeutic antibodies to desired peptide targets, e.g., viral, bacterial or autoantigen peptides, thereby allowing for the production of monoclonal antibodies with very discrete binding properties or even the production of a cocktail of monoclonal antibodies to different peptide targets, e.g., different viral strains. This advantage may especially be useful in the context of the production of a therapeutic or prophylactic vaccine having a desired valency, such as an HPV vaccine that induces protective immunity to different HPV strains.

Fifth, the B cell selection protocol, particularly when used with B cells derived from rabbits, tends to reproducibly yield antigen-specific antibody sequences that are very similar to endogenous human immunoglobulins (around 90% similar at the amino acid level) and that contain CDRs that possess a length very analogous to human immunoglobulins and therefore require little or no sequence modification (typically at most only a few CDR residues may be modified in the parent antibody sequence and no framework exogenous residues introduced) in order to eliminate potential immunogenicity concerns. In particular, preferably the recombinant antibody will contain only the host (rabbit) CDR1 and CDR2 residues required for antigen recognition and the entire CDR3. Thereby, the high antigen binding affinity of the recovered antibody sequences produced according to the B cell and antibody selection protocol remains intact or substantially intact even with humanization.

In sum, these methods can be used to produce antibodies exhibiting higher binding affinities to more distinct epitopes by the use of a more efficient protocol than was previously known.

In a specific embodiment, the present invention provides a method for identifying a single B cell that secretes an antibody specific to a desired antigen and that optionally possesses at least one desired functional property such as affinity, avidity, cytolytic activity, and the like by a process including the following steps:

a. immunizing a host against an antigen;

b. harvesting B cells from the host;

c. enriching the harvested B cells to increase the frequency of antigen-specific cells;

d. creating at least one single cell suspension;

e. culturing a sub-population from the single cell suspension under conditions that favor the survival of a single antigen-specific B cell per culture well;

f. isolating B cells from the sub-population; and g. determining whether the single B cell produces an antibody specific to the antigen.

Typically, these methods will further comprise an additional step of isolating and sequencing, in whole or in part, the polypeptide and nucleic acid sequences encoding the desired antibody. These sequences or modified versions or portions thereof can be expressed in desired host cells in order to produce recombinant antibodies to a desired antigen.

As noted previously, it is believed that the clonal population of B cells predominantly comprises antibody-secreting B cells producing antibody against the desired antigen. It is also believed based on experimental results obtained with several antigens and with different B cell populations that the clonally produced B cells and the isolated antigen-specific B cells derived therefrom produced according to the invention secrete a monoclonal antibody that is typically of relatively high affinity and moreover is capable of efficiently and reproducibly producing a selection of monoclonal antibodies of greater epitopic variability as compared to other methods of deriving monoclonal antibodies from cultured antigen-specific B cells. In an exemplary embodiment the population of immune cells used in such B cell selection methods will be derived from a rabbit. However, other hosts that produce antibodies, including non-human and human hosts, can alternatively be used as a source of immune B cells. It is believed that the use of rabbits as a source of B cells may enhance the diversity of monoclonal antibodies that may be derived by the methods. Also, the antibody sequences derived from rabbits according to the invention typically possess sequences having a high degree of sequence identity to human antibody sequences making them favored for use in humans since they should possess little antigenicity. In the course of humanization, the final humanized antibody contains a much lower foreign/host residue content, usually restricted to a subset of the host CDR residues that differ dramatically due to their nature versus the human target sequence used in the grafting. This enhances the probability of complete activity recovery in the humanized antibody protein.

The methods of antibody selection using an enrichment step disclosed herein include a step of obtaining an immune cell-containing cell population from an immunized host. Methods of obtaining an immune cell-containing cell population from an immunized host are known in the art and generally include inducing an immune response in a host and harvesting cells from the host to obtain one or more cell populations. The response can be elicited by immunizing the host against a desired antigen. Alternatively, the host used as a source of such immune cells can be naturally exposed to the desired antigen such as an individual who has been infected with a particular pathogen such as a bacterium or virus or alternatively has mounted a specific antibody response to a cancer that the individual is afflicted with.

Host animals are well-known in the art and include, but are not limited to, guinea pig, rabbit, mouse, rat, non-human primate, human, as well as other mammals and rodents, chicken, cow, pig, goat, and sheep. Preferably the host is a mammal, more preferably, rabbit, mouse, rat, or human. When exposed to an antigen, the host produces antibodies as part of the native immune response to the antigen. As mentioned, the immune response can occur naturally, as a result of disease, or it can be induced by immunization with the antigen. Immunization can be performed by any method known in the art, such as, by one or more injections of the antigen with or without an agent to enhance immune response, such as complete or incomplete Freund's adjuvant. In another embodiment, the invention also contemplates intrasplenic immunization. As an alternative to immunizing a host animal in vivo, the method can comprise immunizing a host cell culture in vitro.

After allowing time for the immune response (e.g., as measured by serum antibody detection), host animal cells are harvested to obtain one or more cell populations. In a preferred embodiment, a harvested cell population is screened for antibody binding strength and/or antibody functionality. A harvested cell population is preferably from at least one of the spleen, lymph nodes, bone marrow, and/or peripheral blood mononuclear cells (PBMCs). The cells can be harvested from more than one source and pooled. Certain sources may be preferred for certain antigens. For example, the spleen, lymph nodes, and PBMCs are preferred for IL-6; and the lymph nodes are preferred for TNF. The cell population is harvested about 20 to about 90 days or increments therein after immunization, preferably about 50 to about 60 days. A harvested cell population and/or a single cell suspension therefrom can be enriched, screened, and/or cultured for antibody selection. The frequency of antigen-specific cells within a harvested cell population is usually about 1% to about 5%, or increments therein.

In one embodiment, a single cell suspension from a harvested cell population is enriched, preferably by using Miltenyi beads. From the harvested cell population having a frequency of antigen-specific cells of about 1% to about 5%, an enriched cell population is thus derived having a frequency of antigen-specific cells approaching 100%.

Figure 3:
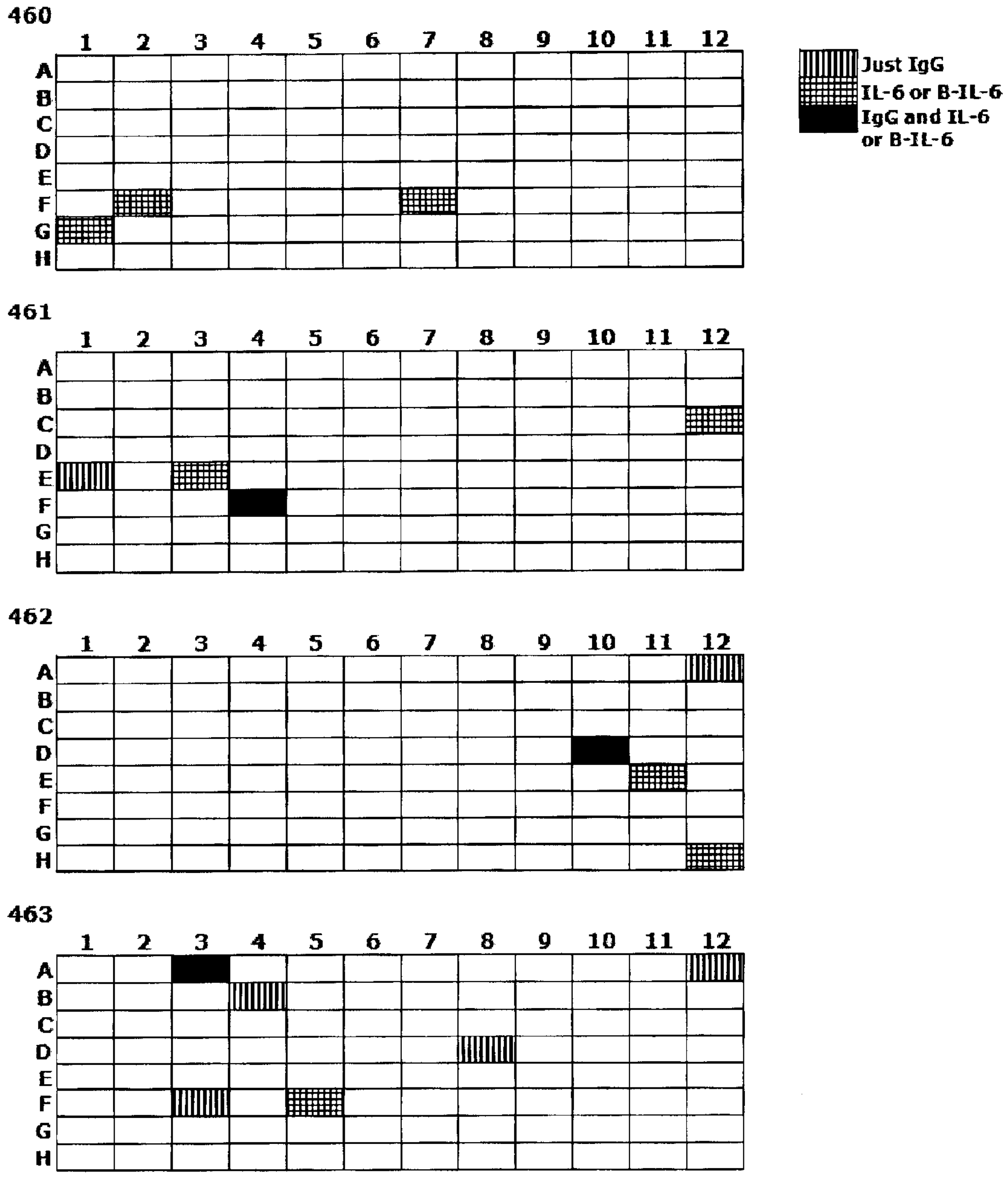
FIG. 3 demonstrates the high correlation between the IgG produced and antigen specificity for an exemplary IL-6 protocol. 9 of 11 wells showed specific IgG correlation with antigen recognition.

The method of antibody selection using an enrichment step includes a step of producing antibodies from at least one antigen-specific cell from an enriched cell population. Methods of producing antibodies in vitro are well known in the art, and any suitable method can be employed. In one embodiment, an enriched cell population, such as an antigen-specific single cell suspension from a harvested cell population, is plated at various cell densities, such as 50, 100, 250, 500, or other increments between 1 and 1000 cells per well. Preferably, the sub-population comprises no more than about 10,000 antigen-specific, antibody-secreting cells, more preferably about 50-10,000, about 50-5,000, about 50-1,000, about 50-500, about 50-250 antigen-specific, antibody-secreting cells, or increments therein. Then, these sub-populations are cultured with suitable medium (e.g., an activated T cell conditioned medium, particularly 1-5% activated rabbit T cell conditioned medium) on a feeder layer, preferably under conditions that favor the survival of a single proliferating antibody-secreting cell per culture well. The feeder layer, generally comprised of irradiated cell matter, e.g., EL4B cells, does not constitute part of the cell population. The cells are cultured in a suitable media for a time sufficient for antibody production, for example about 1 day to about 2 weeks, about 1 day to about 10 days, at least about 3 days, about 3 to about 5 days, about 5 days to about 7 days, at least about 7 days, or other increments therein. In one embodiment, more than one sub-population is cultured simultaneously. Preferably, a single antibody-producing cell and progeny thereof survives in each well, thereby providing a clonal population of antigen-specific B cells in each well. At this stage, the immunoglobulin G (IgG) produced by the clonal population is highly correlative with antigen specificity. In a preferred embodiment, the IgGs exhibit a correlation with antigen specificity that is greater than about 50%, more preferably greater than 70%, 85%, 90%, 95%, 99%, or increments therein. See FIG. 3, which demonstrates an exemplary correlation for IL-6. The correlations were demonstrated by setting up B cell cultures under limiting conditions to establish single antigen-specific antibody products per well. Antigen-specific versus general IgG synthesis was compared. Three populations were observed: IgG that recognized a single format of antigen (biotinylated and direct coating), detectable IgG and antigen recognition irrespective of immobilization, and IgG production alone. IgG production was highly correlated with antigen-specificity.

A supernatant containing the antibodies is optionally collected, which can be enriched, screened, and/or cultured for antibody selection according to the steps described above. In one embodiment, the supernatant is enriched (preferably by an antigen-specificity assay, especially an ELISA assay) and/or screened for antibody functionality.

In another embodiment, the enriched, preferably clonal, antigen-specific B cell population from which a supernatant described above is optionally screened in order to detect the presence of the desired secreted monoclonal antibody is used for the isolation of a few B cells, preferably a single B cell, which is then tested in an appropriate assay in order to confirm the presence of a single antibody-producing B cell in the clonal B cell population. In one embodiment about 1 to about 20 cells are isolated from the clonal B cell population, preferably less than about 15, 12, 10, 5, or 3 cells, or increments therein, most preferably a single cell. The screen is preferably effected by an antigen-specificity assay, especially a halo assay. The halo assay can be performed with the full length protein, or a fragment thereof. The antibody-containing supernatant can also be screened for at least one of: antigen binding affinity; agonism or antagonism of antigen-ligand binding, induction or inhibition of the proliferation of a specific target cell type; induction or inhibition of lysis of a target cell, and induction or inhibition of a biological pathway involving the antigen.

The identified antigen-specific cell can be used to derive the corresponding nucleic acid sequences encoding the desired monoclonal antibody. (An AluI digest can confirm that only a single monoclonal antibody type is produced per well.) As mentioned above, these sequences can be mutated, such as by humanization, in order to render them suitable for use in human medicaments.

As mentioned, the enriched B cell population used in the process can also be further enriched, screened, and/or cultured for antibody selection according to the steps described above which can be repeated or performed in a different order. In a preferred embodiment, at least one cell of an enriched, preferably clonal, antigen-specific cell population is isolated, cultured, and used for antibody selection.

Thus, in one embodiment, the present invention provides a method comprising:

a. harvesting a cell population from an immunized host to obtain a harvested cell population;

b. creating at least one single cell suspension from a harvested cell population;

c. enriching at least one single cell suspension, preferably by chromatography, to form a first enriched cell population;

d. enriching the first enriched cell population, preferably by ELISA assay, to form a second enriched cell population which preferably is clonal, i.e., it contains only a single type of antigen-specific B cell;

e. enriching the second enriched cell population, preferably by halo assay, to form a third enriched cell population containing a single or a few number of B cells that produce an antibody specific to a desired antigen; and f. selecting an antibody produced by an antigen-specific cell isolated from the third enriched cell population.

The method can further include one or more steps of screening the harvested cell population for antibody binding strength (affinity, avidity) and/or antibody functionality. Suitable screening steps include, but are not limited to, assay methods that detect: whether the antibody produced by the identified antigen-specific B cell produces an antibody possessing a minimal antigen binding affinity, whether the antibody agonizes or antagonizes the binding of a desired antigen to a ligand; whether the antibody induces or inhibits the proliferation of a specific cell type; whether the antibody induces or elicits a cytolytic reaction against target cells; whether the antibody binds to a specific epitope; and whether the antibody modulates (inhibits or agonizes) a specific biological pathway or pathways involving the antigen.

Similarly, the method can include one or more steps of screening the second enriched cell population for antibody binding strength and/or antibody functionality.

The method can further include a step of sequencing the polypeptide sequence or the corresponding nucleic acid sequence of the selected antibody. The method can also include a step of producing a recombinant antibody using the sequence, a fragment thereof, or a genetically modified version of the selected antibody. Methods for mutating antibody sequences in order to retain desired properties are well known to those skilled in the art and include humanization, chimerisation, production of single chain antibodies; these mutation methods can yield recombinant antibodies possessing desired effector function, immunogenicity, stability, removal or addition of glycosylation, and the like. The recombinant antibody can be produced by any suitable recombinant cell, including, but not limited to mammalian cells such as CHO, COS, BHK, HEK-293, bacterial cells, yeast cells, plant cells, insect cells, and amphibian cells. In one embodiment, the antibodies are expressed in polyploidal yeast cells, i.e., diploid yeast cells, particularly *Pichia*.

In one embodiment, the method comprises:

a. immunizing a host against an antigen to yield host antibodies;

b. screening the host antibodies for antigen specificity and neutralization;

c. harvesting B cells from the host;

d. enriching the harvested B cells to create an enriched cell population having an increased frequency of antigen-specific cells;

e. culturing one or more sub-populations from the enriched cell population under conditions that favor the survival of a single B cell to produce a clonal population in at least one culture well;

f. determining whether the clonal population produces an antibody specific to the antigen;

g. isolating a single B cell; and h. sequencing the nucleic acid sequence of the antibody produced by the single B cell.

Methods of Humanizing Antibodies

In another embodiment of the invention, there is provided a method for humanizing antibody heavy and light chains. In this embodiment, the following method is followed for the humanization of the heavy and light chains:

Light Chain

1. Identify the amino acid that is the first one following the signal peptide sequence. This is the start of Framework 1. The signal peptide starts at the first initiation methionine and is typically, but not necessarily 22 amino acids in length for rabbit light chain protein sequences. The start of the mature polypeptide can also be determined experimentally by N-terminal protein sequencing, or can be predicted using a prediction algorithm. This is also the start of Framework 1 as classically defined by those in the field.

Example: RbtVL Amino acid residue 1 in FIG. 2, starting 'AYDM . . . '

2. Identify the end of Framework 3. This is typically 86-90 amino acids following the start of Framework 1 and is typically a cysteine residue preceded by two tyrosine residues. This is the end of the Framework 3 as classically defined by those in the field.

Example: RbtVL amino acid residue 88 in FIG. 2, ending as 'TYYC'

3. Use the rabbit light chain sequence of the polypeptide starting from the beginning of Framework 1 to the end of Framework 3 as defined above and perform a sequence homology search for the most similar human antibody protein sequences. This will typically be a search against human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example: RbtVL amino acid sequence from residues numbered 1 through 88 in FIG. 2 is BLASTed against a human antibody germline database. The top three unique returned sequences are shown in FIG. 2 as L12A, V1 and V×02.

4. Generally the most homologous human germline variable light chain sequence is then used as the basis for humanization. However those skilled in the art may decide to use another sequence that wasn't the highest homology as determined by the homology algorithm, based on other factors including sequence gaps and framework similarities.

Example: In FIG. 2, L12A was the most homologous human germline variable light chain sequence and is used as the basis for the humanization of RbtVL.

5. Determine the framework and CDR arrangement (FR1, FR2, FR3, CDR1 & CDR2) for the human homolog being used for the light chain humanization. This is using the traditional layout as described in the field. Align the rabbit variable light chain sequence with the human homolog, while maintaining the layout of the framework and CDR regions.

Example: In FIG. 2, the RbtVL sequence is aligned with the human homologous sequence L12A, and the framework and CDR domains are indicated.

6. Replace the human homologous light chain sequence CDR1 and CDR2 regions with the CDR1 and CDR2 sequences from the rabbit sequence. If there are differences in length between the rabbit and human CDR sequences then use the entire rabbit CDR sequences and their lengths. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted.

Example: In FIG. 2, the CDR1 and CDR2 amino acid residues of the human homologous variable light chain L12A are replaced with the CDR1 and CDR2 amino acid sequences from the RbtVL rabbit antibody light chain sequence. The human L12A frameworks 1, 2 and 3 are unaltered. The resulting humanized sequence is shown below as VLh from residues numbered 1 through 88. Note that the only residues that are different from the L12A human sequence are underlined, and are thus rabbit-derived amino acid residues. In this example only 8 of the 88 residues are different than the human sequence.

7. After framework 3 of the new hybrid sequence created in Step 6, attach the entire CDR3 of the rabbit light chain antibody sequence. The CDR3 sequence can be of various lengths, but is typically 9 to 15 amino acid residues in length. The CDR3 region and the beginning of the following framework 4 region are defined classically and identifiable by those skilled in the art. Typically the beginning of Framework 4, and thus after the end of CDR3 consists of the sequence 'FGGG . . . ', however some variation may exist in these residues.

Example: In FIG. 2, the CDR3 of RbtVL (amino acid residues numbered 89-100) is added after the end of framework 3 in the humanized sequence indicated as VLh.

8. The rabbit light chain framework 4, which is typically the final 11 amino acid residues of the variable light chain and begins as indicated in Step 7 above and typically ends with the amino acid sequence ' . . . VVKR' is replaced with the nearest human light chain framework 4 homolog, usually from germline sequence. Frequently this human light chain framework 4 is of the sequence 'FGGGTKVEIKR'. It is possible that other human light chain framework 4 sequences that are not the most homologous or otherwise different may be used without affecting the specificity, affinity and/or immunogenicity of the resulting humanized antibody. This human light chain framework 4 sequence is added to the end of the variable light chain humanized sequence immediately following the CDR3 sequence from Step 7 above. This is now the end of the variable light chain humanized amino acid sequence.

Example: In FIG. 2, Framework 4 (FR4) of the RbtVL rabbit light chain sequence is shown above a homologous human FR4 sequence. The human FR4 sequence is added to the humanized variable light chain sequence (VLh) right after the end of the CD3 region added in Step 7 above.

Heavy Chain

1. Identify the amino acid that is the first one following the signal peptide sequence. This is the start of Framework 1. The signal peptide starts at the first initiation methionine and is typically 19 amino acids in length for rabbit heavy chain protein sequences. Typically, but not necessarily always, the final 3 amino acid residues of a rabbit heavy chain signal peptide are ' . . . VQC', followed by the start of Framework 1. The start of the mature polypeptide can also be determined experimentally by N-terminal protein sequencing, or can be predicted using a prediction algorithm. This is also the start of Framework 1 as classically defined by those in the field.

Example: RbtVH Amino acid residue 1 in FIG. 2, starting 'QEQL . . . '

2. Identify the end of Framework 3. This is typically 95-100 amino acids following the start of Framework 1 and typically has the final sequence of ' . . . CAR' (although the alanine can also be a valine). This is the end of the Framework 3 as classically defined by those in the field.

Example: RbtVH amino acid residue 98 in FIG. 2, ending as ' . . . FCVR'.

3. Use the rabbit heavy chain sequence of the polypeptide starting from the beginning of Framework 1 to the end of Framework 3 as defined above and perform a sequence homology search for the most similar human antibody protein sequences. This will typically be against a database of human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example: RbtVH amino acid sequence from residues numbered 1 through 98 in FIG. 2 is BLASTed against a human antibody germline database. The top three unique returned sequences are shown in FIG. 2 as 3-64-04, 3-66-04, and 3-53-02.

4. Generally the most homologous human germline variable heavy chain sequence is then used as the basis for humanization. However those skilled in the art may decide to use another sequence that wasn't the most homologous as determined by the homology algorithm, based on other factors including sequence gaps and framework similarities.

Example: 3-64-04 in FIG. 2 was the most homologous human germline variable heavy chain sequence and is used as the basis for the humanization of RbtVH.

5. Determine the framework and CDR arrangement (FR1, FR2, FR3, CDR1 & CDR2) for the human homolog being used for the heavy chain humanization. This is using the traditional layout as described in the field. Align the rabbit variable heavy chain sequence with the human homolog, while maintaining the layout of the framework and CDR regions.

Example: In FIG. 2, the RbtVH sequence is aligned with the human homologous sequence 3-64-04, and the framework and CDR domains are indicated.

6. Replace the human homologous heavy chain sequence CDR1 and CDR2 regions with the CDR1 and CDR2 sequences from the rabbit sequence. If there are differences in length between the rabbit and human CDR sequences then use the entire rabbit CDR sequences and their lengths. In addition, it may be necessary to replace the final three amino acids of the human heavy chain Framework 1 region with the final three amino acids of the rabbit heavy chain Framework 1. Typically but not always, in rabbit heavy chain Framework 1 these three residues follow a Glycine residue preceded by a Serine residue. In addition, it may be necessary replace the final amino acid of the human heavy chain Framework 2 region with the final amino acid of the rabbit heavy chain Framework 2. Typically, but not necessarily always, this is a Glycine residue preceded by an Isoleucine residue in the rabbit heavy chain Framework 2. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted. For example, a tryptophan amino acid residue typically occurs four residues prior to the end of the rabbit heavy chain CDR2 region, whereas in human heavy chain CDR2 this residue is typically a Serine residue. Changing this rabbit tryptophan residue to a the human Serine residue at this position has been demonstrated to have minimal to no effect on the humanized antibody's specificity or affinity, and thus further minimizes the content of rabbit sequence-derived amino acid residues in the humanized sequence.

Example: In FIG. 2, The CDR1 and CDR2 amino acid residues of the human homologous variable heavy chain are replaced with the CDR1 and CDR2 amino acid sequences from the RbtVH rabbit antibody light chain sequence, except for the boxed residue, which is tryptophan in the rabbit sequence (position number 63) and Serine at the same position in the human sequence, and is kept as the human Serine residue. In addition to the CDR1 and CDR2 changes, the final three amino acids of Framework 1 (positions 28-30) as well as the final residue of Framework 2 (position 49) are retained as rabbit amino acid residues instead of human. The resulting humanized sequence is shown below as VHh from residues numbered 1 through 98. Note that the only residues that are different from the 3-64-04 human sequence are underlined, and are thus rabbit-derived amino acid residues. In this example only 15 of the 98 residues are different than the human sequence.

7. After framework 3 of the new hybrid sequence created in Step 6, attach the entire CDR3 of the rabbit heavy chain antibody sequence. The CDR3 sequence can be of various lengths, but is typically 5 to 19 amino acid residues in length. The CDR3 region and the beginning of the following framework 4 region are defined classically and are identifiable by those skilled in the art. Typically the beginning of framework 4, and thus after the end of CDR3 consists of the sequence WGXG . . . (where X is usually Q or P), however some variation may exist in these residues.

Example: The CDR3 of RbtVH (amino acid residues numbered 99-110) is added after the end of framework 3 in the humanized sequence indicated as VHh.

8. The rabbit heavy chain framework 4, which is typically the final 11 amino acid residues of the variable heavy chain and begins as indicated in Step 7 above and typically ends with the amino acid sequence '. . . TVSS' is replaced with the nearest human heavy chain framework 4 homolog, usually from germline sequence. Frequently this human heavy chain framework 4 is of the sequence 'WGQGTLVTVSS'. It is possible that other human heavy chain framework 4 sequences that are not the most homologous or otherwise different may be used without affecting the specificity, affinity and/or immunogenicity of the resulting humanized antibody. This human heavy chain framework 4 sequence is added to the end of the variable heavy chain humanized sequence immediately following the CDR3 sequence from Step 7 above. This is now the end of the variable heavy chain humanized amino acid sequence.

Example: In FIG. 2, framework 4 (FR4) of the RbtVH rabbit heavy chain sequence is shown above a homologous human heavy FR4 sequence. The human FR4 sequence is added to the humanized variable heavy chain sequence (VHh) right after the end of the CD3 region added in Step 7 above.

Methods of Producing Antibodies and Fragments thereof.

The invention is also directed to the production of the antibodies described herein or fragments thereof. Recombinant polypeptides corresponding to the antibodies described herein or fragments thereof are secreted from polyploidal, preferably diploid or tetraploid strains of mating competent yeast. In an exemplary embodiment, the invention is directed to methods for producing these recombinant polypeptides in secreted form for prolonged periods using cultures comprising polyploid yeast, i.e., at least several days to a week, more preferably at least a month or several months, and even more preferably at least 6 months to a year or longer. These polyploid yeast cultures will express at least 10-25 mg/liter of the polypeptide, more preferably at least 50-250 mg/liter, still more preferably at least 500-1000 mg/liter, and most preferably a gram per liter or more of the recombinant polypeptide(s).

In one embodiment of the invention a pair of genetically marked yeast haploid cells are transformed with expression vectors comprising subunits of a desired heteromultimeric protein. One haploid cell comprises a first expression vector, and a second haploid cell comprises a second expression vector. In another embodiment diploid yeast cells will be transformed with one or more expression vectors that provide for the expression and secretion of one or more of the recombinant polypeptides. In still another embodiment a single haploid cell may be transformed with one or more vectors and used to produce a polyploidal yeast by fusion or mating strategies. In yet another embodiment a diploid yeast culture may be transformed with one or more vectors providing for the expression and secretion of a desired polypeptide or polypeptides. These vectors may comprise vectors e.g., linearized plasmids or other linear DNA products that integrate into the yeast cell's genome randomly, through homologous recombination, or using a recombinase such as Cre/Lox or Flp/Frt. Optionally, additional expression vectors may be introduced into the haploid or diploid cells; or the first or second expression vectors may comprise additional coding sequences; for the synthesis of heterotrimers; heterotetramers; etc. The expression levels of the non-identical polypeptides may be individually calibrated, and adjusted through appropriate selection, vector copy number, promoter strength and/or induction and the like. The transformed haploid cells are genetically crossed or fused. The resulting diploid or tetraploid strains are utilized to produce and secrete fully assembled and biologically functional proteins, humanized antibodies described herein or fragments thereof.

The use of diploid or tetraploid cells for protein production provides for unexpected benefits. The cells can be grown for production purposes, i.e. scaled up, and for extended periods of time, in conditions that can be deleterious to the growth of haploid cells, which conditions may include high cell density; growth in minimal media; growth at low temperatures; stable growth in the absence of selective pressure; and which may provide for maintenance of heterologous gene sequence integrity and maintenance of high level expression over time. Without wishing to be bound thereby, the inventors theorize that these benefits may arise, at least in part, from the creation of diploid strains from two distinct parental haploid strains. Such haploid strains can comprise numerous minor autotrophic mutations, which mutations are complemented in the diploid or tetraploid, enabling growth and enhanced production under highly selective conditions.

Transformed mating competent haploid yeast cells provide a genetic method that enables subunit pairing of a desired protein. Haploid yeast strains are transformed with each of two expression vectors, a first vector to direct the synthesis of one polypeptide chain and a second vector to direct the synthesis of a second, non-identical polypeptide chain. The two haploid strains are mated to provide a diploid host where optimized target protein production can be obtained.

Optionally, additional non-identical coding sequence(s) are provided. Such sequences may be present on additional expression vectors or in the first or the second expression vectors. As is known in the art, multiple coding sequences may be independently expressed from individual promoters; or may be coordinately expressed through the inclusion of an "internal ribosome entry site" or "IRES", which is an element that promotes direct internal ribosome entry to the initiation codon, such as ATG, of a cistron (a protein encoding region), thereby leading to the cap-independent translation of the gene. IRES elements functional in yeast are described by Thompson et al. (2001) *P.N.A.S.* 98:12866-12868.

In one embodiment of the invention, antibody sequences are produced in combination with a secretory J chain, which provides for enhanced stability of IgA (see U.S. Pat. Nos. 5,959,177; and 5,202,422).

In a preferred embodiment the two haploid yeast strains are each auxotrophic, and require supplementation of media for growth of the haploid cells. The pair of auxotrophs are complementary, such that the diploid product will grow in the absence of the supplements required for the haploid cells. Many such genetic markers are known in yeast, including requirements for amino acids (e.g. met, lys, his, arg, etc.), nucleosides (e.g. ura3, ade1, etc.); and the like. Amino acid markers may be preferred for the methods of the invention. Alternatively diploid cells which contain the desired vectors can be selected by other means, e.g., by use of other markers, such as green fluorescent protein, antibiotic resistance genes, various dominant selectable markers, and the like.

Two transformed haploid cells may be genetically crossed and diploid strains arising from this mating event selected by their hybrid nutritional requirements and/or antibiotic resistance spectra. Alternatively, populations of the two transformed haploid strains are spheroplasted and fused, and diploid progeny regenerated and selected. By either method, diploid strains can be identified and selectively grown based on their ability to grow in different media than their parents. For example, the diploid cells may be grown in minimal medium that may include antibiotics. The diploid synthesis strategy has certain advantages. Diploid strains have the potential to produce enhanced levels of heterologous protein through broader complementation to underlying mutations, which may impact the production and/or secretion of recombinant protein. Furthermore, once stable strains have been obtained, any antibiotics used to select those strains do not necessarily need to be continuously present in the growth media.

As noted above, in some embodiments a haploid yeast may be transformed with a single or multiple vectors and mated or fused with a non-transformed cell to produce a diploid cell containing the vector or vectors. In other embodiments, a diploid yeast cell may be transformed with one or more vectors that provide for the expression and secretion of a desired heterologous polypeptide by the diploid yeast cell.

In one embodiment of the invention, two haploid strains are transformed with a library of polypeptides, e.g. a library of antibody heavy or light chains. Transformed haploid cells that synthesize the polypeptides are mated with the complementary haploid cells. The resulting diploid cells are screened for functional protein. The diploid cells provide a means of rapidly, conveniently and inexpensively bringing together a large number of combinations of polypeptides for functional testing. This technology is especially applicable for the generation of heterodimeric protein products, where optimized subunit synthesis levels are critical for functional protein expression and secretion.

In another embodiment of the invention, the expression level ratio of the two subunits is regulated in order to maximize product generation. Heterodimer subunit protein levels have been shown previously to impact the final product generation (Simmons L C, J Immunol Methods. 2002 May 1; 263(1-2):133-47). Regulation can be achieved prior to the mating step by selection for a marker present on the expression vector. By stably increasing the copy number of the vector, the expression level can be increased. In some cases, it may be desirable to increase the level of one chain relative to the other, so as to reach a balanced proportion between the subunits of the polypeptide. Antibiotic resistance markers are useful for this purpose, e.g. Zeocin™ (phleomycin) resistance marker, G418 resistance, etc. and provide a means of enrichment for strains that contain multiple integrated copies of an expression vector in a strain by selecting for transformants that are resistant to higher levels of Zeocin™ (phleomycin) or G418. The proper ratio, e.g. 1:1; 1:2; etc. of the subunit genes may be important for efficient protein production. Even when the same promoter is used to transcribe both subunits, many other factors contribute to the final level of protein expressed and therefore, it can be useful to increase the number of copies of one encoded gene relative to the other. Alternatively, diploid strains that produce higher levels of a polypeptide, relative to single copy vector strains, are created by mating two haploid strains, both of which have multiple copies of the expression vectors.

Host cells are transformed with the above-described expression vectors, mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as phosphate, HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Secreted proteins are recovered from the culture medium. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art.

The diploid cells of the invention are grown for production purposes. Such production purposes desirably include growth in minimal media, which media lacks pre-formed amino acids and other complex biomolecules, e.g., media comprising ammonia as a nitrogen source, and glucose as an energy and carbon source, and salts as a source of phosphate, calcium and the like. Preferably such production media lacks selective agents such as antibiotics, amino acids, purines, pyrimidines, etc. The diploid cells can be grown to high cell density, for example at least about 50 g/L; more usually at least about 100 g/L; and may be at least about 300, about 400, about 500 g/L or more.

In one embodiment of the invention, the growth of the subject cells for production purposes is performed at low temperatures, which temperatures may be lowered during log phase, during stationary phase, or both. The term "low temperature" refers to temperatures of at least about 15° C., more usually at least about 17° C., and may be about 20° C., and is usually not more than about 25° C., more usually not more than about 22° C. In another embodiment of the invention, the low temperature is usually not more than about 28° C. Growth temperature can impact the production of full-length secreted proteins in production cultures, and decreasing the culture growth temperature can strongly enhance the intact product yield. The decreased temperature appears to assist intracellular trafficking through the folding and post-translational processing pathways used by the host to generate the target product, along with reduction of cellular protease degradation.

The methods of the invention provide for expression of secreted, active protein, preferably a mammalian protein. In one embodiment, secreted, "active antibodies", as used herein, refers to a correctly folded multimer of at least two properly paired chains, which accurately binds to its cognate antigen. Expression levels of active protein are usually at least about 10-50 mg/liter culture, more usually at least about 100 mg/liter, preferably at least about 500 mg/liter, and may be 1000 mg/liter or more.

The methods of the invention can provide for increased stability of the host and heterologous coding sequences during production. The stability is evidenced, for example, by maintenance of high levels of expression of time, where the starting level of expression is decreased by not more than about 20%, usually not more than 10%, and may be decreased by not more than about 5% over about 20 doublings, 50 doublings, 100 doublings, or more.

The strain stability also provides for maintenance of heterologous gene sequence integrity over time, where the sequence of the active coding sequence and requisite transcriptional regulatory elements are maintained in at least about 99% of the diploid cells, usually in at least about 99.9% of the diploid cells, and preferably in at least about 99.99% of the diploid cells over about 20 doublings, 50 doublings, 100 doublings, or more. Preferably, substantially all of the diploid cells maintain the sequence of the active coding sequence and requisite transcriptional regulatory elements.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

Antibody polypeptides of the invention having IL-6 binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA.

The host cells used to express the antibody polypeptides may be either a bacterial cell such as *E. coli*, or a eukaryotic cell. In a particularly preferred embodiment of the invention, a mammalian cell of a well-defined type for this purpose, such as a myeloma cell or a Chinese hamster ovary (CHO) cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al, Science, 253:792-795 (1991), the contents of which are herein incorporated by reference in its entirety.

Screening Assays

The invention also includes screening assays designed to assist in the identification of diseases and disorders associated with IL-6 in patients exhibiting symptoms of an IL-6 associated disease or disorder.

In one embodiment of the invention, the anti-IL-6 antibodies of the invention, or IL-6 binding fragments thereof, are used to detect the presence of IL-6 in a biological sample obtained from a patient exhibiting symptoms of a disease or disorder associated with IL-6. The presence of IL-6, or elevated levels thereof when compared to pre-disease levels of IL-6 in a comparable biological sample, may be beneficial in diagnosing a disease or disorder associated with IL-6.

Another embodiment of the invention provides a diagnostic or screening assay to assist in diagnosis of diseases or disorders associated with IL-6 in patients exhibiting symptoms of an IL-6 associated disease or disorder identified herein, comprising assaying the level of IL-6 expression in a biological sample from said patient using a post-translationally modified anti-IL-6 antibody or binding fragment thereof. The anti-IL-6 antibody or binding fragment thereof may be post-translationally modified to include a detectable moiety such as set forth previously in the disclosure.

The IL-6 level in the biological sample is determined using a modified anti-IL-6 antibody or binding fragment thereof as set forth herein, and comparing the level of IL-6 in the biological sample against a standard level of IL-6 (e.g., the level in normal biological samples). The skilled clinician would understand that some variability may exist between normal biological samples, and would take that into consideration when evaluating results.

The above-recited assay may also be useful in monitoring a disease or disorder, where the level of IL-6 obtained in a biological sample from a patient believed to have an IL-6 associated disease or disorder is compared with the level of IL-6 in prior biological samples from the same patient, in order to ascertain whether the IL-6 level in said patient has changed with, for example, a treatment regimen.

The invention is also directed to a method of in vivo imaging which detects the presence of cells which express IL-6 comprising administering a diagnostically effective amount of a diagnostic composition. Said in vivo imaging is useful for the detection and imaging of IL-6 expressing tumors or metastases and IL-6 expressing inflammatory sites, for example, and can be used as part of a planning regimen for design of an effective cancer or arthritis treatment protocol. The treatment protocol may include, for example, one or more of radiation, chemotherapy, cytokine therapy, gene therapy, and antibody therapy, as well as an anti-IL-6 antibody or fragment thereof.

A skilled clinician would understand that a biological sample includes, but is not limited to, sera, plasma, urine, saliva, mucous, pleural fluid, synovial fluid and spinal fluid.

Methods of Ameliorating or Reducing Symptoms of or Treating, or Preventing, Diseases and Disorders Associated with, IL-6

In an embodiment of the invention, IL-6 antagonists described herein are useful for ameliorating or reducing the symptoms of, or treating, or preventing, diseases and disorders associated with IL-6. IL-6 antagonists described herein can also be administered in a therapeutically effective amount to patients in need of treatment of diseases and disorders associated with IL-6 in the form of a pharmaceutical composition as described in greater detail below.

In one embodiment of the invention, IL-6 antagonists described herein are useful for ameliorating or reducing the symptoms of, or treating, or preventing, diseases and disorders associated with elevated C-reactive protein (CRP). Such diseases include any disease that exhibits chronic inflammation, e.g., rheumatoid arthritis, juvenile rheumatoid arthritis, psoriasis, psoriatic arthropathy, ankylosing spondylitis, systemic lupus erythematosis, Crohn's disease, ulcerative colitis, pemphigus, dermatomyositis, polymyositis, polymyalgia rheumatica, giant cell arteritis, vasculitis, polyarteritis nodosa, Wegener's granulomatosis, Kawasaki disease, isolated CNS vasculitis, Churg-Strauss arteritis, microscopic polyarteritis, microscopic polyangiitis, Henoch-Schonlein purpura, essential cryoglobulinemic vasculitis, rheumatoid vasculitis, cryoglobulinemia, relapsing polychondritis, Behcet's disease, Takayasu's arteritis, ischemic heart disease, stroke, multiple sclerosis, sepsis, vasculitis secondary to viral infection (e.g., hepatitis B, hepatitis C, HIV, cytomegalovirus, Epstein-Barr virus, Parvo B 19 virus, etc.), Buerger's Disease, cancer, advanced cancer, Osteoarthritis, systemic sclerosis, CREST syndrome, Reiter's disease, Paget's disease of bone, Sjogran's syndrome, diabetes type 1, diabetes type 2, familial Mediterranean fever, autoimmune thrombocytopenia, autoimmune hemolytic anemia, autoimmune thyroid diseases, pernicious anemia, vitiligo, alopecia greata, primary biliary cirrhosis, autoimmune chronic active hepatitis, alcoholic cirrhosis, viral hepatitis including hepatitis B and C, other organ specific autoimmune diseases, burns, idiopathic pulmonary fibrosis, chronic obstructive pulmonary disease, allergic asthma, other allergic conditions or any combination thereof.

In one embodiment of the invention, IL-6 antagonists described herein are useful for ameliorating or reducing the symptoms of, or treating, or preventing, diseases and disorders associated with reduced serum albumin, e.g. rheumatoid arthritis, cancer, advanced cancer, liver disease, renal disease, inflammatory bowel disease, celiac's disease, trauma, burns, other diseases associated with reduced serum albumin, or any combination thereof.

In another embodiment of the invention, IL-6 antagonists described herein are administered to a patient in combination with another active agent. For example, IL-6 antagonist may be co-administered with one or more chemotherapy agents, such as VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux™, Avastin™ Pertuzumab, anti-CD20 antibodies, Rituxan®, ocrelizumab, ofatumumab, DXL625, Herceptin®, or any combination thereof.

In one embodiment of the invention, anti-IL-6 antibodies described herein, or fragments thereof, are useful for ameliorating or reducing the symptoms of, or treating, or preventing, diseases and disorders associated with fatigue. Diseases and disorders associated with fatigue include, but are not limited to, general fatigue, exercise-induced fatigue, cancer-related fatigue, fibromyalgia, inflammatory disease-related fatigue and chronic fatigue syndrome. See, for example, Esper D H, et al, The cancer cachexia syndrome: a review of metabolic and clinical manifestations, Nutr Clin Pract., 2005 August; 20 (4):369-76; Vgontzas A N, et al, IL-6 and its circadian secretion in humans, Neuroimmunomodulation, 2005; 12(3):131-40; Robson-Ansley, P J, et al, Acute interleukin-6 administration impairs athletic performance in healthy, trained male runners, Can J Appl Physiol., 2004 August; 29(4):411-8; Shephard R J., Cytokine responses to physical activity, with particular reference to IL-6: sources, actions, and clinical implications, Crit. Rev Immunol., 2002; 22(3):165-82; Arnold, M C, et al, Using an interleukin-6 challenge to evaluate neuropsychological performance in chronic fatigue syndrome, Psychol Med., 2002 August; 32(6):1075-89; Kurzrock R., The role of cytokines in cancer-related fatigue, Cancer, 2001 Sep. 15; 92(6 Suppl):1684-8; Nishimoto N, et al, Improvement in Castleman's disease by humanized anti-interleukin-6 receptor antibody therapy, Blood, 2000 Jan. 1; 95 (1):56-61; Vgontzas A N, et al, Circadian interleukin-6 secretion and quantity and depth of sleep, J Clin Endocrinol Metab., 1999 August; 84(8):2603-7; and Spath-Schwalbe E, et al, Acute effects of recombinant human interleukin 6 on endocrine and central nervous sleep functions in healthy men, J Clin Endocrinol Metab., 1998 May; 83(5):1573-9; the disclosures of each of which are herein incorporated by reference in their entireties.

In a preferred embodiment of the invention, anti-IL-6 antibodies described herein, or fragments thereof, are useful for ameliorating or reducing the symptoms of, or treating, or preventing, cachexia. Diseases and disorders associated with cachexia include, but are not limited to, cancer-related cachexia, cardiac-related cachexia, respiratory-related cachexia, renal-related cachexia and age-related cachexia. See, for example, Barton, B E., Interleukin-6 and new strategies for the treatment of cancer, hyperproliferative diseases and paraneoplastic syndromes, Expert Opin Ther Targets, 2005 August; 9(4):737-52; Zaki M R, et al, CNTO 328, a monoclonal antibody to IL-6, inhibits human tumor-induced cachexia in nude mice, Int J Cancer, 2004 Sep. 10; 111(4): 592-5; Trikha M, et al, Targeted anti-interleukin-6 monoclonal antibody therapy for cancer: a review of the rationale and clinical evidence, Clin Cancer Res., 2003 Oct. 15; 9(13): 4653-65; Lelli G, et al, Treatment of the cancer anorexia-cachexia syndrome: a critical reappraisal, J. Chemother., 2003 June; 15(3):220-5; Argiles J M, et al, Cytokines in the pathogenesis of cancer cachexia, Curr Opin Clin Nutr Metab Care, 2003 July; 6(4):401-6; Barton B E., IL-6-like cytokines and cancer cachexia: consequences of chronic inflammation, Immunol Res., 2001; 23(1):41-58; Yamashita J I, et al, Medroxyprogesterone acetate and cancer cachexia: interleukin-6 involvement, Breast Cancer, 2000; 7(2):130-5; Yeh S S, et al, Geriatric cachexia: the role of cytokines, Am J Clin Nutr., 1999 August; 70(2):183-97; Strassmann G, et al, Inhibition of experimental cancer cachexia by anti-cytokine and anti-cytokine-receptor therapy, Cytokines Mol. Ther., 1995 June; 1(2):107-13; Fujita J, et al, Anti-interleukin-6 receptor antibody prevents muscle atrophy in colon-26 adenocarcinoma-bearing mice with modulation of lysosomal and ATP-ubiquitin-dependent proteolytic pathways, Int J Cancer, 1996 Nov. 27; 68(5):637-43; Tsujinaka T, et al, Interleukin 6 receptor antibody inhibits muscle atrophy and modulates proteolytic systems in interleukin 6 transgenic mice, J Clin Invest., 1996 Jan. 1; 97(1):244-9; Emilie D, et al, Administration of an anti-interleukin-6 monoclonal antibody to patients with acquired immunodeficiency syndrome and lymphoma: effect on lymphoma growth and on B clinical Symptoms, Blood, 1994 Oct. 15; 84 (8):2472-9; and Strassmann G, et al, Evidence for the involvement of interleukin 6 in experimental cancer cachexia, J Clin Invest., 1992 May; 89(5): 1681-4; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, autoimmune diseases and disorders. Diseases and disorders associated with autoimmunity include, but are not limited to, rheumatoid arthritis, systemic lupus erythematosis (SLE), systemic juvenile idiopathic arthritis, psoriasis, psoriatic arthropathy, ankylosing spondylitis, inflammatory bowel disease (IBD), polymyalgia rheumatica, giant cell arteritis, autoimmune vasculitis, graft versus host disease (GVHD), Sjogren's syndrome, adult onset Still's disease. In a preferred embodiment of the invention, humanized anti-IL-6 antibodies described herein, or fragments thereof, are useful for ameliorating or reducing the symptoms of, or treating, or preventing, rheumatoid arthritis and systemic juvenile idiopathic arthritis. See, for example, Nishimoto N., Clinical studies in patients with Castleman's disease, Crohn's disease, and rheumatoid arthritis in Japan, Clin Rev Allergy Immunol., 2005 June; 28(3):221-30; Nishimoto N, et al, Treatment of rheumatoid arthritis with humanized anti-interleukin-6 receptor antibody: a multicenter, double-blind, placebo-controlled trial, Arthritis Rheum., 2004 June; 50(6):1761-9; Choy E., Interleukin 6 receptor as a target for the treatment of rheumatoid arthritis, Ann Rheum Dis., 2003 November; 62 Suppl 2:ii68-9; Nishimoto N, et al, Toxicity, pharmacokinetics, and dose-finding study of repetitive treatment with the humanized anti-interleukin 6 receptor antibody MRA in rheumatoid arthritis. Phase I/II clinical study, J. Rheumatol., 2003 July; 30(7):1426-35; Mihara M, et al, Humanized antibody to human interleukin-6 receptor inhibits the development of collagen arthritis in cynomolgus monkeys, Clin Immunol., 2001 March; 98(3):319-26; Nishimoto N, et al, Anti-interleukin 6 receptor antibody treatment in rheumatic disease, Ann Rheum Dis., 2000 November; 59 Suppl 1:121-7; Tackey E, et al, Rationale for interleukin-6 blockade in systemic lupus erythematosus, Lupus, 2004; 13(5):339-43; Finck B K, et al, Interleukin 6 promotes murine lupus in NZB/NZW Fl mice, J Clin Invest., 1994 August; 94 (2):585-91; Kitani A, et al, Autostimulatory effects of IL-6 on excessive B cell differentiation in patients with systemic lupus erythematosus: analysis of IL-6 production and IL-6R expression, Clin Exp Immunol., 1992 April; 88(1):75-83; Stuart R A, et al, Elevated serum interleukin-6 levels associated with active disease in systemic connective tissue disorders, Clin Exp Rheumatol., 1995 January-February; 13 (1): 17-22; Mihara M, et al, IL-6 receptor blockage inhibits the onset of autoimmune kidney disease in NZB/W Fl mice, Clin Exp Immunol., 1998 June; 12(3):397-402; Woo P, et al, Open label phase II trial of single, ascending doses of MRA in Caucasian children with severe systemic juvenile idiopathic arthritis: proof of principle of the efficacy of IL-6 receptor blockade in this type of arthritis and demonstration of prolonged clinical improvement, Arthritis Res Ther., 2005; 7(6): RI281-8. Epub 2005 Sep. 15; Yokota S, et al, Clinical study of tocilizumab in children with systemic-onset juvenile idiopathic arthritis, Clin Rev Allergy Immunol., 2005 June; 28(3):231-8; Yokota S, et al, Therapeutic efficacy of humanized recombinant anti-interleukin-6 receptor antibody in children with systemic-onset juvenile idiopathic arthritis, Arthritis Rheum., 2005 March; 52(3):818-25; de Benedetti F, et al, Targeting the interleukin-6 receptor: a new treatment for systemic juvenile idiopathic arthritis?, Arthritis Rheum., 2005 March; 52(3):687-93; De Benedetti F, et al, Is systemic juvenile rheumatoid arthritis an interleukin 6 mediated disease?, J. Rheumatol., 1998 February; 25(2):203-7; Ishihara K, et al, IL-6 in autoimmune disease and chronic inflammatory proliferative disease, Cytokine Growth Factor Rev., 2002 August-October; 13 (4-5):357-68; Gilhar A, et al, In vivo effects of cytokines on psoriatic skin grafted on nude mice involvement of the tumor necrosis factor (TNF) receptor, Clin Exp Immunol., 1996 October; 106(1):134-42; Spadaro A, et al, Interleukin-6 and soluble interleukin-2 receptor in psoriatic arthritis: correlations with clinical and laboratory parameters, Clin Exp Rheumatol., 1996 July-August; 14 (4):413-6; Ameglio F, et al, Interleukin-6 and tumor necrosis factor levels decrease in the suction blister fluids of psoriatic patients during effective therapy, Dermatology, 1994; 189(4): 359-63; Wendling D, et al, Combination therapy of anti-CD4 and anti-IL-6 monoclonal antibodies in a case of severe spondylarthropathy, Br J. Rheumatol., 1996 December; 35(12):1330; Gratacos J, et al, Serum cytokines (IL-6, TNF-alpha, IL-1 beta and IFN-gamma) in ankylosing spondylitis: a close correlation between serum IL-6 and disease activity and severity, Br J. Rheumatol., 1994 October; 33(10):927-31; Ito H., Treatment of Crohn's disease with anti-IL-6 receptor antibody, J. Gastroenterol., 2005 March; 40 Suppl 16:32-4; Ito H, et al, A pilot randomized trial of a human anti-interleukin-6 receptor monoclonal antibody in active Crohn's disease, Gastroenterology, 2004 April; 126(4):989-96; discussion 947; Ito H., IL-6 and Crohn's disease, Curr Drug Targets Inflamm Allergy, 2003 June; 2(2):12530; Ito H, et al, Anti-IL-6 receptor monoclonal antibody inhibits leukocyte recruitment and promotes T-cell apoptosis in a murine model of Crohn's disease, J. Gastroenterol., 2002 November; 37 Suppl 14:56-61; Ito H., Anti-interleukin-6 therapy for Crohn's disease, Curr Pharm Des., 2003; 9(4):295-305; Salvarani C, et al, Acute-phase reactants and the risk of relapse/recurrence in polymyalgia rheumatica: a prospective follow-up study, Arthritis Rheum., 2005 Feb. 15; 53(1):33-8; Roche N E, et al, Correlation of interleukin-6 production and disease activity in polymyalgia rheumatica and giant cell arteritis, Arthritis Rheum., 1993 September; 36(9):1286-94; Gupta M, et al, Cytokine modulation with immune gamma-globulin in peripheral blood of normal children and its implications in Kawasaki disease treatment, J Clin Immunol., 2001 May; 21(3):193-9; Noris M, et al, Interleukin-6 and RANTES in Takayasu arteritis: a guide for therapeutic decisions?, Circulation, 1999 Jul. 6; 100(1):55-60; Besbas N, et al, The role of cytokines in Henoch Schonlein purpura, Scand J. Rheumatol., 1997; 26(6):456-60; Hirohata S, et al, Cerebrospinal fluid interleukin-6 in progressive Neuro-Behcet's syndrome, Clin Immunol Immunopathol., 1997 January; 82(1):12-7; Yamakawa Y, et al, Interleukin-6 (IL-6) in patients with Behcet's disease, J Dermatol Sci., 1996 March; 11(3):189-95; Kim D S., Serum interleukin-6 in Kawasaki disease, Yonsei Med J., 1992 June; 33(2):183-8; Lange, A., et al, Cytokines, adhesion molecules (E-selectin and VCAM-1) and graft-versus-host disease, Arch. Immunol Ther Exp., 1995, 43(2):99-105; Tanaka, J., et al, Cytokine gene expression after allogeneic bone marrow transplantation, Leuk. Lymphoma, 1995 16(5-6):413-418; Dickenson, A M, et al, Predicting outcome in hematological stem cell transplantation, Arch Immunol Ther Exp., 2002 50(6):371-8; Zeiser, R, et al, Immunopathogenesis of acute graft-versus-host disease: implications for novel preventive and therapeutic strategies, Ann Hematol., 2004 83(9):551-65; Dickinson, A M, et al, Genetic polymorphisms predicting the outcome of bone marrow transplants, Br. J. Haematol., 2004 127(5):479-90; and Scheinberg M A, et al, Interleukin 6: a possible marker of disease activity in adult onset Still's disease, Clin Exp Rheumatol., 1996 November-December; 14 (6):653-5, the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, diseases and disorders associated with the skeletal system. Diseases and disorders associated with the skeletal system include, but are not limited to, osteoarthritis, osteoporosis and Paget's disease of bone. In a preferred embodiment of the invention, humanized anti-IL-6 antibodies described herein, or fragments thereof, are useful for ameliorating or reducing the symptoms of, or treating, or preventing, osteoarthritis. See, for example, Malemud C J., Cytokines as therapeutic targets for osteoarthritis, BioDrugs, 2004; 18(1):23-35; Westacott C I, et al, Cytokines in osteoarthritis: mediators or markers of joint destruction?, Semin Arthritis Rheum., 1996 February; 25(4):254-72; Sugiyama T., Involvement of interleukin-6 and prostaglandin E2 in particular osteoporosis of postmenopausal women with rheumatoid arthritis, J Bone Miner Metab., 2001; 19(2):89-96; Abrahamsen B, et al, Cytokines and bone loss in a 5-year longitudinal study-hormone replacement therapy suppresses serum soluble interleukin-6 receptor and increases interleukin-1-receptor antagonist: the Danish Osteoporosis Prevention Study, J Bone Miner Res., 2000 August; 15(8):1545-54; Straub R H, et al, Hormone replacement therapy and interrelation between serum interleukin-6 and body mass index in postmenopausal women: a population-based study, J Clin Endocrinol Metab., 2000 March; 85(3):1340-4; Manolagas S C, The role of IL-6 type cytokines and their receptors in bone, Ann NY Acad. Sci., 1998 May 1; 840:194-204; Ershler W B, et al, Immunologic aspects of osteoporosis, Dev Comp Immunol., 1997 November-December; 21(6):487-99; Mica R L, et al, Increased osteoclast development after estrogen loss: mediation by interleukin-6, Science, 1992 Jul. 3; 257 (5066):88-91; Kallen K J, et al, New developments in IL-6 dependent biology and therapy: where do we stand and what are the options?, Expert Opin Investig Drugs, 1999 September; 8(9):1327-49; Neale S D, et al, The influence of serum cytokines and growth factors on osteoclast formation in Paget's disease, QJM, 2002 April; 95 (4):233-40; Roodman G D, Osteoclast function In Paget's disease and multiple myeloma, Bone, 1995 August; 17(2 Suppl):575-61S; Hoyland J A, et al, Interleukin-6, IL-6 receptor, and IL-6 nuclear factor gene expression in Paget's disease, J Bone Miner Res., 1994 January; 9(1):75-80; and Roodman G D, et al, Interleukin 6. A potential autocrine/paracrine factor in Paget's disease of bone, J Clin Invest., 1992 January; 89(1):46-52; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, diseases and disorders associated with cancer. Diseases and disorders associated with cancer include, but are not limited to, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Müllerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyo sarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sézary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof, as well as drug resistance in cancer chemotherapy and cancer chemotherapy toxicity. See, for example, Hirata T, et al, Humanized anti-interleukin-6 receptor monoclonal antibody induced apoptosis of fresh and cloned human myeloma cells in vitro, Leuk Res., 2003 April; 27(4):343-9, Bataille R, et al, Biologic effects of anti-interleukin-6 murine monoclonal antibody in advanced multiple myeloma, Blood, 1995 Jul. 15; 86 (2):685-91; Goto H, et al, Mouse anti-human interleukin-6 receptor monoclonal antibody inhibits proliferation of fresh human myeloma cells in vitro, Jpn J Cancer Res., 1994 September; 85(9):958-65; Klein B, et al, Murine anti-interleukin-6 monoclonal antibody therapy for a patient with plasma cell leukemia, Blood, 1991 Sep. 1; 78(5):1198-204; Mauray S, et al, Epstein-Barr virus-dependent lymphoproliferative disease: critical role of IL-6, Eur J. Immunol., 2000 July; 30(7):2065-73; Tsunenari T, et al, New xenograft model of multiple myeloma and efficacy of a humanized antibody against human interleukin-6 receptor, Blood, 1997 Sep. 15; 90(6):2437-44; Emilie D, et al, Interleukin-6 production in high-grade B lymphomas: correlation with the presence of malignant immunoblasts in acquired immunodeficiency syndrome and in human immunodeficiency virus-seronegative patients, Blood, 1992 Jul. 15; 80(2):498-504; Emilie D, et al, Administration of an anti-interleukin-6 monoclonal antibody to patients with acquired immunodeficiency syndrome and lymphoma: effect on lymphoma growth and on B clinical Symptoms, Blood, 1994 Oct. 15; 84(8):2472-9; Smith P C, et al, Anti-interleukin-6 monoclonal antibody induces regression of human prostate cancer xenografts in nude mice, Prostate, 2001 Jun. 15; 48(1):47-53; Smith P C, et al, Interleukin-6 and prostate cancer progression, Cytokine Growth Factor Rev., 2001 March; 12(1):33-40; Chung T D, et al, Characterization of the role of IL-6 in the progression of prostate cancer, Prostate, 1999 Feb. 15; 38(3):199-207; Okamoto M, et al, Interleukin-6 as a paracrine and autocrine growth factor in human prostatic carcinoma cells in vitro, Cancer Res., 1997 Jan. 1; 57(1):141-6; Reittie J E, et al, Interleukin-6 inhibits apoptosis and tumor necrosis factor induced proliferation of B-chronic lymphocytic leukemia, Leuk Lymphoma, 1996 June; 22(1-2):83-90, follow 186, color plate VI; Sugiyama H, et al, The expression of IL-6 and its related genes in acute leukemia, Leuk Lymphoma, 1996 March; 21(1-2):49-52; Bataille R, et al, Effects of an anti-interleukin-6 (IL-6) murine monoclonal antibody in a patient with acute monoblastic leukemia, Med Oncol Tumor Pharmacother., 1993; 10(4):185-8; Kedar I, et al, Thalidomide reduces serum C-reactive protein and interleukin-6 and induces response to IL-2 in a fraction of metastatic renal cell cancer patients who failed IL-2-based therapy, Int J Cancer, 2004 Jun. 10; 110(2):260-5; Angelo L S, Talpaz M, Kurzrock R, Autocrine interleukin-6 production in renal cell carcinoma: evidence for the involvement of p53, Cancer Res., 2002 Feb. 1; 62(3):932-40; Nishimoto N, Humanized anti-interleukin-6 receptor antibody treatment of multicentric Castleman disease, Blood, 2005 Oct. 15; 106(8):2627-32, Epub 2005 Jul. 5; Katsume A, et al, Anti-interleukin 6 (IL-6) receptor antibody suppresses Castleman's disease like symptoms emerged in IL-6 transgenic mice, Cytokine, 2002 Dec. 21; 20(6):304-11; Nishimoto N, et al, Improvement in Castleman's disease by humanized anti-interleukin-6 receptor antibody therapy, Blood, 2000 Jan. 1; 95(1):56-61; Screpanti I, Inactivation of the IL-6 gene prevents development of multicentric Castleman's disease in C/EBP beta-deficient mice, J Exp Med., 1996 Oct. 1; 184(4):1561-6; Hsu S M, et al, Expression of interleukin-6 in Castleman's disease, Hum Pathol., 1993 August; 24(8):833-9; Yoshizaki K, et al, Pathogenic significance of interleukin-6 (IL 6/BSF-2) in Castleman's disease, Blood, 1989 September; 74(4):1360-7; Nilsson M B, et al, Interleukin-6, secreted by human ovarian carcinoma cells, is a potent proangiogenic cytokine, Cancer Res., 2005 Dec. 1; 65(23):10794-800; Toutirais O, et al, Constitutive expression of TGF-beta1, interleukin-6 and interleukin-8 by tumor cells as a major component of immune escape in human ovarian carcinoma, Eur Cytokine Netw., 2003 October-December; 14(4):246-55; Obata N H, et al, Effects of interleukin 6 on in vitro cell attachment, migration and invasion of human ovarian carcinoma, Anticancer Res., 1997 January-February; 17 (1A):337-42; Dedoussis G V, et al, Endogenous interleukin 6 conveys resistance to cis-diamminedichloroplatinum-mediated apoptosis of the $K_{562}$ human leukemic cell line, Exp Cell Res., 1999 Jun. 15; 249(2):269-78; Borsellino N, et al, Blocking signaling through the Gp130 receptor chain by interleukin-6 and oncostatin M inhibits PC-3 cell growth and sensitizes the tumor cells to etoposide and cisplatin-mediated cytotoxicity, Cancer, 1999 Jan. 1; 85(1):134-44; Borsellino N, et al, Endogenous interleukin 6 is a resistance factor for cis-diamminedichloroplatinum and etoposide-mediated cytotoxicity of human prostate carcinoma cell lines, Cancer Res., 1995 Oct. 15; 55(20):4633-9; Mizutani Y, et al, Sensitization of human renal cell carcinoma cells to cis-diamminedichloroplatinum(II) by anti-interleukin 6 monoclonal antibody or anti-interleukin 6 receptor monoclonal antibody; Cancer Res., 1995 Feb. 1; 55(3):590-6; Yusuf R Z, et al, Paclitaxel resistance: molecular mechanisms and pharmacologic manipulation, Curr Cancer Drug Targets, 2003 February; 3(1):1-19; Duan Z, et al, Overexpression of IL-6 but not IL-8 increases paclitaxel resistance of U-205 human osteosarcoma cells, Cytokine, 2002 Mar. 7; 17(5):234-42; Conze D, et al, Autocrine production of interleukin 6 causes multidrug resistance in breast cancer cells, Cancer Res., 2001 Dec. 15; 61(24):8851-8; Rossi J F, et al, Optimizing the use of anti-interleukin-6 monoclonal antibody with dexamethasone and 140 mg/m2 of melphalan in multiple myeloma: results of a pilot study including biological aspects, Bone Marrow Transplant, 2005 November; 36(9):771-9; and Tonini G, et al, Oxaliplatin may induce cytokine-release syndrome in colorectal cancer patients, J Biol Regul Homeost Agents, 2002 April-June; 16 (2):105-9; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, ischemic heart disease, atherosclerosis, obesity, diabetes, asthma, multiple sclerosis, Alzheimer's disease, cerebrovascular disease, fever, acute phase response, allergies, anemia, anemia of inflammation (anemia of chronic disease), hypertension, depression, depression associated with a chronic illness, thrombosis, thrombocytosis, acute heart failure, metabolic syndrome, miscarriage, obesity, chronic prostatitis, glomerulonephritis, pelvic inflammatory disease, reperfusion injury, and transplant rejection. See, for example, Tzoulaki I, et al, C-reactive protein, interleukin-6, and soluble adhesion molecules as predictors of progressive peripheral atherosclerosis in the general population: Edinburgh Artery Study, Circulation, 2005 Aug. 16; 112(7):976-83, Epub 2005 Aug. 8; Rattazzi M, et al, C-reactive protein and interleukin-6 in vascular disease: culprits or passive bystanders?, J. Hypertens., 2003 October; 21(10):1787-803; Ito T, et al, HMG-CoA reductase inhibitors reduce interleukin-6 synthesis in human vascular smooth muscle cells, Cardiovasc Drugs Ther., 2002 March; 16(2):121-6; Stenvinkel P, et al, Mortality, malnutrition, and atherosclerosis in ESRD: what is the role of interleukin-6?, Kidney Int Suppl., 2002 May; (80):103-8; Yudkin J S, et al, Inflammation, obesity, stress and coronary heart disease: is interleukin-6 the link?, Atherosclerosis, 2000 February; 148(2):209-14; Huber S A, et al, Interleukin-6 exacerbates early atherosclerosis in mice, Arterioscler Thromb Vasc Biol., 1999 October; 19(10):2364-7; Kado S, et al, Circulating levels of interleukin-6, its soluble receptor and interleukin-6/interleukin-6 receptor complexes in patients with type 2 diabetes mellitus, Acta Diabetol., 1999 June; 36(1-2):67-72; Sukovich D A, et al, Expression of interleukin-6 in atherosclerotic lesions of male ApoE-knockout mice: inhibition by 17beta-estradiol, Arterioscler Thromb Vasc Biol., 1998 September; 8(9):1498-505; Klover P J, et al, Interleukin-6 depletion selectively improves hepatic insulin action in obesity, Endocrinology, 2005 August; 146(8):3417-27, Epub 2005 Apr. 21; Lee Y H, et al, The evolving role of inflammation in obesity and the metabolic syndrome, Curr Diab Rep., 2005 February; 5(1):70-5; Diamant M, et al, The association between abdominal visceral fat and carotid stiffness is mediated by circulating inflammatory markers in uncomplicated type 2 diabetes, J Clin Endocrinol Metab., 2005 March; 90(3):1495-501, Epub 2004 Dec. 21; Bray G A, Medical consequences of obesity, J Clin Endocrinol Metab., 2004 June; 89(6):2583 9; Klover P J, et al, Chronic exposure to interleukin-6 causes hepatic insulin resistance in mice, Diabetes, 2003 November; 52 (11):2784-9; Yudkin J S, et al, Inflammation, obesity, stress and coronary heart disease: is interleukin-6 the link?, Atherosclerosis, 2000 February; 148 (2):209-14; Doganci A, et al, Pathological role of IL-6 in the experimental allergic bronchial asthma in mice, Clin Rev Allergy Immunol., 2005 June; 28(3):257-70; Doganci A, et al, The IL-6R alpha chain controls lung CD4+CD25+ Treg development and function during allergic airway inflammation in vivo, J Clin Invest., 2005 February; 115(2):313 25, (Erratum in: J Clin Invest., 2005 May; 115(5):1388, Lehr, Hans A [added]); Stelmasiak Z, et al, IL 6 and sIL-6R concentration in the cerebrospinal fluid and serum of MS patients, Med Sci Monit., 2001 September-October; 7(5): 914-8; Tilgner J, et al, Continuous interleukin-6 application in vivo via macroencapsulation of interleukin-6-expressing COS-7 cells induces massive gliosis, Glia, 2001 September; 35(3):234-45, Brunello A G, et al, Astrocytic alterations in interleukin-6 Soluble interleukin-6 receptor alpha double-transgenic mice, Am J. Pathol., 2000 November; 157(5):1485-93; Hampel H, et al, Pattern of interleukin-6 receptor complex immunoreactivity between cortical regions of rapid autopsy normal and Alzheimer's disease brain, Eur Arch Psychiatry Clin Neurosci., 2005 August; 255(4):269-78, Epub 2004 Nov. 26; Cacquevel M, et al, Cytokines in neuroinflammation and Alzheimer's disease, Curr Drug Targets, 2004 August; 5(6):529-34; Quintanilla R A, et al, Interleukin 6 induces Alzheimer-type phosphorylation of tau protein by deregulating the cdk5/p35 pathway, Exp Cell Res., 2004 Apr. 15; 295 (1):245-57; Gadient R A, et al, Interleukin-6 (IL-6)—a molecule with both beneficial and destructive potentials, Prog Neurobiol., 1997 August; 52(5):379-90; Hull M, et al, Occurrence of interleukin-6 in cortical plaques of Alzheimer's disease patients may precede transformation of diffuse into neuritic plaques, Ann N Y Acad. Sci., 1996 Jan. 17; 777:205-12; Rallidis L S, et al, Inflammatory markers and in-hospital mortality in acute ischaemic stroke, Atherosclerosis, 2005 Dec. 30; Emsley H C, et al, Interleukin-6 and acute ischaemic stroke, Acta Neurol Scand., 2005 October; 112(4):273-4; Smith C J, et al, Peak plasma interleukin-6 and other peripheral markers of inflammation in the first week of ischaemic stroke correlate with brain infarct volume, stroke severity and long-term outcome, BMC Neurol., 2004 Jan. 15; 4:2; Vila N, et al, Proinflammatory cytokines and early neurological worsening in ischemic stroke, Stroke, 2000 October; 31(10):2325-9; and Tarkowski E, et al, Early intrathecal production of interleukin-6 predicts the size of brain lesion in stroke, Stroke, 1995 August; 26(8):1393-8; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, diseases and disorders associated with cytokine storm. Diseases and disorders associated with cytokine storm include, but are not limited to, graft versus host disease (GVHD), avian influenza, smallpox, pandemic influenza, adult respiratory distress syndrome (ARDS), severe acute respiratory syndrome (SARS), sepsis, and systemic inflammatory response syndrome (SIRS). See, for example, Cecil, R. L., Goldman, L., & Bennett, J. C. (2000). Cecil textbook of medicine. Philadelphia: W.B. Saunders; Ferrara J L, et al., Cytokine storm of graft-versus-host disease: a critical effector role for interleukin-1, Transplant Proc. 1993 February; 25(1 Pt 2):1216-7; Osterholm M T, Preparing for the Next Pandemic, N Engl J. Med. 2005 May 5; 352(18):1839-42; Huang K J, et al., An interferon-gamma-related cytokine storm in SARS patients, J Med. Virol. 2005 February; 75(2): 185-94; and Cheung C Y, et al., Induction of proinflammatory cytokines in human macrophages by influenza A (H5N1) viruses: a mechanism for the unusual severity of human disease? Lancet. 2002 Dec. 7; 360(9348):1831-7.

In another embodiment of the invention, anti-IL-6 antibodies described herein, or fragments thereof, are useful as a wakefulness aid.

Administration

In one embodiment of the invention, the anti-IL-6 antibodies described herein, or IL-6 binding fragments thereof, as well as combinations of said antibody fragments, are administered to a subject at a concentration of between about 0.1 and 20 mg/kg, such as about 0.4 mg/kg, about 0.8 mg/kg, about 1.6 mg/kg, or about 4 mg/kg, of body weight of recipient subject. In a preferred embodiment of the invention, the anti-IL-6 antibodies described herein, or IL-6 binding fragments thereof, as well as combinations of said antibody fragments, are administered to a subject at a concentration of about 0.4 mg/kg of body weight of recipient subject. In a preferred embodiment of the invention, the anti-IL-6 antibodies described herein, or IL-6 binding fragments thereof, as well as combinations of said antibody fragments, are administered to a recipient subject with a frequency of once every twenty-six weeks or less, such as once every sixteen weeks or less, once every eight weeks or less, or once every four weeks, or less. In another preferred embodiment of the invention, the anti-IL-6 antibodies described herein, or IL-6 binding fragments thereof, as well as combinations thereof, are administered to a recipient subject with a frequency at most once per period of approximately one week, such as at most once per period of approximately two weeks, such as at most once per period of approximately four weeks, such as at most once per period of approximately eight weeks, such as at most once per period of approximately twelve weeks, such as at most once per period of approximately sixteen weeks, such as at most once per period of approximately twenty-four weeks.

It is understood that the effective dosage may depend on recipient subject attributes, such as, for example, age, gender, pregnancy status, body mass index, lean body mass, condition or conditions for which the composition is given, other health conditions of the recipient subject that may affect metabolism or tolerance of the composition, levels of IL-6 in the recipient subject, and resistance to the composition (for example, arising from the patient developing antibodies against the composition). A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-IL-6 antibodies described herein, or IL-6 binding fragments thereof, as well as combinations of said antibody fragments, are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-IL-6 antibodies described herein, or IL-6 binding fragments thereof, as well as combinations of said antibody fragments, may be optionally administered in combination with one or more active agents. Such active agents include analgesic, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib. Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Timidazole, Tobramycin, Trimethoprim, Trimethoprim-Sulfamethoxazole, Troleandomycin, Trovafloxacin, and Vancomycin. Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Antiviral agents include abacavir, aciclovir, acyclovir, adefovir, amantadine, amprenavir, an antiretroviral fixed dose combination, an antiretroviral synergistic enhancer, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors, famciclovir, fomivirsen, fosamprenavir, foscarnet, fosfonet, fusion inhibitor, ganciclovir, gardasil, ibacitabine, idoxuridine, imiquimod, immunovir, indinavir, inosine, integrase inhibitor, interferon, interferon type I, interferon type II, interferon type III, lamivudine, lopinavir, loviride, maraviroc, MK-0518, moroxydine, nelfinavir, nevirapine, nexavir, nucleoside analogues, oseltamivir, penciclovir, peramivir, pleconaril, podophyllotoxin, protease inhibitor, reverse transcriptase inhibitor, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine. Any suitable combination of these active agents is also contemplated or a regimen that includes administration thereof in association with an anti-IL-6 antibody according to the invention.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in Remington's Pharmaceutical Sciences, $19^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In one embodiment of the invention that may be used to intravenously administer antibodies of the invention, including Ab1, for cancer indications, the administration formulation comprises, or alternatively consists of, about 10.5 mg/mL of antibody, 25 mM Histidine base, Phosphoric acid q.s. to pH 6, and 250 mM sorbitol.

In another embodiment of the invention that may be used to intravenously administer antibodies of the invention, including Ab1, for cancer indications, the administration formulation comprises, or alternatively consists of, about 10.5 mg/mL of antibody, 12.5 mM Histidine base, 12.5 mM Histidine HCl (or 25 mM Histidine base and Hydrochloric acid q.s. to pH 6), 250 mM sorbitol, and 0.015% (w/w) Polysorbate 80.

In one embodiment of the invention that may be used to subcutaneously administer antibodies of the invention, including Ab1, for rheumatoid arthritis indications, the administration formulation comprises, or alternatively consists of, about 50 or 100 mg/mL of antibody, about 5 mM Histidine base, about 5 mM Histidine HCl to make final pH 6, 250 mM sorbitol, and 0.015% (w/w) Polysorbate 80.

In another embodiment of the invention that may be used to subcutaneously administer antibodies of the invention, including Ab1, for rheumatoid arthritis indications, the administration formulation comprises, or alternatively consists of, about 20 or 100 mg/mL of antibody, about 5 mM Histidine base, about 5 mM Histidine HCl to make final pH 6, 250 to 280 mM sorbitol (or sorbitol in combination with sucrose), and 0.015% (w/w) Polysorbate 80, said formulation having a nitrogen headspace in the shipping vials.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International application Ser. No. 12/124,723, entitled "Novel Rabbit Antibody Humanization Method and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

Certain teachings related to anti-IL-6 antibodies, methods of producing antibodies or fragments thereof using mating competent yeast and corresponding methods were disclosed in U.S. provisional patent application No. 60/924,550, filed May 21, 2007, the disclosure of which is herein incorporated by reference in its entirety.

Certain teachings related to anti-IL-6 antibodies and methods of using those antibodies or fragments thereof to treat thrombosis or hypercoagulation disorders were disclosed in U.S. provisional patent application No. 61/117,861, filed Nov. 25, 2008, the disclosure of which is herein incorporated by reference in its entirety.

Certain anti-IL-6 antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

Each of U.S. Ser. No. 12/502,581 filed on Jul. 14, 2009, U.S. Ser. No. 12/399,156 filed on Mar. 6, 2009, U.S. Ser. No. 12/391,717 filed on Feb. 24, 2009, U.S. Ser. No. 12/366,567 filed on Feb. 5, 2009 is herein incorporated by reference in its entirety.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

Production of Enriched Antigen-Specific B Cell Antibody Culture

Panels of antibodies are derived by immunizing traditional antibody host animals to exploit the native immune response to a target antigen of interest. Typically, the host used for immunization is a rabbit or other host that produces antibodies using a similar maturation process and provides for a population of antigen-specific B cells producing antibodies of comparable diversity, e.g., epitopic diversity. The initial antigen immunization can be conducted using complete Freund's adjuvant (CFA), and the subsequent boosts effected with incomplete adjuvant. At about 50-60 days after immunization, preferably at day 55, antibody titers are tested, and the Antibody Selection (ABS) process is initiated if appropriate titers are established. The two key criteria for ABS initiation are potent antigen recognition and function-modifying activity in the polyclonal sera.

At the time positive antibody titers are established, animals are sacrificed and B cell sources isolated. These sources include: the spleen, lymph nodes, bone marrow, and peripheral blood mononuclear cells (PBMCs). Single cell suspensions are generated, and the cell suspensions are washed to make them compatible for low temperature long term storage. The cells are then typically frozen.

To initiate the antibody identification process, a small fraction of the frozen cell suspensions are thawed, washed, and placed in tissue culture media. These suspensions are then mixed with a biotinylated form of the antigen that was used to generate the animal immune response, and antigen-specific cells are recovered using the Miltenyi magnetic bead cell selection methodology. Specific enrichment is conducted using streptavidin beads. The enriched population is recovered and progressed in the next phase of specific B cell isolation.

Example 2

Production of Clonal, Antigen-Specific B Cell-Containing Culture

Enriched B cells produced according to Example 1 are then plated at varying cell densities per well in a 96 well microtiter plate. Generally, this is at 50, 100, 250, or 500 cells per well with 10 plates per group. The media is supplemented with 4% activated rabbit T cell conditioned media along with 50K frozen irradiated EL4B feeder cells. These cultures are left undisturbed for 5-7 days at which time supernatant-containing secreted antibody is collected and evaluated for target properties in a separate assay setting. The remaining supernatant is left intact, and the plate is frozen at −70° C. Under these conditions, the culture process typically results in wells containing a mixed cell population that comprises a clonal population of antigen-specific B cells, i.e., a single well will only contain a single monoclonal antibody specific to the desired antigen.

Example 3

Screening of Antibody Supernatants for Monoclonal Antibody of Desired Specificity and/or Functional Properties Antibody-containing supernatants derived from the well containing a clonal antigen-specific B cell population produced according to Example 2 are initially screened for antigen recognition using ELISA methods. This includes selective antigen immobilization (e.g., biotinylated antigen capture by streptavidin coated plate), non-specific antigen plate coating, or alternatively, through an antigen build-up strategy (e.g., selective antigen capture followed by binding partner addition to generate a heteromeric protein-antigen complex). Antigen-positive well supernatants are then optionally tested in a function-modifying assay that is strictly dependant on the ligand. One such example is an in vitro protein-protein interaction assay that recreates the natural interaction of the antigen ligand with recombinant receptor protein. Alternatively, a cell-based response that is ligand dependent and easily monitored (e.g., proliferation response) is utilized. Supernatant that displays significant antigen recognition and potency is deemed a positive well. Cells derived from the original positive well are then transitioned to the antibody recovery phase.

Example 4

Recovery of Single, Antibody-Producing B Cell of Desired Antigen Specificity Cells are isolated from a well that contains a clonal population of antigen-specific B cells (produced according to Example 2 or 3), which secrete a single antibody sequence. The isolated cells are then assayed to isolate a single, antibody-secreting cell. Dynal streptavidin beads are coated with biotinylated target antigen under buffered medium to prepare antigen-containing microbeads compatible with cell viability. Next antigen-loaded beads, antibody-producing cells from the positive well, and a fluorescein isothiocyanate (FITC)-labeled anti-host H&L IgG antibody (as noted, the host can be any mammalian host, e.g., rabbit, mouse, rat, etc.) are incubated together at 37° C. This mixture is then re-pipetted in aliquots onto a glass slide such that each aliquot has on average a single, antibody-producing B-cell. The antigen-specific, antibody-secreting cells are then detected through fluorescence microscopy. Secreted antibody is locally concentrated onto the adjacent beads due to the bound antigen and provides localization information based on the strong fluorescent signal. Antibody-secreting cells are identified via FITC detection of antibody-antigen complexes formed adjacent to the secreting cell. The single cell found in the center of this complex is then recovered using a micromanipulator. The cell is snap-frozen in an eppendorf PCR tube for storage at −80° C. until antibody sequence recovery is initiated.

Example 5

Isolation of Antibody Sequences From Antigen-Specific B Cell

Antibody sequences are recovered using a combined RT-PCR based method from a single isolated B-cell produced according to Example 4 or an antigenic specific B cell isolated from the clonal B cell population obtained according to Example 2. Primers are designed to anneal in conserved and constant regions of the target immunoglobulin genes (heavy and light), such as rabbit immunoglobulin sequences, and a two-step nested PCR recovery step is used to obtain the antibody sequence. Amplicons from each well are analyzed for recovery and size integrity. The resulting fragments are then digested with AluI to fingerprint the sequence clonality. Identical sequences display a common fragmentation pattern in their electrophoretic analysis. Significantly, this common fragmentation pattern which proves cell clonality is generally observed even in the wells originally plated up to 1000 cells/well. The original heavy and light chain amplicon fragments are then restriction enzyme digested with HindIII and XhoI or HindIII and BsiWI to prepare the respective pieces of DNA for cloning. The resulting digestions are then ligated into an expression vector and transformed into bacteria for plasmid propagation and production. Colonies are selected for sequence characterization.

Example 6

Recombinant Production of Monoclonal Antibody of Desired Antigen Specificity and/or Functional Properties Correct full-length antibody sequences for each well containing a single monoclonal antibody is established and miniprep DNA is prepared using Qiagen solid-phase methodology. This DNA is then used to transfect mammalian cells to produce recombinant full-length antibody. Crude antibody product is tested for antigen recognition and functional properties to confirm the original characteristics are found in the recombinant antibody protein. Where appropriate, large-scale transient mammalian transfections are completed, and antibody is purified through Protein A affinity chromatography. Kd is assessed using standard methods (e.g., Biacore™) as well as IC50 in a potency assay.

Example 7

Preparation of Antibodies that Bind Human IL-6

By using the antibody selection protocol described herein, one can generate an extensive panel of antibodies. The antibodies have high affinity towards IL-6 (single to double digit pM Kd) and demonstrate potent antagonism of IL-6 in multiple cell-based screening systems (T1165 and HepG2). Furthermore, the collection of antibodies displays distinct modes of antagonism toward IL-6-driven processes.

Immunization Strategy

Rabbits were immunized with huIL-6 (R&R). Immunization consisted of a first subcutaneous (sc) injection of 100 μg in complete Freund's adjuvant (CFA) (Sigma) followed by two boosts, two weeks apart, of 50 μg each in incomplete Freund's adjuvant (IFA) (Sigma). Animals were bled on day 55, and serum titers were determined by ELISA (antigen recognition) and by non-radioactive proliferation assay (Promega) using the T1165 cell line.

Antibody Selection Titer Assessment

Antigen recognition was determined by coating Immulon 4 plates (Thermo) with 1 μg/ml of huIL-6 (50 μl/well) in phosphate buffered saline (PBS, Hyclone) overnight at 4° C. On the day of the assay, plates were washed 3 times with PBS/Tween 20 (PBST tablets, Calbiochem). Plates were then blocked with 200 μl/well of 0.5% fish skin gelatin (FSG, Sigma) in PBS for 30 minutes at 37° C. Blocking solution was removed, and plates were blotted. Serum samples were made (bleeds and pre-bleeds) at a starting dilution of 1:100 (all dilutions were made in FSG 50 μl/well) followed by 1:10 dilutions across the plate (column 12 was left blank for background control). Plates were incubated for 30 minutes at 37° C. Plates were washed 3 times with PBS/Tween 20. Goat anti-rabbit FC-HRP (Pierce) diluted 1:5000 was added to all wells (50 μl/well), and plates were incubated for 30 minutes at 37° C. Plates were washed as described above. 50 μl/well of TMB-Stable stop (Fitzgerald Industries) was added to plates, and color was allowed to develop, generally for 3 to 5 minutes. The development reaction was stopped with 50 μl/well 0.5 M HCl. Plates were read at 450 nm. Optical density (OD) versus dilution was plotted using Graph Pad Prizm software, and titers were determined.

Functional Titer Assessment

The functional activity of the samples was determined by a T1165 proliferation assay. T1165 cells were routinely maintained in modified RPMI medium (Hyclone) supplemented with HEPES, sodium pyruvate, sodium bicarbonate, L-glutamine, high glucose, penicillin/streptomycin, 10% heat inactivated fetal bovine serum (FBS) (all supplements from Hyclone), 2-mercaptoethanol (Sigma), and 10 ng/ml of huIL-6 (R&D). On the day of the assay, cell viability was determined by trypan blue (Invitrogen), and cells were seeded at a fixed density of 20,000 cells/well. Prior to seeding, cells were washed twice in the medium described above without human-IL-6 (by centrifuging at 13000 rpm for 5 minutes and discarding the supernatant). After the last wash, cells were resuspended in the same medium used for washing in a volume equivalent to 50 μl/well. Cells were set aside at room temperature.

In a round-bottom, 96-well plate (Costar), serum samples were added starting at 1:100, followed by a 1:10 dilution across the plate (columns 2 to 10) at 30 μl/well in replicates of 5 (rows B to F: dilution made in the medium described above with no huIL-6). Column 11 was medium only for IL-6 control. 30 μl/well of huIL-6 at 4× concentration of the final EC50 (concentration previously determined) were added to all wells (huIL-6 was diluted in the medium described above). Wells were incubated for 1 hour at 37° C. to allow antibody binding to occur. After 1 hour, 50 μl/well of antibody-antigen (Ab-Ag) complex were transferred to a flat-bottom, 96-well plate (Costar) following the plate map format laid out in the round-bottom plate. On Row G, 50 μl/well of medium were added to all wells (columns 2 to 11) for background control. 50 μl/well of the cell suspension set aside were added to all wells (columns 2 to 11, rows B to G). On Columns 1 and 12 and on rows A and H, 200 μl/well of medium was added to prevent evaporation of test wells and to minimize edge effect. Plates were incubated for 72 h at 37° C. in 4% $CO_2$. At 72 h, 20 μl/well of CellTiter96 (Promega) reagents was added to all test wells per manufacturer protocol, and plates were incubated for 2 h at 37° C. At 2 h, plates were gently mixed on an orbital shaker to disperse cells and to allow homogeneity in the test wells. Plates were read at 490 nm wavelength. Optical density (OD) versus dilution was plotted using Graph Pad Prizm software, and functional titer was determined. A positive assay control plate was conducted as described above using MAB2061 (R&D Systems) at a starting concentration of 1 μg/ml (final concentration) followed by 1:3 dilutions across the plate.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 μm (Fisher) with a plunger of a 20 cc syringe. Cells were collected in the modified RPMI medium described above without huIL-6, but with low glucose. Cells were washed twice by centrifugation. After the last wash, cell density was determined by trypan blue. Cells were centrifuged at 1500 rpm for 10 minutes; the supernatant was discarded. Cells were resuspended in the appropriate volume of 10% dimethyl sulfoxide (DMSO, Sigma) in FBS (Hyclone) and dispensed at 1 ml/vial. Vials were then stored at −70° C. for 24 h prior to being placed in a liquid nitrogen (LN2) tank for long-term storage.

Peripheral blood mononuclear cells (PBMCs) were isolated by mixing whole blood with equal parts of the low glucose medium described above without FBS. 35 ml of the whole blood mixture was carefully layered onto 8 ml of Lymphocyte Rabbit (Cedarlane) into a 45 ml conical tube (Corning) and centrifuged 30 minutes at 2500 rpm at room temperature without brakes. After centrifugation, the PBMC layers were carefully removed using a glass Pasteur pipette (VWR), combined, and placed into a clean 50 ml vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described above.

B Cell Culture

On the day of setting up B cell culture, PBMC, splenocyte, or lymph node vials were thawed for use. Vials were removed from LN2 tank and placed in a 37° C. water bath until thawed. Contents of vials were transferred into 15 ml conical centrifuge tube (Corning) and 10 ml of modified RPMI described above was slowly added to the tube. Cells were centrifuged for 5 minutes at 1.5K rpm, and the supernatant was discarded. Cells were resuspended in 10 ml of fresh media. Cell density and viability was determined by trypan blue. Cells were washed again and resuspended at 1E07 cells/80 μL medium. Biotinylated huIL-6 (B huIL-6) was added to the cell suspension at the final concentration of 3 μg/mL and incubated for 30 minutes at 4° C. Unbound B huIL-6 was removed with two 10 ml washes of phosphate-buffered (PBF):Ca/Mg free PBS (Hyclone), 2 mM ethylenediamine tetraacetic acid (EDTA), 0.5% bovine serum albumin (BSA) (Sigma-biotin free). After the second wash, cells were resuspended at 1E07 cells/80 μL PBF. 20 μL of MACS® streptavidin beads (Milteni)/10E7 cells were added to the cell suspension. Cells were incubated at 4° C. for 15 minutes. Cells were washed once with 2 ml of PBF/10E7 cells. After washing, the cells were resuspended at 1E08 cells/500 μL of PBF and set aside. A MACS® MS column (Milteni) was pre-rinsed with 500 ml of PBF on a magnetic stand (Milteni). Cell suspension was applied to the column through a pre-filter, and unbound fraction was collected. The column was washed with 1.5 ml of PBF buffer. The column was removed from the magnet stand and placed onto a clean, sterile 5 ml Polypropylene Falcon tube. 1 ml of PBF buffer was added to the top of the column, and positive selected cells were collected. The yield and viability of positive and negative cell fraction was determined by trypan blue staining. Positive selection yielded an average of 1% of the starting cell concentration.

A pilot cell screen was established to provide information on seeding levels for the culture. Three 10-plate groups (a total of 30 plates) were seeded at 50, 100, and 200 enriched B cells/well. In addition, each well contained 50K cells/well of irradiated EL-4.B5 cells (5,000 Rads) and an appropriate level of T cell supernatant (ranging from 1-5% depending on preparation) in high glucose modified RPMI medium at a final volume of 250 μL/well. Cultures were incubated for 5 to 7 days at 37° C. in 4% $CO_2$.

Identification of Selective Antibody Secreting B Cells

Cultures were tested for antigen recognition and functional activity between days 5 and 7.

Antigen Recognition Screening

The ELISA format used is as described above except 50 μL of supernatant from the B cell cultures (BCC) wells (all 30 plates) was used as the source of the antibody. The conditioned medium was transferred to antigen-coated plates. After positive wells were identified, the supernatant was removed and transferred to a 96-well master plate(s). The original culture plates were then frozen by removing all the supernatant except 40 μL/well and adding 60 μL/well of 16% DMSO in FBS. Plates were wrapped in paper towels to slow freezing and placed at −70° C.

Functional Activity Screening

Master plates were then screened for functional activity in the T1165 proliferation assay as described before, except row B was media only for background control, row C was media+IL-6 for positive proliferation control, and rows D-G and columns 2-11 were the wells from the BCC (50 μL/well, single points). 40 μL of IL-6 was added to all wells except the media row at 2.5 times the EC50 concentration determined for the assay. After 1 h incubation, the Ab/Ag complex was transferred to a tissue culture (TC) treated, 96-well, flat-bottom plate. 20 μL of cell suspension in modified RPMI medium without huIL-6 (T1165 at 20,000 cells/well) was added to all wells (100 μL final volume per well). Background was subtracted, and observed OD values were transformed into % of inhibition.

B Cell Recovery

Plates containing wells of interest were removed from −70° C., and the cells from each well were recovered with 5-200 μL washes of medium/well. The washes were pooled in a 1.5 ml sterile centrifuge tube, and cells were pelleted for 2 minutes at 1500 rpm.

The tube was inverted, the spin repeated, and the supernatant carefully removed. Cells were resuspended in 100 μL/tube of medium. 100 μL biotinylated IL-6 coated streptavidin M280 dynabeads (Invitrogen) and 16 μL of goat anti-rabbit H&L IgG-FITC diluted 1:100 in medium was added to the cell suspension.

20 μL of cell/beads/FITC suspension was removed, and 5 μL droplets were prepared on a glass slide (Corning) previously treated with Sigmacote (Sigma), 35 to 40 droplets/slide. An impermeable barrier of paraffin oil (JT Baker) was added to submerge the droplets, and the slide was incubated for 90 minutes at 37° C., 4% $CO_2$ in the dark.

Specific B cells that produce antibody can be identified by the fluorescent ring around them due to antibody secretion, recognition of the bead-associated biotinylated antigen, and subsequent detection by the fluorescent-IgG detection reagent. Once a cell of interest was identified, the cell in the center of the fluorescent ring was recovered via a micromanipulator (Eppendorf). The single cell synthesizing and exporting the antibody was transferred into a 250 μL microcentrifuge tube and placed in dry ice. After recovering all cells of interest, these were transferred to −70° C. for long-term storage.

Example 8

Yeast Cell Expression

Antibody genes: Genes were cloned and constructed that directed the synthesis of a chimeric humanized rabbit monoclonal antibody.

Expression vector: The vector contains the following functional components: 1) a mutant ColE1 origin of replication, which facilitates the replication of the plasmid vector in cells of the bacterium *Escherichia coli;* 2) a bacterial Sh ble gene, which confers resistance to the antibiotic Zeocin™ (phleomycin) and serves as the selectable marker for transformations of both *E. coli* and *P. pastoris;* 3) an expression cassette composed of the glyceraldehyde dehydrogenase gene (GAP gene) promoter, fused to sequences encoding the *Saccharomyces cerevisiae* alpha mating factor pre pro secretion leader sequence, followed by sequences encoding a *P. pastoris* transcriptional termination signal from the *P. pastoris* alcohol oxidase I gene (AOX1). The Zeocin™ (phleomycin) resistance marker gene provides a means of enrichment for strains that contain multiple integrated copies of an expression vector in a strain by selecting for transformants that are resistant to higher levels of Zeocin™ (phleomycin).

*P. pastoris* strains: *P. pastoris* strains met1, lys3, ura3 and add 1 may be used. Although any two complementing sets of auxotrophic strains could be used for the construction and maintenance of diploid strains, these two strains are especially suited for this method for two reasons. First, they grow more slowly than diploid strains that are the result of their mating or fusion. Thus, if a small number of haploid add 1 or ura3 cells remain present in a culture or arise through meiosis or other mechanism, the diploid strain should outgrow them in culture.

The second is that it is easy to monitor the sexual state of these strains since diploid Ade+colonies arising from their mating are a normal white or cream color, whereas cells of any strains that are haploid add 1 mutants will form a colony with a distinct pink color. In addition, any strains that are haploid ura3 mutants are resistant to the drug 5-fluoro-orotic acid (FOA) and can be sensitively identified by plating samples of a culture on minimal medium+uracil plates with FOA. On these plates, only uracil-requiring ura3 mutant (presumably haploid) strains can grow and form colonies. Thus, with haploid parent strains marked with add 1 and ura3, one can readily monitor the sexual state of the resulting antibody-producing diploid strains (haploid versus diploid).

Methods

Construction of pGAPZ-alpha expression vectors for transcription of light and heavy chain antibody genes. The humanized light and heavy chain fragments were cloned into the pGAPZ expression vectors through a PCR directed process. The recovered humanized constructs were subjected to amplification under standard KOD polymerase (Novagen) kit conditions ((1) 94° C., 2 minutes; (2) 94° C., 30 seconds (3) 55° C., 30 seconds; (4) 72° C., 30 seconds-cycling through steps 2-4 for 35 times; (5) 72° C. 2 minutes) employing the following primers (1) light chain forward AGCGCTTATTCCGCTATCCAGATGACCCAGTC (SEQ ID NO: 741)—the AfeI site is single underlined. The end of the HSA signal sequence is double underlined, followed by the sequence for the mature variable light chain (not underlined); the reverse CGTACGTTTGATTTCCACCTTG (SEQ ID NO: 742).

Variable light chain reverse primer. BsiWI site is underlined, followed by the reverse complement for the 3' end of the variable light chain. Upon restriction enzyme digest with AfeI and BsiWI this enable insertion in-frame with the pGAPZ vector using the human HAS leader sequence in frame with the human kapp light chain constant region for export. (2) A similar strategy is performed for the heavy chain. The forward primer employed is AGCGCTTATTCCGAGGTGCAGCTGGTGGAGTC (SEQ ID NO: 743). The AfeI site is single underlined. The end of the HSA signal sequence is double underlined, followed by the sequence for the mature variable heavy chain (not underlined). The reverse heavy chain primer is CTCGAGACGGTGACGAGGGT (SEQ ID NO: 744). The XhoI site is underlined, followed by the reverse complement for the 3' end of the variable heavy chain. This enables cloning of the heavy chain in-frame with IgG-γ1 CH1-CH2-CH3 region previous inserted within pGAPZ using a comparable directional cloning strategy.

Transformation of expression vectors into haploid ade1 ura3, met1 and lys3 host strains of *P. pastoris*. All methods used for transformation of haploid *P. pastoris* strains and genetic manipulation of the *P. pastoris* sexual cycle are as described in Higgins, D. R., and Cregg, J. M., Eds. 1998. *Pichia Protocols. Methods in Molecular Biology*. Humana Press, Totowa, N.J.

Prior to transformation, each expression vector is linearized within the GAP promoter sequences with AvrII to direct the integration of the vectors into the GAP promoter locus of the *P. pastoris* genome. Samples of each vector are then individually transformed into electrocompetent cultures of the ade1, ura3, met1 and lys3 strains by electroporation and successful transformants are selected on YPD Zeocin™ (phleomycin) plates by their resistance to this antibiotic. Resulting colonies are selected, streaked for single colonies on YPD Zeocin™ (phleomycin) plates and then examined for the presence of the antibody gene insert by a PCR assay on genomic DNA extracted from each strain for the proper antibody gene insert and/or by the ability of each strain to synthesize an antibody chain by a colony lift/immunoblot method (Wung et al. Biotechniques 21 808-812 (1996). Haploid ade1, met1 and lys3 strains expressing one of the three heavy chain constructs are collected for diploid constructions along with haploid ura3 strain expressing light chain gene. The haploid expressing heavy chain genes are mated with the appropriate light chain haploid ura3 to generate diploid secreting protein.

Mating of haploid strains synthesizing a single antibody chain and selection of diploid derivatives synthesizing tetrameric functional antibodies. To mate *P. pastoris* haploid strains, each ade1 (or met 1 or lys3) heavy chain producing strain to be crossed is streaked across a rich YPD plate and the ura3 light chain producing strain is streaked across a second YPD plate (~10 streaks per plate). After one or two days incubation at 30° C., cells from one plate containing heavy chain strains and one plate containing ura3 light chain strains are transferred to a sterile velvet cloth on a replica-plating block in a cross hatched pattern so that each heavy chain strain contain a patch of cells mixed with each light chain strain. The cross-streaked replica plated cells are then transferred to a mating plate and incubated at 25° C. to stimulate the initiation of mating between strains. After two days, the cells on the mating plates are transferred again to a sterile velvet on a replica-plating block and then transferred to minimal medium plates. These plates are incubated at 30° C. for three days to allow for the selective growth of colonies of prototrophic diploid strains. Colonies that arose are picked and streaked onto a second minimal medium plate to single colony isolate and purify each diploid strain. The resulting diploid cell lines are then examined for antibody production.

Putative diploid strains are tested to demonstrate that they are diploid and contain both expression vectors for antibody production. For diploidy, samples of a strain are spread on mating plates to stimulate them to go through meiosis and form spores. Haploid spore products are collected and tested for phenotype. If a significant percentage of the resulting spore products are single or double auxotrophs it may be concluded that the original strain must have been diploid. Diploid strains are examined for the presence of both antibody genes by extracting genomic DNA from each and utilizing this DNA in PCR reactions specific for each gene.

Fusion of haploid strains synthesizing a single antibody chain and selection of diploid derivatives synthesizing tetrameric functional antibodies. As an alternative to the mating procedure described above, individual cultures of single-chain antibody producing haploid ade1 and ura3 strains are spheroplasted and their resulting spheroplasts fused using polyethylene glycol/$CaCl_2$. The fused haploid strains are then embedded in agar containing 1 M sorbitol and minimal medium to allow diploid strains to regenerate their cell wall and grow into visible colonies. Resulting colonies are picked from the agar, streaked onto a minimal medium plate, and the plates are incubated for two days at 30° C. to generate colonies from single cells of diploid cell lines. The resulting putative diploid cell lines are then examined for diploidy and antibody production as described above.

Purification and analysis of antibodies. A diploid strain for the production of full length antibody is derived through the mating of met 1 light chain and lys3 heavy chain using the methods described above. Culture media from shake-flask or fermenter cultures of diploid *P. pastoris* expression strains are collected and examined for the presence of antibody protein via SDS-PAGE and immunoblotting using antibodies directed against heavy and light chains of human IgG, or specifically against the heavy chain of IgG.

To purify the yeast secreted antibodies, clarified media from antibody producing cultures are passed through a protein A column and after washing with 20 mM sodium phosphate, pH 7.0, binding buffer, protein A bound protein is eluted using 0.1 M glycine HCl buffer, pH 3.0. Fractions containing the most total protein are examined by Coomasie blue strained SDS-PAGE and immunoblotting for antibody protein. Antibody is characterized using the ELISA described above for IL-6 recognition.

Assay for antibody activity. The recombinant yeast-derived humanized antibody is evaluated for functional activity through the IL-6 driven T1165 cell proliferation assay and IL-6 stimulated HepG2 haptoglobin assay described above.

Example 9

Acute Phase Response Neutralization by Intravenous Administration of Anti-IL-6 Antibody Ab1

Figure 4:
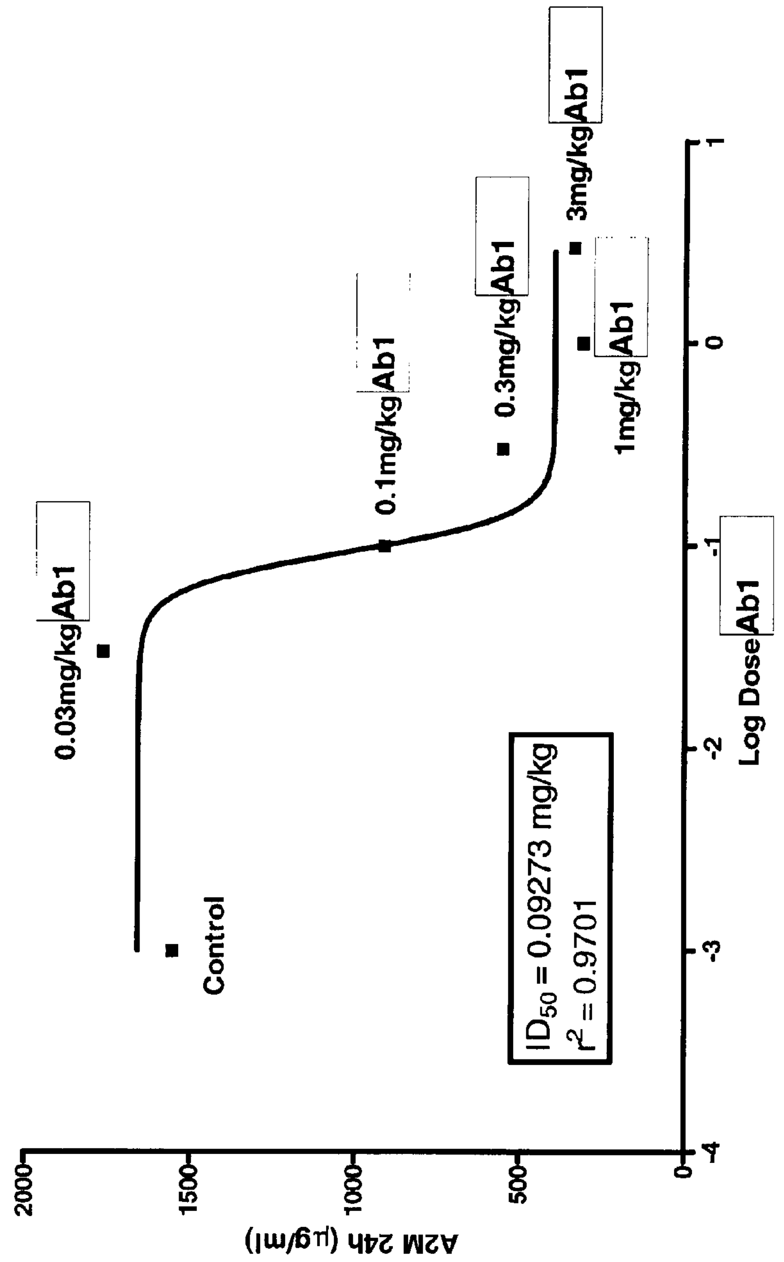
FIG. 4 provides the α-2-macroglobulin (A2M) dose response curve for antibody Ab1 administered intravenously at different doses one hour after a 100 μg/kg s.c. dose of human IL-6.

Human IL-6 can provoke an acute phase response in rats, and one of the major acute phase proteins that is stimulated in the rat is α-2 macroglobulin (A2M). A study was designed to assess the dose of antibody Ab1 required to ablate the A2M response to a single s.c. injection of 100 μg of human IL-6 given one hour after different doses (0.03, 0.1, 0.3, 1, and 3 mg/kg) of antibody Ab1 administered intravenously (n=10 rats/dose level) or polyclonal human IgG1 as the control (n=10 rats). Plasma was recovered and the A2M was quantitated via a commercial sandwich ELISA kit (ICL Inc., Newberg Oreg.; cat. no. E-25A2M). The endpoint was the difference in the plasma concentration of A2M at the 24 hour time point (post-Ab1). The results are presented in FIG. 4.

The IC50 for antibody Ab1 was 0.1 mg/kg with complete suppression of the A2M response at the 0.3 mg/kg. This firmly establishes in vivo neutralization of human IL-6 can be accomplished by antibody Ab1.

Example 10

RXF393 Cachexia Model Study 1

Introduction

The human renal cell cancer cell line, RXF393 produces profound weight loss when transplanted into athymic nude mice. Weight loss begins around day 15 after transplantation with 80% of all animals losing at least 30% of their total body weight by day 18-20 after transplantation. RXF393 secretes human IL-6 and the plasma concentration of human IL-6 in these animals is very high at around 10 ng/ml. Human IL-6 can bind murine soluble IL-6 receptor and activate IL-6 responses in the mouse. Human IL-6 is approximately 10 times less potent than murine IL-6 at activating IL-6 responses in the mouse. The objectives of this study were to determine the effect of antibody Ab1, on survival, body weight, serum amyloid A protein, hematology parameters, and tumor growth in athymic nude mice transplanted with the human renal cell cancer cell line, RXF393.

Methods

Eighty, 6 week old, male athymic nude mice were implanted with RXF393 tumor fragments (30-40 mg) subcutaneously in the right flank. Animals were then divided into eight groups of ten mice. Three groups were given either antibody Ab1 at 3 mg/kg, 10 mg/kg, or 30 mg/kg intravenously weekly on day 1, day 8, day 15 and day 22 after transplantation (progression groups). Another three groups were given either antibody Ab1 at 3 mg/kg, or 10 mg/kg, or 30 mg/kg intravenously weekly on day 8, day 15 and day 22 after transplantation (regression groups). Finally, one control group was given polyclonal human IgG 30 mg/kg and a second control group was given phosphate buffered saline intravenously weekly on day 1, day 8, day 15 and day 22 after transplantation.

Animals were euthanized at either day 28, when the tumor reached 4,000 $mm^3$ or if they became debilitated (>30% loss of body weight). Animals were weighed on days 1, 6 and then daily from days 9 to 28 after transplantation. Mean Percent Body Weight (MPBW) was used as the primary parameter to monitor weight loss during the study. It was calculated as follows: (Body Weight Tumor Weight)/Baseline Body Weight×100. Tumor weight was measured on days 1, 6, 9, 12, 15, 18, 22, 25 and 28 after transplantation. Blood was taken under anesthesia from five mice in each group on days 5 and 13 and all ten mice in each group when euthanized (day 28 in most cases). Blood was analyzed for hematology and serum amyloid A protein (SAA) concentration. An additional group of 10 non-tumor bearing 6 week old, athymic nude male mice had blood samples taken for hematology and SAA concentration estimation to act as a baseline set of values.

Results—Survival

No animals were euthanized or died in any of the antibody Ab1 groups prior to the study termination date of day 28. In the two control groups, 15 animals (7/9 in the polyclonal human IgG group and 8/10 in the phosphate buffered saline group) were found dead or were euthanized because they were very debilitated (>30% loss of body weight). Median survival time in both control groups was 20 days.

Figure 5:
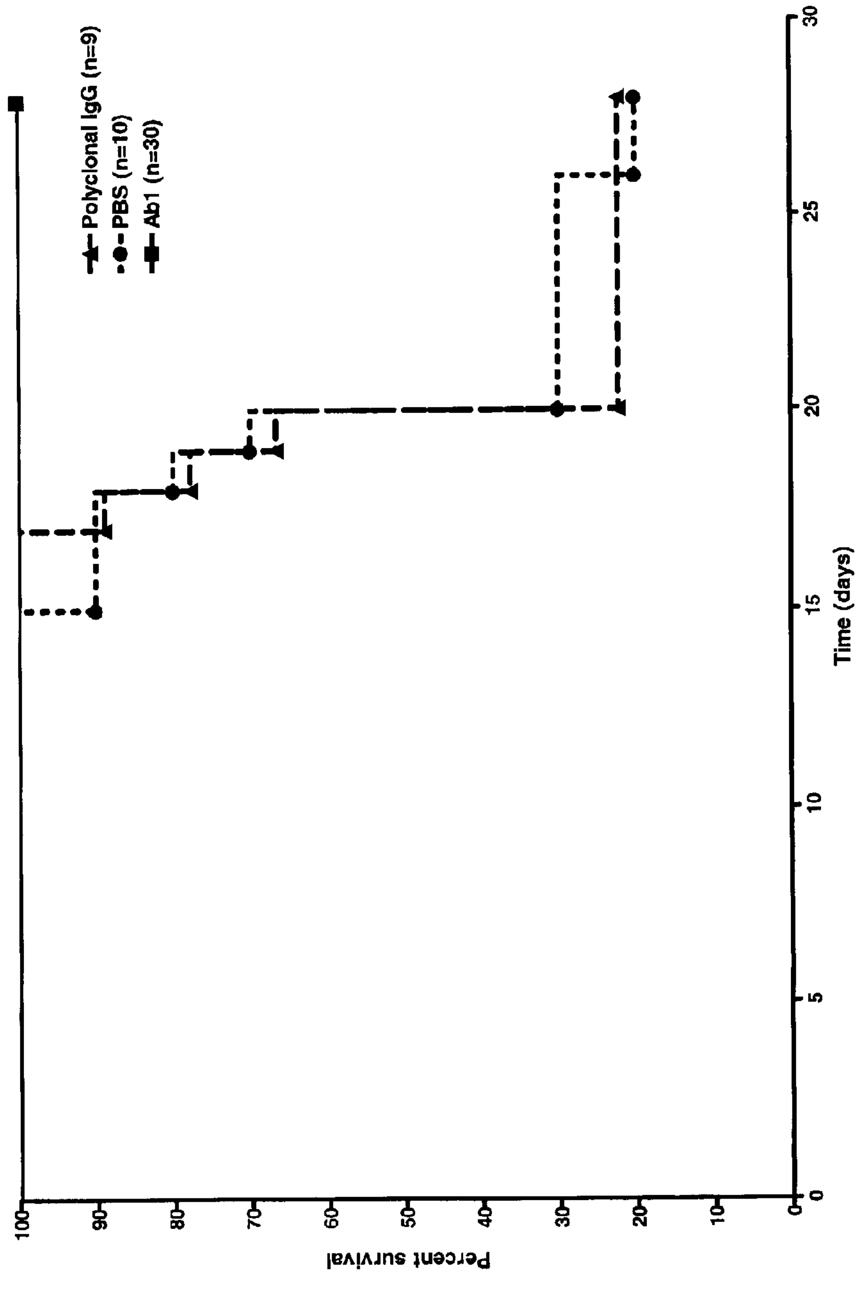
FIG. 5 provides survival data for the antibody Ab1 progression groups versus control groups.

The survival curves for the two control groups and the antibody Ab1 progression (dosed from day 1 of the study) groups are presented in FIG. 5.

Figure 6:
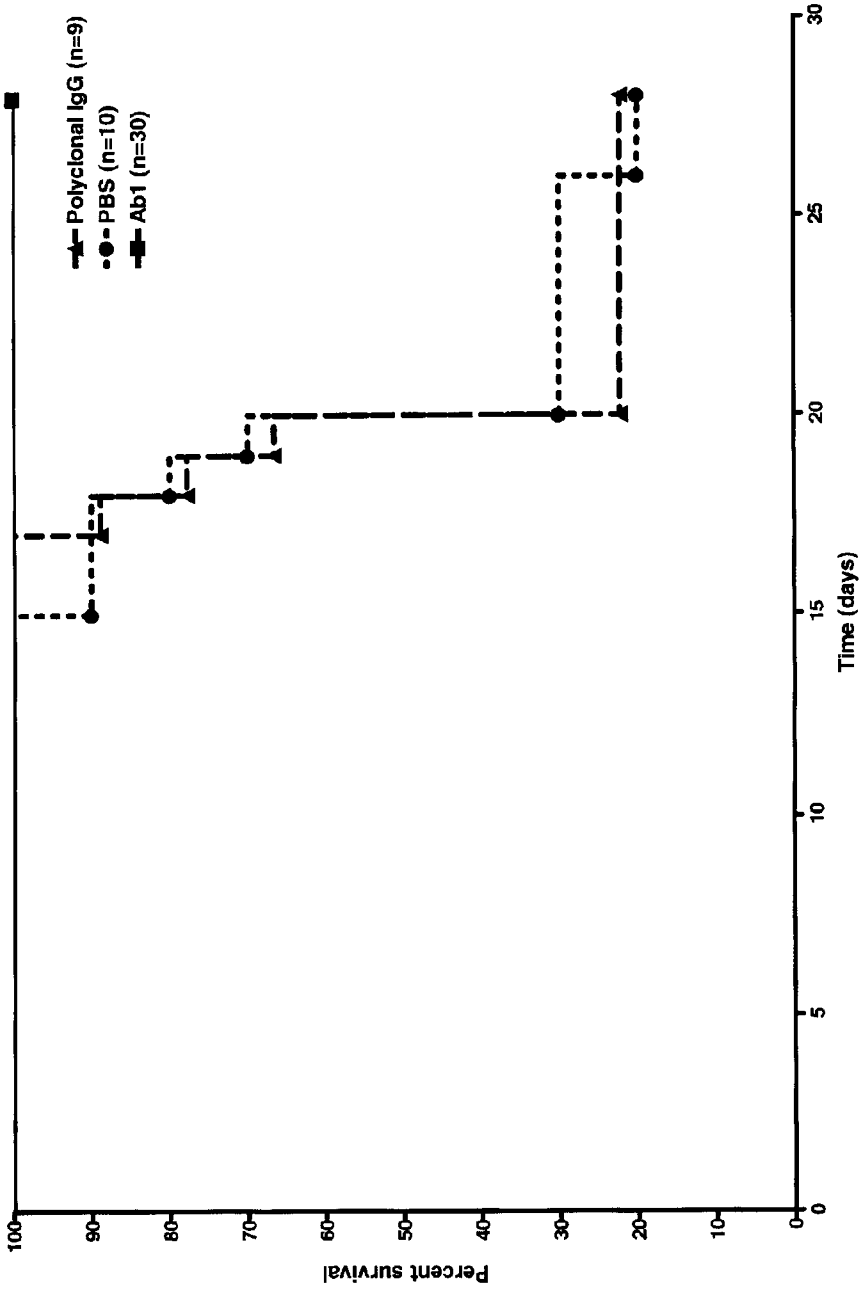
FIG. 6 provides additional survival data for the antibody Ab1 regression groups versus control groups.

The survival curves for the two control groups and the antibody Ab1 regression (dosed from day 8 of the study) groups are presented in FIG. 6.

There was a statistically significant difference between the survival curves for the polyclonal human IgG ($p=0.0038$) and phosphate buffered saline ($p=0.0003$) control groups and the survival curve for the six antibody Ab1 groups. There was no statistically significant difference between the two control groups ($p=0.97$).

Results—Tumor Size

Tumor size in surviving mice was estimated by palpation. For the first 15 days of the study, none of the mice in any group were found dead or were euthanized, and so comparison of tumor sizes between groups on these days was free from sampling bias. No difference in tumor size was observed between the antibody Ab1 progression or regression groups and the control groups through day 15. Comparison of the tumor size between surviving mice in the control and treatment groups subsequent to the onset of mortality in the controls (on day 15) was not undertaken because tumor size the surviving control mice was presumed to be biased and accordingly the results of such comparison would not be meaningful.

As administration of antibody Ab1 promoted survival without any apparent reduction in tumor size, elevated serum IL-6 may contribute to mortality through mechanisms independent of tumor growth. These observations supports the hypothesis that antibody Ab1 can promote cancer patient survivability without directly affecting tumor growth, possibly by enhancing general patient well-being.

Results—Weight Loss

Figure 27:
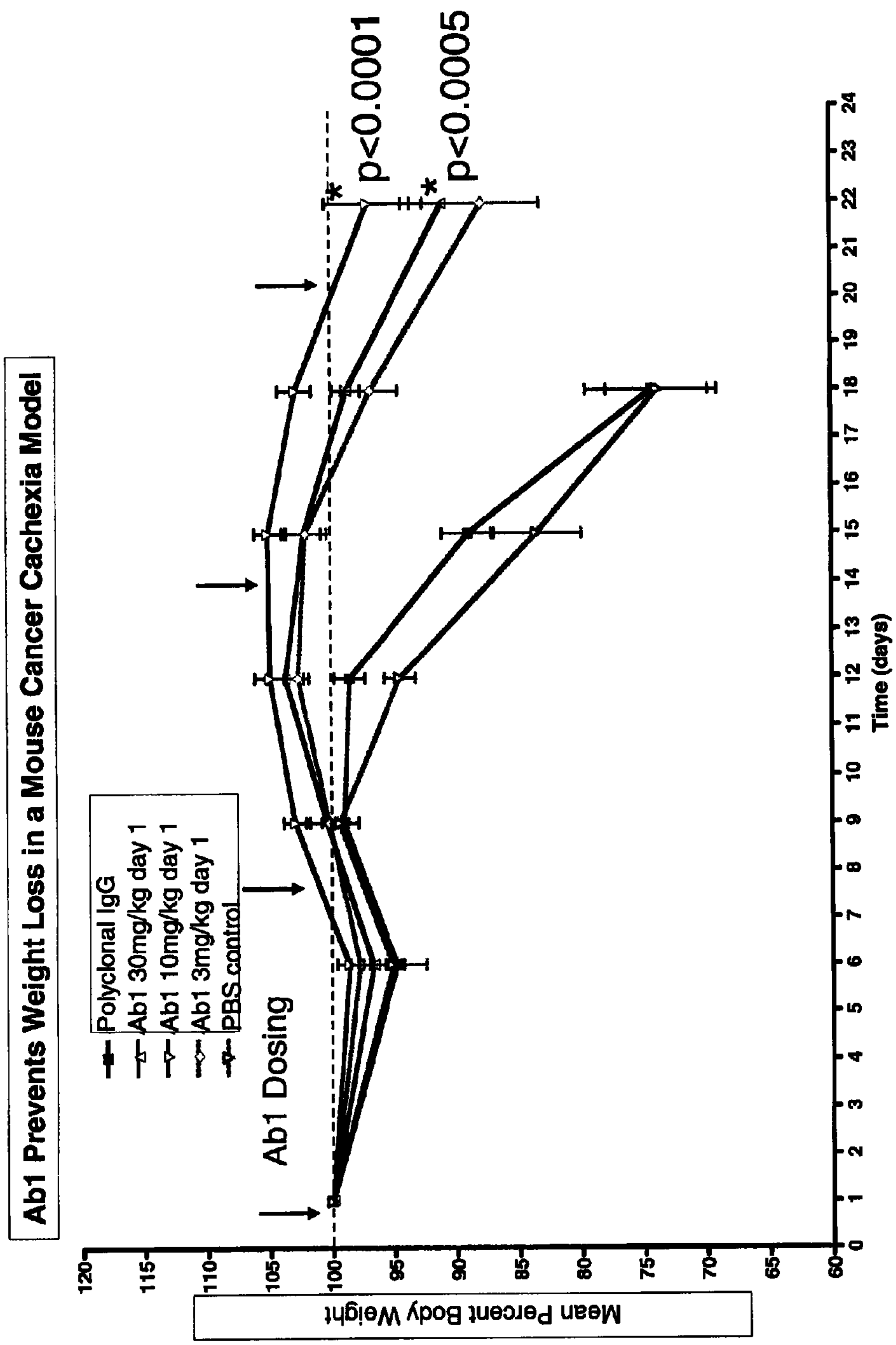
FIG. 27 shows prevention of weight loss by Ab1 in a mouse cancer cachexia model.

Mean Percent Body Weight (MPBW) (±SEM) versus time is shown in FIG. 27. Compared to controls, mice dosed with Ab1 were protected from weight loss. On day 18, MPBW in control mice was 75%, corresponding to an average weight loss of 25%. In contrast, on the same day, MPBW in Ab-1 treatment groups was minimally changed (between 97% and 103%). There was a statistically significant difference between the MPBW curves for the controls (receiving polyclonal human IgG or PBS) and the 10 mg/kg dosage group ($p<0.0001$) or 3 mg/kg and 30 mg/kg dosage groups ($p<0.0005$). There was no statistically significant difference between the two control groups.

Figure 28:
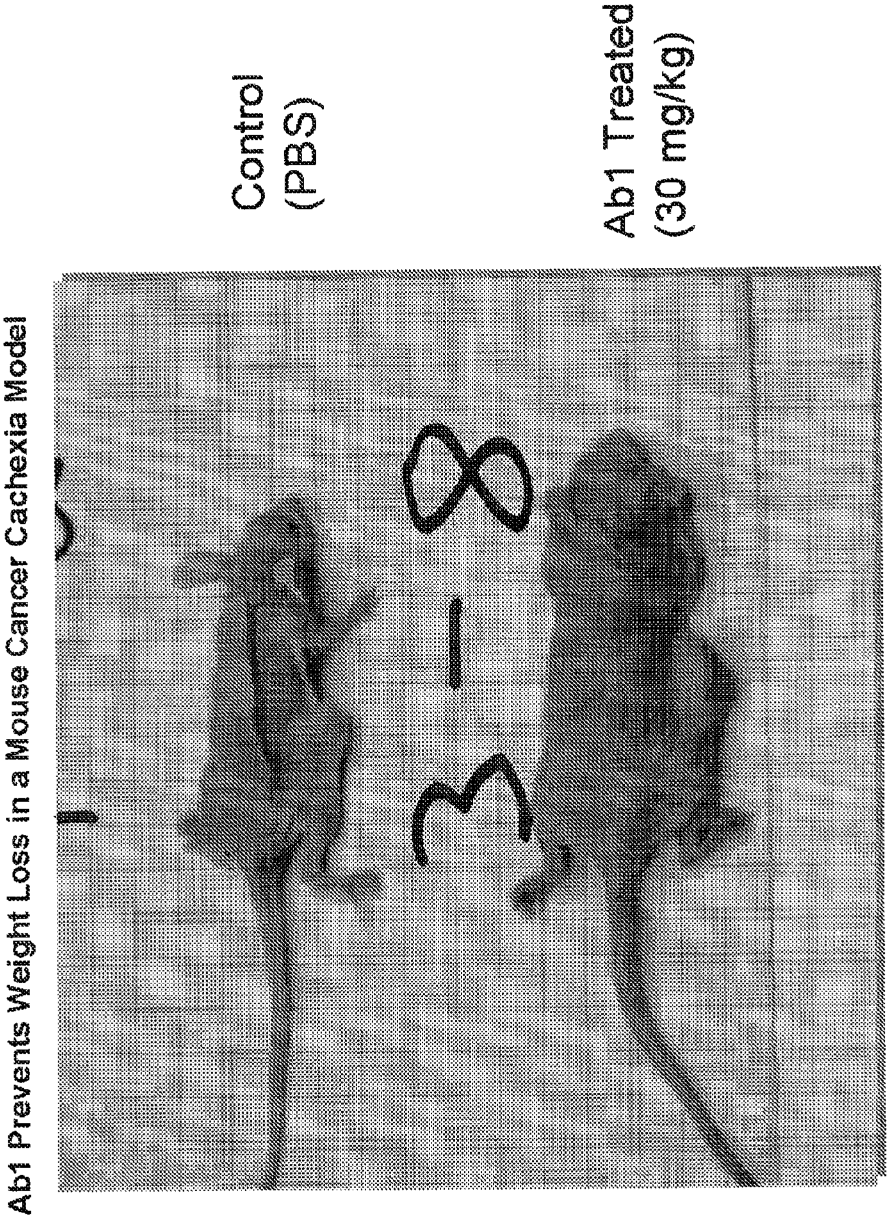
FIG. 28 shows the physical appearance of representative Ab1-treated and control mice in a cancer cachexia model.

Representative photographs of control and Ab1-treated mice (FIG. 28) illustrate the emaciated condition of the control mice, compared to the normal appearance of the Ab1-treated mouse, at the end of the study (note externally visible tumor sites in right flank).

These results suggest that Ab1 may be useful to prevent or treat cachexia caused by elevated IL-6 in humans.

Results—Plasma Serum Amyloid A

Figure 32:
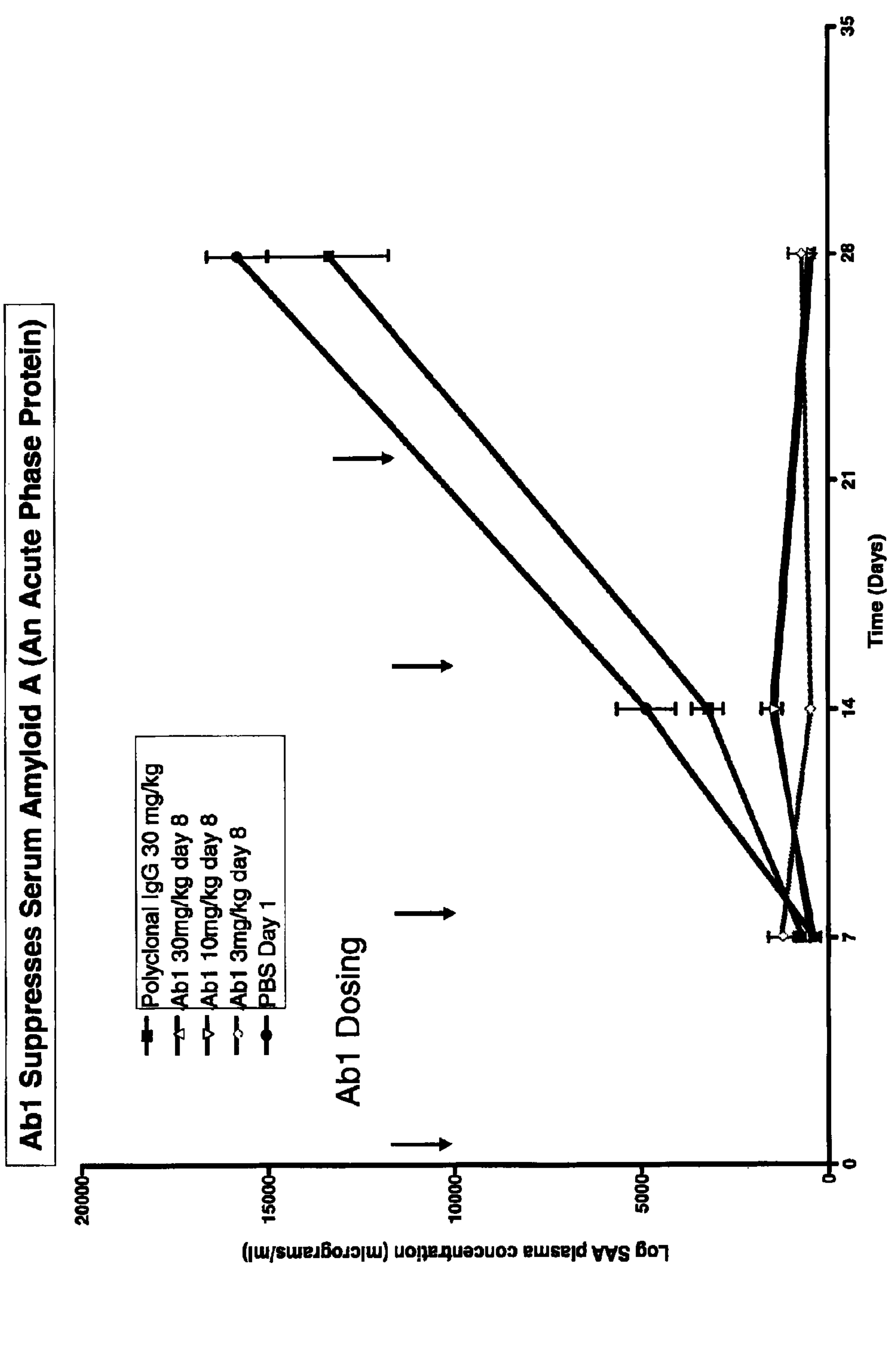
FIG. 32 demonstrates that Ab1 suppresses an acute phase protein (Serum Amyloid A) in mice.

The mean (±SEM) plasma serum amyloid A concentration versus time for the two control groups and the antibody Ab1 progression (dosed from day 1 of the study) and regression (dosed from day 8 of the study) groups are presented in Table 5 and graphically in FIG. 32.

TABLE 5

Mean Plasma SAA - antibody Ab1, all groups versus control groups

| | Mean Plasma SAA ± SEM Day 5 (μg/ml) | Mean Plasma SAA ± SEM Day 13 (μg/ml) | Mean Plasma SAA ± SEM Terminal Bleed (μg/ml) |
|---|---|---|---|
| Polyclonal IgG iv weekly from day 1 | 675 ± 240 (n = 5) | 3198 ± 628 (n = 4) | 13371 ± 2413 (n = 4) |
| PBS iv weekly from day 1 | 355 ± 207 (n = 5) | 4844 ± 1126 (n = 5) | 15826 ± 802 (n = 3) |
| Ab1 30 mg/kg iv weekly from day 1 | 246 ± 100 (n = 5) | 2979 ± 170 (n = 5) | 841 ± 469 (n = 10) |
| Ab1 10 mg/kg iv weekly from day 1 | 3629 ± 624 (n = 5) | 3096 ± 690 (n = 5) | 996 ± 348 (n = 10) |
| Ab1 3 mg/kg iv weekly from day 1 | 106 ± 9 (n = 5) | 1623 ± 595 (n = 4) | 435 ± 70 (n = 9) |
| Ab1 30 mg/kg iv weekly from day 8 | 375 ± 177 (n = 5) | 1492 ± 418 (n = 4) | 498 ± 83 (n = 9) |
| Ab1 10 mg/kg iv weekly from day 8 | 487 ± 170 (n = 5) | 1403 ± 187 (n = 5) | 396 ± 58 (n = 10) |
| Ab1 3 mg/kg iv weekly from day 8 | 1255 ± 516 (n = 5) | 466 ± 157 (n = 5) | 685 ± 350 (n = 5) |

SAA is up-regulated via the stimulation of hIL-6 and this response is directly correlated with circulating levels of hIL-6 derived from the implanted tumor. The surrogate marker provides an indirect readout for active hIL-6. Thus in the two treatment groups described above there are significantly decreased levels of SAA due to the neutralization of tumor-derived hIL-6. This further supports the contention that antibody Ab1 displays in vivo efficacy.

Example 11

RXF393 Cachexia Model Study 2

Introduction

A second study was performed in the RXF-393 cachexia model where treatment with antibody Ab1 was started at a later stage (days 10 and 13 post-transplantation) and with a more prolonged treatment phase (out to 49 days post transplantation). The dosing interval with antibody Ab1 was shortened to 3 days from 7 and also daily food consumption was measured. There was also an attempt to standardize the tumor sizes at the time of initiating dosing with antibody Ab1.

Methods

Eighty, 6 week old, male athymic nude mice were implanted with RXF393 tumor fragments (30-40 mg) subcutaneously in the right flank. 20 mice were selected whose tumors had reached between 270-320 mg in size and divided into two groups. One group received antibody Ab1 at 10 mg/kg i.v. every three days and the other group received polyclonal human IgG 10 mg/kg every 3 days from that time-point (day 10 after transplantation). Another 20 mice were selected when their tumor size had reached 400-527 mg in size and divided into two groups. One group received antibody Ab1 at 10 mg/kg i.v. every three days and the other group received polyclonal human IgG 10 mg/kg every 3 days from that time-point (day 13 after transplantation). The remaining 40 mice took no further part in the study and were euthanized at either day 49, when the tumor reached 4,000 $mm^3$ or if they became very debilitated (>30% loss of body weight).

Animals were weighed every 3-4 days from day 1 to day 49 after transplantation. Mean Percent Body Weight (MPBW) was used as the primary parameter to monitor weight loss during the study. It was calculated as follows: ((Body Weight−Tumor Weight)/Baseline Body Weight)×100. Tumor weight was measured every 3-4 days from day 5 to day 49 after transplantation. Food consumption was measured (amount consumed in 24 hours by weight (g) by each treatment group) every day from day 10 for the 270-320 mg tumor groups and day 13 for the 400-527 mg tumor groups.

Results—Survival

Figure 7:
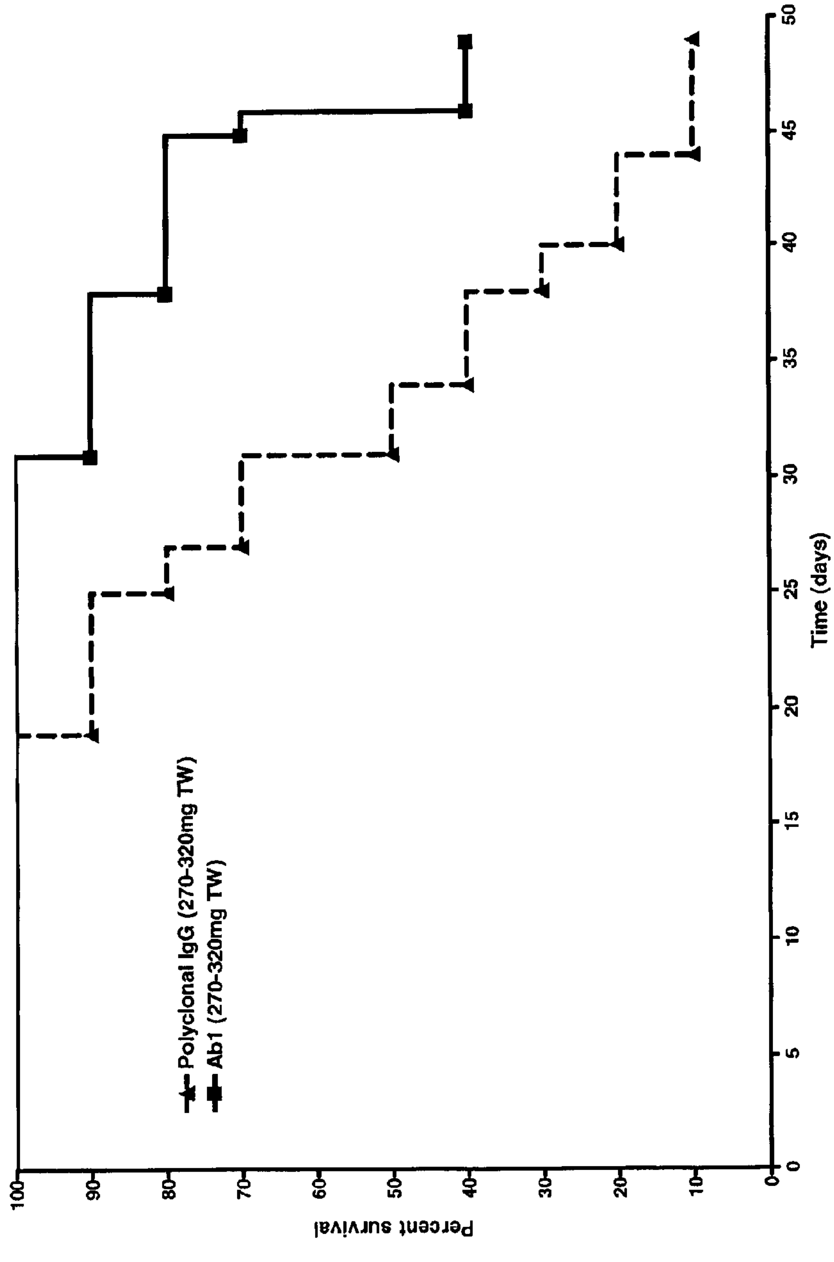
FIG. 7 provides survival data for polyclonal human IgG at 10 mg/kg i.v. every three days (270-320 mg tumor size) versus antibody Ab1 at 10 mg/kg i.v. every three days (270-320 mg tumor size).

The survival curves for antibody Ab1 at 10 mg/kg i.v. every three days (270-320 mg tumor size) and for the polyclonal human IgG 10 mg/kg i.v. every three days (270-320 mg tumor size) are presented in FIG. 7.

Median survival for the antibody Ab1 at 10 mg/kg i.v. every three days (270-320 mg tumor size) was 46 days and for the polyclonal human IgG at 10 mg/kg i.v. every three days (270-320 mg tumor size) was 32.5 days (p=0.0071).

Figure 8:
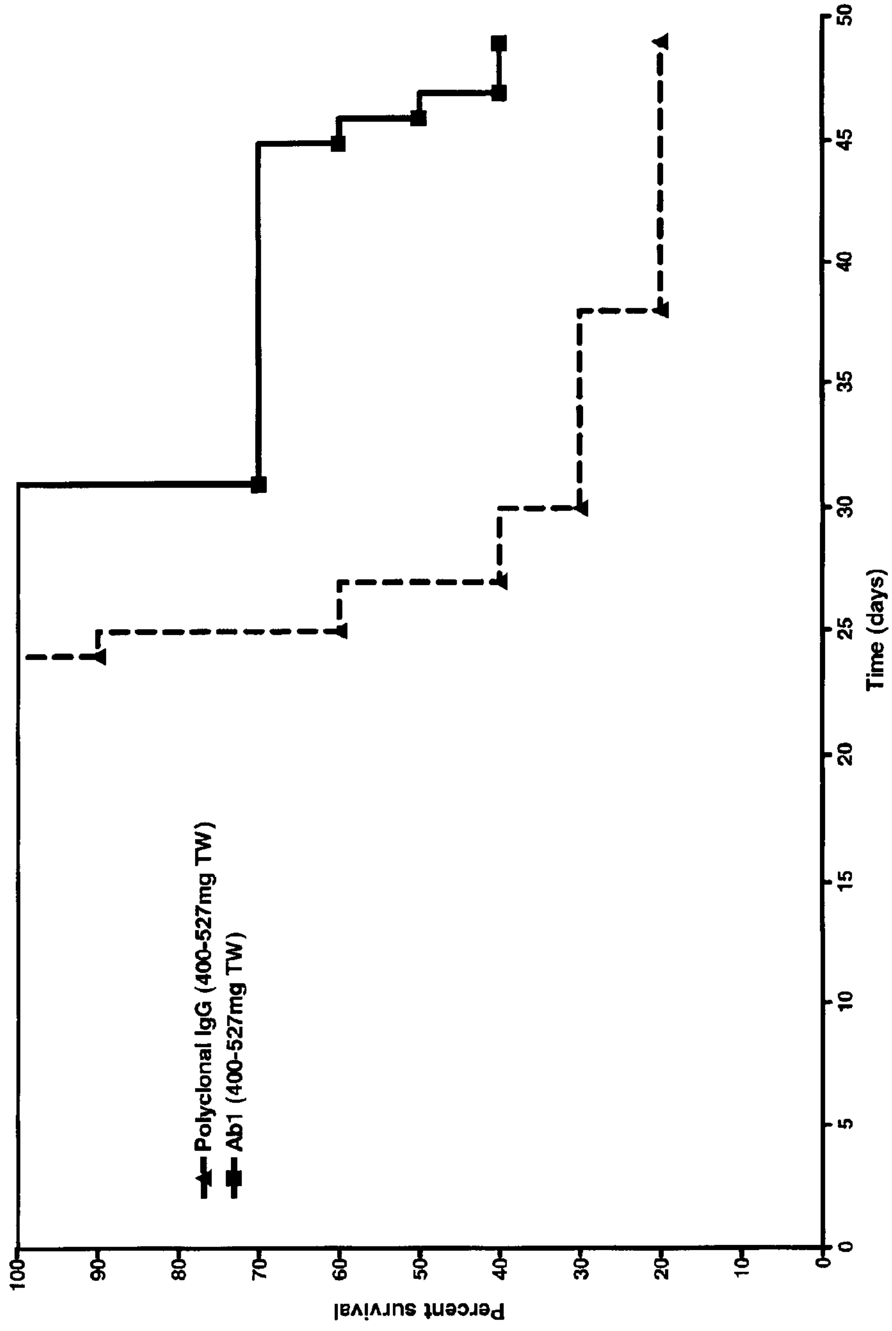
FIG. 8 provides survival data for polyclonal human IgG at 10 mg/kg i.v. every three days (400-527 mg tumor size) versus antibody Ab1 at 10 mg/kg i.v. every three days (400-527 mg tumor size).

The survival curves for the antibody Ab1 at 10 mg/kg i.v. every three days (400-527 mg tumor size) and for the polyclonal human IgG at 10 mg/kg i.v. every three days (400-527 mg tumor size) are presented in FIG. 8. Median survival for the antibody Ab1 at 10 mg/kg i.v. every three days (400-527 mg tumor size) was 46.5 days and for the polyclonal human IgG at 10 mg/kg i.v. every three days (400-527 mg tumor size) was 27 days (p=0.0481).

Example 12

Multi-dose Pharmacokinetic Evaluation of Antibody Ab1 in Non-Human Primates

Antibody Ab1 was dosed in a single bolus infusion to a single male and single female cynomologus monkey in phosphate buffered saline. Plasma samples were removed at fixed time intervals and the level of antibody Ab1 was quantitated through of the use of an antigen capture ELISA assay. Biotinylated IL-6 (50 μl of 3 μg/mL) was captured on Streptavidin coated 96 well microtiter plates. The plates were washed and blocked with 0.5% Fish skin gelatin. Appropriately diluted plasma samples were added and incubated for 1 hour at room temperature. The supernatants removed and an anti-hFc-HRP conjugated secondary antibody applied and left at room temperature.

Figure 9:
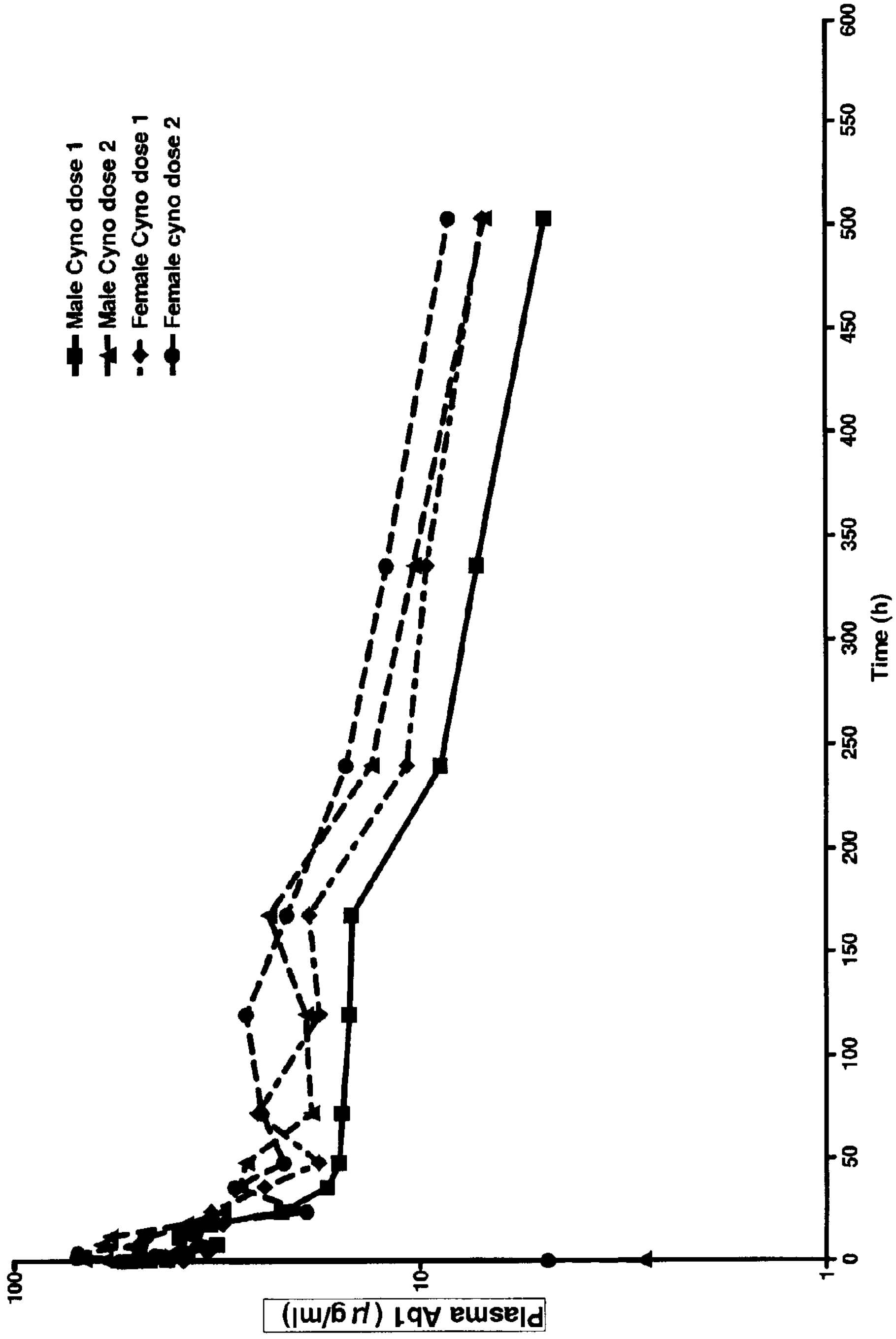
FIG. 9 provides a pharmacokinetic profile of antibody Ab1 in cynomolgus monkey. Plasma levels of antibody Ab1 were quantitated through antigen capture ELISA. This protein displays a half life of between 12 and 17 days consistent with other full length humanized antibodies.
Figure 10A:
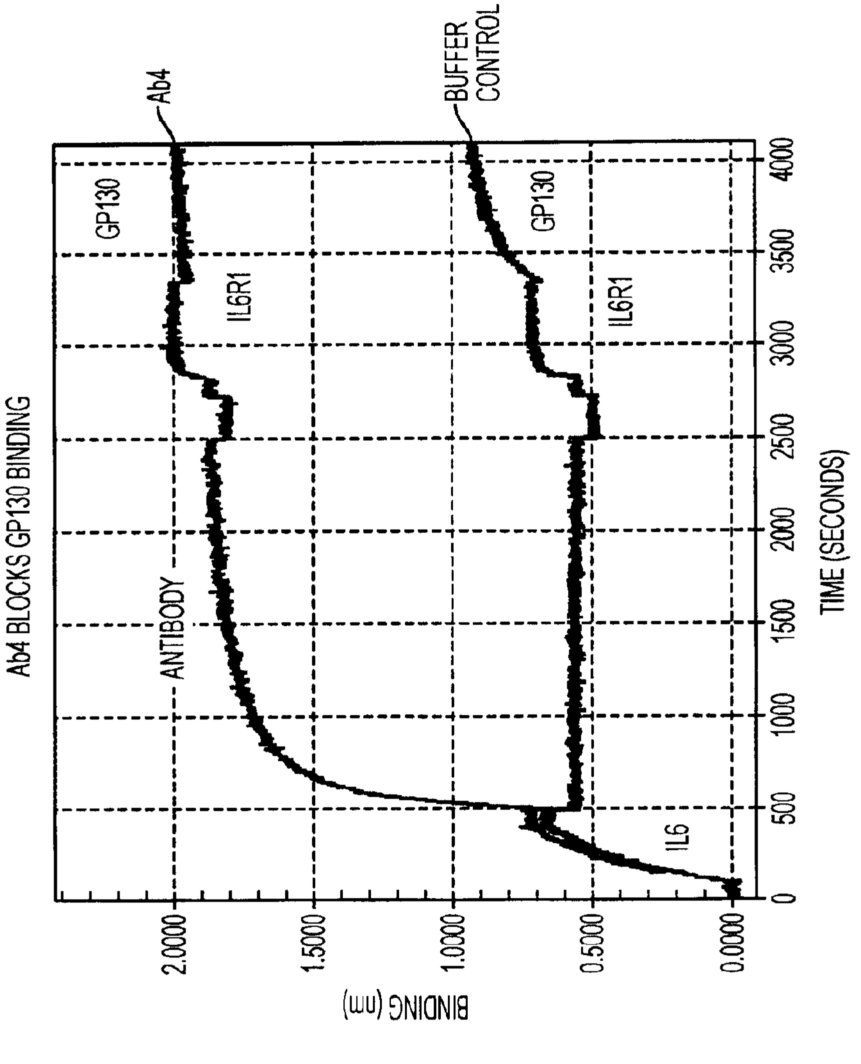
FIG. 10 (A-D) provides binding data for antibodies Ab4, Ab3, Ab8 and Ab2, respectively.
Figure 10B:
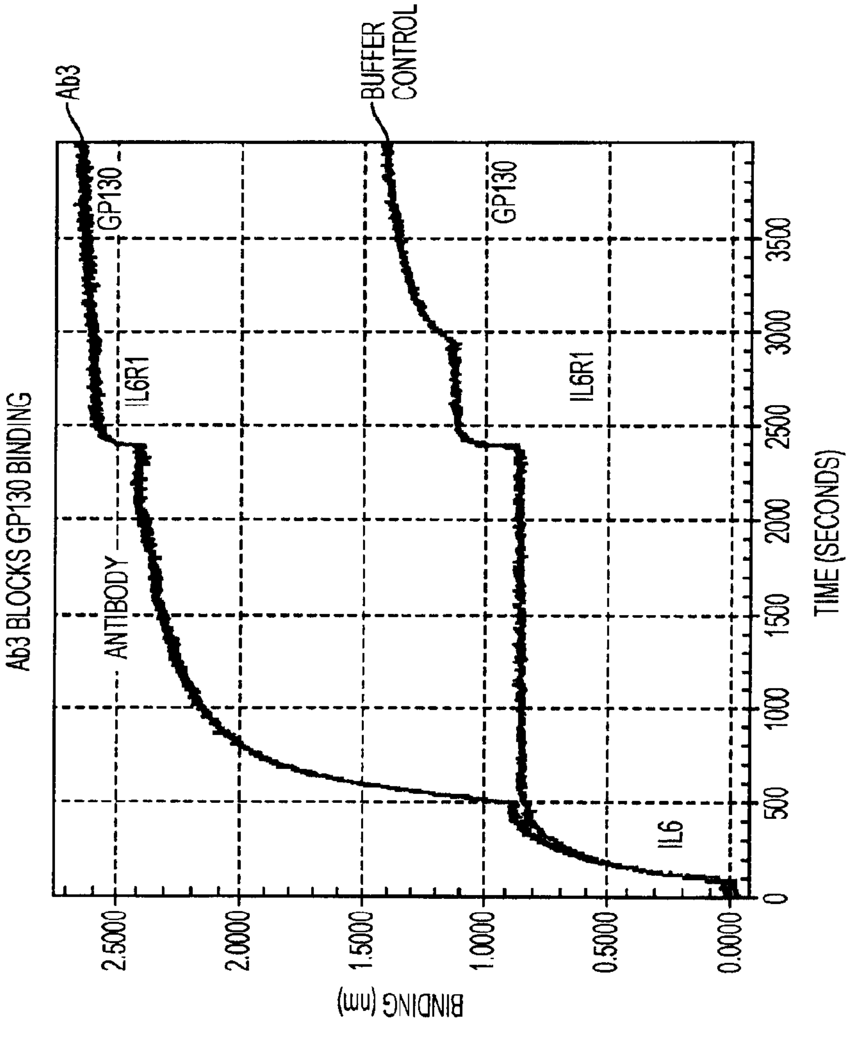
Figure 10C:
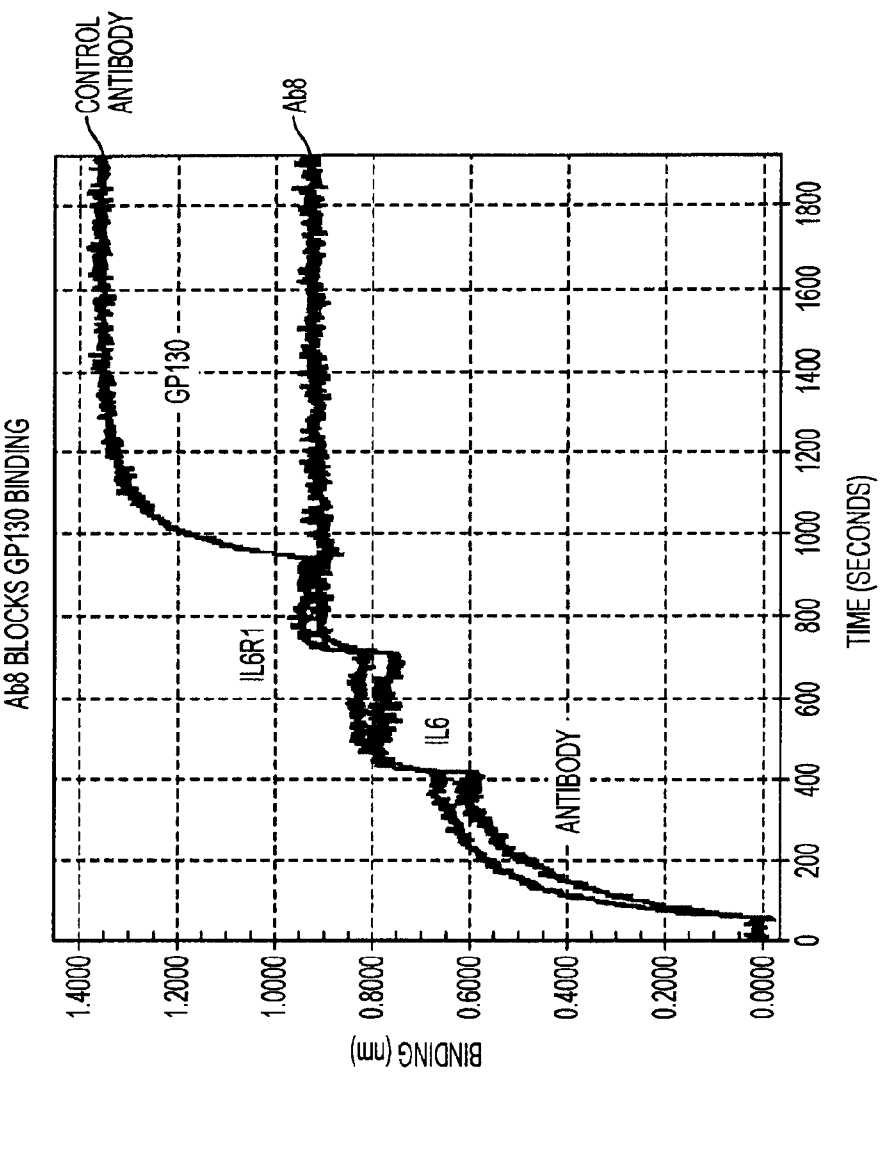
Figure 10D:
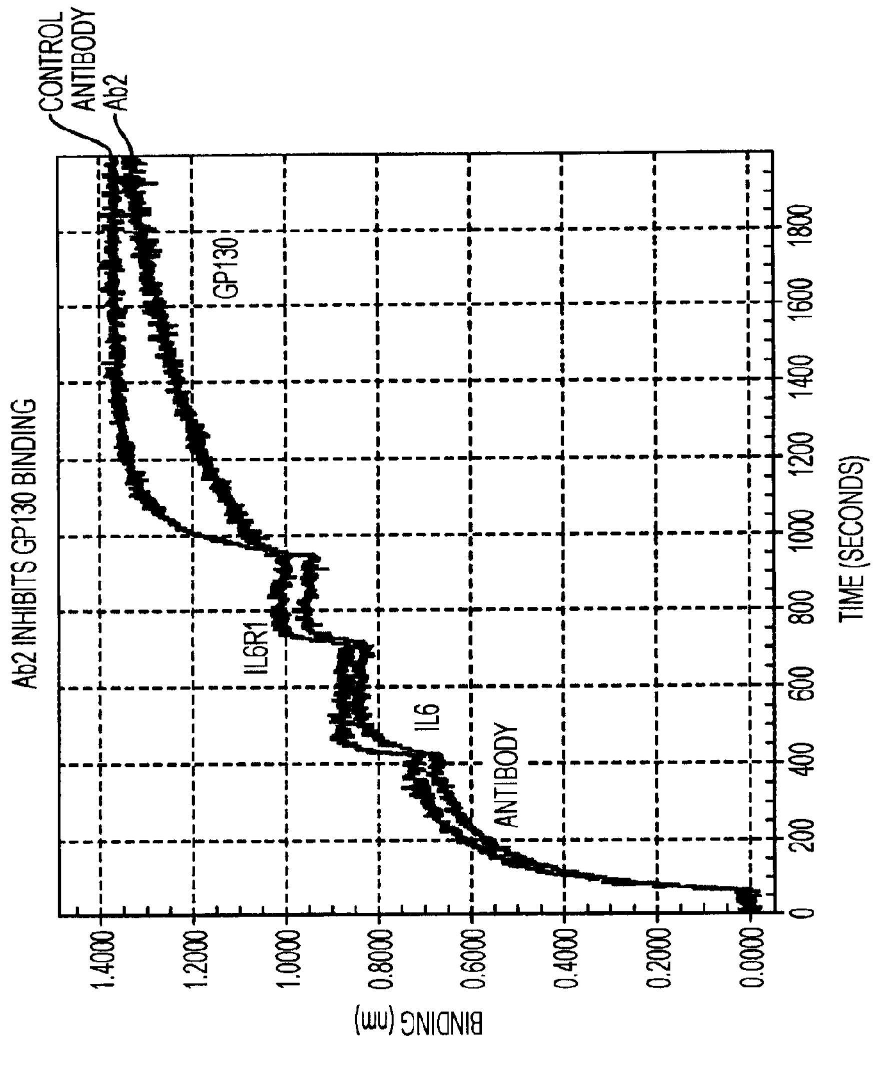
Figure 10E:
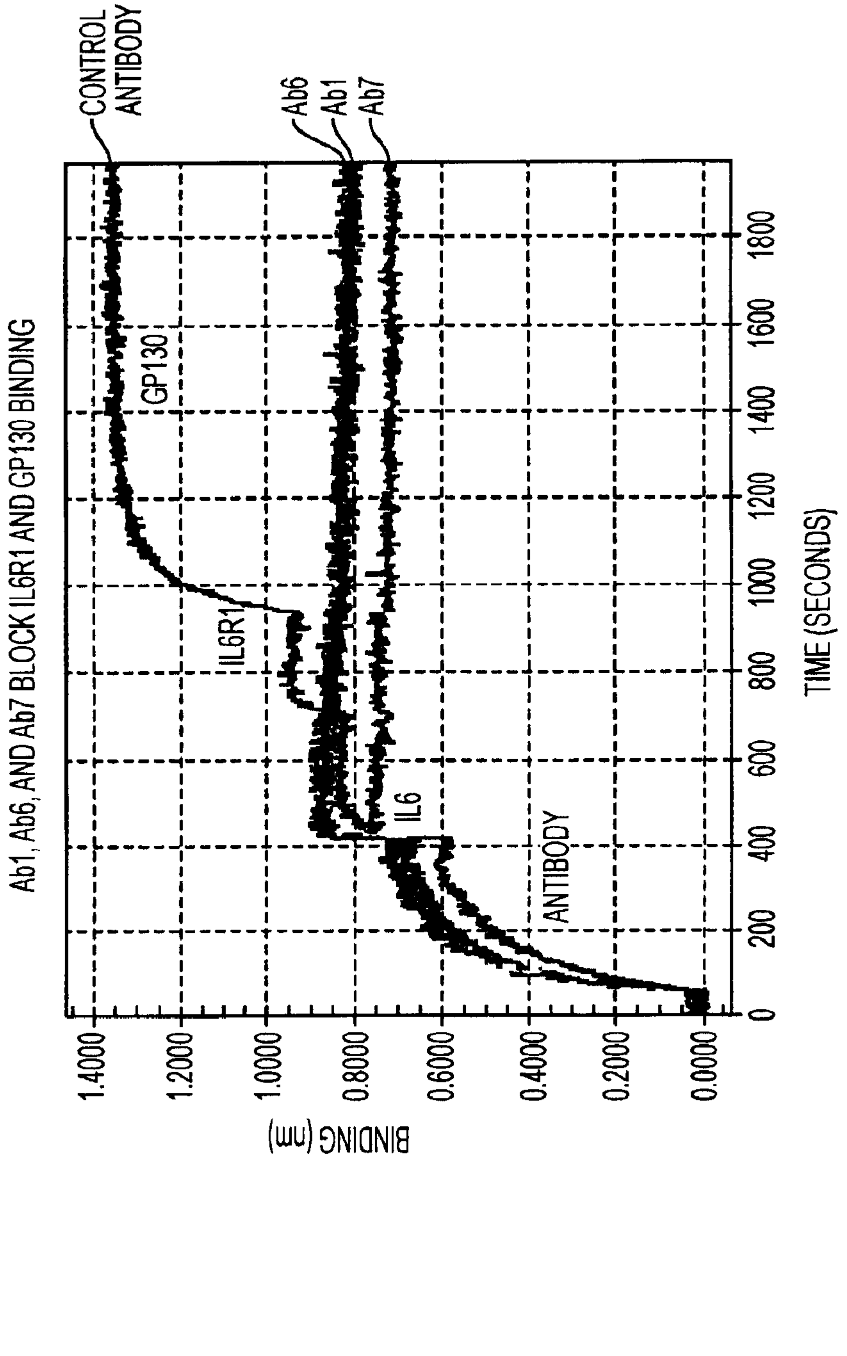

The plates were then aspirated and TMB added to visualize the amount of antibody. The specific levels were then determined through the use of a standard curve. A second dose of antibody Ab1 was administered at day 35 to the same two cynomologus monkeys and the experiment replicated using an identical sampling plan. The resulting concentrations are then plot vs. time as show in FIG. 9.

This humanized full length aglycosylated antibody expressed and purified *Pichia pastoris* displays comparable characteristics to mammalian expressed protein. In addition, multiple doses of this product display reproducible half-lives inferring that this production platform does not generate products that display enhanced immunogenicity.

Example 13

Octet Mechanistic Characterization of Antibody Proteins

IL-6 signaling is dependent upon interactions between IL-6 and two receptors, IL-6R1 (CD126) and gp130 (IL-6 signal transducer). To determine the antibody mechanism of action, mechanistic studies were performed using bio-layer interferometry with an Octet QK instrument (ForteBio; Menlo Park, Calif.). Studies were performed in two different configurations. In the first orientation, biotinylated IL-6 (R&D systems part number 206-IL-001MG/CF, biotinylated using Pierce EZ-link sulfo-NHS-LC-LC-biotin product number 21338 according to manufacturer's protocols) was initially bound to a streptavidin coated biosensor (ForteBio part number 18-5006). Binding is monitored as an increase in signal.

The IL-6 bound to the sensor was then incubated either with the antibody in question or diluent solution alone. The sensor was then incubated with soluble IL-6R1 (R&D systems product number 227-SR-025/CF) molecule. If the IL-6R1 molecule failed to bind, the antibody was deemed to block IL-6/IL-6R1 interactions. These complexes were incubated with gp130 (R&D systems 228-GP-010/CF) in the presence of IL-6R1 for stability purposes. If gp130 did not bind, it was concluded that the antibody blocked gp130 interactions with IL-6.

In the second orientation, the antibody was bound to a biosensor coated with an anti-human IgG1 Fc-specific reagent (ForteBio part number 18-5001). The IL-6 was bound to the immobilized antibody and the sensor was incubated with IL-6R1. If the IL-6R1 did not interact with the IL-6, then it was concluded that the IL-6 binding antibody blocked IL-6/IL-6R1 interactions. In those situations where antibody/IL-6/IL-6R1 was observed, the complex was incubated with gp130 in the presence of IL-6R1. If gp130 did not interact, then it was concluded that the antibody blocked IL-6/gp130 interactions. All studies were performed in a 200 μL final volume, at 30 C and 1000 rpm. For these studies, all proteins were diluted using ForteBio's sample diluent buffer (part number 18-5028).

Results are presented in FIG. 10 (A-E) and FIG. 11.

Example 14

Peptide Mapping

In order to determine the epitope recognized by Ab1 on human IL-6, the antibody was employed in a western-blot based assay. The form of human IL-6 utilized in this example had a sequence of 183 amino acids in length (shown below). A 57-member library of overlapping 15 amino acid peptides encompassing this sequence was commercially synthesized and covalently bound to a PepSpots nitrocellulose membrane (JPT Peptide technologies, Berlin, Germany). The sequences of the overlapping 15 amino acid peptides are shown in FIG. 12. Blots were prepared and probed according to the manufacturer's recommendations.

Figure 13:
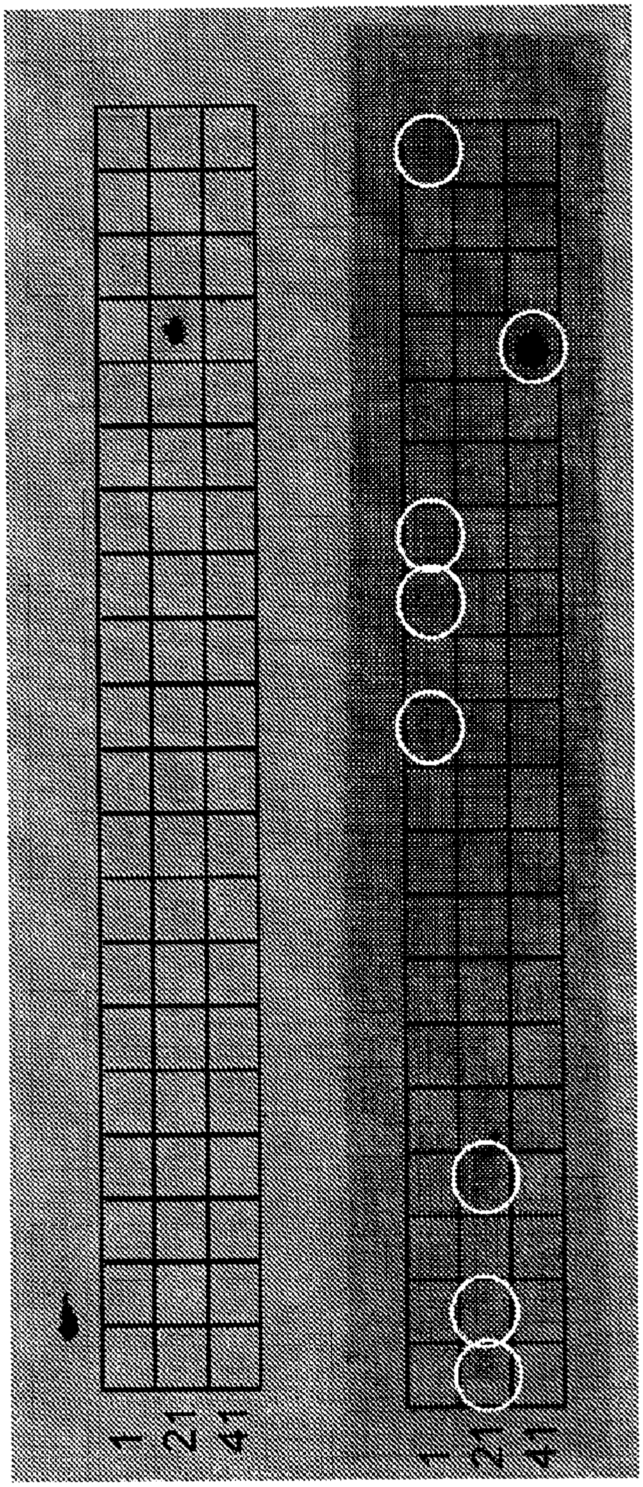
FIG. 13 presents the results of the blots prepared in Example 14.
Figure 14:
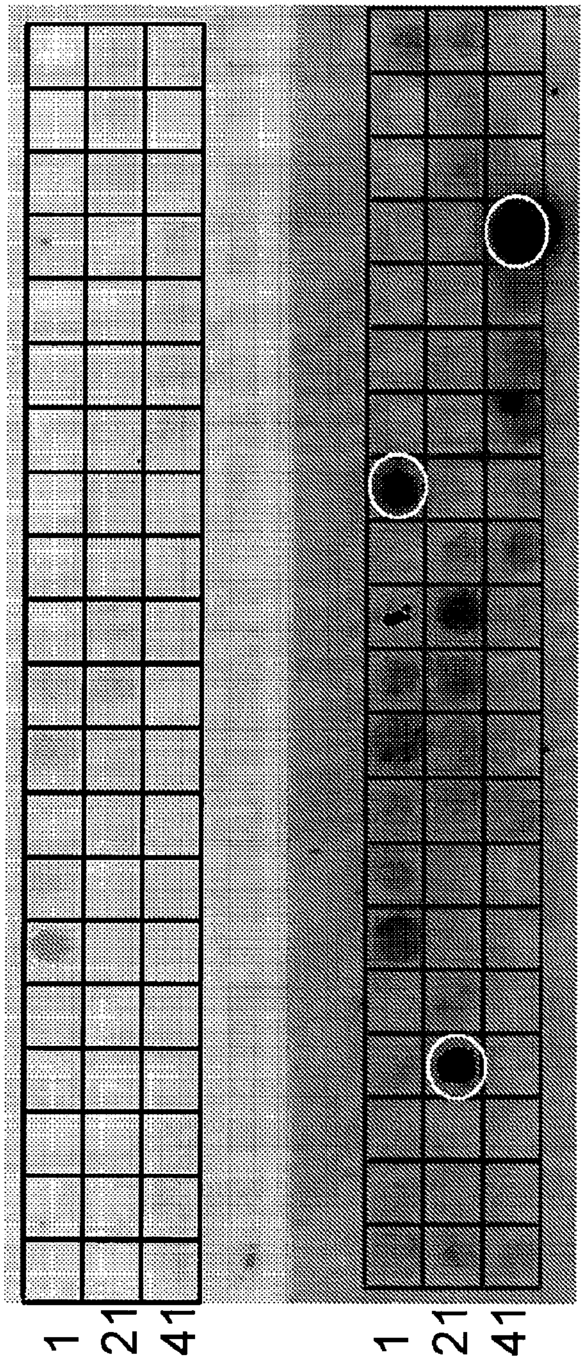
FIG. 14 presents the results of the blots prepared in Example 14.

Briefly, blots were pre-wet in methanol, rinsed in PBS, and blocked for over 2 hours in 10% non-fat milk in PBS/0.05% Tween (Blocking Solution). The Ab1 antibody was used at 1 mg/ml final dilution, and the HRP-conjugated Mouse Anti-Human-Kappa secondary antibody (Southern BioTech #9220-05) was used at a 1:5000 dilution. Antibody dilutions/incubations were performed in blocking solution. Blots were developed using Amersham ECL advance reagents (GE# RPN2135) and chemiluminescent signal documented using a CCD camera (AlphaInnotec). The results of the blots are shown in FIG. 13 and FIG. 14.

The sequence of the form of human IL-6 utilized to generate peptide library is set forth:

```
                                      (SEQ ID NO: 1)
VPPGEDSKDVAAPHRQPLTSSERIDKQIRYILDGISALRKETCNKSNMCE

SSKEALAENNLNLPKMAEKDGCFQSGFNEETCLVKIITGLLEFEVYLEYL

QNRFESSEEQARAVQMSTKVLIQFLQKKAKNLDAITTPDPTTNASLLTKL

QAQNQWLQDMTTHLILRSFKEFLQSSLRALRQM.
```

Example 15

Ab1 has High Affinity for IL-6

Surface plasmon resonance was used to measure association rate ($K_a$), dissociation rate ($K_d$) and dissociation constant ($K_D$) for Ab1 to IL-6 from rat, mouse, dog, human, and cynomolgus monkey at 25° C. (FIG. 15A). The dissociation constant for human IL-6 was 4 pM, indicating very high affinity. As expected, affinity generally decreased with phylogenetic distance from human. The dissociation constants of Ab1 for IL-6 of cynomolgus monkey, rat, and mouse were 31 pM, 1.4 nM, and 0.4 nM, respectively. Ab1 affinity for dog IL-6 below the limit of quantitation of the experiment.

The high affinity of Ab1 for mouse, rat, and cynomolgus monkey IL-6 suggest that Ab1 may be used to inhibit IL-6 of these species. This hypothesis was tested using a cell proliferation assay. In brief, each species's IL-6 was used to stimulate proliferation of T1165 cells, and the concentration at which Ab1 could inhibit 50% of proliferation (IC50) was measured. Inhibition was consistent with the measured dissociation constants (FIG. 15B). These results demonstrate that Ab1 can inhibit the native IL-6 of these species, and suggest the use of these organisms for in vitro or in vivo modeling of IL-6 inhibition by Ab1.

Example 16

Multi-Dose Pharmacokinetic Evaluation of Antibody Ab1 in Healthy Human Volunteers Antibody Ab1 was dosed in a single bolus infusion in histidine and sorbitol to healthy human volunteers. Dosages of 1 mg, 3 mg, 10 mg, 30 mg or 100 mg were administered to each individual in dosage groups containing five to six individuals. Plasma samples were removed at fixed time intervals for up to twelve weeks. Human plasma was collected via venipuncture into a vacuum collection tube containing EDTA. Plasma was separated and used to assess the circulating levels of Ab1 using a monoclonal antibody specific for Ab1, as follows. A 96 well microtiter plate was coated overnight with the monoclonal antibody specific for Ab1 in 1×PBS overnight at 4° C. The remaining steps were conducted at room temperature. The wells were aspirated and subsequently blocked using 0.5% Fish Skin Gelatin (FSG) (Sigma) in 1×PBS for 60 minutes. Human plasma samples were then added and incubated for 60 minutes, then aspirated, then 50 μL of 1 μg/mL biotinylated IL-6 was then added to each well and incubated for 60 minutes. The wells were aspirated, and 50 μL streptavidin-HRP (Pharmingen), diluted 1:5,000 in 0.5% FSG/PBS, was added and incubated for 45 minutes. Development was conducted using standard methods employing TMB for detection. Levels were then determined via comparison to a standard curve prepared in a comparable format.

Figure 16:
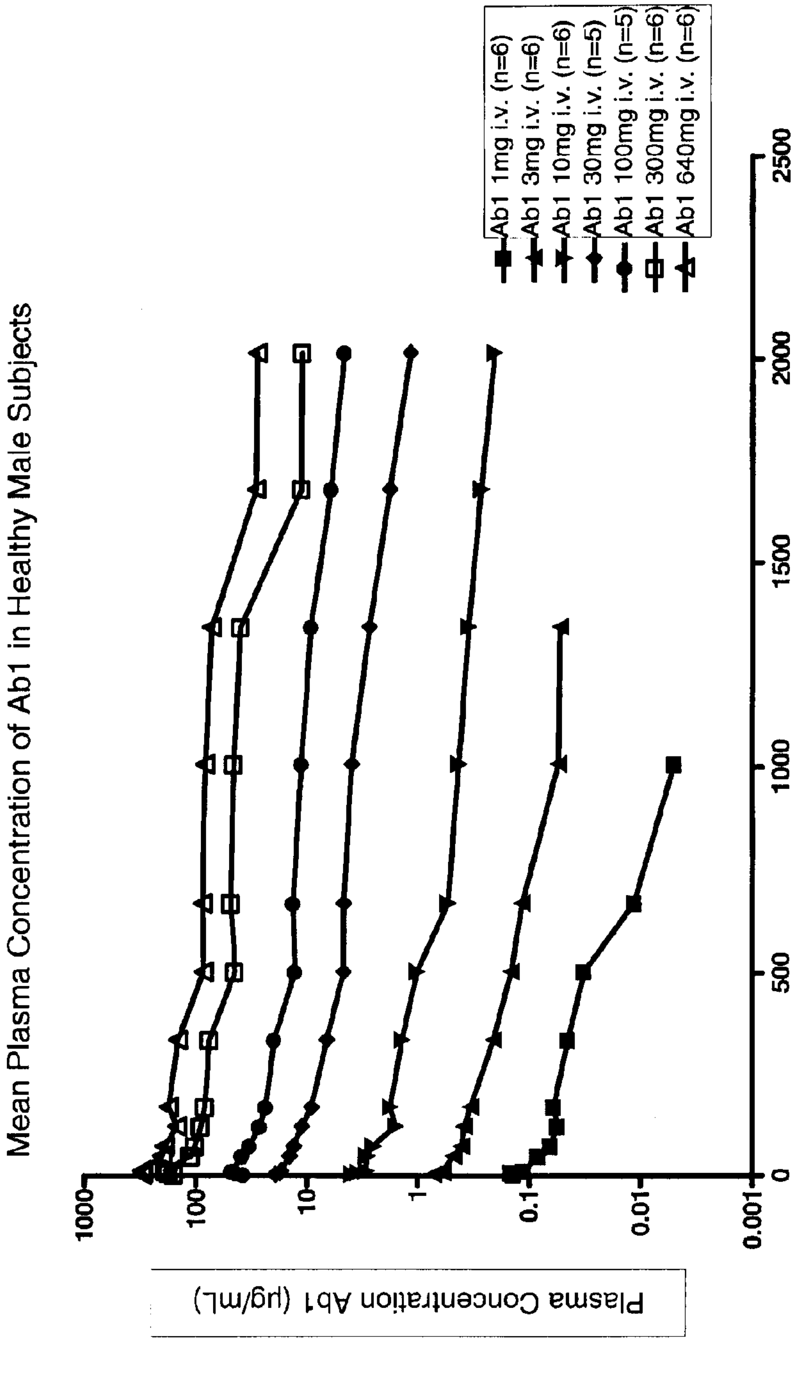
FIG. 16 shows the mean plasma concentration of Ab1 resulting from a single administration of Ab1 to healthy male subjects in several dosage groups.
Figure 17:
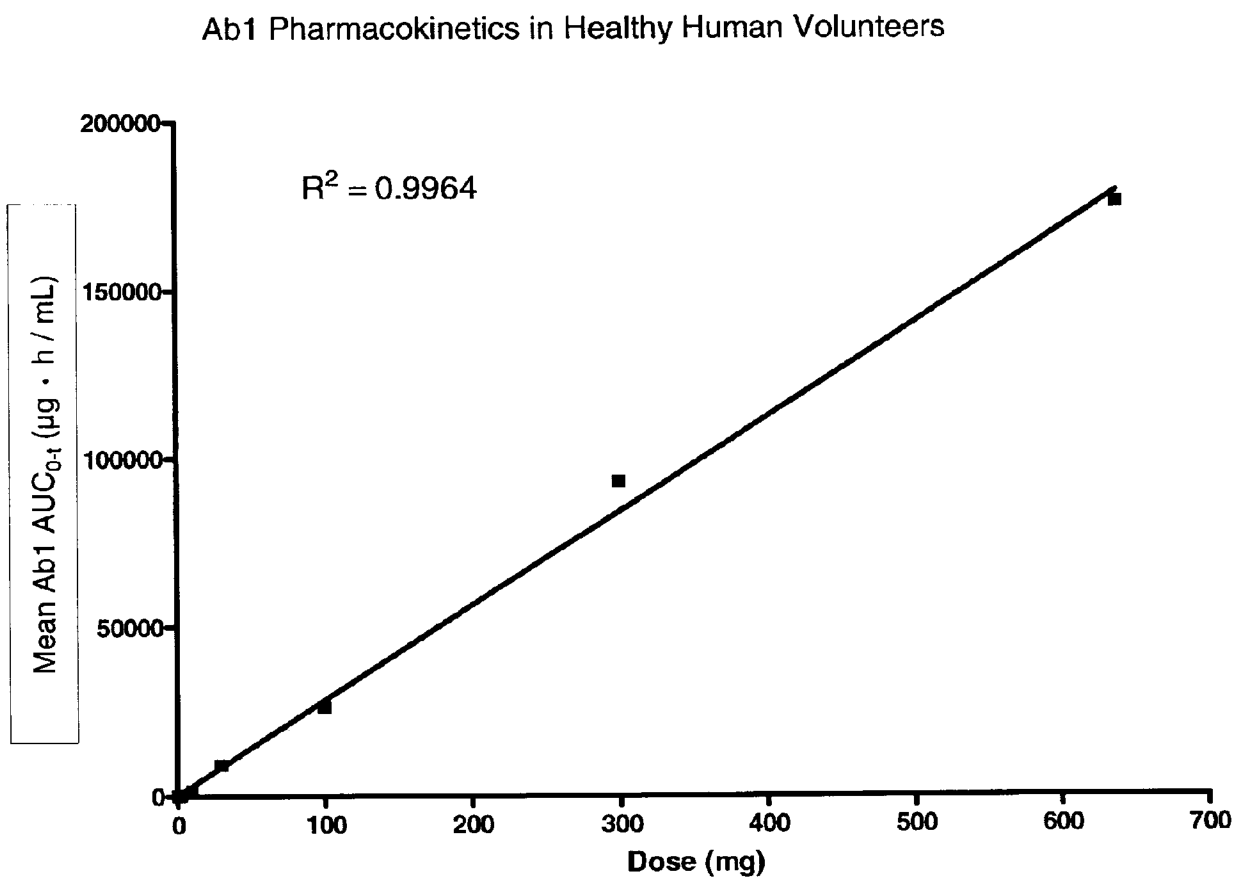
FIG. 17 shows mean area under the plasma Ab1 concentration time curve (AUC) for the dosage groups shown in FIG. 16.
Figure 18:
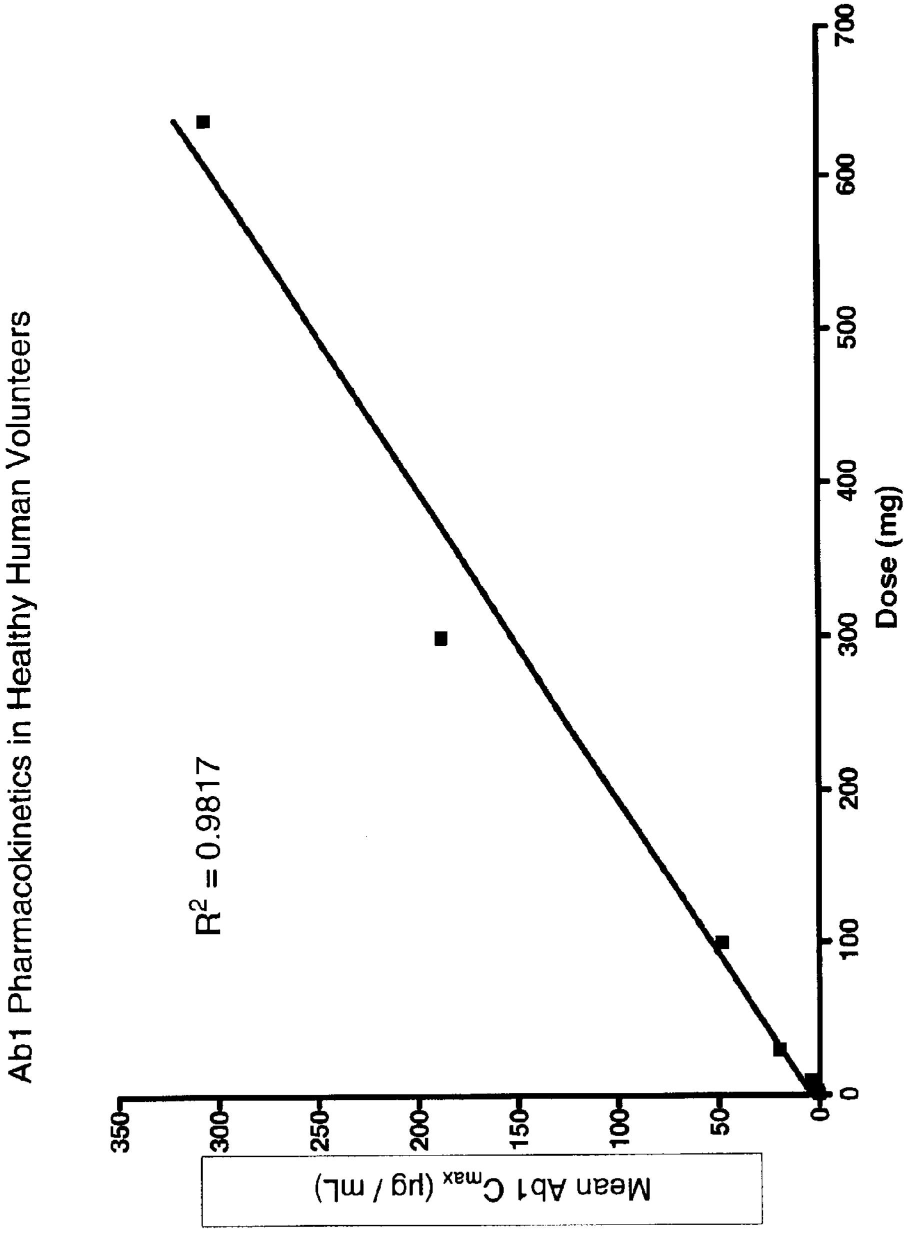
FIG. 18 shows mean peak plasma Ab1 concentration ($C_{max}$) for the dosage groups shown in FIG. 16.

Average plasma concentration of Ab1 for each dosage group versus time is shown in FIG. 16. Mean AUC and $C_{max}$ increased linearly with dosage (FIG. 17 and FIG. 18, respectively). For dosages of 30 mg and above, the average Ab1 half-life in each dosage group was between approximately 25 and 30 days (FIG. 19).

Example 17

Pharmacokinetics of Ab1 in Patients with Advanced Cancer

Antibody Ab1 was dosed in a single bolus infusion in phosphate buffered saline to five individuals with advanced cancer. Each individual received a dosage of 80 mg (n=2) or 160 mg (n=3) of Ab1. Plasma samples were drawn weekly, and the level of antibody Ab1 was quantitated as in Example 16.

Figure 20:
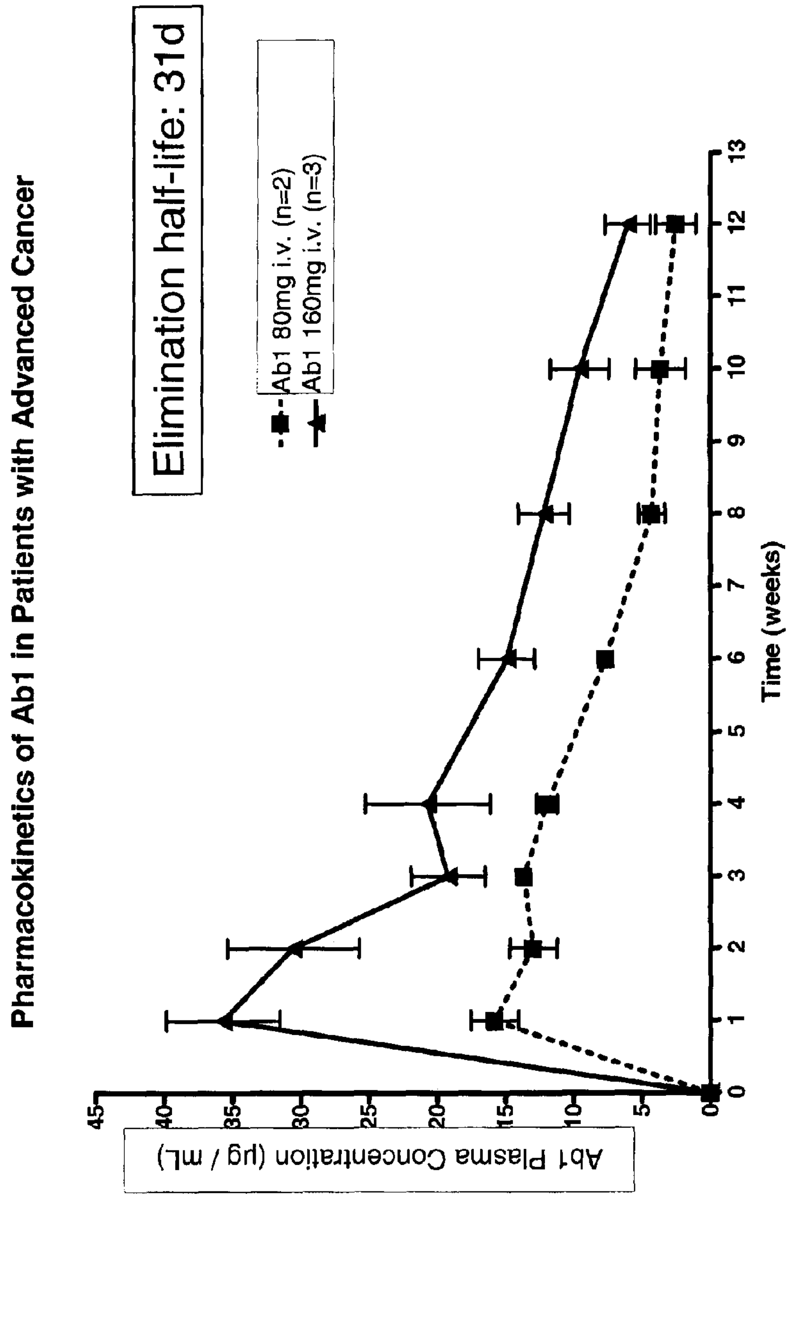
FIG. 20 shows the mean plasma concentration of Ab1 resulting from a single administration of Ab1 to patients with advanced cancer.

Average plasma concentration of Ab1 in these individuals as a function of time is shown in FIG. 20. The average Ab1 half-life was approximately 31 days.

Example 18

Unprecedented Half-Life of Ab1

Overall, the average half-life of Ab1 was approximately 31 days in humans (for dosages of 10 mg and above), and approximately 15-21 days in cynomolgus monkey. The Ab1 half-life in humans and cynomolgus monkeys is unprecedented when compared with the half-lives of other anti-IL-6 antibodies (FIG. 21). As described above, Ab1 was derived from humanization of a rabbit antibody, and is produced from *Pichia pastoris* in an aglycosylated form. These characteristics results in an antibody with very low immunogenicity in humans. Moreover, the lack of glycosylation prevents Ab1 from interacting with the Fc receptor or complement. Without intent to be limited by theory, it is believed that the unprecedented half-life of Ab1 is at least partially attributable to the humanization and lack of glycosylation. The particular sequence and/or structure of the antigen binding surfaces may also contribute to Ab1's half-life.

Example 19

Figure 22:
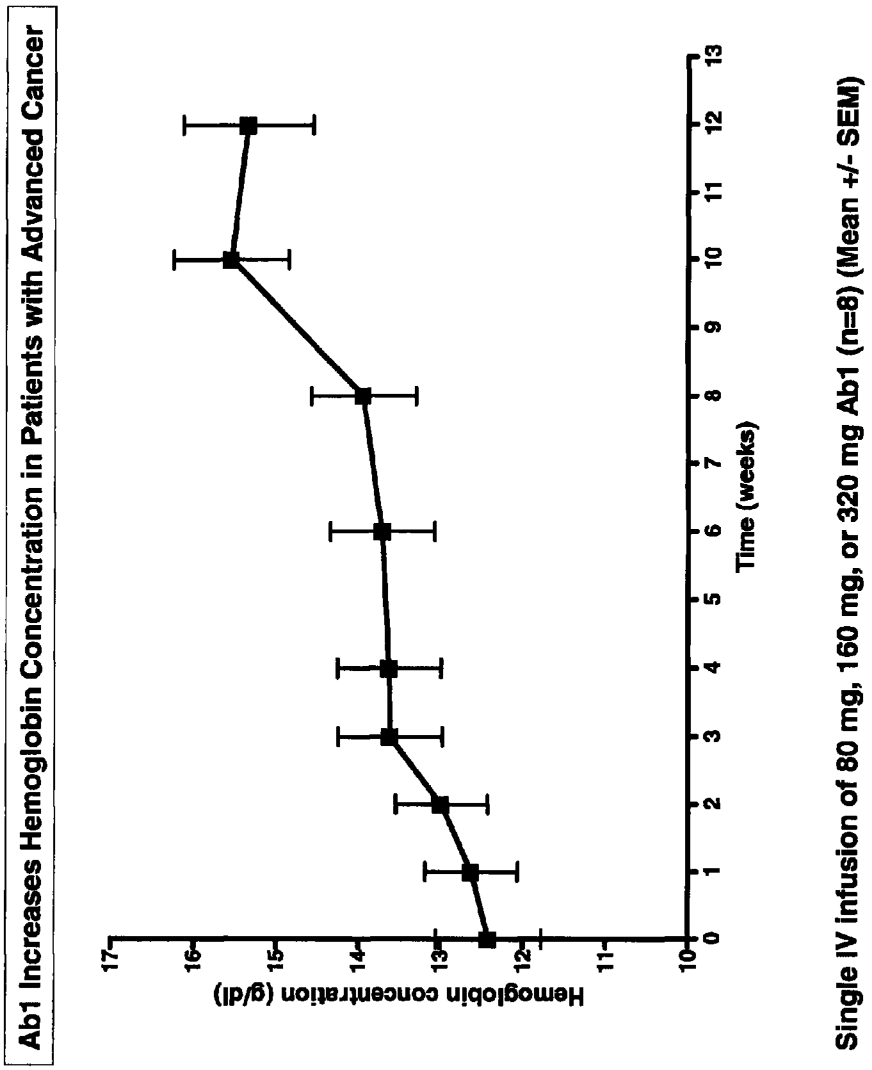
FIG. 22 shows increased hemoglobin concentration following administration of Ab1 to patients with advanced cancer.
Figure 23:
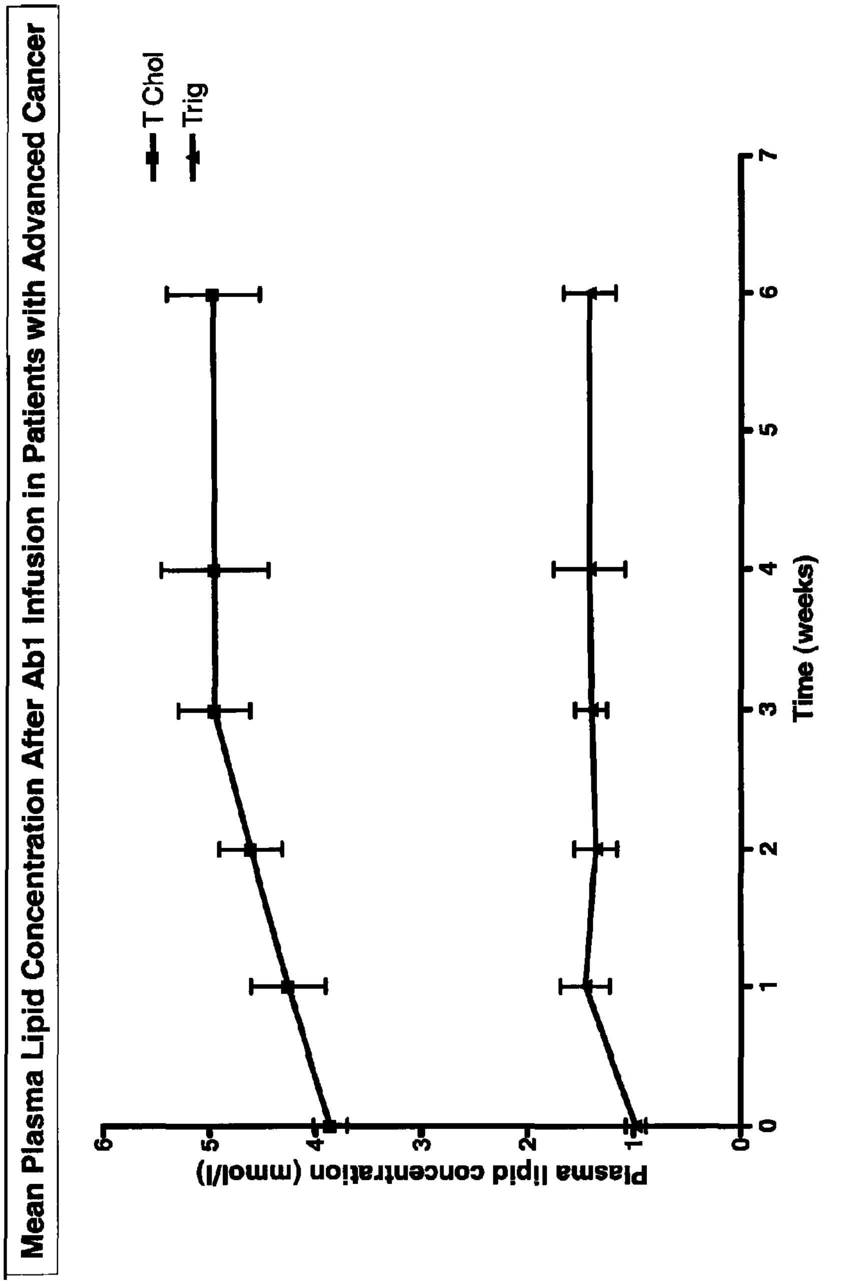
FIG. 23 shows mean plasma lipid concentrations following administration of Ab1 to patients with advanced cancer.
Figure 24:
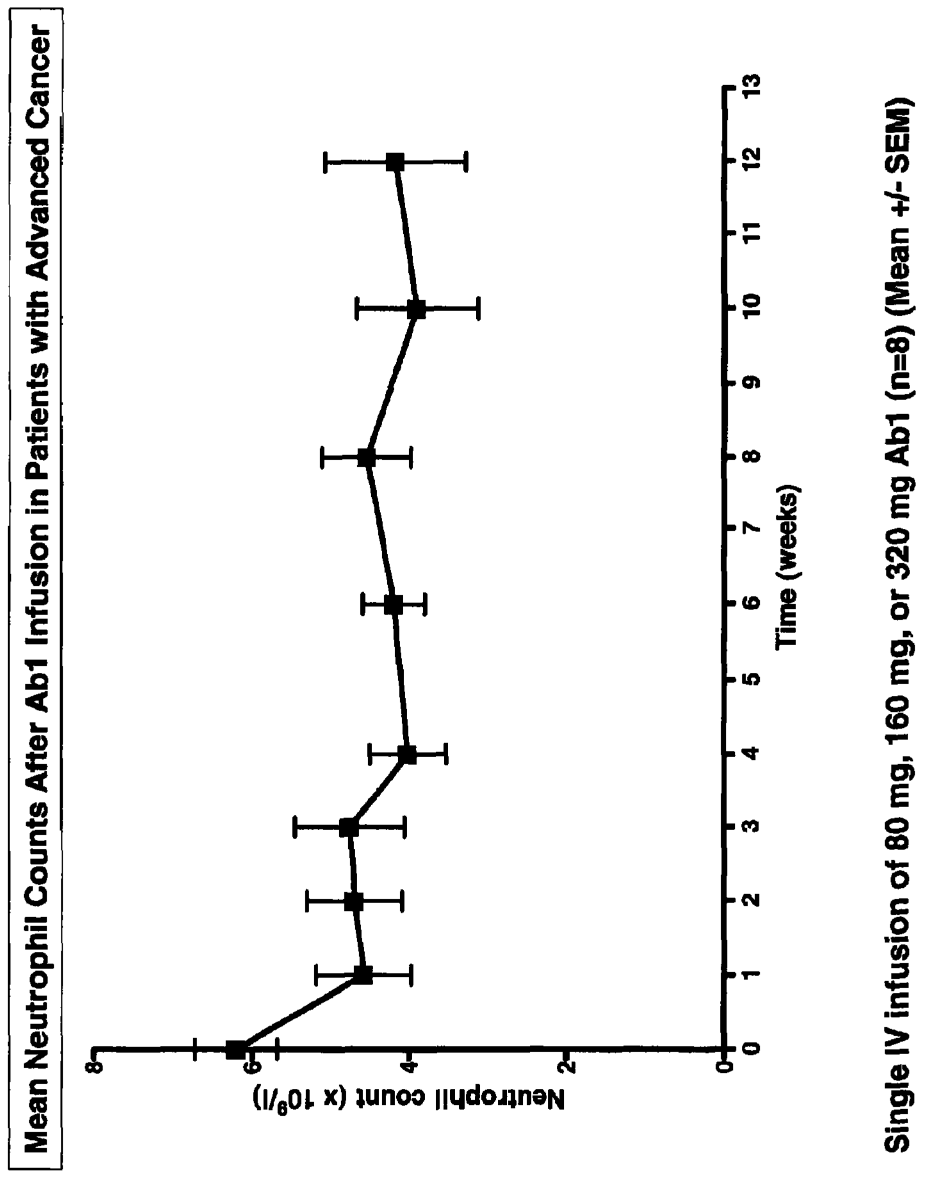
FIG. 24 shows mean neutrophil counts following administration of Ab1 to patients with advanced cancer.

Ab1 Effect on Hemoglobin Concentration, Plasma Lipid Concentration, and Neutrophil Counts in Patients with Advanced Cancer Antibody Ab1 was dosed in a single bolus infusion in phosphate buffered saline to eight individuals with advanced cancer (NSCLC, colorectal cancer, cholangiocarcinoma, or mesothelioma). Each individual received a dosage of 80 mg, 160 mg, or 320 mg of Ab1. Blood samples were removed just prior to infusion and at fixed time intervals for six weeks, and the hemoglobin concentration, plasma lipid concentration, and neutrophil counts were determined. Average hemoglobin concentration rose slightly (FIG. 22), as did total cholesterol and triglycerides (FIG. 23), while mean neutrophil counts fell slightly (FIG. 24).

These results further demonstrate some of the beneficial effects of administration of Ab1 to chronically ill individuals. Because IL-6 is the main cytokine responsible for the anemia of chronic disease (including cancer-related anemia), neutralization of IL-6 by Ab1 increases hemoglobin concentration in these individuals. Similarly, as IL-6 is centrally important in increasing neutrophil counts in inflammation, the observed slight reduction in neutrophil counts further confirms that Ab1 inhibits IL-6. Finally, IL-6 causes anorexia as well as cachexia in these patients; neutralization of IL-6 by Ab1 results in the return of appetite and reversal of cachexia. The increase in plasma lipid concentrations reflects the improved nutritional status of the patients. Taken together, these results further demonstrate that Ab1 effectively reverses these adverse consequences of IL-6 in these patients.

Example 20

Ab1 Suppresses Serum CRP in Healthy Volunteers and in Patients with Advanced Cancer Introduction Serum CRP concentrations have been identified as a strong prognostic indicator in patients with certain forms of cancer. For example, Hashimoto et al. performed univariate and multivariate analysis of preoperative serum CRP concentrations in patients with hepatocellular carcinoma in order to identify factors affecting survival and disease recurrence (Hashimoto, K., et al., Cancer, 103(9):1856-1864 (2005)). Patients were classified into two groups, those with serum CRP levels >1.0 mg/dL ("the CRP positive group") and those with serum CRP levels <1.0 mg/dL ("the CRP negative group"). The authors identified "a significant correlation between preoperative serum CRP level and tumor size." Id. Furthermore, the authors found that "[t]he overall survival and recurrence-free survival rates in the CRP-positive group were significantly lower compared with the rates in the CRP-negative group." Id. The authors concluded that the preoperative CRP level of patients is an independent and significant predictive indicator of poor prognosis and early recurrence in patients with hepatocellular carcinoma.

Similar correlations have been identified by other investigators. For example, Karakiewicz et al. determined that serum CRP was an independent and informative predictor of renal cell carcinoma-specific mortality (Karakiewicz, P. I., et al., Cancer, 110(6):1241-1247 (2007)). Accordingly, there remains a need in the art for methods and/or treatments that reduce serum C-Reactive Protein (CRP) concentrations in cancer patients, and particularly those with advanced cancers.

Methods

Healthy volunteers received a single 1-hour intravenous (IV) infusion of either 100 mg (5 patients), 30 mg (5 patients), 10 mg (6 patients), 3 mg (6 patients) or 1 mg (6 patients) of the Ab1 monoclonal antibody, while another 14 healthy volunteers received intravenous placebo. Comparatively, 2 patients with advanced forms of colorectal cancer received a single 1-hour intravenous (IV) infusion of 80 mg of the Ab1 monoclonal antibody. No further dosages of the Ab1 monoclonal antibody were administered to the test population.

Patients were evaluated prior to administration of the dosage, and thereafter on a weekly basis for at least 5 weeks post dose. At the time of each evaluation, patients were screened for serum CRP concentration.

Results

Healthy Volunteers

Figure 25:
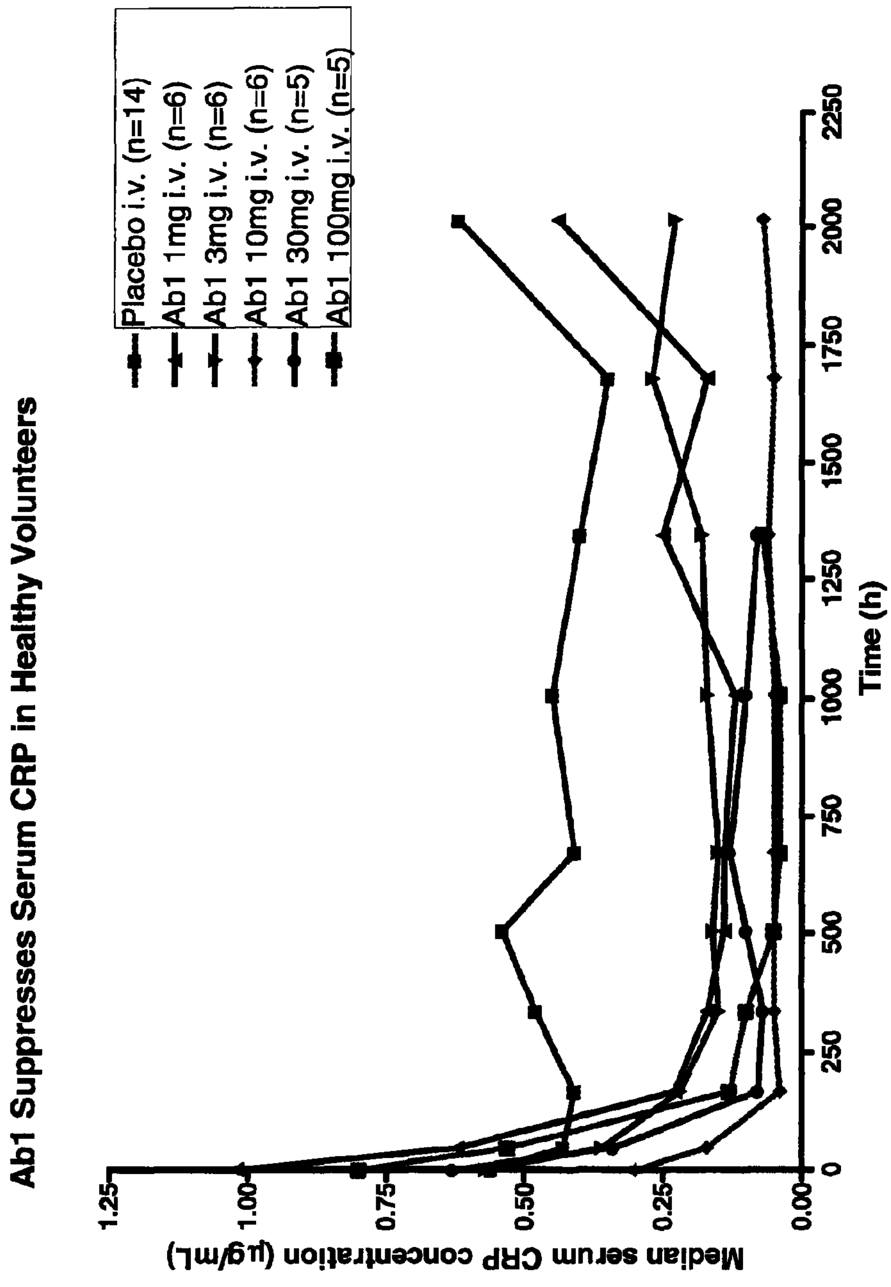
FIG. 25 demonstrates suppression of serum CRP levels in healthy individuals.

As noted above, serum CRP levels are a marker of inflammation; accordingly, baseline CRP levels are typically low in healthy individuals. The low baseline CRP levels can make a further reduction in CRP levels difficult to detect. Nonetheless, a substantial reduction in serum CRP concentrations was detectable in healthy volunteers receiving all concentrations of the Ab1 monoclonal antibody, compared to controls (FIG. 25). The reduction in serum CRP levels was rapid, occurring within one week of antibody administration, and prolonged, continuing at least through the final measurement was taken (8 or 12 weeks from antibody administration).

Cancer Patients

Figure 26A:
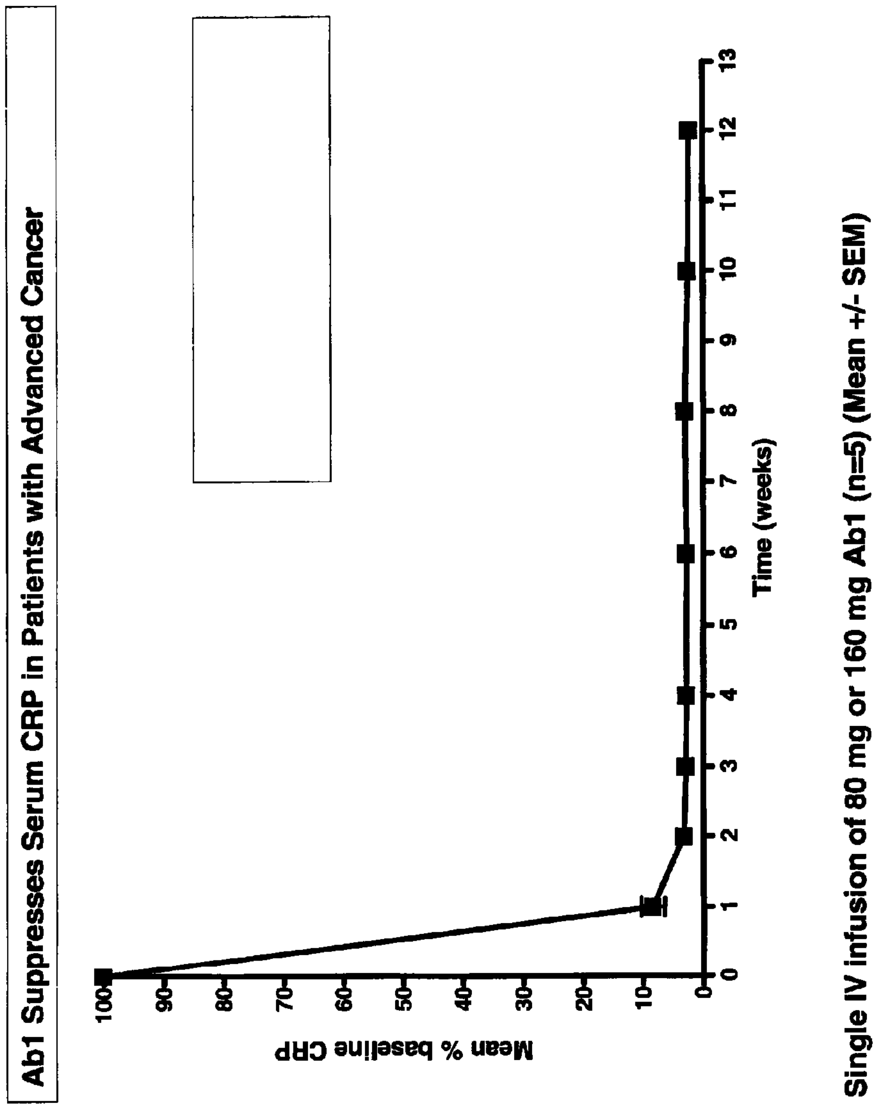
FIG. 26 (A-B) demonstrates suppression of serum CRP levels in advanced cancer patients.
Figure 26B:
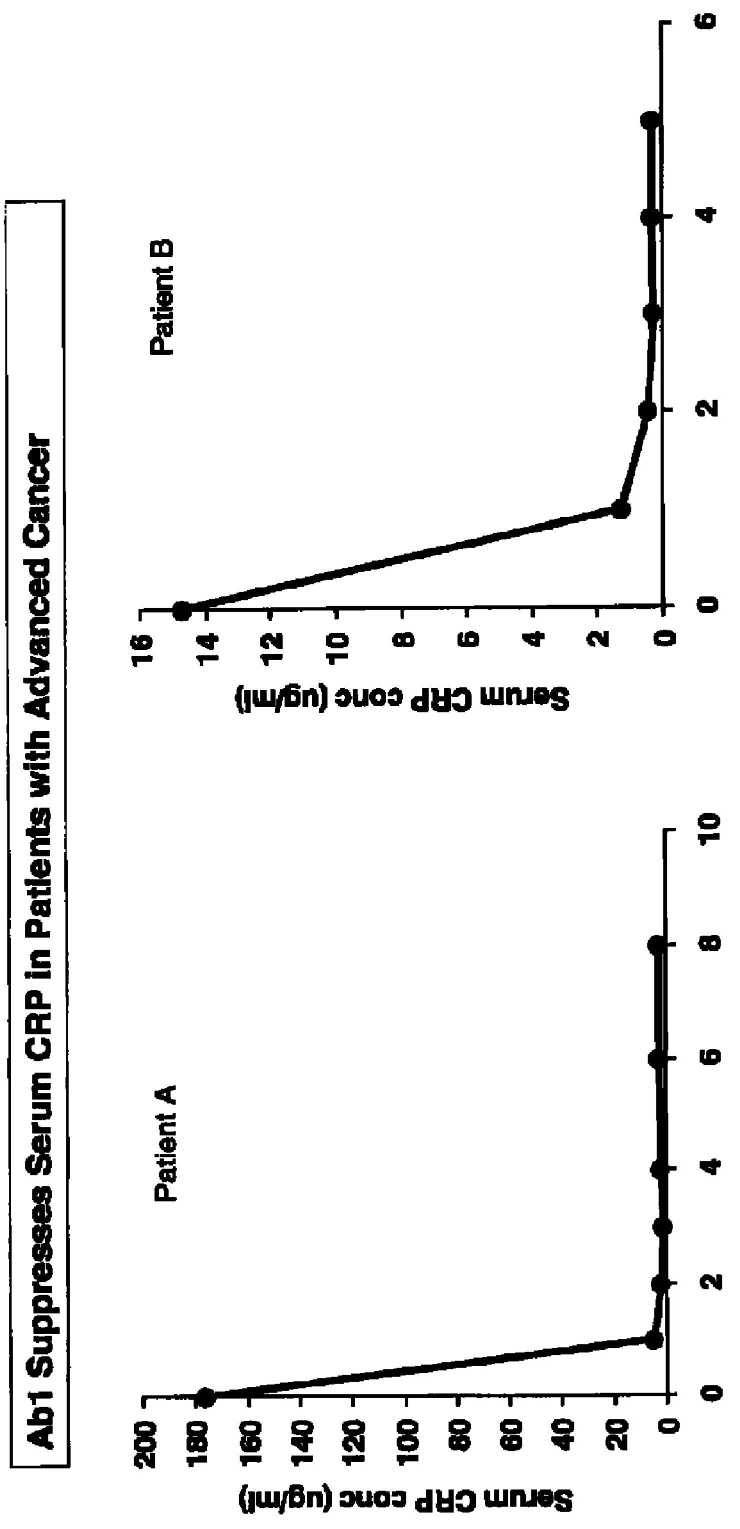

Five advanced cancer patients (colorectal cancer, cholangiocarcinoma, or NSCLC) having elevated serum CRP levels were dosed with 80 mg or 160 mg of Ab1. Serum CRP levels were greatly reduced in these patients (FIG. 26A). The reduction in serum CRP levels was rapid, with 90% of the decrease occurring within one week of Ab1 administration, and prolonged, continuing at least until the final measurement was taken (up to twelve weeks). The CRP levels of two representative individuals are shown in FIG. 26B. In those individuals, the CRP levels were lowered to below the normal reference range (less than 5-6 mg/l) within one week. Thus, administration of Ab1 to advanced cancer patients can cause a rapid and sustained suppression of serum CRP levels.

Example 21

Ab1 Improved Muscular Strength, Improved Weight, and Reduced Fatigue in Patients with Advanced Cancer Introduction Weight loss and fatigue (and accompanying muscular weakness) are very common symptoms of patients with advanced forms of cancer, and these symptoms can worsen as the cancer continues to progress. Fatigue, weight loss and muscular weakness can have significant negative effects on the recovery of patients with advanced forms of cancer, for example by disrupting lifestyles and relationships and affecting the willingness or ability of patients to continue cancer treatments. Known methods of addressing fatigue, weight loss and muscular weakness include regular routines of fitness and exercise, methods of conserving the patient's energy, and treatments that address anemia-induced fatigue and muscular weakness. Nevertheless, there remains a need in the art for methods and/or treatments that improve fatigue, weight loss and muscular weakness in cancer patients.

Methods

Four patients with advanced forms of cancer (colorectal cancer (2), NSCLC (1), cholangiocarcinoma (1) received a single 1-hour intravenous (IV) infusion of either 80 mg or 160 mg of the Ab1 monoclonal antibody. No further dosages of the Ab1 monoclonal antibody were administered to the test population.

Patients were evaluated prior to administration of the dosage, and thereafter for at least 6 weeks post dose. At the time of each evaluation, patients were screened for the following: a.) any change in weight; b.) fatigue as measured using the Facit-F Fatigue Subscale questionnaire a medically recognized test for evaluating fatigue (See, e.g., Cella, D., Lai, J. S., Chang, C. H., Peterman, A., & Slavin, M. (2002). Fatigue in cancer patients compared with fatigue in the general population. Cancer, 94(2), 528-538; Cella, D., Eton, D. T., Lai, F J-S., Peterman, A. H & Merkel, D. E. (2002). Combining anchor and distribution based methods to derive minimal clinically important differences on the Functional Assessment of Cancer Therapy anemia and fatigue scales. Journal of Pain & Symptom Management, 24 (6) 547-561.); and handgrip strength (a medically recognized test for evaluating muscle strength, typically employing a handgrip dynamometer).

Results

Weight Change

Figure 29:
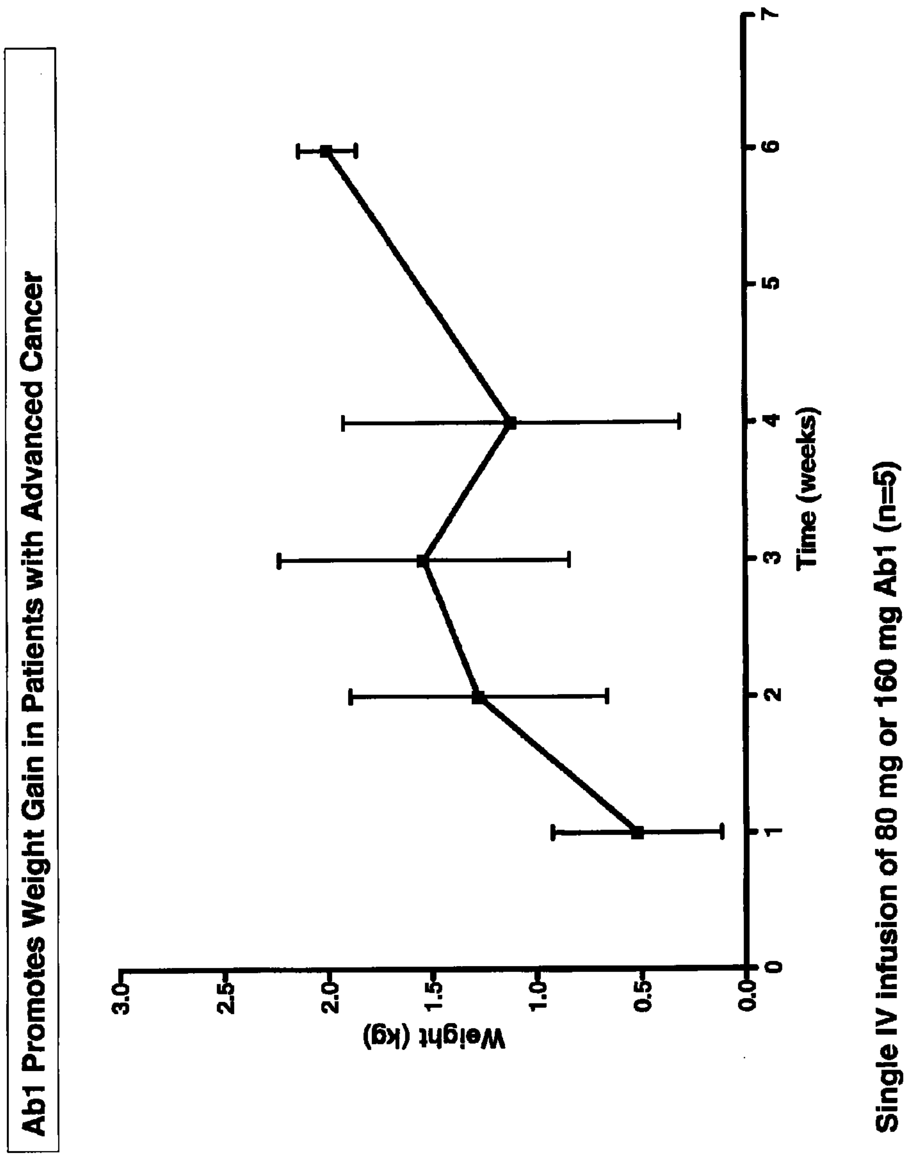
FIG. 29 demonstrates that Ab1 promotes weight gain in advanced cancer patients.

The averaged data for both dosage concentrations (80 mg and 160 mg) of the Ab1 monoclonal antibody demonstrated an increase of about 2 kilograms of weight per patient over the period of 6 weeks (FIG. 29).

Fatigue

Figure 30:
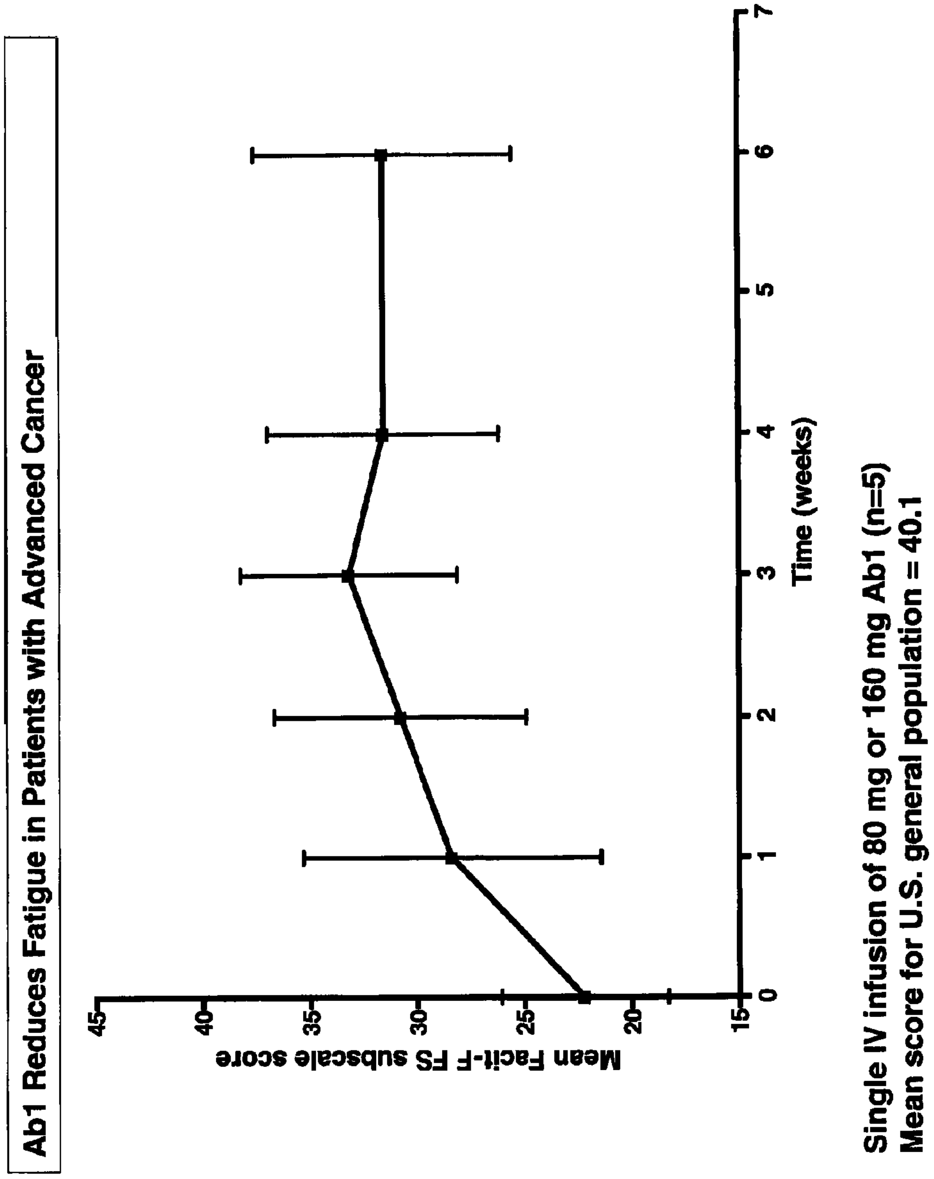
FIG. 30 demonstrates that Ab1 reduces fatigue in advanced cancer patients.

The averaged data for both dosage concentrations (80 mg and 160 mg) of the Ab1 monoclonal antibody demonstrated an increase in the mean Facit-F FS subscale score of at least about 10 points in the patient population over the period of 6 weeks (FIG. 30).

Hand-Grip Strength

Figure 31:
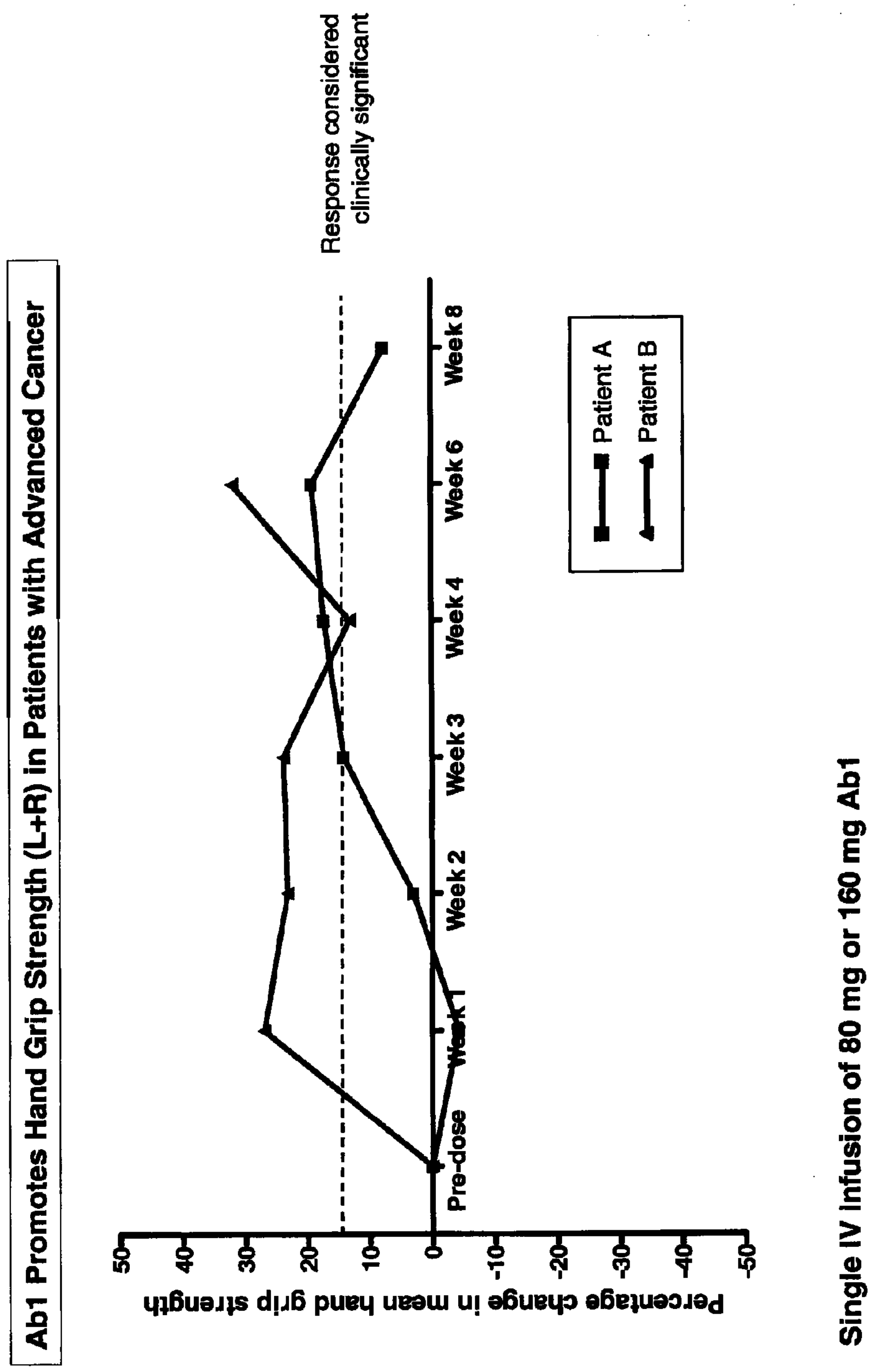
FIG. 31 demonstrates that Ab1 promotes hand grip strength in advanced cancer patients.

The averaged data for both dosage concentrations (80 mg and 160 mg) of the Ab1 monoclonal antibody demonstrated an increase in the mean hand-grip strength of at least about 10 percent in the patient population over the period of 6 weeks (FIG. 31).

Example 22

Ab1For Prevention of Thrombosis

Prior studies have shown that administration of an anti-IL-6 antibody can cause decreased platelet counts. Emilie, D. et al., Blood, 84(8):2472-9 (1994); Blay et al., Int J Cancer, 72(3):424-30 (1997). These results have apparently been viewed as an indicator of potential danger, because further decreases in platelet counts could cause complications such as bleeding. However, Applicants have now discerned that inhibiting IL-6 restores a normal coagulation profile, which Applicants predict will prevent thrombosis. Decreased platelet counts resulting from inhibition of IL-6 is not a sign of potential danger but rather reflects the beneficial restoration of normal coagulation.

The mechanism by which normal coagulation is restored is believed to result from the interplay between IL-6 and the acute phase reaction. In response to elevated IL-6 levels, as for example in a cancer patient, the liver produces acute phase proteins. These acute phase proteins include coagulation factors, such as Factor II, Factor V, Factor VIII, Factor IX, Factor XI, Factor XII, F/fibrin degradation products, thrombin-antithrombin III complex, fibrinogen, plasminogen, prothrombin, and von Willebrand factor. This increase in coagulation factors may be measured directly, or may be inferred from functional measurements of clotting ability. Antagonists of IL-6, such as Ab1, suppresses acute phase proteins, e.g., Serum Amyloid A (see FIG. 32 and Example 10). Applicants now predict that this suppression of acute phase proteins will restore the normal coagulation profile, and thereby prevent thrombosis. The restoration of normal coagulation may cause a slight drop in platelet counts, but the patient will nonetheless retain normal coagulation ability and thus will not have an increased risk of bleeding. Such a treatment will represent a vast improvement over the available anticoagulation therapies whose usefulness is limited by the risk of adverse side-effects, such as major bleeding.

Applicants contemplate that the same beneficial effects of inhibiting IL-6 will be obtained regardless of the method of inhibition. Suitable methods of inhibiting IL-6 include administration of anti-IL-6 antibodies, antisense therapy, soluble IL-6 receptor, etc. either individually or in combinations.

Example 23

Ab1 Increases Plasma Albumin Concentration in Patients with Advanced Cancer

Introduction

Serum albumin concentrations are recognized as predictive indicators of survival and/or recovery success of cancer patients. Hypoalbumenia correlates strongly with poor patient performance in numerous forms of cancer. For example, in one study no patients undergoing systemic chemotherapy for metastatic pancreatic adenocarcinoma and having serum albumin levels less than 3.5 g/dL successfully responded to systemic chemotherapy (Fujishiro, M., et al., Hepatogastroenterology, 47(36):1744-46 (2000)). The authors conclude that "[p]atients with . . . hypoalbuminemia . . . might be inappropriate candidates for systemic chemotherapy and might be treated with other experimental approaches or supportive care." Id.

Similarly, Senior and Maroni state that "[t]he recent appreciation that hypoalbuminemia is the most powerful predictor of mortality in end-stage renal disease highlights the critical importance of ensuring adequate protein intake in this patient population." (J. R. Senior and B. J. Maroni, Am. Soc. Nutr. Sci., 129:313 S-314S (1999)).

In at least one study, attempts to rectify hypoalbuminemia in 27 patients with metastatic cancer by daily intravenous albumin infusion of 20 g until normal serum albumin levels (>3.5 g/dL) were achieved had little success. The authors note that "[a]lbumin infusion for the advanced stage cancer patients has limited value in clinical practice. Patients with PS 4 and hypoalbuminemia have poorer prognosis." (Demirkazik, A., et al., Proc. Am. Soc. Clin. Oncol., 21:Abstr 2892 (2002)).

Accordingly, there remains a need in the art for methods and/or treatments that improve serum albumin concentrations in cancer patients and address hypoalbuminemic states in cancer patients, particularly those with advanced cancers.

Methods

Four patients with advanced forms of cancer (colorectal cancer (2), NSCLC (1), cholangiocarcinoma (1) received a single 1-hour intravenous (IV) infusion of either 80 mg or 160 mg of the Ab1 monoclonal antibody. No further dosages of the Ab1 monoclonal antibody were administered to the test population.

Patients were evaluated prior to administration of the dosage, and thereafter for at least 6 weeks post dose. At the time of each evaluation, patients were screened for plasma albumin concentration.

Results

Figure 33:
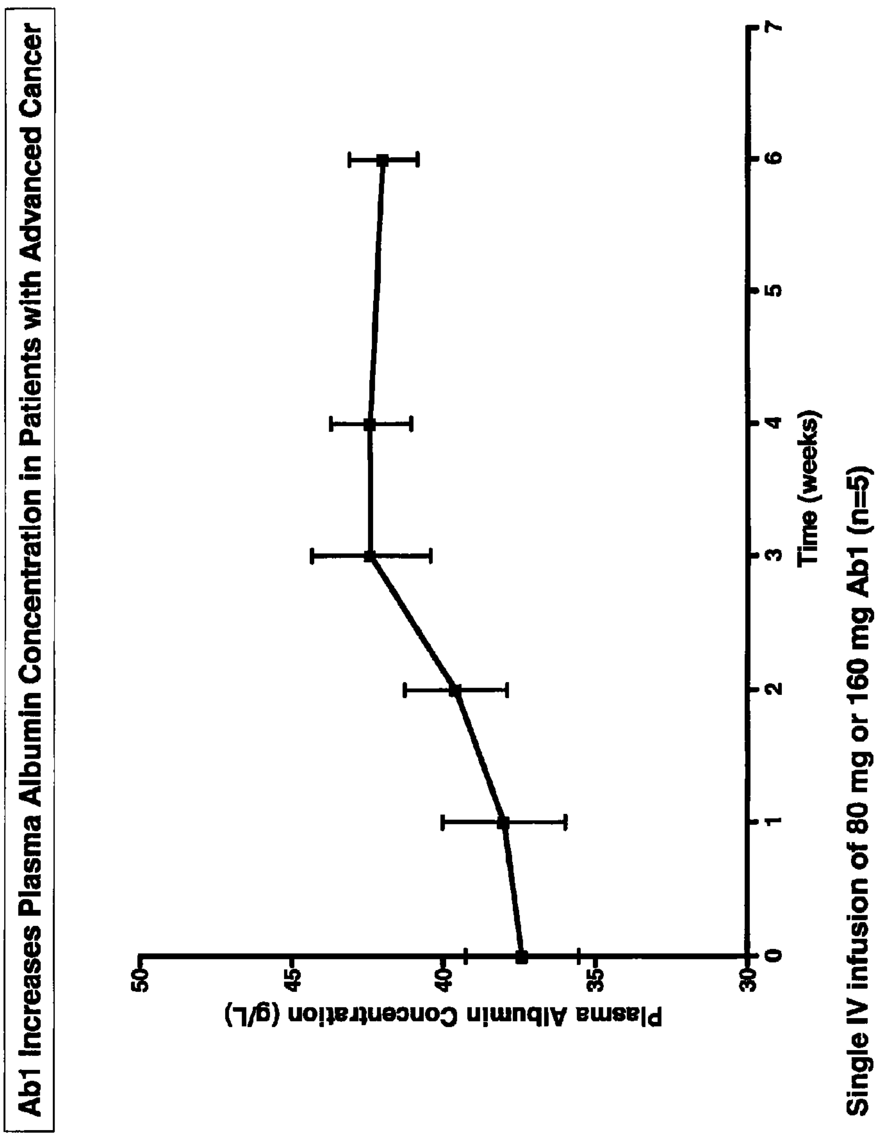
FIG. 33 demonstrates that Ab1 increase plasma albumin concentration in advanced cancer patients.

The averaged data for both dosage concentrations (80 mg and 160 mg) of the Ab1 monoclonal antibody demonstrated an increase of about 5 g/L of plasma albumin concentration per patient over the period of 6 weeks (FIG. 33).

Example 24

Ab1 Increases Hemoglobin in Patients with Advanced Cancer

Figure 38:
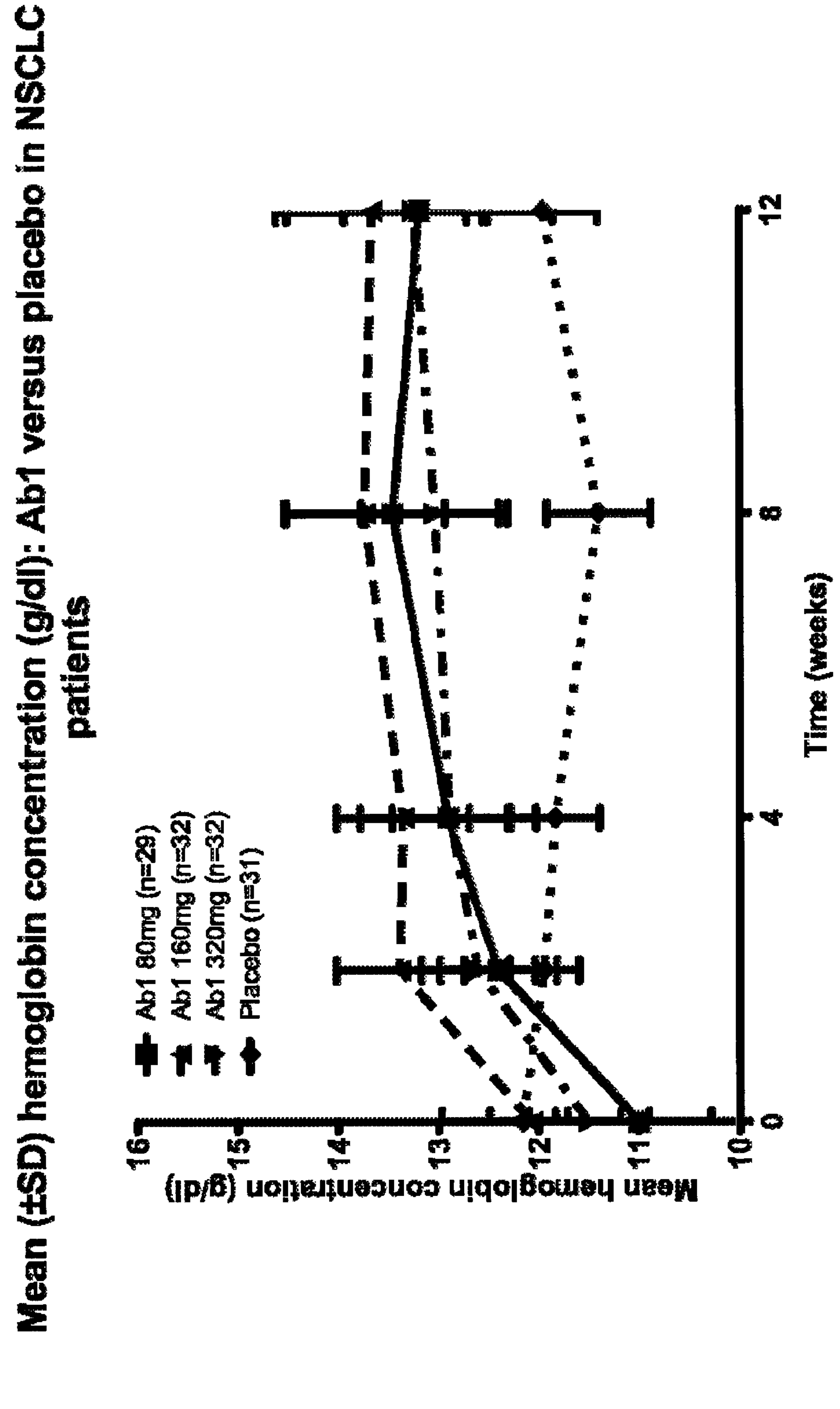
FIG. 38 demonstrates that Ab1 increases mean hemoglobin at 80, 160 and 320 mg after 12 weeks of dosing.
Figure 39:
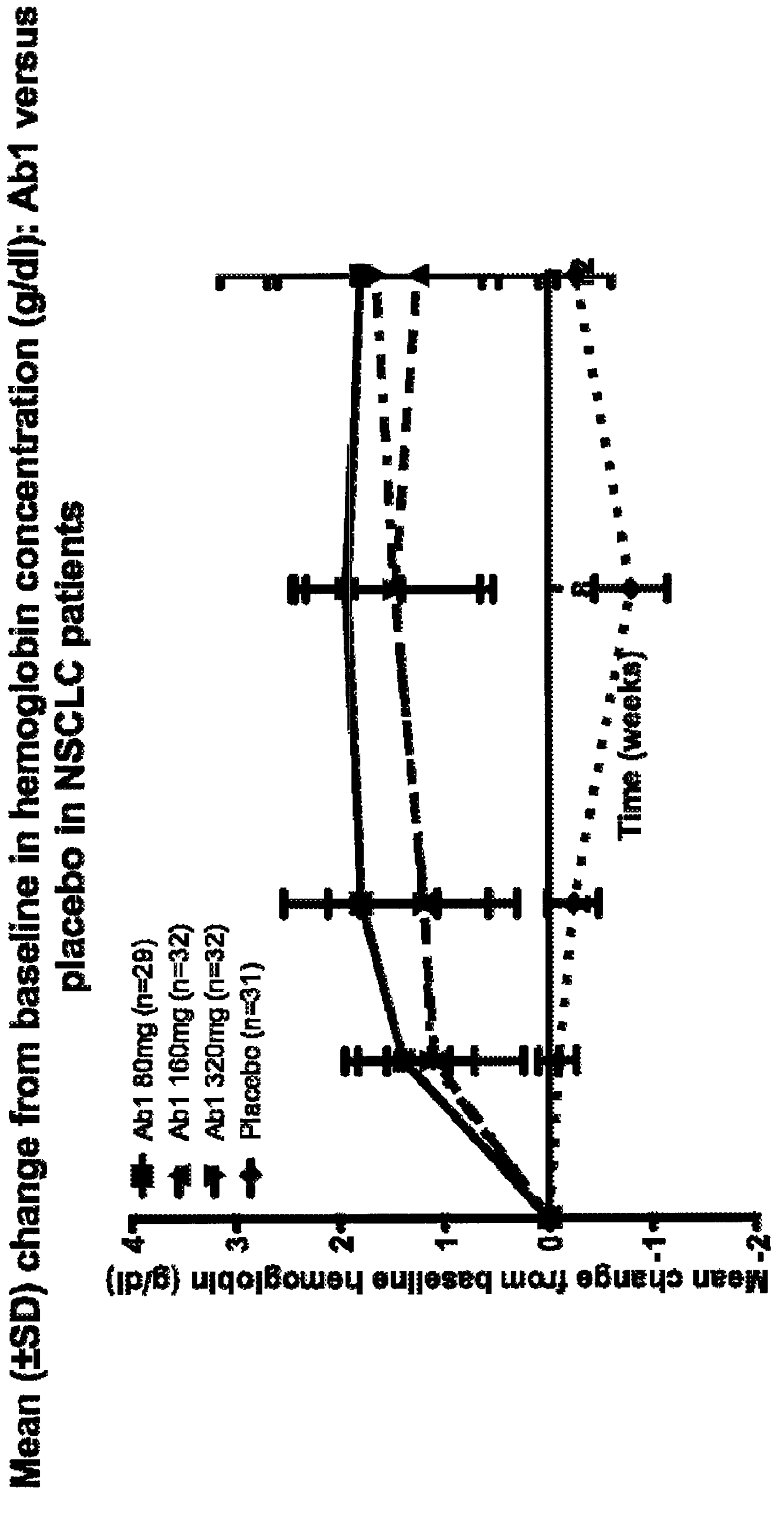
FIG. 39 demonstrates mean change from baseline hemoglobin for the data presented in FIG. 38.

Antibody Ab1 was dosed at 80 mg, 160 mg, or 320 mg of Ab1 in phosphate buffered saline to 93 individuals with non-small cell lung carcinoma. The placebo group of 31 individuals with non-small cell lung carcinoma was dosed with phosphate buffered saline only. Blood samples were removed just prior to dosing (zero week), and at two, four, eight and twelve weeks, and the hemoglobin concentration was determined. Mean hemoglobin concentration rose for those receiving antibody Ab1, while mean hemoglobin concentration of those receiving placebo did not rise after twelve weeks when compared to the concentration just prior to dosing (zero week) (FIGS. 38 and 39).

Figure 40:
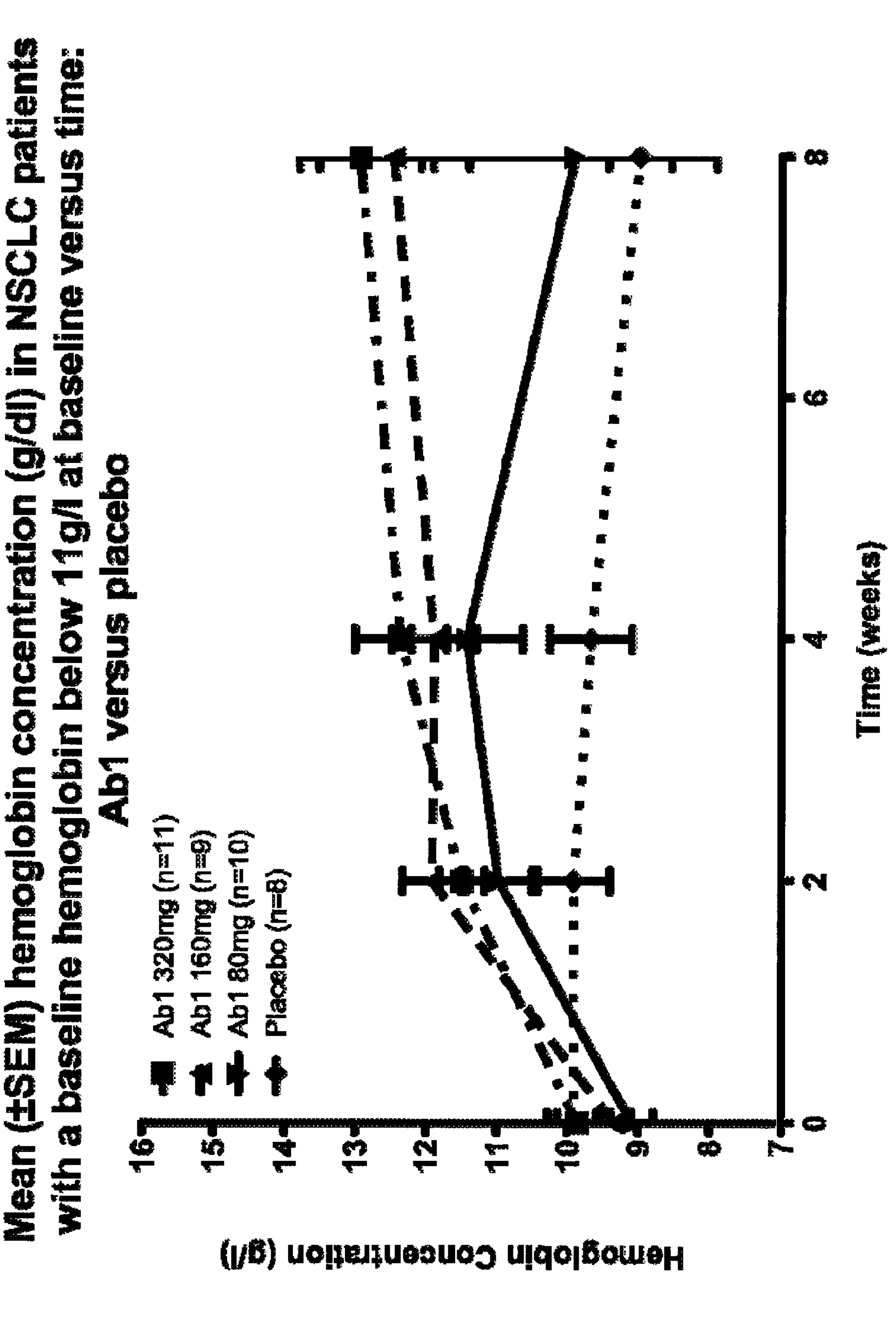
FIG. 40 demonstrates that Ab1 increases mean hemoglobin at 160 and 320 mg after 12 weeks of dosing in patients having baseline hemoglobin below 11 g/l.

A subset of the study population began the study with low levels of hemoglobin, defined as a baseline hemoglobin concentration below 11 g/l. Mean hemoglobin concentration rose above 11 g/l after eight weeks for those receiving antibody Ab1 at dosages of 160 mg and 320 mg, while mean hemoglobin concentration of those receiving antibody Ab1 at dosages of 80 mg or placebo did not rise above 11 g/l after eight weeks (FIG. 40).

These results further demonstrate some of the beneficial effects of administration of Ab1 to chronically ill individuals. Because IL-6 is the main cytokine responsible for the anemia of chronic disease (including cancer-related anemia), neutralization of IL-6 by Ab1 increases hemoglobin concentration in these individuals.

Example 25

Ab1 Increases Hemoglobin in Patients with Rheumatoid Arthritis

Figure 41:
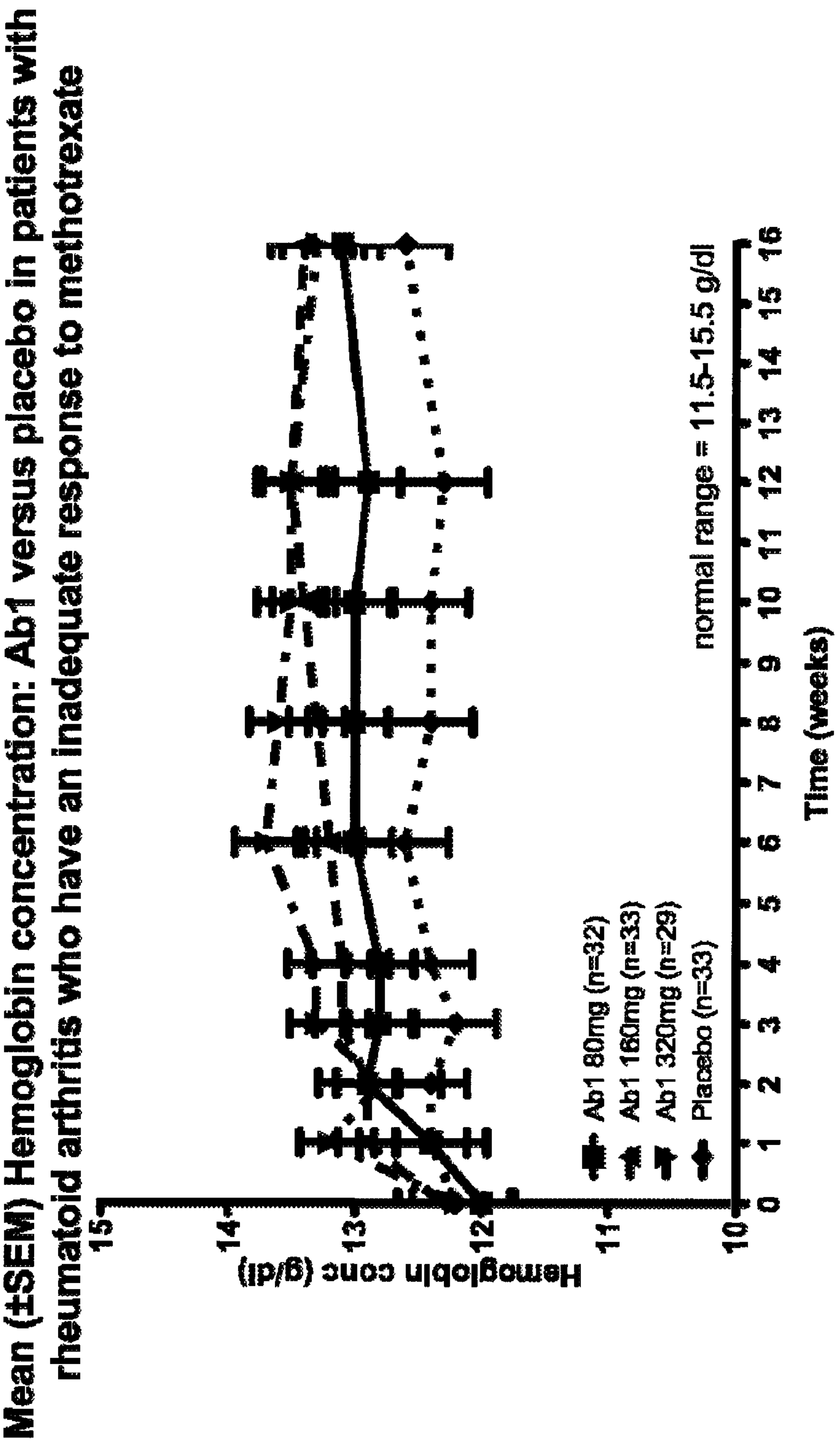
FIG. 41 demonstrates that Ab1 increases mean hemoglobin at 80, 160 and 320 mg after 16 weeks of dosing.

Hemoglobin levels were analyzed in patients with rheumatoid arthritis during treatment with Ab1 antibody. Ab1 antibody was dosed at 80 mg, 160 mg, or 320 mg in phosphate buffered saline to 94 individuals with rheumatoid arthritis. The placebo group of 33 individuals with rheumatoid arthritis was dosed with phosphate buffered saline only. Blood samples were removed just prior to dosing (zero week), and at one, two, three, four, six, eight, ten, twelve, and sixteen weeks, and the hemoglobin concentration was determined. Mean hemoglobin concentration rose for those receiving antibody Ab1, while mean hemoglobin concentration of those receiving placebo did not appreciably rise after sixteen weeks when compared to the concentration just prior to dosing (zero week) (FIG. 41).

These results further demonstrate some of the beneficial effects of administration of Ab1 to chronically ill individuals. Because IL-6 is the main cytokine responsible for the anemia of chronic disease (including cancer-related anemia), neutralization of IL-6 by Ab1 increases hemoglobin concentration.

Example 26

Ab1 Decreases D-dimer Levels in Patients with Advanced Cancer

Introduction

D-dimer concentrations are recognized as useful diagnostic tools in predicting risks of thrombotic events in patients. (Adam et al., 113 Blood 2878-87 (2009)) Patients that are negative for D-dimer have a low probability for thrombosis. For example, D-dimer analysis can rule out suspected lower-extremity deep-vein thrombosis in patients. (Wells et al., 349 N. Engl. J. Med. 1227-35 (2003)) Clinical evaluation in combination with negative D-dimer test can effectively lower the instance of pulmonary embolism to 0.5%. (Van Belle et al., 295 JAMA 172-79 (2006); Kruip et al., 162 Arch. Intern. Med. 1631-35 (2002); Wells et al., 135 Ann. Intern. Med. 98-107 (2001))

D-dimer analysis may have utility in tracking the progress of treating coagulation disorders. One study indicated that anticoagulation treatment for acute venous thromboembolism resulted in a gradual decline in D-dimer concentrations. (Adam et al., 113 Blood 2878-87 (2009); Schutgens et al., 144 J. Lab. Clin. Med. 100-07 (2004)) This discovery led to the conclusion that D-dimer levels monitoring could be used to assess treatment responsiveness. (Adam et al., 113 Blood at 2883)

For patients with cancer, D-dimer analysis may have additional significance, as cancer increases the prevalence of thrombosis. (Adam et al., 113 Blood 2878-87 (2009)) One study with oncology patients indicated that D-dimer concentrations have a high negative predictive value and high sensitivity in diagnosing pulmonary embolism. (King et al., 247 Radiology 854-61 (2008)) Deep-vein thrombosis can similarly be excluded for cancer patients with low probability of developing deep-vein thrombosis and a negative test for D-dimer, although such a combination is less likely for oncology patients. (Lee et al., 123 Thromb. Res. 177-83 (2008)) A higher threshold for a negative D-dimer result may be necessary in cancer patients. (Righini et al., 95 Haemost. 715-19 (2006))

Accordingly, there remains a need in the art for methods and/or treatments of thrombosis that improve D-dimer concentrations in cancer patients and address elevated D-dimer states in cancer patients, particularly those with advanced cancers.

Methods

One-hundred twenty-four patients with non-small cell lung cancer (NSCLC) were divided into 4 treatment groups. Patients in one group received one 1-hour intravenous (IV) infusion of either placebo (n=31), 80 mg (n=29), 160 mg (n=32), or 320 mg (n=32) of the Ab1 monoclonal antibody every 8 weeks over a 24 week duration for a total of 3 doses. Data on D-dimer concentration was collected for the first 8 weeks of treatment. D-dimer data concentration was quantitated by a D-dimer immunoturbidimetric assay. Briefly, the assay is based on the change in turbidity of a microparticle suspension that is measured by photometry. About 1.5 mL of patient sample sodium citrate plasma was collected and stored in a plastic collection tube. A suspension of latex microparticles, coated by covalent bonding with monoclonal antibodies specific for D-dimer, was mixed with the test plasma whose D-dimer level was to be assayed. Antigen-antibody reactions leading to an agglutination of the latex microparticles induced an increase in turbidity of the reaction medium. This increase in turbidity was reflected by an increase in absorbance, the latter being measured photometrically using a STAGO STA analyzer. The increase in absorbance was a function of the D-dimer level present in the test sample.

Results

Figure 42:
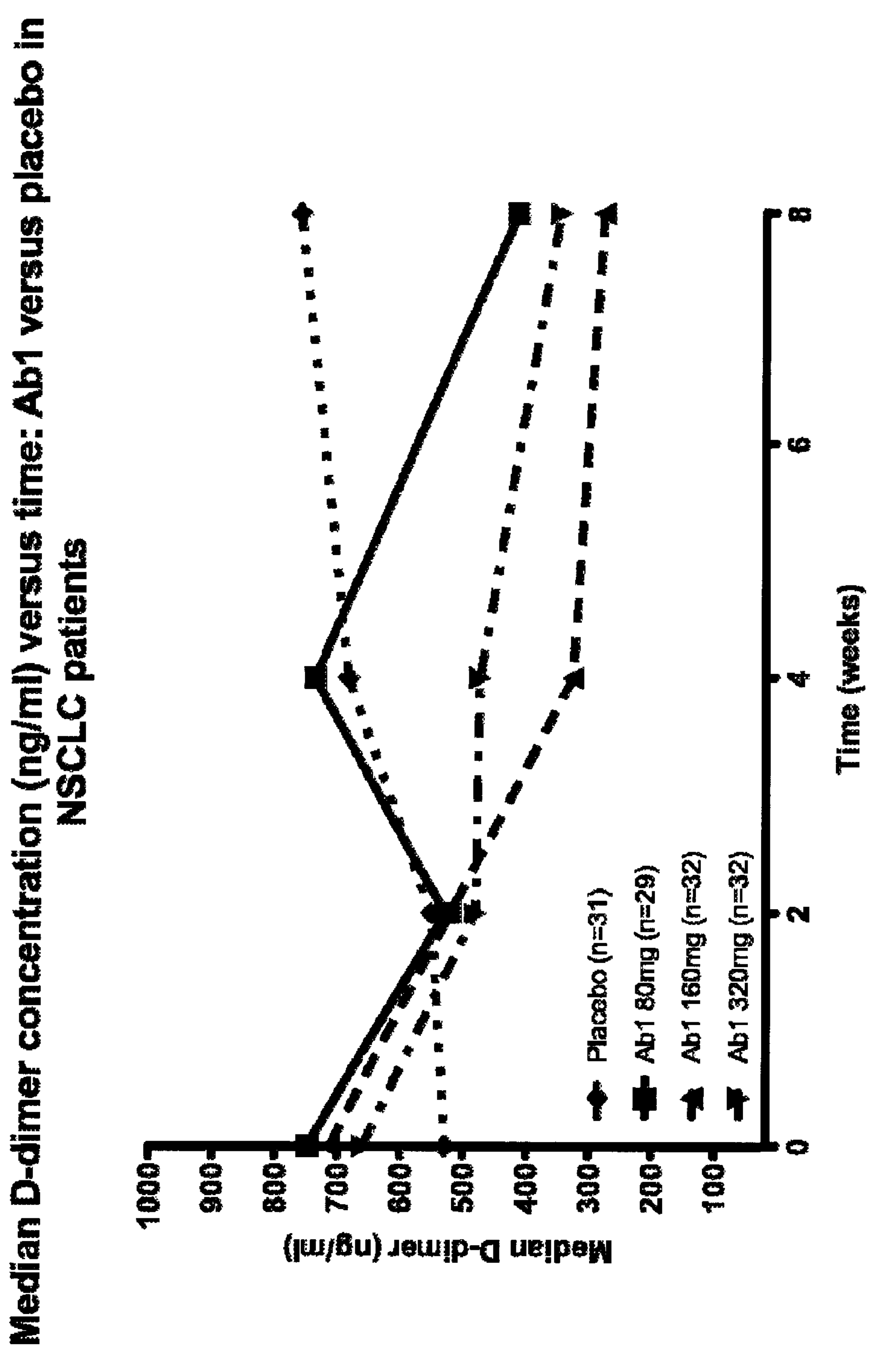
FIG. 42 demonstrates that Ab1 drops D-dimer levels over placebo at 80, 160 and 320 mg after 16 weeks of dosing.
Figure 43:
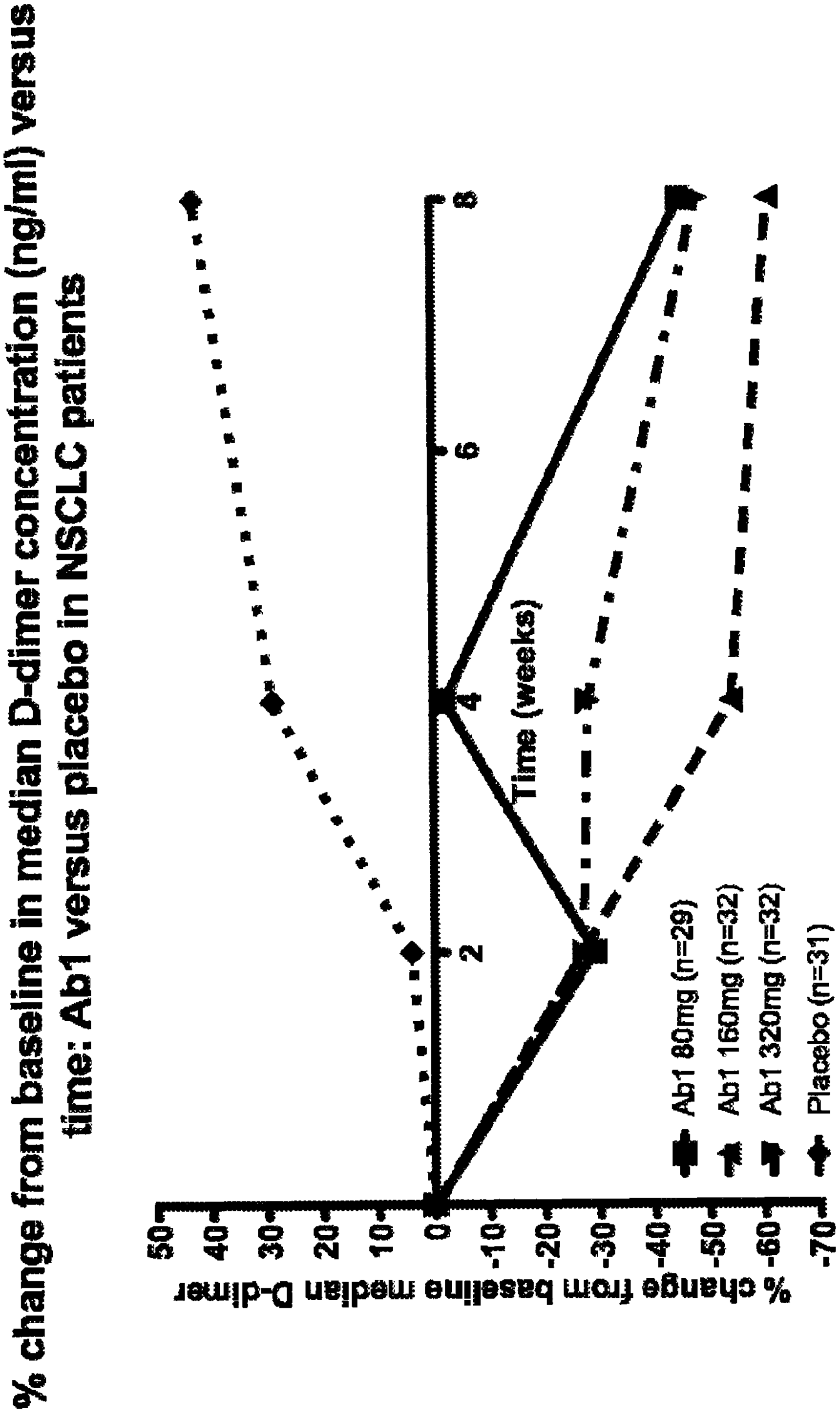
FIG. 43 demonstrates the percent change from baseline in D-dimer concentration from each dosage concentration group corresponding to FIG. 42.

The averaged data for each dosage concentrations (placebo, 80 mg, 160 mg, and 320 mg) of the Ab1 monoclonal antibody are plotted in FIG. 42. Error bars were omitted from the graph for clarity purposes. The percent change from baseline in D-dimer concentration is plotted in FIG. 43. All dosage levels of Ab1 antibody demonstrated a drop in D-dimer levels over placebo over the period of 8 weeks.

Example 27

Ab1 Improved Weight and Reduced Fatigue in Patients with Advanced Cancer

Introduction

Weight loss and fatigue are very common symptoms of patients with advanced forms of cancer, and these symptoms can worsen as the cancer continues to progress. Fatigue and weight loss can have significant negative effects on the recovery of patients with advanced forms of cancer, for example by disrupting lifestyles and relationships and affecting the willingness or ability of patients to continue cancer treatments. Known methods of addressing fatigue and weight loss include regular routines of fitness and exercise, methods of conserving the patient's energy, and treatments that address anemia-induced fatigue. Nevertheless, there remains a need in the art for methods and/or treatments that improve fatigue and weight loss in cancer patients.

Methods

One-hundred twenty-four patients with non-small cell lung cancer (NSCLC) were divided into 4 treatment groups. Patients in one group received one 1-hour intravenous (IV) infusion of either placebo (n=31), 80 mg (n=29), 160 mg (n=32), or 320 mg (n=32) of the Ab1 monoclonal antibody every 8 weeks over a 24 week duration for a total of 3 doses.

Patients were evaluated prior to administration of the dosage, and thereafter for at least 12 weeks post dose. At the time of each evaluation, patients were screened for the following: a.) any change in weight; and b.) fatigue as measured using the Facit-F Fatigue Subscale questionnaire a medically recognized test for evaluating fatigue (See, e.g., Cella, D., Lai, J. S., Chang, C. H., Peterman, A., & Slavin, M. (2002). Fatigue in cancer patients compared with fatigue in the general population. Cancer, 94(2), 528-538; Cella, D., Eton, D. T., Lai, F J-S., Peterman, A. H & Merkel, D. E. (2002). Combining anchor and distribution based methods to derive minimal clinically important differences on the Functional Assessment of Cancer Therapy anemia and fatigue scales. Journal of Pain & Symptom Management, 24 (6) 547-561.).

Results

Weight Change

Figure 44:
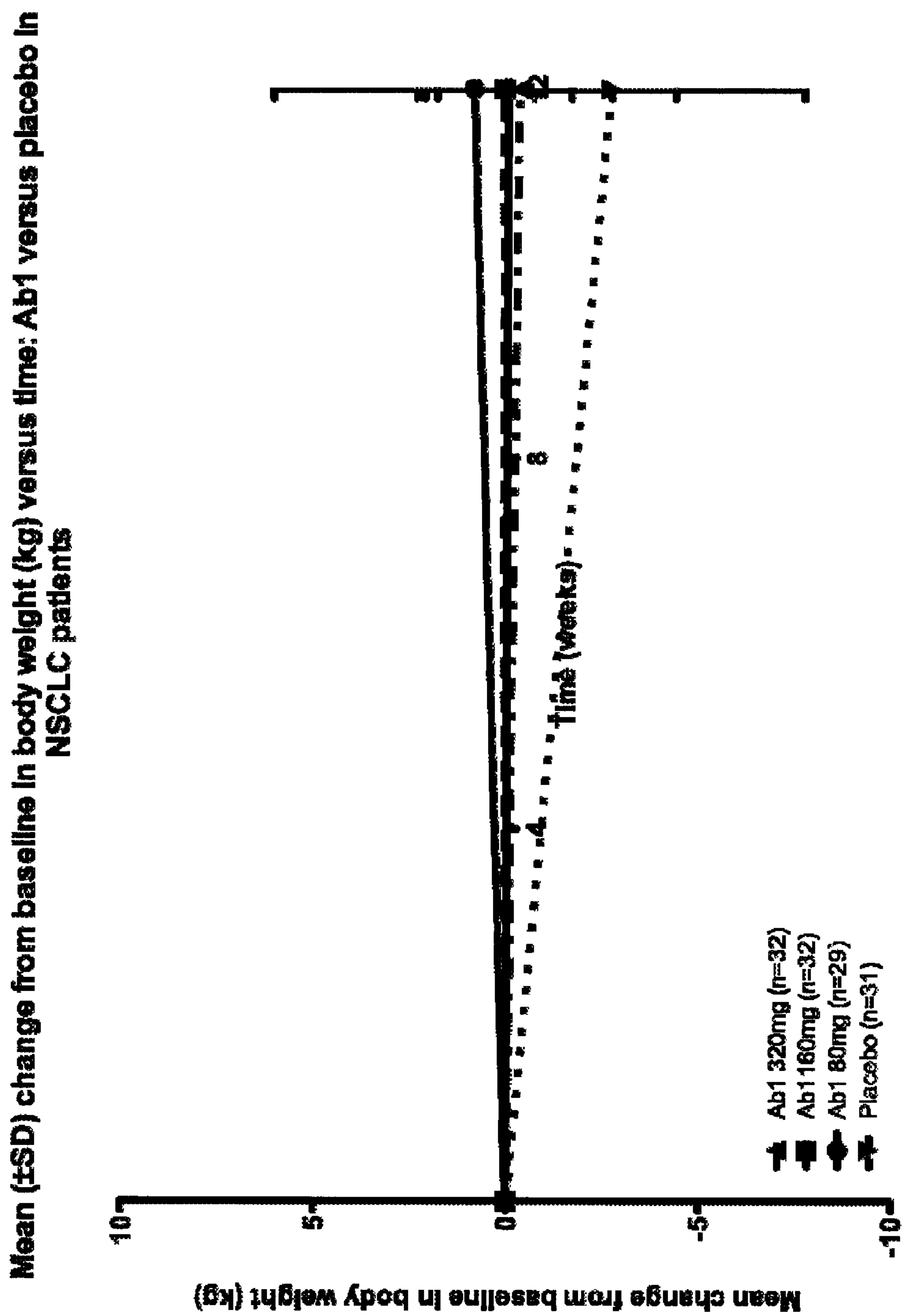
FIG. 44 demonstrates the averaged weight change data from each dosage concentration group (placebo, 80 mg, 160 mg, and 320 mg) of the Ab1 monoclonal antibody over 12 weeks.
Figure 45:
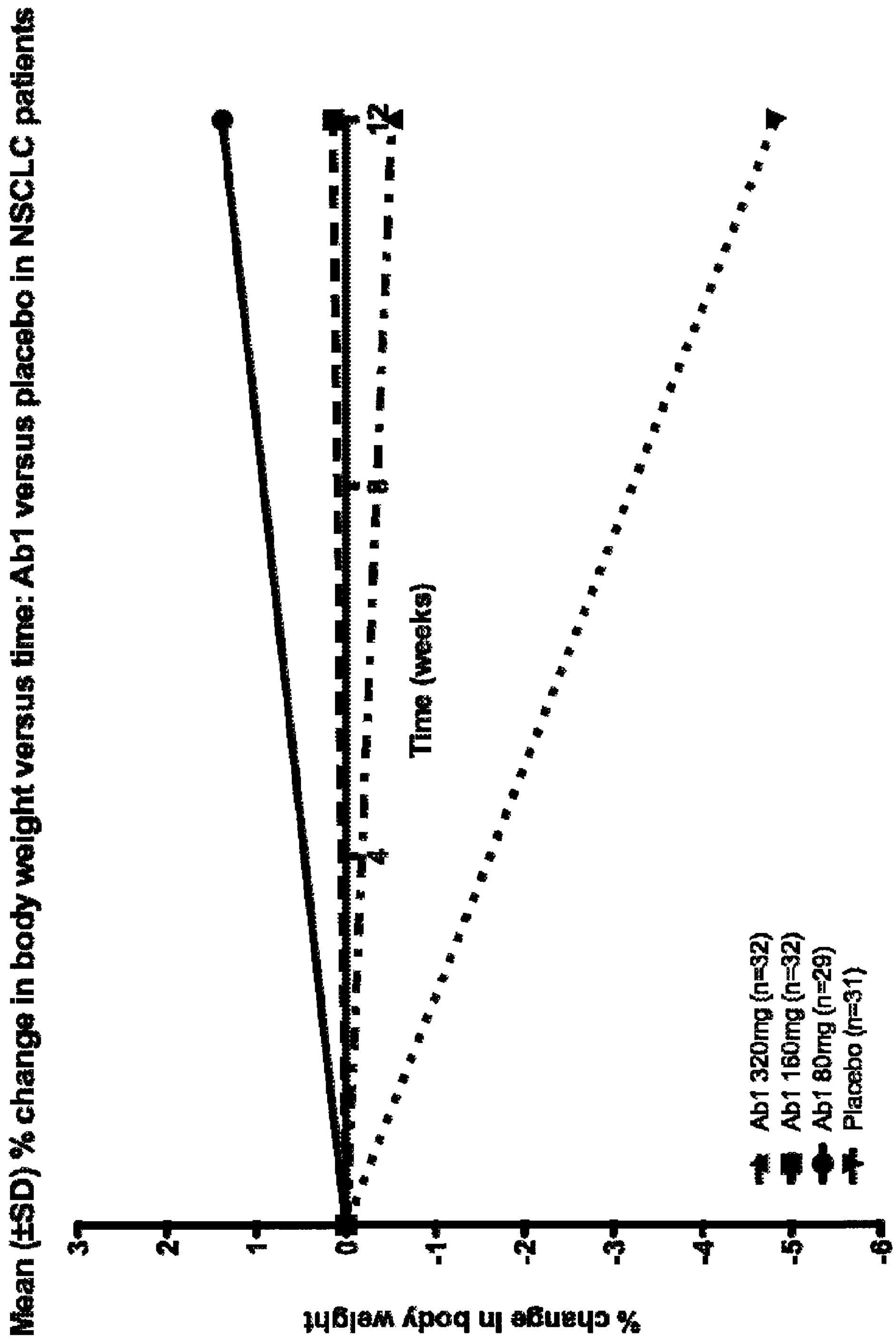
FIG. 45 demonstrates the averaged percent change in body weight from each dosage concentration group corresponding to FIG. 44.
Figure 46:
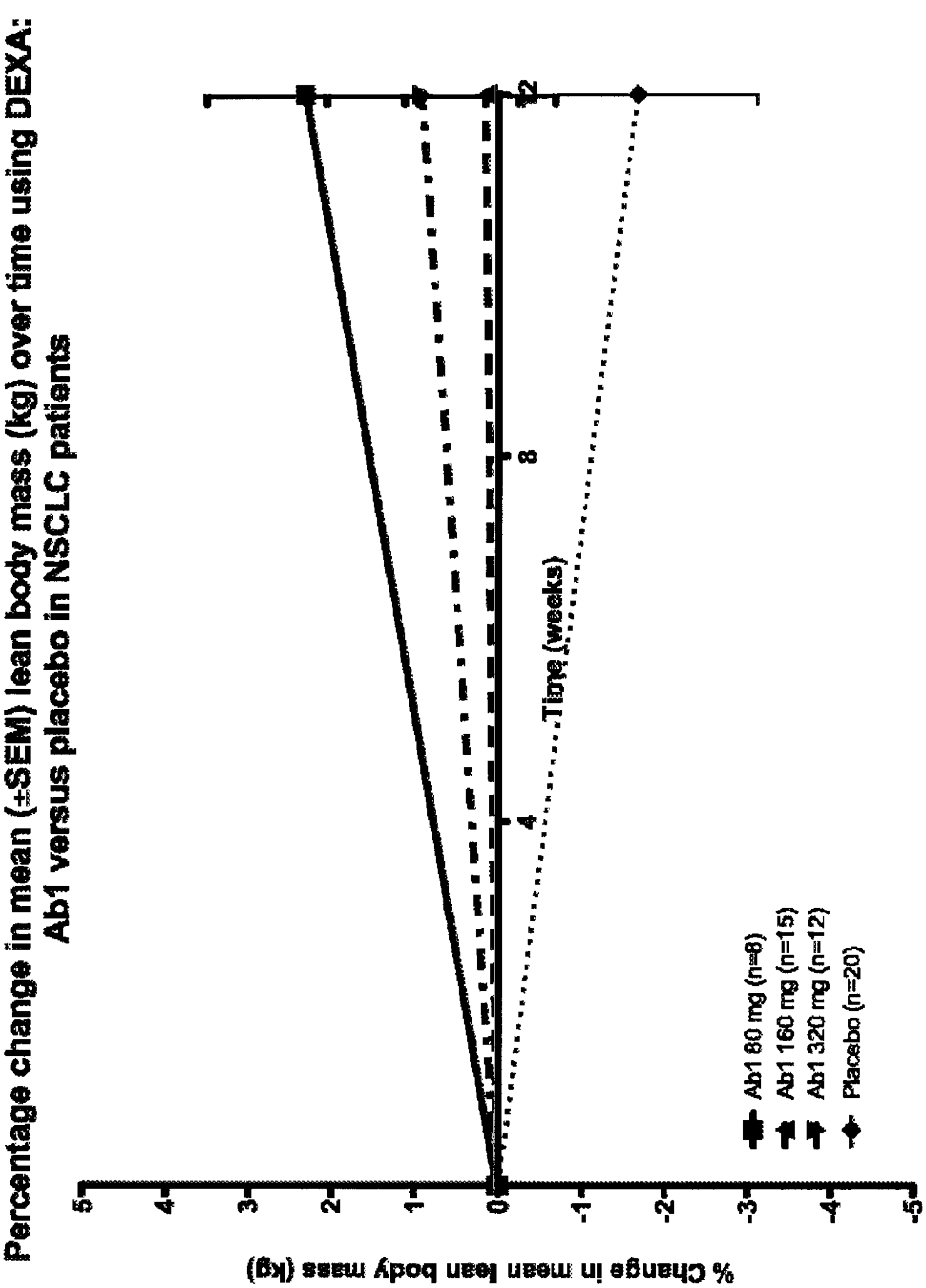
FIG. 46 demonstrates the change in averaged lean body mass data for the dosage concentration groups corresponding to FIG. 44.

The averaged weight change data from each dosage concentration group (placebo, 80 mg, 160 mg, and 320 mg) of the Ab1 monoclonal antibody over 12 weeks is plotted in FIG. 44. The average percent change in body weight from each dosage concentration is plotted in FIG. 45. The averaged lean body mass data for the dosage concentration groups is plotted in FIG. 46.

Fatigue

Figure 47:
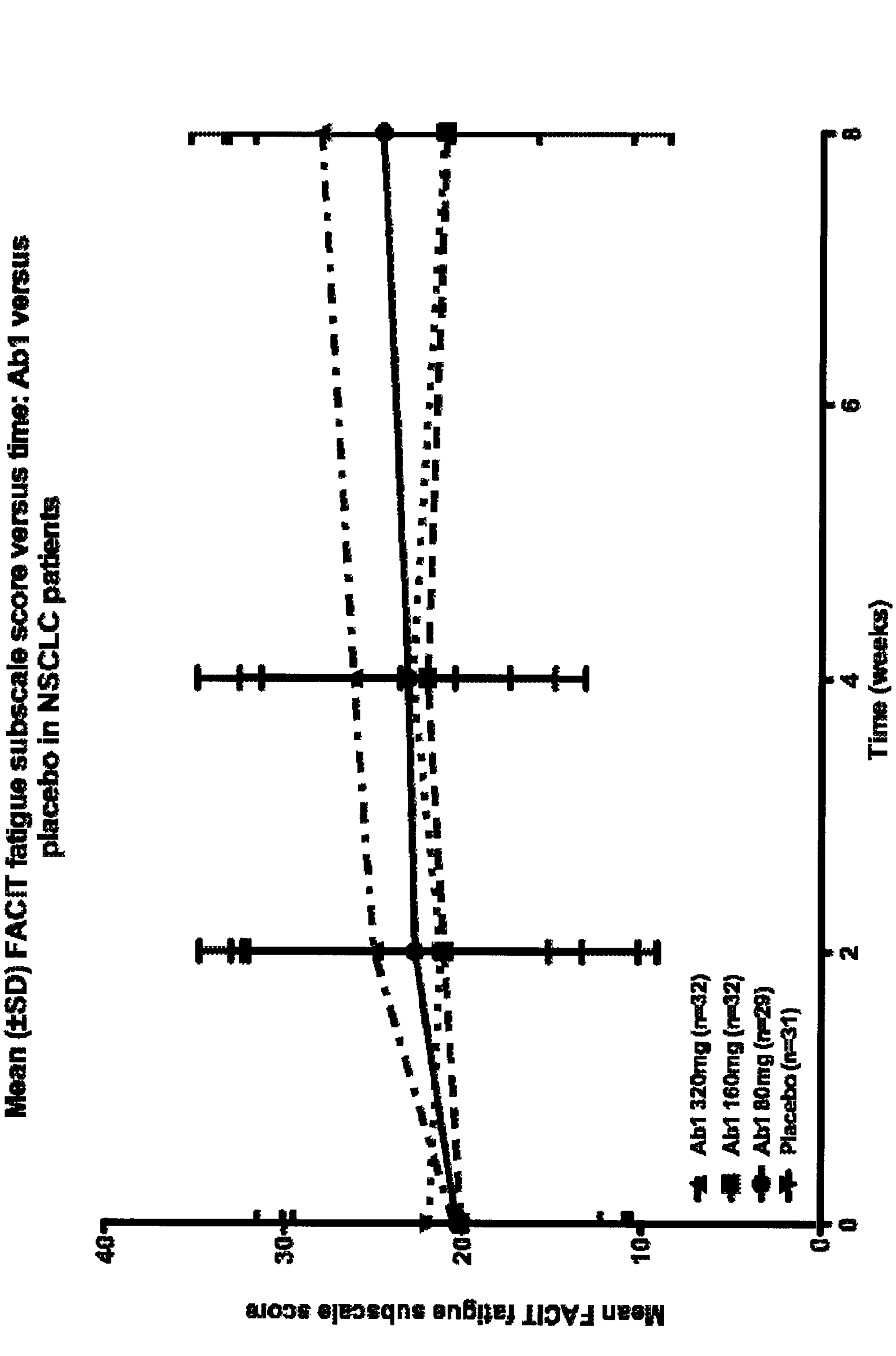
FIG. 47 demonstrates increases in the mean Facit-F FS subscale score for some of the dosage concentration groups in the patient population after dosing at 80, 160 and 320 mg after 8 weeks.
Figure 48:
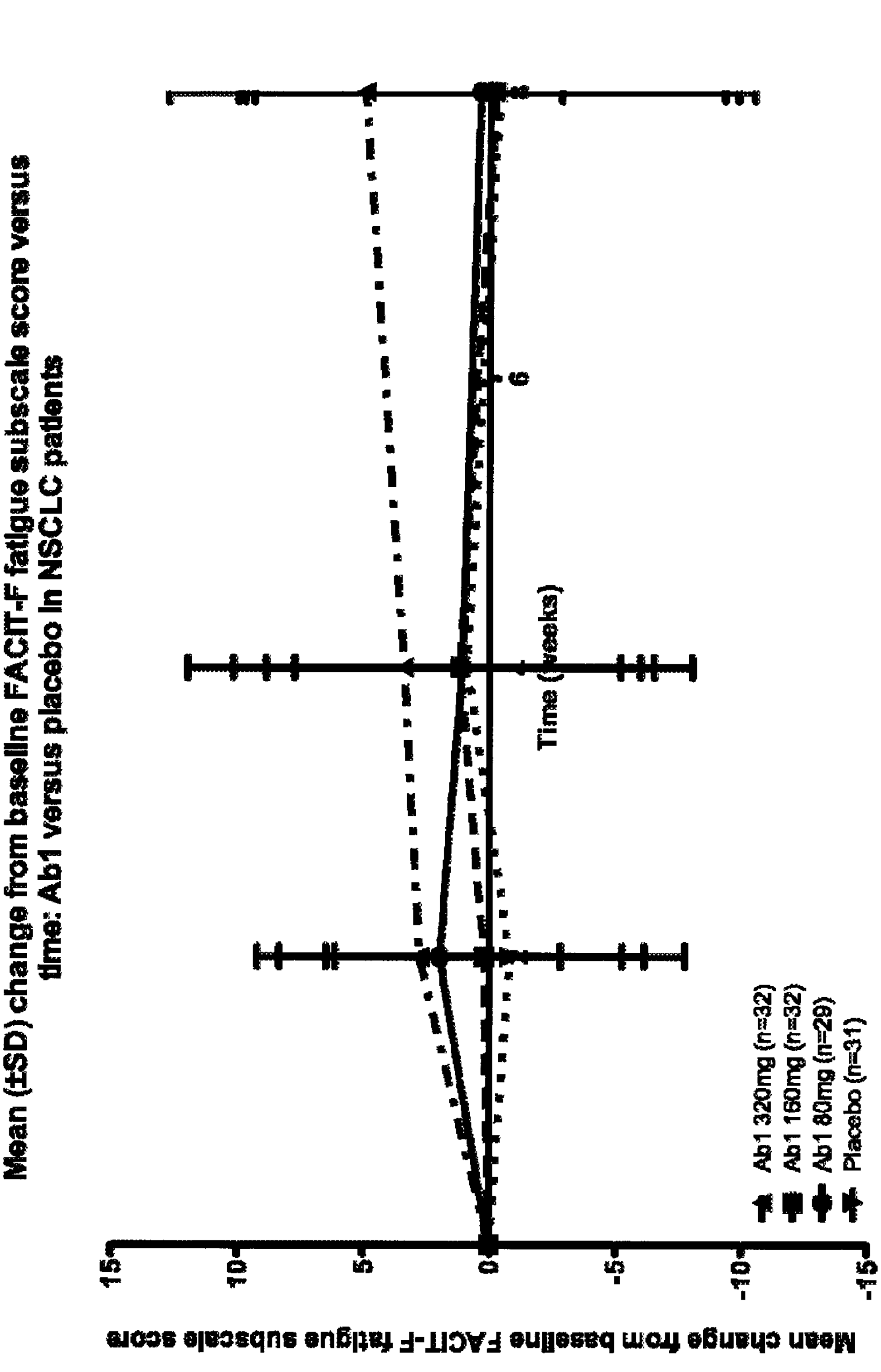
FIG. 48 demonstrates the change from baseline Facit-F FS subscale score corresponding to FIG. 47.

The averaged fatigue from each dosage concentration group (placebo, 80 mg, 160 mg, and 320 mg) of the Ab1 monoclonal antibody demonstrated increases in the mean Facit-F FS subscale score for some of the dosage concentration groups in the patient population over the period of 8 weeks (FIG. 47). The change from baseline Facit-F subscale score is plotted in FIG. 48.

What is claimed is:

1. A method of reducing the risk of hypercoagulation or thrombosis in a subject having an elevated IL-6 level and an elevated D-dimer level by reducing the level of serum D-dimer in said subject, comprising administering to the subject an amount of an IL-6 antagonist, wherein said IL-6 antagonist is an antibody or antibody fragment that specifically binds human IL-6, wherein said antibody or antibody fragment comprises a variable light (VL) region containing the VL complementarity regions, CDR1, CDR2 and CDR3, respectively in SEQ ID NO:4, 5 and 6, and comprises a variable heavy (VH) region containing the VH complementarity regions, CDR1, CDR2 and CDR3, respectively in SEQ ID NO:7, 8 or 120 and 9, and which antibody or fragment is administered in an amount effective to reduce the level amount of serum D-dimer thereby reducing the risk of hypercoagulation or thrombosis in said subject.

2. The method of claim 1, wherein the light chain comprises a polypeptide which is at least 90% identical to the light chain framework region having the sequence contained in SEQ ID NO:699.

3. The method of claim 1, wherein the heavy chain comprises a polypeptide which is at least 90% identical to the heavy chain framework region having the sequence contained in SEQ ID NO:657.

4. The method of claim 1, wherein the light chain comprises a polypeptide which is at least 95% identical to the light chain framework region having the sequence contained in SEQ ID NO:699.

5. The method of claim 1, wherein the heavy chain comprises polypeptide which is at least 95% identical to the heavy chain framework region having the sequence contained in SEQ ID NO:657.

6. The method of claim 1, wherein the light chain comprises polypeptide which is at least 98% identical to the light chain framework region having the sequence contained in SEQ ID NO:699.

7. The method of claim 1, wherein the heavy chain comprises a polypeptide which is at least 98% identical to the heavy chain framework region having the sequence contained in SEQ ID NO:657.

8. The method of claim 1, wherein the light chain comprises a polypeptide which is at least 99% identical to the light chain framework region having the sequence contained in SEQ ID NO:699.

9. The method of claim 1, wherein the heavy chain comprises a polypeptide which is at least 99% identical to the heavy chain framework region having the sequence contained in SEQ ID NO:657.

10. The method of claim 1, wherein the light chain comprises a polypeptide which is identical to the light chain framework region having the sequence contained in SEQ ID NO:699.

11. The method of claim 1, wherein the heavy chain comprises a polypeptide which is identical to the heavy chain framework region having the sequence contained in SEQ ID NO:657.

12. The method of claim 1, wherein the light chain comprises a polypeptide which is identical to the light chain framework region having the sequence contained in SEQ ID NO:2 or 20.

13. The method of claim 1, wherein the heavy chain comprises a polypeptide which is identical to the heavy chain framework region having the sequence contained in SEQ ID NO:3, 18 or 19.

14. The method of claim 1, wherein the light chain comprises a polypeptide which is identical to the light chain framework region having the sequence contained in SEQ ID NO: 20 and he heavy chain comprises a polypeptide which is identical to the heavy chain framework region having the sequence contained in SEQ ID NO: 18 or 19.

15. The method of claim 1 wherein the antibody or fragment comprises human IgG1 constant regions.

16. The method of claim 14 wherein the antibody or fragment comprises human IgG1 constant regions.

17. The method of claim 1 wherein the D-dimer levels are determined before antibody administration.

18. The method of claim 1 wherein said subject also has an elevated C-reactive protein (CRP) level prior to treatment.

19. The method of claim 1 wherein said method further comprises the administration of at least one statin or anti-coagulant.

20. The method of claim 1, wherein the anti-IL-6 antibody or antibody fragment is administered to the subject with a frequency at most once per period of approximately four weeks.

21. The method of claim 1, wherein the subject's coagulation profile is assayed after treatment.

22. The method of claim 1, wherein the subject's coagulation profile is assayed before treatment.

23. The method of claim 1, wherein the anti-IL-6 antibody or antibody fragment has an elimination half-life of at least about 22 days.

24. The method of claim 1, further comprising administration of one or more anti-coagulants or statins.

25. The method of claim 1, wherein the subject's coagulation profile is assessed before or after treatment by measurement of the subject's serum level of one or more of D-dimer, Factor II, Factor V, Factor VIII, Factor IX, Factor XI, Factor XII, F/fibrin degradation products, thrombin-antithrombin III complex, fibrinogen, plasminogen, prothrombin, and von Willebrand factor.

26. The method of claim 1, further comprising measuring the subject's international normalized ratio (INR) prior to administration of the anti-IL-6 antibody or antibody fragment and administering to the subject said anti-IL-6 antibody if the subject's INR is less than about 0.9.

27. The method of claim 1, wherein the subject's serum D-dimer level is lowered to less than the upper limit of the normal reference range within 4 weeks of administering to the subject said anti-IL-6 antibody.

28. The method of claim 1, wherein the subject treated has cancer.

29. The method of claim 1, wherein the subject being treated is undergoing chemotherapy.

30. The method of claim 1, further comprising measuring the level of IL-6 in the subject prior to treatment.

31. The method of claim 1, further comprising measuring the level of C-reactive protein in the subject prior to treatment.

32. The method of claim 21, wherein the subject's coagulation profile is assayed by a method comprising measuring the concentration of D-dimer in the subject's serum.

33. The method of claim 22, wherein the subject's coagulation profile is assayed by a method comprising measuring the concentration of D-dimer in the subject's serum.

34. The method of claim 1, wherein said antibody or fragment inhibits the interaction of IL-6 with gp130.

35. The method of claim 1, wherein said antibody or fragment inhibits the interaction of IL-6 with IL-R 1.

36. The method of claim 1, wherein said antibody or fragment inhibits the interaction of IL-6 with gp 130 and IL-6R1.

37. The method of claim 1, wherein said antibody or fragment neutralizes IL-6 in vivo.

38. The method of claim 14, wherein said antibody or fragment neutralizes IL-6 in vivo.

39. The method of claim 1, wherein said antibody or fragment binds to IL-6 with a dissociation constant ($K_D$) of less than or equal to $5\times10^{-7}$, $10^{-7}$, $5\times10^{-8}$, $10^{-8}$, $5\times10^{-9}$, $10^{-9}$, $5\times10^{-10}$, $10^{-10}$, $5\times10^{-11}$, $10^{-11}$, $5\times10^{-12}$, $10^{-12}$, $5\times10^{-13}$, $10^{-13}$, $5\times10^{-14}$, $10^{-14}$, $5\times10^{-15}$ or $10^{-15}$.

40. The method of claim 1, wherein said antibody or fragment binds to IL-6 with a dissociation constant of less than or equal to $5\times10^{-10}$.

41. The method of claim 1, wherein said antibody or fragment possesses a binding affinity (Kd) less than 50 picomolar.

42. The method of claim 1, wherein said antibody or fragment possesses a $K_{off}$ value less than or equal to $10^{-4}$ $S^{-1}$.

43. The method of claim 1, wherein said antibody or fragment is administered intravenously.

44. The method of claim 14, wherein said antibody or fragment is administered intravenously.

45. The method of claim 1, wherein said antibody or fragment is administered subcutaneously.

46. The method of claim 14, wherein said antibody or fragment is administered subcutaneously.

* * * * *

UNITED STATES PATENT AND TRADEMARK OFFICE

CERTIFICATE OF CORRECTION

PATENT NO. : 8,277,804 B2
APPLICATION NO. : 12/624830
DATED : October 2, 2012
INVENTOR(S) : Jeffrey T. L. Smith It is certified that error appears in the above-identified patent and that said Letters Patent is hereby corrected as shown below:

On the Title page, Column 1, delete "(63) Continuation-in-part of application No. 12/502,581, filed on Jul. 14, 2009, and a continuation-in-part of application No. 12/399,156, filed on Mar. 6, 2009, and a continuation-in-part of application No. 12/391,717, filed on Feb. 24, 2009, and a continuation-in-part of application No. 12/366,567, filed on Feb. 5, 2009."

Signed and Sealed this
Eighteenth Day of June, 2013

Teresa Stanek Rea
*Acting Director of the United States Patent and Trademark Office*

UNITED STATES PATENT AND TRADEMARK OFFICE

CERTIFICATE OF CORRECTION

PATENT NO. : 8,277,804 B2
APPLICATION NO. : 12/624830
DATED : October 2, 2012
INVENTOR(S) : Jeffrey T. L. Smith It is certified that error appears in the above-identified patent and that said Letters Patent is hereby corrected as shown below:

Title Page, Col. 2, (Other Publications), line 6, Delete "laptestsonline" and insert -- labtestsonline --, therefor.

Title Page, Col. 2, (Other Publications), line 25, Delete "understaning" and insert -- understanding --, therefor.

Title Page, Col. 2, (Other Publications), line 29, Delete "HMG-C0A" and insert -- HMG-CoA --, therefor.

In the Claims:

Col. 533, line 12, In Claim 14, Delete "he" and insert -- the --, therefor.

Col. 534, line 22, In Claim 35, Delete "IL-R 1." and insert -- IL-R1. --, therefor.

Col. 534, line 24, In Claim 36, Delete "gp 130" and insert -- gp130 --, therefor.

Signed and Sealed this
Twenty-ninth Day of October, 2013

Teresa Stanek Rea
*Deputy Director of the United States Patent and Trademark Office*

SEQUENCE LISTING

```
<160> NUMBER OF SEQ ID NOS: 744

<210> SEQ ID NO 1
<211> LENGTH: 183
<212> TYPE: PRT
<213> ORGANISM: Homo sapiens

<400> SEQUENCE: 1

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110
```

```
Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180


<210> SEQ ID NO 2
<211> LENGTH: 163
<212> TYPE: PRT
<213> ORGANISM: Oryctolagus cuniculus

<400> SEQUENCE: 2

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Lys Cys Gln Ala Ser
        35                  40                  45

Gln Ser Ile Asn Asn Glu Leu Ser Trp Tyr Gln Gln Lys Pro Gly Gln
    50                  55                  60

Arg Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Ser Leu Arg Asn Ile Asp Asn Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn


<210> SEQ ID NO 3
<211> LENGTH: 166
<212> TYPE: PRT
<213> ORGANISM: Oryctolagus cuniculus

<400> SEQUENCE: 3

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Val Thr Trp Val Arg Gln Ala Pro Gly Lys Gly Leu Glu
    50                  55                  60

Trp Ile Gly Ile Ile Tyr Gly Ser Asp Glu Thr Ala Tyr Ala Thr Trp
65                  70                  75                  80

Ala Ile Gly Arg Phe Thr Ile Ser Lys Thr Ser Thr Thr Val Asp Leu
                85                  90                  95
```

Lys Met Thr Ser Leu Thr Ala Ala Asp Thr Ala Thr Tyr Phe Cys Ala
100 105 110

Arg Asp Asp Ser Ser Asp Trp Asp Ala Lys Phe Asn Leu Trp Gly Gln
115 120 125

Gly Thr Leu Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys
165

<210> SEQ ID NO 4
<211> LENGTH: 11
<212> TYPE: PRT
<213> ORGANISM: Oryctolagus cuniculus

<400> SEQUENCE: 4

Gln Ala Ser Gln Ser Ile Asn Asn Glu Leu Ser
1 5 10

<210> SEQ ID NO 5
<211> LENGTH: 7
<212> TYPE: PRT
<213> ORGANISM: Oryctolagus cuniculus

<400> SEQUENCE: 5

Arg Ala Ser Thr Leu Ala Ser
1 5

<210> SEQ ID NO 6
<211> LENGTH: 12
<212> TYPE: PRT
<213> ORGANISM: Oryctolagus cuniculus

<400> SEQUENCE: 6

Gln Gln Gly Tyr Ser Leu Arg Asn Ile Asp Asn Ala
1 5 10

<210> SEQ ID NO 7
<211> LENGTH: 5
<212> TYPE: PRT
<213> ORGANISM: Oryctolagus cuniculus

<400> SEQUENCE: 7

Asn Tyr Tyr Val Thr
1 5

<210> SEQ ID NO 8
<211> LENGTH: 16
<212> TYPE: PRT
<213> ORGANISM: Oryctolagus cuniculus

<400> SEQUENCE: 8

Ile Ile Tyr Gly Ser Asp Glu Thr Ala Tyr Ala Thr Trp Ala Ile Gly
1 5 10 15

<210> SEQ ID NO 9
<211> LENGTH: 12
<212> TYPE: PRT
<213> ORGANISM: Oryctolagus cuniculus

<400> SEQUENCE: 9

Asp Asp Ser Ser Asp Trp Asp Ala Lys Phe Asn Leu

-continued 1 5 10

<210> SEQ ID NO 10
<211> LENGTH: 491
<212> TYPE: DNA
<213> ORGANISM: Oryctolagus cuniculus

<400> SEQUENCE: 10
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca agtgccaggc cagtcagagc attaacaatg aattatcctg gtatcagcag 180
aaaccagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact t 491

<210> SEQ ID NO 11
<211> LENGTH: 499
<212> TYPE: DNA
<213> ORGANISM: Oryctolagus cuniculus

<400> SEQUENCE: 11
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagcctctg gattctccct cagtaactac tacgtgacct gggtccgcca ggctccaggg 180
aaggggctgg aatggatcgg aatcatttat ggtagtgatg aaacggccta cgcgacctgg 240
gcgataggcc gattcaccat ctccaaaacc tcgaccacgg tggatctgaa aatgaccagt 300
ctgacagccg cggacacggc cacctatttc tgtgccagag atgatagtag tgactgggat 360
gcaaaattta acttgtgggg ccaaggcacc ctggtcaccg tctcgagcgc ctccaccaag 420
ggcccatcgg tcttcccct ggcaccctcc tccaagagca cctctggggg cacagcggcc 480
ctgggctgcc tggtcaagg 499

<210> SEQ ID NO 12
<211> LENGTH: 33
<212> TYPE: DNA
<213> ORGANISM: Oryctolagus cuniculus

<400> SEQUENCE: 12
caggccagtc agagcattaa caatgaatta tcc 33

<210> SEQ ID NO 13
<211> LENGTH: 21
<212> TYPE: DNA
<213> ORGANISM: Oryctolagus cuniculus

<400> SEQUENCE: 13
agggcatcca ctctggcatc t 21

<210> SEQ ID NO 14
<211> LENGTH: 36
<212> TYPE: DNA
<213> ORGANISM: Oryctolagus cuniculus

<400> SEQUENCE: 14
caacagggtt atagtctgag gaatattgat aatgct 36

<210> SEQ ID NO 15
<211> LENGTH: 15
<212> TYPE: DNA
<213> ORGANISM: Oryctolagus cuniculus

<400> SEQUENCE: 15
aactactacg tgacc 15

<210> SEQ ID NO 16
<211> LENGTH: 48
<212> TYPE: DNA
<213> ORGANISM: Oryctolagus cuniculus

<400> SEQUENCE: 16
atcatttatg gtagtgatga aacggcctac gcgacctggg cgataggc 48

<210> SEQ ID NO 17
<211> LENGTH: 36
<212> TYPE: DNA
<213> ORGANISM: Oryctolagus cuniculus

<400> SEQUENCE: 17
gatgatagta gtgactggga tgcaaaattt aacttg 36

<210> SEQ ID NO 18
<211> LENGTH: 109
<212> TYPE: PRT
<213> ORGANISM: Oryctolagus cuniculus

<400> SEQUENCE: 18

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Val Thr Trp Val Arg Gln Ala Pro Gly Lys Gly Leu Glu Trp Val
35 40 45

Gly Ile Ile Tyr Gly Ser Asp Glu Thr Ala Tyr Ala Thr Trp Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu
100 105

<210> SEQ ID NO 19
<211> LENGTH: 109
<212> TYPE: PRT
<213> ORGANISM: Oryctolagus cuniculus

<400> SEQUENCE: 19

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Val Thr Trp Val Arg Gln Ala Pro Gly Lys Gly Leu Glu Trp Val
35 40 45

```
Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105


<210> SEQ ID NO 20
<211> LENGTH: 99
<212> TYPE: PRT
<213> ORGANISM: Oryctolagus cuniculus

<400> SEQUENCE: 20

Ile Gln Met Thr Gln Ser Pro Ser Ser Leu Ser Ala Ser Val Gly Asp
1               5                   10                  15

Arg Val Thr Ile Thr Cys Gln Ala Ser Gln Ser Ile Asn Asn Glu Leu
            20                  25                  30

Ser Trp Tyr Gln Gln Lys Pro Gly Lys Ala Pro Lys Leu Leu Ile Tyr
        35                  40                  45

Arg Ala Ser Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Asp
65                  70                  75                  80

Asp Phe Ala Thr Tyr Tyr Cys Gln Gln Gly Tyr Ser Leu Arg Asn Ile
                85                  90                  95

Asp Asn Ala


<210> SEQ ID NO 21
<211> LENGTH: 170
<212> TYPE: PRT
<213> ORGANISM: Oryctolagus cuniculus

<400> SEQUENCE: 21

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Asn Cys Gln Ala Ser
        35                  40                  45

Glu Thr Ile Tyr Ser Trp Leu Ser Trp Tyr Gln Gln Lys Pro Gly Gln
    50                  55                  60

Pro Pro Lys Leu Leu Ile Tyr Gln Ala Ser Asp Leu Ala Ser Gly Val
65                  70                  75                  80

Pro Ser Arg Phe Ser Gly Ser Gly Ala Gly Thr Glu Tyr Thr Leu Thr
                85                  90                  95

Ile Ser Gly Val Gln Cys Asp Asp Ala Ala Thr Tyr Tyr Cys Gln Gln
            100                 105                 110

Gly Tyr Ser Gly Ser Asn Val Asp Asn Val Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys
                165                 170
```

<210> SEQ ID NO 22
<211> LENGTH: 167
<212> TYPE: PRT
<213> ORGANISM: Oryctolagus cuniculus

<400> SEQUENCE: 22

```
Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Arg Leu Val Thr
            20                  25                  30

Pro Gly Thr Pro Leu Thr Leu Thr Cys Thr Ala Ser Gly Phe Ser Leu
        35                  40                  45

Asn Asp His Ala Met Gly Trp Val Arg Gln Ala Pro Gly Lys Gly Leu
    50                  55                  60

Glu Tyr Ile Gly Phe Ile Asn Ser Gly Gly Ser Ala Arg Tyr Ala Ser
65                  70                  75                  80

Trp Ala Glu Gly Arg Phe Thr Ile Ser Arg Thr Ser Thr Thr Val Asp
                85                  90                  95

Leu Lys Met Thr Ser Leu Thr Thr Glu Asp Thr Ala Thr Tyr Phe Cys
            100                 105                 110

Val Arg Gly Gly Ala Val Trp Ser Ile His Ser Phe Asp Pro Trp Gly
        115                 120                 125

Pro Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys
                165
```

<210> SEQ ID NO 23
<211> LENGTH: 11
<212> TYPE: PRT
<213> ORGANISM: Oryctolagus cuniculus

<400> SEQUENCE: 23

```
Gln Ala Ser Glu Thr Ile Tyr Ser Trp Leu Ser
1               5                   10
```

<210> SEQ ID NO 24
<211> LENGTH: 7
<212> TYPE: PRT
<213> ORGANISM: Oryctolagus cuniculus

<400> SEQUENCE: 24

```
Gln Ala Ser Asp Leu Ala Ser
1               5
```

<210> SEQ ID NO 25
<211> LENGTH: 12
<212> TYPE: PRT
<213> ORGANISM: Oryctolagus cuniculus

<400> SEQUENCE: 25

```
Gln Gln Gly Tyr Ser Gly Ser Asn Val Asp Asn Val
1               5                   10
```

<210> SEQ ID NO 26
<211> LENGTH: 5
<212> TYPE: PRT
<213> ORGANISM: Oryctolagus cuniculus

<400> SEQUENCE: 26

Asp His Ala Met Gly
1 5

<210> SEQ ID NO 27
<211> LENGTH: 16
<212> TYPE: PRT
<213> ORGANISM: Oryctolagus cuniculus

<400> SEQUENCE: 27

Phe Ile Asn Ser Gly Gly Ser Ala Arg Tyr Ala Ser Trp Ala Glu Gly
1 5 10 15

<210> SEQ ID NO 28
<211> LENGTH: 12
<212> TYPE: PRT
<213> ORGANISM: Oryctolagus cuniculus

<400> SEQUENCE: 28

Gly Gly Ala Val Trp Ser Ile His Ser Phe Asp Pro
1 5 10

<210> SEQ ID NO 29
<211> LENGTH: 511
<212> TYPE: DNA
<213> ORGANISM: Oryctolagus cuniculus

<400> SEQUENCE: 29
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca attgccaggc cagtgagacc atttacagtt ggttatcctg gtatcagcag 180
aagccagggc agcctcccaa gctcctgatc taccaggcat ccgatctggc atctggggtc 240
ccatcgcgat tcagcggcag tggggctggg acagagtaca ctctcaccat cagcggcgtg 300
cagtgtgacg atgctgccac ttactactgt caacagggtt atagtggtag taatgttgat 360
aatgttttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tctatcccag agaggccaaa g 511

<210> SEQ ID NO 30
<211> LENGTH: 501
<212> TYPE: DNA
<213> ORGANISM: Oryctolagus cuniculus

<400> SEQUENCE: 30
atggagactg ggctgcgctg gcttctcctg gtcgctgtgc tcaaaggtgt ccagtgtcag 60
gagcagctga aggagtccgg gggtcgcctg gtcacgcctg ggacacccct gacacttacc 120
tgcacagcct ctggattctc cctcaatgac catgcaatgg gctgggtccg ccaggctcca 180
gggaaggggc tggaatacat cggattcatt aatagtggtg gtagcgcacg ctacgcgagc 240
tgggcagaag gccgattcac catctccaga acctcgacca cggtggatct gaaaatgacc 300
agtctgacaa ccgaggacac ggccacctat ttctgtgtca gagggggtgc tgtttggagt 360
attcatagtt ttgatccctg gggcccaggg accctggtca ccgtctcgag cgcctccacc 420
aagggcccat cggtcttccc cctggcaccc tcctccaaga gcacctctgg gggcacagcg 480
gccctgggct gcctggtcaa g 501

<210> SEQ ID NO 31
<211> LENGTH: 33
<212> TYPE: DNA
<213> ORGANISM: Oryctolagus cuniculus

<400> SEQUENCE: 31
caggccagtg agaccattta cagttggtta tcc 33

<210> SEQ ID NO 32
<211> LENGTH: 21
<212> TYPE: DNA
<213> ORGANISM: Oryctolagus cuniculus

<400> SEQUENCE: 32
caggcatccg atctggcatc t 21

<210> SEQ ID NO 33
<211> LENGTH: 36
<212> TYPE: DNA
<213> ORGANISM: Oryctolagus cuniculus

<400> SEQUENCE: 33
caacagggtt atagtggtag taatgttgat aatgtt 36

<210> SEQ ID NO 34
<211> LENGTH: 15
<212> TYPE: DNA
<213> ORGANISM: Oryctolagus cuniculus

<400> SEQUENCE: 34
gaccatgcaa tgggc 15

<210> SEQ ID NO 35
<211> LENGTH: 48
<212> TYPE: DNA
<213> ORGANISM: Oryctolagus cuniculus

<400> SEQUENCE: 35
ttcattaata gtggtggtag cgcacgctac gcgagctggg cagaaggc 48

<210> SEQ ID NO 36
<211> LENGTH: 36
<212> TYPE: DNA
<213> ORGANISM: Oryctolagus cuniculus

<400> SEQUENCE: 36
gggggtgctg tttggagtat tcatagtttt gatccc 36

<210> SEQ ID NO 37
<211> LENGTH: 165
<212> TYPE: PRT
<213> ORGANISM: Oryctolagus cuniculus

<400> SEQUENCE: 37

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Pro
20 25 30

Val Ser Ala Ala Val Gly Gly Thr Val Ser Ile Ser Cys Gln Ala Ser
35 40 45

Gln Ser Val Tyr Asp Asn Asn Tyr Leu Ser Trp Phe Gln Gln Lys Pro
50 55 60

Gly Gln Pro Pro Lys Leu Leu Ile Tyr Gly Ala Ser Thr Leu Ala Ser
65 70 75 80

Gly Val Pro Ser Arg Phe Val Gly Ser Gly Ser Gly Thr Gln Phe Thr
85 90 95

Leu Thr Ile Thr Asp Val Gln Cys Asp Asp Ala Ala Thr Tyr Tyr Cys
100 105 110

Ala Gly Val Tyr Asp Asp Asp Ser Asp Asn Ala Phe Gly Gly Gly Thr
115 120 125

Glu Val Val Val Lys Arg Thr Val Ala Ala Pro Ser Val Phe Ile Phe
130 135 140

Pro Pro Ser Asp Glu Gln Leu Lys Ser Gly Thr Ala Ser Val Val Cys
145 150 155 160

Leu Leu Asn Asn Phe
165

<210> SEQ ID NO 38
<211> LENGTH: 166
<212> TYPE: PRT
<213> ORGANISM: Oryctolagus cuniculus

<400> SEQUENCE: 38

Met Glu Thr Gly Leu Arg Trp Leu Leu Leu Val Ala Val Leu Lys Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Ala Ser Gly Phe Ser Leu Ser
35 40 45

Val Tyr Tyr Met Asn Trp Val Arg Gln Ala Pro Gly Lys Gly Leu Glu
50 55 60

Trp Ile Gly Phe Ile Thr Met Ser Asp Asn Ile Asn Tyr Ala Ser Trp
65 70 75 80

Ala Lys Gly Arg Phe Thr Ile Ser Lys Thr Ser Thr Thr Val Asp Leu
85 90 95

Lys Met Thr Ser Pro Thr Thr Glu Asp Thr Ala Thr Tyr Phe Cys Ala
100 105 110

Arg Ser Arg Gly Trp Gly Thr Met Gly Arg Leu Asp Leu Trp Gly Pro
115 120 125

Gly Thr Leu Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys
165

<210> SEQ ID NO 39
<211> LENGTH: 13
<212> TYPE: PRT
<213> ORGANISM: Oryctolagus cuniculus

<400> SEQUENCE: 39

Gln Ala Ser Gln Ser Val Tyr Asp Asn Asn Tyr Leu Ser
1 5 10

<210> SEQ ID NO 40
<211> LENGTH: 7
<212> TYPE: PRT
<213> ORGANISM: Oryctolagus cuniculus

<400> SEQUENCE: 40

Gly Ala Ser Thr Leu Ala Ser
1 5

<210> SEQ ID NO 41
<211> LENGTH: 11
<212> TYPE: PRT
<213> ORGANISM: Oryctolagus cuniculus

<400> SEQUENCE: 41

Ala Gly Val Tyr Asp Asp Asp Ser Asp Asn Ala
1 5 10

<210> SEQ ID NO 42
<211> LENGTH: 5
<212> TYPE: PRT
<213> ORGANISM: Oryctolagus cuniculus

<400> SEQUENCE: 42

Val Tyr Tyr Met Asn
1 5

<210> SEQ ID NO 43
<211> LENGTH: 16
<212> TYPE: PRT
<213> ORGANISM: Oryctolagus cuniculus

<400> SEQUENCE: 43

Phe Ile Thr Met Ser Asp Asn Ile Asn Tyr Ala Ser Trp Ala Lys Gly
1 5 10 15

<210> SEQ ID NO 44
<211> LENGTH: 12
<212> TYPE: PRT
<213> ORGANISM: Oryctolagus cuniculus

<400> SEQUENCE: 44

Ser Arg Gly Trp Gly Thr Met Gly Arg Leu Asp Leu
1 5 10

<210> SEQ ID NO 45
<211> LENGTH: 496
<212> TYPE: DNA
<213> ORGANISM: Oryctolagus cuniculus

<400> SEQUENCE: 45
atggacacga gggcccccac tcagctgctg gggctcctgc tgctctggct cccaggtgcc 60
acatttgccg ccgtgctgac ccagactcca tctcccgtgt ctgcagctgt gggaggcaca 120
gtcagcatca gttgccaggc cagtcagagt gtttatgaca acaactactt atcctggttt 180
cagcagaaac cagggcagcc tcccaagctc ctgatctatg gtgcatccac tctggcatct 240
ggggtcccat cgcggttcgt gggcagtgga tctgggacac agttcactct caccatcaca 300
gacgtgcagt gtgacgatgc tgccacttac tattgtgcag gcgtttatga tgatgatagt 360
gataatgcct tcggcggagg gaccgaggtg gtggtcaaac gtacggtagc ggccccatct 420
gtcttcatct tcccgccatc tgatgagcag ttgaaatctg gaactgcctc tgttgtgtgc 480
ctgctgaata acttct 496

<210> SEQ ID NO 46
<211> LENGTH: 499
<212> TYPE: DNA
<213> ORGANISM: Oryctolagus cuniculus -continued

<400> SEQUENCE: 46

```
atggagactg ggctgcgctg gcttctcctg gtggctgtgc tcaaaggtgt ccagtgtcag      60
tcgctggagg agtccggggg tcgcctggtc acccctggga cacccctgac actcacctgc     120
acagcctctg gattctccct cagtgtctac tacatgaact gggtccgcca ggctccaggg     180
aaggggctgg aatggatcgg attcattaca atgagtgata atataaatta cgcgagctgg     240
gcgaaaggcc gattcaccat ctccaaaacc tcgaccacgg tggatctgaa aatgaccagt     300
ccgacaaccg aggacacggc cacctatttc tgtgccagga gtcgtggctg gggtacaatg     360
ggtcggttgg atctctgggg cccaggcacc ctcgtcaccg tctcgagcgc ctccaccaag     420
ggcccatcgg tcttccccct ggcaccctcc tccaagagca cctctggggg cacagcggcc     480
ctgggctgcc tggtcaagg                                                  499
```

<210> SEQ ID NO 47
<211> LENGTH: 39
<212> TYPE: DNA
<213> ORGANISM: Oryctolagus cuniculus

<400> SEQUENCE: 47

```
caggccagtc agagtgttta tgacaacaac tacttatcc                             39
```

<210> SEQ ID NO 48
<211> LENGTH: 21
<212> TYPE: DNA
<213> ORGANISM: Oryctolagus cuniculus

<400> SEQUENCE: 48

```
ggtgcatcca ctctggcatc t                                                21
```

<210> SEQ ID NO 49
<211> LENGTH: 33
<212> TYPE: DNA
<213> ORGANISM: Oryctolagus cuniculus

<400> SEQUENCE: 49

```
gcaggcgttt atgatgatga tagtgataat gcc                                   33
```

<210> SEQ ID NO 50
<211> LENGTH: 15
<212> TYPE: DNA
<213> ORGANISM: Oryctolagus cuniculus

<400> SEQUENCE: 50

```
gtctactaca tgaac                                                       15
```

<210> SEQ ID NO 51
<211> LENGTH: 48
<212> TYPE: DNA
<213> ORGANISM: Oryctolagus cuniculus

<400> SEQUENCE: 51

```
ttcattacaa tgagtgataa tataaattac gcgagctggg cgaaaggc                   48
```

<210> SEQ ID NO 52
<211> LENGTH: 36
<212> TYPE: DNA
<213> ORGANISM: Oryctolagus cuniculus

<400> SEQUENCE: 52

```
agtcgtggct ggggtacaat gggtcggttg gatctc                                36
```

<210> SEQ ID NO 53
<211> LENGTH: 164
<212> TYPE: PRT
<213> ORGANISM: Oryctolagus cuniculus

<400> SEQUENCE: 53

Met Asp Thr Arg Ala Pro Thr Gln Leu Leu Gly Leu Leu Leu Leu Trp
1 5 10 15

Leu Pro Gly Ala Ile Cys Asp Pro Val Leu Thr Gln Thr Pro Ser Pro
20 25 30

Val Ser Ala Pro Val Gly Gly Thr Val Ser Ile Ser Cys Gln Ala Ser
35 40 45

Gln Ser Val Tyr Glu Asn Asn Tyr Leu Ser Trp Phe Gln Gln Lys Pro
50 55 60

Gly Gln Pro Pro Lys Leu Leu Ile Tyr Gly Ala Ser Thr Leu Asp Ser
65 70 75 80

Gly Val Pro Ser Arg Phe Lys Gly Ser Gly Ser Gly Thr Gln Phe Thr
85 90 95

Leu Thr Ile Thr Asp Val Gln Cys Asp Asp Ala Ala Thr Tyr Tyr Cys
100 105 110

Ala Gly Val Tyr Asp Asp Asp Ser Asp Asp Ala Phe Gly Gly Gly Thr
115 120 125

Glu Val Val Val Lys Arg Thr Val Ala Ala Pro Ser Val Phe Ile Phe
130 135 140

Pro Pro Ser Asp Glu Gln Leu Lys Ser Gly Thr Ala Ser Val Val Cys
145 150 155 160

Leu Leu Asn Asn

<210> SEQ ID NO 54
<211> LENGTH: 167
<212> TYPE: PRT
<213> ORGANISM: Oryctolagus cuniculus

<400> SEQUENCE: 54

Met Glu Thr Gly Leu Arg Trp Leu Leu Leu Val Ala Val Leu Lys Gly
1 5 10 15

Val Gln Cys Gln Glu Gln Leu Lys Glu Ser Gly Gly Gly Leu Val Thr
20 25 30

Pro Gly Gly Thr Leu Thr Leu Thr Cys Thr Ala Ser Gly Phe Ser Leu
35 40 45

Asn Ala Tyr Tyr Met Asn Trp Val Arg Gln Ala Pro Gly Lys Gly Leu
50 55 60

Glu Trp Ile Gly Phe Ile Thr Leu Asn Asn Asn Val Ala Tyr Ala Asn
65 70 75 80

Trp Ala Lys Gly Arg Phe Thr Phe Ser Lys Thr Ser Thr Thr Val Asp
85 90 95

Leu Lys Met Thr Ser Pro Thr Pro Glu Asp Thr Ala Thr Tyr Phe Cys
100 105 110

Ala Arg Ser Arg Gly Trp Gly Ala Met Gly Arg Leu Asp Leu Trp Gly
115 120 125

His Gly Thr Leu Val Thr Val Ser Ser Ala Ser Thr Lys Gly Pro Ser
130 135 140

Val Phe Pro Leu Ala Pro Ser Ser Lys Ser Thr Ser Gly Gly Thr Ala
145 150 155 160

Ala Leu Gly Cys Leu Val Lys
165

<210> SEQ ID NO 55
<211> LENGTH: 13
<212> TYPE: PRT
<213> ORGANISM: Oryctolagus cuniculus

<400> SEQUENCE: 55

Gln Ala Ser Gln Ser Val Tyr Glu Asn Asn Tyr Leu Ser
1 5 10

<210> SEQ ID NO 56
<211> LENGTH: 7
<212> TYPE: PRT
<213> ORGANISM: Oryctolagus cuniculus

<400> SEQUENCE: 56

Gly Ala Ser Thr Leu Asp Ser
1 5

<210> SEQ ID NO 57
<211> LENGTH: 11
<212> TYPE: PRT
<213> ORGANISM: Oryctolagus cuniculus

<400> SEQUENCE: 57

Ala Gly Val Tyr Asp Asp Asp Ser Asp Asp Ala
1 5 10

<210> SEQ ID NO 58
<211> LENGTH: 5
<212> TYPE: PRT
<213> ORGANISM: Oryctolagus cuniculus

<400> SEQUENCE: 58

Ala Tyr Tyr Met Asn
1 5

<210> SEQ ID NO 59
<211> LENGTH: 16
<212> TYPE: PRT
<213> ORGANISM: Oryctolagus cuniculus

<400> SEQUENCE: 59

Phe Ile Thr Leu Asn Asn Asn Val Ala Tyr Ala Asn Trp Ala Lys Gly
1 5 10 15

<210> SEQ ID NO 60
<211> LENGTH: 12
<212> TYPE: PRT
<213> ORGANISM: Oryctolagus cuniculus

<400> SEQUENCE: 60

Ser Arg Gly Trp Gly Ala Met Gly Arg Leu Asp Leu
1 5 10

<210> SEQ ID NO 61
<211> LENGTH: 494
<212> TYPE: DNA
<213> ORGANISM: Oryctolagus cuniculus

<400> SEQUENCE: 61
atggacacga gggcccccac tcagctgctg gggctcctgc tgctctggct cccaggtgcc 60
atatgtgacc ctgtgctgac ccagactcca tctcccgtat ctgcacctgt gggaggcaca 120
gtcagcatca gttgccaggc cagtcagagt gtttatgaga acaactattt atcctggttt 180
cagcagaaac cagggcagcc tcccaagctc ctgatctatg gtgcatccac tctggattct 240
ggggtcccat cgcggttcaa aggcagtgga tctgggacac agttcactct caccattaca 300
gacgtgcagt gtgacgatgc tgccacttac tattgtgcag gcgtttatga tgatgatagt 360
gatgatgcct tcggcggagg gaccgaggtg gtggtcaaac gtacggtagc ggccccatct 420
gtcttcatct tcccgccatc tgatgagcag ttgaaatctg gaactgcctc tgttgtgtgc 480
ctgctgaata actt 494

<210> SEQ ID NO 62
<211> LENGTH: 502
<212> TYPE: DNA
<213> ORGANISM: Oryctolagus cuniculus

<400> SEQUENCE: 62
atggagactg ggctgcgctg gcttctcctg gtggctgtgc tcaaaggtgt ccagtgtcag 60
gagcagctga aggagtccgg aggaggcctg gtaacgcctg gaggaaccct gacactcacc 120
tgcacagcct ctggattctc cctcaatgcc tactacatga actgggtccg ccaggctcca 180
gggaaggggc tggaatggat cggattcatt actctgaata ataatgtagc ttacgcgaac 240
tgggcgaaag gccgattcac cttctccaaa acctcgacca cggtggatct gaaaatgacc 300
agtccgacac ccgaggacac ggccacctat ttctgtgcca ggagtcgtgg ctggggtgca 360
atgggtcggt tggatctctg gggccatggc accctggtca ccgtctcgag cgcctccacc 420
aagggcccat cggtcttccc cctggcaccc tcctccaaga gcacctctgg gggcacagcg 480
gccctgggct gcctggtcaa gg 502

<210> SEQ ID NO 63
<211> LENGTH: 39
<212> TYPE: DNA
<213> ORGANISM: Oryctolagus cuniculus

<400> SEQUENCE: 63
caggccagtc agagtgttta tgagaacaac tatttatcc 39

<210> SEQ ID NO 64
<211> LENGTH: 21
<212> TYPE: DNA
<213> ORGANISM: Oryctolagus cuniculus

<400> SEQUENCE: 64
ggtgcatcca ctctggattc t 21

<210> SEQ ID NO 65
<211> LENGTH: 33
<212> TYPE: DNA
<213> ORGANISM: Oryctolagus cuniculus

<400> SEQUENCE: 65
gcaggcgttt atgatgatga tagtgatgat gcc 33

<210> SEQ ID NO 66
<211> LENGTH: 15
<212> TYPE: DNA
<213> ORGANISM: Oryctolagus cuniculus

<400> SEQUENCE: 66
gcctactaca tgaac 15

<210> SEQ ID NO 67
<211> LENGTH: 48
<212> TYPE: DNA
<213> ORGANISM: Oryctolagus cuniculus

<400> SEQUENCE: 67
ttcattactc tgaataataa tgtagcttac gcgaactggg cgaaaggc 48

<210> SEQ ID NO 68
<211> LENGTH: 36
<212> TYPE: DNA
<213> ORGANISM: Oryctolagus cuniculus

<400> SEQUENCE: 68
agtcgtggct ggggtgcaat gggtcggttg gatctc 36

<210> SEQ ID NO 69
<211> LENGTH: 164
<212> TYPE: PRT
<213> ORGANISM: Oryctolagus cuniculus

<400> SEQUENCE: 69

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ala Ser
        35                  40                  45

Gln Ser Val Asp Asp Asn Asn Trp Leu Gly Trp Tyr Gln Gln Lys Arg
    50                  55                  60

Gly Gln Pro Pro Lys Tyr Leu Ile Tyr Ser Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Gly Phe Ser Gly Asn Ile Phe Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe
```

<210> SEQ ID NO 70
<211> LENGTH: 164
<212> TYPE: PRT
<213> ORGANISM: Oryctolagus cuniculus

<400> SEQUENCE: 70

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Ser Trp Val Arg Gln Ala Pro Gly Lys Gly Leu Glu
    50                  55                  60

Trp Ile Gly Ile Ile Gly Gly Phe Gly Thr Thr Tyr Tyr Ala Thr Trp
```

```
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Ala
            100                 105                 110

Arg Gly Gly Pro Gly Asn Gly Gly Asp Ile Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp


<210> SEQ ID NO 71
<211> LENGTH: 13
<212> TYPE: PRT
<213> ORGANISM: Oryctolagus cuniculus

<400> SEQUENCE: 71

Gln Ala Ser Gln Ser Val Asp Asp Asn Asn Trp Leu Gly
1               5                   10


<210> SEQ ID NO 72
<211> LENGTH: 7
<212> TYPE: PRT
<213> ORGANISM: Oryctolagus cuniculus

<400> SEQUENCE: 72

Ser Ala Ser Thr Leu Ala Ser
1               5


<210> SEQ ID NO 73
<211> LENGTH: 10
<212> TYPE: PRT
<213> ORGANISM: Oryctolagus cuniculus

<400> SEQUENCE: 73

Ala Gly Gly Phe Ser Gly Asn Ile Phe Ala
1               5                   10


<210> SEQ ID NO 74
<211> LENGTH: 5
<212> TYPE: PRT
<213> ORGANISM: Oryctolagus cuniculus

<400> SEQUENCE: 74

Ser Tyr Ala Met Ser
1               5


<210> SEQ ID NO 75
<211> LENGTH: 16
<212> TYPE: PRT
<213> ORGANISM: Oryctolagus cuniculus

<400> SEQUENCE: 75

Ile Ile Gly Gly Phe Gly Thr Thr Tyr Tyr Ala Thr Trp Ala Lys Gly
1               5                   10                  15


<210> SEQ ID NO 76
<211> LENGTH: 9
<212> TYPE: PRT
<213> ORGANISM: Oryctolagus cuniculus
```

<400> SEQUENCE: 76

Gly Gly Pro Gly Asn Gly Gly Asp Ile
1 5

<210> SEQ ID NO 77
<211> LENGTH: 493
<212> TYPE: DNA
<213> ORGANISM: Oryctolagus cuniculus

<400> SEQUENCE: 77
atggacacga gggcccccac tcagctgctg gggctcctgc tgctctggct cccaggtgcc 60
acatttgccc aagtgctgac ccagactcca tcgcctgtgt ctgcagctgt gggaggcaca 120
gtcaccatca actgccaggc cagtcagagt gttgatgata acaactggtt aggctggtat 180
cagcagaaac gagggcagcc tcccaagtac ctgatctatt ctgcatccac tctggcatct 240
ggggtcccat cgcggttcaa aggcagtgga tctgggacac agttcactct caccatcagc 300
gacctggagt gtgacgatgc tgccacttac tactgtgcag gcggttttag tggtaatatc 360
tttgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tct 493

<210> SEQ ID NO 78
<211> LENGTH: 493
<212> TYPE: DNA
<213> ORGANISM: Oryctolagus cuniculus

<400> SEQUENCE: 78
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gcttctccct cagtagctat gcaatgagct gggtccgcca ggctccagga 180
aaggggctgg agtggatcgg aatcattggt ggttttggta ccacatacta cgcgacctgg 240
gcgaaaggcc gattcaccat ctccaaaacc tcgaccacgg tggatctgag aatcaccagt 300
ccgacaaccg aggacacggc cacctatttc tgtgccagag gtggtcctgg taatggtggt 360
gacatctggg gccaagggac cctggtcacc gtctcgagcg cctccaccaa gggcccatcg 420
gtcttccccc tggcaccctc ctccaagagc acctctgggg gcacagcggc cctgggctgc 480
ctggtcaagg act 493

<210> SEQ ID NO 79
<211> LENGTH: 39
<212> TYPE: DNA
<213> ORGANISM: Oryctolagus cuniculus

<400> SEQUENCE: 79
caggccagtc agagtgttga tgataacaac tggttaggc 39

<210> SEQ ID NO 80
<211> LENGTH: 21
<212> TYPE: DNA
<213> ORGANISM: Oryctolagus cuniculus

<400> SEQUENCE: 80
tctgcatcca ctctggcatc t 21

<210> SEQ ID NO 81
<211> LENGTH: 30

<212> TYPE: DNA
<213> ORGANISM: Oryctolagus cuniculus

<400> SEQUENCE: 81
gcaggcggtt ttagtggtaa tatctttgct 30

<210> SEQ ID NO 82
<211> LENGTH: 15
<212> TYPE: DNA
<213> ORGANISM: Oryctolagus cuniculus

<400> SEQUENCE: 82
agctatgcaa tgagc 15

<210> SEQ ID NO 83
<211> LENGTH: 48
<212> TYPE: DNA
<213> ORGANISM: Oryctolagus cuniculus

<400> SEQUENCE: 83
atcattggtg gttttggtac cacatactac gcgacctggg cgaaaggc 48

<210> SEQ ID NO 84
<211> LENGTH: 27
<212> TYPE: DNA
<213> ORGANISM: Oryctolagus cuniculus

<400> SEQUENCE: 84
ggtggtcctg gtaatggtgg tgacatc 27

<210> SEQ ID NO 85
<211> LENGTH: 164
<212> TYPE: PRT
<213> ORGANISM: Oryctolagus cuniculus

<400> SEQUENCE: 85

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Val Pro Val Gly Gly Thr Val Thr Ile Lys Cys Gln Ser Ser
        35                  40                  45

Gln Ser Val Tyr Asn Asn Phe Leu Ser Trp Tyr Gln Gln Lys Pro Gly
    50                  55                  60

Gln Pro Pro Lys Leu Leu Ile Tyr Gln Ala Ser Lys Leu Ala Ser Gly
65                  70                  75                  80

Val Pro Asp Arg Phe Ser Gly Ser Gly Ser Gly Thr Gln Phe Thr Leu
                85                  90                  95

Thr Ile Ser Gly Val Gln Cys Asp Asp Ala Ala Thr Tyr Tyr Cys Leu
            100                 105                 110

Gly Gly Tyr Asp Asp Asp Ala Asp Asn Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe

<210> SEQ ID NO 86
<211> LENGTH: 170

<212> TYPE: PRT
<213> ORGANISM: Oryctolagus cuniculus

<400> SEQUENCE: 86

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Asp Tyr Ala Met Ser Trp Val Arg Gln Ala Pro Gly Lys Gly Leu Glu
    50                  55                  60

Trp Ile Gly Ile Ile Tyr Ala Gly Ser Gly Ser Thr Trp Tyr Ala Ser
65                  70                  75                  80

Trp Ala Lys Gly Arg Phe Thr Ile Ser Lys Thr Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Asp Gly Tyr Asp Asp Tyr Gly Asp Phe Asp Arg Leu Asp Leu
        115                 120                 125

Trp Gly Pro Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp
                165                 170

<210> SEQ ID NO 87
<211> LENGTH: 12
<212> TYPE: PRT
<213> ORGANISM: Oryctolagus cuniculus

<400> SEQUENCE: 87

Gln Ser Ser Gln Ser Val Tyr Asn Asn Phe Leu Ser
1               5                   10

<210> SEQ ID NO 88
<211> LENGTH: 7
<212> TYPE: PRT
<213> ORGANISM: Oryctolagus cuniculus

<400> SEQUENCE: 88

Gln Ala Ser Lys Leu Ala Ser
1               5

<210> SEQ ID NO 89
<211> LENGTH: 11
<212> TYPE: PRT
<213> ORGANISM: Oryctolagus cuniculus

<400> SEQUENCE: 89

Leu Gly Gly Tyr Asp Asp Asp Ala Asp Asn Ala
1               5                   10

<210> SEQ ID NO 90
<211> LENGTH: 5
<212> TYPE: PRT
<213> ORGANISM: Oryctolagus cuniculus

<400> SEQUENCE: 90

Asp Tyr Ala Met Ser

-continued 1 5

<210> SEQ ID NO 91
<211> LENGTH: 17
<212> TYPE: PRT
<213> ORGANISM: Oryctolagus cuniculus

<400> SEQUENCE: 91

Ile Ile Tyr Ala Gly Ser Gly Ser Thr Trp Tyr Ala Ser Trp Ala Lys
1 5 10 15

Gly

<210> SEQ ID NO 92
<211> LENGTH: 14
<212> TYPE: PRT
<213> ORGANISM: Oryctolagus cuniculus

<400> SEQUENCE: 92

Asp Gly Tyr Asp Asp Tyr Gly Asp Phe Asp Arg Leu Asp Leu
1 5 10

<210> SEQ ID NO 93
<211> LENGTH: 492
<212> TYPE: DNA
<213> ORGANISM: Oryctolagus cuniculus

<400> SEQUENCE: 93
atggacacga gggcccccac tcagctgctg gggctcctgc tgctctggct cccaggtgcc 60
acatttgcag ccgtgctgac ccagacacca tcgcccgtgt ctgtacctgt gggaggcaca 120
gtcaccatca agtgccagtc cagtcagagt gtttataata atttcttatc gtggtatcag 180
cagaaaccag ggcagcctcc caagctcctg atctaccagg catccaaact ggcatctggg 240
gtcccagata ggttcagcgg cagtggatct gggacacagt tcactctcac catcagcggc 300
gtgcagtgtg acgatgctgc cacttactac tgtctaggcg gttatgatga tgatgctgat 360
aatgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tc 492

<210> SEQ ID NO 94
<211> LENGTH: 511
<212> TYPE: DNA
<213> ORGANISM: Oryctolagus cuniculus

<400> SEQUENCE: 94
atggagactg ggctgcgctg gcttctcctg gtcgctgtgc tcaaaggtgt ccagtgtcag 60
tcggtggagg agtccggggg tcgcctggtc acgcctggga cacccctgac gctcacctgc 120
acagtctctg gaatcgacct cagtgactat gcaatgagct gggtccgcca ggctccaggg 180
aaggggctgg aatggatcgg aatcatttat gctggtagtg gtagcacatg gtacgcgagc 240
tgggcgaaag gccgattcac catctccaaa acctcgacca cggtggatct gaaaatcacc 300
agtccgacaa ccgaggacac ggccacctat ttctgtgcca gagatggata cgatgactat 360
ggtgatttcg atcgattgga tctctggggc ccaggcaccc tcgtcaccgt ctcgagcgcc 420
tccaccaagg gcccatcggt cttccccctg gcaccctcct ccaagagcac ctctgggggc 480
acagcggccc tgggctgcct ggtcaaggac t 511

<210> SEQ ID NO 95

<211> LENGTH: 36
<212> TYPE: DNA
<213> ORGANISM: Oryctolagus cuniculus

<400> SEQUENCE: 95
cagtccagtc agagtgttta taataatttc ttatcg 36

<210> SEQ ID NO 96
<211> LENGTH: 21
<212> TYPE: DNA
<213> ORGANISM: Oryctolagus cuniculus

<400> SEQUENCE: 96
caggcatcca aactggcatc t 21

<210> SEQ ID NO 97
<211> LENGTH: 33
<212> TYPE: DNA
<213> ORGANISM: Oryctolagus cuniculus

<400> SEQUENCE: 97
ctaggcggtt atgatgatga tgctgataat gct 33

<210> SEQ ID NO 98
<211> LENGTH: 15
<212> TYPE: DNA
<213> ORGANISM: Oryctolagus cuniculus

<400> SEQUENCE: 98
gactatgcaa tgagc 15

<210> SEQ ID NO 99
<211> LENGTH: 51
<212> TYPE: DNA
<213> ORGANISM: Oryctolagus cuniculus

<400> SEQUENCE: 99
atcatttatg ctggtagtgg tagcacatgg tacgcgagct gggcgaaagg c 51

<210> SEQ ID NO 100
<211> LENGTH: 42
<212> TYPE: DNA
<213> ORGANISM: Oryctolagus cuniculus

<400> SEQUENCE: 100
gatggatacg atgactatgg tgatttcgat cgattggatc tc 42

<210> SEQ ID NO 101
<211> LENGTH: 164
<212> TYPE: PRT
<213> ORGANISM: Oryctolagus cuniculus

<400> SEQUENCE: 101

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Lys Cys Gln Ala Ser
        35                  40                  45

Gln Ser Ile Asn Asn Glu Leu Ser Trp Tyr Gln Gln Lys Ser Gly Gln
    50                  55                  60

Arg Pro Lys Leu Leu Ile Tyr Arg Ala Ser Thr Leu Ala Ser Gly Val
65                  70                  75                  80
```

```
Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Ser Leu Arg Asn Ile Asp Asn Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe


<210> SEQ ID NO 102
<211> LENGTH: 166
<212> TYPE: PRT
<213> ORGANISM: Oryctolagus cuniculus

<400> SEQUENCE: 102

Met Glu Thr Gly Leu Arg Trp Leu Leu Leu Val Ala Val Leu Ser Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Met Thr Trp Val Arg Gln Ala Pro Gly Lys Gly Leu Glu
    50                  55                  60

Trp Ile Gly Met Ile Tyr Gly Ser Asp Glu Thr Ala Tyr Ala Asn Trp
65                  70                  75                  80

Ala Ile Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Asp Asp Ser Ser Asp Trp Asp Ala Lys Phe Asn Leu Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys
                165


<210> SEQ ID NO 103
<211> LENGTH: 11
<212> TYPE: PRT
<213> ORGANISM: Oryctolagus cuniculus

<400> SEQUENCE: 103

Gln Ala Ser Gln Ser Ile Asn Asn Glu Leu Ser
1               5                   10


<210> SEQ ID NO 104
<211> LENGTH: 7
<212> TYPE: PRT
<213> ORGANISM: Oryctolagus cuniculus

<400> SEQUENCE: 104

Arg Ala Ser Thr Leu Ala Ser
1               5
```

<210> SEQ ID NO 105
<211> LENGTH: 12
<212> TYPE: PRT
<213> ORGANISM: Oryctolagus cuniculus

<400> SEQUENCE: 105

Gln Gln Gly Tyr Ser Leu Arg Asn Ile Asp Asn Ala
1 5 10

<210> SEQ ID NO 106
<211> LENGTH: 5
<212> TYPE: PRT
<213> ORGANISM: Oryctolagus cuniculus

<400> SEQUENCE: 106

Asn Tyr Tyr Met Thr
1 5

<210> SEQ ID NO 107
<211> LENGTH: 16
<212> TYPE: PRT
<213> ORGANISM: Oryctolagus cuniculus

<400> SEQUENCE: 107

Met Ile Tyr Gly Ser Asp Glu Thr Ala Tyr Ala Asn Trp Ala Ile Gly
1 5 10 15

<210> SEQ ID NO 108
<211> LENGTH: 12
<212> TYPE: PRT
<213> ORGANISM: Oryctolagus cuniculus

<400> SEQUENCE: 108

Asp Asp Ser Ser Asp Trp Asp Ala Lys Phe Asn Leu
1 5 10

<210> SEQ ID NO 109
<211> LENGTH: 492
<212> TYPE: DNA
<213> ORGANISM: Oryctolagus cuniculus

<400> SEQUENCE: 109
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca aatgccaggc cagtcagagc attaacaatg aattatcctg gtatcagcag 180
aaatcagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tc 492

<210> SEQ ID NO 110
<211> LENGTH: 499
<212> TYPE: DNA
<213> ORGANISM: Oryctolagus cuniculus

<400> SEQUENCE: 110
atggagactg ggctgcgctg gcttctcctg gtcgctgtgc tctcaggtgt ccagtgtcag 60
tcgctggagg agtccggggg tcgcctggtc acgcctggga cacccctgac actcacctgc 120
acagcctctg gattctccct cagtaactac tacatgacct gggtccgcca ggctccaggg 180
aaggggctgg aatggatcgg aatgatttat ggtagtgatg aaacagccta cgcgaactgg 240
gcgataggcc gattcaccat ctccaaaacc tcgaccacgg tggatctgaa aatgaccagt 300
ctgacagccg cggacacggc cacctatttc tgtgccagag atgatagtag tgactgggat 360
gcaaaattta acttgtgggg ccaagggacc ctcgtcaccg tctcgagcgc ctccaccaag 420
ggcccatcgg tcttcccct ggcaccctcc tccaagagca cctctggggg cacagcggcc 480
ctgggctgcc tggtcaagg 499

<210> SEQ ID NO 111
<211> LENGTH: 33
<212> TYPE: DNA
<213> ORGANISM: Oryctolagus cuniculus

<400> SEQUENCE: 111
caggccagtc agagcattaa caatgaatta tcc 33

<210> SEQ ID NO 112
<211> LENGTH: 21
<212> TYPE: DNA
<213> ORGANISM: Oryctolagus cuniculus

<400> SEQUENCE: 112
agggcatcca ctctggcatc t 21

<210> SEQ ID NO 113
<211> LENGTH: 36
<212> TYPE: DNA
<213> ORGANISM: Oryctolagus cuniculus

<400> SEQUENCE: 113
caacagggtt atagtctgag gaatattgat aatgct 36

<210> SEQ ID NO 114
<211> LENGTH: 15
<212> TYPE: DNA
<213> ORGANISM: Oryctolagus cuniculus

<400> SEQUENCE: 114
aactactaca tgacc 15

<210> SEQ ID NO 115
<211> LENGTH: 48
<212> TYPE: DNA
<213> ORGANISM: Oryctolagus cuniculus

<400> SEQUENCE: 115
atgatttatg gtagtgatga aacagcctac gcgaactggg cgataggc 48

<210> SEQ ID NO 116
<211> LENGTH: 36
<212> TYPE: DNA
<213> ORGANISM: Oryctolagus cuniculus

<400> SEQUENCE: 116
gatgatagta gtgactggga tgcaaaattt aacttg 36

<210> SEQ ID NO 117
<211> LENGTH: 109

<212> TYPE: PRT
<213> ORGANISM: Oryctolagus cuniculus

<400> SEQUENCE: 117

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Met Thr Trp Val Arg Gln Ala Pro Gly Lys Gly Leu Glu Trp Val
35 40 45

Gly Met Ile Tyr Gly Ser Asp Glu Thr Ala Tyr Ala Asn Trp Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu
100 105

<210> SEQ ID NO 118
<211> LENGTH: 109
<212> TYPE: PRT
<213> ORGANISM: Oryctolagus cuniculus

<400> SEQUENCE: 118

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Met Thr Trp Val Arg Gln Ala Pro Gly Lys Gly Leu Glu Trp Val
35 40 45

Gly Met Ile Tyr Gly Ser Asp Glu Thr Ala Tyr Ala Asn Ser Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu
100 105

<210> SEQ ID NO 119
<211> LENGTH: 100
<212> TYPE: PRT
<213> ORGANISM: Oryctolagus cuniculus

<400> SEQUENCE: 119

Asp Ile Gln Met Thr Gln Ser Pro Ser Thr Leu Ser Ala Ser Val Gly
1 5 10 15

Asp Arg Val Thr Ile Thr Cys Gln Ala Ser Gln Ser Ile Asn Asn Glu
20 25 30

Leu Ser Trp Tyr Gln Gln Lys Pro Gly Lys Ala Pro Lys Leu Leu Ile
35 40 45

Tyr Arg Ala Ser Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Gly Tyr Ser Leu Arg Asn
85 90 95

```
Ile Asp Asn Ala
            100


<210> SEQ ID NO 120
<211> LENGTH: 16
<212> TYPE: PRT
<213> ORGANISM: Oryctolagus cuniculus

<400> SEQUENCE: 120

Ile Ile Tyr Gly Ser Asp Glu Thr Ala Tyr Ala Thr Ser Ala Ile Gly
1               5                   10                  15


<210> SEQ ID NO 121
<211> LENGTH: 16
<212> TYPE: PRT
<213> ORGANISM: Oryctolagus cuniculus

<400> SEQUENCE: 121

Met Ile Tyr Gly Ser Asp Glu Thr Ala Tyr Ala Asn Ser Ala Ile Gly
1               5                   10                  15


<210> SEQ ID NO 122
<211> LENGTH: 123
<212> TYPE: PRT
<213> ORGANISM: Oryctolagus cuniculus

<400> SEQUENCE: 122

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ser Ser
        35                  40                  45

Gln Ser Val Gly Asn Asn Gln Asp Leu Ser Trp Phe Gln Gln Arg Pro
    50                  55                  60

Gly Gln Pro Pro Lys Leu Leu Ile Tyr Glu Ile Ser Lys Leu Glu Ser
65                  70                  75                  80

Gly Val Pro Ser Arg Phe Ser Gly Ser Gly Ser Gly Thr His Phe Thr
                85                  90                  95

Leu Thr Ile Ser Gly Val Gln Cys Asp Asp Ala Ala Thr Tyr Tyr Cys
            100                 105                 110

Leu Gly Gly Tyr Asp Asp Asp Ala Asp Asn Ala
        115                 120


<210> SEQ ID NO 123
<211> LENGTH: 128
<212> TYPE: PRT
<213> ORGANISM: Oryctolagus cuniculus

<400> SEQUENCE: 123

Met Glu Thr Gly Leu Arg Trp Leu Leu Leu Val Ala Val Leu Lys Gly
1               5                   10                  15

Val Gln Cys His Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Arg Thr Met Ser Trp Val Arg Gln Ala Pro Gly Lys Gly Leu Glu
    50                  55                  60

Trp Ile Gly Tyr Ile Trp Ser Gly Gly Ser Thr Tyr Tyr Ala Thr Trp
65                  70                  75                  80
```

```
Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Leu Gly Asp Thr Gly Gly His Ala Tyr Ala Thr Arg Leu Asn Leu
        115                 120                 125


<210> SEQ ID NO 124
<211> LENGTH: 13
<212> TYPE: PRT
<213> ORGANISM: Oryctolagus cuniculus

<400> SEQUENCE: 124

Gln Ser Ser Gln Ser Val Gly Asn Asn Gln Asp Leu Ser
1               5                   10


<210> SEQ ID NO 125
<211> LENGTH: 7
<212> TYPE: PRT
<213> ORGANISM: Oryctolagus cuniculus

<400> SEQUENCE: 125

Glu Ile Ser Lys Leu Glu Ser
1               5


<210> SEQ ID NO 126
<211> LENGTH: 11
<212> TYPE: PRT
<213> ORGANISM: Oryctolagus cuniculus

<400> SEQUENCE: 126

Leu Gly Gly Tyr Asp Asp Asp Ala Asp Asn Ala
1               5                   10


<210> SEQ ID NO 127
<211> LENGTH: 5
<212> TYPE: PRT
<213> ORGANISM: Oryctolagus cuniculus

<400> SEQUENCE: 127

Ser Arg Thr Met Ser
1               5


<210> SEQ ID NO 128
<211> LENGTH: 16
<212> TYPE: PRT
<213> ORGANISM: Oryctolagus cuniculus

<400> SEQUENCE: 128

Tyr Ile Trp Ser Gly Gly Ser Thr Tyr Tyr Ala Thr Trp Ala Lys Gly
1               5                   10                  15


<210> SEQ ID NO 129
<211> LENGTH: 15
<212> TYPE: PRT
<213> ORGANISM: Oryctolagus cuniculus

<400> SEQUENCE: 129

Leu Gly Asp Thr Gly Gly His Ala Tyr Ala Thr Arg Leu Asn Leu
1               5                   10                  15


<210> SEQ ID NO 130
<211> LENGTH: 369
<212> TYPE: DNA
```

<213> ORGANISM: Oryctolagus cuniculus

<400> SEQUENCE: 130
atggacacga gggcccccac tcagctgctg gggctcctgc tgctctggct cccaggtgcc 60
acatttgcag ccgtgctgac ccagacacca tcacccgtgt ctgcagctgt gggaggcaca 120
gtcaccatca gttgccagtc cagtcagagt gttggtaata accaggactt atcctggttt 180
cagcagagac cagggcagcc tcccaagctc ctgatctacg aaatatccaa actggaatct 240
ggggtcccat cgcggttcag cggcagtgga tctgggacac acttcactct caccatcagc 300
ggcgtacagt gtgacgatgc tgccacttac tactgtctag gcggttatga tgatgatgct 360
gataatgct 369

<210> SEQ ID NO 131
<211> LENGTH: 384
<212> TYPE: DNA
<213> ORGANISM: Oryctolagus cuniculus

<400> SEQUENCE: 131
atggagactg ggctgcgctg gcttctcctg gtcgctgtgc tcaaaggtgt ccagtgtcac 60
tcggtggagg agtccggggg tcgcctggtc acgcctggga cacccctgac actcacctgc 120
acagtctctg gattctccct cagtagtcgt acaatgtcct gggtccgcca ggctccaggg 180
aaggggctgg agtggatcgg atacatttgg agtggtggta gcacatacta cgcgacctgg 240
gcgaaaggcc gattcaccat ctccaaaacc tcgaccacgg tggatctgaa aatcaccagt 300
ccgacaaccg aggacacggc cacctatttc tgtgccagat tgggcgatac tggtggtcac 360
gcttatgcta ctcgcttaaa tctc 384

<210> SEQ ID NO 132
<211> LENGTH: 39
<212> TYPE: DNA
<213> ORGANISM: Oryctolagus cuniculus

<400> SEQUENCE: 132
cagtccagtc agagtgttgg taataaccag gacttatcc 39

<210> SEQ ID NO 133
<211> LENGTH: 21
<212> TYPE: DNA
<213> ORGANISM: Oryctolagus cuniculus

<400> SEQUENCE: 133
gaaatatcca aactggaatc t 21

<210> SEQ ID NO 134
<211> LENGTH: 33
<212> TYPE: DNA
<213> ORGANISM: Oryctolagus cuniculus

<400> SEQUENCE: 134
ctaggcggtt atgatgatga tgctgataat gct 33

<210> SEQ ID NO 135
<211> LENGTH: 15
<212> TYPE: DNA
<213> ORGANISM: Oryctolagus cuniculus

<400> SEQUENCE: 135
agtcgtacaa tgtcc 15

-continued

<210> SEQ ID NO 136
<211> LENGTH: 48
<212> TYPE: DNA
<213> ORGANISM: Oryctolagus cuniculus

<400> SEQUENCE: 136
tacatttgga gtggtggtag cacatactac gcgacctggg cgaaaggc 48

<210> SEQ ID NO 137
<211> LENGTH: 45
<212> TYPE: DNA
<213> ORGANISM: Oryctolagus cuniculus

<400> SEQUENCE: 137
ttgggcgata ctggtggtca cgcttatgct actcgcttaa atctc 45

<210> SEQ ID NO 138
<211> LENGTH: 123
<212> TYPE: PRT
<213> ORGANISM: Oryctolagus cuniculus

<400> SEQUENCE: 138

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Ser
20 25 30

Val Ser Ala Ala Val Gly Gly Thr Val Ser Ile Ser Cys Gln Ser Ser
35 40 45

Gln Ser Val Tyr Ser Asn Lys Tyr Leu Ala Trp Tyr Gln Gln Lys Pro
50 55 60

Gly Gln Pro Pro Lys Leu Leu Ile Tyr Trp Thr Ser Lys Leu Ala Ser
65 70 75 80

Gly Ala Pro Ser Arg Phe Ser Gly Ser Gly Ser Gly Thr Gln Phe Thr
85 90 95

Leu Thr Ile Ser Gly Val Gln Cys Asp Asp Ala Ala Thr Tyr Tyr Cys
100 105 110

Leu Gly Ala Tyr Asp Asp Asp Ala Asp Asn Ala
115 120

<210> SEQ ID NO 139
<211> LENGTH: 126
<212> TYPE: PRT
<213> ORGANISM: Oryctolagus cuniculus

<400> SEQUENCE: 139

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Lys Pro
20 25 30

Asp Glu Thr Leu Thr Leu Thr Cys Thr Ala Ser Gly Phe Ser Leu Glu
35 40 45

Gly Gly Tyr Met Thr Trp Val Arg Gln Ala Pro Gly Lys Gly Leu Glu
50 55 60

Trp Ile Gly Ile Ser Tyr Asp Ser Gly Ser Thr Tyr Tyr Ala Ser Trp
65 70 75 80

Ala Lys Gly Arg Phe Thr Ile Ser Lys Thr Ser Ser Thr Thr Val Asp
85 90 95

Leu Lys Met Thr Ser Leu Thr Thr Glu Asp Thr Ala Thr Tyr Phe Cys
100 105 110

Val Arg Ser Leu Lys Tyr Pro Thr Val Thr Ser Asp Asp Leu
115 120 125

<210> SEQ ID NO 140
<211> LENGTH: 13
<212> TYPE: PRT
<213> ORGANISM: Oryctolagus cuniculus

<400> SEQUENCE: 140

Gln Ser Ser Gln Ser Val Tyr Ser Asn Lys Tyr Leu Ala
1 5 10

<210> SEQ ID NO 141
<211> LENGTH: 7
<212> TYPE: PRT
<213> ORGANISM: Oryctolagus cuniculus

<400> SEQUENCE: 141

Trp Thr Ser Lys Leu Ala Ser
1 5

<210> SEQ ID NO 142
<211> LENGTH: 11
<212> TYPE: PRT
<213> ORGANISM: Oryctolagus cuniculus

<400> SEQUENCE: 142

Leu Gly Ala Tyr Asp Asp Asp Ala Asp Asn Ala
1 5 10

<210> SEQ ID NO 143
<211> LENGTH: 5
<212> TYPE: PRT
<213> ORGANISM: Oryctolagus cuniculus

<400> SEQUENCE: 143

Gly Gly Tyr Met Thr
1 5

<210> SEQ ID NO 144
<211> LENGTH: 16
<212> TYPE: PRT
<213> ORGANISM: Oryctolagus cuniculus

<400> SEQUENCE: 144

Ile Ser Tyr Asp Ser Gly Ser Thr Tyr Tyr Ala Ser Trp Ala Lys Gly
1 5 10 15

<210> SEQ ID NO 145
<211> LENGTH: 12
<212> TYPE: PRT
<213> ORGANISM: Oryctolagus cuniculus

<400> SEQUENCE: 145

Ser Leu Lys Tyr Pro Thr Val Thr Ser Asp Asp Leu
1 5 10

<210> SEQ ID NO 146
<211> LENGTH: 369
<212> TYPE: DNA
<213> ORGANISM: Oryctolagus cuniculus

<400> SEQUENCE: 146
atggacacga gggcccccac tcagctgctg gggctcctgc tgctctggct cccaggtgcc 60
acatttgcag ccgtgctgac ccagacacca tcgtccgtgt ctgcagctgt gggaggcaca 120
gtcagcatca gttgccagtc cagtcagagt gtttatagta ataagtacct agcctggtat 180
cagcagaaac cagggcagcc tcccaagctc ctgatctact ggacatccaa actggcatct 240
ggggccccat cacggttcag cggcagtgga tctgggacac aattcactct caccatcagc 300
ggcgtgcagt gtgacgatgc tgccacttac tactgtctag gcgcttatga tgatgatgct 360
gataatgct 369

<210> SEQ ID NO 147
<211> LENGTH: 378
<212> TYPE: DNA
<213> ORGANISM: Oryctolagus cuniculus

<400> SEQUENCE: 147
atggagactg ggctgcgctg gcttctcctg gtcgctgtgc tcaaaggtgt ccagtgtcag 60
tcggtggaag agtccggggg tcgcctggtc aagcctgacg aaaccctgac actcacctgc 120
acagcctctg gattctccct ggagggcggc tacatgacct gggtccgcca ggctccaggg 180
aaggggctgg aatggatcgg aatcagttat gatagtggta gcacatacta cgcgagctgg 240
gcgaaaggcc gattcaccat ctccaagacc tcgtcgacca cggtggatct gaaaatgacc 300
agtctgacaa ccgaggacac ggccacctat ttctgcgtca gatcactaaa atatcctact 360
gttacttctg atgacttg 378

<210> SEQ ID NO 148
<211> LENGTH: 39
<212> TYPE: DNA
<213> ORGANISM: Oryctolagus cuniculus

<400> SEQUENCE: 148
cagtccagtc agagtgttta tagtaataag tacctagcc 39

<210> SEQ ID NO 149
<211> LENGTH: 21
<212> TYPE: DNA
<213> ORGANISM: Oryctolagus cuniculus

<400> SEQUENCE: 149
tggacatcca aactggcatc t 21

<210> SEQ ID NO 150
<211> LENGTH: 33
<212> TYPE: DNA
<213> ORGANISM: Oryctolagus cuniculus

<400> SEQUENCE: 150
ctaggcgctt atgatgatga tgctgataat gct 33

<210> SEQ ID NO 151
<211> LENGTH: 15
<212> TYPE: DNA
<213> ORGANISM: Oryctolagus cuniculus

<400> SEQUENCE: 151
ggcggctaca tgacc 15

<210> SEQ ID NO 152
<211> LENGTH: 48
<212> TYPE: DNA
<213> ORGANISM: Oryctolagus cuniculus

<400> SEQUENCE: 152
atcagttatg atagtggtag cacatactac gcgagctggg cgaaaggc 48

<210> SEQ ID NO 153
<211> LENGTH: 36
<212> TYPE: DNA
<213> ORGANISM: Oryctolagus cuniculus

<400> SEQUENCE: 153
tcactaaaat atcctactgt tacttctgat gacttg 36

<210> SEQ ID NO 154
<211> LENGTH: 123
<212> TYPE: PRT
<213> ORGANISM: Oryctolagus cuniculus

<400> SEQUENCE: 154

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ser Ser
        35                  40                  45

Gln Ser Val Tyr Asn Asn Asn Asp Leu Ala Trp Tyr Gln Gln Lys Pro
    50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Ala Tyr Tyr Cys
            100                 105                 110

Leu Gly Gly Tyr Asp Asp Asp Ala Asp Asn Ala
        115                 120
```

<210> SEQ ID NO 155
<211> LENGTH: 129
<212> TYPE: PRT
<213> ORGANISM: Oryctolagus cuniculus

<400> SEQUENCE: 155

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Leu Ser Leu Ser
        35                  40                  45

Ser Asn Thr Ile Asn Trp Val Arg Gln Ala Pro Gly Lys Gly Leu Glu
    50                  55                  60

Trp Ile Gly Tyr Ile Trp Ser Gly Gly Ser Thr Tyr Tyr Ala Ser Trp
65                  70                  75                  80

Val Asn Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Gly Gly Tyr Ala Ser Gly Gly Tyr Pro Tyr Ala Thr Arg Leu Asp
        115                 120                 125

Leu
```

<210> SEQ ID NO 156
<211> LENGTH: 13
<212> TYPE: PRT
<213> ORGANISM: Oryctolagus cuniculus

<400> SEQUENCE: 156

Gln Ser Ser Gln Ser Val Tyr Asn Asn Asn Asp Leu Ala
1 5 10

<210> SEQ ID NO 157
<211> LENGTH: 7
<212> TYPE: PRT
<213> ORGANISM: Oryctolagus cuniculus

<400> SEQUENCE: 157

Tyr Ala Ser Thr Leu Ala Ser
1 5

<210> SEQ ID NO 158
<211> LENGTH: 11
<212> TYPE: PRT
<213> ORGANISM: Oryctolagus cuniculus

<400> SEQUENCE: 158

Leu Gly Gly Tyr Asp Asp Asp Ala Asp Asn Ala
1 5 10

<210> SEQ ID NO 159
<211> LENGTH: 5
<212> TYPE: PRT
<213> ORGANISM: Oryctolagus cuniculus

<400> SEQUENCE: 159

Ser Asn Thr Ile Asn
1 5

<210> SEQ ID NO 160
<211> LENGTH: 16
<212> TYPE: PRT
<213> ORGANISM: Oryctolagus cuniculus

<400> SEQUENCE: 160

Tyr Ile Trp Ser Gly Gly Ser Thr Tyr Tyr Ala Ser Trp Val Asn Gly
1 5 10 15

<210> SEQ ID NO 161
<211> LENGTH: 16
<212> TYPE: PRT
<213> ORGANISM: Oryctolagus cuniculus

<400> SEQUENCE: 161

Gly Gly Tyr Ala Ser Gly Gly Tyr Pro Tyr Ala Thr Arg Leu Asp Leu
1 5 10 15

<210> SEQ ID NO 162
<211> LENGTH: 369
<212> TYPE: DNA
<213> ORGANISM: Oryctolagus cuniculus

<400> SEQUENCE: 162
atggacacga gggcccccac tcagctgctg gggctcctgc tgctctggct cccaggtgcc 60
acatttgcag ccgtgctgac ccagacacca tcacccgtgt ctgcagctgt gggaggcaca 120
gtcaccatca gttgccagtc cagtcagagt gtttataata ataacgactt agcctggtat 180
cagcagaaac cagggcagcc tcctaaactc ctgatctatt atgcatccac tctggcatct 240
ggggtcccat cgcggttcaa aggcagtgga tctgggacac agttcactct caccatcagc 300
ggcgtgcagt gtgacgatgc tgccgcttac tactgtctag gcggttatga tgatgatgct 360
gataatgct 369

<210> SEQ ID NO 163
<211> LENGTH: 387
<212> TYPE: DNA
<213> ORGANISM: Oryctolagus cuniculus

<400> SEQUENCE: 163
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtatctg gattatccct cagtagcaat acaataaact gggtccgcca ggctccaggg 180
aaggggctgg agtggatcgg atacatttgg agtggtggta gtacatacta cgcgagctgg 240
gtgaatggtc gattcaccat ctccaaaacc tcgaccacgg tggatctgaa aatcaccagt 300
ccgacaaccg aggacacggc cacctatttc tgtgccagag ggggttacgc tagtggtggt 360
tatccttatg ccactcggtt ggatctc 387

<210> SEQ ID NO 164
<211> LENGTH: 39
<212> TYPE: DNA
<213> ORGANISM: Oryctolagus cuniculus

<400> SEQUENCE: 164
cagtccagtc agagtgttta taataataac gacttagcc 39

<210> SEQ ID NO 165
<211> LENGTH: 21
<212> TYPE: DNA
<213> ORGANISM: Oryctolagus cuniculus

<400> SEQUENCE: 165
tatgcatcca ctctggcatc t 21

<210> SEQ ID NO 166
<211> LENGTH: 33
<212> TYPE: DNA
<213> ORGANISM: Oryctolagus cuniculus

<400> SEQUENCE: 166
ctaggcggtt atgatgatga tgctgataat gct 33

<210> SEQ ID NO 167
<211> LENGTH: 15
<212> TYPE: DNA
<213> ORGANISM: Oryctolagus cuniculus

<400> SEQUENCE: 167
agcaatacaa taaac 15

<210> SEQ ID NO 168
<211> LENGTH: 48
<212> TYPE: DNA
<213> ORGANISM: Oryctolagus cuniculus

<400> SEQUENCE: 168
tacatttgga gtggtggtag tacatactac gcgagctggg tgaatggt 48

<210> SEQ ID NO 169
<211> LENGTH: 48
<212> TYPE: DNA
<213> ORGANISM: Oryctolagus cuniculus

<400> SEQUENCE: 169
gggggttacg ctagtggtgg ttatccttat gccactcggt tggatctc 48

<210> SEQ ID NO 170
<211> LENGTH: 123
<212> TYPE: PRT
<213> ORGANISM: Oryctolagus cuniculus

<400> SEQUENCE: 170

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Ser
20 25 30

Val Ser Ala Ala Val Gly Gly Thr Val Thr Ile Asn Cys Gln Ser Ser
35 40 45

Gln Ser Val Tyr Asn Asn Asp Tyr Leu Ser Trp Tyr Gln Gln Arg Pro
50 55 60

Gly Gln Arg Pro Lys Leu Leu Ile Tyr Gly Ala Ser Lys Leu Ala Ser
65 70 75 80

Gly Val Pro Ser Arg Phe Lys Gly Ser Gly Ser Gly Lys Gln Phe Thr
85 90 95

Leu Thr Ile Ser Gly Val Gln Cys Asp Asp Ala Ala Thr Tyr Tyr Cys
100 105 110

Leu Gly Asp Tyr Asp Asp Asp Ala Asp Asn Thr
115 120

<210> SEQ ID NO 171
<211> LENGTH: 123
<212> TYPE: PRT
<213> ORGANISM: Oryctolagus cuniculus

<400> SEQUENCE: 171

Met Glu Thr Gly Leu Arg Trp Leu Leu Leu Val Ala Val Leu Lys Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Val Ser Gly Phe Thr Leu Ser
35 40 45

Thr Asn Tyr Tyr Leu Ser Trp Val Arg Gln Ala Pro Gly Lys Gly Leu
50 55 60

Glu Trp Ile Gly Ile Ile Tyr Pro Ser Gly Asn Thr Tyr Cys Ala Lys
65 70 75 80

Trp Ala Lys Gly Arg Phe Thr Ile Ser Lys Thr Ser Ser Thr Thr Val
85 90 95

Asp Leu Lys Met Thr Ser Pro Thr Thr Glu Asp Thr Ala Thr Tyr Phe
100 105 110

Cys Ala Arg Asn Tyr Gly Gly Asp Glu Ser Leu
115 120

<210> SEQ ID NO 172
<211> LENGTH: 13
<212> TYPE: PRT
<213> ORGANISM: Oryctolagus cuniculus

<400> SEQUENCE: 172

Gln Ser Ser Gln Ser Val Tyr Asn Asn Asp Tyr Leu Ser
1 5 10

<210> SEQ ID NO 173
<211> LENGTH: 7
<212> TYPE: PRT
<213> ORGANISM: Oryctolagus cuniculus

<400> SEQUENCE: 173

Gly Ala Ser Lys Leu Ala Ser
1 5

<210> SEQ ID NO 174
<211> LENGTH: 11
<212> TYPE: PRT
<213> ORGANISM: Oryctolagus cuniculus

<400> SEQUENCE: 174

Leu Gly Asp Tyr Asp Asp Asp Ala Asp Asn Thr
1 5 10

<210> SEQ ID NO 175
<211> LENGTH: 6
<212> TYPE: PRT
<213> ORGANISM: Oryctolagus cuniculus

<400> SEQUENCE: 175

Thr Asn Tyr Tyr Leu Ser
1 5

<210> SEQ ID NO 176
<211> LENGTH: 16
<212> TYPE: PRT
<213> ORGANISM: Oryctolagus cuniculus

<400> SEQUENCE: 176

Ile Ile Tyr Pro Ser Gly Asn Thr Tyr Cys Ala Lys Trp Ala Lys Gly
1 5 10 15

<210> SEQ ID NO 177
<211> LENGTH: 8
<212> TYPE: PRT
<213> ORGANISM: Oryctolagus cuniculus

<400> SEQUENCE: 177

Asn Tyr Gly Gly Asp Glu Ser Leu
1 5

<210> SEQ ID NO 178
<211> LENGTH: 369
<212> TYPE: DNA
<213> ORGANISM: Oryctolagus cuniculus

<400> SEQUENCE: 178
atggacacga gggcccccac tcagctgctg gggctcctgc tgctctggct cccaggtgcc 60
acatttgcag ccgtgctgac ccagacacca tcctccgtgt ctgcagctgt gggaggcaca 120
gtcaccatca attgccagtc cagtcagagt gtttataata acgactactt atcctggtat 180
caacagaggc cagggcaacg tcccaagctc ctaatctatg gtgcttccaa actggcatct 240
ggggtcccgt cacggttcaa aggcagtgga tctgggaaac agtttactct caccatcagc 300
ggcgtgcagt gtgacgatgc tgccacttac tactgtctgg gcgattatga tgatgatgct 360

-continued gataatact 369

<210> SEQ ID NO 179
<211> LENGTH: 369
<212> TYPE: DNA
<213> ORGANISM: Oryctolagus cuniculus

<400> SEQUENCE: 179
atggagactg ggctgcgctg gcttctcctg gtcgctgtgc tcaaaggtgt ccagtgtcag 60
tcgctggagg agtccggggg tcgcctggtc acgcctggga cacccctgac actcacttgc 120
acagtctctg gattcaccct cagtaccaac tactacctga gctgggtccg ccaggctcca 180
gggaaggggc tagaatggat cggaatcatt tatcctagtg gtaacacata ttgcgcgaag 240
tgggcgaaag gccgattcac catctccaaa acctcgtcga ccacggtgga tctgaaaatg 300
accagtccga caaccgagga cacagccacg tatttctgtg ccagaaatta tggtggtgat 360
gaaagtttg 369

<210> SEQ ID NO 180
<211> LENGTH: 39
<212> TYPE: DNA
<213> ORGANISM: Oryctolagus cuniculus

<400> SEQUENCE: 180
cagtccagtc agagtgttta taataacgac tacttatcc 39

<210> SEQ ID NO 181
<211> LENGTH: 21
<212> TYPE: DNA
<213> ORGANISM: Oryctolagus cuniculus

<400> SEQUENCE: 181
ggtgcttcca aactggcatc t 21

<210> SEQ ID NO 182
<211> LENGTH: 33
<212> TYPE: DNA
<213> ORGANISM: Oryctolagus cuniculus

<400> SEQUENCE: 182
ctgggcgatt atgatgatga tgctgataat act 33

<210> SEQ ID NO 183
<211> LENGTH: 18
<212> TYPE: DNA
<213> ORGANISM: Oryctolagus cuniculus

<400> SEQUENCE: 183
accaactact acctgagc 18

<210> SEQ ID NO 184
<211> LENGTH: 48
<212> TYPE: DNA
<213> ORGANISM: Oryctolagus cuniculus

<400> SEQUENCE: 184
atcatttatc ctagtggtaa cacatattgc gcgaagtggg cgaaaggc 48

<210> SEQ ID NO 185
<211> LENGTH: 24
<212> TYPE: DNA
<213> ORGANISM: Oryctolagus cuniculus

<400> SEQUENCE: 185
aattatggtg gtgatgaaag tttg 24

<210> SEQ ID NO 186
<211> LENGTH: 119
<212> TYPE: PRT
<213> ORGANISM: Oryctolagus cuniculus

<400> SEQUENCE: 186

Met Asp Thr Arg Ala Pro Thr Gln Leu Leu Gly Leu Leu Leu Leu Trp
1 5 10 15

Leu Pro Gly Ala Arg Cys Asp Val Val Met Thr Gln Thr Pro Ala Ser
20 25 30

Val Glu Ala Ala Val Gly Gly Thr Val Thr Ile Lys Cys Gln Ala Ser
35 40 45

Glu Thr Ile Gly Asn Ala Leu Ala Trp Tyr Gln Gln Lys Ser Gly Gln
50 55 60

Pro Pro Lys Leu Leu Ile Tyr Lys Ala Ser Lys Leu Ala Ser Gly Val
65 70 75 80

Pro Ser Arg Phe Lys Gly Ser Gly Ser Gly Thr Glu Tyr Thr Leu Thr
85 90 95

Ile Ser Asp Leu Glu Cys Ala Asp Ala Ala Thr Tyr Tyr Cys Gln Trp
100 105 110

Cys Tyr Phe Gly Asp Ser Val
115

<210> SEQ ID NO 187
<211> LENGTH: 128
<212> TYPE: PRT
<213> ORGANISM: Oryctolagus cuniculus

<400> SEQUENCE: 187

Met Glu Thr Gly Leu Arg Trp Leu Leu Leu Val Thr Val Leu Lys Gly
1 5 10 15

Val Gln Cys Gln Glu Gln Leu Val Glu Ser Gly Gly Gly Leu Val Gln
20 25 30

Pro Glu Gly Ser Leu Thr Leu Thr Cys Thr Ala Ser Gly Phe Asp Phe
35 40 45

Ser Ser Gly Tyr Tyr Met Cys Trp Val Arg Gln Ala Pro Gly Lys Gly
50 55 60

Leu Glu Trp Ile Ala Cys Ile Phe Thr Ile Thr Thr Asn Thr Tyr Tyr
65 70 75 80

Ala Ser Trp Ala Lys Gly Arg Phe Thr Ile Ser Lys Thr Ser Ser Thr
85 90 95

Thr Val Thr Leu Gln Met Thr Ser Leu Thr Ala Ala Asp Thr Ala Thr
100 105 110

Tyr Leu Cys Ala Arg Gly Ile Tyr Ser Asp Asn Asn Tyr Tyr Ala Leu
115 120 125

<210> SEQ ID NO 188
<211> LENGTH: 11
<212> TYPE: PRT
<213> ORGANISM: Oryctolagus cuniculus

<400> SEQUENCE: 188

Gln Ala Ser Glu Thr Ile Gly Asn Ala Leu Ala
1 5 10

<210> SEQ ID NO 189
<211> LENGTH: 7
<212> TYPE: PRT
<213> ORGANISM: Oryctolagus cuniculus

<400> SEQUENCE: 189

Lys Ala Ser Lys Leu Ala Ser
1               5

<210> SEQ ID NO 190
<211> LENGTH: 9
<212> TYPE: PRT
<213> ORGANISM: Oryctolagus cuniculus

<400> SEQUENCE: 190

Gln Trp Cys Tyr Phe Gly Asp Ser Val
1               5

<210> SEQ ID NO 191
<211> LENGTH: 6
<212> TYPE: PRT
<213> ORGANISM: Oryctolagus cuniculus

<400> SEQUENCE: 191

Ser Gly Tyr Tyr Met Cys
1               5

<210> SEQ ID NO 192
<211> LENGTH: 17
<212> TYPE: PRT
<213> ORGANISM: Oryctolagus cuniculus

<400> SEQUENCE: 192

Cys Ile Phe Thr Ile Thr Thr Asn Thr Tyr Tyr Ala Ser Trp Ala Lys
1               5                   10                  15

Gly

<210> SEQ ID NO 193
<211> LENGTH: 11
<212> TYPE: PRT
<213> ORGANISM: Oryctolagus cuniculus

<400> SEQUENCE: 193

Gly Ile Tyr Ser Asp Asn Asn Tyr Tyr Ala Leu
1               5                   10

<210> SEQ ID NO 194
<211> LENGTH: 357
<212> TYPE: DNA
<213> ORGANISM: Oryctolagus cuniculus

<400> SEQUENCE: 194
atggacacga gggcccccac tcagctgctg gggctcctgc tgctctggct cccaggtgcc      60
agatgtgatg ttgtgatgac ccagactcca gcctccgtgg aggcagctgt gggaggcaca     120
gtcaccatca agtgccaggc cagtgagacc attggcaatg cattagcctg gtatcagcag     180
aaatcagggc agcctcccaa gctcctgatc tacaaggcat ccaaactggc atctggggtc     240
ccatcgcggt tcaaaggcag tggatctggg acagagtaca ctctcaccat cagcgacctg     300
gagtgtgccg atgctgccac ttactactgt caatggtgtt attttggtga tagtgtt        357

<210> SEQ ID NO 195
<211> LENGTH: 384
<212> TYPE: DNA

<213> ORGANISM: Oryctolagus cuniculus

<400> SEQUENCE: 195
atggagactg ggctgcgctg gcttctcctg gtcactgtgc tcaaaggtgt ccagtgtcag 60
gagcagctgg tggagtccgg gggaggcctg gtccagcctg agggatccct gacactcacc 120
tgcacagcct ctggattcga cttcagtagc ggctactaca tgtgctgggt ccgccaggct 180
ccagggaagg ggctggagtg gatcgcgtgt attttcacta ttactactaa cacttactac 240
gcgagctggg cgaaaggccg attcaccatc tccaagacct cgtcgaccac ggtgactctg 300
caaatgacca gtctgacagc cgcggacacg gccacctatc tctgtgcgag agggatttat 360
tctgataata attattatgc cttg 384

<210> SEQ ID NO 196
<211> LENGTH: 33
<212> TYPE: DNA
<213> ORGANISM: Oryctolagus cuniculus

<400> SEQUENCE: 196
caggccagtg agaccattgg caatgcatta gcc 33

<210> SEQ ID NO 197
<211> LENGTH: 21
<212> TYPE: DNA
<213> ORGANISM: Oryctolagus cuniculus

<400> SEQUENCE: 197
aaggcatcca aactggcatc t 21

<210> SEQ ID NO 198
<211> LENGTH: 27
<212> TYPE: DNA
<213> ORGANISM: Oryctolagus cuniculus

<400> SEQUENCE: 198
caatggtgtt attttggtga tagtgtt 27

<210> SEQ ID NO 199
<211> LENGTH: 18
<212> TYPE: DNA
<213> ORGANISM: Oryctolagus cuniculus

<400> SEQUENCE: 199
agcggctact acatgtgc 18

<210> SEQ ID NO 200
<211> LENGTH: 51
<212> TYPE: DNA
<213> ORGANISM: Oryctolagus cuniculus

<400> SEQUENCE: 200
tgtattttca ctattactac taacacttac tacgcgagct gggcgaaagg c 51

<210> SEQ ID NO 201
<211> LENGTH: 33
<212> TYPE: DNA
<213> ORGANISM: Oryctolagus cuniculus

<400> SEQUENCE: 201
gggatttatt ctgataataa ttattatgcc ttg 33

<210> SEQ ID NO 202

<211> LENGTH: 119
<212> TYPE: PRT
<213> ORGANISM: Oryctolagus cuniculus

<400> SEQUENCE: 202

Met Asp Thr Arg Ala Pro Thr Gln Leu Leu Gly Leu Leu Leu Leu Trp
1 5 10 15

Leu Pro Gly Ala Arg Cys Asp Val Val Met Thr Gln Thr Pro Ala Ser
20 25 30

Val Glu Ala Ala Val Gly Gly Thr Val Thr Ile Lys Cys Gln Ala Ser
35 40 45

Glu Ser Ile Gly Asn Ala Leu Ala Trp Tyr Gln Gln Lys Pro Gly Gln
50 55 60

Pro Pro Lys Leu Leu Ile Tyr Lys Ala Ser Thr Leu Ala Ser Gly Val
65 70 75 80

Pro Ser Arg Phe Ser Gly Ser Gly Ser Gly Thr Glu Phe Thr Leu Thr
85 90 95

Ile Ser Gly Val Gln Cys Ala Asp Ala Ala Ala Tyr Tyr Cys Gln Trp
100 105 110

Cys Tyr Phe Gly Asp Ser Val
115

<210> SEQ ID NO 203
<211> LENGTH: 128
<212> TYPE: PRT
<213> ORGANISM: Oryctolagus cuniculus

<400> SEQUENCE: 203

Met Glu Thr Gly Leu Arg Trp Leu Leu Leu Val Ala Val Leu Lys Gly
1 5 10 15

Val Gln Cys Gln Gln Gln Leu Val Glu Ser Gly Gly Gly Leu Val Lys
20 25 30

Pro Gly Ala Ser Leu Thr Leu Thr Cys Lys Ala Ser Gly Phe Ser Phe
35 40 45

Ser Ser Gly Tyr Tyr Met Cys Trp Val Arg Gln Ala Pro Gly Lys Gly
50 55 60

Leu Glu Ser Ile Ala Cys Ile Phe Thr Ile Thr Asp Asn Thr Tyr Tyr
65 70 75 80

Ala Asn Trp Ala Lys Gly Arg Phe Thr Ile Ser Lys Pro Ser Ser Pro
85 90 95

Thr Val Thr Leu Gln Met Thr Ser Leu Thr Ala Ala Asp Thr Ala Thr
100 105 110

Tyr Phe Cys Ala Arg Gly Ile Tyr Ser Thr Asp Asn Tyr Tyr Ala Leu
115 120 125

<210> SEQ ID NO 204
<211> LENGTH: 11
<212> TYPE: PRT
<213> ORGANISM: Oryctolagus cuniculus

<400> SEQUENCE: 204

Gln Ala Ser Glu Ser Ile Gly Asn Ala Leu Ala
1 5 10

<210> SEQ ID NO 205
<211> LENGTH: 7
<212> TYPE: PRT
<213> ORGANISM: Oryctolagus cuniculus

<400> SEQUENCE: 205

```
Lys Ala Ser Thr Leu Ala Ser
1               5


<210> SEQ ID NO 206
<211> LENGTH: 9
<212> TYPE: PRT
<213> ORGANISM: Oryctolagus cuniculus

<400> SEQUENCE: 206

Gln Trp Cys Tyr Phe Gly Asp Ser Val
1               5


<210> SEQ ID NO 207
<211> LENGTH: 6
<212> TYPE: PRT
<213> ORGANISM: Oryctolagus cuniculus

<400> SEQUENCE: 207

Ser Gly Tyr Tyr Met Cys
1               5


<210> SEQ ID NO 208
<211> LENGTH: 17
<212> TYPE: PRT
<213> ORGANISM: Oryctolagus cuniculus

<400> SEQUENCE: 208

Cys Ile Phe Thr Ile Thr Asp Asn Thr Tyr Tyr Ala Asn Trp Ala Lys
1               5                   10                  15

Gly


<210> SEQ ID NO 209
<211> LENGTH: 11
<212> TYPE: PRT
<213> ORGANISM: Oryctolagus cuniculus

<400> SEQUENCE: 209

Gly Ile Tyr Ser Thr Asp Asn Tyr Tyr Ala Leu
1               5                   10


<210> SEQ ID NO 210
<211> LENGTH: 357
<212> TYPE: DNA
<213> ORGANISM: Oryctolagus cuniculus

<400> SEQUENCE: 210

atggacacga gggcccccac tcagctgctg gggctcctgc tgctctggct cccaggtgcc      60

agatgtgatg ttgtgatgac ccagactcca gcctccgtgg aggcagctgt gggaggcaca     120

gtcaccatca agtgccaggc cagtgagagc attggcaatg cattagcctg gtatcagcag     180

aaaccagggc agcctcccaa gctcctgatc tacaaggcat ccactctggc atctggggtc     240

ccatcgcggt tcagcggcag tggatctggg acagagttca ctctcaccat cagcggcgtg     300

cagtgtgccg atgctgccgc ttactactgt caatggtgtt attttggtga tagtgtt       357


<210> SEQ ID NO 211
<211> LENGTH: 384
<212> TYPE: DNA
<213> ORGANISM: Oryctolagus cuniculus

<400> SEQUENCE: 211

atggagactg ggctgcgctg gcttctcctg gtcgctgtgc tcaaaggtgt ccagtgtcag      60
```

```
cagcagctgg tggagtccgg gggaggcctg gtcaagccgg gggcatccct gacactcacc    120

tgcaaagcct ctggattctc cttcagtagc ggctactaca tgtgctgggt ccgccaggct    180

ccagggaagg ggctggagtc gatcgcatgc atttttacta ttactgataa cacttactac    240

gcgaactggg cgaaaggccg attcaccatc tccaagccct cgtcgcccac ggtgactctg    300

caaatgacca gtctgacagc cgcggacacg gccacctatt tctgtgcgag ggggatttat    360

tctactgata attattatgc cttg                                            384


<210> SEQ ID NO 212
<211> LENGTH: 33
<212> TYPE: DNA
<213> ORGANISM: Oryctolagus cuniculus

<400> SEQUENCE: 212

caggccagtg agagcattgg caatgcatta gcc                                   33


<210> SEQ ID NO 213
<211> LENGTH: 21
<212> TYPE: DNA
<213> ORGANISM: Oryctolagus cuniculus

<400> SEQUENCE: 213

aaggcatcca ctctggcatc t                                                21


<210> SEQ ID NO 214
<211> LENGTH: 27
<212> TYPE: DNA
<213> ORGANISM: Oryctolagus cuniculus

<400> SEQUENCE: 214

caatggtgtt attttggtga tagtgtt                                          27


<210> SEQ ID NO 215
<211> LENGTH: 18
<212> TYPE: DNA
<213> ORGANISM: Oryctolagus cuniculus

<400> SEQUENCE: 215

agcggctact acatgtgc                                                    18


<210> SEQ ID NO 216
<211> LENGTH: 51
<212> TYPE: DNA
<213> ORGANISM: Oryctolagus cuniculus

<400> SEQUENCE: 216

tgcattttta ctattactga taacacttac tacgcgaact gggcgaaagg c               51


<210> SEQ ID NO 217
<211> LENGTH: 33
<212> TYPE: DNA
<213> ORGANISM: Oryctolagus cuniculus

<400> SEQUENCE: 217

gggatttatt ctactgataa ttattatgcc ttg                                   33


<210> SEQ ID NO 218
<211> LENGTH: 123
<212> TYPE: PRT
<213> ORGANISM: Oryctolagus cuniculus

<400> SEQUENCE: 218
```

```
Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Val Ser Ser Tyr Leu Asn Trp Tyr Gln Gln Lys Pro Gly Gln
    50                  55                  60

Pro Pro Lys Leu Leu Ile Tyr Arg Ala Ser Thr Leu Glu Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Cys
            100                 105                 110

Thr Tyr Gly Thr Ser Ser Ser Tyr Gly Ala Ala
        115                 120
```

<210> SEQ ID NO 219
<211> LENGTH: 133
<212> TYPE: PRT
<213> ORGANISM: Oryctolagus cuniculus

<400> SEQUENCE: 219

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Ser Leu Ser
        35                  40                  45

Ser Asn Ala Ile Ser Trp Val Arg Gln Ala Pro Gly Lys Gly Leu Glu
    50                  55                  60

Trp Ile Gly Ile Ile Ser Tyr Ser Gly Thr Thr Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Asp Asp Pro Thr Thr Val Met Val Met Leu Ile Pro Phe Gly
        115                 120                 125

Ala Gly Met Asp Leu
    130
```

<210> SEQ ID NO 220
<211> LENGTH: 11
<212> TYPE: PRT
<213> ORGANISM: Oryctolagus cuniculus

<400> SEQUENCE: 220

```
Gln Ala Ser Gln Ser Val Ser Ser Tyr Leu Asn
1               5                   10
```

<210> SEQ ID NO 221
<211> LENGTH: 7
<212> TYPE: PRT
<213> ORGANISM: Oryctolagus cuniculus

<400> SEQUENCE: 221

```
Arg Ala Ser Thr Leu Glu Ser
1               5
```

<210> SEQ ID NO 222
<211> LENGTH: 13
<212> TYPE: PRT
<213> ORGANISM: Oryctolagus cuniculus

<400> SEQUENCE: 222

Gln Cys Thr Tyr Gly Thr Ser Ser Ser Tyr Gly Ala Ala
1 5 10

<210> SEQ ID NO 223
<211> LENGTH: 5
<212> TYPE: PRT
<213> ORGANISM: Oryctolagus cuniculus

<400> SEQUENCE: 223

Ser Asn Ala Ile Ser
1 5

<210> SEQ ID NO 224
<211> LENGTH: 16
<212> TYPE: PRT
<213> ORGANISM: Oryctolagus cuniculus

<400> SEQUENCE: 224

Ile Ile Ser Tyr Ser Gly Thr Thr Tyr Tyr Ala Ser Trp Ala Lys Gly
1 5 10 15

<210> SEQ ID NO 225
<211> LENGTH: 19
<212> TYPE: PRT
<213> ORGANISM: Oryctolagus cuniculus

<400> SEQUENCE: 225

Asp Asp Pro Thr Thr Val Met Val Met Leu Ile Pro Phe Gly Ala Gly
1 5 10 15

Met Asp Leu

<210> SEQ ID NO 226
<211> LENGTH: 369
<212> TYPE: DNA
<213> ORGANISM: Oryctolagus cuniculus

<400> SEQUENCE: 226
atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca agtgccaggc cagtcagagc gttagtagct acttaaactg gtatcagcag 180
aaaccagggc agcctcccaa gctcctgatc tacagggcat ccactctgga atctggggtc 240
ccatcgcggt tcaaaggcag tggatctggg acagagttca ctctcaccat cagcgacctg 300
gagtgtgccg atgctgccac ttactactgt caatgtactt atggtactag tagtagttat 360
ggtgctgct 369

<210> SEQ ID NO 227
<211> LENGTH: 399
<212> TYPE: DNA
<213> ORGANISM: Oryctolagus cuniculus

<400> SEQUENCE: 227
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120

-continued accgtctctg gtatctccct cagtagcaat gcaataagct gggtccgcca ggctccaggg 180
aaggggctgg aatggatcgg aatcattagt tatagtggta ccacatacta cgcgagctgg 240
gcgaaaggcc gattcaccat ctccaaaacc tcgtcgacca cggtggatct gaaaatcact 300
agtccgacaa ccgaggacac ggccacctac ttctgtgcca gagatgaccc tacgacagtt 360
atggttatgt tgataccttt tggagccggc atggacctc 399

<210> SEQ ID NO 228
<211> LENGTH: 33
<212> TYPE: DNA
<213> ORGANISM: Oryctolagus cuniculus

<400> SEQUENCE: 228
caggccagtc agagcgttag tagctactta aac 33

<210> SEQ ID NO 229
<211> LENGTH: 21
<212> TYPE: DNA
<213> ORGANISM: Oryctolagus cuniculus

<400> SEQUENCE: 229
agggcatcca ctctggaatc t 21

<210> SEQ ID NO 230
<211> LENGTH: 39
<212> TYPE: DNA
<213> ORGANISM: Oryctolagus cuniculus

<400> SEQUENCE: 230
caatgtactt atggtactag tagtagttat ggtgctgct 39

<210> SEQ ID NO 231
<211> LENGTH: 15
<212> TYPE: DNA
<213> ORGANISM: Oryctolagus cuniculus

<400> SEQUENCE: 231
agcaatgcaa taagc 15

<210> SEQ ID NO 232
<211> LENGTH: 48
<212> TYPE: DNA
<213> ORGANISM: Oryctolagus cuniculus

<400> SEQUENCE: 232
atcattagtt atagtggtac cacatactac gcgagctggg cgaaaggc 48

<210> SEQ ID NO 233
<211> LENGTH: 57
<212> TYPE: DNA
<213> ORGANISM: Oryctolagus cuniculus

<400> SEQUENCE: 233
gatgacccta cgacagttat ggttatgttg ataccttttg gagccggcat ggacctc 57

<210> SEQ ID NO 234
<211> LENGTH: 125
<212> TYPE: PRT
<213> ORGANISM: Oryctolagus cuniculus

<400> SEQUENCE: 234

Met Asp Thr Arg Ala Pro Thr Gln Leu Leu Gly Leu Leu Leu Leu Trp

```
1               5                   10                  15

Leu Pro Gly Ala Thr Phe Ala Gln Val Leu Thr Gln Thr Ala Ser Pro
            20                  25                  30

Val Ser Ala Ala Val Gly Gly Thr Val Thr Ile Asn Cys Gln Ala Ser
        35                  40                  45

Gln Ser Val Tyr Lys Asn Asn Tyr Leu Ser Trp Tyr Gln Gln Lys Pro
    50                  55                  60

Gly Gln Pro Pro Lys Gly Leu Ile Tyr Ser Ala Ser Thr Leu Asp Ser
65                  70                  75                  80

Gly Val Pro Leu Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Asp Cys Ser Ser Gly Asp Cys Tyr Ala
        115                 120                 125


<210> SEQ ID NO 235
<211> LENGTH: 119
<212> TYPE: PRT
<213> ORGANISM: Oryctolagus cuniculus

<400> SEQUENCE: 235

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Glu Gly Ser Leu Thr Leu Thr Cys Thr Ala Ser Gly Phe Ser Phe Ser
        35                  40                  45

Ser Tyr Trp Met Cys Trp Val Arg Gln Ala Pro Gly Lys Gly Leu Glu
    50                  55                  60

Trp Ile Ala Cys Ile Val Thr Gly Asn Gly Asn Thr Tyr Tyr Ala Asn
65                  70                  75                  80

Trp Ala Lys Gly Arg Phe Thr Ile Ser Lys Thr Ser Ser Thr Thr Val
                85                  90                  95

Thr Leu Gln Met Thr Ser Leu Thr Ala Ala Asp Thr Ala Thr Tyr Phe
            100                 105                 110

Cys Ala Lys Ala Tyr Asp Leu
        115


<210> SEQ ID NO 236
<211> LENGTH: 13
<212> TYPE: PRT
<213> ORGANISM: Oryctolagus cuniculus

<400> SEQUENCE: 236

Gln Ala Ser Gln Ser Val Tyr Lys Asn Asn Tyr Leu Ser
1               5                   10


<210> SEQ ID NO 237
<211> LENGTH: 7
<212> TYPE: PRT
<213> ORGANISM: Oryctolagus cuniculus

<400> SEQUENCE: 237

Ser Ala Ser Thr Leu Asp Ser
1               5


<210> SEQ ID NO 238
<211> LENGTH: 13
```

<212> TYPE: PRT
<213> ORGANISM: Oryctolagus cuniculus

<400> SEQUENCE: 238

Leu Gly Ser Tyr Asp Cys Ser Ser Gly Asp Cys Tyr Ala
1 5 10

<210> SEQ ID NO 239
<211> LENGTH: 5
<212> TYPE: PRT
<213> ORGANISM: Oryctolagus cuniculus

<400> SEQUENCE: 239

Ser Tyr Trp Met Cys
1 5

<210> SEQ ID NO 240
<211> LENGTH: 17
<212> TYPE: PRT
<213> ORGANISM: Oryctolagus cuniculus

<400> SEQUENCE: 240

Cys Ile Val Thr Gly Asn Gly Asn Thr Tyr Tyr Ala Asn Trp Ala Lys
1 5 10 15

Gly

<210> SEQ ID NO 241
<211> LENGTH: 4
<212> TYPE: PRT
<213> ORGANISM: Oryctolagus cuniculus

<400> SEQUENCE: 241

Ala Tyr Asp Leu
1

<210> SEQ ID NO 242
<211> LENGTH: 375
<212> TYPE: DNA
<213> ORGANISM: Oryctolagus cuniculus

<400> SEQUENCE: 242
atggacacga gggcccccac tcagctgctg gggctcctgc tgctctggct cccaggtgcc 60
acatttgccc aagtgctgac ccagactgca tcgcccgtgt ctgcagctgt gggaggcaca 120
gtcaccatca actgccaggc cagtcagagt gtttataaga acaactactt atcctggtat 180
cagcagaaac cagggcagcc tcccaaaggc ctgatctatt ctgcatcgac tctagattct 240
ggggtcccat tgcggttcag cggcagtgga tctgggacac agttcactct caccatcagc 300
gacgtgcagt gtgacgatgc tgccacttac tactgtctag gcagttatga ttgtagtagt 360
ggtgattgtt atgct 375

<210> SEQ ID NO 243
<211> LENGTH: 357
<212> TYPE: DNA
<213> ORGANISM: Oryctolagus cuniculus

<400> SEQUENCE: 243
atggagactg ggctgcgctg gcttctcctg gtcgctgtgc tcaaaggtgt ccagtgtcag 60
tcgttggagg agtccggggg agacctggtc aagcctgagg gatccctgac actcacctgc 120
acagcctctg gattctcctt cagtagctac tggatgtgct gggtccgcca ggctccaggg 180
aaggggctgg agtggatcgc atgcattgtt actggtaatg gtaacactta ctacgcgaac 240
tgggcgaaag gccgattcac catctccaaa acctcgtcga ccacggtgac tctgcaaatg 300
accagtctga cagccgcgga cacggccacc tatttttgtg cgaaagccta tgacttg 357

<210> SEQ ID NO 244
<211> LENGTH: 39
<212> TYPE: DNA
<213> ORGANISM: Oryctolagus cuniculus

<400> SEQUENCE: 244
caggccagtc agagtgttta taagaacaac tacttatcc 39

<210> SEQ ID NO 245
<211> LENGTH: 21
<212> TYPE: DNA
<213> ORGANISM: Oryctolagus cuniculus

<400> SEQUENCE: 245
tctgcatcga ctctagattc t 21

<210> SEQ ID NO 246
<211> LENGTH: 39
<212> TYPE: DNA
<213> ORGANISM: Oryctolagus cuniculus

<400> SEQUENCE: 246
ctaggcagtt atgattgtag tagtggtgat tgttatgct 39

<210> SEQ ID NO 247
<211> LENGTH: 15
<212> TYPE: DNA
<213> ORGANISM: Oryctolagus cuniculus

<400> SEQUENCE: 247
agctactgga tgtgc 15

<210> SEQ ID NO 248
<211> LENGTH: 51
<212> TYPE: DNA
<213> ORGANISM: Oryctolagus cuniculus

<400> SEQUENCE: 248
tgcattgtta ctggtaatgg taacacttac tacgcgaact gggcgaaagg c 51

<210> SEQ ID NO 249
<211> LENGTH: 12
<212> TYPE: DNA
<213> ORGANISM: Oryctolagus cuniculus

<400> SEQUENCE: 249
gcctatgact tg 12

<210> SEQ ID NO 250
<211> LENGTH: 123
<212> TYPE: PRT
<213> ORGANISM: Oryctolagus cuniculus

<400> SEQUENCE: 250

Met Asp Thr Arg Ala Pro Thr Gln Leu Leu Gly Leu Leu Leu Leu Trp
1 5 10 15

Leu Pro Gly Ser Thr Phe Ala Ala Val Leu Thr Gln Thr Pro Ser Pro
20 25 30

Val Ser Ala Ala Val Gly Gly Thr Val Ser Ile Ser Cys Gln Ala Ser

```
        35                  40                  45

Gln Ser Val Tyr Asp Asn Asn Tyr Leu Ser Trp Tyr Gln Gln Lys Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Thr Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Phe Asn Asp Asp Ser Asp Asp Ala
        115                 120


<210> SEQ ID NO 251
<211> LENGTH: 125
<212> TYPE: PRT
<213> ORGANISM: Oryctolagus cuniculus

<400> SEQUENCE: 251

Met Glu Thr Gly Leu Arg Trp Leu Leu Leu Val Ala Val Pro Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Leu Ser Gly Phe Ser Leu Ser
        35                  40                  45

Ala Tyr Tyr Met Ser Trp Val Arg Gln Ala Pro Gly Lys Gly Leu Glu
    50                  55                  60

Trp Ile Gly Phe Ile Thr Leu Ser Asp His Ile Ser Tyr Ala Arg Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Ser Arg Gly Trp Gly Ala Met Gly Arg Leu Asp Leu
        115                 120                 125


<210> SEQ ID NO 252
<211> LENGTH: 13
<212> TYPE: PRT
<213> ORGANISM: Oryctolagus cuniculus

<400> SEQUENCE: 252

Gln Ala Ser Gln Ser Val Tyr Asp Asn Asn Tyr Leu Ser
1               5                   10


<210> SEQ ID NO 253
<211> LENGTH: 7
<212> TYPE: PRT
<213> ORGANISM: Oryctolagus cuniculus

<400> SEQUENCE: 253

Gly Ala Ser Thr Leu Ala Ser
1               5


<210> SEQ ID NO 254
<211> LENGTH: 11
<212> TYPE: PRT
<213> ORGANISM: Oryctolagus cuniculus

<400> SEQUENCE: 254

Ala Gly Val Phe Asn Asp Asp Ser Asp Asp Ala
```

-continued

```
1               5                   10


<210> SEQ ID NO 255
<211> LENGTH: 5
<212> TYPE: PRT
<213> ORGANISM: Oryctolagus cuniculus

<400> SEQUENCE: 255

Ala Tyr Tyr Met Ser
1               5


<210> SEQ ID NO 256
<211> LENGTH: 16
<212> TYPE: PRT
<213> ORGANISM: Oryctolagus cuniculus

<400> SEQUENCE: 256

Phe Ile Thr Leu Ser Asp His Ile Ser Tyr Ala Arg Trp Ala Lys Gly
1               5                   10                  15


<210> SEQ ID NO 257
<211> LENGTH: 12
<212> TYPE: PRT
<213> ORGANISM: Oryctolagus cuniculus

<400> SEQUENCE: 257

Ser Arg Gly Trp Gly Ala Met Gly Arg Leu Asp Leu
1               5                   10


<210> SEQ ID NO 258
<211> LENGTH: 369
<212> TYPE: DNA
<213> ORGANISM: Oryctolagus cuniculus

<400> SEQUENCE: 258

atggacacga gggcccccac tcagctgctg gggctcctgc tgctctggct cccaggttcc      60

acatttgccg ccgtgctgac ccagactcca tctcccgtgt ctgcagctgt gggaggcaca     120

gtcagcatca gttgccaggc cagtcagagt gtttatgaca acaactattt atcctggtat     180

cagcagaaac caggacagcc tcccaagctc ctgatctatg gtgcatccac tctggcatct     240

ggggtcccat cgcggttcaa aggcacggga tctgggacac agttcactct caccatcaca     300

gacgtgcagt gtgacgatgc tgccacttac tattgtgcag gcgtttttaa tgatgatagt     360

gatgatgcc                                                            369


<210> SEQ ID NO 259
<211> LENGTH: 375
<212> TYPE: DNA
<213> ORGANISM: Oryctolagus cuniculus

<400> SEQUENCE: 259

atggagactg ggctgcgctg gcttctcctg gtcgctgtgc ccaaaggtgt ccagtgtcag      60

tcgctggagg agtccggggg tcgcctggtc acgcctggga cacccctgac actcacctgc     120

acactctctg gattctccct cagtgcatac tatatgagct gggtccgcca ggctccaggg     180

aaggggctgg aatggatcgg attcattact ctgagtgatc atatatctta cgcgaggtgg     240

gcgaaaggcc gattcaccat ctccaaaacc tcgaccacgg tggatctgaa aatgaccagt     300

ccgacaaccg aggacacggc cacctatttc tgtgccagga gtcgtggctg ggtgcaatg     360

ggtcggttgg atctc                                                     375
```

<210> SEQ ID NO 260
<211> LENGTH: 39
<212> TYPE: DNA
<213> ORGANISM: Oryctolagus cuniculus

<400> SEQUENCE: 260
caggccagtc agagtgttta tgacaacaac tatttatcc 39

<210> SEQ ID NO 261
<211> LENGTH: 21
<212> TYPE: DNA
<213> ORGANISM: Oryctolagus cuniculus

<400> SEQUENCE: 261
ggtgcatcca ctctggcatc t 21

<210> SEQ ID NO 262
<211> LENGTH: 33
<212> TYPE: DNA
<213> ORGANISM: Oryctolagus cuniculus

<400> SEQUENCE: 262
gcaggcgttt ttaatgatga tagtgatgat gcc 33

<210> SEQ ID NO 263
<211> LENGTH: 15
<212> TYPE: DNA
<213> ORGANISM: Oryctolagus cuniculus

<400> SEQUENCE: 263
gcatactata tgagc 15

<210> SEQ ID NO 264
<211> LENGTH: 48
<212> TYPE: DNA
<213> ORGANISM: Oryctolagus cuniculus

<400> SEQUENCE: 264
ttcattactc tgagtgatca tatatcttac gcgaggtggg cgaaaggc 48

<210> SEQ ID NO 265
<211> LENGTH: 36
<212> TYPE: DNA
<213> ORGANISM: Oryctolagus cuniculus

<400> SEQUENCE: 265
agtcgtggct ggggtgcaat gggtcggttg gatctc 36

<210> SEQ ID NO 266
<211> LENGTH: 123
<212> TYPE: PRT
<213> ORGANISM: Oryctolagus cuniculus

<400> SEQUENCE: 266

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ala Ser
        35                  40                  45

Gln Ser Val Tyr Asn Asn Lys Asn Leu Ala Trp Tyr Gln Gln Lys Ser
    50                  55                  60

Gly Gln Pro Pro Lys Leu Leu Ile Tyr Trp Ala Ser Thr Leu Ala Ser
```

```
65                  70                  75                  80

Gly Val Ser Ser Arg Phe Ser Gly Ser Gly Ser Gly Thr Gln Phe Thr
                85                  90                  95

Leu Thr Val Ser Gly Val Gln Cys Asp Asp Ala Ala Thr Tyr Tyr Cys
            100                 105                 110

Leu Gly Val Phe Asp Asp Asp Ala Asp Asn Ala
        115                 120
```

<210> SEQ ID NO 267
<211> LENGTH: 121
<212> TYPE: PRT
<213> ORGANISM: Oryctolagus cuniculus

<400> SEQUENCE: 267

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Ser Met Thr Trp Val Arg Gln Ala Pro Gly Lys Gly Leu Glu
    50                  55                  60

Tyr Ile Gly Val Ile Gly Thr Ser Gly Ser Thr Tyr Tyr Ala Thr Trp
65                  70                  75                  80

Ala Lys Gly Arg Phe Thr Ile Ser Arg Thr Ser Thr Thr Val Ala Leu
                85                  90                  95

Lys Ile Thr Ser Pro Thr Thr Glu Asp Thr Ala Thr Tyr Phe Cys Val
            100                 105                 110

Arg Ser Leu Ser Ser Ile Thr Phe Leu
        115                 120
```

<210> SEQ ID NO 268
<211> LENGTH: 13
<212> TYPE: PRT
<213> ORGANISM: Oryctolagus cuniculus

<400> SEQUENCE: 268

```
Gln Ala Ser Gln Ser Val Tyr Asn Asn Lys Asn Leu Ala
1               5                   10
```

<210> SEQ ID NO 269
<211> LENGTH: 7
<212> TYPE: PRT
<213> ORGANISM: Oryctolagus cuniculus

<400> SEQUENCE: 269

```
Trp Ala Ser Thr Leu Ala Ser
1               5
```

<210> SEQ ID NO 270
<211> LENGTH: 11
<212> TYPE: PRT
<213> ORGANISM: Oryctolagus cuniculus

<400> SEQUENCE: 270

```
Leu Gly Val Phe Asp Asp Asp Ala Asp Asn Ala
1               5                   10
```

<210> SEQ ID NO 271
<211> LENGTH: 5
<212> TYPE: PRT

<213> ORGANISM: Oryctolagus cuniculus

<400> SEQUENCE: 271

Ser Tyr Ser Met Thr
1               5

<210> SEQ ID NO 272
<211> LENGTH: 16
<212> TYPE: PRT
<213> ORGANISM: Oryctolagus cuniculus

<400> SEQUENCE: 272

Val Ile Gly Thr Ser Gly Ser Thr Tyr Tyr Ala Thr Trp Ala Lys Gly
1               5                   10                  15

<210> SEQ ID NO 273
<211> LENGTH: 8
<212> TYPE: PRT
<213> ORGANISM: Oryctolagus cuniculus

<400> SEQUENCE: 273

Ser Leu Ser Ser Ile Thr Phe Leu
1               5

<210> SEQ ID NO 274
<211> LENGTH: 369
<212> TYPE: DNA
<213> ORGANISM: Oryctolagus cuniculus

<400> SEQUENCE: 274
atggacacga gggcccccac tcagctgctg gggctcctgc tgctctggct cccaggtgcc 60
acattcgcag ccgtgctgac ccagacacca tcgcccgtgt ctgcggctgt gggaggcaca 120
gtcaccatca gttgccaggc cagtcagagt gtttataaca acaaaaaattt agcctggtat 180 cagcagaaat cagggcagcc tcccaagctc ctgatctact gggcatccac tctggcatct 240
ggggtctcat cgcggttcag cggcagtgga tctgggacac agttcactct caccgtcagc 300
ggcgtgcagt gtgacgatgc tgccacttac tactgtctag gcgtttttga tgatgatgct 360
gataatgct 369

<210> SEQ ID NO 275
<211> LENGTH: 363
<212> TYPE: DNA
<213> ORGANISM: Oryctolagus cuniculus

<400> SEQUENCE: 275
atggagactg ggctgcgctg gcttctcctg gtcgctgtgc tcaaaggtgt ccaatgtcag 60
tcggtggagg agtccggggg tcgcctggtc acgcctggga cacccctgac actcacctgc 120
acagcctctg gattctccct cagtagctac tccatgacct gggtccgcca ggctccaggg 180
aaggggctgg aatatatcgg agtcattggt actagtggta gcacatacta cgcgacctgg 240
gcgaaaggcc gattcaccat ctccagaacc tcgaccacgg tggctctgaa aatcaccagt 300
ccgacaaccg aggacacggc cacctatttc tgtgtcagga gtctttcttc tattactttc 360
ttg 363

<210> SEQ ID NO 276
<211> LENGTH: 39
<212> TYPE: DNA
<213> ORGANISM: Oryctolagus cuniculus

<400> SEQUENCE: 276
caggccagtc agagtgttta taacaacaaa aatttagcc 39

<210> SEQ ID NO 277
<211> LENGTH: 21
<212> TYPE: DNA
<213> ORGANISM: Oryctolagus cuniculus

<400> SEQUENCE: 277
tgggcatcca ctctggcatc t 21

<210> SEQ ID NO 278
<211> LENGTH: 33
<212> TYPE: DNA
<213> ORGANISM: Oryctolagus cuniculus

<400> SEQUENCE: 278
ctaggcgttt ttgatgatga tgctgataat gct 33

<210> SEQ ID NO 279
<211> LENGTH: 15
<212> TYPE: DNA
<213> ORGANISM: Oryctolagus cuniculus

<400> SEQUENCE: 279
agctactcca tgacc 15

<210> SEQ ID NO 280
<211> LENGTH: 48
<212> TYPE: DNA
<213> ORGANISM: Oryctolagus cuniculus

<400> SEQUENCE: 280
gtcattggta ctagtggtag cacatactac gcgacctggg cgaaaggc 48

<210> SEQ ID NO 281
<211> LENGTH: 24
<212> TYPE: DNA
<213> ORGANISM: Oryctolagus cuniculus

<400> SEQUENCE: 281
agtctttctt ctattacttt cttg 24

<210> SEQ ID NO 282
<211> LENGTH: 120
<212> TYPE: PRT
<213> ORGANISM: Oryctolagus cuniculus

<400> SEQUENCE: 282

```
Met Asp Thr Arg Ala Pro Thr Gln Leu Leu Gly Leu Leu Leu Leu Trp
1               5                   10                  15

Leu Pro Gly Ala Arg Cys Ala Phe Glu Leu Thr Gln Thr Pro Ala Ser
            20                  25                  30

Val Glu Ala Ala Val Gly Gly Thr Val Thr Ile Asn Cys Gln Ala Ser
        35                  40                  45

Gln Asn Ile Tyr Arg Tyr Leu Ala Trp Tyr Gln Gln Lys Pro Gly Gln
    50                  55                  60

Pro Pro Lys Phe Leu Ile Tyr Leu Ala Ser Thr Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Ser
```

-continued

```
            100                 105                 110

Tyr Tyr Ser Ser Asn Ser Val Ala
        115                 120


<210> SEQ ID NO 283
<211> LENGTH: 128
<212> TYPE: PRT
<213> ORGANISM: Oryctolagus cuniculus

<400> SEQUENCE: 283

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Asp Leu Val Gln
            20                  25                  30

Pro Glu Gly Ser Leu Thr Leu Thr Cys Thr Ala Ser Glu Leu Asp Phe
        35                  40                  45

Ser Ser Gly Tyr Trp Ile Cys Trp Val Arg Gln Val Pro Gly Lys Gly
    50                  55                  60

Leu Glu Trp Ile Gly Cys Ile Tyr Thr Gly Ser Ser Gly Ser Thr Phe
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Gly Tyr Ser Gly Phe Gly Tyr Phe Lys Leu
        115                 120                 125


<210> SEQ ID NO 284
<211> LENGTH: 11
<212> TYPE: PRT
<213> ORGANISM: Oryctolagus cuniculus

<400> SEQUENCE: 284

Gln Ala Ser Gln Asn Ile Tyr Arg Tyr Leu Ala
1               5                   10


<210> SEQ ID NO 285
<211> LENGTH: 7
<212> TYPE: PRT
<213> ORGANISM: Oryctolagus cuniculus

<400> SEQUENCE: 285

Leu Ala Ser Thr Leu Ala Ser
1               5


<210> SEQ ID NO 286
<211> LENGTH: 10
<212> TYPE: PRT
<213> ORGANISM: Oryctolagus cuniculus

<400> SEQUENCE: 286

Gln Ser Tyr Tyr Ser Ser Asn Ser Val Ala
1               5                   10


<210> SEQ ID NO 287
<211> LENGTH: 6
<212> TYPE: PRT
<213> ORGANISM: Oryctolagus cuniculus

<400> SEQUENCE: 287

Ser Gly Tyr Trp Ile Cys
1               5
```

<210> SEQ ID NO 288
<211> LENGTH: 18
<212> TYPE: PRT
<213> ORGANISM: Oryctolagus cuniculus

<400> SEQUENCE: 288

Cys Ile Tyr Thr Gly Ser Ser Gly Ser Thr Phe Tyr Ala Ser Trp Ala
1 5 10 15

Lys Gly

<210> SEQ ID NO 289
<211> LENGTH: 10
<212> TYPE: PRT
<213> ORGANISM: Oryctolagus cuniculus

<400> SEQUENCE: 289

Gly Tyr Ser Gly Phe Gly Tyr Phe Lys Leu
1 5 10

<210> SEQ ID NO 290
<211> LENGTH: 360
<212> TYPE: DNA
<213> ORGANISM: Oryctolagus cuniculus

<400> SEQUENCE: 290
atggacacga gggcccccac tcagctgctg gggctcctgc tgctctggct cccaggtgcc 60
agatgtgcat tcgaattgac ccagactcca gcctccgtgg aggcagctgt gggaggcaca 120
gtcaccatca attgccaggc cagtcagaac atttatagat acttagcctg gtatcagcag 180
aaaccagggc agcctcccaa gttcctgatc tatctggcat ctactctggc atctggggtc 240
ccatcgcggt ttaaaggcag tggatctggg acagagttca ctctcaccat cagcgacctg 300
gagtgtgccg atgctgccac ttactactgt caaagttatt atagtagtaa tagtgtcgct 360

<210> SEQ ID NO 291
<211> LENGTH: 384
<212> TYPE: DNA
<213> ORGANISM: Oryctolagus cuniculus

<400> SEQUENCE: 291
atggagactg ggctgcgctg gcttctcctg gtcgctgtgc tcaaaggtgt ccagtgtcag 60
gagcagctgg tggagtccgg gggagacctg gtccagcctg agggatccct gacactcacc 120
tgcacagctt ctgagttaga cttcagtagc ggctactgga tatgctgggt ccgccaggtt 180
ccagggaagg ggctggagtg gatcggatgc atttatactg gtagtagtgg tagcactttt 240
tacgcgagtt gggcgaaagg ccgattcacc atctccaaaa cctcgtcgac cacggtgact 300
ctgcaaatga ccagtctgac agccgcggac acggccacct atttctgtgc gagaggttat 360
agtggctttg gttactttaa gttg 384

<210> SEQ ID NO 292
<211> LENGTH: 33
<212> TYPE: DNA
<213> ORGANISM: Oryctolagus cuniculus

<400> SEQUENCE: 292
caggccagtc agaacattta tagatactta gcc 33

<210> SEQ ID NO 293
<211> LENGTH: 21

<212> TYPE: DNA
<213> ORGANISM: Oryctolagus cuniculus

<400> SEQUENCE: 293
ctggcatcta ctctggcatc t 21

<210> SEQ ID NO 294
<211> LENGTH: 30
<212> TYPE: DNA
<213> ORGANISM: Oryctolagus cuniculus

<400> SEQUENCE: 294
caaagttatt atagtagtaa tagtgtcgct 30

<210> SEQ ID NO 295
<211> LENGTH: 18
<212> TYPE: DNA
<213> ORGANISM: Oryctolagus cuniculus

<400> SEQUENCE: 295
agcggctact ggatatgc 18

<210> SEQ ID NO 296
<211> LENGTH: 54
<212> TYPE: DNA
<213> ORGANISM: Oryctolagus cuniculus

<400> SEQUENCE: 296
tgcatttata ctggtagtag tggtagcact ttttacgcga gttgggcgaa aggc 54

<210> SEQ ID NO 297
<211> LENGTH: 30
<212> TYPE: DNA
<213> ORGANISM: Oryctolagus cuniculus

<400> SEQUENCE: 297
ggttatagtg gctttggtta ctttaagttg 30

<210> SEQ ID NO 298
<211> LENGTH: 122
<212> TYPE: PRT
<213> ORGANISM: Oryctolagus cuniculus

<400> SEQUENCE: 298

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Glu Asp Ile Tyr Arg Leu Leu Ala Trp Tyr Gln Gln Lys Pro Gly Gln
    50                  55                  60

Pro Pro Lys Leu Leu Ile Tyr Asp Ser Ser Asp Leu Ala Ser Gly Val
65                  70                  75                  80

Pro Ser Arg Phe Lys Gly Ser Gly Ser Gly Thr Glu Phe Thr Leu Ala
                85                  90                  95

Ile Ser Gly Val Gln Cys Asp Asp Ala Ala Thr Tyr Tyr Cys Gln Gln
            100                 105                 110

Ala Trp Ser Tyr Ser Asp Ile Asp Asn Ala
        115                 120
```

<210> SEQ ID NO 299
<211> LENGTH: 123
<212> TYPE: PRT
<213> ORGANISM: Oryctolagus cuniculus

<400> SEQUENCE: 299

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Tyr Met Ser Trp Val Arg Gln Ala Pro Gly Lys Gly Leu Glu
    50                  55                  60

Trp Ile Gly Ile Ile Thr Thr Ser Gly Asn Thr Phe Tyr Ala Ser Trp
65                  70                  75                  80

Ala Lys Gly Arg Leu Thr Ile Ser Arg Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Thr Ser Asp Ile Phe Tyr Tyr Arg Asn Leu
        115                 120
```

<210> SEQ ID NO 300
<211> LENGTH: 11
<212> TYPE: PRT
<213> ORGANISM: Oryctolagus cuniculus

<400> SEQUENCE: 300

```
Gln Ala Ser Glu Asp Ile Tyr Arg Leu Leu Ala
1               5                   10
```

<210> SEQ ID NO 301
<211> LENGTH: 7
<212> TYPE: PRT
<213> ORGANISM: Oryctolagus cuniculus

<400> SEQUENCE: 301

```
Asp Ser Ser Asp Leu Ala Ser
1               5
```

<210> SEQ ID NO 302
<211> LENGTH: 12
<212> TYPE: PRT
<213> ORGANISM: Oryctolagus cuniculus

<400> SEQUENCE: 302

```
Gln Gln Ala Trp Ser Tyr Ser Asp Ile Asp Asn Ala
1               5                   10
```

<210> SEQ ID NO 303
<211> LENGTH: 5
<212> TYPE: PRT
<213> ORGANISM: Oryctolagus cuniculus

<400> SEQUENCE: 303

```
Ser Tyr Tyr Met Ser
1               5
```

<210> SEQ ID NO 304
<211> LENGTH: 16
<212> TYPE: PRT
<213> ORGANISM: Oryctolagus cuniculus

<400> SEQUENCE: 304

Ile Ile Thr Thr Ser Gly Asn Thr Phe Tyr Ala Ser Trp Ala Lys Gly
1 5 10 15

<210> SEQ ID NO 305
<211> LENGTH: 10
<212> TYPE: PRT
<213> ORGANISM: Oryctolagus cuniculus

<400> SEQUENCE: 305

Thr Ser Asp Ile Phe Tyr Tyr Arg Asn Leu
1 5 10

<210> SEQ ID NO 306
<211> LENGTH: 366
<212> TYPE: DNA
<213> ORGANISM: Oryctolagus cuniculus

<400> SEQUENCE: 306
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cagtgaggac atttataggt tattggcctg gtatcaacag 180
aaaccagggc agcctcccaa gctcctgatc tatgattcat ccgatctggc atctggggtc 240
ccatcgcggt tcaaaggcag tggatctggg acagagttca ctctcgccat cagcggtgtg 300
cagtgtgacg atgctgccac ttactactgt caacaggctt ggagttatag tgatattgat 360
aatgct 366

<210> SEQ ID NO 307
<211> LENGTH: 369
<212> TYPE: DNA
<213> ORGANISM: Oryctolagus cuniculus

<400> SEQUENCE: 307
atggagactg ggctgcgctg gcttctcctg gtcgctgtgc tcaaaggtgt ccagtgtcag 60
tcggtggagg agtccggggg tcgcctggtc acgccgggga cacccctgac actcacctgc 120
acagcctctg gattctccct cagtagctac tacatgagct gggtccgcca ggctccaggg 180
aaggggctgg aatggatcgg aatcattact actagtggta atacatttta cgcgagctgg 240
gcgaaaggcc ggctcaccat ctccagaacc tcgaccacgg tggatctgaa aatcaccagt 300
ccgacaaccg aggacacggc cacctatttc tgtgccagaa cttctgatat tttttattat 360
cgtaacttg 369

<210> SEQ ID NO 308
<211> LENGTH: 33
<212> TYPE: DNA
<213> ORGANISM: Oryctolagus cuniculus

<400> SEQUENCE: 308
caggccagtg aggacattta taggttattg gcc 33

<210> SEQ ID NO 309
<211> LENGTH: 21
<212> TYPE: DNA
<213> ORGANISM: Oryctolagus cuniculus

<400> SEQUENCE: 309
gattcatccg atctggcatc t 21

<210> SEQ ID NO 310
<211> LENGTH: 36
<212> TYPE: DNA
<213> ORGANISM: Oryctolagus cuniculus

<400> SEQUENCE: 310
caacaggctt ggagttatag tgatattgat aatgct 36

<210> SEQ ID NO 311
<211> LENGTH: 15
<212> TYPE: DNA
<213> ORGANISM: Oryctolagus cuniculus

<400> SEQUENCE: 311
agctactaca tgagc 15

<210> SEQ ID NO 312
<211> LENGTH: 48
<212> TYPE: DNA
<213> ORGANISM: Oryctolagus cuniculus

<400> SEQUENCE: 312
atcattacta ctagtggtaa tacattttac gcgagctggg cgaaaggc 48

<210> SEQ ID NO 313
<211> LENGTH: 30
<212> TYPE: DNA
<213> ORGANISM: Oryctolagus cuniculus

<400> SEQUENCE: 313
acttctgata tttttatta tcgtaacttg 30

<210> SEQ ID NO 314
<211> LENGTH: 123
<212> TYPE: PRT
<213> ORGANISM: Oryctolagus cuniculus

<400> SEQUENCE: 314

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Ala Ser Pro
            20                  25                  30

Val Ser Ala Ala Val Gly Ala Thr Val Thr Ile Asn Cys Gln Ser Ser
        35                  40                  45

Gln Ser Val Tyr Asn Asp Met Asp Leu Ala Trp Phe Gln Gln Lys Pro
    50                  55                  60

Gly Gln Pro Pro Lys Leu Leu Ile Tyr Ser Ala Ser Thr Leu Ala Ser
65                  70                  75                  80

Gly Val Pro Ser Arg Phe Ser Gly Ser Gly Ser Gly Thr Glu Phe Thr
                85                  90                  95

Leu Thr Ile Ser Gly Val Gln Cys Asp Asp Ala Ala Thr Tyr Tyr Cys
            100                 105                 110

Leu Gly Ala Phe Asp Asp Asp Ala Asp Asn Thr
        115                 120
```

<210> SEQ ID NO 315
<211> LENGTH: 129
<212> TYPE: PRT
<213> ORGANISM: Oryctolagus cuniculus

<400> SEQUENCE: 315

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Thr
        35                  40                  45

Arg His Ala Ile Thr Trp Val Arg Gln Ala Pro Gly Lys Gly Leu Glu
    50                  55                  60

Trp Ile Gly Cys Ile Trp Ser Gly Gly Ser Thr Tyr Tyr Ala Thr Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Ala
            100                 105                 110

Arg Val Ile Gly Asp Thr Ala Gly Tyr Ala Tyr Phe Thr Gly Leu Asp
        115                 120                 125

Leu


<210> SEQ ID NO 316
<211> LENGTH: 13
<212> TYPE: PRT
<213> ORGANISM: Oryctolagus cuniculus

<400> SEQUENCE: 316

Gln Ser Ser Gln Ser Val Tyr Asn Asp Met Asp Leu Ala
1               5                   10


<210> SEQ ID NO 317
<211> LENGTH: 7
<212> TYPE: PRT
<213> ORGANISM: Oryctolagus cuniculus

<400> SEQUENCE: 317

Ser Ala Ser Thr Leu Ala Ser
1               5


<210> SEQ ID NO 318
<211> LENGTH: 11
<212> TYPE: PRT
<213> ORGANISM: Oryctolagus cuniculus

<400> SEQUENCE: 318

Leu Gly Ala Phe Asp Asp Asp Ala Asp Asn Thr
1               5                   10


<210> SEQ ID NO 319
<211> LENGTH: 5
<212> TYPE: PRT
<213> ORGANISM: Oryctolagus cuniculus

<400> SEQUENCE: 319

Arg His Ala Ile Thr
1               5


<210> SEQ ID NO 320
<211> LENGTH: 16
<212> TYPE: PRT
<213> ORGANISM: Oryctolagus cuniculus

<400> SEQUENCE: 320

Cys Ile Trp Ser Gly Gly Ser Thr Tyr Tyr Ala Thr Trp Ala Lys Gly
```

-continued

```
1               5                   10                  15

<210> SEQ ID NO 321
<211> LENGTH: 16
<212> TYPE: PRT
<213> ORGANISM: Oryctolagus cuniculus

<400> SEQUENCE: 321

Val Ile Gly Asp Thr Ala Gly Tyr Ala Tyr Phe Thr Gly Leu Asp Leu
1               5                   10                  15

<210> SEQ ID NO 322
<211> LENGTH: 369
<212> TYPE: DNA
<213> ORGANISM: Oryctolagus cuniculus

<400> SEQUENCE: 322

atggacacga gggcccccac tcagctgctg gggctcctgc tgctctggct cccaggtgcc     60

acgtttgcag ccgtgctgac ccagactgca tcacccgtgt ctgccgctgt gggagccaca    120

gtcaccatca actgccagtc cagtcagagt gtttataatg acatggactt agcctggttt    180

cagcagaaac cagggcagcc tcccaagctc ctgatctatt ctgcatccac tctggcatct    240

ggggtcccat cgcggttcag cggcagtgga tctgggacag agttcactct caccatcagc    300

ggcgtgcagt gtgacgatgc tgccacttac tactgtctag gcgcttttga tgatgatgct    360

gataatact                                                            369

<210> SEQ ID NO 323
<211> LENGTH: 387
<212> TYPE: DNA
<213> ORGANISM: Oryctolagus cuniculus

<400> SEQUENCE: 323

atggagactg ggctgcgctg gcttctcctg gtcgctgtgc tcaaaggtgt ccagtgtcag     60

tcggtggagg agtccggggg tcgcctggtc acgcctggga cacccctgac actcacctgc    120

acagtctctg gattctccct cactaggcat gcaataacct gggtccgcca ggctccaggg    180

aaggggctgg aatggatcgg atgcatttgg agtggtggta gcacatacta cgcgacctgg    240

gcgaaaggcc gattcaccat ctccaaaacc tcgaccacgg tggatctcag aatcaccagt    300

ccgacaaccg aggacacggc cacctacttc tgtgccagag tcattggcga tactgctggt    360

tatgcttatt ttacggggct tgacttg                                        387

<210> SEQ ID NO 324
<211> LENGTH: 39
<212> TYPE: DNA
<213> ORGANISM: Oryctolagus cuniculus

<400> SEQUENCE: 324

cagtccagtc agagtgttta taatgacatg gacttagcc                            39

<210> SEQ ID NO 325
<211> LENGTH: 21
<212> TYPE: DNA
<213> ORGANISM: Oryctolagus cuniculus

<400> SEQUENCE: 325

tctgcatcca ctctggcatc t                                               21

<210> SEQ ID NO 326
<211> LENGTH: 33
```

<212> TYPE: DNA
<213> ORGANISM: Oryctolagus cuniculus

<400> SEQUENCE: 326
ctaggcgctt ttgatgatga tgctgataat act 33

<210> SEQ ID NO 327
<211> LENGTH: 15
<212> TYPE: DNA
<213> ORGANISM: Oryctolagus cuniculus

<400> SEQUENCE: 327
aggcatgcaa taacc 15

<210> SEQ ID NO 328
<211> LENGTH: 48
<212> TYPE: DNA
<213> ORGANISM: Oryctolagus cuniculus

<400> SEQUENCE: 328
tgcatttgga gtggtggtag cacatactac gcgacctggg cgaaaggc 48

<210> SEQ ID NO 329
<211> LENGTH: 48
<212> TYPE: DNA
<213> ORGANISM: Oryctolagus cuniculus

<400> SEQUENCE: 329
gtcattggcg atactgctgg ttatgcttat tttacggggc ttgacttg 48

<210> SEQ ID NO 330
<211> LENGTH: 121
<212> TYPE: PRT
<213> ORGANISM: Oryctolagus cuniculus

<400> SEQUENCE: 330

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Val Tyr Asn Trp Leu Ser Trp Tyr Gln Gln Lys Pro Gly Gln
    50                  55                  60

Pro Pro Lys Leu Leu Ile Tyr Thr Ala Ser Ser Leu Ala Ser Gly Val
65                  70                  75                  80

Pro Ser Arg Phe Ser Gly Ser Gly Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Thr Ser Asp Val Asp Asn Val
        115                 120
```

<210> SEQ ID NO 331
<211> LENGTH: 130
<212> TYPE: PRT
<213> ORGANISM: Oryctolagus cuniculus

<400> SEQUENCE: 331

```
Met Glu Thr Gly Leu Arg Trp Leu Leu Leu Val Ala Val Leu Lys Gly
1               5                   10                  15
```

```
Val Gln Cys Gln Ser Leu Glu Glu Ala Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Tyr Ala Met Gly Trp Val Arg Gln Ala Pro Gly Lys Gly Leu Glu
    50                  55                  60

Tyr Ile Gly Ile Ile Ser Ser Ser Gly Ser Thr Tyr Tyr Ala Thr Trp
65                  70                  75                  80

Ala Lys Gly Arg Phe Thr Ile Ser Gln Ala Ser Ser Thr Thr Val Asp
                85                  90                  95

Leu Lys Ile Thr Ser Pro Thr Thr Glu Asp Ser Ala Thr Tyr Phe Cys
            100                 105                 110

Ala Arg Gly Gly Ala Gly Ser Gly Gly Val Trp Leu Leu Asp Gly Phe
        115                 120                 125

Asp Pro
    130


<210> SEQ ID NO 332
<211> LENGTH: 11
<212> TYPE: PRT
<213> ORGANISM: Oryctolagus cuniculus

<400> SEQUENCE: 332

Gln Ala Ser Gln Ser Val Tyr Asn Trp Leu Ser
1               5                   10


<210> SEQ ID NO 333
<211> LENGTH: 7
<212> TYPE: PRT
<213> ORGANISM: Oryctolagus cuniculus

<400> SEQUENCE: 333

Thr Ala Ser Ser Leu Ala Ser
1               5


<210> SEQ ID NO 334
<211> LENGTH: 11
<212> TYPE: PRT
<213> ORGANISM: Oryctolagus cuniculus

<400> SEQUENCE: 334

Gln Gln Gly Tyr Thr Ser Asp Val Asp Asn Val
1               5                   10


<210> SEQ ID NO 335
<211> LENGTH: 5
<212> TYPE: PRT
<213> ORGANISM: Oryctolagus cuniculus

<400> SEQUENCE: 335

Ser Tyr Ala Met Gly
1               5


<210> SEQ ID NO 336
<211> LENGTH: 16
<212> TYPE: PRT
<213> ORGANISM: Oryctolagus cuniculus

<400> SEQUENCE: 336

Ile Ile Ser Ser Ser Gly Ser Thr Tyr Tyr Ala Thr Trp Ala Lys Gly
1               5                   10                  15
```

<210> SEQ ID NO 337
<211> LENGTH: 16
<212> TYPE: PRT
<213> ORGANISM: Oryctolagus cuniculus

<400> SEQUENCE: 337

Gly Gly Ala Gly Ser Gly Gly Val Trp Leu Leu Asp Gly Phe Asp Pro
1 5 10 15

<210> SEQ ID NO 338
<211> LENGTH: 363
<212> TYPE: DNA
<213> ORGANISM: Oryctolagus cuniculus

<400> SEQUENCE: 338
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cagtcagagt gtttataatt ggttatcctg gtatcagcag 180
aaaccagggc agcctcccaa gctcctgatc tatactgcat ccagtctggc atctggggtc 240
ccatcgcggt tcagtggcag tggatctggg acagagttca ctctcaccat cagcggcgtg 300
gagtgtgccg atgctgccac ttactactgt caacagggtt atactagtga tgttgataat 360
gtt 363

<210> SEQ ID NO 339
<211> LENGTH: 390
<212> TYPE: DNA
<213> ORGANISM: Oryctolagus cuniculus

<400> SEQUENCE: 339
atggagactg ggctgcgctg gcttctcctg gtcgctgtgc tcaaaggtgt ccagtgtcag 60
tcgctggagg aggccggggg tcgcctggtc acgcctggga cacccctgac actcacctgc 120
acagtctctg gaatcgacct cagtagctat gcaatgggct gggtccgcca ggctccaggg 180
aaggggctgg aatacatcgg aatcattagt agtagtggta gcacatacta cgcgacctgg 240
gcgaaaggcc gattcaccat ctcacaagcc tcgtcgacca cggtggatct gaaaattacc 300
agtccgacaa ccgaggactc ggccacatat ttctgtgcca gagggggtgc tggtagtggt 360
ggtgtttggc tgcttgatgg ttttgatccc 390

<210> SEQ ID NO 340
<211> LENGTH: 33
<212> TYPE: DNA
<213> ORGANISM: Oryctolagus cuniculus

<400> SEQUENCE: 340
caggccagtc agagtgttta taattggtta tcc 33

<210> SEQ ID NO 341
<211> LENGTH: 21
<212> TYPE: DNA
<213> ORGANISM: Oryctolagus cuniculus

<400> SEQUENCE: 341
actgcatcca gtctggcatc t 21

<210> SEQ ID NO 342
<211> LENGTH: 33
<212> TYPE: DNA
<213> ORGANISM: Oryctolagus cuniculus

<400> SEQUENCE: 342
caacagggtt atactagtga tgttgataat gtt 33

<210> SEQ ID NO 343
<211> LENGTH: 15
<212> TYPE: DNA
<213> ORGANISM: Oryctolagus cuniculus

<400> SEQUENCE: 343
agctatgcaa tgggc 15

<210> SEQ ID NO 344
<211> LENGTH: 48
<212> TYPE: DNA
<213> ORGANISM: Oryctolagus cuniculus

<400> SEQUENCE: 344
atcattagta gtagtggtag cacatactac gcgacctggg cgaaaggc 48

<210> SEQ ID NO 345
<211> LENGTH: 48
<212> TYPE: DNA
<213> ORGANISM: Oryctolagus cuniculus

<400> SEQUENCE: 345
gggggtgctg gtagtggtgg tgtttggctg cttgatggtt ttgatccc 48

<210> SEQ ID NO 346
<211> LENGTH: 123
<212> TYPE: PRT
<213> ORGANISM: Oryctolagus cuniculus

<400> SEQUENCE: 346

```
Met Asp Thr Arg Ala Pro Thr Gln Leu Leu Gly Leu Leu Leu Leu Trp
1               5                   10                  15

Leu Pro Gly Ala Lys Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Asn Ile Tyr Asn Trp Leu Ala Trp Tyr Gln Gln Lys Pro Gly
    50                  55                  60

Gln Pro Pro Lys Leu Leu Ile Tyr Thr Val Gly Asp Leu Ala Ser Gly
65                  70                  75                  80

Val Ser Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Gln Gly Tyr Ser Ser Ser Tyr Val Asp Asn Val
        115                 120
```

<210> SEQ ID NO 347
<211> LENGTH: 130
<212> TYPE: PRT
<213> ORGANISM: Oryctolagus cuniculus

<400> SEQUENCE: 347

```
Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Arg Leu Val Thr
            20                  25                  30
```

```
Pro Gly Thr Pro Leu Thr Leu Thr Cys Thr Val Ser Gly Phe Ser Leu
        35                  40                  45

Asn Asp Tyr Ala Val Gly Trp Phe Arg Gln Ala Pro Gly Lys Gly Leu
    50                  55                  60

Glu Trp Ile Gly Tyr Ile Arg Ser Ser Gly Thr Thr Ala Tyr Ala Thr
65                  70                  75                  80

Trp Ala Lys Gly Arg Phe Thr Ile Ser Ala Thr Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Gly Gly Ala Gly Ser Ser Gly Val Trp Ile Leu Asp Gly Phe
        115                 120                 125

Ala Pro
    130


<210> SEQ ID NO 348
<211> LENGTH: 11
<212> TYPE: PRT
<213> ORGANISM: Oryctolagus cuniculus

<400> SEQUENCE: 348

Gln Ala Ser Glu Asn Ile Tyr Asn Trp Leu Ala
1               5                   10


<210> SEQ ID NO 349
<211> LENGTH: 7
<212> TYPE: PRT
<213> ORGANISM: Oryctolagus cuniculus

<400> SEQUENCE: 349

Thr Val Gly Asp Leu Ala Ser
1               5


<210> SEQ ID NO 350
<211> LENGTH: 12
<212> TYPE: PRT
<213> ORGANISM: Oryctolagus cuniculus

<400> SEQUENCE: 350

Gln Gln Gly Tyr Ser Ser Ser Tyr Val Asp Asn Val
1               5                   10


<210> SEQ ID NO 351
<211> LENGTH: 5
<212> TYPE: PRT
<213> ORGANISM: Oryctolagus cuniculus

<400> SEQUENCE: 351

Asp Tyr Ala Val Gly
1               5


<210> SEQ ID NO 352
<211> LENGTH: 16
<212> TYPE: PRT
<213> ORGANISM: Oryctolagus cuniculus

<400> SEQUENCE: 352

Tyr Ile Arg Ser Ser Gly Thr Thr Ala Tyr Ala Thr Trp Ala Lys Gly
1               5                   10                  15


<210> SEQ ID NO 353
<211> LENGTH: 16
<212> TYPE: PRT
```

<213> ORGANISM: Oryctolagus cuniculus

<400> SEQUENCE: 353

Gly Gly Ala Gly Ser Ser Gly Val Trp Ile Leu Asp Gly Phe Ala Pro
1 5 10 15

<210> SEQ ID NO 354
<211> LENGTH: 369
<212> TYPE: DNA
<213> ORGANISM: Oryctolagus cuniculus

<400> SEQUENCE: 354
atggacacga gggcccccac tcagctgctg gggctcctgc tgctctggct cccaggtgcc 60
aaatgtgccg atgttgtgat gacccagact ccagcctccg tgtctgcagc tgtgggaggc 120
acagtcacca tcaattgcca ggccagtgag aacatttata attggttagc ctggtatcag 180
cagaaaccag ggcagcctcc caagctcctg atctatactg taggcgatct ggcatctggg 240
gtctcatcgc ggttcaaagg cagtggatct gggacagagt tcactctcac catcagcgac 300
ctggagtgtg ccgatgctgc cacttactat tgtcaacagg gttatagtag tagttatgtt 360
gataatgtt 369

<210> SEQ ID NO 355
<211> LENGTH: 390
<212> TYPE: DNA
<213> ORGANISM: Oryctolagus cuniculus

<400> SEQUENCE: 355
atggagactg ggctgcgctg gcttctcctg gtcgctgtgc tcaaaggtgt ccagtgtcag 60
gagcagctga aggagtccgg gggtcgcctg gtcacgcctg ggacacccct gacactcacc 120
tgcacagtct ctggattctc cctcaatgac tatgcagtgg gctggttccg ccaggctcca 180
gggaaggggc tggaatggat cggatacatt cgtagtagtg gtaccacagc ctacgcgacc 240
tgggcgaaag gccgattcac catctccgct acctcgacca cggtggatct gaaaatcacc 300
agtccgacaa ccgaggacac ggccacctat ttctgtgcca gagggggtgc tggtagtagt 360
ggtgtgtgga tccttgatgg ttttgctccc 390

<210> SEQ ID NO 356
<211> LENGTH: 33
<212> TYPE: DNA
<213> ORGANISM: Oryctolagus cuniculus

<400> SEQUENCE: 356
caggccagtg agaacattta taattggtta gcc 33

<210> SEQ ID NO 357
<211> LENGTH: 21
<212> TYPE: DNA
<213> ORGANISM: Oryctolagus cuniculus

<400> SEQUENCE: 357
actgtaggcg atctggcatc t 21

<210> SEQ ID NO 358
<211> LENGTH: 36
<212> TYPE: DNA
<213> ORGANISM: Oryctolagus cuniculus

<400> SEQUENCE: 358
caacagggtt atagtagtag ttatgttgat aatgtt 36

<210> SEQ ID NO 359
<211> LENGTH: 15
<212> TYPE: DNA
<213> ORGANISM: Oryctolagus cuniculus

<400> SEQUENCE: 359
gactatgcag tgggc 15

<210> SEQ ID NO 360
<211> LENGTH: 48
<212> TYPE: DNA
<213> ORGANISM: Oryctolagus cuniculus

<400> SEQUENCE: 360
tacattcgta gtagtggtac cacagcctac gcgacctggg cgaaaggc 48

<210> SEQ ID NO 361
<211> LENGTH: 48
<212> TYPE: DNA
<213> ORGANISM: Oryctolagus cuniculus

<400> SEQUENCE: 361
gggggtgctg gtagtagtgg tgtgtggatc cttgatggtt ttgctccc 48

<210> SEQ ID NO 362
<211> LENGTH: 121
<212> TYPE: PRT
<213> ORGANISM: Oryctolagus cuniculus

<400> SEQUENCE: 362

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Ser
20 25 30

Val Ser Ala Ala Val Gly Gly Thr Val Thr Ile Asn Cys Gln Ala Ser
35 40 45

Gln Ser Val Tyr Gln Asn Asn Tyr Leu Ser Trp Phe Gln Gln Lys Pro
50 55 60

Gly Gln Pro Pro Lys Leu Leu Ile Tyr Gly Ala Ala Thr Leu Ala Ser
65 70 75 80

Gly Val Pro Ser Arg Phe Lys Gly Ser Gly Ser Gly Thr Gln Phe Thr
85 90 95

Leu Thr Ile Ser Asp Leu Glu Cys Asp Asp Ala Ala Thr Tyr Tyr Cys
100 105 110

Ala Gly Ala Tyr Arg Asp Val Asp Ser
115 120

<210> SEQ ID NO 363
<211> LENGTH: 130
<212> TYPE: PRT
<213> ORGANISM: Oryctolagus cuniculus

<400> SEQUENCE: 363

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Thr Ala Ser Gly Phe Ser Phe Thr
35 40 45

```
Ser Thr Tyr Tyr Ile Tyr Trp Val Arg Gln Ala Pro Gly Lys Gly Leu
    50                  55                  60

Glu Trp Ile Ala Cys Ile Asp Ala Gly Ser Ser Gly Ser Thr Tyr Tyr
65                  70                  75                  80

Ala Thr Trp Val Asn Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Lys Trp Asp Tyr Gly Gly Asn Val Gly Trp Gly Tyr
        115                 120                 125

Asp Leu
    130


<210> SEQ ID NO 364
<211> LENGTH: 13
<212> TYPE: PRT
<213> ORGANISM: Oryctolagus cuniculus

<400> SEQUENCE: 364

Gln Ala Ser Gln Ser Val Tyr Gln Asn Asn Tyr Leu Ser
1               5                   10


<210> SEQ ID NO 365
<211> LENGTH: 7
<212> TYPE: PRT
<213> ORGANISM: Oryctolagus cuniculus

<400> SEQUENCE: 365

Gly Ala Ala Thr Leu Ala Ser
1               5


<210> SEQ ID NO 366
<211> LENGTH: 9
<212> TYPE: PRT
<213> ORGANISM: Oryctolagus cuniculus

<400> SEQUENCE: 366

Ala Gly Ala Tyr Arg Asp Val Asp Ser
1               5


<210> SEQ ID NO 367
<211> LENGTH: 6
<212> TYPE: PRT
<213> ORGANISM: Oryctolagus cuniculus

<400> SEQUENCE: 367

Ser Thr Tyr Tyr Ile Tyr
1               5


<210> SEQ ID NO 368
<211> LENGTH: 18
<212> TYPE: PRT
<213> ORGANISM: Oryctolagus cuniculus

<400> SEQUENCE: 368

Cys Ile Asp Ala Gly Ser Ser Gly Ser Thr Tyr Tyr Ala Thr Trp Val
1               5                   10                  15

Asn Gly


<210> SEQ ID NO 369
<211> LENGTH: 13
<212> TYPE: PRT
<213> ORGANISM: Oryctolagus cuniculus
```

<400> SEQUENCE: 369

Trp Asp Tyr Gly Gly Asn Val Gly Trp Gly Tyr Asp Leu
1 5 10

<210> SEQ ID NO 370
<211> LENGTH: 363
<212> TYPE: DNA
<213> ORGANISM: Oryctolagus cuniculus

<400> SEQUENCE: 370
atggacacga gggcccccac tcagctgctg gggctcctgc tgctctggct cccaggtgcc 60
acatttgctc aagtgctgac ccagactcca tcctccgtgt ctgcagctgt gggaggcaca 120
gtcaccatca attgccaggc cagtcagagt gtttatcaga acaactactt atcctggttt 180
cagcagaaac cagggcagcc tcccaagctc ctgatctatg gtgcggccac tctggcatct 240
ggggtcccat cgcggttcaa aggcagtgga tctgggacac agttcactct caccatcagc 300
gacctggagt gtgacgatgc tgccacttac tactgtgcag gcgcttatag ggatgtggat 360
tct 363

<210> SEQ ID NO 371
<211> LENGTH: 390
<212> TYPE: DNA
<213> ORGANISM: Oryctolagus cuniculus

<400> SEQUENCE: 371
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
acagcctctg gattctcctt tactagtacc tactacatct actgggtccg ccaggctcca 180
gggaaggggc tggagtggat cgcatgtatt gatgctggta gtagtggtag cacttactac 240
gcgacctggg tgaatggccg attcaccatc tccaaaacct cgtcgaccac ggtgactctg 300
caaatgacca gtctgacagc cgcggacacg gccacctatt tctgtgcgaa atgggattat 360
ggtggtaatg ttggttgggg ttatgacttg 390

<210> SEQ ID NO 372
<211> LENGTH: 39
<212> TYPE: DNA
<213> ORGANISM: Oryctolagus cuniculus

<400> SEQUENCE: 372
caggccagtc agagtgttta tcagaacaac tacttatcc 39

<210> SEQ ID NO 373
<211> LENGTH: 21
<212> TYPE: DNA
<213> ORGANISM: Oryctolagus cuniculus

<400> SEQUENCE: 373
ggtgcggcca ctctggcatc t 21

<210> SEQ ID NO 374
<211> LENGTH: 27
<212> TYPE: DNA
<213> ORGANISM: Oryctolagus cuniculus

<400> SEQUENCE: 374
gcaggcgctt atagggatgt ggattct 27

<210> SEQ ID NO 375
<211> LENGTH: 18
<212> TYPE: DNA
<213> ORGANISM: Oryctolagus cuniculus

<400> SEQUENCE: 375
agtacctact acatctac 18

<210> SEQ ID NO 376
<211> LENGTH: 54
<212> TYPE: DNA
<213> ORGANISM: Oryctolagus cuniculus

<400> SEQUENCE: 376
tgtattgatg ctggtagtag tggtagcact tactacgcga cctgggtgaa tggc 54

<210> SEQ ID NO 377
<211> LENGTH: 39
<212> TYPE: DNA
<213> ORGANISM: Oryctolagus cuniculus

<400> SEQUENCE: 377
tgggattatg gtggtaatgt tggttggggt tatgacttg 39

<210> SEQ ID NO 378
<211> LENGTH: 120
<212> TYPE: PRT
<213> ORGANISM: Oryctolagus cuniculus

<400> SEQUENCE: 378

```
Met Asp Thr Arg Ala Pro Thr Gln Leu Leu Gly Leu Leu Leu Leu Trp
1               5                   10                  15

Leu Pro Gly Ala Arg Cys Ala Phe Glu Leu Thr Gln Thr Pro Ser Ser
            20                  25                  30

Val Glu Ala Ala Val Gly Gly Thr Val Thr Ile Lys Cys Gln Ala Ser
        35                  40                  45

Gln Ser Ile Ser Ser Tyr Leu Ala Trp Tyr Gln Gln Lys Pro Gly Gln
    50                  55                  60

Pro Pro Lys Phe Leu Ile Tyr Arg Ala Ser Thr Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Ser
            100                 105                 110

Tyr Tyr Asp Ser Val Ser Asn Pro
        115                 120
```

<210> SEQ ID NO 379
<211> LENGTH: 127
<212> TYPE: PRT
<213> ORGANISM: Oryctolagus cuniculus

<400> SEQUENCE: 379

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Glu Gly Ser Leu Thr Leu Thr Cys Lys Ala Ser Gly Leu Asp Leu Gly
        35                  40                  45

Thr Tyr Trp Phe Met Cys Trp Val Arg Gln Ala Pro Gly Lys Gly Leu
```

```
    50                  55                  60

Glu Trp Ile Ala Cys Ile Tyr Thr Gly Ser Ser Gly Ser Thr Phe Tyr
65                  70                  75                  80

Ala Ser Trp Val Asn Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Gly Tyr Ser Gly Tyr Gly Tyr Phe Lys Leu
        115                 120                 125


<210> SEQ ID NO 380
<211> LENGTH: 11
<212> TYPE: PRT
<213> ORGANISM: Oryctolagus cuniculus

<400> SEQUENCE: 380

Gln Ala Ser Gln Ser Ile Ser Ser Tyr Leu Ala
1               5                   10


<210> SEQ ID NO 381
<211> LENGTH: 7
<212> TYPE: PRT
<213> ORGANISM: Oryctolagus cuniculus

<400> SEQUENCE: 381

Arg Ala Ser Thr Leu Ala Ser
1               5


<210> SEQ ID NO 382
<211> LENGTH: 10
<212> TYPE: PRT
<213> ORGANISM: Oryctolagus cuniculus

<400> SEQUENCE: 382

Gln Ser Tyr Tyr Asp Ser Val Ser Asn Pro
1               5                   10


<210> SEQ ID NO 383
<211> LENGTH: 6
<212> TYPE: PRT
<213> ORGANISM: Oryctolagus cuniculus

<400> SEQUENCE: 383

Thr Tyr Trp Phe Met Cys
1               5


<210> SEQ ID NO 384
<211> LENGTH: 18
<212> TYPE: PRT
<213> ORGANISM: Oryctolagus cuniculus

<400> SEQUENCE: 384

Cys Ile Tyr Thr Gly Ser Ser Gly Ser Thr Phe Tyr Ala Ser Trp Val
1               5                   10                  15

Asn Gly


<210> SEQ ID NO 385
<211> LENGTH: 10
<212> TYPE: PRT
<213> ORGANISM: Oryctolagus cuniculus

<400> SEQUENCE: 385

Gly Tyr Ser Gly Tyr Gly Tyr Phe Lys Leu
```

-continued 1 5 10

<210> SEQ ID NO 386
<211> LENGTH: 360
<212> TYPE: DNA
<213> ORGANISM: Oryctolagus cuniculus

<400> SEQUENCE: 386
atggacacga gggcccccac tcagctgctg gggctcctgc tgctctggct cccaggtgcc 60
agatgtgcat tcgaattgac ccagactcca tcctccgtgg aggcagctgt gggaggcaca 120
gtcaccatca agtgccaggc cagtcagagc attagtagtt acttagcctg gtatcagcag 180
aaaccagggc agcctcccaa gttcctgatc tacagggcgt ccactctggc atctggggtc 240
ccatcgcgat tcaaaggcag tggatctggg acagagttca ctctcaccat cagcgacctg 300
gagtgtgccg atgctgccac ttactactgt caaagctatt atgatagtgt ttcaaatcct 360

<210> SEQ ID NO 387
<211> LENGTH: 381
<212> TYPE: DNA
<213> ORGANISM: Oryctolagus cuniculus

<400> SEQUENCE: 387
atggagactg ggctgcgctg gcttctcctg gtcgctgtgc tcaaaggtgt ccagtgtcag 60
tcgttggagg agtccggggg agacctggtc aagcctgagg gatccctgac actcacctgc 120
aaagcctctg gactcgacct cggtacctac tggttcatgt gctgggtccg ccaggctcca 180
gggaaggggc tggagtggat cgcttgtatt tatactggta gtagtggttc cactttctac 240
gcgagctggg tgaatggccg attcaccatc tccaaaacct cgtcgaccac ggtgactctg 300
caaatgacca gtctgacagc cgcggacacg gccacttatt tttgtgcgag aggttatagt 360
ggttatggtt attttaagtt g 381

<210> SEQ ID NO 388
<211> LENGTH: 33
<212> TYPE: DNA
<213> ORGANISM: Oryctolagus cuniculus

<400> SEQUENCE: 388
caggccagtc agagcattag tagttactta gcc 33

<210> SEQ ID NO 389
<211> LENGTH: 21
<212> TYPE: DNA
<213> ORGANISM: Oryctolagus cuniculus

<400> SEQUENCE: 389
agggcgtcca ctctggcatc t 21

<210> SEQ ID NO 390
<211> LENGTH: 30
<212> TYPE: DNA
<213> ORGANISM: Oryctolagus cuniculus

<400> SEQUENCE: 390
caaagctatt atgatagtgt ttcaaatcct 30

<210> SEQ ID NO 391
<211> LENGTH: 18
<212> TYPE: DNA
<213> ORGANISM: Oryctolagus cuniculus

<400> SEQUENCE: 391
acctactggt tcatgtgc 18

<210> SEQ ID NO 392
<211> LENGTH: 54
<212> TYPE: DNA
<213> ORGANISM: Oryctolagus cuniculus

<400> SEQUENCE: 392
tgtatttata ctggtagtag tggttccact ttctacgcga gctgggtgaa tggc 54

<210> SEQ ID NO 393
<211> LENGTH: 30
<212> TYPE: DNA
<213> ORGANISM: Oryctolagus cuniculus

<400> SEQUENCE: 393
ggttatagtg gttatggtta ttttaagttg 30

<210> SEQ ID NO 394
<211> LENGTH: 124
<212> TYPE: PRT
<213> ORGANISM: Oryctolagus cuniculus

<400> SEQUENCE: 394

```
Met Asp Thr Arg Ala Pro Thr Gln Leu Leu Gly Leu Leu Leu Leu Trp
1               5                   10                  15

Leu Pro Gly Val Thr Phe Ala Ile Glu Met Thr Gln Ser Pro Phe Ser
            20                  25                  30

Val Ser Ala Ala Val Gly Gly Thr Val Ser Ile Ser Cys Gln Ala Ser
        35                  40                  45

Gln Ser Val Tyr Lys Asn Asn Gln Leu Ser Trp Tyr Gln Gln Lys Ser
    50                  55                  60

Gly Gln Pro Pro Lys Leu Leu Ile Tyr Gly Ala Ser Ala Leu Ala Ser
65                  70                  75                  80

Gly Val Pro Ser Arg Phe Lys Gly Ser Gly Ser Gly Thr Glu Phe Thr
                85                  90                  95

Leu Thr Ile Ser Asp Val Gln Cys Asp Asp Ala Ala Thr Tyr Tyr Cys
            100                 105                 110

Ala Gly Ala Ile Thr Gly Ser Ile Asp Thr Asp Gly
        115                 120
```

<210> SEQ ID NO 395
<211> LENGTH: 130
<212> TYPE: PRT
<213> ORGANISM: Oryctolagus cuniculus

<400> SEQUENCE: 395

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Thr Ser Gly Phe Ser Phe Ser
        35                  40                  45

Ser Ser Tyr Phe Ile Cys Trp Val Arg Gln Ala Pro Gly Lys Gly Leu
    50                  55                  60

Glu Trp Ile Ala Cys Ile Tyr Gly Gly Asp Gly Ser Thr Tyr Tyr Ala
65                  70                  75                  80

Ser Trp Ala Lys Gly Arg Phe Thr Ile Ser Lys Thr Ser Ser Thr Thr
```

```
                85                  90                  95

Val Thr Leu Gln Met Thr Ser Leu Thr Ala Ala Asp Thr Ala Thr Tyr
            100                 105                 110

Phe Cys Ala Arg Glu Trp Ala Tyr Ser Gln Gly Tyr Phe Gly Ala Phe
        115                 120                 125

Asp Leu
    130


<210> SEQ ID NO 396
<211> LENGTH: 13
<212> TYPE: PRT
<213> ORGANISM: Oryctolagus cuniculus

<400> SEQUENCE: 396

Gln Ala Ser Gln Ser Val Tyr Lys Asn Asn Gln Leu Ser
1               5                   10


<210> SEQ ID NO 397
<211> LENGTH: 7
<212> TYPE: PRT
<213> ORGANISM: Oryctolagus cuniculus

<400> SEQUENCE: 397

Gly Ala Ser Ala Leu Ala Ser
1               5


<210> SEQ ID NO 398
<211> LENGTH: 12
<212> TYPE: PRT
<213> ORGANISM: Oryctolagus cuniculus

<400> SEQUENCE: 398

Ala Gly Ala Ile Thr Gly Ser Ile Asp Thr Asp Gly
1               5                   10


<210> SEQ ID NO 399
<211> LENGTH: 6
<212> TYPE: PRT
<213> ORGANISM: Oryctolagus cuniculus

<400> SEQUENCE: 399

Ser Ser Tyr Phe Ile Cys
1               5


<210> SEQ ID NO 400
<211> LENGTH: 17
<212> TYPE: PRT
<213> ORGANISM: Oryctolagus cuniculus

<400> SEQUENCE: 400

Cys Ile Tyr Gly Gly Asp Gly Ser Thr Tyr Tyr Ala Ser Trp Ala Lys
1               5                   10                  15

Gly


<210> SEQ ID NO 401
<211> LENGTH: 14
<212> TYPE: PRT
<213> ORGANISM: Oryctolagus cuniculus

<400> SEQUENCE: 401

Glu Trp Ala Tyr Ser Gln Gly Tyr Phe Gly Ala Phe Asp Leu
1               5                   10
```

<210> SEQ ID NO 402
<211> LENGTH: 372
<212> TYPE: DNA
<213> ORGANISM: Oryctolagus cuniculus

<400> SEQUENCE: 402
atggacacga gggcccccac tcagctgctg gggctcctgc tgctctggct cccaggtgtc 60
acatttgcca tcgaaatgac ccagagtcca ttctccgtgt ctgcagctgt gggaggcaca 120
gtcagcatca gttgccaggc cagtcagagt gtttataaga acaaccaatt atcctggtat 180
cagcagaaat cagggcagcc tcccaagctc ctgatctatg gtgcatcggc tctggcatct 240
ggggtcccat cgcggttcaa aggcagtgga tctgggacag agttcactct caccatcagc 300
gacgtgcagt gtgacgatgc tgccacttac tactgtgcag gcgctattac tggtagtatt 360
gatacggatg gt 372

<210> SEQ ID NO 403
<211> LENGTH: 390
<212> TYPE: DNA
<213> ORGANISM: Oryctolagus cuniculus

<400> SEQUENCE: 403
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
acaacttctg gattctcctt cagtagcagc tacttcattt gctgggtccg ccaggctcca 180
gggaaggggc tggagtggat cgcatgcatt tatggtggtg atggcagcac atactacgcg 240
agctgggcga aaggccgatt caccatctcc aaaacctcgt cgaccacggt gacgctgcaa 300
atgaccagtc tgacagccgc ggacacggcc acctatttct gtgcgagaga atgggcatat 360
agtcaaggtt attttggtgc ttttgatctc 390

<210> SEQ ID NO 404
<211> LENGTH: 39
<212> TYPE: DNA
<213> ORGANISM: Oryctolagus cuniculus

<400> SEQUENCE: 404
caggccagtc agagtgttta taagaacaac caattatcc 39

<210> SEQ ID NO 405
<211> LENGTH: 21
<212> TYPE: DNA
<213> ORGANISM: Oryctolagus cuniculus

<400> SEQUENCE: 405
ggtgcatcgg ctctggcatc t 21

<210> SEQ ID NO 406
<211> LENGTH: 36
<212> TYPE: DNA
<213> ORGANISM: Oryctolagus cuniculus

<400> SEQUENCE: 406
gcaggcgcta ttactggtag tattgatacg gatggt 36

<210> SEQ ID NO 407
<211> LENGTH: 18
<212> TYPE: DNA
<213> ORGANISM: Oryctolagus cuniculus

<400> SEQUENCE: 407
agcagctact tcatttgc 18

<210> SEQ ID NO 408
<211> LENGTH: 51
<212> TYPE: DNA
<213> ORGANISM: Oryctolagus cuniculus

<400> SEQUENCE: 408
tgcatttatg gtggtgatgg cagcacatac tacgcgagct gggcgaaagg c 51

<210> SEQ ID NO 409
<211> LENGTH: 42
<212> TYPE: DNA
<213> ORGANISM: Oryctolagus cuniculus

<400> SEQUENCE: 409
gaatgggcat atagtcaagg ttattttggt gcttttgatc tc 42

<210> SEQ ID NO 410
<211> LENGTH: 124
<212> TYPE: PRT
<213> ORGANISM: Oryctolagus cuniculus

<400> SEQUENCE: 410

Met Asp Thr Arg Ala Pro Thr Gln Leu Leu Gly Leu Leu Leu Leu Trp
1 5 10 15

Leu Pro Gly Ala Arg Cys Asp Val Val Met Thr Gln Thr Pro Ala Ser
20 25 30

Val Glu Ala Ala Val Gly Gly Thr Val Thr Ile Lys Cys Gln Ala Ser
35 40 45

Glu Asp Ile Ser Ser Tyr Leu Ala Trp Tyr Gln Gln Lys Pro Gly Gln
50 55 60

Pro Pro Lys Leu Leu Ile Tyr Ala Ala Ser Asn Leu Glu Ser Gly Val
65 70 75 80

Ser Ser Arg Phe Lys Gly Ser Gly Ser Gly Thr Glu Tyr Thr Leu Thr
85 90 95

Ile Ser Asp Leu Glu Cys Ala Asp Ala Ala Thr Tyr Tyr Cys Gln Cys
100 105 110

Thr Tyr Gly Thr Ile Ser Ile Ser Asp Gly Asn Ala
115 120

<210> SEQ ID NO 411
<211> LENGTH: 124
<212> TYPE: PRT
<213> ORGANISM: Oryctolagus cuniculus

<400> SEQUENCE: 411

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Phe Met Thr Trp Val Arg Gln Ala Pro Gly Glu Gly Leu Glu
50 55 60

Tyr Ile Gly Phe Ile Asn Pro Gly Gly Ser Ala Tyr Tyr Ala Ser Trp
65 70 75 80

Val Lys Gly Arg Phe Thr Ile Ser Lys Ser Ser Thr Thr Val Asp Leu
85 90 95

```
Lys Ile Thr Ser Pro Thr Thr Glu Asp Thr Ala Thr Tyr Phe Cys Ala
            100                 105                 110

Arg Val Leu Ile Val Ser Tyr Gly Ala Phe Thr Ile
        115                 120


<210> SEQ ID NO 412
<211> LENGTH: 11
<212> TYPE: PRT
<213> ORGANISM: Oryctolagus cuniculus

<400> SEQUENCE: 412

Gln Ala Ser Glu Asp Ile Ser Ser Tyr Leu Ala
1               5                   10


<210> SEQ ID NO 413
<211> LENGTH: 7
<212> TYPE: PRT
<213> ORGANISM: Oryctolagus cuniculus

<400> SEQUENCE: 413

Ala Ala Ser Asn Leu Glu Ser
1               5


<210> SEQ ID NO 414
<211> LENGTH: 14
<212> TYPE: PRT
<213> ORGANISM: Oryctolagus cuniculus

<400> SEQUENCE: 414

Gln Cys Thr Tyr Gly Thr Ile Ser Ile Ser Asp Gly Asn Ala
1               5                   10


<210> SEQ ID NO 415
<211> LENGTH: 5
<212> TYPE: PRT
<213> ORGANISM: Oryctolagus cuniculus

<400> SEQUENCE: 415

Ser Tyr Phe Met Thr
1               5


<210> SEQ ID NO 416
<211> LENGTH: 16
<212> TYPE: PRT
<213> ORGANISM: Oryctolagus cuniculus

<400> SEQUENCE: 416

Phe Ile Asn Pro Gly Gly Ser Ala Tyr Tyr Ala Ser Trp Val Lys Gly
1               5                   10                  15


<210> SEQ ID NO 417
<211> LENGTH: 11
<212> TYPE: PRT
<213> ORGANISM: Oryctolagus cuniculus

<400> SEQUENCE: 417

Val Leu Ile Val Ser Tyr Gly Ala Phe Thr Ile
1               5                   10


<210> SEQ ID NO 418
<211> LENGTH: 372
<212> TYPE: DNA
<213> ORGANISM: Oryctolagus cuniculus

<400> SEQUENCE: 418
```

atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca agtgccaggc cagtgaggat attagtagct acttagcctg gtatcagcag 180
aaaccagggc agcctcccaa gctcctgatc tatgctgcat ccaatctgga atctggggtc 240
tcatcgcgat tcaaaggcag tggatctggg acagagtaca ctctcaccat cagcgacctg 300
gagtgtgccg atgctgccac ctattactgt caatgtactt atggtactat ttctattagt 360
gatggtaatg ct 372

<210> SEQ ID NO 419
<211> LENGTH: 372
<212> TYPE: DNA
<213> ORGANISM: Oryctolagus cuniculus

<400> SEQUENCE: 419
atggagactg ggctgcgctg gcttctcctg gtcgctgtgc tcaaaggtgt ccaatgtcag 60
tcggtggagg agtccggggg tcgcctggtc acgcctggga cacccctgac actcacctgc 120
acagtctctg gattctccct cagtagctac ttcatgacct gggtccgcca ggctccaggg 180
gaggggctgg aatacatcgg attcattaat cctggtggta gcgcttacta cgcgagctgg 240
gtgaaaggcc gattcaccat ctccaagtcc tcgaccacgg tagatctgaa aatcaccagt 300
ccgacaaccg aggacacggc cacctatttc tgtgccaggg ttctgattgt ttcttatgga 360
gcctttacca tc 372

<210> SEQ ID NO 420
<211> LENGTH: 33
<212> TYPE: DNA
<213> ORGANISM: Oryctolagus cuniculus

<400> SEQUENCE: 420
caggccagtg aggatattag tagctactta gcc 33

<210> SEQ ID NO 421
<211> LENGTH: 21
<212> TYPE: DNA
<213> ORGANISM: Oryctolagus cuniculus

<400> SEQUENCE: 421
gctgcatcca atctggaatc t 21

<210> SEQ ID NO 422
<211> LENGTH: 42
<212> TYPE: DNA
<213> ORGANISM: Oryctolagus cuniculus

<400> SEQUENCE: 422
caatgtactt atggtactat ttctattagt gatggtaatg ct 42

<210> SEQ ID NO 423
<211> LENGTH: 15
<212> TYPE: DNA
<213> ORGANISM: Oryctolagus cuniculus

<400> SEQUENCE: 423
agctacttca tgacc 15

<210> SEQ ID NO 424
<211> LENGTH: 48

<212> TYPE: DNA
<213> ORGANISM: Oryctolagus cuniculus

<400> SEQUENCE: 424
ttcattaatc ctggtggtag cgcttactac gcgagctggg tgaaaggc 48

<210> SEQ ID NO 425
<211> LENGTH: 33
<212> TYPE: DNA
<213> ORGANISM: Oryctolagus cuniculus

<400> SEQUENCE: 425
gttctgattg tttcttatgg agcctttacc atc 33

<210> SEQ ID NO 426
<211> LENGTH: 124
<212> TYPE: PRT
<213> ORGANISM: Oryctolagus cuniculus

<400> SEQUENCE: 426

Met Asp Thr Arg Ala Pro Thr Gln Leu Leu Gly Leu Leu Leu Leu Trp
1 5 10 15

Leu Pro Gly Ala Arg Cys Asp Val Val Met Thr Gln Thr Pro Ala Ser
20 25 30

Val Ser Ala Ala Val Gly Gly Thr Val Thr Ile Lys Cys Gln Ala Ser
35 40 45

Glu Asp Ile Glu Ser Tyr Leu Ala Trp Tyr Gln Gln Lys Pro Gly Gln
50 55 60

Pro Pro Lys Leu Leu Ile Tyr Gly Ala Ser Asn Leu Glu Ser Gly Val
65 70 75 80

Ser Ser Arg Phe Lys Gly Ser Gly Ser Gly Thr Glu Phe Thr Leu Thr
85 90 95

Ile Ser Asp Leu Glu Cys Ala Asp Ala Ala Thr Tyr Tyr Cys Gln Cys
100 105 110

Thr Tyr Gly Ile Ile Ser Ile Ser Asp Gly Asn Ala
115 120

<210> SEQ ID NO 427
<211> LENGTH: 124
<212> TYPE: PRT
<213> ORGANISM: Oryctolagus cuniculus

<400> SEQUENCE: 427

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Phe Met Thr Trp Val Arg Gln Ala Pro Gly Glu Gly Leu Glu
50 55 60

Tyr Ile Gly Phe Met Asn Thr Gly Asp Asn Ala Tyr Tyr Ala Ser Trp
65 70 75 80

Ala Lys Gly Arg Phe Thr Ile Ser Lys Thr Ser Thr Thr Val Asp Leu
85 90 95

Lys Ile Thr Ser Pro Thr Thr Glu Asp Thr Ala Thr Tyr Phe Cys Ala
100 105 110

Arg Val Leu Val Val Ala Tyr Gly Ala Phe Asn Ile
115 120

<210> SEQ ID NO 428
<211> LENGTH: 11
<212> TYPE: PRT
<213> ORGANISM: Oryctolagus cuniculus

<400> SEQUENCE: 428

Gln Ala Ser Glu Asp Ile Glu Ser Tyr Leu Ala
1 5 10

<210> SEQ ID NO 429
<211> LENGTH: 7
<212> TYPE: PRT
<213> ORGANISM: Oryctolagus cuniculus

<400> SEQUENCE: 429

Gly Ala Ser Asn Leu Glu Ser
1 5

<210> SEQ ID NO 430
<211> LENGTH: 14
<212> TYPE: PRT
<213> ORGANISM: Oryctolagus cuniculus

<400> SEQUENCE: 430

Gln Cys Thr Tyr Gly Ile Ile Ser Ile Ser Asp Gly Asn Ala
1 5 10

<210> SEQ ID NO 431
<211> LENGTH: 5
<212> TYPE: PRT
<213> ORGANISM: Oryctolagus cuniculus

<400> SEQUENCE: 431

Ser Tyr Phe Met Thr
1 5

<210> SEQ ID NO 432
<211> LENGTH: 16
<212> TYPE: PRT
<213> ORGANISM: Oryctolagus cuniculus

<400> SEQUENCE: 432

Phe Met Asn Thr Gly Asp Asn Ala Tyr Tyr Ala Ser Trp Ala Lys Gly
1 5 10 15

<210> SEQ ID NO 433
<211> LENGTH: 11
<212> TYPE: PRT
<213> ORGANISM: Oryctolagus cuniculus

<400> SEQUENCE: 433

Val Leu Val Val Ala Tyr Gly Ala Phe Asn Ile
1 5 10

<210> SEQ ID NO 434
<211> LENGTH: 372
<212> TYPE: DNA
<213> ORGANISM: Oryctolagus cuniculus

<400> SEQUENCE: 434
atggacacga gggcccccac tcagctgctg gggctcctgc tgctctggct cccaggtgcc 60
agatgtgatg ttgtgatgac ccagactcca gcctccgtgt ctgcagctgt gggaggcaca 120
gtcaccatca agtgccaggc cagtgaggac attgaaagct atctagcctg gtatcagcag 180
aaaccagggc agcctcccaa gctcctgatc tatggtgcat ccaatctgga atctggggtc 240
tcatcgcggt tcaaaggcag tggatctggg acagagttca ctctcaccat cagcgacctg 300
gagtgtgccg atgctgccac ttactattgt caatgcactt atggtattat tagtattagt 360
gatggtaatg ct 372

<210> SEQ ID NO 435
<211> LENGTH: 372
<212> TYPE: DNA
<213> ORGANISM: Oryctolagus cuniculus

<400> SEQUENCE: 435
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtgtctg gattctccct cagtagctac ttcatgacct gggtccgcca ggctccaggg 180
gaggggctgg aatacatcgg attcatgaat actggtgata acgcatacta cgcgagctgg 240
gcgaaaggcc gattcaccat ctccaaaacc tcgaccacgg tggatctgaa aatcaccagt 300
ccgacaaccg aggacacggc cacctatttc tgtgccaggg ttcttgttgt tgcttatgga 360
gcctttaaca tc 372

<210> SEQ ID NO 436
<211> LENGTH: 33
<212> TYPE: DNA
<213> ORGANISM: Oryctolagus cuniculus

<400> SEQUENCE: 436
caggccagtg aggacattga aagctatcta gcc 33

<210> SEQ ID NO 437
<211> LENGTH: 21
<212> TYPE: DNA
<213> ORGANISM: Oryctolagus cuniculus

<400> SEQUENCE: 437
ggtgcatcca atctggaatc t 21

<210> SEQ ID NO 438
<211> LENGTH: 42
<212> TYPE: DNA
<213> ORGANISM: Oryctolagus cuniculus

<400> SEQUENCE: 438
caatgcactt atggtattat tagtattagt gatggtaatg ct 42

<210> SEQ ID NO 439
<211> LENGTH: 15
<212> TYPE: DNA
<213> ORGANISM: Oryctolagus cuniculus

<400> SEQUENCE: 439
agctacttca tgacc 15

<210> SEQ ID NO 440
<211> LENGTH: 48
<212> TYPE: DNA
<213> ORGANISM: Oryctolagus cuniculus

<400> SEQUENCE: 440
ttcatgaata ctggtgataa cgcatactac gcgagctggg cgaaaggc 48

<210> SEQ ID NO 441
<211> LENGTH: 33
<212> TYPE: DNA
<213> ORGANISM: Oryctolagus cuniculus

<400> SEQUENCE: 441
gttcttgttg ttgcttatgg agcctttaac atc 33

<210> SEQ ID NO 442
<211> LENGTH: 124
<212> TYPE: PRT
<213> ORGANISM: Oryctolagus cuniculus

<400> SEQUENCE: 442

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Pro
20 25 30

Val Ser Glu Pro Val Gly Gly Thr Val Ser Ile Ser Cys Gln Ser Ser
35 40 45

Lys Ser Val Met Asn Asn Asn Tyr Leu Ala Trp Tyr Gln Gln Lys Pro
50 55 60

Gly Gln Pro Pro Lys Leu Leu Ile Tyr Gly Ala Ser Asn Leu Ala Ser
65 70 75 80

Gly Val Pro Ser Arg Phe Ser Gly Ser Gly Ser Gly Thr Gln Phe Thr
85 90 95

Leu Thr Ile Ser Asp Val Gln Cys Asp Asp Ala Ala Thr Tyr Tyr Cys
100 105 110

Gln Gly Gly Tyr Thr Gly Tyr Ser Asp His Gly Thr
115 120

<210> SEQ ID NO 443
<211> LENGTH: 127
<212> TYPE: PRT
<213> ORGANISM: Oryctolagus cuniculus

<400> SEQUENCE: 443

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Lys Pro
20 25 30

Asp Glu Thr Leu Thr Leu Thr Cys Thr Val Ser Gly Ile Asp Leu Ser
35 40 45

Ser Tyr Pro Met Asn Trp Val Arg Gln Ala Pro Gly Lys Gly Leu Glu
50 55 60

Trp Ile Gly Phe Ile Asn Thr Gly Gly Thr Ile Val Tyr Ala Ser Trp
65 70 75 80

Ala Lys Gly Arg Phe Thr Ile Ser Lys Thr Ser Thr Thr Val Asp Leu
85 90 95

Lys Met Thr Ser Pro Thr Thr Glu Asp Thr Ala Thr Tyr Phe Cys Ala
100 105 110

Arg Gly Ser Tyr Val Ser Ser Gly Tyr Ala Tyr Tyr Phe Asn Val
115 120 125

<210> SEQ ID NO 444
<211> LENGTH: 13
<212> TYPE: PRT
<213> ORGANISM: Oryctolagus cuniculus

<400> SEQUENCE: 444

Gln Ser Ser Lys Ser Val Met Asn Asn Asn Tyr Leu Ala
1 5 10

<210> SEQ ID NO 445
<211> LENGTH: 7
<212> TYPE: PRT
<213> ORGANISM: Oryctolagus cuniculus

<400> SEQUENCE: 445

Gly Ala Ser Asn Leu Ala Ser
1 5

<210> SEQ ID NO 446
<211> LENGTH: 12
<212> TYPE: PRT
<213> ORGANISM: Oryctolagus cuniculus

<400> SEQUENCE: 446

Gln Gly Gly Tyr Thr Gly Tyr Ser Asp His Gly Thr
1 5 10

<210> SEQ ID NO 447
<211> LENGTH: 5
<212> TYPE: PRT
<213> ORGANISM: Oryctolagus cuniculus

<400> SEQUENCE: 447

Ser Tyr Pro Met Asn
1 5

<210> SEQ ID NO 448
<211> LENGTH: 16
<212> TYPE: PRT
<213> ORGANISM: Oryctolagus cuniculus

<400> SEQUENCE: 448

Phe Ile Asn Thr Gly Gly Thr Ile Val Tyr Ala Ser Trp Ala Lys Gly
1 5 10 15

<210> SEQ ID NO 449
<211> LENGTH: 14
<212> TYPE: PRT
<213> ORGANISM: Oryctolagus cuniculus

<400> SEQUENCE: 449

Gly Ser Tyr Val Ser Ser Gly Tyr Ala Tyr Tyr Phe Asn Val
1 5 10

<210> SEQ ID NO 450
<211> LENGTH: 372
<212> TYPE: DNA
<213> ORGANISM: Oryctolagus cuniculus

<400> SEQUENCE: 450
atggacacga gggcccccac tcagctgctg gggctcctgc tgctctggct cccaggtgcc 60
acatttgccg ccgtgctgac ccagactcca tctcccgtgt ctgaacctgt gggaggcaca 120
gtcagcatca gttgccagtc cagtaagagt gttatgaata acaactactt agcctggtat 180
cagcagaaac cagggcagcc tcccaagctc ctgatctatg gtgcatccaa tctggcatct 240
ggggtcccat cacggttcag cggcagtgga tctgggacac agttcactct caccatcagc 300
gacgtgcagt gtgacgatgc tgccacttac tactgtcaag gcggttatac tggttatagt 360
gatcatggga ct 372

<210> SEQ ID NO 451
<211> LENGTH: 381
<212> TYPE: DNA
<213> ORGANISM: Oryctolagus cuniculus

<400> SEQUENCE: 451
atggagactg ggctgcgctg gcttctcctg gtcgctgtgc tcaaaggtgt ccagtgtcag 60
tcggtggagg agtccggggg tcgcctggtc aagcctgacg aaaccctgac actcacctgc 120
acagtctctg gaatcgacct cagtagctat ccaatgaact gggtccgcca ggctccaggg 180
aaggggctgg aatggatcgg attcattaat actggtggta ccatagtcta cgcgagctgg 240
gcaaaaggcc gattcaccat ctccaaaacc tcgaccacgg tggatctgaa aatgaccagt 300
ccgacaaccg aggacacggc cacctatttc tgtgccagag gcagttatgt ttcatctggt 360
tatgcctact attttaatgt c 381

<210> SEQ ID NO 452
<211> LENGTH: 39
<212> TYPE: DNA
<213> ORGANISM: Oryctolagus cuniculus

<400> SEQUENCE: 452
cagtccagta agagtgttat gaataacaac tacttagcc 39

<210> SEQ ID NO 453
<211> LENGTH: 21
<212> TYPE: DNA
<213> ORGANISM: Oryctolagus cuniculus

<400> SEQUENCE: 453
ggtgcatcca atctggcatc t 21

<210> SEQ ID NO 454
<211> LENGTH: 36
<212> TYPE: DNA
<213> ORGANISM: Oryctolagus cuniculus

<400> SEQUENCE: 454
caaggcggtt atactggtta tagtgatcat gggact 36

<210> SEQ ID NO 455
<211> LENGTH: 15
<212> TYPE: DNA
<213> ORGANISM: Oryctolagus cuniculus

<400> SEQUENCE: 455
agctatccaa tgaac 15

<210> SEQ ID NO 456
<211> LENGTH: 48
<212> TYPE: DNA
<213> ORGANISM: Oryctolagus cuniculus

<400> SEQUENCE: 456
ttcattaata ctggtggtac catagtctac gcgagctggg caaaaggc 48

<210> SEQ ID NO 457
<211> LENGTH: 42
<212> TYPE: DNA
<213> ORGANISM: Oryctolagus cuniculus

<400> SEQUENCE: 457
ggcagttatg tttcatctgg ttatgcctac tattttaatg tc 42

<210> SEQ ID NO 458
<211> LENGTH: 121
<212> TYPE: PRT
<213> ORGANISM: Oryctolagus cuniculus

<400> SEQUENCE: 458

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Ser Ile Ser Cys Gln Ser Ser
        35                  40                  45

Gln Ser Val Tyr Asn Asn Asn Trp Leu Ser Trp Phe Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Gln Cys Asp Asp Val Ala Thr Tyr Tyr Cys
            100                 105                 110

Ala Gly Gly Tyr Leu Asp Ser Val Ile
        115                 120
```

<210> SEQ ID NO 459
<211> LENGTH: 126
<212> TYPE: PRT
<213> ORGANISM: Oryctolagus cuniculus

<400> SEQUENCE: 459

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Ser Ile Asn Trp Val Arg Gln Ala Pro Gly Lys Gly Leu Glu
    50                  55                  60

Trp Ile Gly Ile Ile Ala Asn Ser Gly Thr Thr Phe Tyr Ala Asn Trp
65                  70                  75                  80

Ala Lys Gly Arg Phe Thr Val Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Glu Ser Gly Met Tyr Asn Glu Tyr Gly Lys Phe Asn Ile
        115                 120                 125
```

<210> SEQ ID NO 460
<211> LENGTH: 13
<212> TYPE: PRT
<213> ORGANISM: Oryctolagus cuniculus

<400> SEQUENCE: 460

```
Gln Ser Ser Gln Ser Val Tyr Asn Asn Asn Trp Leu Ser
1               5                   10
```

<210> SEQ ID NO 461
<211> LENGTH: 7
<212> TYPE: PRT
<213> ORGANISM: Oryctolagus cuniculus

<400> SEQUENCE: 461

Lys Ala Ser Thr Leu Ala Ser
1               5

<210> SEQ ID NO 462
<211> LENGTH: 9
<212> TYPE: PRT
<213> ORGANISM: Oryctolagus cuniculus

<400> SEQUENCE: 462

Ala Gly Gly Tyr Leu Asp Ser Val Ile
1               5

<210> SEQ ID NO 463
<211> LENGTH: 5
<212> TYPE: PRT
<213> ORGANISM: Oryctolagus cuniculus

<400> SEQUENCE: 463

Thr Tyr Ser Ile Asn
1               5

<210> SEQ ID NO 464
<211> LENGTH: 16
<212> TYPE: PRT
<213> ORGANISM: Oryctolagus cuniculus

<400> SEQUENCE: 464

Ile Ile Ala Asn Ser Gly Thr Thr Phe Tyr Ala Asn Trp Ala Lys Gly
1               5                   10                  15

<210> SEQ ID NO 465
<211> LENGTH: 13
<212> TYPE: PRT
<213> ORGANISM: Oryctolagus cuniculus

<400> SEQUENCE: 465

Glu Ser Gly Met Tyr Asn Glu Tyr Gly Lys Phe Asn Ile
1               5                   10

<210> SEQ ID NO 466
<211> LENGTH: 363
<212> TYPE: DNA
<213> ORGANISM: Oryctolagus cuniculus

<400> SEQUENCE: 466
atggacacga gggcccccac tcagctgctg gggctcctgc tgctctggct cccaggtgcc      60
acatttgccg ccgtgctgac ccagactcca tctcccgtgt ctgcagctgt gggaggcaca     120
gtcagcatca gttgccagtc cagtcagagt gtttataata acaactggtt atcctggttt     180
cagcagaaac cagggcagcc tcccaagctc ctgatctaca aggcatccac tctggcatct     240
ggggtcccat cgcggttcaa aggcagtgga tctgggacac agttcactct caccatcagc     300
gacgtgcagt gtgacgatgt tgccacttac tactgtgcgg gcggttatct tgatagtgtt     360
att                                                                   363

<210> SEQ ID NO 467
<211> LENGTH: 378

<212> TYPE: DNA
<213> ORGANISM: Oryctolagus cuniculus

<400> SEQUENCE: 467
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gattctccct cagtacctat tcaataaact gggtccgcca ggctccaggg 180
aagggcctgg aatggatcgg aatcattgct aatagtggta ccacattcta cgcgaactgg 240
gcgaaaggcc gattcaccgt ctccaaaacc tcgaccacgg tggatctgaa aatcaccagt 300
ccgacaaccg aggacacggc cacctatttc tgtgccagag agagtggaat gtacaatgaa 360
tatggtaaat ttaacatc 378

<210> SEQ ID NO 468
<211> LENGTH: 39
<212> TYPE: DNA
<213> ORGANISM: Oryctolagus cuniculus

<400> SEQUENCE: 468
cagtccagtc agagtgttta taataacaac tggttatcc 39

<210> SEQ ID NO 469
<211> LENGTH: 21
<212> TYPE: DNA
<213> ORGANISM: Oryctolagus cuniculus

<400> SEQUENCE: 469
aaggcatcca ctctggcatc t 21

<210> SEQ ID NO 470
<211> LENGTH: 27
<212> TYPE: DNA
<213> ORGANISM: Oryctolagus cuniculus

<400> SEQUENCE: 470
gcgggcggtt atcttgatag tgttatt 27

<210> SEQ ID NO 471
<211> LENGTH: 15
<212> TYPE: DNA
<213> ORGANISM: Oryctolagus cuniculus

<400> SEQUENCE: 471
acctattcaa taaac 15

<210> SEQ ID NO 472
<211> LENGTH: 48
<212> TYPE: DNA
<213> ORGANISM: Oryctolagus cuniculus

<400> SEQUENCE: 472
atcattgcta atagtggtac cacattctac gcgaactggg cgaaaggc 48

<210> SEQ ID NO 473
<211> LENGTH: 39
<212> TYPE: DNA
<213> ORGANISM: Oryctolagus cuniculus

<400> SEQUENCE: 473
gagagtggaa tgtacaatga atatggtaaa tttaacatc 39

<210> SEQ ID NO 474
<211> LENGTH: 122
<212> TYPE: PRT
<213> ORGANISM: Oryctolagus cuniculus

<400> SEQUENCE: 474

```
Met Asp Thr Arg Ala Pro Thr Gln Leu Leu Gly Leu Leu Leu Leu Trp
1               5                   10                  15

Leu Pro Gly Ala Arg Cys Ala Ser Asp Met Thr Gln Thr Pro Ser Ser
            20                  25                  30

Val Ser Ala Ala Val Gly Gly Thr Val Thr Ile Asn Cys Gln Ala Ser
        35                  40                  45

Glu Asn Ile Tyr Ser Phe Leu Ala Trp Tyr Gln Gln Lys Pro Gly Gln
    50                  55                  60

Pro Pro Lys Leu Leu Ile Phe Lys Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

Ile Ser Asp Leu Glu Cys Asp Asp Ala Ala Thr Tyr Tyr Cys Gln Gln
            100                 105                 110

Gly Ala Thr Val Tyr Asp Ile Asp Asn Asn
        115                 120
```

<210> SEQ ID NO 475
<211> LENGTH: 128
<212> TYPE: PRT
<213> ORGANISM: Oryctolagus cuniculus

<400> SEQUENCE: 475

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ala Tyr Ala Met Ile Trp Val Arg Gln Ala Pro Gly Glu Gly Leu Glu
    50                  55                  60

Trp Ile Thr Ile Ile Tyr Pro Asn Gly Ile Thr Tyr Tyr Ala Asn Trp
65                  70                  75                  80

Ala Lys Gly Arg Phe Thr Val Ser Lys Thr Ser Thr Ala Met Asp Leu
                85                  90                  95

Lys Ile Thr Ser Pro Thr Thr Glu Asp Thr Ala Thr Tyr Phe Cys Ala
            100                 105                 110

Arg Asp Ala Glu Ser Ser Lys Asn Ala Tyr Trp Gly Tyr Phe Asn Val
        115                 120                 125
```

<210> SEQ ID NO 476
<211> LENGTH: 11
<212> TYPE: PRT
<213> ORGANISM: Oryctolagus cuniculus

<400> SEQUENCE: 476

```
Gln Ala Ser Glu Asn Ile Tyr Ser Phe Leu Ala
1               5                   10
```

<210> SEQ ID NO 477
<211> LENGTH: 7
<212> TYPE: PRT
<213> ORGANISM: Oryctolagus cuniculus

<400> SEQUENCE: 477

Lys Ala Ser Thr Leu Ala Ser
1 5

<210> SEQ ID NO 478
<211> LENGTH: 12
<212> TYPE: PRT
<213> ORGANISM: Oryctolagus cuniculus

<400> SEQUENCE: 478

Gln Gln Gly Ala Thr Val Tyr Asp Ile Asp Asn Asn
1 5 10

<210> SEQ ID NO 479
<211> LENGTH: 5
<212> TYPE: PRT
<213> ORGANISM: Oryctolagus cuniculus

<400> SEQUENCE: 479

Ala Tyr Ala Met Ile
1 5

<210> SEQ ID NO 480
<211> LENGTH: 16
<212> TYPE: PRT
<213> ORGANISM: Oryctolagus cuniculus

<400> SEQUENCE: 480

Ile Ile Tyr Pro Asn Gly Ile Thr Tyr Tyr Ala Asn Trp Ala Lys Gly
1 5 10 15

<210> SEQ ID NO 481
<211> LENGTH: 15
<212> TYPE: PRT
<213> ORGANISM: Oryctolagus cuniculus

<400> SEQUENCE: 481

Asp Ala Glu Ser Ser Lys Asn Ala Tyr Trp Gly Tyr Phe Asn Val
1 5 10 15

<210> SEQ ID NO 482
<211> LENGTH: 366
<212> TYPE: DNA
<213> ORGANISM: Oryctolagus cuniculus

<400> SEQUENCE: 482
atggacacga gggcccccac tcagctgctg gggctcctgc tgctctggct cccaggtgcc 60
agatgtgcct ctgatatgac ccagactcca tcctccgtgt ctgcagctgt gggaggcaca 120
gtcaccatca attgccaggc cagtgagaac atttatagct ttttggcctg gtatcagcag 180
aaaccagggc agcctcccaa gctcctgatc ttcaaggctt ccactctggc atctggggtc 240
tcatcgcggt tcaaaggcag tggatctggg acacagttca ctctcaccat cagcgacctg 300
gagtgtgacg atgctgccac ttactactgt caacagggtg ctactgtgta tgatattgat 360
aataat 366

<210> SEQ ID NO 483
<211> LENGTH: 384
<212> TYPE: DNA
<213> ORGANISM: Oryctolagus cuniculus

<400> SEQUENCE: 483
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagtttctg gaatcgacct cagtgcctat gcaatgatct gggtccgcca ggctccaggg 180
gaggggctgg aatggatcac aatcatttat cctaatggta tcacatacta cgcgaactgg 240
gcgaaaggcc gattcaccgt ctccaaaacc tcgaccgcga tggatctgaa aatcaccagt 300
ccgacaaccg aggacacggc cacctatttc tgtgccagag atgcagaaag tagtaagaat 360
gcttattggg gctactttaa cgtc 384

<210> SEQ ID NO 484
<211> LENGTH: 33
<212> TYPE: DNA
<213> ORGANISM: Oryctolagus cuniculus

<400> SEQUENCE: 484
caggccagtg agaacattta tagctttttg gcc 33

<210> SEQ ID NO 485
<211> LENGTH: 21
<212> TYPE: DNA
<213> ORGANISM: Oryctolagus cuniculus

<400> SEQUENCE: 485
aaggcttcca ctctggcatc t 21

<210> SEQ ID NO 486
<211> LENGTH: 36
<212> TYPE: DNA
<213> ORGANISM: Oryctolagus cuniculus

<400> SEQUENCE: 486
caacagggtg ctactgtgta tgatattgat aataat 36

<210> SEQ ID NO 487
<211> LENGTH: 15
<212> TYPE: DNA
<213> ORGANISM: Oryctolagus cuniculus

<400> SEQUENCE: 487
gcctatgcaa tgatc 15

<210> SEQ ID NO 488
<211> LENGTH: 48
<212> TYPE: DNA
<213> ORGANISM: Oryctolagus cuniculus

<400> SEQUENCE: 488
atcatttatc ctaatggtat cacatactac gcgaactggg cgaaaggc 48

<210> SEQ ID NO 489
<211> LENGTH: 45
<212> TYPE: DNA
<213> ORGANISM: Oryctolagus cuniculus

<400> SEQUENCE: 489
gatgcagaaa gtagtaagaa tgcttattgg ggctacttta acgtc 45

<210> SEQ ID NO 490
<211> LENGTH: 122
<212> TYPE: PRT
<213> ORGANISM: Oryctolagus cuniculus

<400> SEQUENCE: 490

```
Met Asp Thr Arg Ala Pro Thr Gln Leu Leu Gly Leu Leu Leu Leu Trp
1               5                   10                  15

Leu Pro Gly Ala Arg Cys Ala Ser Asp Met Thr Gln Thr Pro Ser Ser
            20                  25                  30

Val Ser Ala Ala Val Gly Gly Thr Val Thr Ile Asn Cys Gln Ala Ser
        35                  40                  45

Glu Asn Ile Tyr Ser Phe Leu Ala Trp Tyr Gln Gln Lys Pro Gly Gln
    50                  55                  60

Pro Pro Lys Leu Leu Ile Phe Arg Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

Ile Ser Asp Leu Glu Cys Asp Asp Ala Ala Thr Tyr Tyr Cys Gln Gln
            100                 105                 110

Gly Ala Thr Val Tyr Asp Ile Asp Asn Asn
        115                 120


<210> SEQ ID NO 491
<211> LENGTH: 128
<212> TYPE: PRT
<213> ORGANISM: Oryctolagus cuniculus

<400> SEQUENCE: 491

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ala Tyr Ala Met Ile Trp Val Arg Gln Ala Pro Gly Glu Gly Leu Glu
    50                  55                  60

Trp Ile Thr Ile Ile Tyr Pro Asn Gly Ile Thr Tyr Tyr Ala Asn Trp
65                  70                  75                  80

Ala Lys Gly Arg Phe Thr Val Ser Lys Thr Ser Thr Ala Met Asp Leu
                85                  90                  95

Lys Ile Thr Ser Pro Thr Thr Glu Asp Thr Ala Thr Tyr Phe Cys Ala
            100                 105                 110

Arg Asp Ala Glu Ser Ser Lys Asn Ala Tyr Trp Gly Tyr Phe Asn Val
        115                 120                 125


<210> SEQ ID NO 492
<211> LENGTH: 11
<212> TYPE: PRT
<213> ORGANISM: Oryctolagus cuniculus

<400> SEQUENCE: 492

Gln Ala Ser Glu Asn Ile Tyr Ser Phe Leu Ala
1               5                   10


<210> SEQ ID NO 493
<211> LENGTH: 7
<212> TYPE: PRT
<213> ORGANISM: Oryctolagus cuniculus

<400> SEQUENCE: 493

Arg Ala Ser Thr Leu Ala Ser
1               5
```

<210> SEQ ID NO 494
<211> LENGTH: 12
<212> TYPE: PRT
<213> ORGANISM: Oryctolagus cuniculus

<400> SEQUENCE: 494

Gln Gln Gly Ala Thr Val Tyr Asp Ile Asp Asn Asn
1 5 10

<210> SEQ ID NO 495
<211> LENGTH: 5
<212> TYPE: PRT
<213> ORGANISM: Oryctolagus cuniculus

<400> SEQUENCE: 495

Ala Tyr Ala Met Ile
1 5

<210> SEQ ID NO 496
<211> LENGTH: 16
<212> TYPE: PRT
<213> ORGANISM: Oryctolagus cuniculus

<400> SEQUENCE: 496

Ile Ile Tyr Pro Asn Gly Ile Thr Tyr Tyr Ala Asn Trp Ala Lys Gly
1 5 10 15

<210> SEQ ID NO 497
<211> LENGTH: 15
<212> TYPE: PRT
<213> ORGANISM: Oryctolagus cuniculus

<400> SEQUENCE: 497

Asp Ala Glu Ser Ser Lys Asn Ala Tyr Trp Gly Tyr Phe Asn Val
1 5 10 15

<210> SEQ ID NO 498
<211> LENGTH: 366
<212> TYPE: DNA
<213> ORGANISM: Oryctolagus cuniculus

<400> SEQUENCE: 498
atggacacga gggcccccac tcagctgctg gggctcctgc tgctctggct cccaggtgcc 60
agatgtgcct ctgatatgac ccagactcca tcctccgtgt ctgcagctgt gggaggcaca 120
gtcaccatca attgccaggc cagtgagaac atttatagct ttttggcctg gtatcagcag 180
aaaccagggc agcctcccaa gctcctgatc ttcagggctt ccactctggc atctggggtc 240
tcatcgcggt tcaaaggcag tggatctggg acacagttca ctctcaccat cagcgacctg 300
gagtgtgacg atgctgccac ttactactgt caacagggtg ctactgtgta tgatattgat 360
aataat 366

<210> SEQ ID NO 499
<211> LENGTH: 384
<212> TYPE: DNA
<213> ORGANISM: Oryctolagus cuniculus

<400> SEQUENCE: 499
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagtttctg gaatcgacct cagtgcctat gcaatgatct gggtccgcca ggctccaggg 180
gaggggctgg aatggatcac aatcatttat cctaatggta tcacatacta cgcgaactgg 240
gcgaaaggcc gattcaccgt ctccaaaacc tcgaccgcga tggatctgaa aatcaccagt 300
ccgacaaccg aggacacggc cacctatttc tgtgccagag atgcagaaag tagtaagaat 360
gcttattggg gctactttaa cgtc 384

<210> SEQ ID NO 500
<211> LENGTH: 33
<212> TYPE: DNA
<213> ORGANISM: Oryctolagus cuniculus

<400> SEQUENCE: 500
caggccagtg agaacattta tagctttttg gcc 33

<210> SEQ ID NO 501
<211> LENGTH: 21
<212> TYPE: DNA
<213> ORGANISM: Oryctolagus cuniculus

<400> SEQUENCE: 501
agggcttcca ctctggcatc t 21

<210> SEQ ID NO 502
<211> LENGTH: 36
<212> TYPE: DNA
<213> ORGANISM: Oryctolagus cuniculus

<400> SEQUENCE: 502
caacagggtg ctactgtgta tgatattgat aataat 36

<210> SEQ ID NO 503
<211> LENGTH: 15
<212> TYPE: DNA
<213> ORGANISM: Oryctolagus cuniculus

<400> SEQUENCE: 503
gcctatgcaa tgatc 15

<210> SEQ ID NO 504
<211> LENGTH: 48
<212> TYPE: DNA
<213> ORGANISM: Oryctolagus cuniculus

<400> SEQUENCE: 504
atcatttatc ctaatggtat cacatactac gcgaactggg cgaaaggc 48

<210> SEQ ID NO 505
<211> LENGTH: 45
<212> TYPE: DNA
<213> ORGANISM: Oryctolagus cuniculus

<400> SEQUENCE: 505
gatgcagaaa gtagtaagaa tgcttattgg ggctacttta acgtc 45

<210> SEQ ID NO 506
<211> LENGTH: 124
<212> TYPE: PRT
<213> ORGANISM: Oryctolagus cuniculus

<400> SEQUENCE: 506

Met Asp Thr Arg Ala Pro Thr Gln Leu Leu Gly Leu Leu Leu Leu Trp
1 5 10 15

Leu Pro Gly Ala Thr Phe Ala Ile Glu Met Thr Gln Thr Pro Ser Pro
20 25 30

```
Val Ser Ala Ala Val Gly Gly Thr Val Thr Ile Asn Cys Gln Ala Ser
        35                  40                  45

Glu Ser Val Phe Asn Asn Met Leu Ser Trp Tyr Gln Gln Lys Pro Gly
    50                  55                  60

His Ser Pro Lys Leu Leu Ile Tyr Asp Ala Ser Asp Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Gly Val Glu Cys Asp Asp Ala Ala Thr Tyr Tyr Cys Ala
            100                 105                 110

Gly Tyr Lys Ser Asp Ser Asn Asp Gly Asp Asn Val
        115                 120


<210> SEQ ID NO 507
<211> LENGTH: 123
<212> TYPE: PRT
<213> ORGANISM: Oryctolagus cuniculus

<400> SEQUENCE: 507

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Arg Asn Ser Ile Thr Trp Val Arg Gln Ala Pro Gly Glu Gly Leu Glu
    50                  55                  60

Trp Ile Gly Ile Ile Thr Gly Ser Gly Arg Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Gly His Pro Gly Leu Gly Ser Gly Asn Ile
        115                 120


<210> SEQ ID NO 508
<211> LENGTH: 12
<212> TYPE: PRT
<213> ORGANISM: Oryctolagus cuniculus

<400> SEQUENCE: 508

Gln Ala Ser Glu Ser Val Phe Asn Asn Met Leu Ser
1               5                   10


<210> SEQ ID NO 509
<211> LENGTH: 7
<212> TYPE: PRT
<213> ORGANISM: Oryctolagus cuniculus

<400> SEQUENCE: 509

Asp Ala Ser Asp Leu Ala Ser
1               5


<210> SEQ ID NO 510
<211> LENGTH: 13
<212> TYPE: PRT
<213> ORGANISM: Oryctolagus cuniculus

<400> SEQUENCE: 510
```

```
Ala Gly Tyr Lys Ser Asp Ser Asn Asp Gly Asp Asn Val
1               5                   10


<210> SEQ ID NO 511
<211> LENGTH: 5
<212> TYPE: PRT
<213> ORGANISM: Oryctolagus cuniculus

<400> SEQUENCE: 511

Arg Asn Ser Ile Thr
1               5


<210> SEQ ID NO 512
<211> LENGTH: 16
<212> TYPE: PRT
<213> ORGANISM: Oryctolagus cuniculus

<400> SEQUENCE: 512

Ile Ile Thr Gly Ser Gly Arg Thr Tyr Tyr Ala Asn Trp Ala Lys Gly
1               5                   10                  15


<210> SEQ ID NO 513
<211> LENGTH: 10
<212> TYPE: PRT
<213> ORGANISM: Oryctolagus cuniculus

<400> SEQUENCE: 513

Gly His Pro Gly Leu Gly Ser Gly Asn Ile
1               5                   10


<210> SEQ ID NO 514
<211> LENGTH: 372
<212> TYPE: DNA
<213> ORGANISM: Oryctolagus cuniculus

<400> SEQUENCE: 514

atggacacga gggcccccac tcagctgctg gggctcctgc tgctctggct cccaggtgcc     60

acatttgcca ttgaaatgac ccagactcca tcccccgtgt ctgccgctgt gggaggcaca    120

gtcaccatca attgccaggc cagtgagagt gtttttaata atatgttatc ctggtatcag    180

cagaaaccag ggcactctcc taagctcctg atctatgatg catccgatct ggcatctggg    240

gtcccatcgc ggttcaaagg cagtggatct gggacacagt tcactctcac catcagtggc    300

gtggagtgtg acgatgctgc cacttactat tgtgcagggt ataaaagtga tagtaatgat    360

ggcgataatg tt                                                        372


<210> SEQ ID NO 515
<211> LENGTH: 369
<212> TYPE: DNA
<213> ORGANISM: Oryctolagus cuniculus

<400> SEQUENCE: 515

atggagactg ggctgcgctg gcttctcctg gtcgctgtgc tcaaaggtgt ccagtgtcag     60

tcgctggagg agtccggggg tcgcctggtc acgcctggga cacccctgac actcacctgc    120

acagtctctg gattctccct caacaggaat tcaataacct gggtccgcca ggctccaggg    180

gaggggctgg aatggatcgg aatcattact ggtagtggta gaacgtacta cgcgaactgg    240

gcaaaaggcc gattcaccat ctccaaaacc tcgaccacgg tggatctgaa aatgaccagt    300

ccgacaaccg aggacacggc cacctatttc tgtgccagag gccatcctgg tcttggtagt    360

ggtaacatc                                                            369
```

<210> SEQ ID NO 516
<211> LENGTH: 36
<212> TYPE: DNA
<213> ORGANISM: Oryctolagus cuniculus

<400> SEQUENCE: 516
caggccagtg agagtgtttt taataatatg ttatcc 36

<210> SEQ ID NO 517
<211> LENGTH: 21
<212> TYPE: DNA
<213> ORGANISM: Oryctolagus cuniculus

<400> SEQUENCE: 517
gatgcatccg atctggcatc t 21

<210> SEQ ID NO 518
<211> LENGTH: 39
<212> TYPE: DNA
<213> ORGANISM: Oryctolagus cuniculus

<400> SEQUENCE: 518
gcagggtata aaagtgatag taatgatggc gataatgtt 39

<210> SEQ ID NO 519
<211> LENGTH: 15
<212> TYPE: DNA
<213> ORGANISM: Oryctolagus cuniculus

<400> SEQUENCE: 519
aggaattcaa taacc 15

<210> SEQ ID NO 520
<211> LENGTH: 48
<212> TYPE: DNA
<213> ORGANISM: Oryctolagus cuniculus

<400> SEQUENCE: 520
atcattactg gtagtggtag aacgtactac gcgaactggg caaaaggc 48

<210> SEQ ID NO 521
<211> LENGTH: 30
<212> TYPE: DNA
<213> ORGANISM: Oryctolagus cuniculus

<400> SEQUENCE: 521
ggccatcctg gtcttggtag tggtaacatc 30

<210> SEQ ID NO 522
<211> LENGTH: 121
<212> TYPE: PRT
<213> ORGANISM: Oryctolagus cuniculus

<400> SEQUENCE: 522

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Ile Asn Cys Gln Ser Ser
        35                  40                  45

Gln Ser Val Tyr Asn Asn Tyr Leu Ser Trp Tyr Gln Gln Lys Pro Gly
    50                  55                  60
```

```
Gln Pro Pro Lys Leu Leu Ile Tyr Thr Ala Ser Ser Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Glu Val Gln Cys Asp Asp Ala Ala Thr Tyr Tyr Cys Gln
            100                 105                 110

Gly Tyr Tyr Ser Gly Pro Ile Ile Thr
        115                 120


<210> SEQ ID NO 523
<211> LENGTH: 122
<212> TYPE: PRT
<213> ORGANISM: Oryctolagus cuniculus

<400> SEQUENCE: 523

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Tyr Ile Gln Trp Val Arg Gln Ala Pro Gly Glu Gly Leu Glu
    50                  55                  60

Trp Ile Gly Ile Ile Tyr Ala Gly Gly Ser Ala Tyr Tyr Ala Thr Trp
65                  70                  75                  80

Ala Asn Gly Arg Phe Thr Ile Ala Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Ala Arg Gly Thr Phe Asp Gly Tyr Glu Leu
        115                 120


<210> SEQ ID NO 524
<211> LENGTH: 12
<212> TYPE: PRT
<213> ORGANISM: Oryctolagus cuniculus

<400> SEQUENCE: 524

Gln Ser Ser Gln Ser Val Tyr Asn Asn Tyr Leu Ser
1               5                   10


<210> SEQ ID NO 525
<211> LENGTH: 7
<212> TYPE: PRT
<213> ORGANISM: Oryctolagus cuniculus

<400> SEQUENCE: 525

Thr Ala Ser Ser Leu Ala Ser
1               5


<210> SEQ ID NO 526
<211> LENGTH: 10
<212> TYPE: PRT
<213> ORGANISM: Oryctolagus cuniculus

<400> SEQUENCE: 526

Gln Gly Tyr Tyr Ser Gly Pro Ile Ile Thr
1               5                   10


<210> SEQ ID NO 527
```

<211> LENGTH: 5
<212> TYPE: PRT
<213> ORGANISM: Oryctolagus cuniculus

<400> SEQUENCE: 527

Asn Tyr Tyr Ile Gln
1 5

<210> SEQ ID NO 528
<211> LENGTH: 16
<212> TYPE: PRT
<213> ORGANISM: Oryctolagus cuniculus

<400> SEQUENCE: 528

Ile Ile Tyr Ala Gly Gly Ser Ala Tyr Tyr Ala Thr Trp Ala Asn Gly
1 5 10 15

<210> SEQ ID NO 529
<211> LENGTH: 8
<212> TYPE: PRT
<213> ORGANISM: Oryctolagus cuniculus

<400> SEQUENCE: 529

Gly Thr Phe Asp Gly Tyr Glu Leu
1 5

<210> SEQ ID NO 530
<211> LENGTH: 363
<212> TYPE: DNA
<213> ORGANISM: Oryctolagus cuniculus

<400> SEQUENCE: 530
atggacacga gggcccccac tcagctgctg gggctcctgc tgctctggct cccaggtgcc 60
acatttgcgc aagtgctgac ccagactgca tcgtccgtgt ctgcagctgt gggaggcaca 120
gtcaccatca attgccagtc cagtcagagt gtttataata actacttatc ctggtatcag 180
cagaaaccag ggcagcctcc caagctcctg atctatactg catccagcct ggcatctggg 240
gtcccatcgc ggttcaaagg cagtggatct gggacacagt tcactctcac catcagcgaa 300
gtgcagtgtg acgatgctgc cacttactac tgtcaaggct attatagtgg tcctataatt 360
act 363

<210> SEQ ID NO 531
<211> LENGTH: 366
<212> TYPE: DNA
<213> ORGANISM: Oryctolagus cuniculus

<400> SEQUENCE: 531
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagcctctg gattctccct caataactac tacatacaat gggtccgcca ggctccaggg 180
gaggggctgg aatggatcgg gatcatttat gctggtggta gcgcatacta cgcgacctgg 240
gcaaacggcc gattcaccat cgccaaaacc tcgtcgacca cggtggatct gaagatgacc 300
agtctgacaa ccgaggacac ggccacctat ttctgtgcca gagggacatt tgatggttat 360
gagttg 366

<210> SEQ ID NO 532
<211> LENGTH: 36
<212> TYPE: DNA
<213> ORGANISM: Oryctolagus cuniculus

<400> SEQUENCE: 532
cagtccagtc agagtgttta taataactac ttatcc 36

<210> SEQ ID NO 533
<211> LENGTH: 21
<212> TYPE: DNA
<213> ORGANISM: Oryctolagus cuniculus

<400> SEQUENCE: 533
actgcatcca gcctggcatc t 21

<210> SEQ ID NO 534
<211> LENGTH: 30
<212> TYPE: DNA
<213> ORGANISM: Oryctolagus cuniculus

<400> SEQUENCE: 534
caaggctatt atagtggtcc tataattact 30

<210> SEQ ID NO 535
<211> LENGTH: 15
<212> TYPE: DNA
<213> ORGANISM: Oryctolagus cuniculus

<400> SEQUENCE: 535
aactactaca tacaa 15

<210> SEQ ID NO 536
<211> LENGTH: 48
<212> TYPE: DNA
<213> ORGANISM: Oryctolagus cuniculus

<400> SEQUENCE: 536
atcatttatg ctggtggtag cgcatactac gcgacctggg caaacggc 48

<210> SEQ ID NO 537
<211> LENGTH: 24
<212> TYPE: DNA
<213> ORGANISM: Oryctolagus cuniculus

<400> SEQUENCE: 537
gggacatttg atggttatga gttg 24

<210> SEQ ID NO 538
<211> LENGTH: 122
<212> TYPE: PRT
<213> ORGANISM: Oryctolagus cuniculus

<400> SEQUENCE: 538

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Val Pro Val Gly Asp Thr Val Thr Ile Ser Cys Gln Ser Ser
        35                  40                  45

Glu Ser Val Tyr Ser Asn Asn Leu Leu Ser Trp Tyr Gln Gln Lys Pro
    50                  55                  60

Gly Gln Pro Pro Lys Leu Leu Ile Tyr Arg Ala Ser Asn Leu Ala Ser
65                  70                  75                  80

Gly Val Pro Ser Arg Phe Lys Gly Ser Gly Ser Gly Thr Gln Phe Thr
                85                  90                  95
```

```
Leu Thr Ile Ser Gly Ala Gln Cys Asp Asp Ala Ala Thr Tyr Tyr Cys
            100                 105                 110

Gln Gly Tyr Tyr Ser Gly Val Ile Asn Ser
        115                 120


<210> SEQ ID NO 539
<211> LENGTH: 124
<212> TYPE: PRT
<213> ORGANISM: Oryctolagus cuniculus

<400> SEQUENCE: 539

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Phe Met Ser Trp Val Arg Gln Ala Pro Gly Glu Gly Leu Glu
    50                  55                  60

Tyr Ile Gly Phe Ile Asn Pro Gly Gly Ser Ala Tyr Tyr Ala Ser Trp
65                  70                  75                  80

Ala Ser Gly Arg Leu Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ile Leu Ile Val Ser Tyr Gly Ala Phe Thr Ile
        115                 120


<210> SEQ ID NO 540
<211> LENGTH: 13
<212> TYPE: PRT
<213> ORGANISM: Oryctolagus cuniculus

<400> SEQUENCE: 540

Gln Ser Ser Glu Ser Val Tyr Ser Asn Asn Leu Leu Ser
1               5                   10


<210> SEQ ID NO 541
<211> LENGTH: 7
<212> TYPE: PRT
<213> ORGANISM: Oryctolagus cuniculus

<400> SEQUENCE: 541

Arg Ala Ser Asn Leu Ala Ser
1               5


<210> SEQ ID NO 542
<211> LENGTH: 10
<212> TYPE: PRT
<213> ORGANISM: Oryctolagus cuniculus

<400> SEQUENCE: 542

Gln Gly Tyr Tyr Ser Gly Val Ile Asn Ser
1               5                   10


<210> SEQ ID NO 543
<211> LENGTH: 5
<212> TYPE: PRT
<213> ORGANISM: Oryctolagus cuniculus

<400> SEQUENCE: 543
```

Ser Tyr Phe Met Ser
1 5

<210> SEQ ID NO 544
<211> LENGTH: 16
<212> TYPE: PRT
<213> ORGANISM: Oryctolagus cuniculus

<400> SEQUENCE: 544

Phe Ile Asn Pro Gly Gly Ser Ala Tyr Tyr Ala Ser Trp Ala Ser Gly
1 5 10 15

<210> SEQ ID NO 545
<211> LENGTH: 11
<212> TYPE: PRT
<213> ORGANISM: Oryctolagus cuniculus

<400> SEQUENCE: 545

Ile Leu Ile Val Ser Tyr Gly Ala Phe Thr Ile
1 5 10

<210> SEQ ID NO 546
<211> LENGTH: 366
<212> TYPE: DNA
<213> ORGANISM: Oryctolagus cuniculus

<400> SEQUENCE: 546
atggacacga gggcccccac tcagctgctg gggctcctgc tgctctggct cccaggtgcc 60
acatttgccc aagtgctgac ccagactcca tcccctgtgt ctgtccctgt gggagacaca 120
gtcaccatca gttgccagtc cagtgagagc gtttatagta ataacctctt atcctggtat 180
cagcagaaac cagggcagcc tcccaagctc ctgatctaca gggcatccaa tctggcatct 240
ggtgtcccat cgcggttcaa aggcagtgga tctgggacac agttcactct caccatcagc 300
ggcgcacagt gtgacgatgc tgccacttac tactgtcaag gctattatag tggtgtcatt 360
aatagt 366

<210> SEQ ID NO 547
<211> LENGTH: 372
<212> TYPE: DNA
<213> ORGANISM: Oryctolagus cuniculus

<400> SEQUENCE: 547
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtgtctg gattctccct cagtagctac ttcatgagct gggtccgcca ggctccaggg 180
gaggggctgg aatacatcgg attcattaat cctggtggta gcgcatacta cgcgagctgg 240
gcgagtggcc gactcaccat ctccaaaacc tcgaccacgg tagatctgaa aatcaccagt 300
ccgacaaccg aggacacggc cacctatttc tgtgccagga ttcttattgt ttcttatgga 360
gcctttacca tc 372

<210> SEQ ID NO 548
<211> LENGTH: 39
<212> TYPE: DNA
<213> ORGANISM: Oryctolagus cuniculus

<400> SEQUENCE: 548
cagtccagtg agagcgttta tagtaataac ctcttatcc 39

<210> SEQ ID NO 549
<211> LENGTH: 21
<212> TYPE: DNA
<213> ORGANISM: Oryctolagus cuniculus

<400> SEQUENCE: 549
agggcatcca atctggcatc t 21

<210> SEQ ID NO 550
<211> LENGTH: 30
<212> TYPE: DNA
<213> ORGANISM: Oryctolagus cuniculus

<400> SEQUENCE: 550
caaggctatt atagtggtgt cattaatagt 30

<210> SEQ ID NO 551
<211> LENGTH: 15
<212> TYPE: DNA
<213> ORGANISM: Oryctolagus cuniculus

<400> SEQUENCE: 551
agctacttca tgagc 15

<210> SEQ ID NO 552
<211> LENGTH: 48
<212> TYPE: DNA
<213> ORGANISM: Oryctolagus cuniculus

<400> SEQUENCE: 552
ttcattaatc ctggtggtag cgcatactac gcgagctggg cgagtggc 48

<210> SEQ ID NO 553
<211> LENGTH: 33
<212> TYPE: DNA
<213> ORGANISM: Oryctolagus cuniculus

<400> SEQUENCE: 553
attcttattg tttcttatgg agcctttacc atc 33

<210> SEQ ID NO 554
<211> LENGTH: 122
<212> TYPE: PRT
<213> ORGANISM: Oryctolagus cuniculus

<400> SEQUENCE: 554

Met Asp Thr Arg Ala Pro Thr Gln Leu Leu Gly Leu Leu Leu Leu Trp
1 5 10 15

Leu Pro Gly Ala Arg Cys Ala Tyr Asp Met Thr Gln Thr Pro Ala Ser
20 25 30

Val Glu Val Ala Val Gly Gly Thr Val Thr Ile Lys Cys Gln Ala Thr
35 40 45

Glu Ser Ile Gly Asn Glu Leu Ser Trp Tyr Gln Gln Lys Pro Gly Gln
50 55 60

Ala Pro Lys Leu Leu Ile Tyr Ser Ala Ser Thr Leu Ala Ser Gly Val
65 70 75 80

Pro Ser Arg Phe Lys Gly Ser Gly Ser Gly Thr Gln Phe Thr Leu Thr
85 90 95

Ile Thr Gly Val Glu Cys Asp Asp Ala Ala Thr Tyr Tyr Cys Gln Gln
100 105 110

Gly Tyr Ser Ser Ala Asn Ile Asp Asn Ala
115 120

<210> SEQ ID NO 555
<211> LENGTH: 128
<212> TYPE: PRT
<213> ORGANISM: Oryctolagus cuniculus

<400> SEQUENCE: 555

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Lys Tyr Tyr Met Ser Trp Val Arg Gln Ala Pro Glu Lys Gly Leu Lys
    50                  55                  60

Tyr Ile Gly Tyr Ile Asp Ser Thr Thr Val Asn Thr Tyr Tyr Ala Thr
65                  70                  75                  80

Trp Ala Arg Gly Arg Phe Thr Ile Ser Lys Thr Ser Thr Thr Val Asp
                85                  90                  95

Leu Lys Ile Thr Ser Pro Thr Ser Glu Asp Thr Ala Thr Tyr Phe Cys
            100                 105                 110

Ala Arg Gly Ser Thr Tyr Phe Thr Asp Gly Gly His Arg Leu Asp Leu
        115                 120                 125

<210> SEQ ID NO 556
<211> LENGTH: 11
<212> TYPE: PRT
<213> ORGANISM: Oryctolagus cuniculus

<400> SEQUENCE: 556

Gln Ala Thr Glu Ser Ile Gly Asn Glu Leu Ser
1               5                   10

<210> SEQ ID NO 557
<211> LENGTH: 7
<212> TYPE: PRT
<213> ORGANISM: Oryctolagus cuniculus

<400> SEQUENCE: 557

Ser Ala Ser Thr Leu Ala Ser
1               5

<210> SEQ ID NO 558
<211> LENGTH: 12
<212> TYPE: PRT
<213> ORGANISM: Oryctolagus cuniculus

<400> SEQUENCE: 558

Gln Gln Gly Tyr Ser Ser Ala Asn Ile Asp Asn Ala
1               5                   10

<210> SEQ ID NO 559
<211> LENGTH: 5
<212> TYPE: PRT
<213> ORGANISM: Oryctolagus cuniculus

<400> SEQUENCE: 559

Lys Tyr Tyr Met Ser
1               5

<210> SEQ ID NO 560
<211> LENGTH: 17

<212> TYPE: PRT
<213> ORGANISM: Oryctolagus cuniculus

<400> SEQUENCE: 560

Tyr Ile Asp Ser Thr Thr Val Asn Thr Tyr Tyr Ala Thr Trp Ala Arg
1 5 10 15

Gly

<210> SEQ ID NO 561
<211> LENGTH: 14
<212> TYPE: PRT
<213> ORGANISM: Oryctolagus cuniculus

<400> SEQUENCE: 561

Gly Ser Thr Tyr Phe Thr Asp Gly Gly His Arg Leu Asp Leu
1 5 10

<210> SEQ ID NO 562
<211> LENGTH: 366
<212> TYPE: DNA
<213> ORGANISM: Oryctolagus cuniculus

<400> SEQUENCE: 562
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cactgagagc attggcaatg agttatcctg gtatcagcag 180
aaaccagggc aggctcccaa gctcctgatc tattctgcat ccactctggc atctggggtc 240
ccatcgcggt tcaaaggcag tggatctggg acacagttca ctctcaccat caccggcgtg 300
gagtgtgatg atgctgccac ttactactgt caacagggtt atagtagtgc taatattgat 360
aatgct 366

<210> SEQ ID NO 563
<211> LENGTH: 384
<212> TYPE: DNA
<213> ORGANISM: Oryctolagus cuniculus

<400> SEQUENCE: 563
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
accgtctctg gattctccct cagtaagtac tacatgagct gggtccgcca ggctccagag 180
aaggggctga aatacatcgg atacattgat agtactactg ttaatacata ctacgcgacc 240
tgggcgagag gccgattcac catctccaaa acctcgacca cggtggatct gaagatcacc 300
agtccgacaa gtgaggacac ggccacctat ttctgtgcca gaggaagtac ttattttact 360
gatggaggcc atcggttgga tctc 384

<210> SEQ ID NO 564
<211> LENGTH: 33
<212> TYPE: DNA
<213> ORGANISM: Oryctolagus cuniculus

<400> SEQUENCE: 564
caggccactg agagcattgg caatgagtta tcc 33

<210> SEQ ID NO 565
<211> LENGTH: 21
<212> TYPE: DNA
<213> ORGANISM: Oryctolagus cuniculus

<400> SEQUENCE: 565
tctgcatcca ctctggcatc t 21

<210> SEQ ID NO 566
<211> LENGTH: 36
<212> TYPE: DNA
<213> ORGANISM: Oryctolagus cuniculus

<400> SEQUENCE: 566
caacagggtt atagtagtgc taatattgat aatgct 36

<210> SEQ ID NO 567
<211> LENGTH: 15
<212> TYPE: DNA
<213> ORGANISM: Oryctolagus cuniculus

<400> SEQUENCE: 567
aagtactaca tgagc 15

<210> SEQ ID NO 568
<211> LENGTH: 51
<212> TYPE: DNA
<213> ORGANISM: Oryctolagus cuniculus

<400> SEQUENCE: 568
tacattgata gtactactgt taatacatac tacgcgacct gggcgagagg c 51

<210> SEQ ID NO 569
<211> LENGTH: 42
<212> TYPE: DNA
<213> ORGANISM: Oryctolagus cuniculus

<400> SEQUENCE: 569
ggaagtactt attttactga tggaggccat cggttggatc tc 42

<210> SEQ ID NO 570
<211> LENGTH: 122
<212> TYPE: PRT
<213> ORGANISM: Oryctolagus cuniculus

<400> SEQUENCE: 570

Met Asp Thr Arg Ala Pro Thr Gln Leu Leu Gly Leu Leu Leu Leu Trp
1 5 10 15

Leu Pro Gly Ala Arg Cys Ala Tyr Asp Met Thr Gln Thr Pro Ala Ser
20 25 30

Val Glu Val Ala Val Gly Gly Thr Val Thr Ile Lys Cys Gln Ala Thr
35 40 45

Glu Ser Ile Gly Asn Glu Leu Ser Trp Tyr Gln Gln Lys Pro Gly Gln
50 55 60

Ala Pro Lys Leu Leu Ile Tyr Ser Ala Ser Thr Leu Ala Ser Gly Val
65 70 75 80

Pro Ser Arg Phe Lys Gly Ser Gly Ser Gly Thr Gln Phe Thr Leu Thr
85 90 95

Ile Thr Gly Val Glu Cys Asp Asp Ala Ala Thr Tyr Tyr Cys Gln Gln
100 105 110

Gly Tyr Ser Ser Ala Asn Ile Asp Asn Ala
115 120

<210> SEQ ID NO 571
<211> LENGTH: 124

<212> TYPE: PRT
<213> ORGANISM: Oryctolagus cuniculus

<400> SEQUENCE: 571

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Asn Met Gly Trp Val Arg Gln Ala Pro Gly Lys Gly Leu Glu
    50                  55                  60

Trp Ile Gly Ser Ile Thr Ile Asp Gly Arg Thr Tyr Tyr Ala Ser Trp
65                  70                  75                  80

Ala Lys Gly Arg Phe Thr Val Ser Lys Ser Ser Thr Thr Val Asp Leu
                85                  90                  95

Lys Met Thr Ser Leu Thr Thr Gly Asp Thr Ala Thr Tyr Phe Cys Ala
            100                 105                 110

Arg Ile Leu Ile Val Ser Tyr Gly Ala Phe Thr Ile
        115                 120

<210> SEQ ID NO 572
<211> LENGTH: 11
<212> TYPE: PRT
<213> ORGANISM: Oryctolagus cuniculus

<400> SEQUENCE: 572

Gln Ala Thr Glu Ser Ile Gly Asn Glu Leu Ser
1               5                   10

<210> SEQ ID NO 573
<211> LENGTH: 7
<212> TYPE: PRT
<213> ORGANISM: Oryctolagus cuniculus

<400> SEQUENCE: 573

Ser Ala Ser Thr Leu Ala Ser
1               5

<210> SEQ ID NO 574
<211> LENGTH: 12
<212> TYPE: PRT
<213> ORGANISM: Oryctolagus cuniculus

<400> SEQUENCE: 574

Gln Gln Gly Tyr Ser Ser Ala Asn Ile Asp Asn Ala
1               5                   10

<210> SEQ ID NO 575
<211> LENGTH: 5
<212> TYPE: PRT
<213> ORGANISM: Oryctolagus cuniculus

<400> SEQUENCE: 575

Thr Tyr Asn Met Gly
1               5

<210> SEQ ID NO 576
<211> LENGTH: 16
<212> TYPE: PRT
<213> ORGANISM: Oryctolagus cuniculus

<400> SEQUENCE: 576

Ser Ile Thr Ile Asp Gly Arg Thr Tyr Tyr Ala Ser Trp Ala Lys Gly
1 5 10 15

<210> SEQ ID NO 577
<211> LENGTH: 11
<212> TYPE: PRT
<213> ORGANISM: Oryctolagus cuniculus

<400> SEQUENCE: 577

Ile Leu Ile Val Ser Tyr Gly Ala Phe Thr Ile
1 5 10

<210> SEQ ID NO 578
<211> LENGTH: 366
<212> TYPE: DNA
<213> ORGANISM: Oryctolagus cuniculus

<400> SEQUENCE: 578
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cactgagagc attggcaatg agttatcctg gtatcagcag 180
aaaccagggc aggctcccaa gctcctgatc tattctgcat ccactctggc atctggggtc 240
ccatcgcggt tcaaaggcag tggatctggg acacagttca ctctcaccat caccggcgtg 300
gagtgtgatg atgctgccac ttactactgt caacagggtt atagtagtgc taatattgat 360
aatgct 366

<210> SEQ ID NO 579
<211> LENGTH: 372
<212> TYPE: DNA
<213> ORGANISM: Oryctolagus cuniculus

<400> SEQUENCE: 579
atggagactg ggctgcgctg gcttctcctg gtcgctgtgc tcaaaggtgt ccagtgtcag 60
tcgctggagg agtccggggg tcgcctggta acgcctggga cacccctgac actcacctgc 120
acagtctctg gattctccct cagtacctac aacatgggct gggtccgcca ggctccaggg 180
aaggggctgg aatggatcgg aagtattact attgatggtc gcacatacta cgcgagctgg 240
gcgaaaggcc gattcaccgt ctccaaaagc tcgaccacgg tggatctgaa aatgaccagt 300
ctgacaaccg gggacacggc cacctatttc tgtgccagga ttcttattgt ttcttatggg 360
gcctttacca tc 372

<210> SEQ ID NO 580
<211> LENGTH: 33
<212> TYPE: DNA
<213> ORGANISM: Oryctolagus cuniculus

<400> SEQUENCE: 580
caggccactg agagcattgg caatgagtta tcc 33

<210> SEQ ID NO 581
<211> LENGTH: 21
<212> TYPE: DNA
<213> ORGANISM: Oryctolagus cuniculus

<400> SEQUENCE: 581
tctgcatcca ctctggcatc t 21

<210> SEQ ID NO 582
<211> LENGTH: 36
<212> TYPE: DNA
<213> ORGANISM: Oryctolagus cuniculus

<400> SEQUENCE: 582
caacagggtt atagtagtgc taatattgat aatgct 36

<210> SEQ ID NO 583
<211> LENGTH: 15
<212> TYPE: DNA
<213> ORGANISM: Oryctolagus cuniculus

<400> SEQUENCE: 583
acctacaaca tgggc 15

<210> SEQ ID NO 584
<211> LENGTH: 48
<212> TYPE: DNA
<213> ORGANISM: Oryctolagus cuniculus

<400> SEQUENCE: 584
agtattacta ttgatggtcg cacatactac gcgagctggg cgaaaggc 48

<210> SEQ ID NO 585
<211> LENGTH: 33
<212> TYPE: DNA
<213> ORGANISM: Oryctolagus cuniculus

<400> SEQUENCE: 585
attcttattg tttcttatgg ggcctttacc atc 33

<210> SEQ ID NO 586
<211> LENGTH: 105
<212> TYPE: PRT
<213> ORGANISM: Artificial Sequence
<220> FEATURE:
<223> OTHER INFORMATION: Kappa constant domain

<400> SEQUENCE: 586

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 587
<211> LENGTH: 315
<212> TYPE: DNA
<213> ORGANISM: Artificial Sequence
<220> FEATURE:
<223> OTHER INFORMATION: Kappa constant domain

<400> SEQUENCE: 587

-continued

```
gtggctgcac catctgtctt catcttcccg ccatctgatg agcagttgaa atctggaact     60

gcctctgttg tgtgcctgct gaataacttc tatcccagag aggccaaagt acagtggaag    120

gtggataacg ccctccaatc gggtaactcc caggagagtg tcacagagca ggacagcaag    180

gacagcacct acagcctcag cagcaccctg acgctgagca aagcagacta cgagaaacac    240

aaagtctacg cctgcgaagt cacccatcag ggcctgagct cgcccgtcac aaagagcttc    300

aacaggggag agtgt                                                     315
```

<210> SEQ ID NO 588
<211> LENGTH: 330
<212> TYPE: PRT
<213> ORGANISM: Artificial Sequence
<220> FEATURE:
<223> OTHER INFORMATION: Gamma-1 constant domain

<400> SEQUENCE: 588

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

-continued

```
305                 310                 315                 320

Gln Lys Ser Leu Ser Leu Ser Pro Gly Lys
                325                 330
```

```
<210> SEQ ID NO 589
<211> LENGTH: 990
<212> TYPE: DNA
<213> ORGANISM: Artificial Sequence
<220> FEATURE:
<223> OTHER INFORMATION: Gamma-1 constant domain

<400> SEQUENCE: 589

gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacgcc     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggaggag     720

atgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctac agcaagctca ccgtggacaa gagcaggtgg     900

cagcagggga acgtcttctc atgctccgtg atgcatgagg ctctgcacaa ccactacacg     960

cagaagagcc tctccctgtc tccgggtaaa                                      990
```

```
<210> SEQ ID NO 590
<211> LENGTH: 15
<212> TYPE: PRT
<213> ORGANISM: Homo sapiens

<400> SEQUENCE: 590

Val Pro Pro Gly Glu Asp Ser Lys Asp Val Ala Ala Pro His Arg
1               5                   10                  15
```

```
<210> SEQ ID NO 591
<211> LENGTH: 15
<212> TYPE: PRT
<213> ORGANISM: Homo sapiens

<400> SEQUENCE: 591

Gly Glu Asp Ser Lys Asp Val Ala Ala Pro His Arg Gln Pro Leu
1               5                   10                  15
```

```
<210> SEQ ID NO 592
<211> LENGTH: 15
<212> TYPE: PRT
<213> ORGANISM: Homo sapiens

<400> SEQUENCE: 592

Ser Lys Asp Val Ala Ala Pro His Arg Gln Pro Leu Thr Ser Ser
```

1 5 10 15

<210> SEQ ID NO 593
<211> LENGTH: 15
<212> TYPE: PRT
<213> ORGANISM: Homo sapiens

<400> SEQUENCE: 593

Val Ala Ala Pro His Arg Gln Pro Leu Thr Ser Ser Glu Arg Ile
1 5 10 15

<210> SEQ ID NO 594
<211> LENGTH: 15
<212> TYPE: PRT
<213> ORGANISM: Homo sapiens

<400> SEQUENCE: 594

Pro His Arg Gln Pro Leu Thr Ser Ser Glu Arg Ile Asp Lys Gln
1 5 10 15

<210> SEQ ID NO 595
<211> LENGTH: 15
<212> TYPE: PRT
<213> ORGANISM: Homo sapiens

<400> SEQUENCE: 595

Gln Pro Leu Thr Ser Ser Glu Arg Ile Asp Lys Gln Ile Arg Tyr
1 5 10 15

<210> SEQ ID NO 596
<211> LENGTH: 15
<212> TYPE: PRT
<213> ORGANISM: Homo sapiens

<400> SEQUENCE: 596

Thr Ser Ser Glu Arg Ile Asp Lys Gln Ile Arg Tyr Ile Leu Asp
1 5 10 15

<210> SEQ ID NO 597
<211> LENGTH: 15
<212> TYPE: PRT
<213> ORGANISM: Homo sapiens

<400> SEQUENCE: 597

Glu Arg Ile Asp Lys Gln Ile Arg Tyr Ile Leu Asp Gly Ile Ser
1 5 10 15

<210> SEQ ID NO 598
<211> LENGTH: 15
<212> TYPE: PRT
<213> ORGANISM: Homo sapiens

<400> SEQUENCE: 598

Asp Lys Gln Ile Arg Tyr Ile Leu Asp Gly Ile Ser Ala Leu Arg
1 5 10 15

<210> SEQ ID NO 599
<211> LENGTH: 15
<212> TYPE: PRT
<213> ORGANISM: Homo sapiens

<400> SEQUENCE: 599

Ile Arg Tyr Ile Leu Asp Gly Ile Ser Ala Leu Arg Lys Glu Thr
1 5 10 15

<210> SEQ ID NO 600
<211> LENGTH: 15
<212> TYPE: PRT
<213> ORGANISM: Homo sapiens

<400> SEQUENCE: 600

Ile Leu Asp Gly Ile Ser Ala Leu Arg Lys Glu Thr Cys Asn Lys
1 5 10 15

<210> SEQ ID NO 601
<211> LENGTH: 15
<212> TYPE: PRT
<213> ORGANISM: Homo sapiens

<400> SEQUENCE: 601

Gly Ile Ser Ala Leu Arg Lys Glu Thr Cys Asn Lys Ser Asn Met
1 5 10 15

<210> SEQ ID NO 602
<211> LENGTH: 15
<212> TYPE: PRT
<213> ORGANISM: Homo sapiens

<400> SEQUENCE: 602

Ala Leu Arg Lys Glu Thr Cys Asn Lys Ser Asn Met Cys Glu Ser
1 5 10 15

<210> SEQ ID NO 603
<211> LENGTH: 15
<212> TYPE: PRT
<213> ORGANISM: Homo sapiens

<400> SEQUENCE: 603

Lys Glu Thr Cys Asn Lys Ser Asn Met Cys Glu Ser Ser Lys Glu
1 5 10 15

<210> SEQ ID NO 604
<211> LENGTH: 15
<212> TYPE: PRT
<213> ORGANISM: Homo sapiens

<400> SEQUENCE: 604

Cys Asn Lys Ser Asn Met Cys Glu Ser Ser Lys Glu Ala Leu Ala
1 5 10 15

<210> SEQ ID NO 605
<211> LENGTH: 15
<212> TYPE: PRT
<213> ORGANISM: Homo sapiens

<400> SEQUENCE: 605

Ser Asn Met Cys Glu Ser Ser Lys Glu Ala Leu Ala Glu Asn Asn
1 5 10 15

<210> SEQ ID NO 606
<211> LENGTH: 15
<212> TYPE: PRT
<213> ORGANISM: Homo sapiens

<400> SEQUENCE: 606

Cys Glu Ser Ser Lys Glu Ala Leu Ala Glu Asn Asn Leu Asn Leu
1 5 10 15

<210> SEQ ID NO 607
<211> LENGTH: 15
<212> TYPE: PRT

<213> ORGANISM: Homo sapiens

<400> SEQUENCE: 607

Ser Lys Glu Ala Leu Ala Glu Asn Asn Leu Asn Leu Pro Lys Met
1 5 10 15

<210> SEQ ID NO 608
<211> LENGTH: 15
<212> TYPE: PRT
<213> ORGANISM: Homo sapiens

<400> SEQUENCE: 608

Ala Leu Ala Glu Asn Asn Leu Asn Leu Pro Lys Met Ala Glu Lys
1 5 10 15

<210> SEQ ID NO 609
<211> LENGTH: 15
<212> TYPE: PRT
<213> ORGANISM: Homo sapiens

<400> SEQUENCE: 609

Glu Asn Asn Leu Asn Leu Pro Lys Met Ala Glu Lys Asp Gly Cys
1 5 10 15

<210> SEQ ID NO 610
<211> LENGTH: 15
<212> TYPE: PRT
<213> ORGANISM: Homo sapiens

<400> SEQUENCE: 610

Leu Asn Leu Pro Lys Met Ala Glu Lys Asp Gly Cys Phe Gln Ser
1 5 10 15

<210> SEQ ID NO 611
<211> LENGTH: 15
<212> TYPE: PRT
<213> ORGANISM: Homo sapiens

<400> SEQUENCE: 611

Pro Lys Met Ala Glu Lys Asp Gly Cys Phe Gln Ser Gly Phe Asn
1 5 10 15

<210> SEQ ID NO 612
<211> LENGTH: 15
<212> TYPE: PRT
<213> ORGANISM: Homo sapiens

<400> SEQUENCE: 612

Ala Glu Lys Asp Gly Cys Phe Gln Ser Gly Phe Asn Glu Glu Thr
1 5 10 15

<210> SEQ ID NO 613
<211> LENGTH: 15
<212> TYPE: PRT
<213> ORGANISM: Homo sapiens

<400> SEQUENCE: 613

Asp Gly Cys Phe Gln Ser Gly Phe Asn Glu Glu Thr Cys Leu Val
1 5 10 15

<210> SEQ ID NO 614
<211> LENGTH: 15
<212> TYPE: PRT
<213> ORGANISM: Homo sapiens

<400> SEQUENCE: 614

Phe Gln Ser Gly Phe Asn Glu Glu Thr Cys Leu Val Lys Ile Ile
1 5 10 15

<210> SEQ ID NO 615
<211> LENGTH: 15
<212> TYPE: PRT
<213> ORGANISM: Homo sapiens

<400> SEQUENCE: 615

Gly Phe Asn Glu Glu Thr Cys Leu Val Lys Ile Ile Thr Gly Leu
1 5 10 15

<210> SEQ ID NO 616
<211> LENGTH: 15
<212> TYPE: PRT
<213> ORGANISM: Homo sapiens

<400> SEQUENCE: 616

Glu Glu Thr Cys Leu Val Lys Ile Ile Thr Gly Leu Leu Glu Phe
1 5 10 15

<210> SEQ ID NO 617
<211> LENGTH: 15
<212> TYPE: PRT
<213> ORGANISM: Homo sapiens

<400> SEQUENCE: 617

Cys Leu Val Lys Ile Ile Thr Gly Leu Leu Glu Phe Glu Val Tyr
1 5 10 15

<210> SEQ ID NO 618
<211> LENGTH: 15
<212> TYPE: PRT
<213> ORGANISM: Homo sapiens

<400> SEQUENCE: 618

Lys Ile Ile Thr Gly Leu Leu Glu Phe Glu Val Tyr Leu Glu Tyr
1 5 10 15

<210> SEQ ID NO 619
<211> LENGTH: 15
<212> TYPE: PRT
<213> ORGANISM: Homo sapiens

<400> SEQUENCE: 619

Thr Gly Leu Leu Glu Phe Glu Val Tyr Leu Glu Tyr Leu Gln Asn
1 5 10 15

<210> SEQ ID NO 620
<211> LENGTH: 15
<212> TYPE: PRT
<213> ORGANISM: Homo sapiens

<400> SEQUENCE: 620

Leu Glu Phe Glu Val Tyr Leu Glu Tyr Leu Gln Asn Arg Phe Glu
1 5 10 15

<210> SEQ ID NO 621
<211> LENGTH: 15
<212> TYPE: PRT
<213> ORGANISM: Homo sapiens

<400> SEQUENCE: 621

Glu Val Tyr Leu Glu Tyr Leu Gln Asn Arg Phe Glu Ser Ser Glu
1 5 10 15

<210> SEQ ID NO 622
<211> LENGTH: 15
<212> TYPE: PRT
<213> ORGANISM: Homo sapiens

<400> SEQUENCE: 622

Leu Glu Tyr Leu Gln Asn Arg Phe Glu Ser Ser Glu Glu Gln Ala
1 5 10 15

<210> SEQ ID NO 623
<211> LENGTH: 15
<212> TYPE: PRT
<213> ORGANISM: Homo sapiens

<400> SEQUENCE: 623

Leu Gln Asn Arg Phe Glu Ser Ser Glu Glu Gln Ala Arg Ala Val
1 5 10 15

<210> SEQ ID NO 624
<211> LENGTH: 15
<212> TYPE: PRT
<213> ORGANISM: Homo sapiens

<400> SEQUENCE: 624

Arg Phe Glu Ser Ser Glu Glu Gln Ala Arg Ala Val Gln Met Ser
1 5 10 15

<210> SEQ ID NO 625
<211> LENGTH: 15
<212> TYPE: PRT
<213> ORGANISM: Homo sapiens

<400> SEQUENCE: 625

Ser Ser Glu Glu Gln Ala Arg Ala Val Gln Met Ser Thr Lys Val
1 5 10 15

<210> SEQ ID NO 626
<211> LENGTH: 15
<212> TYPE: PRT
<213> ORGANISM: Homo sapiens

<400> SEQUENCE: 626

Glu Gln Ala Arg Ala Val Gln Met Ser Thr Lys Val Leu Ile Gln
1 5 10 15

<210> SEQ ID NO 627
<211> LENGTH: 15
<212> TYPE: PRT
<213> ORGANISM: Homo sapiens

<400> SEQUENCE: 627

Arg Ala Val Gln Met Ser Thr Lys Val Leu Ile Gln Phe Leu Gln
1 5 10 15

<210> SEQ ID NO 628
<211> LENGTH: 15
<212> TYPE: PRT
<213> ORGANISM: Homo sapiens

<400> SEQUENCE: 628

Gln Met Ser Thr Lys Val Leu Ile Gln Phe Leu Gln Lys Lys Ala
1 5 10 15

<210> SEQ ID NO 629

<211> LENGTH: 15
<212> TYPE: PRT
<213> ORGANISM: Homo sapiens

<400> SEQUENCE: 629

Thr Lys Val Leu Ile Gln Phe Leu Gln Lys Lys Ala Lys Asn Leu
1 5 10 15

<210> SEQ ID NO 630
<211> LENGTH: 15
<212> TYPE: PRT
<213> ORGANISM: Homo sapiens

<400> SEQUENCE: 630

Leu Ile Gln Phe Leu Gln Lys Lys Ala Lys Asn Leu Asp Ala Ile
1 5 10 15

<210> SEQ ID NO 631
<211> LENGTH: 15
<212> TYPE: PRT
<213> ORGANISM: Homo sapiens

<400> SEQUENCE: 631

Phe Leu Gln Lys Lys Ala Lys Asn Leu Asp Ala Ile Thr Thr Pro
1 5 10 15

<210> SEQ ID NO 632
<211> LENGTH: 15
<212> TYPE: PRT
<213> ORGANISM: Homo sapiens

<400> SEQUENCE: 632

Lys Lys Ala Lys Asn Leu Asp Ala Ile Thr Thr Pro Asp Pro Thr
1 5 10 15

<210> SEQ ID NO 633
<211> LENGTH: 15
<212> TYPE: PRT
<213> ORGANISM: Homo sapiens

<400> SEQUENCE: 633

Lys Asn Leu Asp Ala Ile Thr Thr Pro Asp Pro Thr Thr Asn Ala
1 5 10 15

<210> SEQ ID NO 634
<211> LENGTH: 15
<212> TYPE: PRT
<213> ORGANISM: Homo sapiens

<400> SEQUENCE: 634

Asp Ala Ile Thr Thr Pro Asp Pro Thr Thr Asn Ala Ser Leu Leu
1 5 10 15

<210> SEQ ID NO 635
<211> LENGTH: 15
<212> TYPE: PRT
<213> ORGANISM: Homo sapiens

<400> SEQUENCE: 635

Thr Thr Pro Asp Pro Thr Thr Asn Ala Ser Leu Leu Thr Lys Leu
1 5 10 15

<210> SEQ ID NO 636
<211> LENGTH: 15
<212> TYPE: PRT
<213> ORGANISM: Homo sapiens

<400> SEQUENCE: 636

Asp Pro Thr Thr Asn Ala Ser Leu Leu Thr Lys Leu Gln Ala Gln
1 5 10 15

<210> SEQ ID NO 637
<211> LENGTH: 15
<212> TYPE: PRT
<213> ORGANISM: Homo sapiens

<400> SEQUENCE: 637

Thr Asn Ala Ser Leu Leu Thr Lys Leu Gln Ala Gln Asn Gln Trp
1 5 10 15

<210> SEQ ID NO 638
<211> LENGTH: 15
<212> TYPE: PRT
<213> ORGANISM: Homo sapiens

<400> SEQUENCE: 638

Ser Leu Leu Thr Lys Leu Gln Ala Gln Asn Gln Trp Leu Gln Asp
1 5 10 15

<210> SEQ ID NO 639
<211> LENGTH: 15
<212> TYPE: PRT
<213> ORGANISM: Homo sapiens

<400> SEQUENCE: 639

Thr Lys Leu Gln Ala Gln Asn Gln Trp Leu Gln Asp Met Thr Thr
1 5 10 15

<210> SEQ ID NO 640
<211> LENGTH: 15
<212> TYPE: PRT
<213> ORGANISM: Homo sapiens

<400> SEQUENCE: 640

Gln Ala Gln Asn Gln Trp Leu Gln Asp Met Thr Thr His Leu Ile
1 5 10 15

<210> SEQ ID NO 641
<211> LENGTH: 15
<212> TYPE: PRT
<213> ORGANISM: Homo sapiens

<400> SEQUENCE: 641

Asn Gln Trp Leu Gln Asp Met Thr Thr His Leu Ile Leu Arg Ser
1 5 10 15

<210> SEQ ID NO 642
<211> LENGTH: 15
<212> TYPE: PRT
<213> ORGANISM: Homo sapiens

<400> SEQUENCE: 642

Leu Gln Asp Met Thr Thr His Leu Ile Leu Arg Ser Phe Lys Glu
1 5 10 15

<210> SEQ ID NO 643
<211> LENGTH: 15
<212> TYPE: PRT
<213> ORGANISM: Homo sapiens

<400> SEQUENCE: 643

Met Thr Thr His Leu Ile Leu Arg Ser Phe Lys Glu Phe Leu Gln
1 5 10 15

<210> SEQ ID NO 644
<211> LENGTH: 15
<212> TYPE: PRT
<213> ORGANISM: Homo sapiens

<400> SEQUENCE: 644

His Leu Ile Leu Arg Ser Phe Lys Glu Phe Leu Gln Ser Ser Leu
1 5 10 15

<210> SEQ ID NO 645
<211> LENGTH: 15
<212> TYPE: PRT
<213> ORGANISM: Homo sapiens

<400> SEQUENCE: 645

Leu Arg Ser Phe Lys Glu Phe Leu Gln Ser Ser Leu Arg Ala Leu
1 5 10 15

<210> SEQ ID NO 646
<211> LENGTH: 15
<212> TYPE: PRT
<213> ORGANISM: Homo sapiens

<400> SEQUENCE: 646

Phe Lys Glu Phe Leu Gln Ser Ser Leu Arg Ala Leu Arg Gln Met
1 5 10 15

<210> SEQ ID NO 647
<211> LENGTH: 111
<212> TYPE: PRT
<213> ORGANISM: Oryctolagus cuniculus

<400> SEQUENCE: 647

Ala Tyr Asp Met Thr Gln Thr Pro Ala Ser Val Ser Ala Ala Val Gly
1 5 10 15

Gly Thr Val Thr Ile Lys Cys Gln Ala Ser Gln Ser Ile Asn Asn Glu
20 25 30

Leu Ser Trp Tyr Gln Gln Lys Pro Gly Gln Arg Pro Lys Leu Leu Ile
35 40 45

Tyr Arg Ala Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Gln Gly Tyr Ser Leu Arg Asn
85 90 95

Ile Asp Asn Ala Phe Gly Gly Gly Thr Glu Val Val Val Lys Arg
100 105 110

<210> SEQ ID NO 648
<211> LENGTH: 88
<212> TYPE: PRT
<213> ORGANISM: Homo sapiens

<400> SEQUENCE: 648

Ala Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Leu Leu Ile

```
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85


<210> SEQ ID NO 649
<211> LENGTH: 88
<212> TYPE: PRT
<213> ORGANISM: Homo sapiens

<400> SEQUENCE: 649

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys
                85


<210> SEQ ID NO 650
<211> LENGTH: 88
<212> TYPE: PRT
<213> ORGANISM: Homo sapiens

<400> SEQUENCE: 650

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys
                85


<210> SEQ ID NO 651
<211> LENGTH: 111
<212> TYPE: PRT
<213> ORGANISM: Artificial Sequence
<220> FEATURE:
<223> OTHER INFORMATION: Humanized antibody

<400> SEQUENCE: 651

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
```

```
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg
            100                 105                 110


<210> SEQ ID NO 652
<211> LENGTH: 117
<212> TYPE: PRT
<213> ORGANISM: Oryctolagus cuniculus

<400> SEQUENCE: 652

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Val Thr Trp Val Arg Gln Ala Pro Gly Lys Gly Leu Glu Trp Ile Gly
        35                  40                  45

Ile Ile Tyr Gly Ser Asp Glu Thr Ala Tyr Ala Thr Trp Ala Ile Gly
    50                  55                  60

Arg Phe Thr Ile Ser Lys Thr Ser Thr Thr Val Asp Leu Lys Met Thr
65                  70                  75                  80

Ser Leu Thr Ala Ala Asp Thr Ala Thr Tyr Phe Cys Ala Arg Asp Asp
                85                  90                  95

Ser Ser Asp Trp Asp Ala Lys Phe Asn Leu Trp Gly Gln Gly Thr Leu
            100                 105                 110

Val Thr Val Ser Ser
        115


<210> SEQ ID NO 653
<211> LENGTH: 97
<212> TYPE: PRT
<213> ORGANISM: Homo sapiens

<400> SEQUENCE: 653

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg


<210> SEQ ID NO 654
<211> LENGTH: 97
<212> TYPE: PRT
<213> ORGANISM: Homo sapiens
```

<400> SEQUENCE: 654

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Val Ser Ser Asn
20 25 30

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg

<210> SEQ ID NO 655
<211> LENGTH: 98
<212> TYPE: PRT
<213> ORGANISM: Homo sapiens

<400> SEQUENCE: 655

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Val Ile Tyr Ser Gly Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 656
<211> LENGTH: 120
<212> TYPE: PRT
<213> ORGANISM: Artificial sequence
<220> FEATURE:
<223> OTHER INFORMATION: Humanized antibody

<400> SEQUENCE: 656

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Val Thr Trp Val Arg Gln Ala Pro Gly Lys Gly Leu Glu Trp Val
35 40 45

Gly Ile Ile Tyr Gly Ser Asp Glu Thr Ala Tyr Ala Thr Trp Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu Trp Gly Gln
100 105 110

```
Gly Thr Leu Val Thr Val Ser Ser
        115                 120


<210> SEQ ID NO 657
<211> LENGTH: 120
<212> TYPE: PRT
<213> ORGANISM: Artificial sequence
<220> FEATURE:
<223> OTHER INFORMATION: Humanized antibody

<400> SEQUENCE: 657

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser
        115                 120


<210> SEQ ID NO 658
<211> LENGTH: 166
<212> TYPE: PRT
<213> ORGANISM: Oryctolagus cuniculus

<400> SEQUENCE: 658

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Val Thr Trp Val Arg Gln Ala Pro Gly Lys Gly Leu Glu
    50                  55                  60

Trp Ile Gly Ile Ile Tyr Gly Ser Asp Glu Thr Ala Tyr Ala Thr Ser
65                  70                  75                  80

Ala Ile Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Asp Asp Ser Ser Asp Trp Asp Ala Lys Phe Asn Leu Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys
                165
```

<210> SEQ ID NO 659
<211> LENGTH: 16
<212> TYPE: PRT
<213> ORGANISM: Oryctolagus cuniculus

<400> SEQUENCE: 659

```
Ile Ile Tyr Gly Ser Asp Glu Thr Ala Tyr Ala Thr Ser Ala Ile Gly
1               5                   10                  15
```

<210> SEQ ID NO 660
<211> LENGTH: 122
<212> TYPE: PRT
<213> ORGANISM: Oryctolagus cuniculus

<400> SEQUENCE: 660

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Lys Cys Gln Ala Ser
        35                  40                  45

Gln Ser Ile Asn Asn Glu Leu Ser Trp Tyr Gln Gln Lys Pro Gly Gln
    50                  55                  60

Arg Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Ser Leu Arg Asn Ile Asp Asn Ala
        115                 120
```

<210> SEQ ID NO 661
<211> LENGTH: 125
<212> TYPE: PRT
<213> ORGANISM: Oryctolagus cuniculus

<400> SEQUENCE: 661

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Val Thr Trp Val Arg Gln Ala Pro Gly Lys Gly Leu Glu
    50                  55                  60

Trp Ile Gly Ile Ile Tyr Gly Ser Asp Glu Thr Ala Tyr Ala Thr Trp
65                  70                  75                  80

Ala Ile Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Asp Asp Ser Ser Asp Trp Asp Ala Lys Phe Asn Leu
        115                 120                 125
```

<210> SEQ ID NO 662
<211> LENGTH: 366
<212> TYPE: DNA
<213> ORGANISM: Oryctolagus cuniculus

<400> SEQUENCE: 662
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca agtgccaggc cagtcagagc attaacaatg aattatcctg gtatcagcag 180
aaaccagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgct 366

<210> SEQ ID NO 663
<211> LENGTH: 375
<212> TYPE: DNA
<213> ORGANISM: Oryctolagus cuniculus

<400> SEQUENCE: 663
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagcctctg gattctccct cagtaactac tacgtgacct gggtccgcca ggctccaggg 180
aaggggctgg aatggatcgg aatcatttat ggtagtgatg aaacggccta cgcgacctgg 240
gcgataggcc gattcaccat ctccaaaacc tcgaccacgg tggatctgaa aatgaccagt 300
ctgacagccg cggacacggc cacctatttc tgtgccagag atgatagtag tgactgggat 360
gcaaaattta acttg 375

<210> SEQ ID NO 664
<211> LENGTH: 450
<212> TYPE: PRT
<213> ORGANISM: Oryctolagus cuniculus

<400> SEQUENCE: 664

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Trp Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

-continued

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 665
<211> LENGTH: 450
<212> TYPE: PRT
<213> ORGANISM: Oryctolagus cuniculus

<400> SEQUENCE: 665

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
```

```
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 666
<211> LENGTH: 216
<212> TYPE: PRT
<213> ORGANISM: Oryctolagus cuniculus

<400> SEQUENCE: 666

Ile Gln Met Thr Gln Ser Pro Ser Ser Leu Ser Ala Ser Val Gly Asp
1               5                   10                  15

Arg Val Thr Ile Thr Cys Gln Ala Ser Gln Ser Ile Asn Asn Glu Leu
```

20 25 30

Ser Trp Tyr Gln Gln Lys Pro Gly Lys Ala Pro Lys Leu Leu Ile Tyr
35 40 45

Arg Ala Ser Thr Leu Ala Ser Gly Val Pro Ser Arg Phe Ser Gly Ser
50 55 60

Gly Ser Gly Thr Asp Phe Thr Leu Thr Ile Ser Ser Leu Gln Pro Asp
65 70 75 80

Asp Phe Ala Thr Tyr Tyr Cys Gln Gln Gly Tyr Ser Leu Arg Asn Ile
85 90 95

Asp Asn Ala Phe Gly Gly Gly Thr Lys Val Glu Ile Lys Arg Thr Val
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val Asp Asn Ala Leu Gln Ser Gly Asn
145 150 155 160

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys
180 185 190

Val Tyr Ala Cys Glu Val Thr His Gln Gly Leu Ser Ser Pro Val Thr
195 200 205

Lys Ser Phe Asn Arg Gly Glu Cys
210 215

<210> SEQ ID NO 667
<211> LENGTH: 122
<212> TYPE: PRT
<213> ORGANISM: Oryctolagus cuniculus

<400> SEQUENCE: 667

Met Asp Thr Arg Ala Pro Thr Gln Leu Leu Gly Leu Leu Leu Leu Trp
1 5 10 15

Leu Pro Gly Ala Arg Cys Ala Tyr Asp Met Thr Gln Thr Pro Ala Ser
20 25 30

Val Glu Val Ala Val Gly Gly Thr Val Thr Ile Asn Cys Gln Ala Ser
35 40 45

Glu Thr Ile Tyr Ser Trp Leu Ser Trp Tyr Gln Gln Lys Pro Gly Gln
50 55 60

Pro Pro Lys Leu Leu Ile Tyr Gln Ala Ser Asp Leu Ala Ser Gly Val
65 70 75 80

Pro Ser Arg Phe Ser Gly Ser Gly Ala Gly Thr Glu Tyr Thr Leu Thr
85 90 95

Ile Ser Gly Val Gln Cys Asp Asp Ala Ala Thr Tyr Tyr Cys Gln Gln
100 105 110

Gly Tyr Ser Gly Ser Asn Val Asp Asn Val
115 120

<210> SEQ ID NO 668
<211> LENGTH: 126
<212> TYPE: PRT
<213> ORGANISM: Oryctolagus cuniculus

<400> SEQUENCE: 668

Met Glu Thr Gly Leu Arg Trp Leu Leu Leu Val Ala Val Leu Lys Gly
1 5 10 15

-continued

```
Val Gln Cys Gln Glu Gln Leu Lys Glu Ser Gly Gly Arg Leu Val Thr
            20                  25                  30

Pro Gly Thr Pro Leu Thr Leu Thr Cys Thr Ala Ser Gly Phe Ser Leu
        35                  40                  45

Asn Asp His Ala Met Gly Trp Val Arg Gln Ala Pro Gly Lys Gly Leu
    50                  55                  60

Glu Tyr Ile Gly Phe Ile Asn Ser Gly Gly Ser Ala Arg Tyr Ala Ser
65                  70                  75                  80

Trp Ala Glu Gly Arg Phe Thr Ile Ser Arg Thr Ser Thr Thr Val Asp
                85                  90                  95

Leu Lys Met Thr Ser Leu Thr Thr Glu Asp Thr Ala Thr Tyr Phe Cys
            100                 105                 110

Val Arg Gly Gly Ala Val Trp Ser Ile His Ser Phe Asp Pro
        115                 120                 125
```

<210> SEQ ID NO 669
<211> LENGTH: 366
<212> TYPE: DNA
<213> ORGANISM: Oryctolagus cuniculus

<400> SEQUENCE: 669

```
atggacacga gggcccccac tcagctgctg gggctcctgc tgctctggct cccaggtgcc     60

agatgtgcct atgatatgac ccagactcca gcctctgtgg aggtagctgt gggaggcaca    120

gtcaccatca attgccaggc cagtgagacc atttacagtt ggttatcctg gtatcagcag    180

aagccagggc agcctcccaa gctcctgatc taccaggcat ccgatctggc atctggggtc    240

ccatcgcgat tcagcggcag tggggctggg acagagtaca ctctcaccat cagcggcgtg    300

cagtgtgacg atgctgccac ttactactgt caacagggtt atagtggtag taatgttgat    360

aatgtt                                                               366
```

<210> SEQ ID NO 670
<211> LENGTH: 378
<212> TYPE: DNA
<213> ORGANISM: Oryctolagus cuniculus

<400> SEQUENCE: 670

```
atggagactg ggctgcgctg gcttctcctg gtcgctgtgc tcaaaggtgt ccagtgtcag     60

gagcagctga aggagtccgg gggtcgcctg gtcacgcctg ggacacccct gacacttacc    120

tgcacagcct ctggattctc cctcaatgac catgcaatgg gctgggtccg ccaggctcca    180

gggaaggggc tggaatacat cggattcatt aatagtggtg gtagcgcacg ctacgcgagc    240

tgggcagaag gccgattcac catctccaga acctcgacca cggtggatct gaaaatgacc    300

agtctgacaa ccgaggacac ggccacctat ttctgtgtca gagggggtgc tgtttggagt    360

attcatagtt ttgatccc                                                  378
```

<210> SEQ ID NO 671
<211> LENGTH: 123
<212> TYPE: PRT
<213> ORGANISM: Oryctolagus cuniculus

<400> SEQUENCE: 671

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30
```

```
Val Ser Ala Ala Val Gly Gly Thr Val Ser Ile Ser Cys Gln Ala Ser
        35                  40                  45

Gln Ser Val Tyr Asp Asn Asn Tyr Leu Ser Trp Phe Gln Gln Lys Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Val Gly Ser Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Asp Ser Asp Asn Ala
        115                 120
```

<210> SEQ ID NO 672
<211> LENGTH: 125
<212> TYPE: PRT
<213> ORGANISM: Oryctolagus cuniculus

<400> SEQUENCE: 672

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Val Tyr Tyr Met Asn Trp Val Arg Gln Ala Pro Gly Lys Gly Leu Glu
    50                  55                  60

Trp Ile Gly Phe Ile Thr Met Ser Asp Asn Ile Asn Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Ser Arg Gly Trp Gly Thr Met Gly Arg Leu Asp Leu
        115                 120                 125
```

<210> SEQ ID NO 673
<211> LENGTH: 369
<212> TYPE: DNA
<213> ORGANISM: Oryctolagus cuniculus

<400> SEQUENCE: 673

```
atggacacga gggcccccac tcagctgctg gggctcctgc tgctctggct cccaggtgcc      60

acatttgccg ccgtgctgac ccagactcca tctcccgtgt ctgcagctgt gggaggcaca     120

gtcagcatca gttgccaggc cagtcagagt gtttatgaca acaactactt atcctggttt     180

cagcagaaac cagggcagcc tcccaagctc ctgatctatg gtgcatccac tctggcatct     240

ggggtcccat cgcggttcgt gggcagtgga tctgggacac agttcactct caccatcaca     300

gacgtgcagt gtgacgatgc tgccacttac tattgtgcag gcgtttatga tgatgatagt     360

gataatgcc                                                             369
```

<210> SEQ ID NO 674
<211> LENGTH: 375
<212> TYPE: DNA
<213> ORGANISM: Oryctolagus cuniculus

<400> SEQUENCE: 674

```
atggagactg ggctgcgctg gcttctcctg gtggctgtgc tcaaaggtgt ccagtgtcag     60

tcgctggagg agtccggggg tcgcctggtc acccctggga cacccctgac actcacctgc    120

acagcctctg gattctccct cagtgtctac tacatgaact gggtccgcca ggctccaggg    180

aaggggctgg aatggatcgg attcattaca atgagtgata atataaatta cgcgagctgg    240

gcgaaaggcc gattcaccat ctccaaaacc tcgaccacgg tggatctgaa aatgaccagt    300

ccgacaaccg aggacacggc cacctatttc tgtgccagga gtcgtggctg ggtacaatg     360

ggtcggttgg atctc                                                     375


<210> SEQ ID NO 675
<211> LENGTH: 123
<212> TYPE: PRT
<213> ORGANISM: Oryctolagus cuniculus

<400> SEQUENCE: 675

Met Asp Thr Arg Ala Pro Thr Gln Leu Leu Gly Leu Leu Leu Leu Trp
1               5                   10                  15

Leu Pro Gly Ala Ile Cys Asp Pro Val Leu Thr Gln Thr Pro Ser Pro
            20                  25                  30

Val Ser Ala Pro Val Gly Gly Thr Val Ser Ile Ser Cys Gln Ala Ser
        35                  40                  45

Gln Ser Val Tyr Glu Asn Asn Tyr Leu Ser Trp Phe Gln Gln Lys Pro
    50                  55                  60

Gly Gln Pro Pro Lys Leu Leu Ile Tyr Gly Ala Ser Thr Leu Asp Ser
65                  70                  75                  80

Gly Val Pro Ser Arg Phe Lys Gly Ser Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Asp Ser Asp Asp Ala
        115                 120


<210> SEQ ID NO 676
<211> LENGTH: 126
<212> TYPE: PRT
<213> ORGANISM: Oryctolagus cuniculus

<400> SEQUENCE: 676

Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Gly Leu Val Thr
            20                  25                  30

Pro Gly Gly Thr Leu Thr Leu Thr Cys Thr Ala Ser Gly Phe Ser Leu
        35                  40                  45

Asn Ala Tyr Tyr Met Asn Trp Val Arg Gln Ala Pro Gly Lys Gly Leu
    50                  55                  60

Glu Trp Ile Gly Phe Ile Thr Leu Asn Asn Asn Val Ala Tyr Ala Asn
65                  70                  75                  80

Trp Ala Lys Gly Arg Phe Thr Phe Ser Lys Thr Ser Thr Thr Val Asp
                85                  90                  95

Leu Lys Met Thr Ser Pro Thr Pro Glu Asp Thr Ala Thr Tyr Phe Cys
            100                 105                 110

Ala Arg Ser Arg Gly Trp Gly Ala Met Gly Arg Leu Asp Leu
        115                 120                 125


<210> SEQ ID NO 677
```

<211> LENGTH: 369
<212> TYPE: DNA
<213> ORGANISM: Oryctolagus cuniculus

<400> SEQUENCE: 677
atggacacga gggcccccac tcagctgctg gggctcctgc tgctctggct cccaggtgcc 60
atatgtgacc ctgtgctgac ccagactcca tctcccgtat ctgcacctgt gggaggcaca 120
gtcagcatca gttgccaggc cagtcagagt gtttatgaga acaactattt atcctggttt 180
cagcagaaac cagggcagcc tcccaagctc ctgatctatg gtgcatccac tctggattct 240
ggggtcccat cgcggttcaa aggcagtgga tctgggacac agttcactct caccattaca 300
gacgtgcagt gtgacgatgc tgccacttac tattgtgcag gcgtttatga tgatgatagt 360
gatgatgcc 369

<210> SEQ ID NO 678
<211> LENGTH: 378
<212> TYPE: DNA
<213> ORGANISM: Oryctolagus cuniculus

<400> SEQUENCE: 678
atggagactg ggctgcgctg gcttctcctg gtggctgtgc tcaaaggtgt ccagtgtcag 60
gagcagctga aggagtccgg aggaggcctg gtaacgcctg gaggaaccct gacactcacc 120
tgcacagcct ctggattctc cctcaatgcc tactacatga actgggtccg ccaggctcca 180
gggaaggggc tggaatggat cggattcatt actctgaata ataatgtagc ttacgcgaac 240
tgggcgaaag gccgattcac cttctccaaa acctcgacca cggtggatct gaaaatgacc 300
agtccgacac ccgaggacac ggccacctat ttctgtgcca ggagtcgtgg ctggggtgca 360
atgggtcggt tggatctc 378

<210> SEQ ID NO 679
<211> LENGTH: 122
<212> TYPE: PRT
<213> ORGANISM: Oryctolagus cuniculus

<400> SEQUENCE: 679

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Pro
20 25 30

Val Ser Ala Ala Val Gly Gly Thr Val Thr Ile Asn Cys Gln Ala Ser
35 40 45

Gln Ser Val Asp Asp Asn Asn Trp Leu Gly Trp Tyr Gln Gln Lys Arg
50 55 60

Gly Gln Pro Pro Lys Tyr Leu Ile Tyr Ser Ala Ser Thr Leu Ala Ser
65 70 75 80

Gly Val Pro Ser Arg Phe Lys Gly Ser Gly Ser Gly Thr Gln Phe Thr
85 90 95

Leu Thr Ile Ser Asp Leu Glu Cys Asp Asp Ala Ala Thr Tyr Tyr Cys
100 105 110

Ala Gly Gly Phe Ser Gly Asn Ile Phe Ala
115 120

<210> SEQ ID NO 680
<211> LENGTH: 122
<212> TYPE: PRT
<213> ORGANISM: Oryctolagus cuniculus

<400> SEQUENCE: 680

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Ala Met Ser Trp Val Arg Gln Ala Pro Gly Lys Gly Leu Glu
50 55 60

Trp Ile Gly Ile Ile Gly Gly Phe Gly Thr Thr Tyr Tyr Ala Thr Trp
65 70 75 80

Ala Lys Gly Arg Phe Thr Ile Ser Lys Thr Ser Thr Thr Val Asp Leu
85 90 95

Arg Ile Thr Ser Pro Thr Thr Glu Asp Thr Ala Thr Tyr Phe Cys Ala
100 105 110

Arg Gly Gly Pro Gly Asn Gly Gly Asp Ile
115 120

<210> SEQ ID NO 681
<211> LENGTH: 366
<212> TYPE: DNA
<213> ORGANISM: Oryctolagus cuniculus

<400> SEQUENCE: 681
atggacacga gggcccccac tcagctgctg gggctcctgc tgctctggct cccaggtgcc 60
acatttgccc aagtgctgac ccagactcca tcgcctgtgt ctgcagctgt gggaggcaca 120
gtcaccatca actgccaggc cagtcagagt gttgatgata acaactggtt aggctggtat 180
cagcagaaac gagggcagcc tcccaagtac ctgatctatt ctgcatccac tctggcatct 240
ggggtcccat cgcggttcaa aggcagtgga tctgggacac agttcactct caccatcagc 300
gacctggagt gtgacgatgc tgccacttac tactgtgcag gcggttttag tggtaatatc 360
tttgct 366

<210> SEQ ID NO 682
<211> LENGTH: 366
<212> TYPE: DNA
<213> ORGANISM: Oryctolagus cuniculus

<400> SEQUENCE: 682
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gcttctccct cagtagctat gcaatgagct gggtccgcca ggctccagga 180
aaggggctgg agtggatcgg aatcattggt ggttttggta ccacatacta cgcgacctgg 240
gcgaaaggcc gattcaccat ctccaaaacc tcgaccacgg tggatctgag aatcaccagt 300
ccgacaaccg aggacacggc cacctatttc tgtgccagag gtggtcctgg taatggtggt 360
gacatc 366

<210> SEQ ID NO 683
<211> LENGTH: 122
<212> TYPE: PRT
<213> ORGANISM: Oryctolagus cuniculus

<400> SEQUENCE: 683

Met Asp Thr Arg Ala Pro Thr Gln Leu Leu Gly Leu Leu Leu Leu Trp
1 5 10 15

```
Leu Pro Gly Ala Thr Phe Ala Ala Val Leu Thr Gln Thr Pro Ser Pro
            20                  25                  30

Val Ser Val Pro Val Gly Gly Thr Val Thr Ile Lys Cys Gln Ser Ser
        35                  40                  45

Gln Ser Val Tyr Asn Asn Phe Leu Ser Trp Tyr Gln Gln Lys Pro Gly
    50                  55                  60

Gln Pro Pro Lys Leu Leu Ile Tyr Gln Ala Ser Lys Leu Ala Ser Gly
65                  70                  75                  80

Val Pro Asp Arg Phe Ser Gly Ser Gly Ser Gly Thr Gln Phe Thr Leu
                85                  90                  95

Thr Ile Ser Gly Val Gln Cys Asp Asp Ala Ala Thr Tyr Tyr Cys Leu
            100                 105                 110

Gly Gly Tyr Asp Asp Asp Ala Asp Asn Ala
        115                 120
```

<210> SEQ ID NO 684
<211> LENGTH: 128
<212> TYPE: PRT
<213> ORGANISM: Oryctolagus cuniculus

<400> SEQUENCE: 684

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Asp Tyr Ala Met Ser Trp Val Arg Gln Ala Pro Gly Lys Gly Leu Glu
    50                  55                  60

Trp Ile Gly Ile Ile Tyr Ala Gly Ser Gly Ser Thr Trp Tyr Ala Ser
65                  70                  75                  80

Trp Ala Lys Gly Arg Phe Thr Ile Ser Lys Thr Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Asp Gly Tyr Asp Asp Tyr Gly Asp Phe Asp Arg Leu Asp Leu
        115                 120                 125
```

<210> SEQ ID NO 685
<211> LENGTH: 366
<212> TYPE: DNA
<213> ORGANISM: Oryctolagus cuniculus

<400> SEQUENCE: 685

```
atggacacga gggcccccac tcagctgctg gggctcctgc tgctctggct cccaggtgcc      60

acatttgcag ccgtgctgac ccagacacca tcgcccgtgt ctgtacctgt gggaggcaca     120

gtcaccatca agtgccagtc cagtcagagt gtttataata atttcttatc gtggtatcag     180

cagaaaccag ggcagcctcc caagctcctg atctaccagg catccaaact ggcatctggg     240

gtcccagata ggttcagcgg cagtggatct gggacacagt tcactctcac catcagcggc     300

gtgcagtgtg acgatgctgc cacttactac tgtctaggcg gttatgatga tgatgctgat     360

aatgct                                                                366
```

<210> SEQ ID NO 686
<211> LENGTH: 384
<212> TYPE: DNA

<213> ORGANISM: Oryctolagus cuniculus

<400> SEQUENCE: 686
atggagactg ggctgcgctg gcttctcctg gtcgctgtgc tcaaaggtgt ccagtgtcag 60
tcggtggagg agtccggggg tcgcctggtc acgcctggga cacccctgac gctcacctgc 120
acagtctctg gaatcgacct cagtgactat gcaatgagct gggtccgcca ggctccaggg 180
aaggggctgg aatggatcgg aatcatttat gctggtagtg gtagcacatg gtacgcgagc 240
tgggcgaaag gccgattcac catctccaaa acctcgacca cggtggatct gaaaatcacc 300
agtccgacaa ccgaggacac ggccacctat ttctgtgcca gagatggata cgatgactat 360
ggtgatttcg atcgattgga tctc 384

<210> SEQ ID NO 687
<211> LENGTH: 122
<212> TYPE: PRT
<213> ORGANISM: Oryctolagus cuniculus

<400> SEQUENCE: 687

Met Asp Thr Arg Ala Pro Thr Gln Leu Leu Gly Leu Leu Leu Leu Trp
1 5 10 15

Leu Pro Gly Ala Arg Cys Ala Tyr Asp Met Thr Gln Thr Pro Ala Ser
20 25 30

Val Ser Ala Ala Val Gly Gly Thr Val Thr Ile Lys Cys Gln Ala Ser
35 40 45

Gln Ser Ile Asn Asn Glu Leu Ser Trp Tyr Gln Gln Lys Ser Gly Gln
50 55 60

Arg Pro Lys Leu Leu Ile Tyr Arg Ala Ser Thr Leu Ala Ser Gly Val
65 70 75 80

Ser Ser Arg Phe Lys Gly Ser Gly Ser Gly Thr Glu Phe Thr Leu Thr
85 90 95

Ile Ser Asp Leu Glu Cys Ala Asp Ala Ala Thr Tyr Tyr Cys Gln Gln
100 105 110

Gly Tyr Ser Leu Arg Asn Ile Asp Asn Ala
115 120

<210> SEQ ID NO 688
<211> LENGTH: 125
<212> TYPE: PRT
<213> ORGANISM: Oryctolagus cuniculus

<400> SEQUENCE: 688

Met Glu Thr Gly Leu Arg Trp Leu Leu Leu Val Ala Val Leu Ser Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Ala Ser Gly Phe Ser Leu Ser
35 40 45

Asn Tyr Tyr Met Thr Trp Val Arg Gln Ala Pro Gly Lys Gly Leu Glu
50 55 60

Trp Ile Gly Met Ile Tyr Gly Ser Asp Glu Thr Ala Tyr Ala Asn Trp
65 70 75 80

Ala Ile Gly Arg Phe Thr Ile Ser Lys Thr Ser Thr Thr Val Asp Leu
85 90 95

Lys Met Thr Ser Leu Thr Ala Ala Asp Thr Ala Thr Tyr Phe Cys Ala
100 105 110

Arg Asp Asp Ser Ser Asp Trp Asp Ala Lys Phe Asn Leu 115 120 125

<210> SEQ ID NO 689
<211> LENGTH: 366
<212> TYPE: DNA
<213> ORGANISM: Oryctolagus cuniculus

<400> SEQUENCE: 689
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca aatgccaggc cagtcagagc attaacaatg aattatcctg gtatcagcag 180
aaatcagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgct 366

<210> SEQ ID NO 690
<211> LENGTH: 375
<212> TYPE: DNA
<213> ORGANISM: Oryctolagus cuniculus

<400> SEQUENCE: 690
atggagactg ggctgcgctg gcttctcctg gtcgctgtgc tctcaggtgt ccagtgtcag 60
tcgctggagg agtccggggg tcgcctggtc acgcctggga cacccctgac actcacctgc 120
acagcctctg gattctccct cagtaactac tacatgacct gggtccgcca ggctccaggg 180
aaggggctgg aatggatcgg aatgatttat ggtagtgatg aaacagccta cgcgaactgg 240
gcgataggcc gattcaccat ctccaaaacc tcgaccacgg tggatctgaa aatgaccagt 300
ctgacagccg cggacacggc cacctatttc tgtgccagag atgatagtag tgactgggat 360
gcaaaattta acttg 375

<210> SEQ ID NO 691
<211> LENGTH: 450
<212> TYPE: PRT
<213> ORGANISM: Oryctolagus cuniculus

<400> SEQUENCE: 691

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Met Thr Trp Val Arg Gln Ala Pro Gly Lys Gly Leu Glu Trp Val
35 40 45

Gly Met Ile Tyr Gly Ser Asp Glu Thr Ala Tyr Ala Asn Trp Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 692
<211> LENGTH: 450
<212> TYPE: PRT
<213> ORGANISM: Oryctolagus cuniculus

<400> SEQUENCE: 692

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Met Thr Trp Val Arg Gln Ala Pro Gly Lys Gly Leu Glu Trp Val
        35                  40                  45

Gly Met Ile Tyr Gly Ser Asp Glu Thr Ala Tyr Ala Asn Ser Ala Ile
    50                  55                  60
```

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 693
<211> LENGTH: 217
<212> TYPE: PRT
```

<213> ORGANISM: Oryctolagus cuniculus

<400> SEQUENCE: 693

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 694
<211> LENGTH: 33
<212> TYPE: DNA
<213> ORGANISM: Oryctolagus cuniculus

<400> SEQUENCE: 694
caggccagtc agagcattaa caatgagtta tcc 33

<210> SEQ ID NO 695
<211> LENGTH: 36
<212> TYPE: DNA
<213> ORGANISM: Oryctolagus cuniculus

<400> SEQUENCE: 695
caacagggtt atagtctgag gaacattgat aatgct 36

<210> SEQ ID NO 696
<211> LENGTH: 48
<212> TYPE: DNA
<213> ORGANISM: Oryctolagus cuniculus

<400> SEQUENCE: 696
atcatctatg gtagtgatga aaccgcctac gctacctccg ctataggc 48

<210> SEQ ID NO 697
<211> LENGTH: 36
<212> TYPE: DNA

<213> ORGANISM: Oryctolagus cuniculus

<400> SEQUENCE: 697
gatgatagta gtgactggga tgcaaagttc aacttg 36

<210> SEQ ID NO 698
<211> LENGTH: 336
<212> TYPE: DNA
<213> ORGANISM: Oryctolagus cuniculus

<400> SEQUENCE: 698
gctatccaga tgacccagtc tccttcctcc ctgtctgcat ctgtaggaga cagagtcacc 60
atcacttgcc aggccagtca gagcattaac aatgagttat cctggtatca gcagaaacca 120
gggaaagccc ctaagctcct gatctatagg gcatccactc tggcatctgg ggtcccatca 180
aggttcagcg gcagtggatc tgggacagac ttcactctca ccatcagcag cctgcagcct 240
gatgattttg caacttatta ctgccaacag ggttatagtc tgaggaacat tgataatgct 300
ttcggcggag ggaccaaggt ggaaatcaaa cgtacg 336

<210> SEQ ID NO 699
<211> LENGTH: 112
<212> TYPE: PRT
<213> ORGANISM: Oryctolagus cuniculus

<400> SEQUENCE: 699

Ala Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asn Glu
20 25 30

Leu Ser Trp Tyr Gln Gln Lys Pro Gly Lys Ala Pro Lys Leu Leu Ile
35 40 45

Tyr Arg Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Asp Asp Phe Ala Thr Tyr Tyr Cys Gln Gln Gly Tyr Ser Leu Arg Asn
85 90 95

Ile Asp Asn Ala Phe Gly Gly Gly Thr Lys Val Glu Ile Lys Arg Thr
100 105 110

<210> SEQ ID NO 700
<211> LENGTH: 360
<212> TYPE: DNA
<213> ORGANISM: Oryctolagus cuniculus

<400> SEQUENCE: 700
gaggtgcagc tggtggagtc tgggggaggc ttggtccagc ctggggggtc cctgagactc 60
tcctgtgcag cctctggatt ctccctcagt aactactacg tgacctgggt ccgtcaggct 120
ccagggaagg ggctggagtg ggtcggcatc atctatggta gtgatgaaac cgcctacgct 180
acctccgcta taggccgatt caccatctcc agagacaatt ccaagaacac cctgtatctt 240
caaatgaaca gcctgagagc tgaggacact gctgtgtatt actgtgctag agatgatagt 300
agtgactggg atgcaaagtt caacttgtgg ggccaaggga ccctcgtcac cgtctcgagc 360

<210> SEQ ID NO 701
<211> LENGTH: 651
<212> TYPE: DNA
<213> ORGANISM: Oryctolagus cuniculus

<400> SEQUENCE: 701

```
gctatccaga tgacccagtc tccttcctcc ctgtctgcat ctgtaggaga cagagtcacc      60
atcacttgcc aggccagtca gagcattaac aatgagttat cctggtatca gcagaaacca     120
gggaaagccc ctaagctcct gatctatagg gcatccactc tggcatctgg ggtcccatca     180
aggttcagcg gcagtggatc tgggacagac ttcactctca ccatcagcag cctgcagcct     240
gatgattttg caacttatta ctgccaacag ggttatagtc tgaggaacat tgataatgct     300
ttcggcggag ggaccaaggt ggaaatcaaa cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t              651
```

<210> SEQ ID NO 702
<211> LENGTH: 217
<212> TYPE: PRT
<213> ORGANISM: Oryctolagus cuniculus

<400> SEQUENCE: 702

```
Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 703
<211> LENGTH: 1350
<212> TYPE: DNA
<213> ORGANISM: Oryctolagus cuniculus

<400> SEQUENCE: 703
gaggtgcagc tggtggagtc tgggggaggc ttggtccagc ctggggggtc cctgagactc 60
tcctgtgcag cctctggatt ctccctcagt aactactacg tgacctgggt ccgtcaggct 120
ccagggaagg ggctggagtg ggtcggcatc atctatggta gtgatgaaac cgcctacgct 180
acctccgcta taggccgatt caccatctcc agagacaatt ccaagaacac cctgtatctt 240
caaatgaaca gcctgagagc tgaggacact gctgtgtatt actgtgctag agatgatagt 300
agtgactggg atgcaaagtt caacttgtgg ggccaaggga ccctcgtcac cgtctcgagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacgcc 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

<210> SEQ ID NO 704
<211> LENGTH: 450
<212> TYPE: PRT
<213> ORGANISM: Oryctolagus cuniculus

<400> SEQUENCE: 704

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Val Thr Trp Val Arg Gln Ala Pro Gly Lys Gly Leu Glu Trp Val
35 40 45

Gly Ile Ile Tyr Gly Ser Asp Glu Thr Ala Tyr Ala Thr Ser Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 705
<211> LENGTH: 705
<212> TYPE: DNA
<213> ORGANISM: Oryctolagus cuniculus

<400> SEQUENCE: 705
atgaagtggg taacctttat ttcccttctg tttctcttta gcagcgctta ttccgctatc 60
cagatgaccc agtctccttc ctccctgtct gcatctgtag gagacagagt caccatcact 120
tgccaggcca gtcagagcat taacaatgag ttatcctggt atcagcagaa accagggaaa 180
gcccctaagc tcctgatcta tagggcatcc actctggcat ctggggtccc atcaaggttc 240

-continued

```
agcggcagtg gatctgggac agacttcact ctcaccatca gcagcctgca gcctgatgat    300

tttgcaactt attactgcca acagggttat agtctgagga acattgataa tgctttcggc    360

ggagggacca aggtggaaat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705
```

<210> SEQ ID NO 706
<211> LENGTH: 235
<212> TYPE: PRT
<213> ORGANISM: Oryctolagus cuniculus

<400> SEQUENCE: 706

```
Met Lys Trp Val Thr Phe Ile Ser Leu Leu Phe Leu Phe Ser Ser Ala
1               5                   10                  15

Tyr Ser Ala Ile Gln Met Thr Gln Ser Pro Ser Ser Leu Ser Ala Ser
            20                  25                  30

Val Gly Asp Arg Val Thr Ile Thr Cys Gln Ala Ser Gln Ser Ile Asn
        35                  40                  45

Asn Glu Leu Ser Trp Tyr Gln Gln Lys Pro Gly Lys Ala Pro Lys Leu
    50                  55                  60

Leu Ile Tyr Arg Ala Ser Thr Leu Ala Ser Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Asp Asp Phe Ala Thr Tyr Tyr Cys Gln Gln Gly Tyr Ser Leu
            100                 105                 110

Arg Asn Ile Asp Asn Ala Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 707
<211> LENGTH: 1404
<212> TYPE: DNA
<213> ORGANISM: Oryctolagus cuniculus

<400> SEQUENCE: 707

```
atgaagtggg taacctttat ttcccttctg tttctcttta gcagcgctta ttccgaggtg     60

cagctggtgg agtctggggg aggcttggtc cagcctgggg ggtccctgag actctcctgt    120
```

```
gcagcctctg gattctccct cagtaactac tacgtgacct gggtccgtca ggctccaggg    180

aaggggctgg agtgggtcgg catcatctat ggtagtgatg aaaccgccta cgctacctcc    240

gctataggcc gattcaccat ctccagagac aattccaaga acaccctgta tcttcaaatg    300

aacagcctga gagctgagga cactgctgtg tattactgtg ctagagatga tagtagtgac    360

tgggatgcaa agttcaactt gtggggccaa gggaccctcg tcaccgtctc gagcgcctcc    420

accaagggcc catcggtctt ccccctggca ccctcctcca agagcacctc tgggggcaca    480

gcggccctgg gctgcctggt caaggactac ttccccgaac cggtgacggt gtcgtggaac    540

tcaggcgccc tgaccagcgg cgtgcacacc ttcccggctg tcctacagtc ctcaggactc    600

tactccctca gcagcgtggt gaccgtgccc tccagcagct tgggcaccca gacctacatc    660

tgcaacgtga atcacaagcc cagcaacacc aaggtggaca agagagttga gcccaaatct    720

tgtgacaaaa ctcacacatg cccaccgtgc ccagcacctg aactcctggg gggaccgtca    780

gtcttcctct tccccccaaa acccaaggac accctcatga tctcccggac ccctgaggtc    840

acatgcgtgg tggtggacgt gagccacgaa gaccctgagg tcaagttcaa ctggtacgtg    900

gacggcgtgg aggtgcataa tgccaagaca aagccgcggg aggagcagta cgccagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catcccggga ggagatgacc   1140

aagaaccagg tcagcctgac ctgcctggtc aaaggcttct atcccagcga catcgccgtg   1200

gagtgggaga gcaatgggca gccggagaac aactacaaga ccacgcctcc cgtgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaa                                          1404
```

<210> SEQ ID NO 708
<211> LENGTH: 468
<212> TYPE: PRT
<213> ORGANISM: Oryctolagus cuniculus

<400> SEQUENCE: 708

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
            20                  25                  30

Gly Gly Ser Leu Arg Leu Ser Cys Ala Ala Ser Gly Phe Ser Leu Ser
        35                  40                  45

Asn Tyr Tyr Val Thr Trp Val Arg Gln Ala Pro Gly Lys Gly Leu Glu
    50                  55                  60

Trp Val Gly Ile Ile Tyr Gly Ser Asp Glu Thr Ala Tyr Ala Thr Ser
65                  70                  75                  80

Ala Ile Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Arg Asp Asp Ser Ser Asp Trp Asp Ala Lys Phe Asn Leu Trp
        115                 120                 125

Gly Gln Gly Thr Leu Val Thr Val Ser Ser Ala Ser Thr Lys Gly Pro
    130                 135                 140
```

-continued

Ser Val Phe Pro Leu Ala Pro Ser Ser Lys Ser Thr Ser Gly Gly Thr
145 150 155 160

Ala Ala Leu Gly Cys Leu Val Lys Asp Tyr Phe Pro Glu Pro Val Thr
165 170 175

Val Ser Trp Asn Ser Gly Ala Leu Thr Ser Gly Val His Thr Phe Pro
180 185 190

Ala Val Leu Gln Ser Ser Gly Leu Tyr Ser Leu Ser Ser Val Val Thr
195 200 205

Val Pro Ser Ser Ser Leu Gly Thr Gln Thr Tyr Ile Cys Asn Val Asn
210 215 220

His Lys Pro Ser Asn Thr Lys Val Asp Lys Arg Val Glu Pro Lys Ser
225 230 235 240

Cys Asp Lys Thr His Thr Cys Pro Pro Cys Pro Ala Pro Glu Leu Leu
245 250 255

Gly Gly Pro Ser Val Phe Leu Phe Pro Pro Lys Pro Lys Asp Thr Leu
260 265 270

Met Ile Ser Arg Thr Pro Glu Val Thr Cys Val Val Val Asp Val Ser
275 280 285

His Glu Asp Pro Glu Val Lys Phe Asn Trp Tyr Val Asp Gly Val Glu
290 295 300

Val His Asn Ala Lys Thr Lys Pro Arg Glu Glu Gln Tyr Ala Ser Thr
305 310 315 320

Tyr Arg Val Val Ser Val Leu Thr Val Leu His Gln Asp Trp Leu Asn
325 330 335

Gly Lys Glu Tyr Lys Cys Lys Val Ser Asn Lys Ala Leu Pro Ala Pro
340 345 350

Ile Glu Lys Thr Ile Ser Lys Ala Lys Gly Gln Pro Arg Glu Pro Gln
355 360 365

Val Tyr Thr Leu Pro Pro Ser Arg Glu Glu Met Thr Lys Asn Gln Val
370 375 380

Ser Leu Thr Cys Leu Val Lys Gly Phe Tyr Pro Ser Asp Ile Ala Val
385 390 395 400

Glu Trp Glu Ser Asn Gly Gln Pro Glu Asn Asn Tyr Lys Thr Thr Pro
405 410 415

Pro Val Leu Asp Ser Asp Gly Ser Phe Phe Leu Tyr Ser Lys Leu Thr
420 425 430

Val Asp Lys Ser Arg Trp Gln Gln Gly Asn Val Phe Ser Cys Ser Val
435 440 445

Met His Glu Ala Leu His Asn His Tyr Thr Gln Lys Ser Leu Ser Leu
450 455 460

Ser Pro Gly Lys
465

<210> SEQ ID NO 709
<211> LENGTH: 111
<212> TYPE: PRT
<213> ORGANISM: Oryctolagus cuniculus

<400> SEQUENCE: 709

Ala Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asn Glu
20 25 30

Leu Ser Trp Tyr Gln Gln Lys Pro Gly Lys Ala Pro Lys Leu Leu Ile
35 40 45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg
            100                 105                 110

<210> SEQ ID NO 710
<211> LENGTH: 11
<212> TYPE: PRT
<213> ORGANISM: Homo sapiens

<400> SEQUENCE: 710

Arg Ala Ser Gln Gly Ile Arg Asn Asp Leu Gly
1               5                   10

<210> SEQ ID NO 711
<211> LENGTH: 11
<212> TYPE: PRT
<213> ORGANISM: Homo sapiens

<400> SEQUENCE: 711

Arg Ala Ser Gln Gly Ile Ser Asn Tyr Leu Ala
1               5                   10

<210> SEQ ID NO 712
<211> LENGTH: 11
<212> TYPE: PRT
<213> ORGANISM: Homo sapiens

<400> SEQUENCE: 712

Arg Ala Ser Gln Ser Ile Ser Ser Trp Leu Ala
1               5                   10

<210> SEQ ID NO 713
<211> LENGTH: 7
<212> TYPE: PRT
<213> ORGANISM: Homo sapiens

<400> SEQUENCE: 713

Ala Ala Ser Ser Leu Gln Ser
1               5

<210> SEQ ID NO 714
<211> LENGTH: 7
<212> TYPE: PRT
<213> ORGANISM: Homo sapiens

<400> SEQUENCE: 714

Ala Ala Ser Thr Leu Gln Ser
1               5

<210> SEQ ID NO 715
<211> LENGTH: 7
<212> TYPE: PRT
<213> ORGANISM: Homo sapiens

<400> SEQUENCE: 715

Lys Ala Ser Ser Leu Glu Ser
1               5

<210> SEQ ID NO 716

<211> LENGTH: 5
<212> TYPE: PRT
<213> ORGANISM: Homo sapiens

<400> SEQUENCE: 716

Ser Asn Tyr Met Ser
1 5

<210> SEQ ID NO 717
<211> LENGTH: 16
<212> TYPE: PRT
<213> ORGANISM: Homo sapiens

<400> SEQUENCE: 717

Val Ile Tyr Ser Gly Gly Ser Thr Tyr Tyr Ala Asp Ser Val Lys Gly
1 5 10 15

<210> SEQ ID NO 718
<211> LENGTH: 17
<212> TYPE: PRT
<213> ORGANISM: Homo sapiens

<400> SEQUENCE: 718

Val Ile Tyr Ser Gly Gly Ser Ser Thr Tyr Tyr Ala Asp Ser Val Lys
1 5 10 15

Gly

<210> SEQ ID NO 719
<211> LENGTH: 330
<212> TYPE: PRT
<213> ORGANISM: Artificial Sequence
<220> FEATURE:
<223> OTHER INFORMATION: Gamma-1 constant domain

<400> SEQUENCE: 719

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn

-continued

```
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 720
<211> LENGTH: 297
<212> TYPE: DNA
<213> ORGANISM: Oryctolagus cuniculus

<400> SEQUENCE: 720

atccagatga cccagtctcc ttcctccctg tctgcatctg taggagacag agtcaccatc      60

acttgccagg ccagtcagag cattaacaat gagttatcct ggtatcagca gaaaccaggg     120

aaagccccta agctcctgat ctatagggca tccactctgg catctggggt cccatcaagg     180

ttcagcggca gtggatctgg gacagacttc actctcacca tcagcagcct gcagcctgat     240

gattttgcaa cttattactg ccaacagggt tatagtctga ggaacattga taatgct        297


<210> SEQ ID NO 721
<211> LENGTH: 333
<212> TYPE: DNA
<213> ORGANISM: Oryctolagus cuniculus

<400> SEQUENCE: 721

gcctatgata tgacccagac tccagcctcg gtgtctgcag ctgtgggagg cacagtcacc      60

atcaagtgcc aggccagtca gagcattaac aatgaattat cctggtatca gcagaaacca     120

gggcagcgtc ccaagctcct gatctatagg gcatccactc tggcatctgg ggtctcatcg     180

cggttcaaag gcagtggatc tgggacagag ttcactctca ccatcagcga cctggagtgt     240

gccgatgctg ccacttacta ctgtcaacag ggttatagtc tgaggaatat tgataatgct     300

ttcggcggag ggaccgaggt ggtggtcaaa cgt                                  333


<210> SEQ ID NO 722
<211> LENGTH: 648
<212> TYPE: DNA
<213> ORGANISM: Oryctolagus cuniculus

<400> SEQUENCE: 722

atccagatga cccagtctcc ttcctccctg tctgcatctg taggagacag agtcaccatc      60

acttgccagg ccagtcagag cattaacaat gagttatcct ggtatcagca gaaaccaggg     120

aaagccccta agctcctgat ctatagggca tccactctgg catctggggt cccatcaagg     180

ttcagcggca gtggatctgg gacagacttc actctcacca tcagcagcct gcagcctgat     240
```

gattttgcaa cttattactg ccaacagggt tatagtctga ggaacattga taatgctttc 300
ggcggaggga ccaaggtgga aatcaaacgt acggtggctg caccatctgt cttcatcttc 360
ccgccatctg atgagcagtt gaaatctgga actgcctctg ttgtgtgcct gctgaataac 420
ttctatccca gagaggccaa agtacagtgg aaggtggata acgccctcca atcgggtaac 480
tcccaggaga gtgtcacaga gcaggacagc aaggacagca cctacagcct cagcagcacc 540
ctgacgctga gcaaagcaga ctacgagaaa cacaaagtct acgcctgcga agtcacccat 600
cagggcctga gctcgcccgt cacaaagagc ttcaacaggg gagagtgt 648

<210> SEQ ID NO 723
<211> LENGTH: 333
<212> TYPE: DNA
<213> ORGANISM: Oryctolagus cuniculus

<400> SEQUENCE: 723
gctatccaga tgacccagtc tccttcctcc ctgtctgcat ctgtaggaga cagagtcacc 60
atcacttgcc aggccagtca gagcattaac aatgagttat cctggtatca gcagaaacca 120
gggaaagccc ctaagctcct gatctatagg gcatccactc tggcatctgg ggtcccatca 180
aggttcagcg gcagtggatc tgggacagac ttcactctca ccatcagcag cctgcagcct 240
gatgattttg caacttatta ctgccaacag ggttatagtc tgaggaacat tgataatgct 300
ttcggcggag ggaccaaggt ggaaatcaaa cgt 333

<210> SEQ ID NO 724
<211> LENGTH: 327
<212> TYPE: DNA
<213> ORGANISM: Oryctolagus cuniculus

<400> SEQUENCE: 724
gaggtgcagc tggtggagtc tgggggaggc ttggtccagc ctgggggggtc cctgagactc 60 tcctgtgcag cctctggatt ctccctcagt aactactacg tgacctgggt ccgtcaggct 120
ccagggaagg ggctggagtg ggtcggcatc atctatggta gtgatgaaac cgcctacgct 180
acctccgcta taggccgatt caccatctcc agagacaatt ccaagaacac cctgtatctt 240
caaatgaaca gcctgagagc tgaggacact gctgtgtatt actgtgctag agatgatagt 300
agtgactggg atgcaaagtt caacttg 327

<210> SEQ ID NO 725
<211> LENGTH: 351
<212> TYPE: DNA
<213> ORGANISM: Oryctolagus cuniculus

<400> SEQUENCE: 725
cagtcgctgg aggagtccgg gggtcgcctg gtcacgcctg ggacacccct gacactcacc 60
tgcacagcct ctggattctc cctcagtaac tactacgtga cctgggtccg ccaggctcca 120
gggaaggggc tggaatggat cggaatcatt tatggtagtg atgaaacggc ctacgcgacc 180
tgggcgatag gccgattcac catctccaaa acctcgacca cggtggatct gaaaatgacc 240
agtctgacag ccgcggacac ggccacctat ttctgtgcca gagatgatag tagtgactgg 300
gatgcaaaat ttaacttgtg gggccaaggc accctggtca ccgtctcgag c 351

<210> SEQ ID NO 726
<211> LENGTH: 224
<212> TYPE: PRT
<213> ORGANISM: Homo sapiens

<400> SEQUENCE: 726

Met Glu Lys Leu Leu Cys Phe Leu Val Leu Thr Ser Leu Ser His Ala
1 5 10 15

Phe Gly Gln Thr Asp Met Ser Arg Lys Ala Phe Val Phe Pro Lys Glu
20 25 30

Ser Asp Thr Ser Tyr Val Ser Leu Lys Ala Pro Leu Thr Lys Pro Leu
35 40 45

Lys Ala Phe Thr Val Cys Leu His Phe Tyr Thr Glu Leu Ser Ser Thr
50 55 60

Arg Gly Tyr Ser Ile Phe Ser Tyr Ala Thr Lys Arg Gln Asp Asn Glu
65 70 75 80

Ile Leu Ile Phe Trp Ser Lys Asp Ile Gly Tyr Ser Phe Thr Val Gly
85 90 95

Gly Ser Glu Ile Leu Phe Glu Val Pro Glu Val Thr Val Ala Pro Val
100 105 110

His Ile Cys Thr Ser Trp Glu Ser Ala Ser Gly Ile Val Glu Phe Trp
115 120 125

Val Asp Gly Lys Pro Arg Val Arg Lys Ser Leu Lys Lys Gly Tyr Thr
130 135 140

Val Gly Ala Glu Ala Ser Ile Ile Leu Gly Gln Glu Gln Asp Ser Phe
145 150 155 160

Gly Gly Asn Phe Glu Gly Ser Gln Ser Leu Val Gly Asp Ile Gly Asn
165 170 175

Val Asn Met Trp Asp Phe Val Leu Ser Pro Asp Glu Ile Asn Thr Ile
180 185 190

Tyr Leu Gly Gly Pro Phe Ser Pro Asn Val Leu Asn Trp Arg Ala Leu
195 200 205

Lys Tyr Glu Val Gln Gly Glu Val Phe Thr Lys Pro Gln Leu Trp Pro
210 215 220

<210> SEQ ID NO 727
<211> LENGTH: 468
<212> TYPE: PRT
<213> ORGANISM: Homo sapiens

<400> SEQUENCE: 727

Met Leu Ala Val Gly Cys Ala Leu Leu Ala Ala Leu Leu Ala Ala Pro
1 5 10 15

Gly Ala Ala Leu Ala Pro Arg Arg Cys Pro Ala Gln Glu Val Ala Arg
20 25 30

Gly Val Leu Thr Ser Leu Pro Gly Asp Ser Val Thr Leu Thr Cys Pro
35 40 45

Gly Val Glu Pro Glu Asp Asn Ala Thr Val His Trp Val Leu Arg Lys
50 55 60

Pro Ala Ala Gly Ser His Pro Ser Arg Trp Ala Gly Met Gly Arg Arg
65 70 75 80

Leu Leu Leu Arg Ser Val Gln Leu His Asp Ser Gly Asn Tyr Ser Cys
85 90 95

Tyr Arg Ala Gly Arg Pro Ala Gly Thr Val His Leu Leu Val Asp Val
100 105 110

Pro Pro Glu Glu Pro Gln Leu Ser Cys Phe Arg Lys Ser Pro Leu Ser
115 120 125

Asn Val Val Cys Glu Trp Gly Pro Arg Ser Thr Pro Ser Leu Thr Thr
130 135 140

Lys Ala Val Leu Leu Val Arg Lys Phe Gln Asn Ser Pro Ala Glu Asp

-continued

```
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465


<210> SEQ ID NO 728
<211> LENGTH: 918
<212> TYPE: PRT
<213> ORGANISM: Homo sapiens

<400> SEQUENCE: 728

Met Leu Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
```

-continued

```
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480
```

-continued

```
Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910
```

-continued

```
Gly Gly Tyr Met Pro Gln
        915


<210> SEQ ID NO 729
<211> LENGTH: 111
<212> TYPE: PRT
<213> ORGANISM: Oryctolagus cuniculus

<400> SEQUENCE: 729

Ala Tyr Asp Met Thr Gln Thr Pro Ala Ser Val Glu Val Ala Val Gly
1               5                   10                  15

Gly Thr Val Thr Ile Asn Cys Gln Ala Ser Glu Thr Ile Tyr Ser Trp
            20                  25                  30

Leu Ser Trp Tyr Gln Gln Lys Pro Gly Gln Pro Pro Lys Leu Leu Ile
        35                  40                  45

Tyr Gln Ala Ser Asp Leu Ala Ser Gly Val Pro Ser Arg Phe Ser Gly
    50                  55                  60

Ser Gly Ala Gly Thr Glu Tyr Thr Leu Thr Ile Ser Gly Val Gln Cys
65                  70                  75                  80

Asp Asp Ala Ala Thr Tyr Tyr Cys Gln Gln Gly Tyr Ser Gly Ser Asn
                85                  90                  95

Val Asp Asn Val Phe Gly Gly Gly Thr Glu Val Val Val Lys Arg
            100                 105                 110


<210> SEQ ID NO 730
<211> LENGTH: 88
<212> TYPE: PRT
<213> ORGANISM: Homo sapiens

<400> SEQUENCE: 730

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys
                85


<210> SEQ ID NO 731
<211> LENGTH: 88
<212> TYPE: PRT
<213> ORGANISM: Homo sapiens

<400> SEQUENCE: 731

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

```
65                  70                  75                  80

Asp Asp Phe Ala Thr Tyr Tyr Cys
                85


<210> SEQ ID NO 732
<211> LENGTH: 88
<212> TYPE: PRT
<213> ORGANISM: Homo sapiens

<400> SEQUENCE: 732

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85


<210> SEQ ID NO 733
<211> LENGTH: 111
<212> TYPE: PRT
<213> ORGANISM: Artificial Sequence
<220> FEATURE:
<223> OTHER INFORMATION: Humanized antibody

<400> SEQUENCE: 733

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Thr Ile Tyr Ser Trp
            20                  25                  30

Leu Ser Trp Tyr Gln Gln Lys Pro Gly Lys Ala Pro Lys Leu Leu Ile
        35                  40                  45

Tyr Gln Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Gly Ser Asn
                85                  90                  95

Val Asp Asn Val Phe Gly Gly Gly Thr Lys Val Glu Ile Lys Arg
            100                 105                 110


<210> SEQ ID NO 734
<211> LENGTH: 11
<212> TYPE: PRT
<213> ORGANISM: Homo sapiens

<400> SEQUENCE: 734

Phe Gly Gly Gly Thr Lys Val Glu Ile Lys Arg
1               5                   10


<210> SEQ ID NO 735
<211> LENGTH: 118
<212> TYPE: PRT
<213> ORGANISM: Oryctolagus cuniculus

<400> SEQUENCE: 735
```

Gln Glu Gln Leu Lys Glu Ser Gly Gly Arg Leu Val Thr Pro Gly Thr
1 5 10 15

Pro Leu Thr Leu Thr Cys Thr Ala Ser Gly Phe Ser Leu Asn Asp His
20 25 30

Ala Met Gly Trp Val Arg Gln Ala Pro Gly Lys Gly Leu Glu Tyr Ile
35 40 45

Gly Phe Ile Asn Ser Gly Gly Ser Ala Arg Tyr Ala Ser Trp Ala Glu
50 55 60

Gly Arg Phe Thr Ile Ser Arg Thr Ser Thr Thr Val Asp Leu Lys Met
65 70 75 80

Thr Ser Leu Thr Thr Glu Asp Thr Ala Thr Tyr Phe Cys Val Arg Gly
85 90 95

Gly Ala Val Trp Ser Ile His Ser Phe Asp Pro Trp Gly Pro Gly Thr
100 105 110

Leu Val Thr Val Ser Ser
115

<210> SEQ ID NO 736
<211> LENGTH: 98
<212> TYPE: PRT
<213> ORGANISM: Homo sapiens

<400> SEQUENCE: 736

Gln Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 737
<211> LENGTH: 97
<212> TYPE: PRT
<213> ORGANISM: Homo sapiens

<400> SEQUENCE: 737

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Ser Asn
20 25 30

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg

<210> SEQ ID NO 738
<211> LENGTH: 97
<212> TYPE: PRT
<213> ORGANISM: Homo sapiens

<400> SEQUENCE: 738

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 739
<211> LENGTH: 120
<212> TYPE: PRT
<213> ORGANISM: Artificial Sequence
<220> FEATURE:
<223> OTHER INFORMATION: Humanized antibody

<400> SEQUENCE: 739

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Leu Asn Asp His
            20                  25                  30

Ala Met Gly Trp Val Arg Gln Ala Pro Gly Lys Gly Leu Glu Tyr Val
        35                  40                  45

Gly Phe Ile Asn Ser Gly Gly Ser Ala Arg Tyr Ala Ser Ser Ala Glu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Ala Val Trp Ser Ile His Ser Phe Asp Pro Trp Gly Gln
            100                 105                 110

Gly Thr Leu Val Thr Val Ser Ser
        115                 120

<210> SEQ ID NO 740
<211> LENGTH: 11
<212> TYPE: PRT
<213> ORGANISM: Homo sapiens

<400> SEQUENCE: 740

Trp Gly Gln Gly Thr Leu Val Thr Val Ser Ser
1               5                   10

<210> SEQ ID NO 741
<211> LENGTH: 32
<212> TYPE: DNA
<213> ORGANISM: Artificial Sequence
<220> FEATURE:

-continued

```
<223> OTHER INFORMATION: PCR Primer

<400> SEQUENCE: 741

agcgcttatt ccgctatcca gatgacccag tc                                 32


<210> SEQ ID NO 742
<211> LENGTH: 22
<212> TYPE: DNA
<213> ORGANISM: Artificial Sequence
<220> FEATURE:
<223> OTHER INFORMATION: PCR Primer

<400> SEQUENCE: 742

cgtacgtttg atttccacct tg                                            22


<210> SEQ ID NO 743
<211> LENGTH: 32
<212> TYPE: DNA
<213> ORGANISM: Artificial Sequence
<220> FEATURE:
<223> OTHER INFORMATION: PCR Primer

<400> SEQUENCE: 743

agcgcttatt ccgaggtgca gctggtggag tc                                 32


<210> SEQ ID NO 744
<211> LENGTH: 20
<212> TYPE: DNA
<213> ORGANISM: Artificial Sequence
<220> FEATURE:
<223> OTHER INFORMATION: PCR Primer

<400> SEQUENCE: 744

ctcgagacgg tgacgagggt                                               20
```